United States Patent
McDonald et al.

(10) Patent No.: US 9,611,252 B2
(45) Date of Patent: *Apr. 4, 2017

(54) THERAPEUTIC INHIBITORY COMPOUNDS

(71) Applicant: LifeSci Pharmaceuticals, Inc., Bridgetown, St. Michael (BB)

(72) Inventors: Andrew McDonald, New York, NY (US); Shawn Qian, Foster City, CA (US)

(73) Assignee: LIFESCI PHARMACEUTICALS, INC., St. Michael (BB)

( * ) Notice: Subject to any disclaimer, the term of this patent is extended or adjusted under 35 U.S.C. 154(b) by 0 days.

This patent is subject to a terminal disclaimer.

(21) Appl. No.: 15/042,102

(22) Filed: Feb. 11, 2016

(65) Prior Publication Data

US 2016/0200704 A1    Jul. 14, 2016

Related U.S. Application Data

(63) Continuation-in-part of application No. PCT/US2014/072851, filed on Dec. 30, 2014.

(60) Provisional application No. 62/190,223, filed on Jul. 8, 2015, provisional application No. 62/187,786, filed on Jul. 1, 2015, provisional application No. 62/025,203, filed on Jul. 16, 2014, provisional application No. 61/921,995, filed on Dec. 30, 2013.

(51) Int. Cl.
  *C07D 401/14*  (2006.01)
  *C07D 413/14*  (2006.01)
  *C07D 471/04*  (2006.01)

(52) U.S. Cl.
  CPC ......... *C07D 401/14* (2013.01); *C07D 413/14* (2013.01); *C07D 471/04* (2013.01)

(58) Field of Classification Search
  None
  See application file for complete search history.

(56) References Cited

U.S. PATENT DOCUMENTS

| | | |
|---|---|---|
| 5,846,514 A | 12/1998 | Foster et al. |
| 6,334,997 B1 | 1/2002 | Foster et al. |
| 2009/0099184 A1 | 4/2009 | Delombaert et al. |
| 2009/0270407 A1 | 10/2009 | Tseng et al. |
| 2011/0118236 A1* | 5/2011 | Mochizuki ........... C07D 231/56 514/214.02 |
| 2011/0124626 A1 | 5/2011 | Pooni et al. |
| 2014/0350034 A1 | 11/2014 | Brandl et al. |

FOREIGN PATENT DOCUMENTS

| | | |
|---|---|---|
| WO | WO-2010108733 A1 | 9/2010 |
| WO | WO-2013040436 A2 | 3/2013 |
| WO | WO-2014086805 A1 | 6/2014 |
| WO | WO-2015022546 A1 | 2/2015 |
| WO | WO-2015103317 A1 | 7/2015 |
| WO | WO-2016011209 A1 | 1/2016 |

OTHER PUBLICATIONS

Berge et al. Pharmaceutical Salts. Journal of Pharmaceutical Sciences 66(1):1-19 (Jan. 1977).
Bork et al. Treatment of 193 episodes of laryngeal edema with C1 inhibitor concentrate in patients with hereditary angioedema. Arch. Intern. Med. 161:714-718 (2001).
Bork et al. Treatment with C1 inhibitor concentrate in abdominal pain attacks of patients with hereditary angioedema. Transfusion 45:1774-1784 (2005).
Bundgard et al. Design of Prodrugs pp. 7-9, 21-24 (1985).
Chemical Abstracts Search (Jul. 7, 2015).
Colman et al. Effect of cleavage of the heavy chain of human plasma kallikrein on its functional properties. Blood 65:311-318 (1985).
COOL. Characterization of the human blood coagulation factor XII gene. Intron/exon gene organization and analysis of the 5'-flanking region. The Journal of Biological Chemistry 262(28):13662-13673 (1987).
Cugno et al. C1-inhibitor deficiency and angioedema: molecular mechanisms and clinical progress. Trends Mol. Med. 15(2):69-78 (2009).
Cugno et al. Generation of plasmin during acute attacks of hereditary angioedema. The Journal of Laboratory and Clinical Medicine 121(1):38-43 (1993).
Evans. Synthesis of radiolabeled compounds. J Radioanal Chem 64(1-2): 9-32 (1981).
Gao. Extracellular carbonic anhydrase mediates hemorrhagic retinal and cerebral vascular permeability through prekallikrein activation. Nat Med 13(2):181-188 (2007).
Higuchi et al. Pro-drugs as Novel Delivery Systems. A.C.S. Symposium Series vol. 14 (1975).
Kabalka et al. The Synthesis of Radiolabeled Compounds via Organometallic Intermediates. Tetrahedron 45(21):6601-6621 (1989).
Kaplan et al. Angioedema. J. Am. Acad. Dermatol. 53(3):373-388 (2005).
Kaplan et al. The intrinsic coagulation/kinin-forming cascade: assembly in plasma and cell surfaces in inflammation. Advances in Immunology 66:225-272 (1997).
Liu et al. Intraocular hemorrhage causes retinal vascular dysfunction via plasma kallikrein. Invest. Ophthalmol. Vis. Sci. 54(2):1086-1094 (2013).

(Continued)

*Primary Examiner* — Kortney L Klinkel
*Assistant Examiner* — William Lee
(74) *Attorney, Agent, or Firm* — Wilson, Sonsini, Goodrich & Rosati

(57) ABSTRACT

Provided herein are heterocyclic derivative compounds and pharmaceutical compositions comprising said compounds that are useful for inhibiting plasma kallikrein. Furthermore, the subject compounds and compositions are useful for the treatment of diseases wherein the inhibition of plasma kallikrein inhibition has been implicated, such as angioedema and the like.

20 Claims, No Drawings

(56) References Cited

OTHER PUBLICATIONS

Liu et al. Plasma kallikrein-kinin system and diabetic retinopathy. Biol Chem 394(3):319-328 (2013).
Mehta et al. Signaling mechanisms regulating endothelial permeability. Physiol. Rev. 86(1):279-367 (2006).
Muller et al. Novel roles for factor XII-driven plasma contact activation system. Curr. Opin. Hematol. 15:516-521 (2008).
Ny et al. The structure of the human tissue-type plasminogen activator gene: correlation of intron and exon structures to functional and structural domains. PNAS USA 81(17):5355-5359 (1984).
PCT/US2014/072851 International Search Report and Written Opinion dated May 15, 2015.
PCT/US2015/40659 International Search Report and Written Opinion dated Oct. 16, 2015.
Phipps et al. Plasma kallikrein mediates angiotensin II type 1 receptor-stimulated retinal vascular permeability. Hypertension 53:175-181 (2009).
Pixley et al. The regulation of human factor XIIa by plasma proteinase inhibitors. The Journal of Biological Chemistry 260(3):1723-1729 (1985).
Sandoval et al. Ca(2+) signalling and PKCalpha activate increased endothelial permeability by disassembly of VE-cadherin junctions. J. Physiol. 533(pt 2):433-445 (2001).
Schapira et al. Protection of human plasma kallikrein from inactivation by C1 inhibitor and other protease inhibitors. The role of high molecular weight kininogen. Biochemistry 20:2738-2743 (1981).
Stahl et al. Handbook of Pharmaceutical Salts. Verlag Helvetica Chimica Acta, Zurich, 2002.
Stavrou. Factor XII: what does it contribute to our understanding of the physiology and pathophysiology of hemostasis & thrombosis. Thrombosis Research 125(3):210-215 (2010).
Storoni et al. Selective Inhibition of Plasma Kallikrein Protects brain from Reperfusion Injury. JPET 381:849-954 (2006).
Co-pending U.S. Appl. No. 15/199,785, filed Jun. 30, 2016.
Liu et al. Author response: retinal microglia. Invest. Ophthalmol. Vis. Sci. 54(2):pii (2013).
Liu et al. Hyperoxia causes regression of vitreous neovascularization by downregulating VEGF/VEGFR2 pathway. Invest. Ophthalmol. Vis. Sci. 54(2):918-931 (2013).
Liu et al. TGFβ signaling induces expression of Gadd45b in retinal ganglion cells. Invest. Ophthalmol. Vis. Sci. 54(2):1061-1069 (2013).
PCT/US2014/072851 International Preliminary Report on Patentability dated Jul. 14, 2016.
PCT/IB2016/01048 International Search Report and Written Opinion dated Nov. 15, 2016.

* cited by examiner

THERAPEUTIC INHIBITORY COMPOUNDS

CROSS-REFERENCE

This application claims the benefit of U.S. application Ser. No. 62/190,223, filed Jul. 8, 2015; and U.S. application Ser. No. 62/187,786, filed Jul. 1, 2015; and is a continuation-in-part of International Application No. PCT/US2014/072851, filed Dec. 30, 2014, which claims the benefit of U.S. application Ser. No. 62/025,203, filed Jul. 16, 2014; and U.S. application Ser. No. 61/921,995 filed Dec. 30, 2013; each of which are hereby incorporated by reference in their entirety.

BACKGROUND

A need exists in the medicinal arts for the effective treatment of diseases and disorders related to the vascular system. Such diseases and disorders include, but are not limited to, angioedema, macular edema and brain edema.

BRIEF SUMMARY OF THE INVENTION

Provided herein are heterocyclic derivative compounds and pharmaceutical compositions comprising said compounds. The subject compounds and compositions are useful for inhibiting plasma kallikrein.

One embodiment provides a compound, or a pharmaceutically acceptable salt thereof, having the structure of Formula (I):

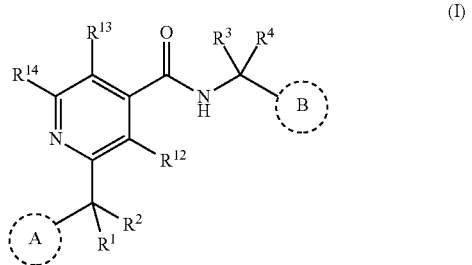

wherein,

Ring A is an optionally substituted bicyclic heteroaryl ring;

Ring B is an optionally substituted monocyclic heteroaryl ring or optionally substituted bicyclic heteroaryl ring;

each $R^{12}$, $R^{13}$, or $R^{14}$ is independently selected from hydrogen, cyano, halo, hydroxy, azido, amino, nitro, —$CO_2H$, —S(O)—$R^{20}$, —S—$R^{20}$, —S(O)$_2$—$R^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —CO—$R^{20}$, —$CO_2$—$R^{20}$, —CO($NR^{21}$)$_2$, —$SO_2(NR^{21})_2$, —C(=$NR^{22}$)—($NR^{21}$)$_2$, or optionally substituted alkynyl;

each $R^1$ or $R^2$ is independently selected from hydrogen, halo, hydroxy, amino, —$CO_2H$, —S(O)—$R^{20}$, —S—$R^{20}$, —S(O)$_2$—$R^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —CO—$R^{20}$, —$CO_2$—$R^{20}$, —CO($NR^{21}$)$_2$, —$SO_2(NR^{21})_2$, —C(=$NR^{22}$)—($NR^{21}$)$_2$, or optionally substituted alkynyl; or optionally, $R^1$ and $R^2$ are optionally substituted C1-C5 alkyl and join to form a ring; or optionally, $R^1$ and $R^2$ together form an oxo;

each $R^3$ or $R^4$ is independently selected from hydrogen, —$CO_2H$, optionally substituted alkyl, optionally substituted cycloalkyl, optionally substituted alkenyl, optionally substituted aryl, optionally substituted heteroaryl, optionally substituted heterocyclyl, —CO—$R^{20}$, —$CO_2$—$R^{20}$, —CO($NR^{21}$)$_2$, —$SO_2(NR^{21})_2$, —C(=$NR^{22}$)—($NR^{21}$)$_2$, or optionally substituted alkynyl; or optionally, $R^3$ and $R^4$ are optionally substituted C1-C5 alkyl and join to form a ring;

each $R^{20}$ is selected from optionally substituted alkyl, optionally substituted cycloalkyl, optionally substituted aryl, optionally substituted heteroaryl, or optionally substituted heterocyclyl;

each $R^{21}$ is selected from hydrogen, optionally substituted alkyl, optionally substituted cycloalkyl, optionally substituted aryl, optionally substituted heteroaryl, or optionally substituted heterocyclyl; and each $R^{22}$ is selected from hydrogen, —CN, optionally substituted alkyl, optionally substituted cycloalkyl, optionally substituted aryl, optionally substituted heteroaryl, or optionally substituted heterocyclyl; with the provision that the compound of Formula (I) is not 2-[[4,5,6,7-tetrahydro-3-(trifluoromethyl)-1H-indazol-1-yl]methyl]-N-(2-thienylmethyl)-4-pyridinecarboxamide.

One embodiment provides a compound, or a pharmaceutically acceptable salt thereof, having the structure of Formula (Ia):

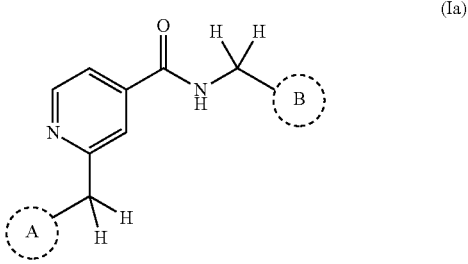

wherein,

Ring A is an optionally substituted bicyclic heteroaryl ring; and

Ring B is an optionally substituted monocyclic heteroaryl ring or optionally substituted bicyclic heteroaryl ring; with the provision that the compound of Formula (Ia) is not 2-[[4,5,6,7-tetrahydro-3-(trifluoromethyl)-1H-indazol-1-yl]methyl]-N-(2-thienylmethyl)-4-pyridinecarboxamide.

One embodiment provides a pharmaceutical composition comprising a compound of Formula (I), or a pharmaceutically acceptable salt thereof, and a pharmaceutically acceptable excipient.

One embodiment provides a method of inhibiting kallikrein enzyme comprising contacting the kallikrein enzyme with a compound of Formula (I).

One embodiment provides a method for treating angioedema in a patient in need thereof comprising administering to the patient a composition comprising a compound of Formula (I), or a pharmaceutically acceptable salt thereof.

One embodiment provides a pharmaceutical composition comprising a compound of Formula (Ia), or a pharmaceutically acceptable salt thereof, and a pharmaceutically acceptable excipient.

One embodiment provides a method of inhibiting kallikrein enzyme comprising contacting the kallikrein enzyme with a compound of Formula (Ia).

One embodiment provides a method for treating angioedema in a patient in need thereof comprising administering to the patient a composition comprising a compound of Formula (Ia), or a pharmaceutically acceptable salt thereof.

INCORPORATION BY REFERENCE

All publications, patents, and patent applications mentioned in this specification are herein incorporated by reference for the specific purposes identified herein.

DETAILED DESCRIPTION OF THE INVENTION

As used herein and in the appended claims, the singular forms "a," "and," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range, in some instances, will vary between 1% and 15% of the stated number or numerical range. The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

DEFINITIONS

As used in the specification and appended claims, unless specified to the contrary, the following terms have the meaning indicated below.

"Amino" refers to the —NH$_2$ radical.
"Cyano" refers to the —CN radical.
"Nitro" refers to the —NO$_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Hydrazino" refers to the =N—NH$_2$ radical.

"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —OR$^a$, —SR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —OC(O)—N(R$^a$)$_2$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$R$^a$ (where t is 1 or 2) and —S(O)$_t$N(R$^a$)$_2$ (where t is 1 or 2) where each R$^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —OR$^a$, —

$SR^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —O$R^a$, —
$SR^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group is through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —O$R^a$, —
$SR^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. In certain embodiments, an alkynylene comprises two to eight carbon atoms (e.g., $C_2$-$C_8$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms (e.g., $C_2$-$C_3$ alkynylene). In other embodiments, an alkynylene comprises two carbon atom (e.g., $C_2$ alkylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene). Unless stated otherwise specifically in the specification, an alkynylene chain is optionally substituted by one or more of the following substituents: halo, cyano, nitro, oxo, thioxo, imino, oximo, trimethylsilanyl, —O$R^a$, —
$SR^a$, —OC(O)—$R^a$, —N($R^a$)$_2$, —C(O)$R^a$, —C(O)O$R^a$, —C(O)N($R^a$)$_2$, —N($R^a$)C(O)O$R^a$, —OC(O)—N($R^a$)$_2$, —N($R^a$)C(O)$R^a$, —N($R^a$)S(O)$_t$$R^a$ (where t is 1 or 2), —S(O)$_t$O$R^a$ (where t is 1 or 2), —S(O)$_t$$R^a$ (where t is 1 or 2) and —S(O)$_t$N($R^a$)$_2$ (where t is 1 or 2) where each $R^a$ is independently hydrogen, alkyl (optionally substituted with halogen, hydroxy, methoxy, or trifluoromethyl), fluoroalkyl, carbocyclyl (optionally substituted with halogen, hydroxy, methoxy, or trifluoromethyl), carbocyclylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl).

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aralkyl" refers to a radical of the formula $-R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula $-R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula $-R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Aralkoxy" refers to a radical bonded through an oxygen atom of the formula $-O-R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Carbocyclyl" refers to a stable non-aromatic monocyclic or polycyclic hydrocarbon radical consisting solely of carbon and hydrogen atoms, which includes fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. Carbocyclyl is saturated (i.e., containing single C—C bonds only) or unsaturated (i.e., containing one or more double bonds or triple bonds). A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1]heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, $-R^b-OR^a$, $-R^b-OC(O)-R^a$, $-R^b-OC(O)-OR^a$, $-R^b-OC(O)-N(R^a)_2$, $-R^b-N(R^a)_2$, $-R^b-C(O)R^a$, $-R^b-C(O)OR^a$, $-R^b-C(O)N(R^a)_2$, $-R^b-O-R^c-C(O)N(R^a)_2$, $-R^b-N(R^a)C(O)OR^a$, $-R^b-N(R^a)C(O)R^a$, $-R^b-N(R^a)S(O)_tR^a$ (where t is 1 or 2), $-R^b-S(O)_tR^a$ (where t is 1 or 2), $-R^b-S(O)_tOR^a$ (where t is 1 or 2) and $-R^b-S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical is optionally substituted as defined above.

"Carbocyclylalkynyl" refers to a radical of the formula —$R^c$-carbocyclyl where $R^c$ is an alkynylene chain as defined above. The alkynylene chain and the carbocyclyl radical is optionally substituted as defined above.

"Carbocyclylalkoxy" refers to a radical bonded through an oxygen atom of the formula —O—$R^c$-carbocyclyl where $R^c$ is an alkylene chain as defined above. The alkylene chain and the carbocyclyl radical is optionally substituted as defined above.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to,

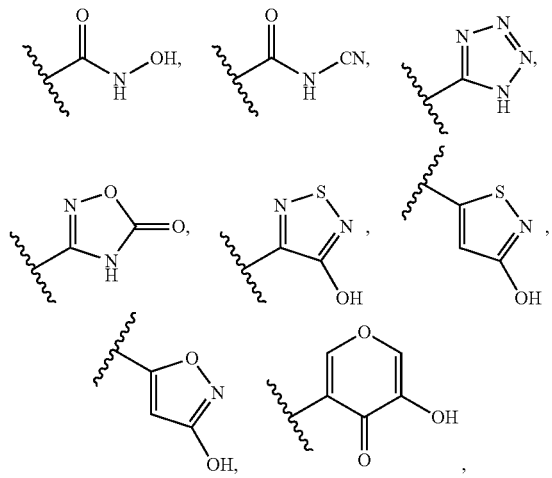

and the like.

"Halo" or "halogen" refers to bromo, chloro, fluoro or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" refers to a stable 3- to 18-membered non-aromatic ring radical that comprises two to twelve carbon atoms and from one to six heteroatoms selected from nitrogen, oxygen and sulfur. Unless stated otherwise specifically in the specification, the heterocyclyl radical is a monocyclic, bicyclic, tricyclic or tetracyclic ring system, which optionally includes fused or bridged ring systems. The heteroatoms in the heterocyclyl radical are optionally oxidized. One or more nitrogen atoms, if present, are optionally quaternized. The heterocyclyl radical is partially or fully saturated. The heterocyclyl is attached to the rest of the molecule through any atom of the ring(s). Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)$C(O)$OR^a$, —$R^b$—$N(R^a)$C(O)$R^a$, —$R^b$—$N(R^a)$S(O)$_tR^a$ (where t is 1 or 2), —$R^b$—S(O)$_tR^a$ (where t is 1 or 2), —$R^b$—S(O)$_tOR^a$ (where t is 1 or 2) and —$R^b$—S(O)$_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heterocyclyl" or "N-attached heterocyclyl" refers to a heterocyclyl radical as defined above containing at least one nitrogen and where the point of attachment of the heterocyclyl radical to the rest of the molecule is through a nitrogen atom in the heterocyclyl radical. An N-heterocyclyl radical is optionally substituted as described above for heterocyclyl radicals. Examples of such N-heterocyclyl radicals include, but are not limited to, 1-morpholinyl, 1-piperidinyl, 1-piperazinyl, 1-pyrrolidinyl, pyrazolidinyl, imidazolinyl, and imidazolidinyl.

"C-heterocyclyl" or "C-attached heterocyclyl" refers to a heterocyclyl radical as defined above containing at least one heteroatom and where the point of attachment of the heterocyclyl radical to the rest of the molecule is through a carbon atom in the heterocyclyl radical. A C-heterocyclyl radical is optionally substituted as described above for heterocyclyl radicals. Examples of such C-heterocyclyl radicals include, but are not limited to, 2-morpholinyl, 2- or 3- or 4-piperidinyl, 2-piperazinyl, 2- or 3-pyrrolidinyl, and the like.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—C(O)$R^a$, —$R^b$—C(O)$OR^a$, —$R^b$—C(O)$N(R^a)_2$, —$R^b$—O—$R^c$—C(O)$N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl (optionally substituted with halogen, hydroxy, methoxy, or trifluoromethyl), fluoroalkyl, cycloalkyl (optionally substituted with halogen, hydroxy, methoxy, or trifluoromethyl), cycloalkylalkyl (optionally substituted with halogen, hydroxy, methoxy, or trifluoromethyl), aryl (optionally substituted with halogen, hydroxy, methoxy, or trifluoromethyl), aralkyl (optionally substituted with halogen, hydroxy, methoxy, or trifluoromethyl), heterocyclyl (optionally substituted with halogen, hydroxy, methoxy, or trifluoromethyl), heterocyclylalkyl (optionally substituted with halogen, hydroxy, methoxy, or trifluoromethyl), heteroaryl (optionally substituted with halogen, hydroxy, methoxy, or trifluoromethyl), or heteroarylalkyl (optionally substituted with halogen, hydroxy, methoxy, or trifluoromethyl), each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An N-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

The compounds disclosed herein, in some embodiments, contain one or more asymmetric centers and thus give rise to enantiomers, diastereomers, and other stereoisomeric forms that are defined, in terms of absolute stereochemistry, as (R)- or (S)-. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans.) Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

The compounds disclosed herein, in some embodiments, are used in different enriched isotopic forms, e.g., enriched in the content of $^2$H, $^3$H, $^{11}$C, $^{13}$C and/or $^{14}$C. In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2$H), tritium ($^3$H), iodine-125 ($^{125}$I) or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are all contemplated. All isotopic variations of the compounds of the present invention, whether radioactive or not, are encompassed within the scope of the present invention.

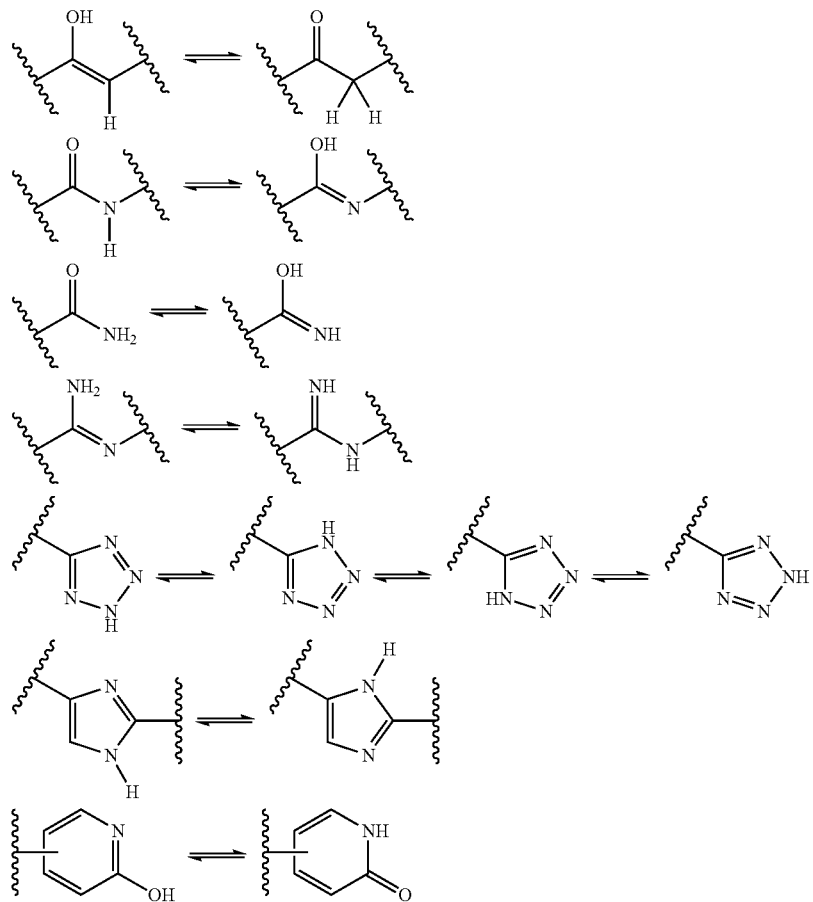

In certain embodiments, the compounds disclosed herein have some or all of the $^1$H atoms replaced with $^2$H atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)]2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commerically from chemical vendors, such as Aldrich Chemical Co.

Deuterium-transfer reagents suitable for use in nucleophilic substitution reactions, such as iodomethane-d$_3$ (CD$_3$I), are readily available and may be employed to transfer a deuterium-substituted carbon atom under nucleophilic substitution reaction conditions to the reaction substrate. The use of CD$_3$I is illustrated, by way of example only, in the reaction schemes below.

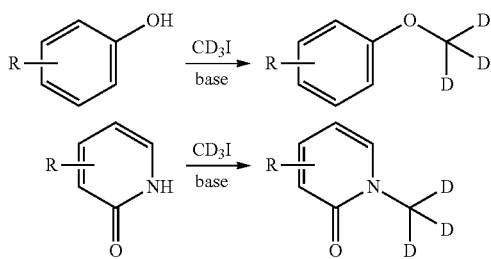

Deuterium-transfer reagents, such as lithium aluminum deuteride (LiAlD$_4$), are employed to transfer deuterium under reducing conditions to the reaction substrate. The use of LiAlD$_4$ is illustrated, by way of example only, in the reaction schemes below.

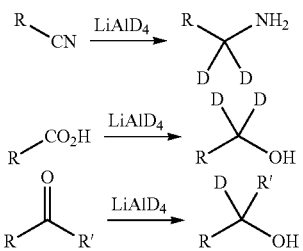

Deuterium gas and palladium catalyst are employed to reduce unsaturated carbon-carbon linkages and to perform a reductive substitution of aryl carbon-halogen bonds as illustrated, by way of example only, in the reaction schemes below.

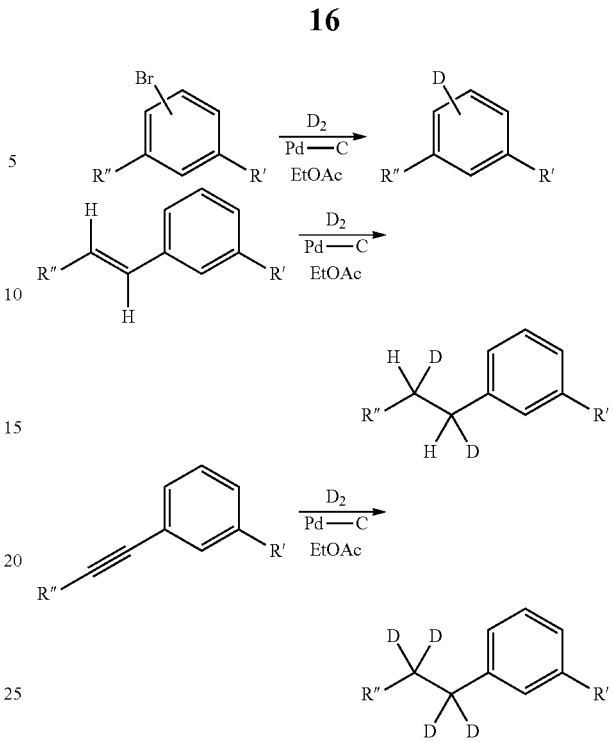

In one embodiment, the compounds disclosed herein contain one deuterium atom. In another embodiment, the compounds disclosed herein contain two deuterium atoms. In another embodiment, the compounds disclosed herein contain three deuterium atoms. In another embodiment, the compounds disclosed herein contain four deuterium atoms. In another embodiment, the compounds disclosed herein contain five deuterium atoms. In another embodiment, the compounds disclosed herein contain six deuterium atoms. In another embodiment, the compounds disclosed herein contain more than six deuterium atoms. In another embodiment, the compound disclosed herein is fully substituted with deuterium atoms and contains no non-exchangeable $^1$H hydrogen atoms. In one embodiment, the level of deuterium incorporation is determined by synthetic methods in which a deuterated synthetic building block is used as a starting material.

"Pharmaceutically acceptable salt" includes both acid and base addition salts. A pharmaceutically acceptable salt of any one of the kallikrein inhibitory compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and. aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

As used herein, "treatment" or "treating," or "palliating" or "ameliorating" are used interchangeably. These terms refer to an approach for obtaining beneficial or desired results including but not limited to therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is still afflicted with the underlying disorder. For prophylactic benefit, the compositions are, in some embodiments, administered to a patient at risk of developing a particular disease, or to a patient reporting one or more of the physiological symptoms of a disease, even though a diagnosis of this disease has not been made.

"Prodrug" is meant to indicate a compound that is, in some embodiments, converted under physiological conditions or by solvolysis to a biologically active compound described herein. Thus, the term "prodrug" refers to a precursor of a biologically active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of alcohol or amine functional groups in the active compounds and the like.

Kallikrein Inhibitory Compounds

Provided herein are heterocyclic derivative compounds and pharmaceutical compositions comprising said compounds. The subject compounds and compositions are useful for inhibiting plasma kallikrein.

One embodiment provides a compound, or a pharmaceutically acceptable salt thereof, having the structure of Formula (I):

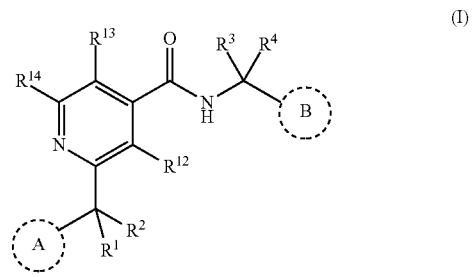

wherein,

Ring A is an optionally substituted bicyclic heterocyclic or heteroaryl ring;

Ring B is an optionally substituted monocyclic heterocyclic or heteroaryl ring or optionally substituted bicyclic heterocyclic or heteroaryl ring;

each $R^{12}$, $R^{13}$, or $R^{14}$ is independently selected from hydrogen, cyano, halo, hydroxy, azido, amino, nitro, —$CO_2H$, —$S(O)$—$R^{20}$, —$S$—$R^{20}$, —$S(O)_2$—$R^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —CO—$R^{20}$, —$CO_2$—$R^{20}$, —$CO(NR^{21})_2$, —$SO_2(NR^{21})_2$, —$C(=NR^{22})$—$(NR^{21})_2$, or optionally substituted alkynyl;

each $R^1$ or $R^2$ is independently selected from hydrogen, halo, hydroxy, amino, —$CO_2H$, —$S(O)$—$R^{20}$, —$S$—$R^{20}$, —$S(O)_2$—$R^{20}$, optionally substituted alkoxy, optionally substituted aryloxy, optionally substituted heteroaryloxy, optionally substituted (heterocyclyl)-O—, optionally substituted alkyl, optionally substituted cycloalkyl, optionally substituted alkenyl, optionally substituted aryl, optionally substituted heteroaryl, optionally substituted heterocyclyl, optionally substituted alkylamino, optionally substituted dialkylamino, —$CO$—$R^{20}$, —$CO_2$—$R^{20}$, —$CO(NR^{21})_2$, —$SO_2(NR^{21})_2$, —$C(=NR^{22})$—$(NR^{21})_2$, or optionally substituted alkynyl; or optionally, $R^1$ and $R^2$ are optionally substituted C1-C5 alkyl and join to form a ring; or optionally, $R^1$ and $R^2$ together form an oxo;

each $R^3$ or $R^4$ is independently selected from hydrogen, —$CO_2H$, optionally substituted alkyl, optionally substituted cycloalkyl, optionally substituted alkenyl, optionally substituted aryl, optionally substituted heteroaryl, optionally substituted heterocyclyl, —$CO$—$R^{20}$, —$CO_2$—$R^{20}$, —$CO(NR^{21})_2$, —$SO_2(NR^{21})_2$, —$C(=NR^{22})$—$(NR^{21})_2$, or optionally substituted alkynyl; or optionally, $R^3$ and $R^4$ are optionally substituted C1-C5 alkyl and join to form a ring;

each $R^{20}$ is selected from optionally substituted alkyl, optionally substituted cycloalkyl, optionally substituted aryl, optionally substituted heteroaryl, or optionally substituted heterocyclyl;

each $R^{21}$ is selected from hydrogen, optionally substituted alkyl, optionally substituted cycloalkyl, optionally substituted aryl, optionally substituted heteroaryl, or optionally substituted heterocyclyl; and each $R^{22}$ is selected from hydrogen, —CN, optionally substituted alkyl, optionally substituted cycloalkyl, optionally substituted aryl, optionally substituted heteroaryl, or optionally substituted heterocyclyl; with the provision that the compound of Formula (I) is not 2-[[4,5,6,7-tetrahydro-3-(trifluoromethyl)-1H-indazol-1-yl]methyl]-N-(2-thienylmethyl)-4-pyridinecarboxamide.

Another embodiment provides the compound, or a pharmaceutically acceptable salt thereof, having the structure of Formula (I), wherein Ring A is an optionally substituted bicyclic heterocyclic ring.

Another embodiment provides the compound, or a pharmaceutically acceptable salt thereof, having the structure of Formula (I), wherein Ring A is an optionally substituted bicyclic heteroaryl ring.

Another embodiment provides the compound, or a pharmaceutically acceptable salt thereof, having the structure of Formula (I), wherein Ring B is an optionally substituted monocyclic heterocyclic ring.

Another embodiment provides the compound, or a pharmaceutically acceptable salt thereof, having the structure of Formula (I), wherein Ring B is an optionally substituted monocyclic heteroaryl ring.

Another embodiment provides the compound, or a pharmaceutically acceptable salt thereof, having the structure of Formula (I), wherein Ring B is an optionally substituted bicyclic heterocyclic ring.

Another embodiment provides the compound, or a pharmaceutically acceptable salt thereof, having the structure of Formula (I), wherein Ring B is an optionally substituted bicyclic heteroaryl ring.

Another embodiment provides the compound, or a pharmaceutically acceptable salt thereof, having the structure of Formula (I), wherein $R^{12}$ is hydrogen.

Another embodiment provides the compound, or a pharmaceutically acceptable salt thereof, having the structure of Formula (I), wherein $R^{14}$ is independently selected from —$S(O)$—$R^2$, —$S$—$R^{20}$, —$S(O)_2$—$R^{20}$, optionally substituted alkoxy, optionally substituted aryloxy, optionally substituted heteroaryloxy, optionally substituted (heterocyclyl)-O—, optionally substituted heteroaryl, optionally substituted heterocyclyl, optionally substituted alkylamino, optionally substituted dialkylamino, —$CO$—$R^{20}$, —$CO_2$—$R^{20}$, —$CO(NR^{21})_2$, —$SO_2(NR^{21})_2$, or —$C(=NR^{22})$—$(NR^{21})_2$. Another embodiment provides the compound, or a pharmaceutically acceptable salt thereof, having the structure of Formula (I), wherein $R^{14}$ is independently selected from optionally substituted alkyl, optionally substituted cycloalkyl, optionally substituted alkenyl, optionally substituted aryl, optionally substituted heteroaryl, optionally substituted heterocyclyl, or optionally substituted alkynyl. Another embodiment provides the compound, or a pharmaceutically acceptable salt thereof, having the structure of Formula (I), wherein $R^{14}$ is hydrogen. Another embodiment provides the compound, or a pharmaceutically acceptable salt thereof, having the structure of Formula (I), wherein $R^{14}$ is optionally substituted alkyl, or optionally substituted cycloalkyl.

Another embodiment provides the compound, or a pharmaceutically acceptable salt thereof, having the structure of Formula (I), wherein $R^{13}$ is independently selected from —$S(O)$—$R^{20}$, —$S$—$R^{20}$, —$S(O)_2$—$R^{20}$, optionally substituted alkoxy, optionally substituted aryloxy, optionally substituted heteroaryloxy, optionally substituted (heterocyclyl)-O—, optionally substituted heteroaryl, optionally substituted heterocyclyl, optionally substituted alkylamino, optionally substituted dialkylamino, —$CO$—$R^{20}$, —$CO_2$—$R^{20}$, —$CO(NR^{21})_2$, —$SO_2(NR^{21})_2$, or —$C(=NR^{22})$—$(NR^{21})_2$. Another embodiment provides the compound, or a pharmaceutically acceptable salt thereof, having the structure of Formula (I), wherein $R^{13}$ is independently selected from optionally substituted alkyl, optionally substituted cycloalkyl, optionally substituted alkenyl, optionally substituted aryl, optionally substituted heteroaryl, optionally substituted heterocyclyl, or optionally substituted alkynyl. Another embodiment provides the compound, or a pharmaceutically acceptable salt thereof, having the structure of Formula (I), wherein $R^{13}$ is hydrogen. Another embodiment provides the compound, or a pharmaceutically acceptable salt thereof, having the structure of Formula (I), wherein $R^{13}$ is optionally substituted alkyl, or optionally substituted cycloalkyl.

Another embodiment provides the compound, or a pharmaceutically acceptable salt thereof, having the structure of Formula (I), wherein $R^3$ and $R^4$ are hydrogen. Another embodiment provides the compound, or a pharmaceutically acceptable salt thereof, having the structure of Formula (I), wherein $R^3$ is hydrogen. Another embodiment provides the compound, or a pharmaceutically acceptable salt thereof, having the structure of Formula (I), wherein $R^4$ is hydrogen. Another embodiment provides the compound, or a pharmaceutically acceptable salt thereof, having the structure of Formula (I), wherein $R^3$ is optionally substituted alkyl. Another embodiment provides the compound, or a pharmaceutically acceptable salt thereof, having the structure of Formula (I), wherein $R^4$ is optionally substituted alkyl.

Another embodiment provides the compound, or a pharmaceutically acceptable salt thereof, having the structure of Formula (I), wherein R¹ and R² are hydrogen. Another embodiment provides the compound, or a pharmaceutically acceptable salt thereof, having the structure of Formula (I), wherein R¹ is hydrogen. Another embodiment provides the compound, or a pharmaceutically acceptable salt thereof, having the structure of Formula (I), wherein R² is hydrogen. Another embodiment provides the compound, or a pharmaceutically acceptable salt thereof, having the structure of Formula (I), wherein R¹ is optionally substituted alkyl. Another embodiment provides the compound, or a pharmaceutically acceptable salt thereof, having the structure of Formula (I), wherein R² is optionally substituted alkyl. Another embodiment provides the compound, or a pharmaceutically acceptable salt thereof, having the structure of Formula (I), wherein R¹ is optionally substituted alkoxy. Another embodiment provides the compound, or a pharmaceutically acceptable salt thereof, having the structure of Formula (I), wherein R² is optionally substituted alkoxy.

One embodiment provides a compound, or a pharmaceutically acceptable salt thereof, having the structure of Formula (Ia):

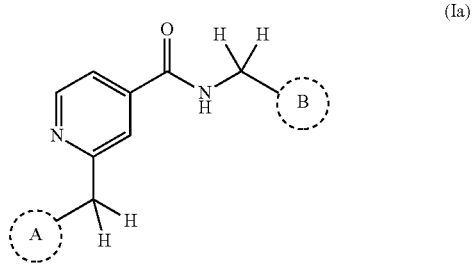

(Ia)

wherein,

Ring A is an optionally substituted bicyclic heterocyclic or heteroaryl ring; and Ring B is an optionally substituted monocyclic heterocyclic or heteroaryl ring or optionally substituted bicyclic heterocyclic or heteroaryl ring; with the provision that the compound of Formula (I) is not 2-[[4,5,6,7-tetrahydro-3-(trifluoromethyl)-1H-indazol-1-yl]methyl]-N-(2-thienylmethyl)-4-pyridinecarboxamide.

Another embodiment provides the compound, or a pharmaceutically acceptable salt thereof, having the structure of Formula (Ia), wherein Ring A is an optionally substituted bicyclic heterocyclic ring.

Another embodiment provides the compound, or a pharmaceutically acceptable salt thereof, having the structure of Formula (Ia), wherein Ring A is an optionally substituted bicyclic heteroaryl ring.

Another embodiment provides the compound, or a pharmaceutically acceptable salt thereof, having the structure of Formula (Ia), wherein Ring B is an optionally substituted monocyclic heterocyclic ring.

Another embodiment provides the compound, or a pharmaceutically acceptable salt thereof, having the structure of Formula (Ia), wherein Ring B is an optionally substituted monocyclic heteroaryl ring.

Another embodiment provides the compound, or a pharmaceutically acceptable salt thereof, having the structure of Formula (Ia), wherein Ring B is an optionally substituted bicyclic heterocyclic ring.

Another embodiment provides the compound, or a pharmaceutically acceptable salt thereof, having the structure of Formula (Ia), wherein Ring B is an optionally substituted bicyclic heteroaryl ring.

Another embodiment provides the compound, or a pharmaceutically acceptable salt thereof, having the structure of Formula (I) or (Ia), wherein Ring B is not thiophenyl.

Another embodiment provides the compound, or a pharmaceutically acceptable salt thereof, having the structure of Formula (I) or (Ia), wherein Ring A is not tetrahydro-1H-indazol-1-yl.

Another embodiment provides the compound, or a pharmaceutically acceptable salt thereof, having the structure of Formula (I) or (Ia), wherein Ring A is selected from optionally substituted quinolyl, optionally substituted indolyl, optionally substituted indazolyl, optionally substituted benzimidazolyl, optionally substituted isoquinolyl, optionally substituted cinnolinyl, optionally substituted phthalazinyl, optionally substituted quinazolinyl, optionally substituted naphthyridinyl, or optionally substituted benzoisoxazolyl. Another embodiment provides the compound, or a pharmaceutically acceptable salt thereof, having the structure of Formula (I) or (Ia), wherein Ring A is selected from optionally substituted benzo[d]isoxazol-7-yl, optionally substituted 4-aminoquinazolin-5-yl, optionally substituted indol-5-yl; optionally substituted quinolin-3-yl; quinoxalin-2-yl; optionally substituted isoquinolin-1(2H)-on-2-yl; or optionally substituted quinolin-6-yl. Another embodiment provides the compound, or a pharmaceutically acceptable salt thereof, having the structure of Formula (I) or (Ia), wherein Ring A is an optionally substituted quinolin-6-yl. Another embodiment provides the compound, or a pharmaceutically acceptable salt thereof, having the structure of Formula (I) or (Ia), wherein the optionally substituted quinolin-6-yl is substituted with at least one substituent selected from optionally substituted C1-C3 alkyl, halogen, —CN, —SO₂Me, —SO₂NH₂, —CONH₂, —CH₂NHAc, —CO₂Me, —CO₂H, —CH₂OH, —CH₂NH₂, —NH₂, —OH, or —OMe. Another embodiment provides the compound, or a pharmaceutically acceptable salt thereof, having the structure of Formula (I) or (Ia), wherein the optionally substituted quinolin-6-yl is substituted at least at the 3-position. Another embodiment provides the compound, or a pharmaceutically acceptable salt thereof, having the structure of Formula (I) or (Ia), wherein the quinolin-6-yl is selected from 3-chloroquinolin-6-yl, 3-methylquinolin-6-yl, 3-trifluoromethylquinolin-6-yl, 3-fluoroquinolin-6-yl, or 3-cyanoquinolin-6-yl. Another embodiment provides the compound, or a pharmaceutically acceptable salt thereof, having the structure of Formula (I) or (Ia), wherein Ring A is an optionally substituted quinolin-3-yl. Another embodiment provides the compound, or a pharmaceutically acceptable salt thereof, having the structure of Formula (I) or (Ia), wherein the optionally substituted quinolin-3-yl is substituted at least at the 6-position or the 7-position. Another embodiment provides the compound, or a pharmaceutically acceptable salt thereof, having the structure of Formula (I) or (Ia), wherein the optionally substituted quinolin-3-yl is substituted with at least one substituent selected from optionally substituted C1-C3 alkyl, halogen, —CN, —SO₂Me, —SO₂NH₂, —CONH₂, —CH₂NHAc, —CO₂Me, —CO₂H, —CH₂OH, —CH₂NH₂, —NH₂, —OH, or —OMe.

Another embodiment provides the compound, or a pharmaceutically acceptable salt thereof, having the structure of Formula (I) or (Ia), wherein Ring B is selected from an optionally substituted monocyclic heteroaryl ring. Another embodiment provides the compound, or a pharmaceutically acceptable salt thereof, having the structure of Formula (I) or (Ia), wherein the optionally substituted monocyclic heteroaryl ring is selected from optionally substituted imidazolyl, optionally substituted pyrazolyl, optionally substituted pyridinyl, optionally substituted pyridazinyl, optionally substituted pyrimidinyl, or optionally substituted pyrazinyl. Another embodiment provides the compound, or a pharmaceutically acceptable salt thereof, having the structure of Formula (I) or (Ia), wherein the optionally substituted monocyclic heteroaryl ring is an optionally substituted pyridinyl. Another embodiment provides the compound, or a pharmaceutically acceptable salt thereof, having the structure of Formula (I) or (Ia), wherein the optionally substituted pyridinyl is an optionally substituted aminopyridinyl. Another embodiment provides the compound, or a pharmaceutically acceptable salt thereof, having the structure of Formula (I) or (Ia), wherein the optionally substituted aminopyridinyl is an optionally substituted 6-aminopyridin-3-yl. Another embodiment provides the compound, or a pharmaceutically acceptable salt thereof, having the structure of Formula (I) or (Ia), wherein Ring B is selected from an optionally substituted bicyclic heteroaryl ring. Another embodiment provides the compound, or a pharmaceutically acceptable salt thereof, having the structure of Formula (I) or (Ia), wherein the optionally substituted bicyclic heteroaryl ring is selected from optionally substituted quinolinyl, optionally substituted isoquinolinyl, optionally substituted quinazolinyl, optionally substituted indolyl, optionally substituted indazolyl, optionally substituted 1H-pyrrolo[2,3-b]pyridinyl, optionally substituted benzoxazolyl, optionally substituted benzoisoxazolyl, or optionally substituted benzimidazolyl. Another embodiment provides the compound, or a pharmaceutically acceptable salt thereof, having the structure of Formula (I) or (Ia), wherein the optionally substituted bicyclic heteroaryl ring is an optionally substituted indolyl. Another embodiment provides the compound, or a pharmaceutically acceptable salt thereof, having the structure of Formula (I) or (Ia), wherein the optionally substituted bicyclic heteroaryl ring is an optionally substituted indazolyl. Another embodiment provides the compound, or a pharmaceutically acceptable salt thereof, having the structure of Formula (I) or (Ia), wherein the optionally substituted indolyl is an optionally substituted indol-5-yl. Another embodiment provides the compound, or a pharmaceutically acceptable salt thereof, having the structure of Formula (I) or (Ia), wherein the optionally substituted indazolyl is an optionally substituted indazol-5-yl. Another embodiment provides the compound, or a pharmaceutically acceptable salt thereof, having the structure of Formula (I) or (Ia), wherein the optionally substituted bicyclic heteroaryl ring is an optionally substituted 1H-pyrrolo[2,3-b]pyridinyl. Another embodiment provides the compound, or a pharmaceutically acceptable salt thereof, having the structure of Formula (I) or (Ia), wherein Ring A is selected from optionally substituted quinolyl; and Ring B is selected from an optionally substituted indolyl, an optionally substituted indazolyl, and an optionally substituted 1H-pyrrolo[2,3-b]pyridinyl.

In some embodiments, the kallikrein inhibitory compound described in Formula (I) has a structure provided in Table 1.

TABLE 1

| Chemical Synthesis Example | Structure | Name |
|---|---|---|
| 1 | 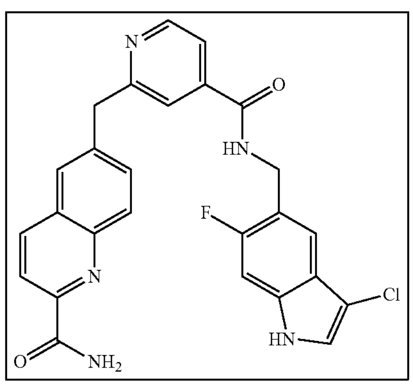 [SMILES: NC(=O)c1ccc2cc(Cc3cc(C(=O)NCc4cc5c(Cl)c[nH]c5cc4F)ccn3)ccc2n1] | 6-((4-(((3-chloro-6-fluoro-1H-indol-5-yl)methyl)carbamoyl)pyridin-2-yl)methyl)quinoline-2-carboxamide |
| 2 | 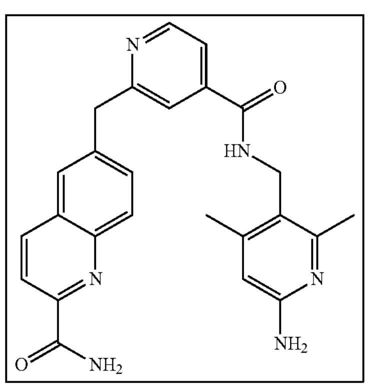 [SMILES: Cc1cc(N)nc(C)c1CNC(=O)c1ccnc(Cc2ccc3nc(C(N)=O)ccc3c2)c1] | 6-((4-(((6-amino-2,4-dimethylpyridin-3-yl)methyl)carbamoyl)pyridin-2-yl)methyl)quinoline-2-carboxamide |

TABLE 1-continued

| Chemical Synthesis Example | Structure | Name |
|---|---|---|
| 3 | 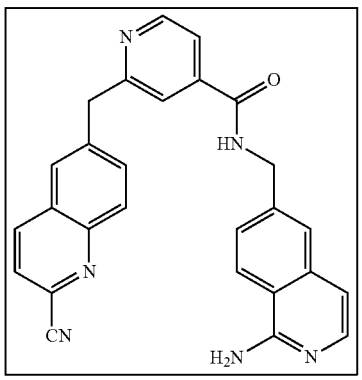 [SMILES: N#Cc1ccc2cc(Cc3cc(C(=O)NCc4ccc5c(N)nccc5c4)ccn3)ccc2n1] | N-((1-aminoisoquinolin-6-yl)methyl)-2-((2-cyanoquinolin-6-yl)methyl)isonicotinamide |
| 4 | 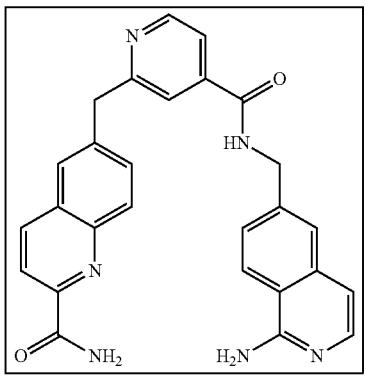 [SMILES: NC(=O)c1ccc2cc(Cc3cc(C(=O)NCc4ccc5c(N)nccc5c4)ccn3)ccc2n1] | 6-((4-(((1-aminoisoquinolin-6-yl)methyl)carbamoyl)pyridin-2-yl)methyl)quinoline-2-carboxamide |
| 5 | 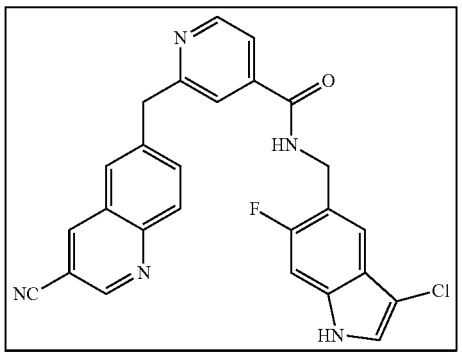 [SMILES: N#Cc1cnc2ccc(Cc3cc(C(=O)NCc4cc5c(Cl)c[nH]c5cc4F)ccn3)cc2c1] | N-((3-chloro-6-fluoro-1H-indol-5-yl)methyl)-2-((3-cyanoquinolin-6-yl)methyl)isonicotinamide |
| 6 | 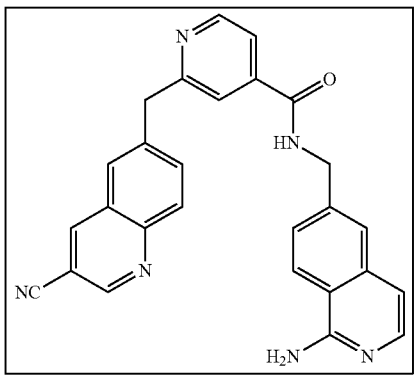 [SMILES: N#Cc1cnc2ccc(Cc3cc(C(=O)NCc4ccc5c(N)nccc5c4)ccn3)cc2c1] | N-((1-aminoisoquinolin-6-yl)methyl)-2-((3-cyanoquinolin-6-yl)methyl)isonicotinamide |

TABLE 1-continued

| Chemical Synthesis Example | Structure | Name |
|---|---|---|
| 7 | 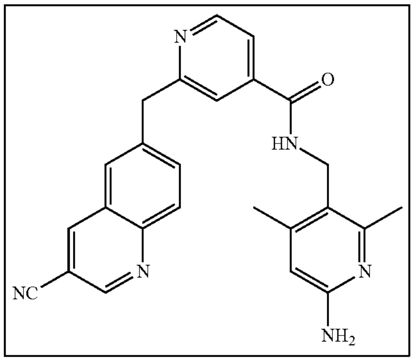 [SMILES: Cc1cc(N)nc(C)c1CNC(=O)c1ccnc(Cc2ccc3ncc(C#N)cc3c2)c1] | N-((6-amino-2,4-dimethylpyridin-3-yl)methyl)-2-((3-cyanoquinolin-6-yl)methyl)isonicotinamide |
| 8 | 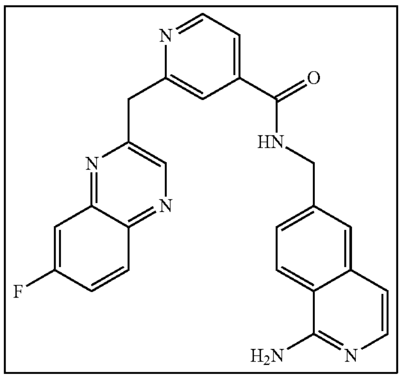 [SMILES: Nc1nccc2cc(CNC(=O)c3ccnc(Cc4cnc5ccc(F)cc5n4)c3)ccc12] | N-((1-aminoisoquinolin-6-yl)methyl)-2-((7-fluoroquinoxalin-2-yl)methyl)isonicotinamide |
| 9 | 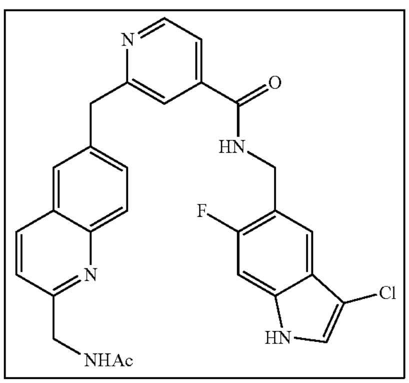 [SMILES: CC(=O)NCc1ccc2cc(Cc3cc(C(=O)NCc4cc5c(Cl)c[nH]c5cc4F)ccn3)ccc2n1] | 2-((2-(acetamidomethyl)quinolin-6-yl)methyl)-N-((3-chloro-6-fluoro-1H-indol-5-yl)methyl)isonicotinamide |
| 10 | 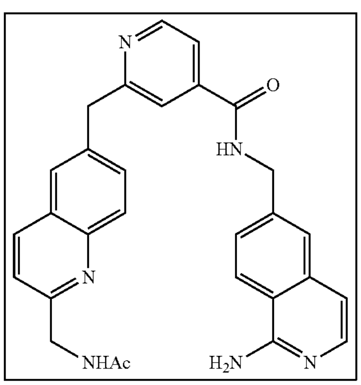 [SMILES: CC(=O)NCc1ccc2cc(Cc3cc(C(=O)NCc4ccc5c(N)nccc5c4)ccn3)ccc2n1] | 2-((2-(acetamidomethyl)quinolin-6-yl)methyl)-N-((1-aminoisoquinolin-6-yl)methyl)isonicotinamide |

TABLE 1-continued

| Chemical Synthesis Example | Structure | Name |
|---|---|---|
| 11 | 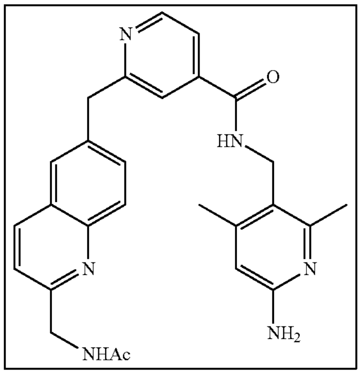 [SMILES: CC(=O)NCc1ccc2cc(Cc3cc(C(=O)NCc4c(C)cc(N)nc4C)ccn3)ccc2n1] | 2-((2-(acetamidomethyl)quinolin-6-yl)methyl)-N-((6-amino-2,4-dimethylpyridin-3-yl)methyl)isonicotinamide |
| 12 | 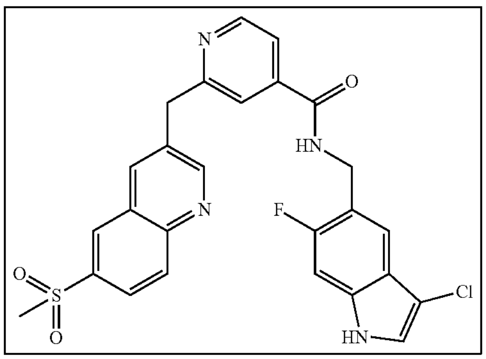 [SMILES: CS(=O)(=O)c1ccc2ncc(Cc3cc(C(=O)NCc4cc5c(Cl)c[nH]c5cc4F)ccn3)cc2c1] | N-((3-chloro-6-fluoro-1H-indol-5-yl)methyl)-2-((6-(methylsulfonyl)quinolin-3-yl)methyl)isonicotinamide |
| 13 | 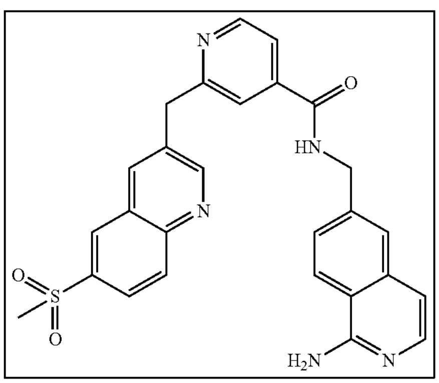 [SMILES: CS(=O)(=O)c1ccc2ncc(Cc3cc(C(=O)NCc4ccc5c(N)nccc5c4)ccn3)cc2c1] | N-((1-aminoisoquinolin-6-yl)methyl)-2-((6-(methylsulfonyl)quinolin-3-yl)methyl)isonicotinamide |
| 14 | 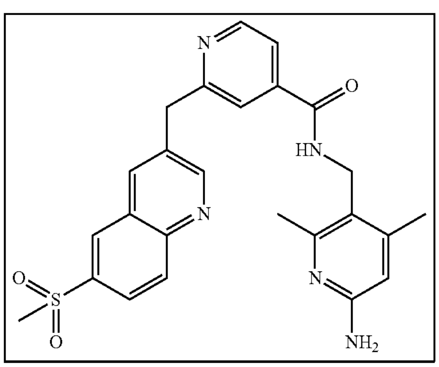 [SMILES: Cc1cc(N)nc(C)c1CNC(=O)c1ccnc(Cc2cnc3ccc(S(C)(=O)=O)cc3c2)c1] | N-((6-amino-2,4-dimethylpyridin-3-yl)methyl)-2-((6-(methylsulfonyl)quinolin-3-yl)methyl)isonicotinamide |

TABLE 1-continued

| Chemical Synthesis Example | Structure | Name |
|---|---|---|
| 15 | 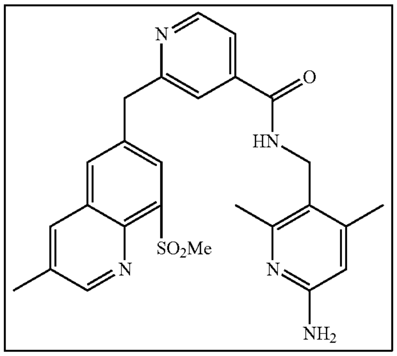 | N-((6-amino-2,4-dimethylpyridin-3-yl)methyl)-2-((3-methyl-8-(methylsulfonyl)quinolin-6-yl)methyl)isonicotinamide |
| 16 | 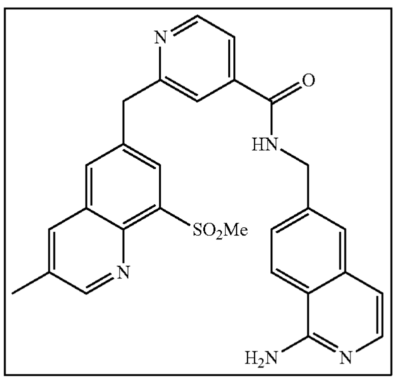 [SMILES: Cc1cnc2c(S(C)(=O)=O)cc(Cc3cc(C(=O)NCc4ccc5c(N)nccc5c4)ccn3)cc2c1] | N-((1-aminoisoquinolin-6-yl)methyl)-2-((3-methyl-8-(methylsulfonyl)quinolin-6-yl)methyl)isonicotinamide |
| 17 | 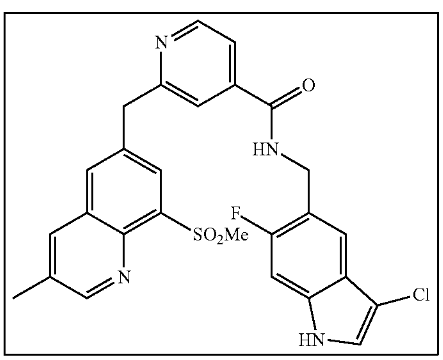 [SMILES: Cc1cnc2c(S(C)(=O)=O)cc(Cc3cc(C(=O)NCc4cc5c(Cl)c[nH]c5cc4F)ccn3)cc2c1] | N-((3-chloro-6-fluoro-1H-indol-5-yl)methyl)-2-((3-methyl-8-(methylsulfonyl)quinolin-6-yl)methyl)isonicotinamide |
| 18 | 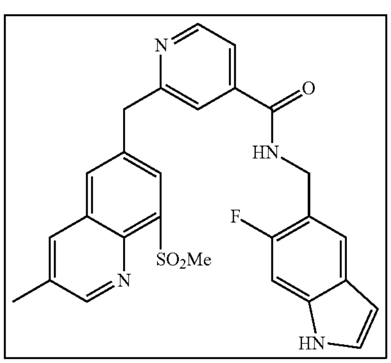 [SMILES: Cc1cnc2c(S(C)(=O)=O)cc(Cc3cc(C(=O)NCc4cc5cc[nH]c5cc4F)ccn3)cc2c1] | N-((6-fluoro-1H-indol-5-yl)methyl)-2-((3-methyl-8-(methylsulfonyl)quinolin-6-yl)methyl)isonicotinamide |

TABLE 1-continued

| Chemical Synthesis Example | Structure | Name |
|---|---|---|
| 19 | 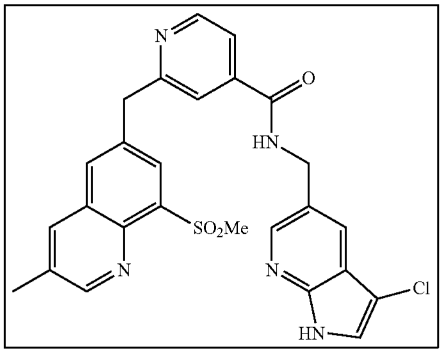 [SMILES: Cc1cnc2c(S(C)(=O)=O)cc(Cc3cc(C(=O)NCc4cnc5[nH]cc(Cl)c5c4)ccn3)cc2c1] | N-((3-chloro-1H-pyrrolo[2,3-b]pyridin-5-yl)methyl)-2-((3-methyl-8-(methylsulfonyl)quinolin-6-yl)methyl)isonicotinamide |
| 20 | 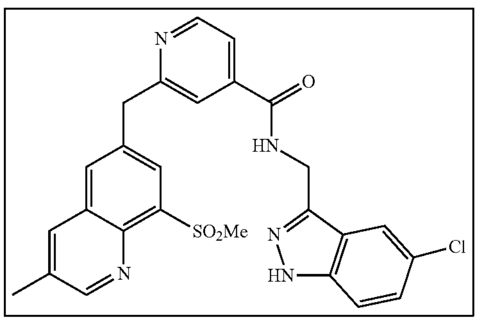 [SMILES: Cc1cnc2c(S(C)(=O)=O)cc(Cc3cc(C(=O)NCc4n[nH]c5ccc(Cl)cc45)ccn3)cc2c1] | N-((5-chloro-1H-indazol-3-yl)methyl)-2-((3-methyl-8-(methylsulfonyl)quinolin-6-yl)methyl)isonicotinamide |
| 21 | 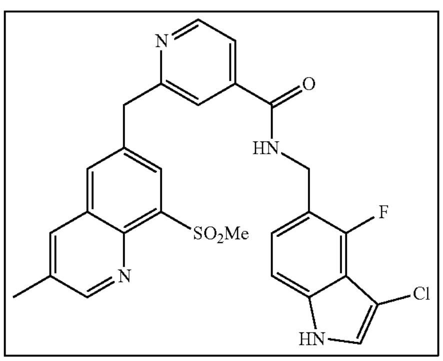 [SMILES: Cc1cnc2c(S(C)(=O)=O)cc(Cc3cc(C(=O)NCc4ccc5[nH]cc(Cl)c5c4F)ccn3)cc2c1] | N-((3-chloro-4-fluoro-1H-indol-5-yl)methyl)-2-((3-methyl-8-(methylsulfonyl)quinolin-6-yl)methyl)isonicotinamide |
| 22 | 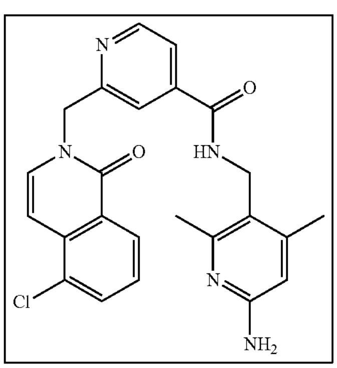 [SMILES: Cc1cc(N)nc(C)c1CNC(=O)c1ccnc(Cn2ccc3c(Cl)cccc3c2=O)c1] | N-((6-amino-2,4-dimethylpyridin-3-yl)methyl)-2-((5-chloro-1-oxoisoquinolin-2(1H)-yl)methyl)isonicotinamide |

TABLE 1-continued

| Chemical Synthesis Example | Structure | Name |
|---|---|---|
| 23 | 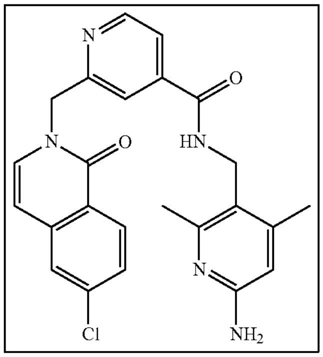 [SMILES: Cc1cc(N)nc(C)c1CNC(=O)c1ccnc(Cn2ccc3cc(Cl)ccc3c2=O)c1] | N-((6-amino-2,4-dimethylpyridin-3-yl)methyl)-2-((6-chloro-1-oxoisoquinolin-2(1H)-yl)methyl)isonicotinamide |
| 24 | 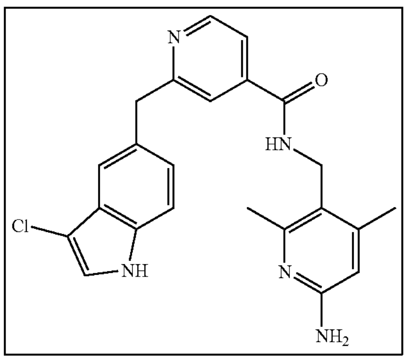 [SMILES: Cc1cc(N)nc(C)c1CNC(=O)c1ccnc(Cc2ccc3[nH]cc(Cl)c3c2)c1] | N-((6-amino-2,4-dimethylpyridin-3-yl)methyl)-2-((3-chloro-1H-indol-5-yl)methyl)isonicotinamide |
| 25 | 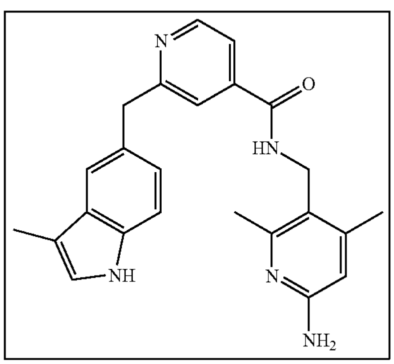 | N-((6-amino-2,4-dimethylpyridin-3-yl)methyl)-2-((3-methyl-1H-indol-5-yl)methyl)isonicotinamide |
| 26 | 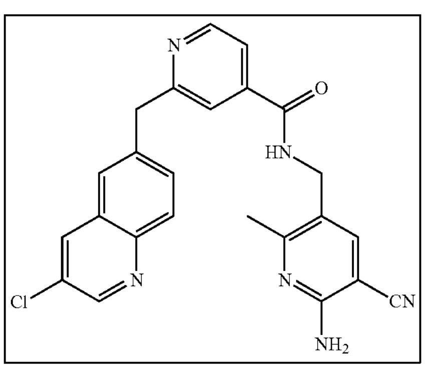 [SMILES: Cc1nc(N)c(C#N)cc1CNC(=O)c1ccnc(Cc2ccc3ncc(Cl)cc3c2)c1] | N-((6-amino-5-cyano-2-methylpyridin-3-yl)methyl)-2-((3-chloroquinolin-6-yl)methyl)isonicotinamide |

TABLE 1-continued

| Chemical Synthesis Example | Structure | Name |
|---|---|---|
| 27 | 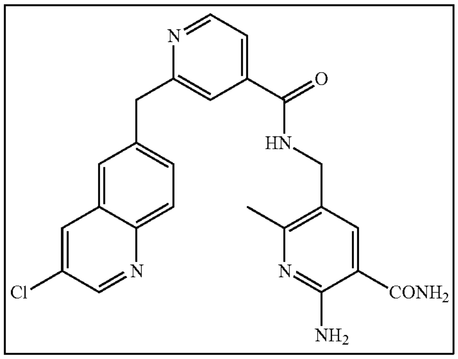 [SMILES: Cc1nc(N)c(C(N)=O)cc1CNC(=O)c1ccnc(Cc2ccc3ncc(Cl)cc3c2)c1] | 2-amino-5-((2-((3-chloroquinolin-6-yl)methyl)isonicotinamido)methyl)-6-methylnicotinamide |
| 28 | 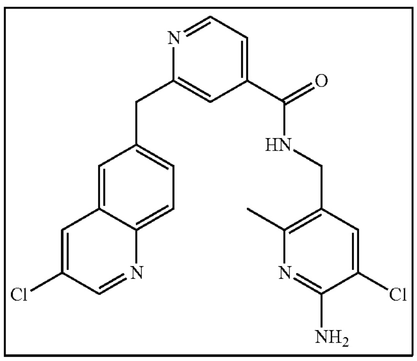 [SMILES: Cc1nc(N)c(Cl)cc1CNC(=O)c1ccnc(Cc2ccc3ncc(Cl)cc3c2)c1] | N-((6-amino-5-chloro-2-methylpyridin-3-yl)methyl)-2-((3-chloroquinolin-6-yl)methyl)isonicotinamide |
| 29 | 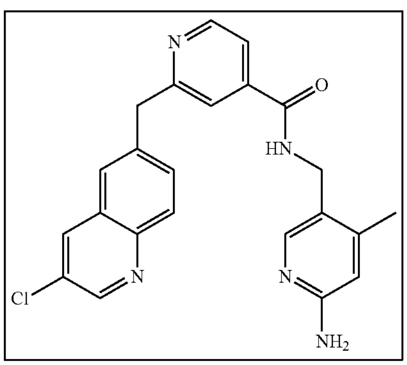 | N-((6-amino-4-methylpyridin-3-yl)methyl)-2-((3-chloroquinolin-6-yl)methyl)isonicotinamide |
| 30 | 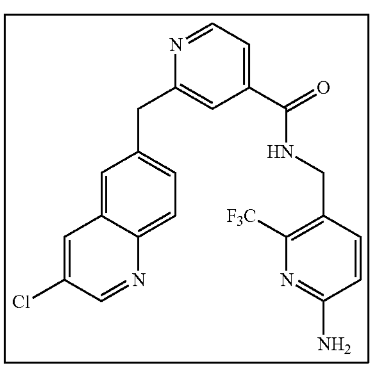 | N-((6-amino-2-(trifluoromethyl)pyridin-3-yl)methyl)-2-((3-chloroquinolin-6-yl)methyl)isonicotinamide |

TABLE 1-continued

| Chemical Synthesis Example | Structure | Name |
|---|---|---|
| 31 | 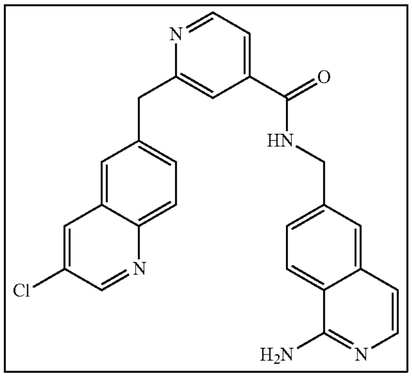 [SMILES: Nc1nccc2cc(CNC(=O)c3ccnc(Cc4ccc5ncc(Cl)cc5c4)c3)ccc12] | N-((1-aminoisoquinolin-6-yl)methyl)-2-((3-chloroquinolin-6-yl)methyl)isonicotinamide |
| 32 | 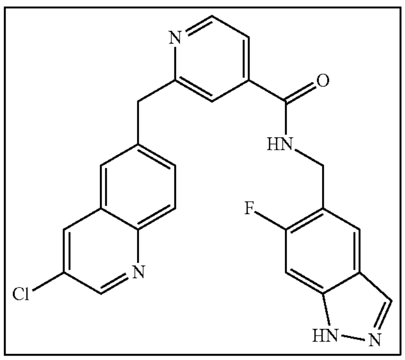 [SMILES: O=C(NCc1cc2cn[nH]c2cc1F)c1ccnc(Cc2ccc3ncc(Cl)cc3c2)c1] | 2-((3-chloroquinolin-6-yl)methyl)-N-((6-fluoro-1H-indazol-5-yl)methyl)isonicotinamide |
| 33 | 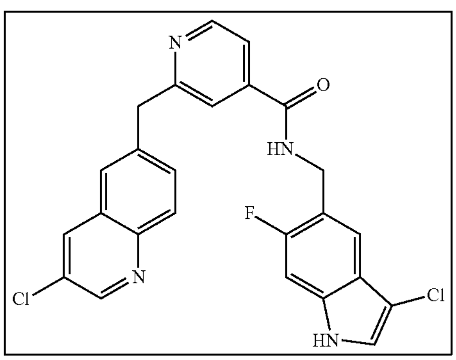 [SMILES: O=C(NCc1cc2c(Cl)c[nH]c2cc1F)c1ccnc(Cc2ccc3ncc(Cl)cc3c2)c1] | N-((3-chloro-6-fluoro-1H-indol-5-yl)methyl)-2-((3-chloroquinolin-6-yl)methyl)isonicotinamide |
| 34 | 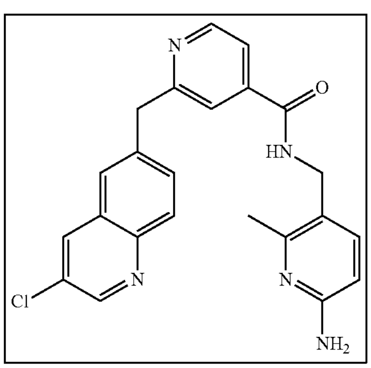 [SMILES: Cc1nc(N)ccc1CNC(=O)c1ccnc(Cc2ccc3ncc(Cl)cc3c2)c1] | N-((6-amino-2-methylpyridin-3-yl)methyl)-2-((3-chloroquinolin-6-yl)methyl)isonicotinamide |

TABLE 1-continued

| Chemical Synthesis Example | Structure | Name |
|---|---|---|
| 35 | 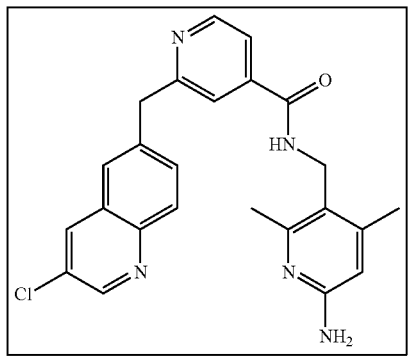 [SMILES: Cc1cc(N)nc(C)c1CNC(=O)c1ccnc(Cc2ccc3ncc(Cl)cc3c2)c1] | N-((6-amino-2,4-dimethylpyridin-3-yl)methyl)-2-((3-chloroquinolin-6-yl)methyl)isonicotinamide |
| 36 | 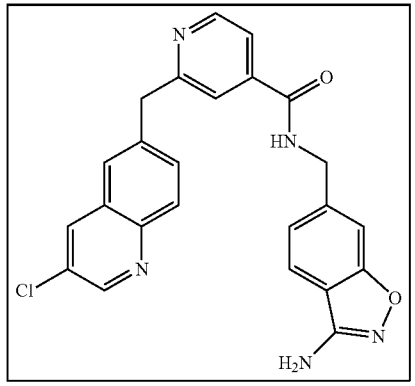 [SMILES: Nc1noc2cc(CNC(=O)c3ccnc(Cc4ccc5ncc(Cl)cc5c4)c3)ccc12] | N-((3-aminobenzo[d]isoxazol-6-yl)methyl)-2-((3-chloroquinolin-6-yl)methyl)isonicotinamide |
| 37 | 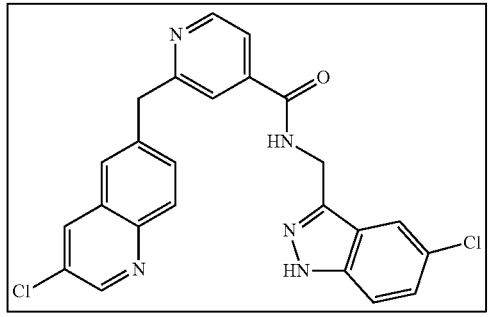 [SMILES: O=C(NCc1n[nH]c2ccc(Cl)cc12)c1ccnc(Cc2ccc3ncc(Cl)cc3c2)c1] | N-((5-chloro-1H-indazol-3-yl)methyl)-2-((3-chloroquinolin-6-yl)methyl)isonicotinamide |
| 38 | 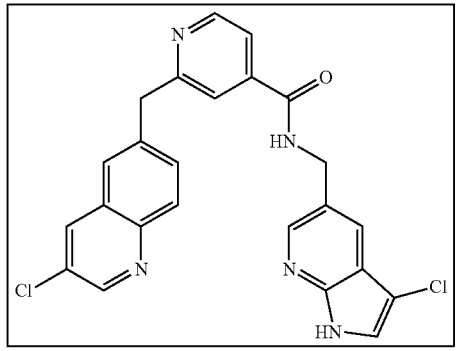 [SMILES: O=C(NCc1cnc2[nH]cc(Cl)c2c1)c1ccnc(Cc2ccc3ncc(Cl)cc3c2)c1] | N-((3-chloro-1H-pyrrolo[2,3-b]pyridin-5-yl)methyl)-2-((3-chloroquinolin-6-yl)methyl)isonicotinamide |

TABLE 1-continued

| Chemical Synthesis Example | Structure | Name |
|---|---|---|
| 39 | 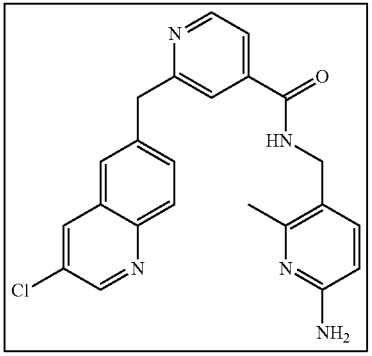 [SMILES: Cc1nc(N)ccc1CNC(=O)c1ccnc(Cc2ccc3ncc(Cl)cc3c2)c1] | N-((6-amino-2-methylpyridin-3-yl)methyl)-2-((3-chloroquinolin-6-yl)methyl)isonicotinamide |
| 40 | 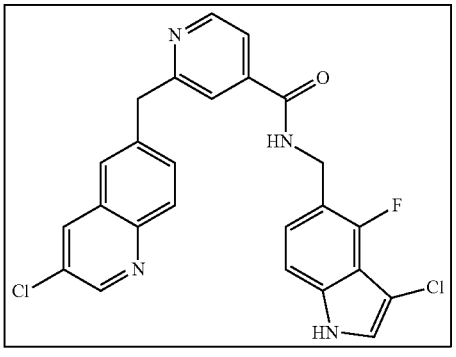 [SMILES: O=C(NCc1ccc2[nH]cc(Cl)c2c1F)c1ccnc(Cc2ccc3ncc(Cl)cc3c2)c1] | N-((3-chloro-4-fluoro-1H-indol-5-yl)methyl)-2-((3-chloroquinolin-6-yl)methyl)isonicotinamide |
| 41 | 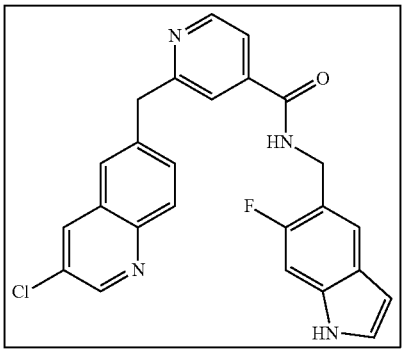 [SMILES: O=C(NCc1cc2cc[nH]c2cc1F)c1ccnc(Cc2ccc3ncc(Cl)cc3c2)c1] | 2-((3-chloroquinolin-6-yl)methyl)-N-((6-fluoro-1H-indol-5-yl)methyl)isonicotinamide |
| 42 | 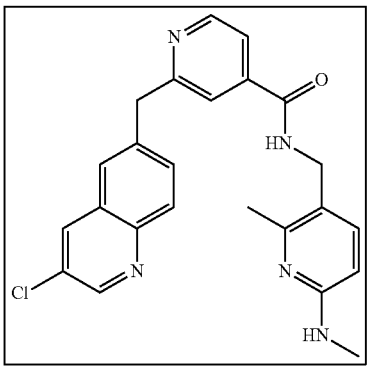 [SMILES: CNc1ccc(CNC(=O)c2ccnc(Cc3ccc4ncc(Cl)cc4c3)c2)c(C)n1] | 2-((3-chloroquinolin-6-yl)methyl)-N-((2-methyl-6-(methylamino)pyridin-3-yl)methyl)isonicotinamide |

TABLE 1-continued

| Chemical Synthesis Example | Structure | Name |
|---|---|---|
| 43 | 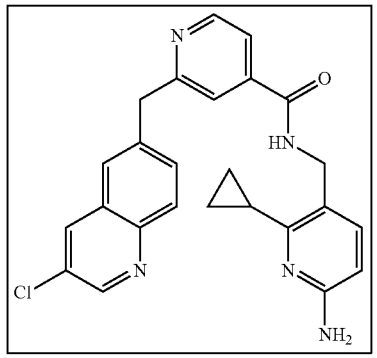 [SMILES: Nc1ccc(CNC(=O)c2ccnc(Cc3ccc4ncc(Cl)cc4c3)c2)c(C2CC2)n1] | N-((6-amino-2-cyclopropylpyridin-3-yl)methyl)-2-((3-chloroquinolin-6-yl)methyl)isonicotinamide |
| 44 | 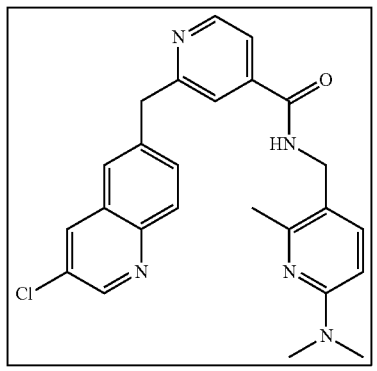 [SMILES: Cc1nc(N(C)C)ccc1CNC(=O)c1ccnc(Cc2ccc3ncc(Cl)cc3c2)c1] | 2-((3-chloroquinolin-6-yl)methyl)-N-((6-(dimethylamino)-2-methylpyridin-3-yl)methyl)isonicotinamide |
| 45 | 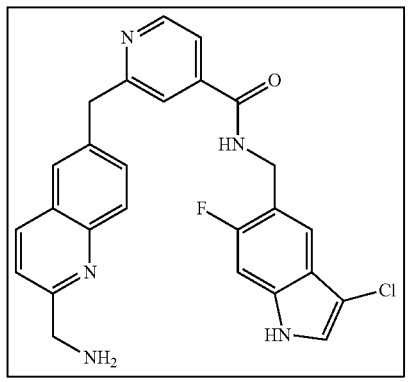 [SMILES: NCc1ccc2cc(Cc3cc(C(=O)NCc4cc5c(Cl)c[nH]c5cc4F)ccn3)ccc2n1] | 2-((2-(aminomethyl)quinolin-6-yl)methyl)-N-((3-chloro-6-fluoro-1H-indol-5-yl)methyl)isonicotinamide |
| 46 | 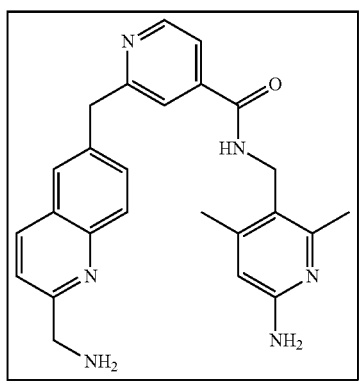 [SMILES: Cc1cc(N)nc(C)c1CNC(=O)c1ccnc(Cc2ccc3nc(CN)ccc3c2)c1] | N-((6-amino-2,4-dimethylpyridin-3-yl)methyl)-2-((2-(aminomethyl)quinolin-6-yl)methyl)isonicotinamide |

TABLE 1-continued

| Chemical Synthesis Example | Structure | Name |
|---|---|---|
| 47 | 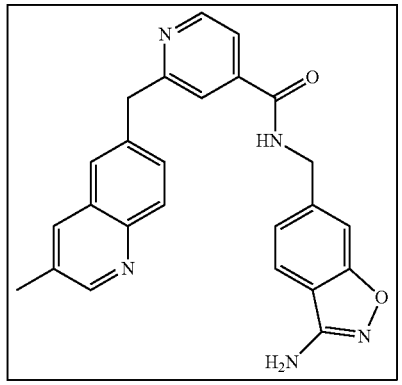 [SMILES: Cc1cnc2ccc(Cc3cc(C(=O)NCc4ccc5c(N)noc5c4)ccn3)cc2c1] | N-((3-aminobenzo[d]isoxazol-6-yl)methyl)-2-((3-methylquinolin-6-yl)methyl)isonicotinamide |
| 48 | 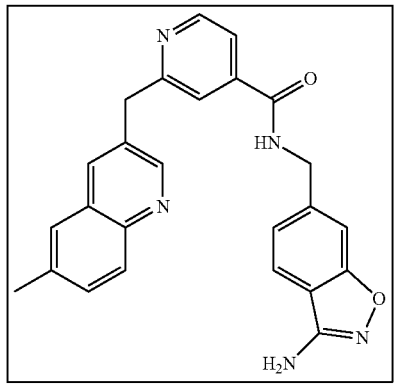 [SMILES: Cc1ccc2ncc(Cc3cc(C(=O)NCc4ccc5c(N)noc5c4)ccn3)cc2c1] | N-((3-aminobenzo[d]isoxazol-6-yl)methyl)-2-((6-methylquinolin-3-yl)methyl)isonicotinamide |
| 49 | 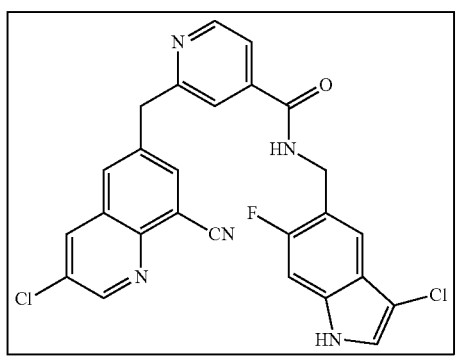 [SMILES: N#Cc1cc(Cc2cc(C(=O)NCc3cc4c(Cl)c[nH]c4cc3F)ccn2)cc2cc(Cl)cnc12] | N-((3-chloro-6-fluoro-1H-indol-5-yl)methyl)-2-((3-chloro-8-cyanoquinolin-6-yl)methyl)isonicotinamide |
| 50 | 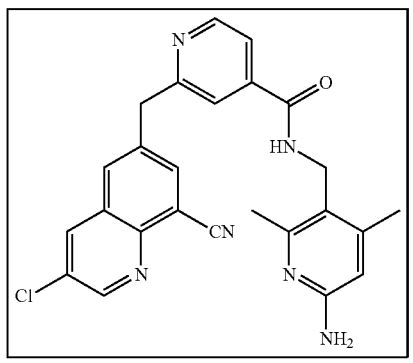 | N-((6-amino-2,4-dimethylpyridin-3-yl)methyl)-2-((3-chloro-8-cyanoquinolin-6-yl)methyl)isonicotinamide |

TABLE 1-continued

| Chemical Synthesis Example | Structure | Name |
|---|---|---|
| 51 | 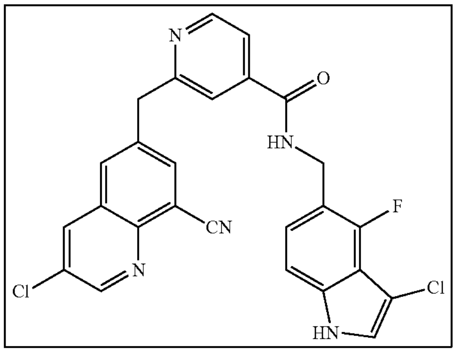 [SMILES: N#Cc1cc(Cc2cc(C(=O)NCc3ccc4[nH]cc(Cl)c4c3F)ccn2)cc2cc(Cl)cnc12] | N-((3-chloro-4-fluoro-1H-indol-5-yl)methyl)-2-((3-chloro-8-cyanoquinolin-6-yl)methyl)isonicotinamide |
| 52 | 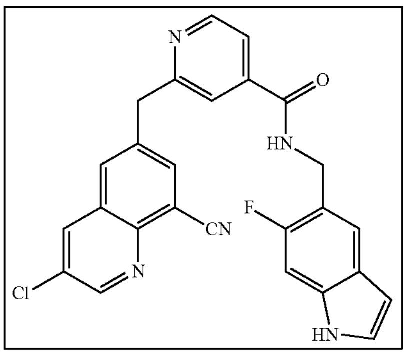 [SMILES: N#Cc1cc(Cc2cc(C(=O)NCc3cc4cc[nH]c4cc3F)ccn2)cc2cc(Cl)cnc12] | 2-((3-chloro-8-cyanoquinolin-6-yl)methyl)-N-((6-fluoro-1H-indol-5-yl)methyl)isonicotinamide |
| 53 | 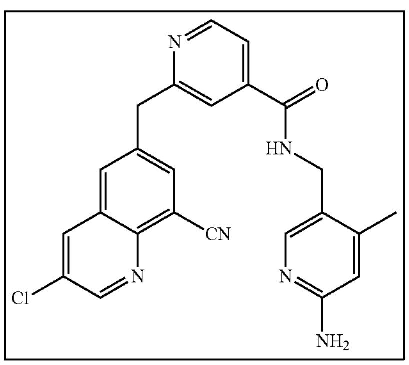 [SMILES: Cc1cc(N)ncc1CNC(=O)c1ccnc(Cc2cc(C#N)c3ncc(Cl)cc3c2)c1] | N-((6-amino-4-methylpyridin-3-yl)methyl)-2-((3-chloro-8-cyanoquinolin-6-yl)methyl)isonicotinamide |
| 54 | 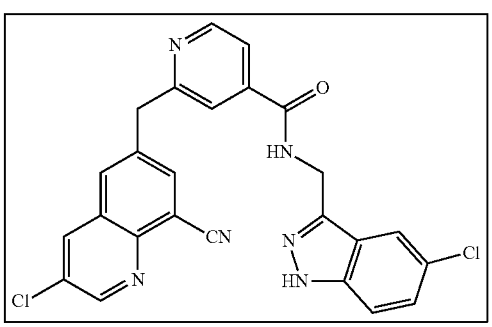 [SMILES: N#Cc1cc(Cc2cc(C(=O)NCc3n[nH]c4ccc(Cl)cc34)ccn2)cc2cc(Cl)cnc12] | N-((5-chloro-1H-indazol-3-yl)methyl)-2-((3-chloro-8-cyanoquinolin-6-yl)methyl)isonicotinamide |

TABLE 1-continued

| Chemical Synthesis Example | Structure | Name |
|---|---|---|
| 55 | 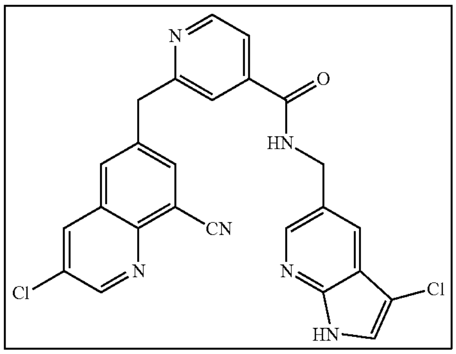 [SMILES: N#Cc1cc(Cc2cc(C(=O)NCc3cnc4[nH]cc(Cl)c4c3)ccn2)cc2cc(Cl)cnc12] | N-((3-chloro-1H-pyrrolo[2,3-b]pyridin-5-yl)methyl)-2-((3-chloro-8-cyanoquinolin-6-yl)methyl)isonicotinamide |
| 56 | 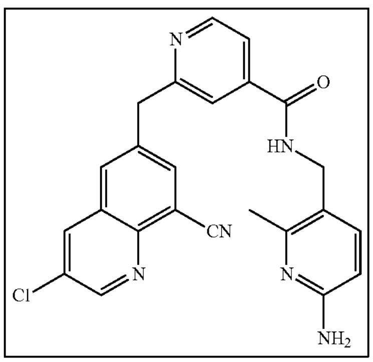 [SMILES: Cc1nc(N)ccc1CNC(=O)c1ccnc(Cc2cc(C#N)c3ncc(Cl)cc3c2)c1] | N-((6-amino-2-methylpyridin-3-yl)methyl)-2-((3-chloro-8-cyanoquinolin-6-yl)methyl)isonicotinamide |
| 57 | 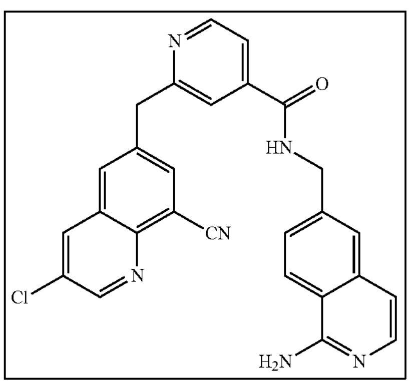 [SMILES: N#Cc1cc(Cc2cc(C(=O)NCc3ccc4c(N)nccc4c3)ccn2)cc2cc(Cl)cnc12] | N-((1-aminoisoquinolin-6-yl)methyl)-2-((3-chloro-8-cyanoquinolin-6-yl)methyl)isonicotinamide |
| 58 | 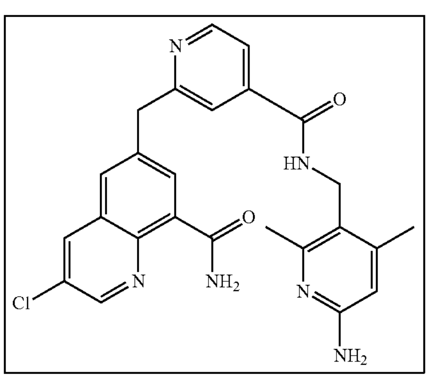 [SMILES: Cc1cc(N)nc(C)c1CNC(=O)c1ccnc(Cc2cc(C(N)=O)c3ncc(Cl)cc3c2)c1] | 6-((4-(((6-amino-2,4-dimethylpyridin-3-yl)methyl)carbamoyl)pyridin-2-yl)methyl)-3-chloroquinoline-8-carboxamide |

TABLE 1-continued

| Chemical Synthesis Example | Structure | Name |
|---|---|---|
| 59 | 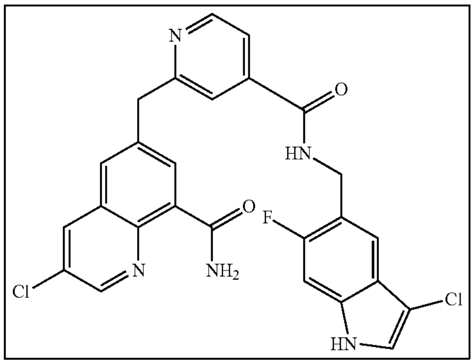 [SMILES: NC(=O)c1cc(Cc2cc(C(=O)NCc3cc4c(Cl)c[nH]c4cc3F)ccn2)cc2cc(Cl)cnc12] | 3-chloro-6-((4-(((3-chloro-6-fluoro-1H-indol-5-yl)methyl)carbamoyl)pyridin-2-yl)methyl)quinoline-8-carboxamide |
| 60 | 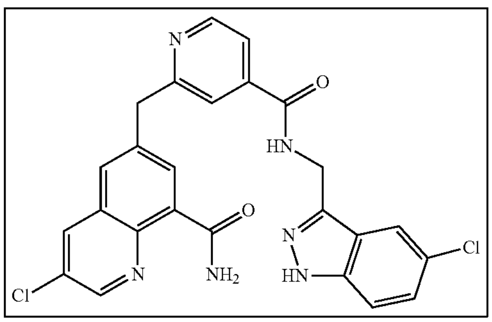 [SMILES: NC(=O)c1cc(Cc2cc(C(=O)NCc3n[nH]c4ccc(Cl)cc34)ccn2)cc2cc(Cl)cnc12] | 3-chloro-6-((4-(((5-chloro-1H-indazol-3-yl)methyl)carbamoyl)pyridin-2-yl)methyl)quinoline-8-carboxamide |
| 61 | 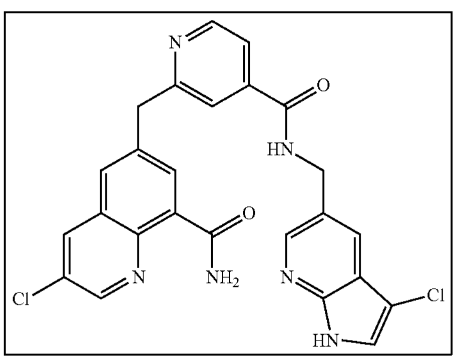 [SMILES: NC(=O)c1cc(Cc2cc(C(=O)NCc3cnc4[nH]cc(Cl)c4c3)ccn2)cc2cc(Cl)cnc12] | 3-chloro-6-((4-(((3-chloro-1H-pyrrolo[2,3-b]pyridin-5-yl)methyl)carbamoyl)pyridin-2-yl)methyl)quinoline-8-carboxamide |
| 62 | 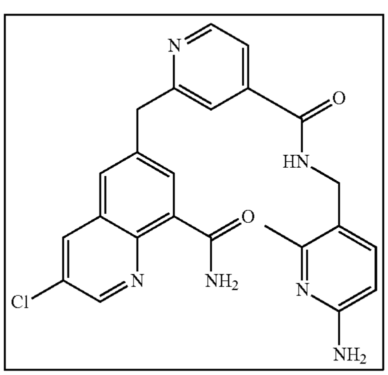 [SMILES: Cc1nc(N)ccc1CNC(=O)c1ccnc(Cc2cc(C(N)=O)c3ncc(Cl)cc3c2)c1] | 6-((4-(((6-amino-2-methylpyridin-3-yl)methyl)carbamoyl)pyridin-2-yl)methyl)-3-chloroquinoline-8-carboxamide |

TABLE 1-continued

| Chemical Synthesis Example | Structure | Name |
|---|---|---|
| 63 | 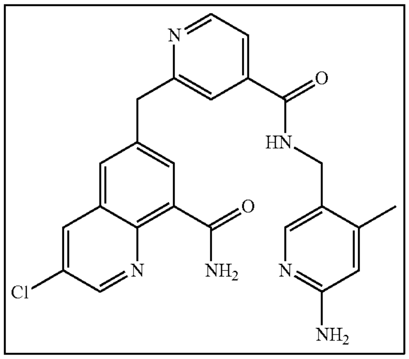 [SMILES: Cc1cc(N)ncc1CNC(=O)c1ccnc(Cc2cc(C(N)=O)c3ncc(Cl)cc3c2)c1] | 6-((4-(((6-amino-4-methylpyridin-3-yl)methyl)carbamoyl)pyridin-2-yl)methyl)-3-chloroquinoline-8-carboxamide |
| 64 | 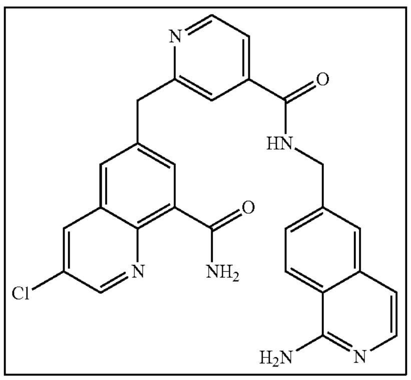 [SMILES: NC(=O)c1cc(Cc2cc(C(=O)NCc3ccc4c(N)nccc4c3)ccn2)cc2cc(Cl)cnc12] | 6-((4-(((1-aminoisoquinolin-6-yl)methyl)carbamoyl)pyridin-2-yl)methyl)-3-chloroquinoline-8-carboxamide |
| 65 | 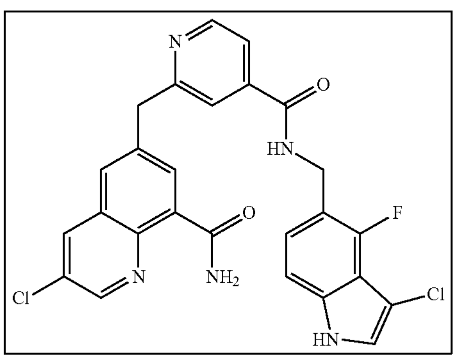 [SMILES: NC(=O)c1cc(Cc2cc(C(=O)NCc3ccc4[nH]cc(Cl)c4c3F)ccn2)cc2cc(Cl)cnc12] | 3-chloro-6-((4-(((3-chloro-4-fluoro-1H-indol-5-yl)methyl)carbamoyl)pyridin-2-yl)methyl)quinoline-8-carboxamide |
| 66 | 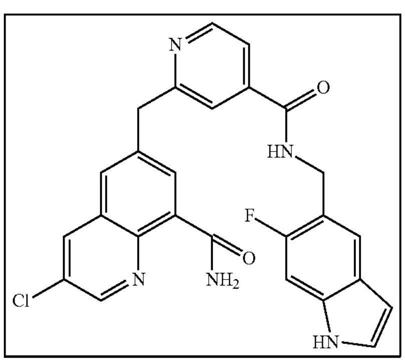 [SMILES: NC(=O)c1cc(Cc2cc(C(=O)NCc3cc4cc[nH]c4cc3F)ccn2)cc2cc(Cl)cnc12] | 3-chloro-6-((4-(((6-fluoro-1H-indol-5-yl)methyl)carbamoyl)pyridin-2-yl)methyl)quinoline-8-carboxamide |

TABLE 1-continued

| Chemical Synthesis Example | Structure | Name |
|---|---|---|
| 67 | 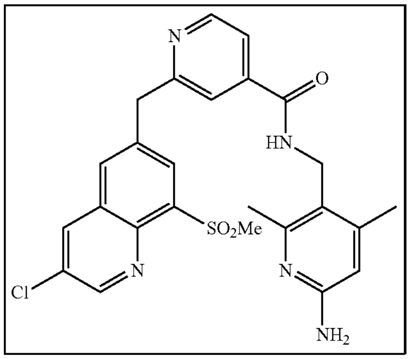 [SMILES: Cc1cc(N)nc(C)c1CNC(=O)c1ccnc(Cc2cc(S(C)(=O)=O)c3ncc(Cl)cc3c2)c1] | N-((6-amino-2,4-dimethylpyridin-3-yl)methyl)-2-((3-chloro-8-(methylsulfonyl)quinolin-6-yl)methyl)isonicotinamide |
| 68 | 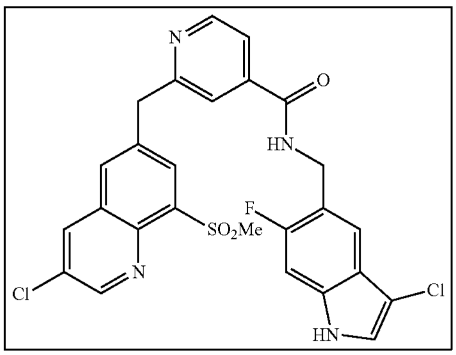 [SMILES: CS(=O)(=O)c1cc(Cc2cc(C(=O)NCc3cc4c(Cl)c[nH]c4cc3F)ccn2)cc2cc(Cl)cnc12] | N-((3-chloro-6-fluoro-1H-indol-5-yl)methyl)-2-((3-chloro-8-(methylsulfonyl)quinolin-6-yl)methyl)isonicotinamide |
| 69 | 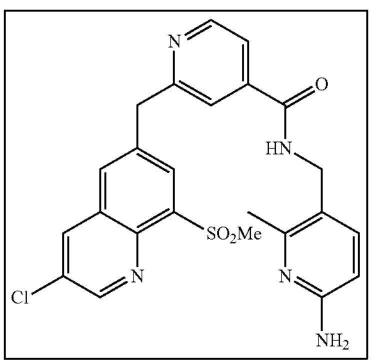 [SMILES: Cc1nc(N)ccc1CNC(=O)c1ccnc(Cc2cc(S(C)(=O)=O)c3ncc(Cl)cc3c2)c1] | N-((6-amino-2-methylpyridin-3-yl)methyl)-2-((3-chloro-8-(methylsulfonyl)quinolin-6-yl)methyl)isonicotinamide |
| 70 | 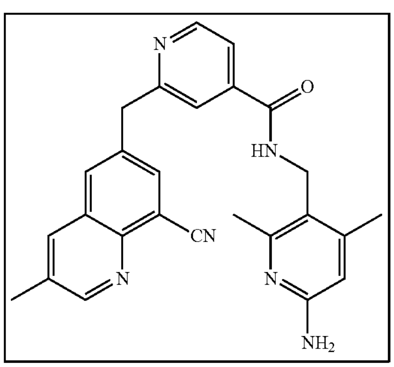 | N-((6-amino-2,4-dimethylpyridin-3-yl)methyl)-2-((8-cyano-3-methylquinolin-6-yl)methyl)isonicotinamide |

TABLE 1-continued

| Chemical Synthesis Example | Structure | Name |
|---|---|---|
| 71 | 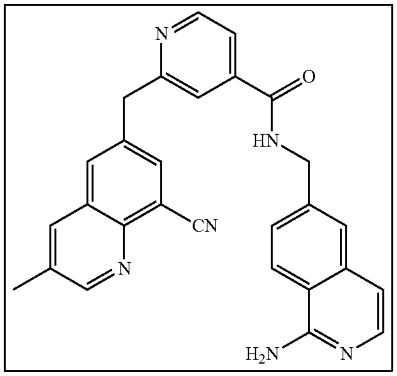 [SMILES: Cc1cnc2c(C#N)cc(Cc3cc(C(=O)NCc4ccc5c(N)nccc5c4)ccn3)cc2c1] | N-((1-aminoisoquinolin-6-yl)methyl)-2-((8-cyano-3-methylquinolin-6-yl)methyl)isonicotinamide |
| 72 | 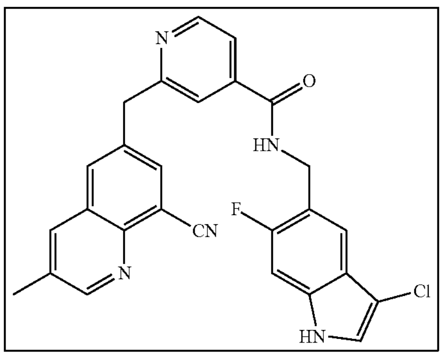 [SMILES: Cc1cnc2c(C#N)cc(Cc3cc(C(=O)NCc4cc5c(Cl)c[nH]c5cc4F)ccn3)cc2c1] | N-((3-chloro-6-fluoro-1H-indol-5-yl)methyl)-2-((8-cyano-3-methylquinolin-6-yl)methyl)isonicotinamide |
| 73 | 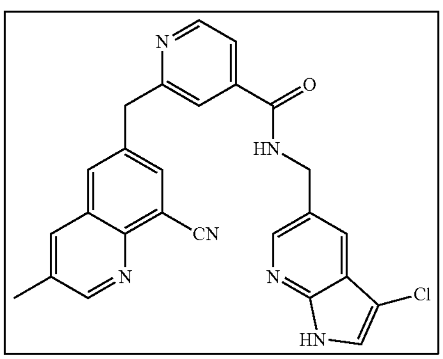 [SMILES: Cc1cnc2c(C#N)cc(Cc3cc(C(=O)NCc4cnc5[nH]cc(Cl)c5c4)ccn3)cc2c1] | N-((3-chloro-1H-pyrrolo[2,3-b]pyridin-5-yl)methyl)-2-((8-cyano-3-methylquinolin-6-yl)methyl)isonicotinamide |
| 74 | 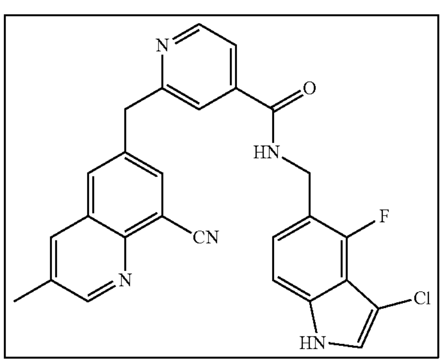 [SMILES: Cc1cnc2c(C#N)cc(Cc3cc(C(=O)NCc4ccc5[nH]cc(Cl)c5c4F)ccn3)cc2c1] | N-((3-chloro-4-fluoro-1H-indol-5-yl)methyl)-2-((8-cyano-3-methylquinolin-6-yl)methyl)isonicotinamide |

TABLE 1-continued

| Chemical Synthesis Example | Structure | Name |
|---|---|---|
| 75 | 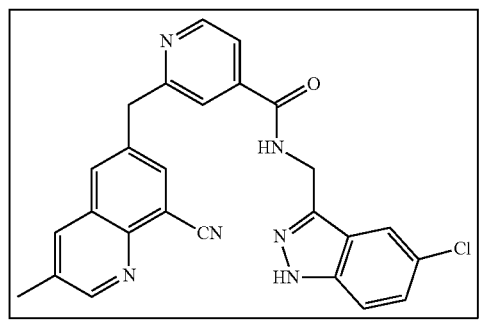 [SMILES: Cc1cnc2c(C#N)cc(Cc3cc(C(=O)NCc4n[nH]c5ccc(Cl)cc45)ccn3)cc2c1] | N-((5-chloro-1H-indazol-3-yl)methyl)-2-((8-cyano-3-methylquinolin-6-yl)methyl)isonicotinamide |
| 76 | 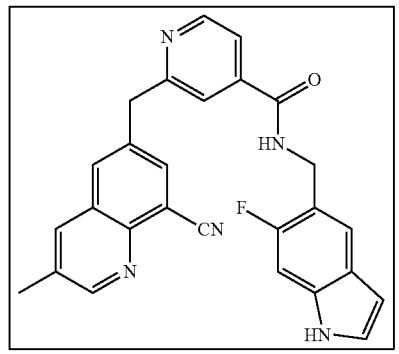 [SMILES: Cc1cnc2c(C#N)cc(Cc3cc(C(=O)NCc4cc5cc[nH]c5cc4F)ccn3)cc2c1] | 2-((8-cyano-3-methylquinolin-6-yl)methyl)-N-((6-fluoro-1H-indol-5-yl)methyl)isonicotinamide |
| 77 | 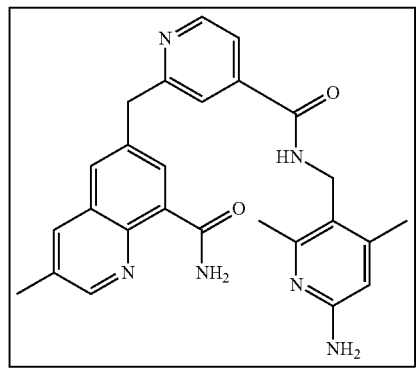 | 6-((4-(((6-amino-2,4-dimethylpyridin-3-yl)methyl)carbamoyl)pyridin-2-yl)methyl)-3-methylquinoline-8-carboxamide |
| 78 | 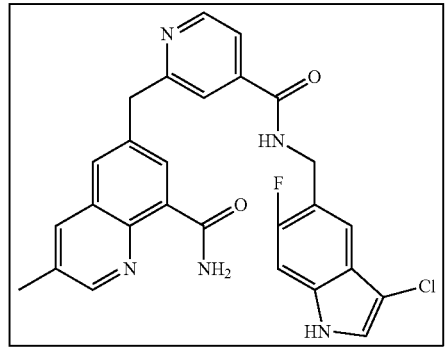 [SMILES: Cc1cnc2c(C(N)=O)cc(Cc3cc(C(=O)NCc4cc5c(Cl)c[nH]c5cc4F)ccn3)cc2c1] | 6-((4-(((3-chloro-6-fluoro-1H-indol-5-yl)methyl)carbamoyl)pyridin-2-yl)methyl)-3-methylquinoline-8-carboxamide |

TABLE 1-continued

| Chemical Synthesis Example | Structure | Name |
|---|---|---|
| 79 | 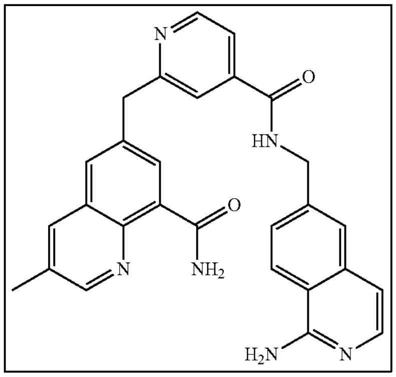 [SMILES: Cc1cnc2c(C(N)=O)cc(Cc3cc(C(=O)NCc4ccc5c(N)nccc5c4)ccn3)cc2c1] | 6-((4-(((1-aminoisoquinolin-6-yl)methyl)carbamoyl)pyridin-2-yl)methyl)-3-methylquinoline-8-carboxamide |
| 80 | 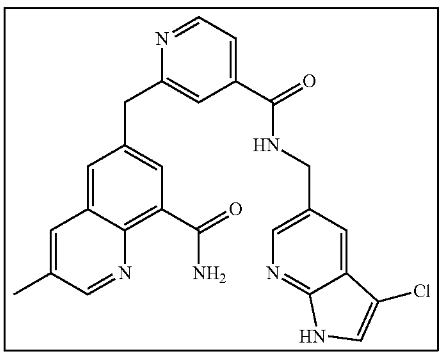 [SMILES: Cc1cnc2c(C(N)=O)cc(Cc3cc(C(=O)NCc4cnc5[nH]cc(Cl)c5c4)ccn3)cc2c1] | 6-((4-(((3-chloro-1H-pyrrolo[2,3-b]pyridin-5-yl)methyl)carbamoyl)pyridin-2-yl)methyl)-3-methylquinoline-8-carboxamide |
| 81 | 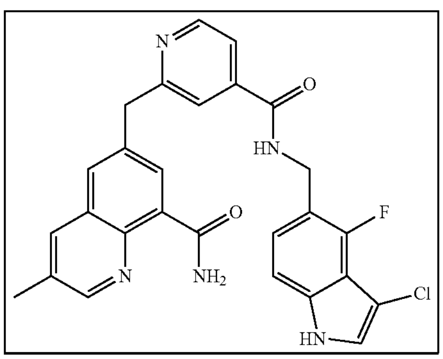 [SMILES: Cc1cnc2c(C(N)=O)cc(Cc3cc(C(=O)NCc4ccc5[nH]cc(Cl)c5c4F)ccn3)cc2c1] | 6-((4-(((3-chloro-4-fluoro-1H-indol-5-yl)methyl)carbamoyl)pyridin-2-yl)methyl)-3-methylquinoline-8-carboxamide |
| 82 | 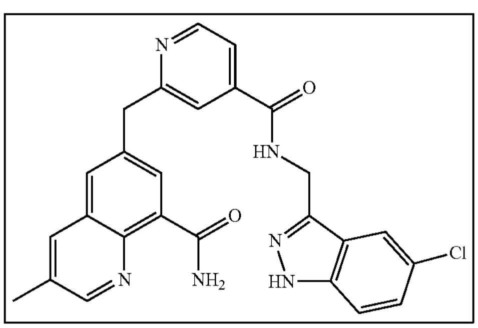 [SMILES: Cc1cnc2c(C(N)=O)cc(Cc3cc(C(=O)NCc4n[nH]c5ccc(Cl)cc45)ccn3)cc2c1] | 6-((4-(((5-chloro-1H-indazol-3-yl)methyl)carbamoyl)pyridin-2-yl)methyl)-3-methylquinoline-8-carboxamide |

TABLE 1-continued

| Chemical Synthesis Example | Structure | Name |
|---|---|---|
| 83 | 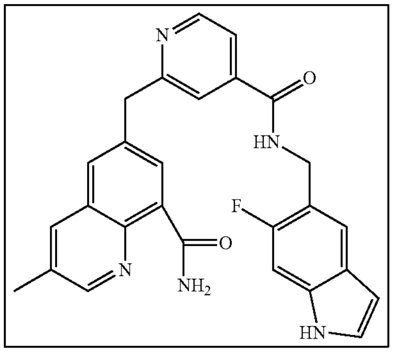 [SMILES: Cc1cnc2c(C(N)=O)cc(Cc3cc(C(=O)NCc4cc5cc[nH]c5cc4F)ccn3)cc2c1] | 6-((4-(((6-fluoro-1H-indol-5-yl)methyl)carbamoyl)pyridin-2-yl)methyl)-3-methylquinoline-8-carboxamide |
| 84 | 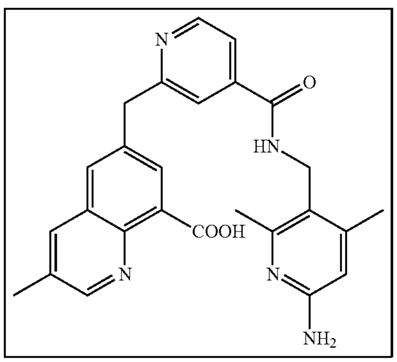 | 6-((4-(((6-amino-2,4-dimethylpyridin-3-yl)methyl)carbamoyl)pyridin-2-yl)methyl)-3-methylquinoline-8-carboxylic acid |
| 85 | 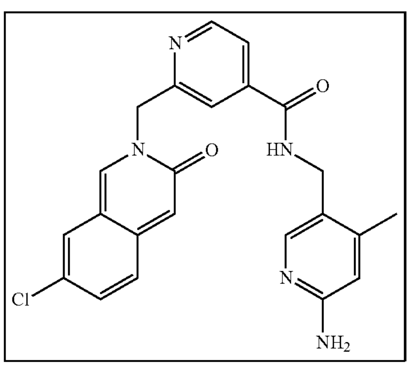 [SMILES: Cc1cc(N)ncc1CNC(=O)c1ccnc(Cn2cc3cc(Cl)ccc3cc2=O)c1] | N-((6-amino-4-methylpyridin-3-yl)methyl)-2-((7-chloro-3-oxoisoquinolin-2(3H)-yl)methyl)isonicotinamide |
| 86 | 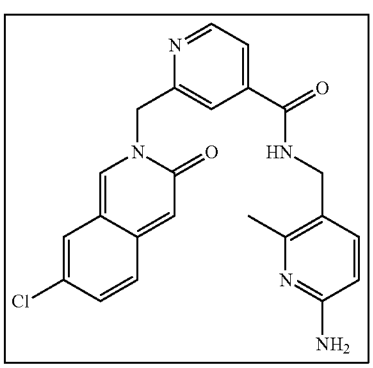 [SMILES: Cc1nc(N)ccc1CNC(=O)c1ccnc(Cn2cc3cc(Cl)ccc3cc2=O)c1] | N-((6-amino-2-methylpyridin-3-yl)methyl)-2-((7-chloro-3-oxoisoquinolin-2(3H)-yl)methyl)isonicotinamide |

TABLE 1-continued

| Chemical Synthesis Example | Structure | Name |
|---|---|---|
| 87 | 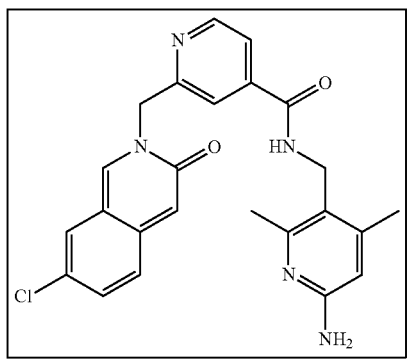 [SMILES: Cc1cc(N)nc(C)c1CNC(=O)c1ccnc(Cn2cc3cc(Cl)ccc3cc2=O)c1] | N-((6-amino-2,4-dimethylpyridin-3-yl)methyl)-2-((7-chloro-3-oxoisoquinolin-2(3H)-yl)methyl)isonicotinamide |
| 88 | 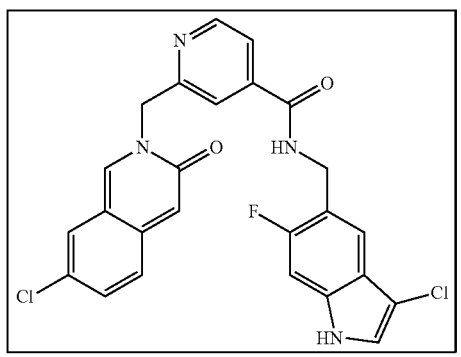 [SMILES: O=C(NCc1cc2c(Cl)c[nH]c2cc1F)c1ccnc(Cn2cc3cc(Cl)ccc3cc2=O)c1] | 2-((7-chloro-3-oxoisoquinolin-2(3H)-yl)methyl)-N-((3-chloro-6-fluoro-1H-indol-5-yl)methyl)isonicotinamide |
| 89 | 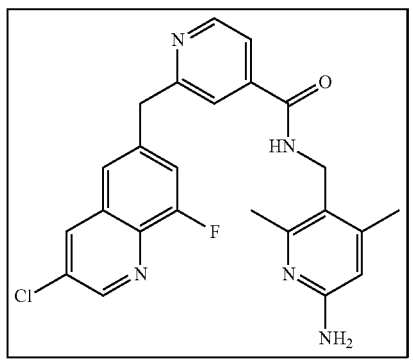 | N-((6-amino-2,4-dimethylpyridin-3-yl)methyl)-2-((3-chloro-8-fluoroquinolin-6-yl)methyl)isonicotinamide |
| 90 | 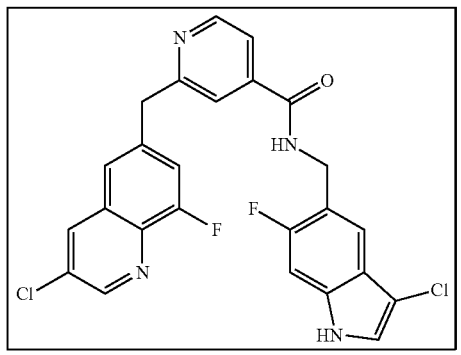 [SMILES: O=C(NCc1cc2c(Cl)c[nH]c2cc1F)c1ccnc(Cc2cc(F)c3ncc(Cl)cc3c2)c1] | N-((3-chloro-6-fluoro-1H-indol-5-yl)methyl)-2-((3-chloro-8-fluoroquinolin-6-yl)methyl)isonicotinamide |

TABLE 1-continued

| Chemical Synthesis Example | Structure | Name |
|---|---|---|
| 91 | 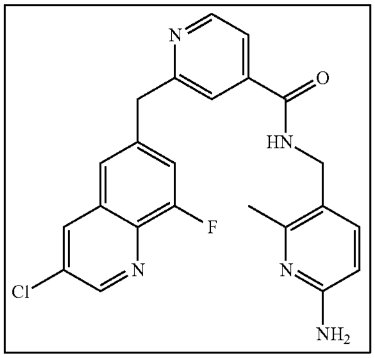 [SMILES: Cc1nc(N)ccc1CNC(=O)c1ccnc(Cc2cc(F)c3ncc(Cl)cc3c2)c1] | N-((6-amino-2-methylpyridin-3-yl)methyl)-2-((3-chloro-8-fluoroquinolin-6-yl)methyl)isonicotinamide |
| 92 | 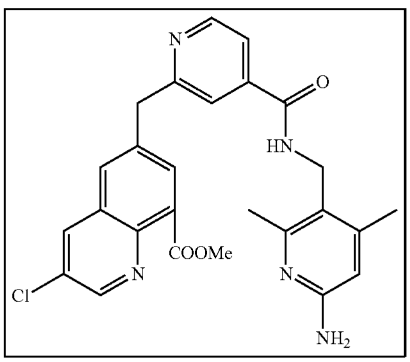 [SMILES: COC(=O)c1cc(Cc2cc(C(=O)NCc3c(C)cc(N)nc3C)ccn2)cc2cc(Cl)cnc12] | methyl 6-((4-(((6-amino-2,4-dimethylpyridin-3-yl)methyl)carbamoyl)pyridin-2-yl)methyl)-3-chloroquinoline-8-carboxylate |
| 93 | 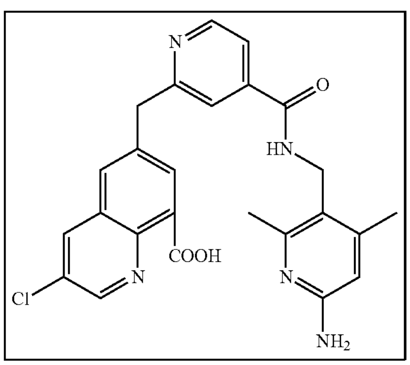 [SMILES: Cc1cc(N)nc(C)c1CNC(=O)c1ccnc(Cc2cc(C(=O)O)c3ncc(Cl)cc3c2)c1] | 6-((4-(((6-amino-2,4-dimethylpyridin-3-yl)methyl)carbamoyl)pyridin-2-yl)methyl)-3-chloroquinoline-8-carboxylic acid |
| 94 | 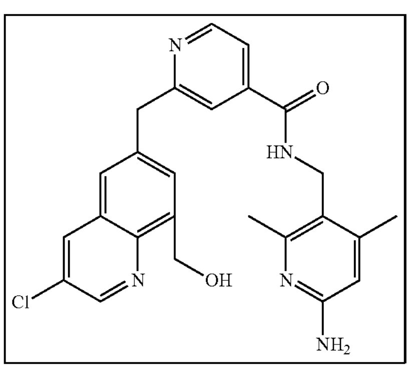 [SMILES: Cc1cc(N)nc(C)c1CNC(=O)c1ccnc(Cc2cc(CO)c3ncc(Cl)cc3c2)c1] | N-((6-amino-2,4-dimethylpyridin-3-yl)methyl)-2-((3-chloro-8-(hydroxymethyl)quinolin-6-yl)methyl)isonicotinamide |

TABLE 1-continued

| Chemical Synthesis Example | Structure | Name |
|---|---|---|
| 95 | 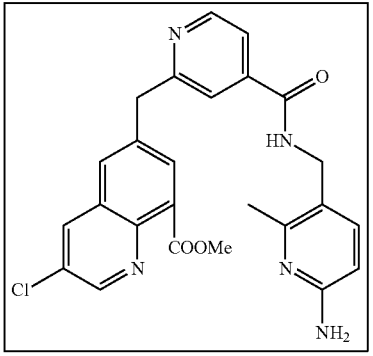 [SMILES: COC(=O)c1cc(Cc2cc(C(=O)NCc3ccc(N)nc3C)ccn2)cc2cc(Cl)cnc12] | methyl 6-((4-(((6-amino-2-methylpyridin-3-yl)methyl)carbamoyl)pyridin-2-yl)methyl)-3-chloroquinoline-8-carboxylate |
| 96 | 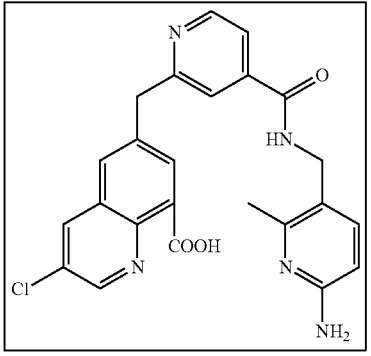 [SMILES: Cc1nc(N)ccc1CNC(=O)c1ccnc(Cc2cc(C(=O)O)c3ncc(Cl)cc3c2)c1] | 6-((4-(((6-amino-2-methylpyridin-3-yl)methyl)carbamoyl)pyridin-2-yl)methyl)-3-chloroquinoline-8-carboxylic acid |
| 97 | 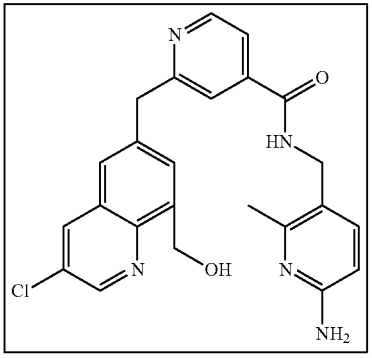 [SMILES: Cc1nc(N)ccc1CNC(=O)c1ccnc(Cc2cc(CO)c3ncc(Cl)cc3c2)c1] | N-((6-amino-2-methylpyridin-3-yl)methyl)-2-((3-chloro-8-(hydroxymethyl)quinolin-6-yl)methyl)isonicotinamide |
| 98 | 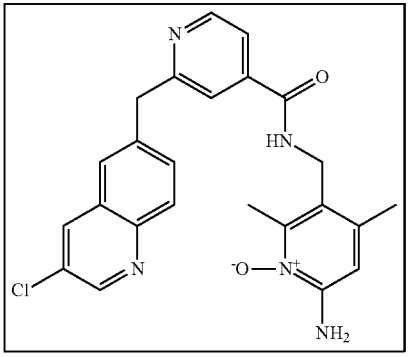 | 6-amino-3-((2-((3-chloroquinolin-6-yl)methyl)isonicotinamido)methyl)-2,4-dimethylpyridine 1-oxide |

TABLE 1-continued

| Chemical Synthesis Example | Structure | Name |
|---|---|---|
| 99 | 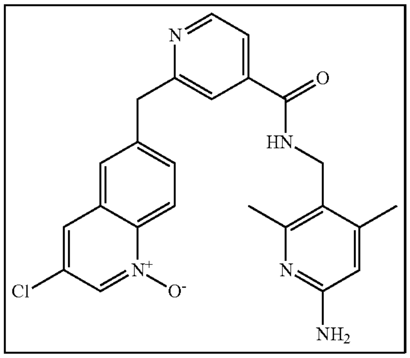 [SMILES: Cc1cc(N)nc(C)c1CNC(=O)c1ccnc(Cc2ccc3c(cc(Cl)c[n+]3[O-])c2)c1] | 6-((4-(((6-amino-2,4-dimethylpyridin-3-yl)methyl)carbamoyl)pyridin-2-yl)methyl)-3-chloroquinoline 1-oxide |
| 100 | 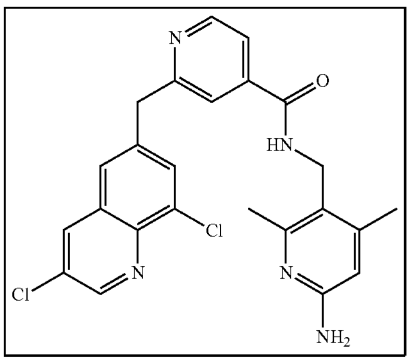 [SMILES: Cc1cc(N)nc(C)c1CNC(=O)c1ccnc(Cc2cc(Cl)c3ncc(Cl)cc3c2)c1] | N-((6-amino-2,4-dimethylpyridin-3-yl)methyl)-2-((3,8-dichloroquinolin-6-yl)methyl)isonicotinamide |
| 101 | 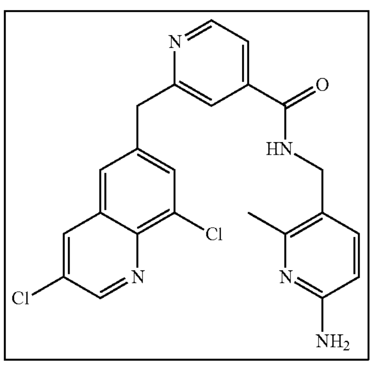 [SMILES: Cc1nc(N)ccc1CNC(=O)c1ccnc(Cc2cc(Cl)c3ncc(Cl)cc3c2)c1] | N-((6-amino-2-methylpyridin-3-yl)methyl)-2-((3,8-dichloroquinolin-6-yl)methyl)isonicotinamide |
| 102 | 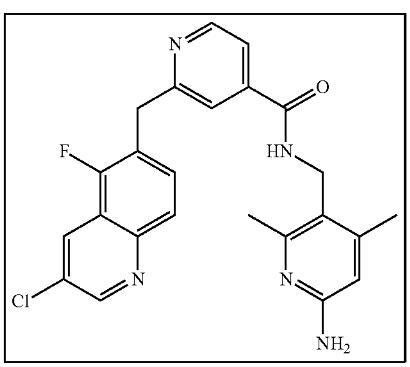 [SMILES: Cc1cc(N)nc(C)c1CNC(=O)c1ccnc(Cc2ccc3ncc(Cl)cc3c2F)c1] | N-((6-amino-2,4-dimethylpyridin-3-yl)methyl)-2-((3-chloro-5-fluoroquinolin-6-yl)methyl)isonicotinamide |

TABLE 1-continued

| Chemical Synthesis Example | Structure | Name |
|---|---|---|
| 103 | 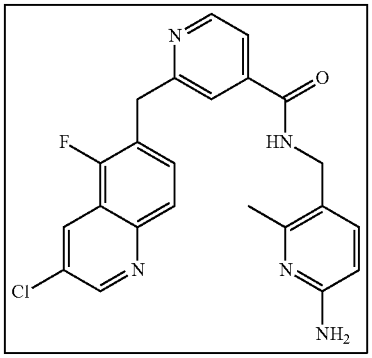 [SMILES: Cc1nc(N)ccc1CNC(=O)c1ccnc(Cc2ccc3ncc(Cl)cc3c2F)c1] | N-((6-amino-2-methylpyridin-3-yl)methyl)-2-((3-chloro-5-fluoroquinolin-6-yl)methyl)isonicotinamide |
| 104 | 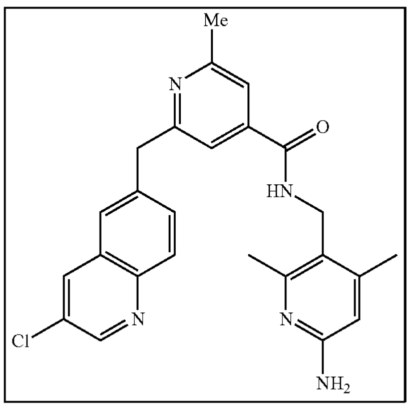 [SMILES: Cc1cc(C(=O)NCc2c(C)cc(N)nc2C)cc(Cc2ccc3ncc(Cl)cc3c2)n1] | N-((6-amino-2,4-dimethylpyridin-3-yl)methyl)-2-((3-chloroquinolin-6-yl)methyl)-6-methylisonicotinamide |
| 105 | 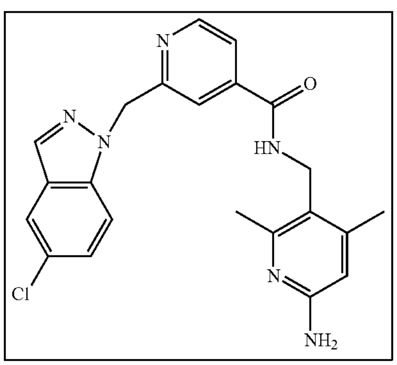 [SMILES: Cc1cc(N)nc(C)c1CNC(=O)c1ccnc(Cn2ncc3cc(Cl)ccc32)c1] | N-((6-amino-2,4-dimethylpyridin-3-yl)methyl)-2-((5-chloro-1H-indazol-1-yl)methyl)isonicotinamide |
| 106 | 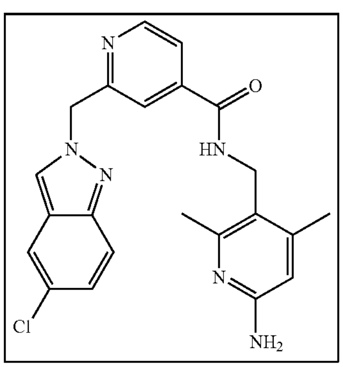 [SMILES: Cc1cc(N)nc(C)c1CNC(=O)c1ccnc(Cn2cc3cc(Cl)ccc3n2)c1] | N-((6-amino-2,4-dimethylpyridin-3-yl)methyl)-2-((5-chloro-2H-indazol-2-yl)methyl)isonicotinamide |

TABLE 1-continued

| Chemical Synthesis Example | Structure | Name |
|---|---|---|
| 107 | 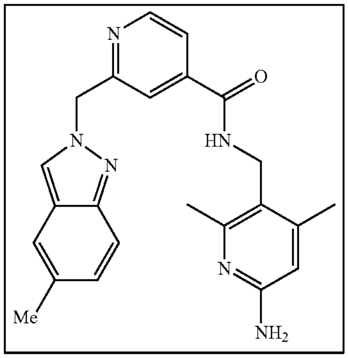 [SMILES: Cc1ccc2nn(Cc3cc(C(=O)NCc4c(C)cc(N)nc4C)ccn3)cc2c1] | N-((6-amino-2,4-dimethylpyridin-3-yl)methyl)-2-((5-methyl-2H-indazol-2-yl)methyl)isonicotinamide |
| 108 | 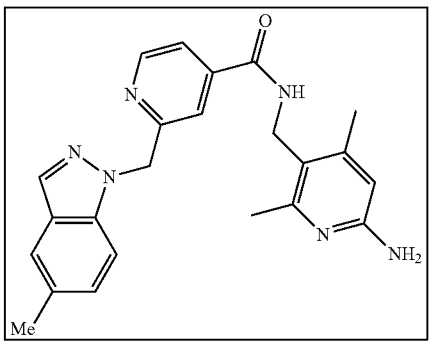 [SMILES: Cc1ccc2c(cnn2Cc2cc(C(=O)NCc3c(C)cc(N)nc3C)ccn2)c1] | N-((6-amino-2,4-dimethylpyridin-3-yl)methyl)-2-((5-methyl-1H-indazol-1-yl)methyl)isonicotinamide |
| 109 | 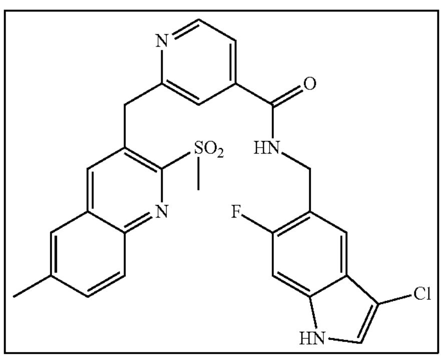 [SMILES: Cc1ccc2nc(S(C)(=O)=O)c(Cc3cc(C(=O)NCc4cc5c(Cl)c[nH]c5cc4F)ccn3)cc2c1] | N-((3-chloro-6-fluoro-1H-indol-5-yl)methyl)-2-((6-methyl-2-(methylsulfonyl)quinolin-3-yl)methyl)isonicotinamide |
| 110 | 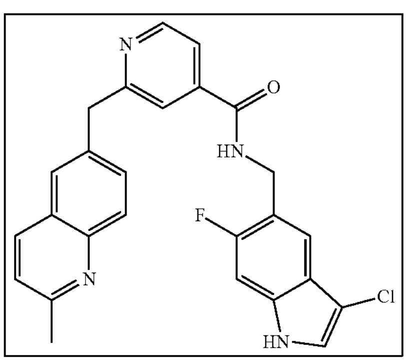 [SMILES: Cc1ccc2cc(Cc3cc(C(=O)NCc4cc5c(Cl)c[nH]c5cc4F)ccn3)ccc2n1] | N-((3-chloro-6-fluoro-1H-indol-5-yl)methyl)-2-((2-methylquinolin-6-yl)methyl)isonicotinamide |

TABLE 1-continued

| Chemical Synthesis Example | Structure | Name |
|---|---|---|
| 111 | 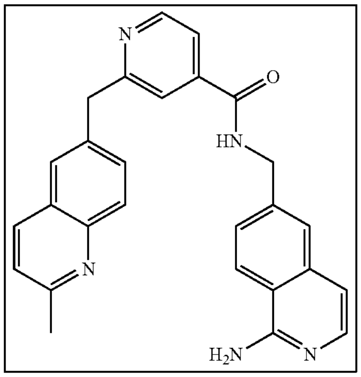 [SMILES: Cc1ccc2cc(Cc3cc(C(=O)NCc4ccc5c(N)nccc5c4)ccn3)ccc2n1] | N-((1-aminoisoquinolin-6-yl)methyl)-2-((2-methylquinolin-6-yl)methyl)isonicotinamide |
| 112 | 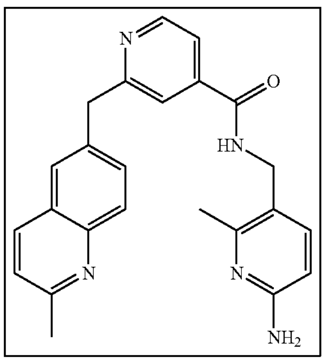 [SMILES: Cc1ccc2cc(Cc3cc(C(=O)NCc4ccc(N)nc4C)ccn3)ccc2n1] | N-((6-amino-2-methylpyridin-3-yl)methyl)-2-((2-methylquinolin-6-yl)methyl)isonicotinamide |
| 113 | 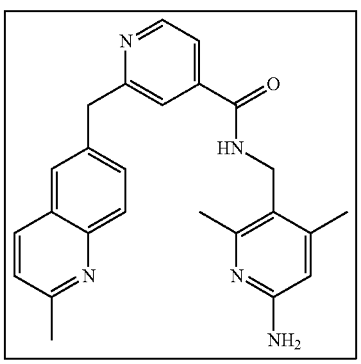 [SMILES: Cc1ccc2cc(Cc3cc(C(=O)NCc4c(C)cc(N)nc4C)ccn3)ccc2n1] | N-((6-amino-2,4-dimethylpyridin-3-yl)methyl)-2-((2-methylquinolin-6-yl)methyl)isonicotinamide |
| 114 | 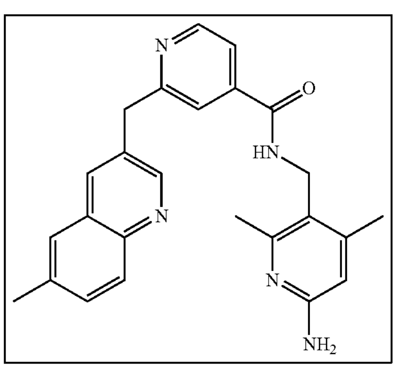 | N-((6-amino-2,4-dimethylpyridin-3-yl)methyl)-2-((6-methylquinolin-3-yl)methyl)isonicotinamide |

TABLE 1-continued

| Chemical Synthesis Example | Structure | Name |
|---|---|---|
| 115 | 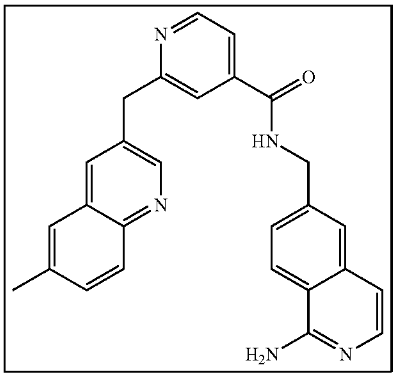 [SMILES: Cc1ccc2ncc(Cc3cc(C(=O)NCc4ccc5c(N)nccc5c4)ccn3)cc2c1] | N-((1-aminoisoquinolin-6-yl)methyl)-2-((6-methylquinolin-3-yl)methyl)isonicotinamide |
| 116 | 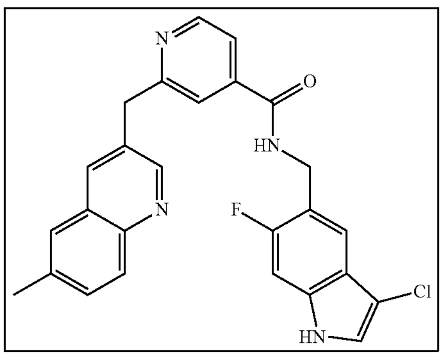 [SMILES: Cc1ccc2ncc(Cc3cc(C(=O)NCc4cc5c(Cl)c[nH]c5cc4F)ccn3)cc2c1] | N-((3-chloro-6-fluoro-1H-indol-5-yl)methyl)-2-((6-methylquinolin-3-yl)methyl)isonicotinamide |
| 117 | 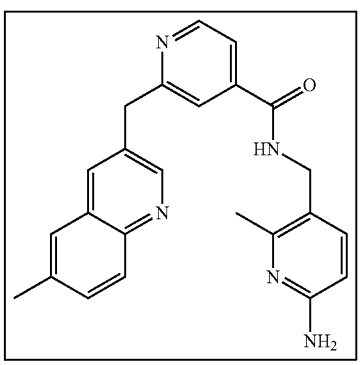 [SMILES: Cc1ccc2ncc(Cc3cc(C(=O)NCc4ccc(N)nc4C)ccn3)cc2c1] | N-((6-amino-2-methylpyridin-3-yl)methyl)-2-((6-methylquinolin-3-yl)methyl)isonicotinamide |
| 118 | 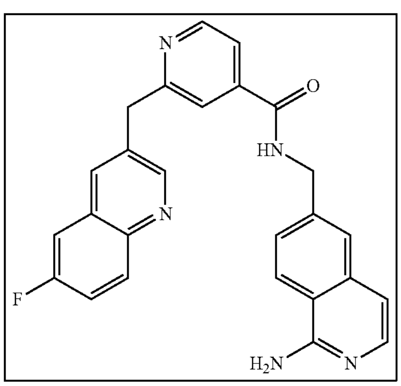 [SMILES: Nc1nccc2cc(CNC(=O)c3ccnc(Cc4cnc5ccc(F)cc5c4)c3)ccc12] | N-((1-aminoisoquinolin-6-yl)methyl)-2-((6-fluoroquinolin-3-yl)methyl)isonicotinamide |

TABLE 1-continued

| Chemical Synthesis Example | Structure | Name |
|---|---|---|
| 119 | 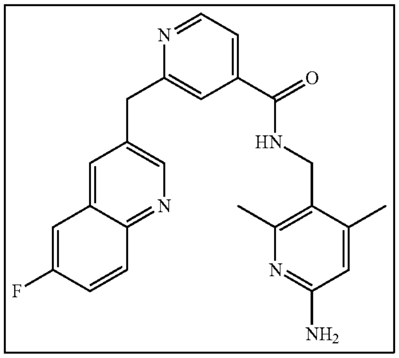 [SMILES: Cc1cc(N)nc(C)c1CNC(=O)c1ccnc(Cc2cnc3ccc(F)cc3c2)c1] | N-((6-amino-2,4-dimethylpyridin-3-yl)methyl)-2-((6-fluoroquinolin-3-yl)methyl)isonicotinamide |
| 120 | 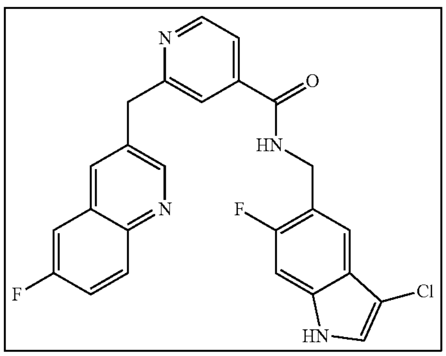 [SMILES: O=C(NCc1cc2c(Cl)c[nH]c2cc1F)c1ccnc(Cc2cnc3ccc(F)cc3c2)c1] | N-((3-chloro-6-fluoro-1H-indol-5-yl)methyl)-2-((6-fluoroquinolin-3-yl)methyl)isonicotinamide |
| 121 | 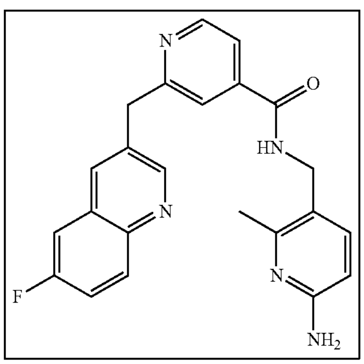 [SMILES: Cc1nc(N)ccc1CNC(=O)c1ccnc(Cc2cnc3ccc(F)cc3c2)c1] | N-((6-amino-2-methylpyridin-3-yl)methyl)-2-((6-fluoroquinolin-3-yl)methyl)isonicotinamide |
| 122 | 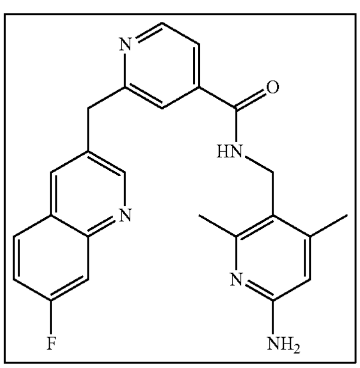 [SMILES: Cc1cc(N)nc(C)c1CNC(=O)c1ccnc(Cc2cnc3cc(F)ccc3c2)c1] | N-((6-amino-2,4-dimethylpyridin-3-yl)methyl)-2-((7-fluoroquinolin-3-yl)methyl)isonicotinamide |

TABLE 1-continued

| Chemical Synthesis Example | Structure | Name |
|---|---|---|
| 123 | 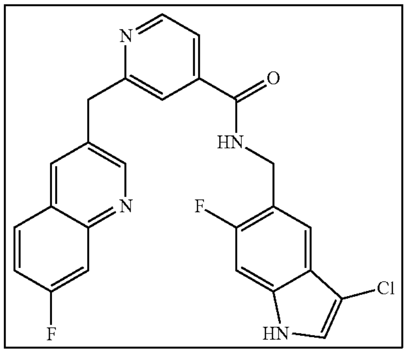 [SMILES: O=C(NCc1cc2c(Cl)c[nH]c2cc1F)c1ccnc(Cc2cnc3cc(F)ccc3c2)c1] | N-((3-chloro-6-fluoro-1H-indol-5-yl)methyl)-2-((7-fluoroquinolin-3-yl)methyl)isonicotinamide |
| 124 | 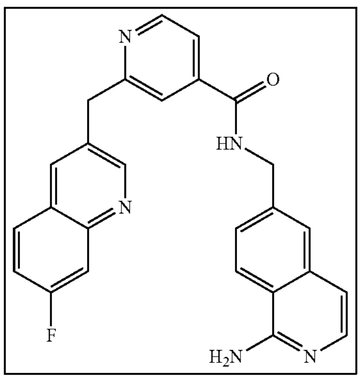 [SMILES: Nc1nccc2cc(CNC(=O)c3ccnc(Cc4cnc5cc(F)ccc5c4)c3)ccc12] | N-((1-aminoisoquinolin-6-yl)methyl)-2-((7-fluoroquinolin-3-yl)methyl)isonicotinamide |
| 125 | 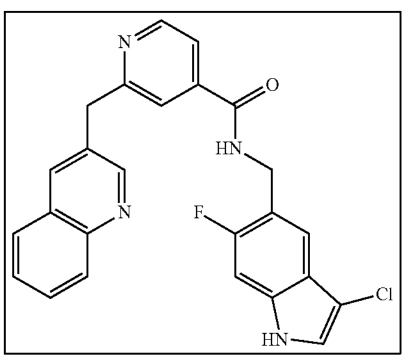 [SMILES: O=C(NCc1cc2c(Cl)c[nH]c2cc1F)c1ccnc(Cc2cnc3ccccc3c2)c1] | N-((3-chloro-6-fluoro-1H-indol-5-yl)methyl)-2-(quinolin-3-ylmethyl)isonicotinamide |
| 126 | 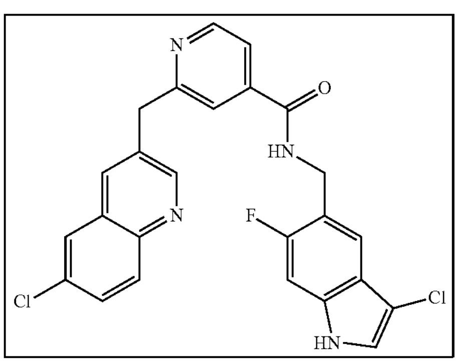 [SMILES: O=C(NCc1cc2c(Cl)c[nH]c2cc1F)c1ccnc(Cc2cnc3ccc(Cl)cc3c2)c1] | N-((3-chloro-6-fluoro-1H-indol-5-yl)methyl)-2-((6-chloroquinolin-3-yl)methyl)isonicotinamide |

TABLE 1-continued

| Chemical Synthesis Example | Structure | Name |
|---|---|---|
| 127 | 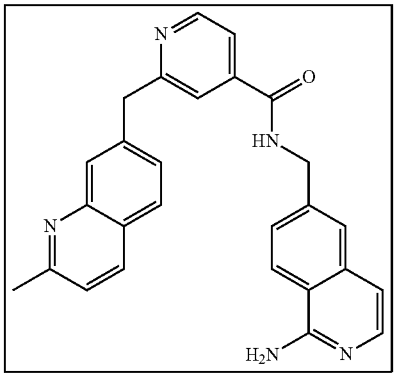 [SMILES: Cc1ccc2ccc(Cc3cc(C(=O)NCc4ccc5c(N)nccc5c4)ccn3)cc2n1] | N-((1-aminoisoquinolin-6-yl)methyl)-2-((2-methylquinolin-7-yl)methyl)isonicotinamide |
| 128 | 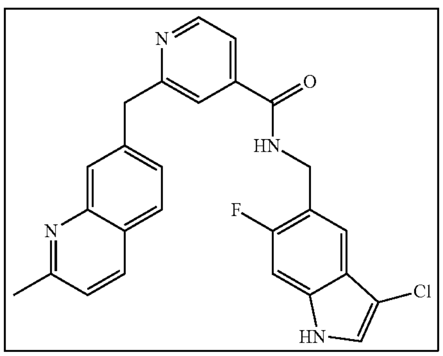 [SMILES: Cc1ccc2ccc(Cc3cc(C(=O)NCc4cc5c(Cl)c[nH]c5cc4F)ccn3)cc2n1] | N-((3-chloro-6-fluoro-1H-indol-5-yl)methyl)-2-((2-methylquinolin-7-yl)methyl)isonicotinamide |
| 129 | 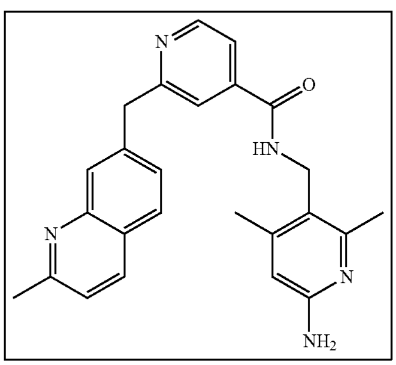 | N-((6-amino-2,4-dimethylpyridin-3-yl)methyl)-2-((2-methylquinolin-7-yl)methyl)isonicotinamide |
| 130 | 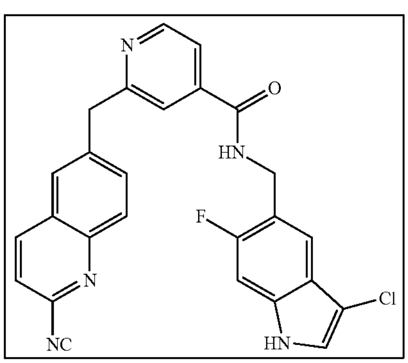 | N-((3-chloro-6-fluoro-1H-indol-5-yl)methyl)-2-((2-isocyanoquinolin-6-yl)methyl)isonicotinamide |

TABLE 1-continued

| Chemical Synthesis Example | Structure | Name |
|---|---|---|
| 131 | 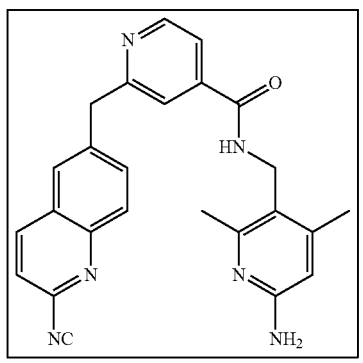 | N-((6-amino-2,4-dimethylpyridin-3-yl)methyl)-2-((2-isocyanoquinolin-6-yl)methyl)isonicotinamide |
| 132 | 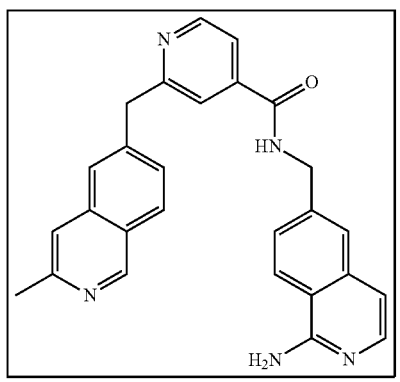 [SMILES: Cc1cc2cc(Cc3cc(C(=O)NCc4ccc5c(N)nccc5c4)ccn3)ccc2cn1] | N-((1-aminoisoquinolin-6-yl)methyl)-2-((3-methylisoquinolin-6-yl)methyl)isonicotinamide |
| 133 | 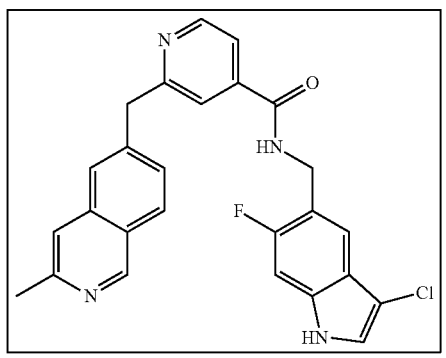 [SMILES: Cc1cc2cc(Cc3cc(C(=O)NCc4cc5c(Cl)c[nH]c5cc4F)ccn3)ccc2cn1] | N-((3-chloro-6-fluoro-1H-indol-5-yl)methyl)-2-((3-methylisoquinolin-6-yl)methyl)isonicotinamide |
| 134 | 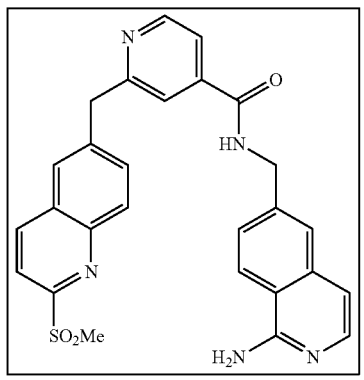 [SMILES: CS(=O)(=O)c1ccc2cc(Cc3cc(C(=O)NCc4ccc5c(N)nccc5c4)ccn3)ccc2n1] | N-((1-aminoisoquinolin-6-yl)methyl)-2-((2-(methylsulfonyl)quinolin-6-yl)methyl)isonicotinamide |

TABLE 1-continued

| Chemical Synthesis Example | Structure | Name |
|---|---|---|
| 135 | 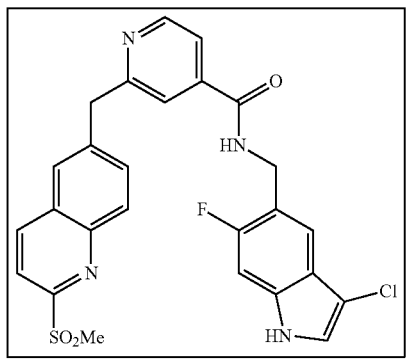 [SMILES: CS(=O)(=O)c1ccc2cc(Cc3cc(C(=O)NCc4cc5c(Cl)c[nH]c5cc4F)ccn3)ccc2n1] | N-((3-chloro-6-fluoro-1H-indol-5-yl)methyl)-2-((2-(methylsulfonyl)quinolin-6-yl)methyl)isonicotinamide |
| 136 | 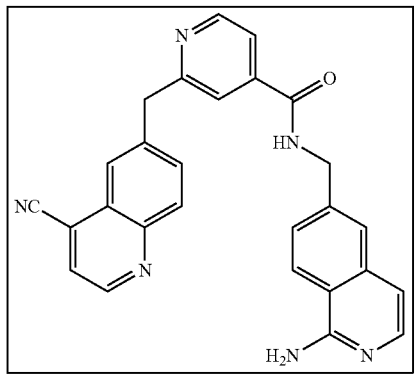 [SMILES: N#Cc1ccnc2ccc(Cc3cc(C(=O)NCc4ccc5c(N)nccc5c4)ccn3)cc12] | N-((1-aminoisoquinolin-6-yl)methyl)-2-((4-cyanoquinolin-6-yl)methyl)isonicotinamide |
| 137 | 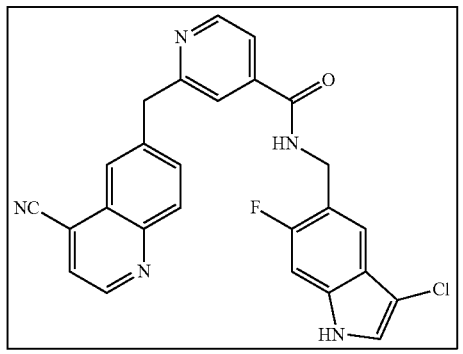 [SMILES: N#Cc1ccnc2ccc(Cc3cc(C(=O)NCc4cc5c(Cl)c[nH]c5cc4F)ccn3)cc12] | N-((3-chloro-6-fluoro-1H-indol-5-yl)methyl)-2-((4-cyanoquinolin-6-yl)methyl)isonicotinamide |
| 138 | 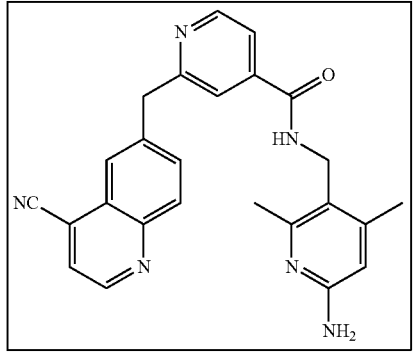 [SMILES: Cc1cc(N)nc(C)c1CNC(=O)c1ccnc(Cc2ccc3nccc(C#N)c3c2)c1] | N-((6-amino-2,4-dimethylpyridin-3-yl)methyl)-2-((4-cyanoquinolin-6-yl)methyl)isonicotinamide |

TABLE 1-continued

| Chemical Synthesis Example | Structure | Name |
|---|---|---|
| 139 | 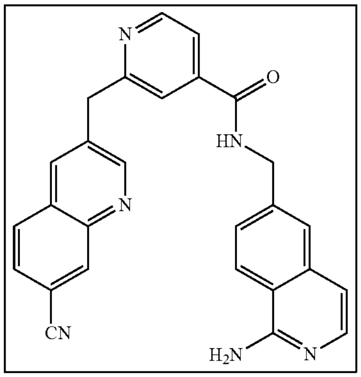 [SMILES: N#Cc1ccc2cc(Cc3cc(C(=O)NCc4ccc5c(N)nccc5c4)ccn3)cnc2c1] | N-((1-aminoisoquinolin-6-yl)methyl)-2-((7-chloroquinolin-3-yl)methyl)isonicotinamide |
| 140 | 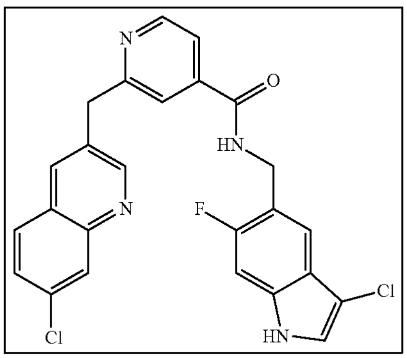 [SMILES: O=C(NCc1cc2c(Cl)c[nH]c2cc1F)c1ccnc(Cc2cnc3cc(Cl)ccc3c2)c1] | N-((3-chloro-6-fluoro-1H-indol-5-yl)methyl)-2-((7-chloroquinolin-3-yl)methyl)isonicotinamide |
| 141 | 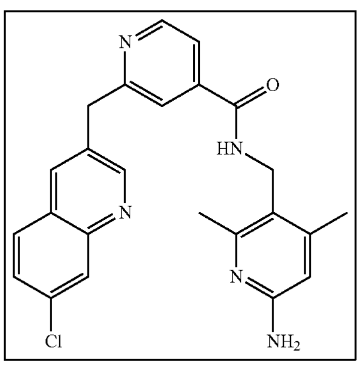 | N-((6-amino-2,4-dimethylpyridin-3-yl)methyl)-2-((7-chloroquinolin-3-yl)methyl)isonicotinamide |
| 142 | 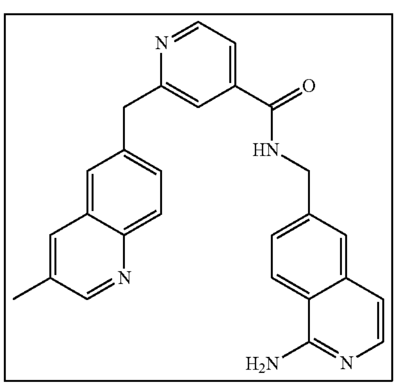 [SMILES: Cc1cnc2ccc(Cc3cc(C(=O)NCc4ccc5c(N)nccc5c4)ccn3)cc2c1] | N-((1-aminoisoquinolin-6-yl)methyl)-2-((3-methylquinolin-6-yl)methyl)isonicotinamide |

TABLE 1-continued

| Chemical Synthesis Example | Structure | Name |
|---|---|---|
| 143 | 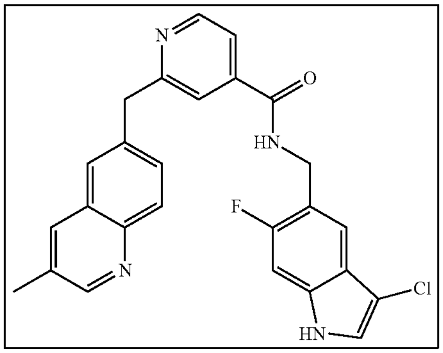 [SMILES: Cc1cnc2ccc(Cc3cc(C(=O)NCc4cc5c(Cl)c[nH]c5cc4F)ccn3)cc2c1] | N-((3-chloro-6-fluoro-1H-indol-5-yl)methyl)-2-((3-methylquinolin-6-yl)methyl)isonicotinamide |
| 144 | 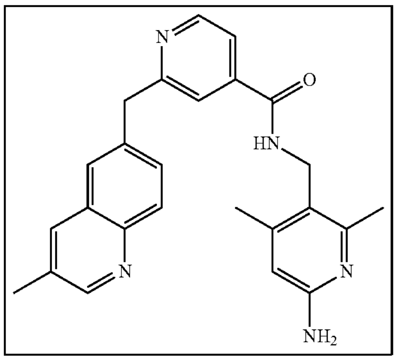 | N-((6-amino-2,4-dimethylpyridin-3-yl)methyl)-2-((3-methylquinolin-6-yl)methyl)isonicotinamide |
| 145 | 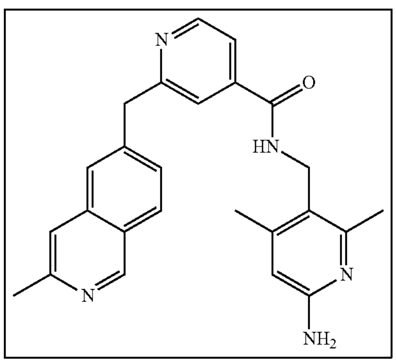 | N-((6-amino-2,4-dimethylpyridin-3-yl)methyl)-2-((3-methylisoquinolin-6-yl)methyl)isonicotinamide |
| 146 | 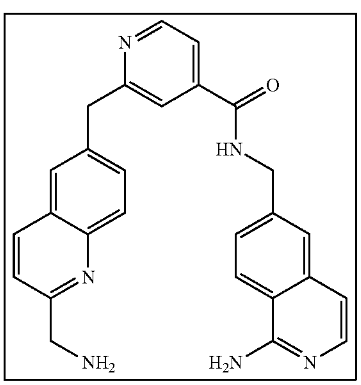 [SMILES: NCc1ccc2cc(Cc3cc(C(=O)NCc4ccc5c(N)nccc5c4)ccn3)ccc2n1] | N-((1-aminoisoquinolin-6-yl)methyl)-2-((2-(aminomethyl)quinolin-6-yl)methyl)isonicotinamide |

In some embodiments, the compound described herein has the structure provided in Table 2.

TABLE 2

| Name | Structure |
|---|---|
| N-((1-aminoisoquinolin-6-yl)methyl)-2-((3-fluoroquinolin-6-yl)methyl)isonicotinamide | 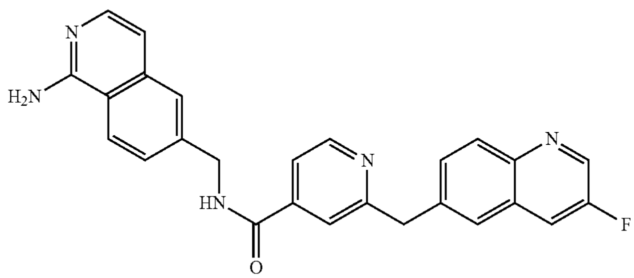 [SMILES: Nc1nccc2cc(CNC(=O)c3ccnc(Cc4ccc5ncc(F)cc5c4)c3)ccc12] |
| N-((1-aminoisoquinolin-6-yl)methyl)-2-((6-cyanoquinolin-3-yl)methyl)isonicotinamide | 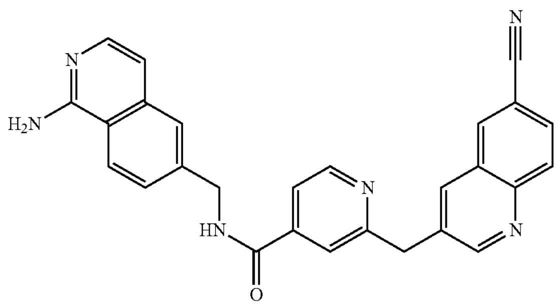 [SMILES: N#Cc1ccc2ncc(Cc3cc(C(=O)NCc4ccc5c(N)nccc5c4)ccn3)cc2c1] |
| 3-((4-(((1-aminoisoquinolin-6-yl)methyl)carbamoyl)pyridin-2-yl)methyl)quinoline-6-carboxamide | 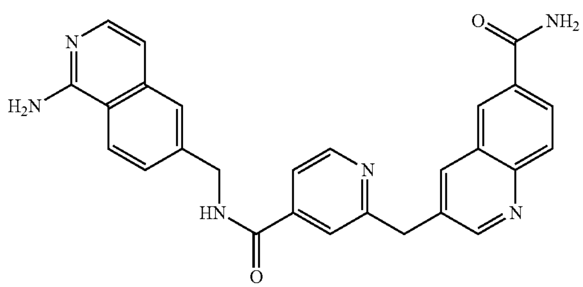 [SMILES: NC(=O)c1ccc2ncc(Cc3cc(C(=O)NCc4ccc5c(N)nccc5c4)ccn3)cc2c1] |
| N-((1-aminoisoquinolin-6-yl)methyl)-2-((6-chloroquinolin-3-yl)methyl)isonicotinamide | 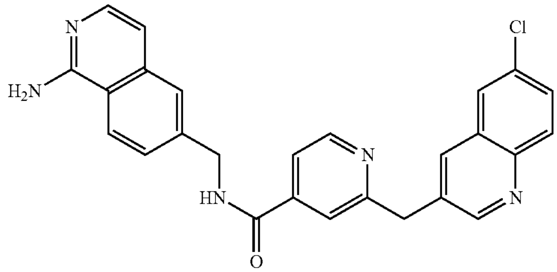 [SMILES: Nc1nccc2cc(CNC(=O)c3ccnc(Cc4cnc5ccc(Cl)cc5c4)c3)ccc12] |
| N-((1-aminoisoquinolin-6-yl)methyl)-2-((6-(hydroxymethyl)quinolin-3-yl)methyl)isonicotinamide | 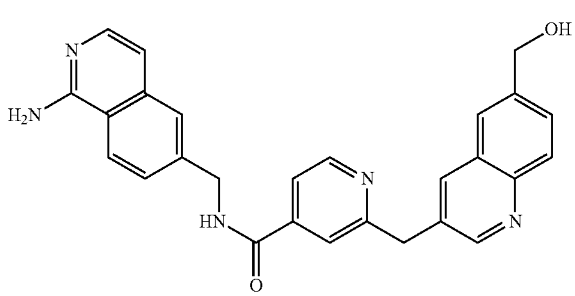 [SMILES: Nc1nccc2cc(CNC(=O)c3ccnc(Cc4cnc5ccc(CO)cc5c4)c3)ccc12] |

TABLE 2-continued

| Name | Structure |
|---|---|
| N-((1-aminoisoquinolin-6-yl)methyl)-2-((6-(aminomethyl)quinolin-3-yl)methyl)isonicotinamide | 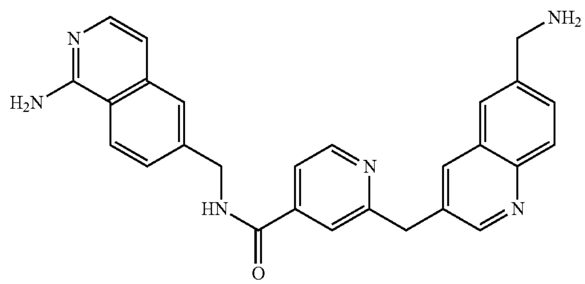 [SMILES: NCc1ccc2ncc(Cc3cc(C(=O)NCc4ccc5c(N)nccc5c4)ccn3)cc2c1] |
| 6-((4-(((1-aminoisoquinolin-6-yl)methyl)carbamoyl)pyridin-2-yl)methyl)quinoline-3-carboxamide | 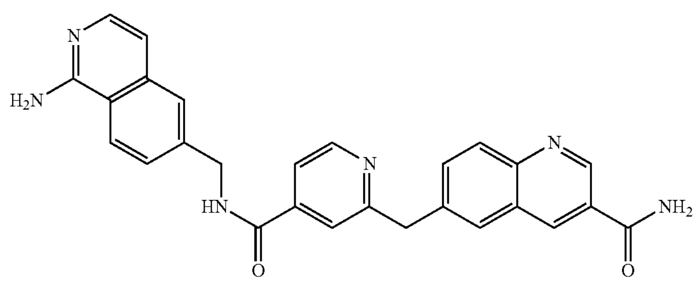 [SMILES: NC(=O)c1cnc2ccc(Cc3cc(C(=O)NCc4ccc5c(N)nccc5c4)ccn3)cc2c1] |
| N-((1-aminoisoquinolin-6-yl)methyl)-2-((3-(hydroxymethyl)quinolin-6-yl)methyl)isonicotinamide | 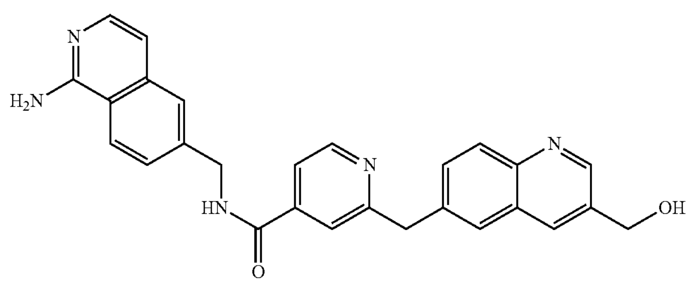 [SMILES: Nc1nccc2cc(CNC(=O)c3ccnc(Cc4ccc5ncc(CO)cc5c4)c3)ccc12] |
| N-((1-aminoisoquinolin-6-yl)methyl)-2-((3-(aminomethyl)quinolin-6-yl)methyl)isonicotinamide | 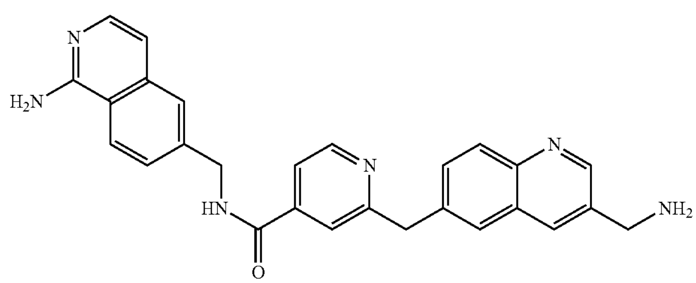 [SMILES: NCc1cnc2ccc(Cc3cc(C(=O)NCc4ccc5c(N)nccc5c4)ccn3)cc2c1] |
| N-((1-aminoisoquinolin-6-yl)methyl)-2-((3-methyl-8-sulfamoylquinolin-6-yl)methyl)isonicotinamide | 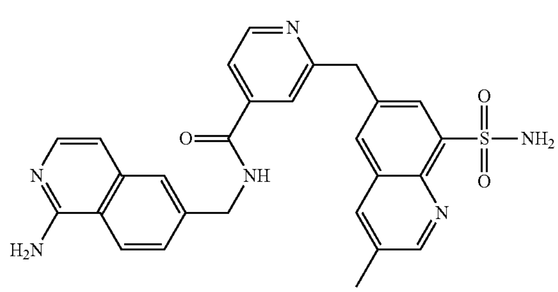 [SMILES: Cc1cnc2c(S(N)(=O)=O)cc(Cc3cc(C(=O)NCc4ccc5c(N)nccc5c4)ccn3)cc2c1] |

TABLE 2-continued

| Name | Structure |
|---|---|
| 6-((4-(((1-aminoisoquinolin-6-yl)methyl)carbamoyl)pyridin-2-yl)methyl)-3-methylquinoline-8-carboxylic acid | 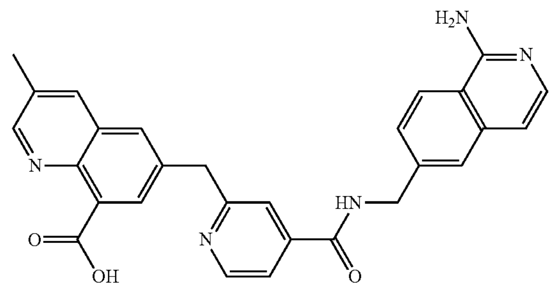 [SMILES: Cc1cnc2c(C(=O)O)cc(Cc3cc(C(=O)NCc4ccc5c(N)nccc5c4)ccn3)cc2c1] |
| N-((6-amino-2-methylpyridin-3-yl)methyl)-2-((3-methyl-8-(methylsulfonyl)quinolin-6-yl)methyl)isonicotinamide | 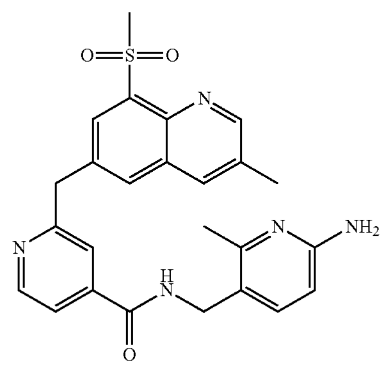 [SMILES: Cc1cnc2c(S(C)(=O)=O)cc(Cc3cc(C(=O)NCc4ccc(N)nc4C)ccn3)cc2c1] |
| N-((6-amino-4-methylpyridin-3-yl)methyl)-2-((3-methyl-8-(methylsulfonyl)quinolin-6-yl)methyl)isonicotinamide | 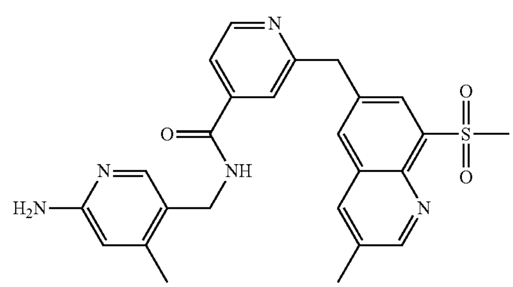 [SMILES: Cc1cnc2c(S(C)(=O)=O)cc(Cc3cc(C(=O)NCc4cnc(N)cc4C)ccn3)cc2c1] |
| N-((6-amino-2-methyl-4-(trifluoromethyl)pyridin-3-yl)methyl)-2-((3-methyl-8-(methylsulfonyl)quinolin-6-yl)methyl)isonicotinamide | 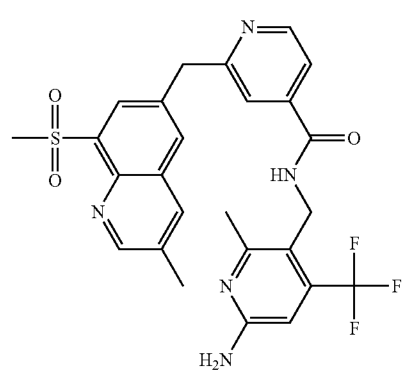 [SMILES: Cc1cnc2c(S(C)(=O)=O)cc(Cc3cc(C(=O)NCc4c(C(F)(F)F)cc(N)nc4C)ccn3)cc2c1] |

TABLE 2-continued

| Name | Structure |
|---|---|
| N-((6-amino-4-cyano-2-methylpyridin-3-yl)methyl)-2-((3-methyl-8-(methylsulfonyl)quinolin-6-yl)methyl)isonicotinamide | 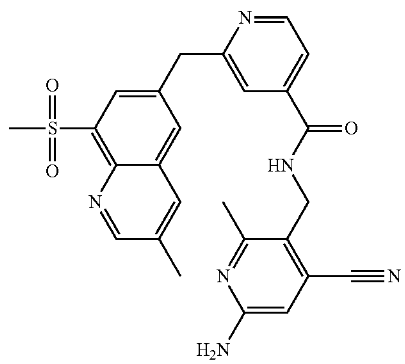 [SMILES: Cc1cnc2c(S(C)(=O)=O)cc(Cc3cc(C(=O)NCc4c(C#N)cc(N)nc4C)ccn3)cc2c1] |
| N-((6-amino-4-methyl-2-(trifluoromethyl)pyridin-3-yl)methyl)-2-((3-methyl-8-(methylsulfonyl)quinolin-6-yl)methyl)isonicotinamide | 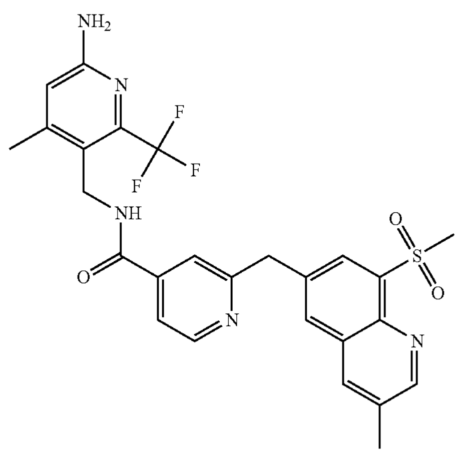 |
| N-((6-amino-2-cyano-4-methylpyridin-3-yl)methyl)-2-((3-methyl-8-(methylsulfonyl)quinolin-6-yl)methyl)isonicotinamide | 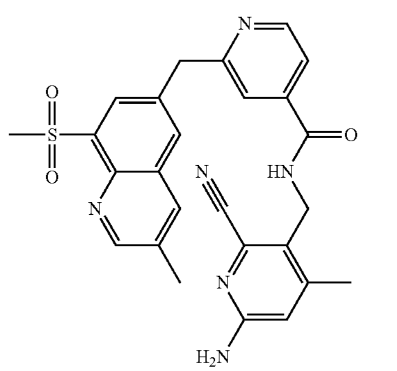 |
| N-((6-amino-5-fluoro-2-methylpyridin-3-yl)methyl)-2-((3-methyl-8-(methylsulfonyl)quinolin-6-yl)methyl)isonicotinamide | 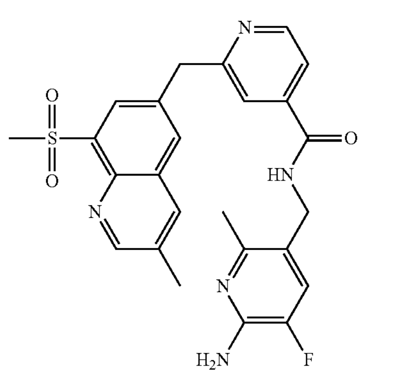 |

TABLE 2-continued

| Name | Structure |
|---|---|
| N-((6-amino-5-chloro-2-methylpyridin-3-yl)methyl)-2-((3-methyl-8-(methylsulfonyl)quinolin-6-yl)methyl)isonicotinamide | 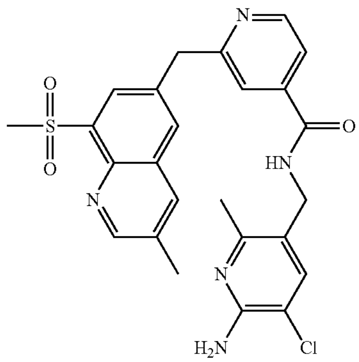 [SMILES: Cc1cnc2c(S(C)(=O)=O)cc(Cc3cc(C(=O)NCc4cc(Cl)c(N)nc4C)ccn3)cc2c1] |
| N-((6-amino-5-cyano-2-methylpyridin-3-yl)methyl)-2-((3-methyl-8-(methylsulfonyl)quinolin-6-yl)methyl)isonicotinamide | 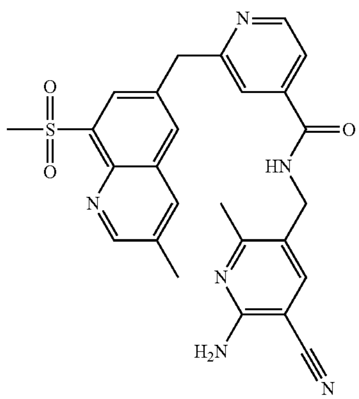 [SMILES: Cc1cnc2c(S(C)(=O)=O)cc(Cc3cc(C(=O)NCc4cc(C#N)c(N)nc4C)ccn3)cc2c1] |
| N-((6-amino-2-methyl-5-(trifluoromethyl)pyridin-3-yl)methyl)-2-((3-methyl-8-(methylsulfonyl)quinolin-6-yl)methyl)isonicotinamide | 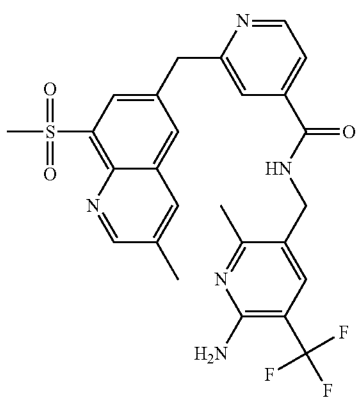 |
| N-((1-aminoisoquinolin-6-yl)methyl)-2-((3-fluoro-8-(methylsulfonyl)quinolin-6-yl)methyl)isonicotinamide | 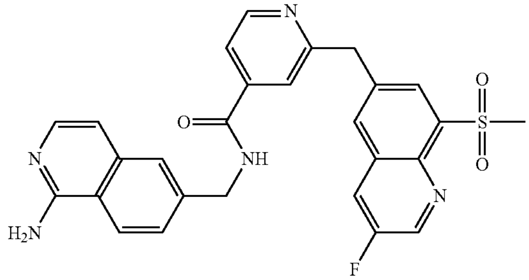 [SMILES: CS(=O)(=O)c1cc(Cc2cc(C(=O)NCc3ccc4c(N)nccc4c3)ccn2)cc2cc(F)cnc12] |

TABLE 2-continued

| Name | Structure |
|---|---|
| N-((1-aminoisoquinolin-6-yl)methyl)-2-((3-fluoro-8-sulfamoylquinolin-6-yl)methyl)isonicotinamide | 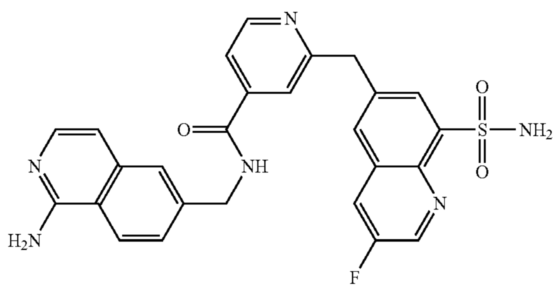 [SMILES: Nc1nccc2cc(CNC(=O)c3ccnc(Cc4cc(S(N)(=O)=O)c5ncc(F)cc5c4)c3)ccc12] |
| 6-((4-(((1-aminoisoquinolin-6-yl)methyl)carbamoyl)pyridin-2-yl)methyl)-3-fluoroquinoline-8-carboxylic acid | 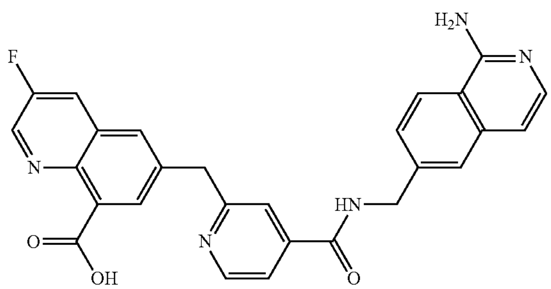 [SMILES: Nc1nccc2cc(CNC(=O)c3ccnc(Cc4cc(C(=O)O)c5ncc(F)cc5c4)c3)ccc12] |
| N-((3-chloro-1H-pyrrolo[2,3-b]pyridin-5-yl)methyl)-2-((3-fluoro-8-(methylsulfonyl)quinolin-6-yl)methyl)isonicotinamide | 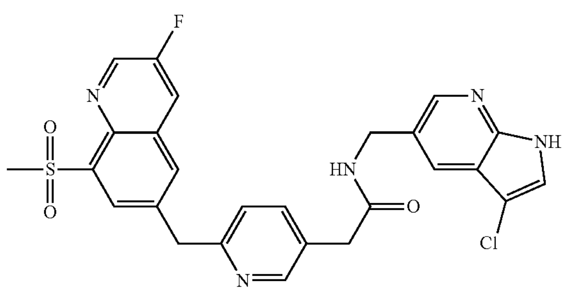 [SMILES: CS(=O)(=O)c1cc(Cc2ccc(CC(=O)NCc3cnc4[nH]cc(Cl)c4c3)cn2)cc2cc(F)cnc12] |
| N-((3-chloro-6-fluoro-1H-indol-5-yl)methyl)-2-((3-fluoro-8-(methylsulfonyl)quinolin-6-yl)methyl)isonicotinamide | 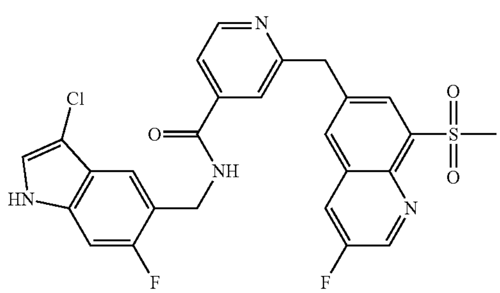 [SMILES: CS(=O)(=O)c1cc(Cc2cc(C(=O)NCc3cc4c(Cl)c[nH]c4cc3F)ccn2)cc2cc(F)cnc12] |
| N-((6-amino-2,4-dimethylpyridin-3-yl)methyl)-2-((3-fluoro-8-(methylsulfonyl)quinolin-6-yl)methyl)isonicotinamide | 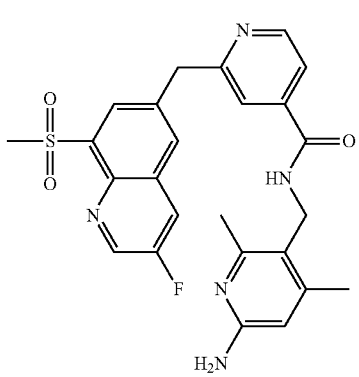 |

TABLE 2-continued

| Name | Structure |
|---|---|
| N-((5-chloro-1H-indazol-3-yl)methyl)-2-((3-fluoro-8-(methylsulfonyl)quinolin-6-yl)methyl)isonicotinamide | 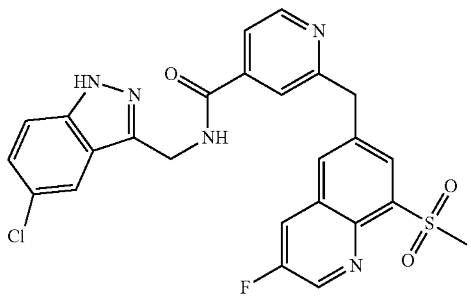 [SMILES: CS(=O)(=O)c1cc(Cc2cc(C(=O)NCc3n[nH]c4ccc(Cl)cc34)ccn2)cc2cc(F)cnc12] |
| N-((6-amino-2-methylpyridin-3-yl)methyl)-2-((3-fluoro-8-(methylsulfonyl)quinolin-6-yl)methyl)isonicotinamide | 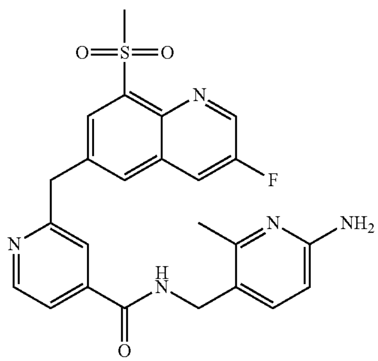 [SMILES: Cc1nc(N)ccc1CNC(=O)c1ccnc(Cc2cc(S(C)(=O)=O)c3ncc(F)cc3c2)c1] |
| N-((6-amino-4-methylpyridin-3-yl)methyl)-2-((3-fluoro-8-(methylsulfonyl)quinolin-6-yl)methyl)isonicotinamide | 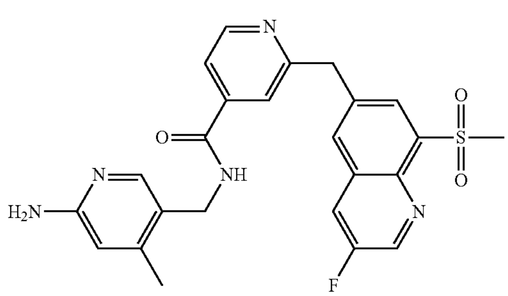 [SMILES: Cc1cc(N)ncc1CNC(=O)c1ccnc(Cc2cc(S(C)(=O)=O)c3ncc(F)cc3c2)c1] |
| N-((6-amino-2-methyl-4-(trifluoromethyl)pyridin-3-yl)methyl)-2-((3-fluoro-8-(methylsulfonyl)quinolin-6-yl)methyl)isonicotinamide | 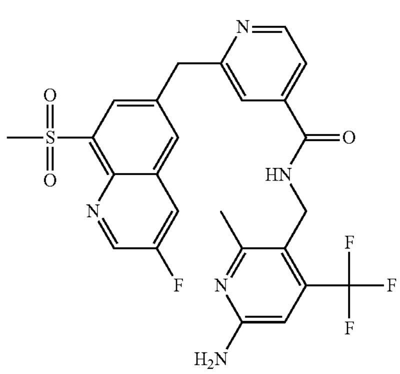 |

TABLE 2-continued

| Name | Structure |
|---|---|
| N-((6-amino-4-cyano-2-methylpyridin-3-yl)methyl)-2-((3-fluoro-8-(methylsulfonyl)quinolin-6-yl)methyl)isonicotinamide | 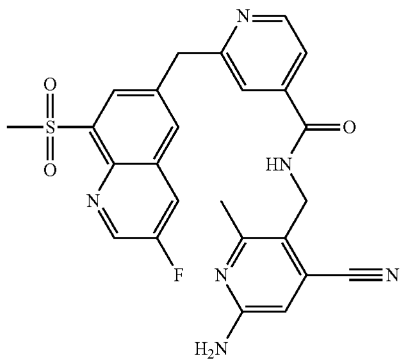 |
| N-((6-amino-4-methyl-2-(trifluoromethyl)pyridin-3-yl)methyl)-2-((3-fluoro-8-(methylsulfonyl)quinolin-6-yl)methyl)isonicotinamide | 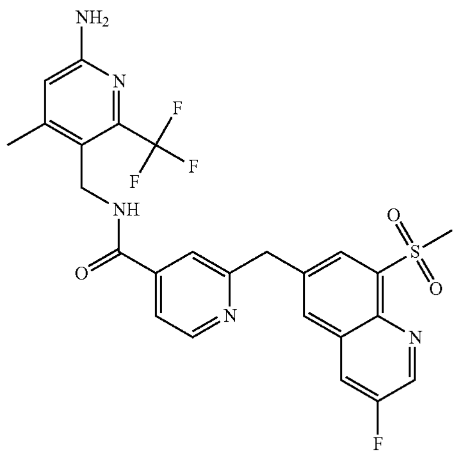 |
| N-((6-amino-2-cyano-4-methylpyridin-3-yl)methyl)-2-((3-fluoro-8-(methylsulfonyl)quinolin-6-yl)methyl)isonicotinamide | 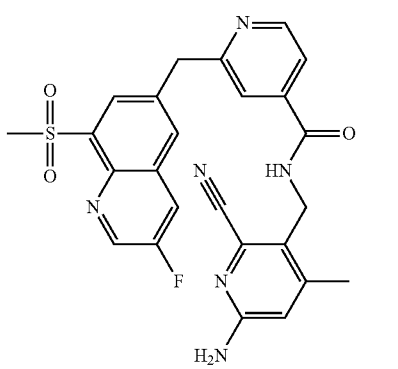 |
| N-((6-amino-5-fluoro-2-methylpyridin-3-yl)methyl)-2-((3-fluoro-8-(methylsulfonyl)quinolin-6-yl)methyl)isonicotinamide | 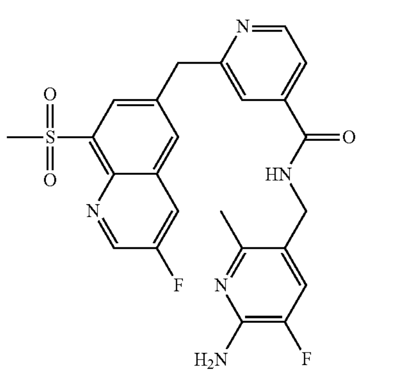 |

TABLE 2-continued

| Name | Structure |
|---|---|
| N-((6-amino-5-chloro-2-methylpyridin-3-yl)methyl)-2-((3-fluoro-8-(methylsulfonyl)quinolin-6-yl)methyl)isonicotinamide | 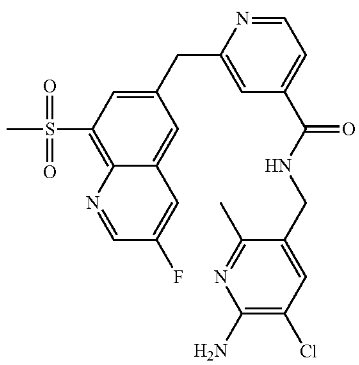 [SMILES: Cc1nc(N)c(Cl)cc1CNC(=O)c1ccnc(Cc2cc(S(C)(=O)=O)c3ncc(F)cc3c2)c1] |
| N-((6-amino-5-cyano-2-methylpyridin-3-yl)methyl)-2-((3-fluoro-8-(methylsulfonyl)quinolin-6-yl)methyl)isonicotinamide | 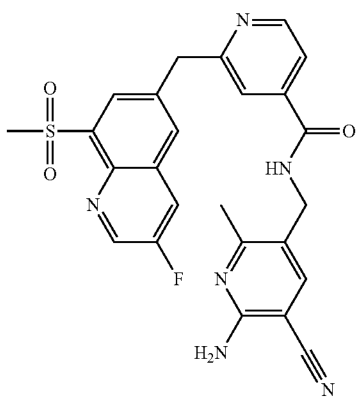 [SMILES: Cc1nc(N)c(C#N)cc1CNC(=O)c1ccnc(Cc2cc(S(C)(=O)=O)c3ncc(F)cc3c2)c1] |
| N-((6-amino-2-methyl-5-(trifluoromethyl)pyridin-3-yl)methyl)-2-((3-fluoro-8-(methylsulfonyl)quinolin-6-yl)methyl)isonicotinamide | 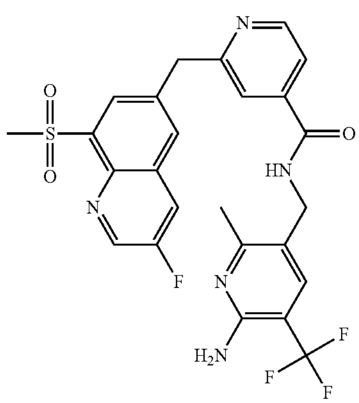 [SMILES: Cc1nc(N)c(C(F)(F)F)cc1CNC(=O)c1ccnc(Cc2cc(S(C)(=O)=O)c3ncc(F)cc3c2)c1] |
| N-((3-chloro-4-fluoro-1H-indol-5-yl)methyl)-2-((3-fluoro-8-(methylsulfonyl)quinolin-6-yl)methyl)isonicotinamide | 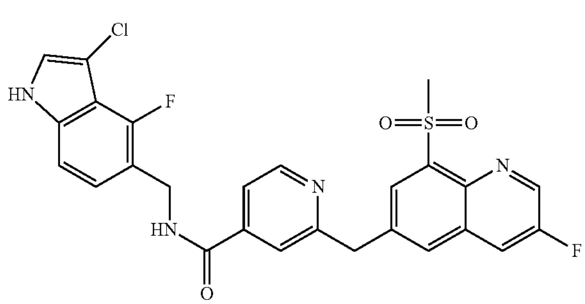 [SMILES: CS(=O)(=O)c1cc(Cc2cc(C(=O)NCc3ccc4[nH]cc(Cl)c4c3F)ccn2)cc2cc(F)cnc12] |

TABLE 2-continued

| Name | Structure |
|---|---|
| N-((6-amino-2-methylpyridin-3-yl)methyl)-2-((3-methylquinolin-6-yl)methyl)isonicotinamide | 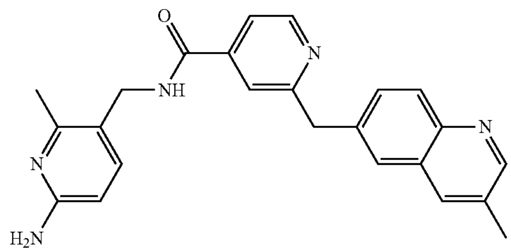 [SMILES: Cc1cnc2ccc(Cc3cc(C(=O)NCc4ccc(N)nc4C)ccn3)cc2c1] |
| N-((6-amino-4-methylpyridin-3-yl)methyl)-2-((3-methylquinolin-6-yl)methyl)isonicotinamide | 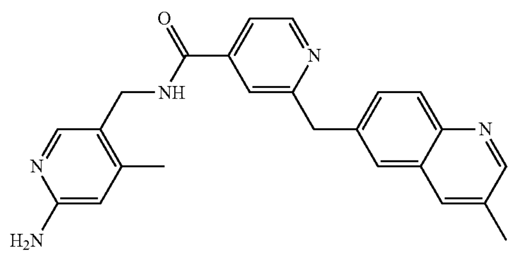 [SMILES: Cc1cnc2ccc(Cc3cc(C(=O)NCc4cnc(N)cc4C)ccn3)cc2c1] |
| N-((3-chloro-1H-pyrrolo[2,3-b]pyridin-5-yl)methyl)-2-((3-methylquinolin-6-yl)methyl)isonicotinamide | 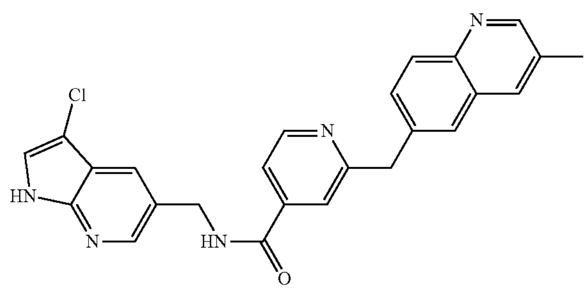 [SMILES: Cc1cnc2ccc(Cc3cc(C(=O)NCc4cnc5[nH]cc(Cl)c5c4)ccn3)cc2c1] |
| N-((5-chloro-1H-indazol-3-yl)methyl)-2-((3-methylquinolin-6-yl)methyl)isonicotinamide | 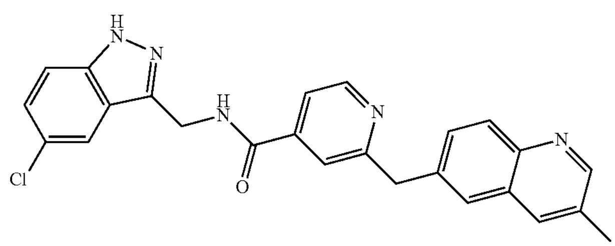 [SMILES: Cc1cnc2ccc(Cc3cc(C(=O)NCc4n[nH]c5ccc(Cl)cc45)ccn3)cc2c1] |
| N-((3-chloro-4-fluoro-1H-indol-5-yl)methyl)-2-((3-methylquinolin-6-yl)methyl)isonicotinamide | 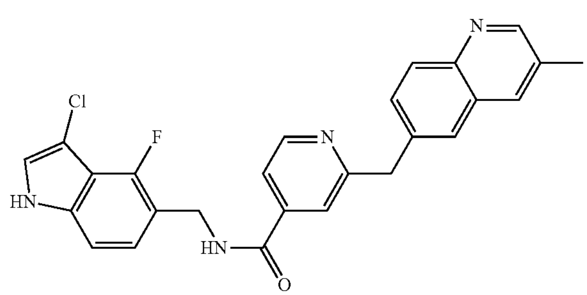 [SMILES: Cc1cnc2ccc(Cc3cc(C(=O)NCc4ccc5[nH]cc(Cl)c5c4F)ccn3)cc2c1] |
| N-((6-fluoro-1H-indol-5-yl)methyl)-2-((3-methylquinolin-6-yl)methyl)isonicotinamide | 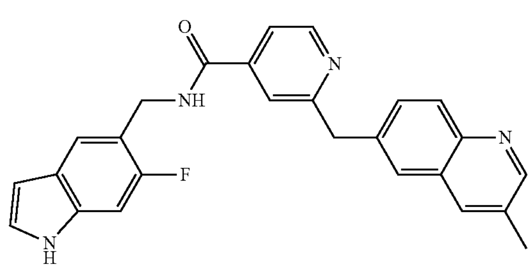 [SMILES: Cc1cnc2ccc(Cc3cc(C(=O)NCc4cc5cc[nH]c5cc4F)ccn3)cc2c1] |

TABLE 2-continued

| Name | Structure |
|---|---|
| N-((6-fluoro-1H-indazol-5-yl)methyl)-2-((3-methylquinolin-6-yl)methyl)isonicotinamide | 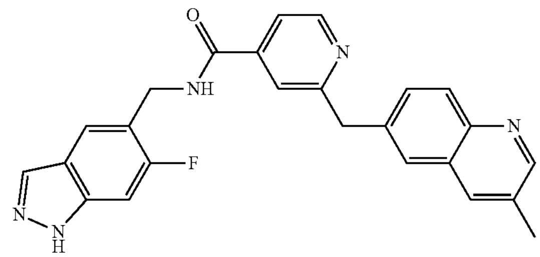 [SMILES: Cc1cnc2ccc(Cc3cc(C(=O)NCc4cc5cn[nH]c5cc4F)ccn3)cc2c1] |
| N-((1H-pyrrolo[2,3-b]pyridin-5-yl)methyl)-2-((3-methylquinolin-6-yl)methyl)isonicotinamide | 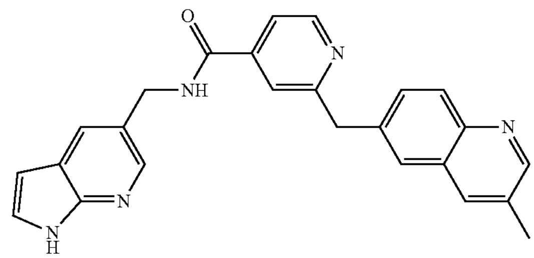 |
| N-((3-chloro-1H-indol-5-yl)methyl)-2-((3-methylquinolin-6-yl)methyl)isonicotinamide | 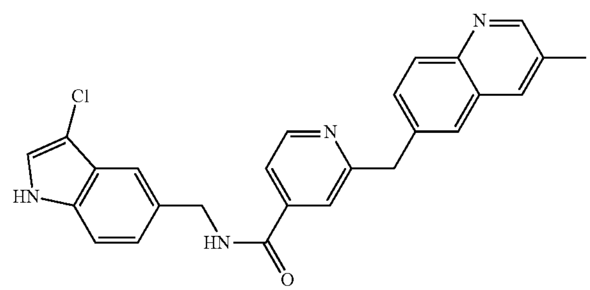 [SMILES: Cc1cnc2ccc(Cc3cc(C(=O)NCc4ccc5[nH]cc(Cl)c5c4)ccn3)cc2c1] |
| N-((5-chloro-1H-indol-3-yl)methyl)-2-((3-methylquinolin-6-yl)methyl)isonicotinamide | 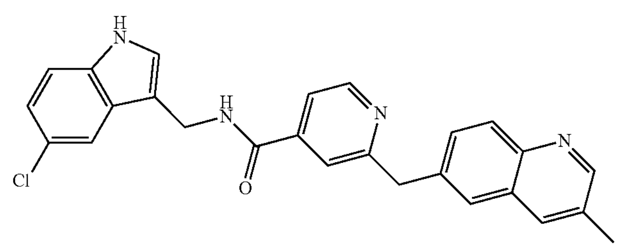 |
| N-((3-chloro-6-methyl-1H-indol-5-yl)methyl)-2-((3-methylquinolin-6-yl)methyl)isonicotinamide | 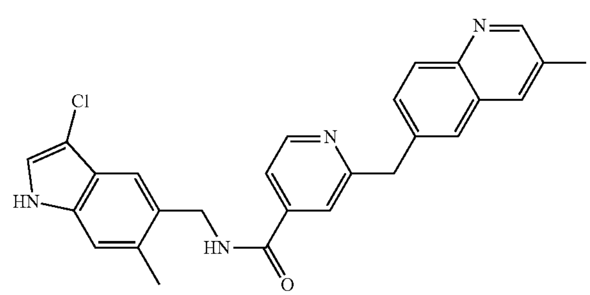 [SMILES: Cc1cnc2ccc(Cc3cc(C(=O)NCc4cc5c(Cl)c[nH]c5cc4C)ccn3)cc2c1] |

TABLE 2-continued

| Name | Structure |
|---|---|
| N-((3-chloro-6-methyl-1H-pyrrolo[2,3-b]pyridin-5-yl)methyl)-2-((3-methylquinolin-6-yl)methyl)isonicotinamide | 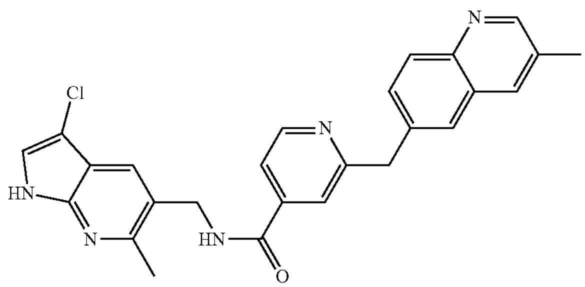 [SMILES: Cc1cnc2ccc(Cc3cc(C(=O)NCc4cc5c(Cl)c[nH]c5nc4C)ccn3)cc2c1] |
| N-((3-chloro-1H-pyrrolo[3,2-b]pyridin-5-yl)methyl)-2-((3-methylquinolin-6-yl)methyl)isonicotinamide | 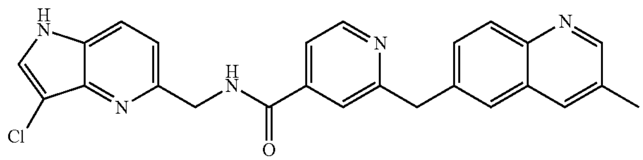 [SMILES: Cc1cnc2ccc(Cc3cc(C(=O)NCc4ccc5[nH]cc(Cl)c5n4)ccn3)cc2c1] |
| N-((1H-pyrrolo[3,2-b]pyridin-5-yl)methyl)-2-((3-methylquinolin-6-yl)methyl)isonicotinamide | 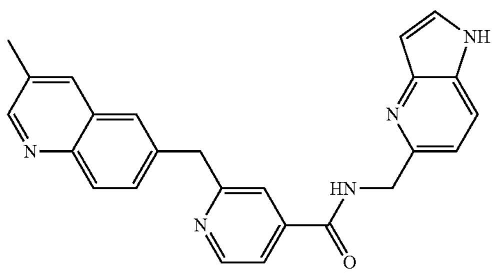 [SMILES: Cc1cnc2ccc(Cc3cc(C(=O)NCc4ccc5[nH]ccc5n4)ccn3)cc2c1] |
| N-((6-amino-2-methylpyridin-3-yl)methyl)-2-((3-fluoroquinolin-6-yl)methyl)isonicotinamide | 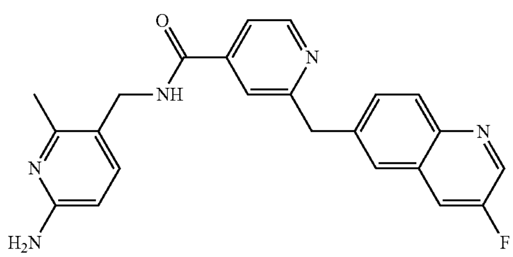 |
| N-((6-amino-4-methylpyridin-3-yl)methyl)-2-((3-fluoroquinolin-6-yl)methyl)isonicotinamide | 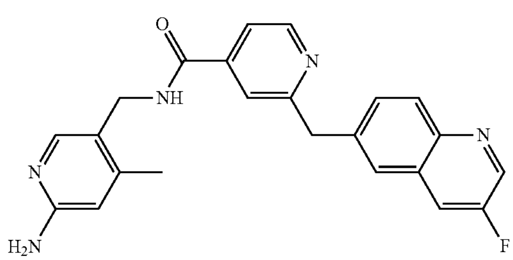 |
| N-((6-amino-2,4-dimethylpyridin-3-yl)methyl)-2-((3-fluoroquinolin-6-yl)methyl)isonicotinamide | 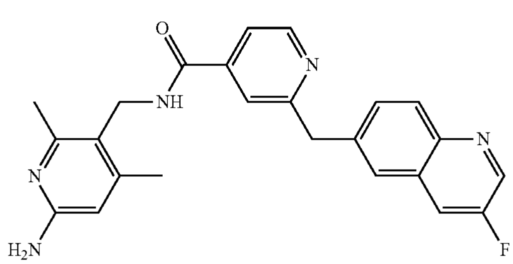 [SMILES: Cc1cc(N)nc(C)c1CNC(=O)c1ccnc(Cc2ccc3ncc(F)cc3c2)c1] |

TABLE 2-continued

| Name | Structure |
| --- | --- |
| N-((3-chloro-1H-pyrrolo[2,3-b]pyridin-5-yl)methyl)-2-((3-fluoroquinolin-6-yl)methyl)isonicotinamide | 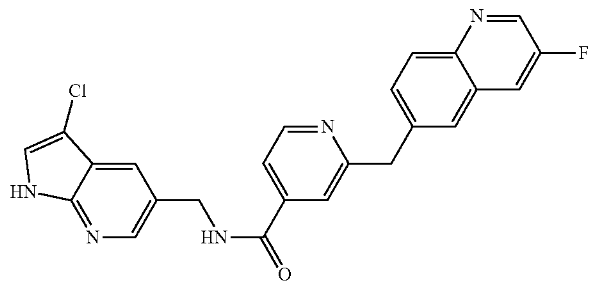 [SMILES: O=C(NCc1cnc2[nH]cc(Cl)c2c1)c1ccnc(Cc2ccc3ncc(F)cc3c2)c1] |
| N-((5-chloro-1H-indazol-3-yl)methyl)-2-((3-fluoroquinolin-6-yl)methyl)isonicotinamide | 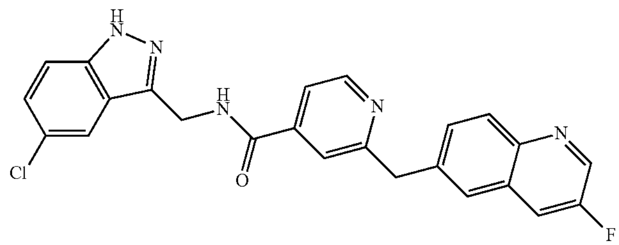 [SMILES: O=C(NCc1n[nH]c2ccc(Cl)cc12)c1ccnc(Cc2ccc3ncc(F)cc3c2)c1] |
| N-((3-chloro-4-fluoro-1H-indol-5-yl)methyl)-2-((3-fluoroquinolin-6-yl)methyl)isonicotinamide | 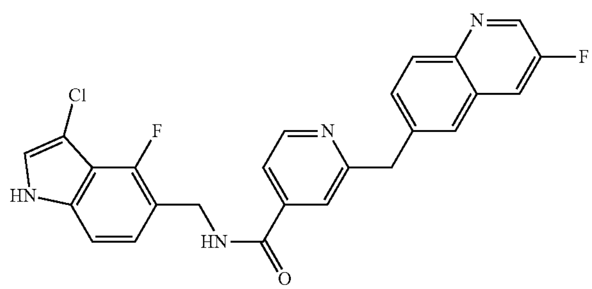 [SMILES: O=C(NCc1ccc2[nH]cc(Cl)c2c1F)c1ccnc(Cc2ccc3ncc(F)cc3c2)c1] |
| N-((3-chloro-1H-pyrrolo[2,3-b]pyridin-5-yl)methyl)-2-((3-chloro-8-(methylsulfonyl)quinolin-6-yl)methyl)isonicotinamide | 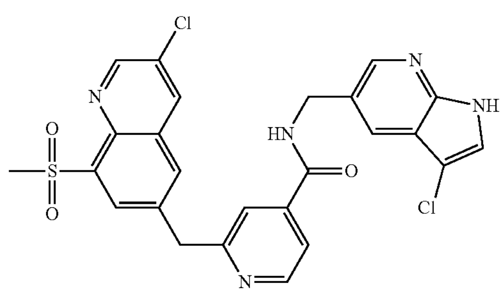 [SMILES: CS(=O)(=O)c1cc(Cc2cc(C(=O)NCc3cnc4[nH]cc(Cl)c4c3)ccn2)cc2cc(Cl)cnc12] |
| N-((5-chloro-1H-indazol-3-yl)methyl)-2-((3-chloro-8-(methylsulfonyl)quinolin-6-yl)methyl)isonicotinamide | 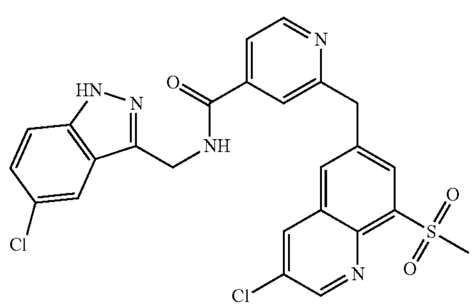 [SMILES: CS(=O)(=O)c1cc(Cc2cc(C(=O)NCc3n[nH]c4ccc(Cl)cc34)ccn2)cc2cc(Cl)cnc12] |

TABLE 2-continued

| Name | Structure |
|---|---|
| N-((6-fluoro-1H-indol-5-yl)methyl)-2-((3-fluoroquinolin-6-yl)methyl)isonicotinamide | 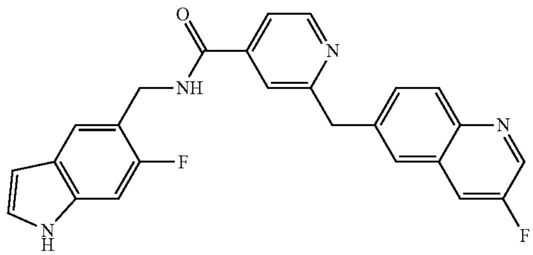 [SMILES: O=C(NCc1cc2cc[nH]c2cc1F)c1ccnc(Cc2ccc3ncc(F)cc3c2)c1] |
| N-((6-fluoro-1H-indazol-5-yl)methyl)-2-((3-fluoroquinolin-6-yl)methyl)isonicotinamide | 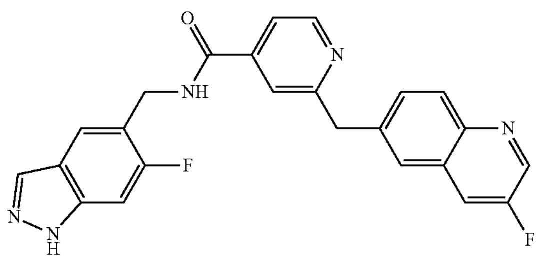 [SMILES: O=C(NCc1cc2cn[nH]c2cc1F)c1ccnc(Cc2ccc3ncc(F)cc3c2)c1] |
| N-((1H-pyrrolo[2,3-b]pyridin-5-yl)methyl)-2-((3-fluoroquinolin-6-yl)methyl)isonicotinamide | 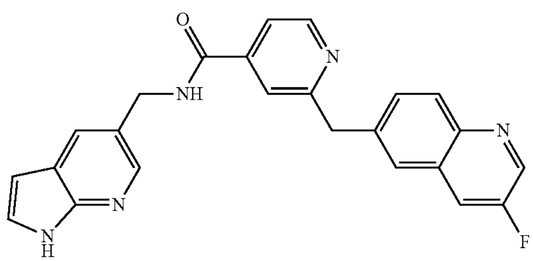 [SMILES: O=C(NCc1cnc2[nH]ccc2c1)c1ccnc(Cc2ccc3ncc(F)cc3c2)c1] |
| N-((3-chloro-1H-indol-5-yl)methyl)-2-((3-fluoroquinolin-6-yl)methyl)isonicotinamide | 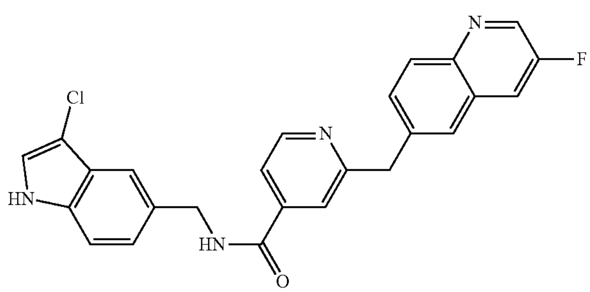 [SMILES: O=C(NCc1ccc2[nH]cc(Cl)c2c1)c1ccnc(Cc2ccc3ncc(F)cc3c2)c1] |
| N-((5-chloro-1H-indol-3-yl)methyl)-2-((3-fluoroquinolin-6-yl)methyl)isonicotinamide | 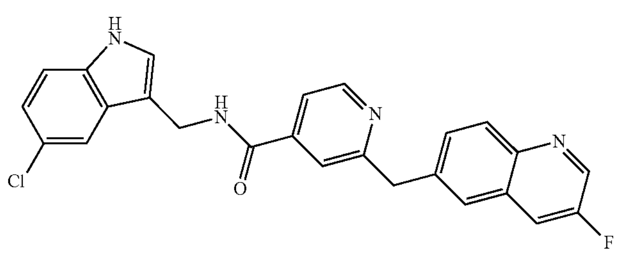 [SMILES: O=C(NCc1c[nH]c2ccc(Cl)cc12)c1ccnc(Cc2ccc3ncc(F)cc3c2)c1] |
| N-((3-chloro-6-methyl-1H-indol-5-yl)methyl)-2-((3-fluoroquinolin-6-yl)methyl)isonicotinamide | 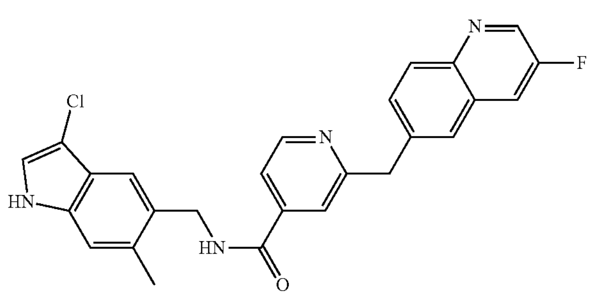 |

TABLE 2-continued

| Name | Structure |
|---|---|
| N-((3-chloro-6-methyl-1H-pyrrolo[2,3-b]pyridin-5-yl)methyl)-2-((3-fluoroquinolin-6-yl)methyl)isonicotinamide | 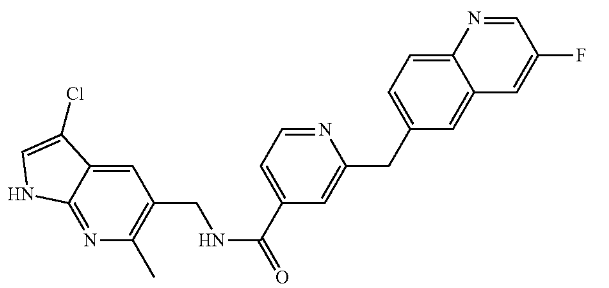 [SMILES: Cc1nc2[nH]cc(Cl)c2cc1CNC(=O)c1ccnc(Cc2ccc3ncc(F)cc3c2)c1] |
| N-((3-chloro-1H-pyrrolo[3,2-b]pyridin-5-yl)methyl)-2-((3-fluoroquinolin-6-yl)methyl)isonicotinamide | 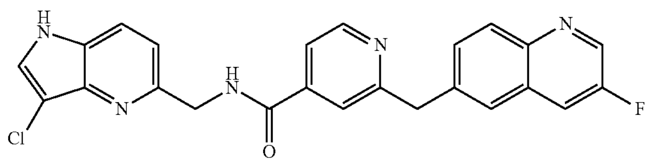 [SMILES: O=C(NCc1ccc2[nH]cc(Cl)c2n1)c1ccnc(Cc2ccc3ncc(F)cc3c2)c1] |
| N-((1H-pyrrolo[3,2-b]pyridin-5-yl)methyl)-2-((3-fluoroquinolin-6-yl)methyl)isonicotinamide | 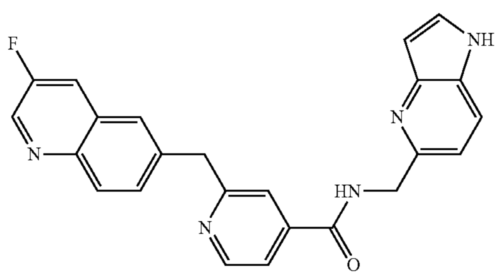 [SMILES: O=C(NCc1ccc2[nH]ccc2n1)c1ccnc(Cc2ccc3ncc(F)cc3c2)c1] |
| N-((1H-benzo[d]imidazol-5-yl)methyl)-2-((3-methylquinolin-6-yl)methyl)isonicotinamide | 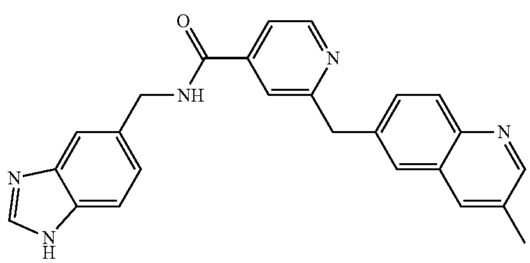 [SMILES: Cc1cnc2ccc(Cc3cc(C(=O)NCc4ccc5[nH]cnc5c4)ccn3)cc2c1] |
| N-((3-amino-1H-indazol-6-yl)methyl)-2-((3-methylquinolin-6-yl)methyl)isonicotinamide | 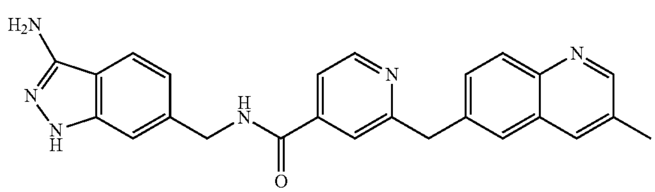 [SMILES: Cc1cnc2ccc(Cc3cc(C(=O)NCc4ccc5c(N)n[nH]c5c4)ccn3)cc2c1] |
| N-((2-aminobenzo[d]oxazol-6-yl)methyl)-2-((3-methylquinolin-6-yl)methyl)isonicotinamide | 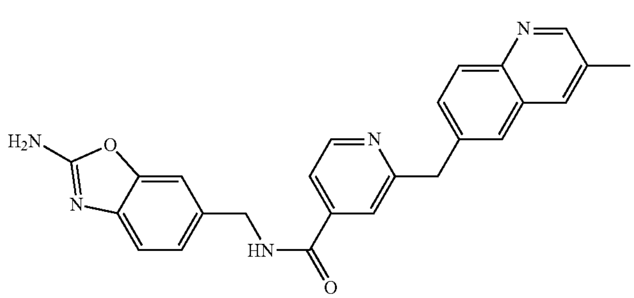 [SMILES: Cc1cnc2ccc(Cc3cc(C(=O)NCc4ccc5nc(N)oc5c4)ccn3)cc2c1] |

TABLE 2-continued

| Name | Structure |
|---|---|
| N-((2-aminobenzo[d]oxazol-5-yl)methyl)-2-((3-methylquinolin-6-yl)methyl)isonicotinamide | 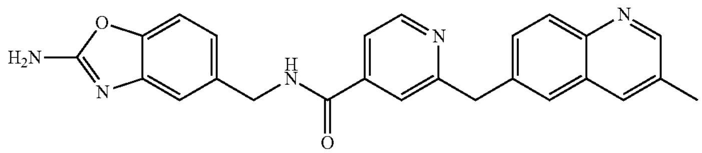 [SMILES: Cc1cnc2ccc(Cc3cc(C(=O)NCc4ccc5oc(N)nc5c4)ccn3)cc2c1] |
| N-((1-aminoisoquinolin-6-yl)methyl)-2-((3-methyl-8-(methylsulfonyl)isoquinolin-6-yl)methyl)isonicotinamide | 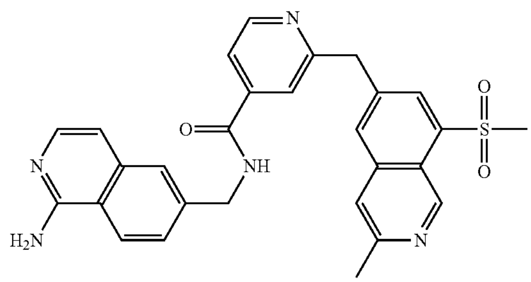 [SMILES: Cc1cc2cc(Cc3cc(C(=O)NCc4ccc5c(N)nccc5c4)ccn3)cc(S(C)(=O)=O)c2cn1] |
| N-((1-aminoisoquinolin-6-yl)methyl)-2-((3-methyl-8-sulfamoylisoquinolin-6-yl)methyl)isonicotinamide | 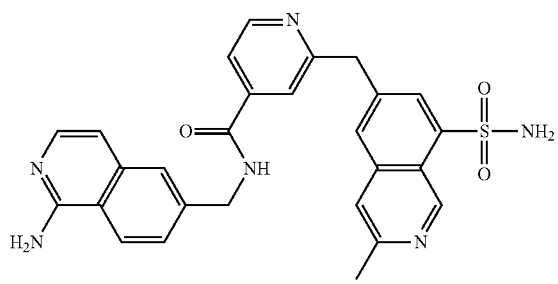 [SMILES: Cc1cc2cc(Cc3cc(C(=O)NCc4ccc5c(N)nccc5c4)ccn3)cc(S(N)(=O)=O)c2cn1] |
| 6-((4-(((1-aminoisoquinolin-6-yl)methyl)carbamoyl)pyridin-2-yl)methyl)-3-methylisoquinoline-8-carboxylic acid | 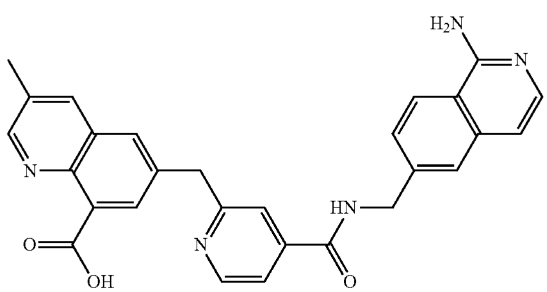 [SMILES: Cc1cnc2c(C(=O)O)cc(Cc3cc(C(=O)NCc4ccc5c(N)nccc5c4)ccn3)cc2c1] |
| N-((3-chloro-1H-pyrrolo[2,3-b]pyridin-5-yl)methyl)-2-((3-methyl-8-(methylsulfonyl)isoquinolin-6-yl)methyl)isonicotinamide | 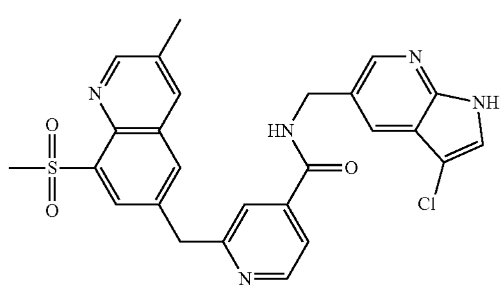 [SMILES: Cc1cnc2c(S(C)(=O)=O)cc(Cc3cc(C(=O)NCc4cnc5[nH]cc(Cl)c5c4)ccn3)cc2c1] |
| N-((3-chloro-6-fluoro-1H-indol-5-yl)methyl)-2-((3-methyl-8-(methylsulfonyl)isoquinolin-6-yl)methyl)isonicotinamide | 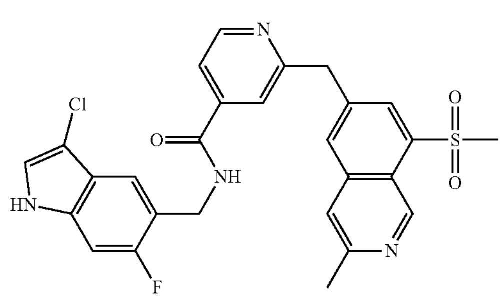 [SMILES: Cc1cc2cc(Cc3cc(C(=O)NCc4cc5c(Cl)c[nH]c5cc4F)ccn3)cc(S(C)(=O)=O)c2cn1] |

TABLE 2-continued

| Name | Structure |
|---|---|
| N-((6-amino-2,4-dimethylpyridin-3-yl)methyl)-2-((3-methyl-8-(methylsulfonyl)isoquinolin-6-yl)methyl)isonicotinamide | 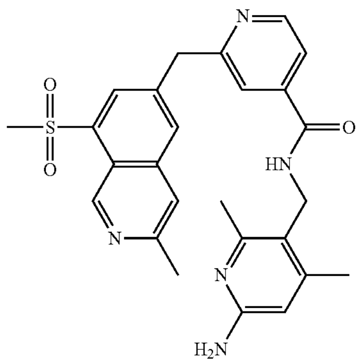 |
| N-((5-chloro-1H-indazol-3-yl)methyl)-2-((3-methyl-8-(methylsulfonyl)isoquinolin-6-yl)methyl)isonicotinamide | 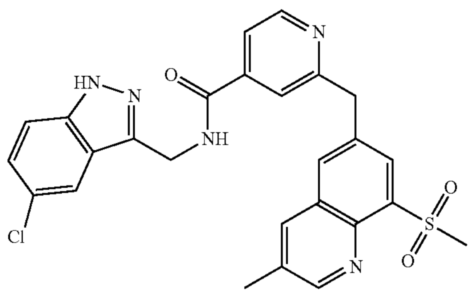 [SMILES: Cc1cnc2c(S(C)(=O)=O)cc(Cc3cc(C(=O)NCc4n[nH]c5ccc(Cl)cc45)ccn3)cc2c1] |
| N-((3-chloro-4-fluoro-1H-indol-5-yl)methyl)-2-((3-methyl-8-(methylsulfonyl)isoquinolin-6-yl)methyl)isonicotinamide | 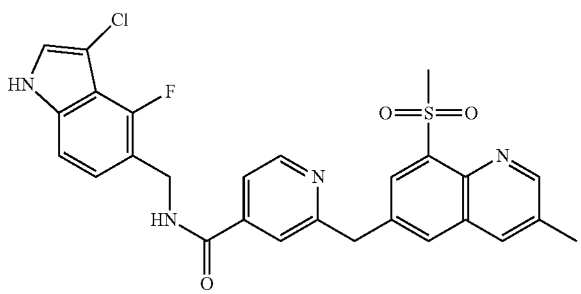 [SMILES: Cc1cnc2c(S(C)(=O)=O)cc(Cc3cc(C(=O)NCc4ccc5[nH]cc(Cl)c5c4F)ccn3)cc2c1] |
| N-((1-aminoisoquinolin-6-yl)methyl)-2-((2-methyl-8-(methylsulfonyl)quinolin-6-yl)methyl)isonicotinamide | 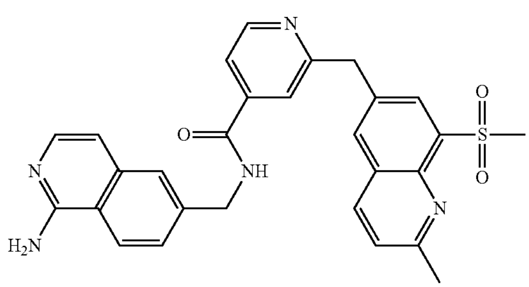 [SMILES: Cc1ccc2cc(Cc3cc(C(=O)NCc4ccc5c(N)nccc5c4)ccn3)cc(S(C)(=O)=O)c2n1] |
| N-((1-aminoisoquinolin-6-yl)methyl)-2-((2-methyl-8-sulfamoylquinolin-6-yl)methyl)isonicotinamide | 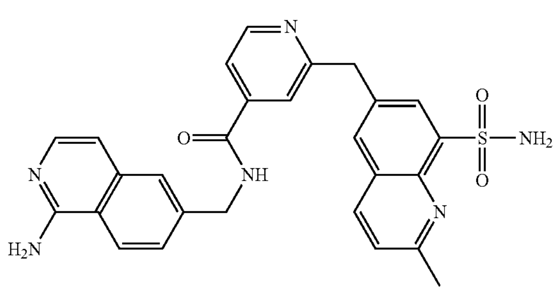 [SMILES: Cc1ccc2cc(Cc3cc(C(=O)NCc4ccc5c(N)nccc5c4)ccn3)cc(S(N)(=O)=O)c2n1] |

TABLE 2-continued

| Name | Structure |
|---|---|
| 6-((4-(((1-aminoisoquinolin-6-yl)methyl)carbamoyl)pyridin-2-yl)methyl)-2-methylquinoline-8-carboxylic acid | 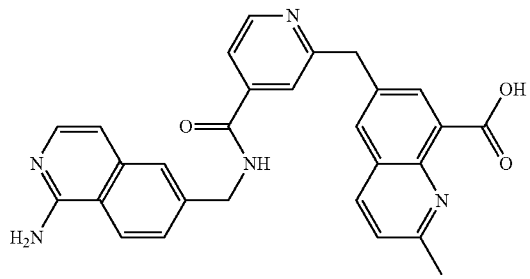 [SMILES: Cc1ccc2cc(Cc3cc(C(=O)NCc4ccc5c(N)nccc5c4)ccn3)cc(C(=O)O)c2n1] |
| N-((3-chloro-1H-pyrrolo[2,3-b]pyridin-5-yl)methyl)-2-((2-methyl-8-(methylsulfonyl)quinolin-6-yl)methyl)isonicotinamide | 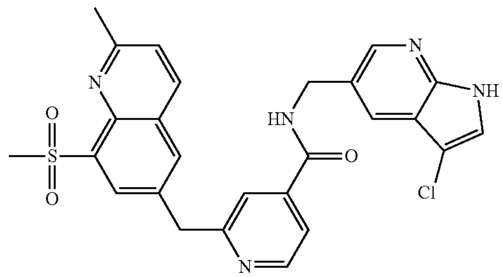 [SMILES: Cc1ccc2cc(Cc3cc(C(=O)NCc4cnc5[nH]cc(Cl)c5c4)ccn3)cc(S(C)(=O)=O)c2n1] |
| N-((3-chloro-6-fluoro-1H-indol-5-yl)methyl)-2-((2-methyl-8-(methylsulfonyl)quinolin-6-yl)methyl)isonicotinamide | 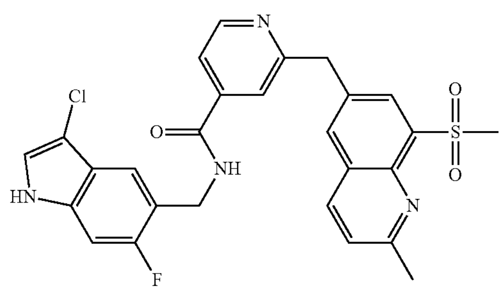 [SMILES: Cc1ccc2cc(Cc3cc(C(=O)NCc4cc5c(Cl)c[nH]c5cc4F)ccn3)cc(S(C)(=O)=O)c2n1] |
| N-((6-amino-2,4-dimethylpyridin-3-yl)methyl)-2-((2-methyl-8-(methylsulfonyl)quinolin-6-yl)methyl)isonicotinamide | 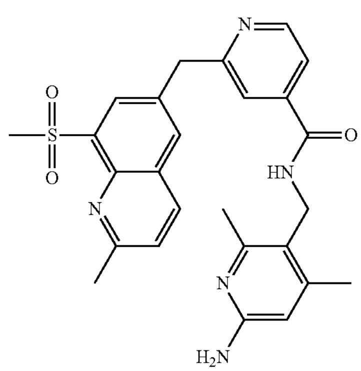 |

TABLE 2-continued

| Name | Structure |
|---|---|
| N-((5-chloro-1H-indazol-3-yl)methyl)-2-((2-methyl-8-(methylsulfonyl)quinolin-6-yl)methyl)isonicotinamide | 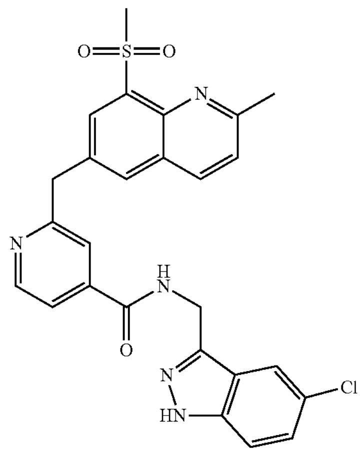 [SMILES: Cc1ccc2cc(Cc3cc(C(=O)NCc4n[nH]c5ccc(Cl)cc45)ccn3)cc(S(C)(=O)=O)c2n1] |
| N-((3-chloro-4-fluoro-1H-indol-5-yl)methyl)-2-((2-methyl-8-(methylsulfonyl)quinolin-6-yl)methyl)isonicotinamide | 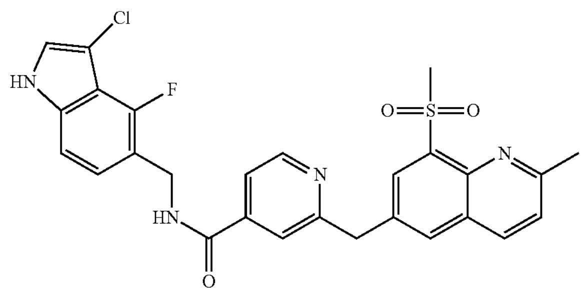 [SMILES: Cc1ccc2cc(Cc3cc(C(=O)NCc4ccc5[nH]cc(Cl)c5c4F)ccn3)cc(S(C)(=O)=O)c2n1] |
| N-((6-amino-4-cyano-2-methylpyridin-3-yl)methyl)-2-((3-methylquinolin-6-yl)methyl)isonicotinamide | 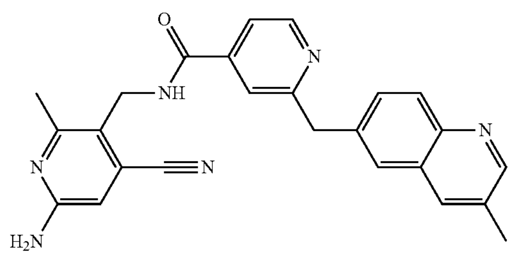 |
| N-((6-amino-2-methyl-4-(trifluoromethyl)pyridin-3-yl)methyl)-2-((3-methylquinolin-6-yl)methyl)isonicotinamide | 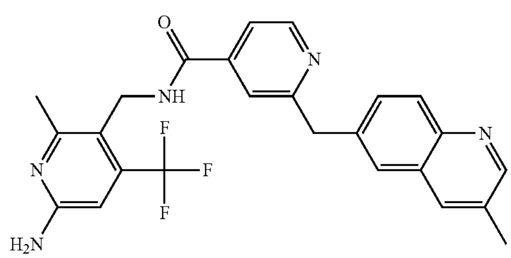 |
| N-((6-amino-5-fluoro-2-methylpyridin-3-yl)methyl)-2-((3-methylquinolin-6-yl)methyl)isonicotinamide | 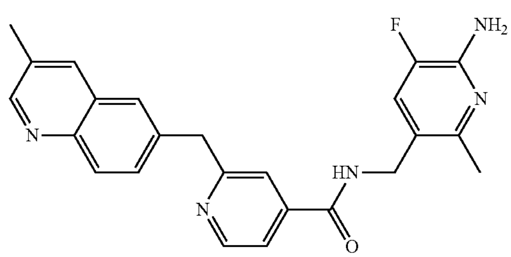 |

TABLE 2-continued

| Name | Structure |
|---|---|
| N-((6-amino-5-chloro-2-methylpyridin-3-yl)methyl)-2-((3-methylquinolin-6-yl)methyl)isonicotinamide | 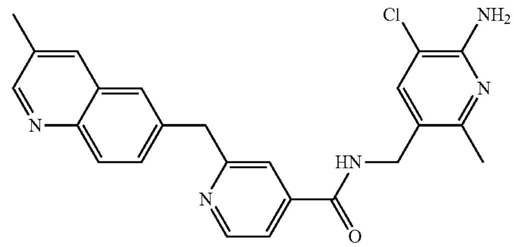 [SMILES: Cc1cnc2ccc(Cc3cc(C(=O)NCc4cc(F)c(N)nc4C)ccn3)cc2c1] |
| N-((6-amino-2-methyl-5-(trifluoromethyl)pyridin-3-yl)methyl)-2-((3-methylquinolin-6-yl)methyl)isonicotinamide | 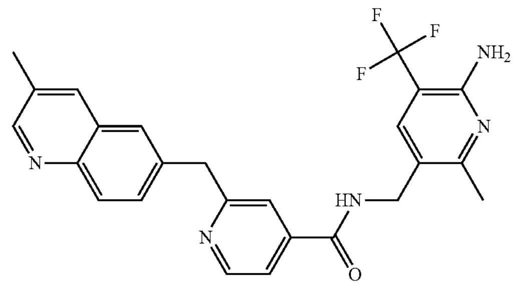 [SMILES: Cc1cnc2ccc(Cc3cc(C(=O)NCc4cc(C(F)(F)F)c(N)nc4C)ccn3)cc2c1] |
| N-((6-amino-5-cyano-2-methylpyridin-3-yl)methyl)-2-((3-methylquinolin-6-yl)methyl)isonicotinamide | 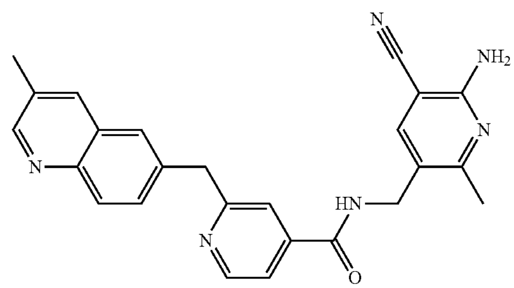 [SMILES: Cc1cnc2ccc(Cc3cc(C(=O)NCc4cc(C#N)c(N)nc4C)ccn3)cc2c1] |
| N-((6-amino-2-cyano-4-methylpyridin-3-yl)methyl)-2-((3-methylquinolin-6-yl)methyl)isonicotinamide | 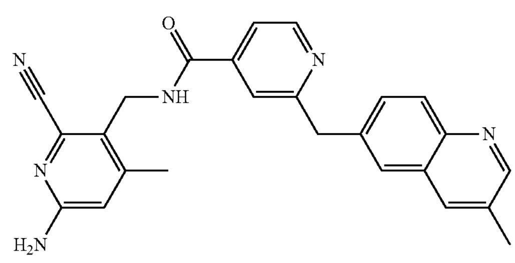 [SMILES: Cc1cnc2ccc(Cc3cc(C(=O)NCc4c(C)cc(N)nc4C#N)ccn3)cc2c1] |
| N-((6-amino-4-methyl-2-(trifluoromethyl)pyridin-3-yl)methyl)-2-((3-methylquinolin-6-yl)methyl)isonicotinamide | 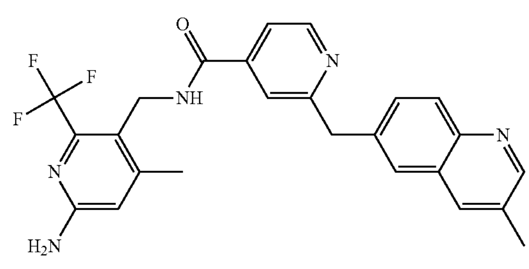 [SMILES: Cc1cnc2ccc(Cc3cc(C(=O)NCc4c(C)cc(N)nc4C(F)(F)F)ccn3)cc2c1] |
| N-((6-amino-4-cyano-2-methylpyridin-3-yl)methyl)-2-((3-fluoroquinolin-6-yl)methyl)isonicotinamide | 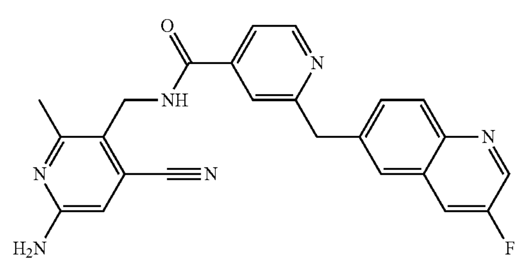 |

TABLE 2-continued

| Name | Structure |
|---|---|
| N-((6-amino-2-methyl-4-(trifluoromethyl)pyridin-3-yl)methyl)-2-((3-fluoroquinolin-6-yl)methyl)isonicotinamide | 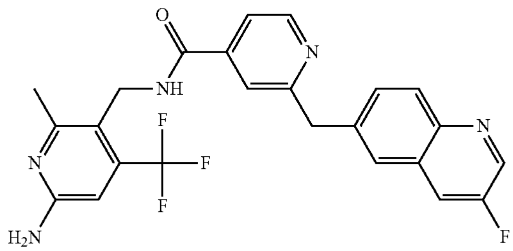 |
| N-((6-amino-5-fluoro-2-methylpyridin-3-yl)methyl)-2-((3-fluoroquinolin-6-yl)methyl)isonicotinamide | 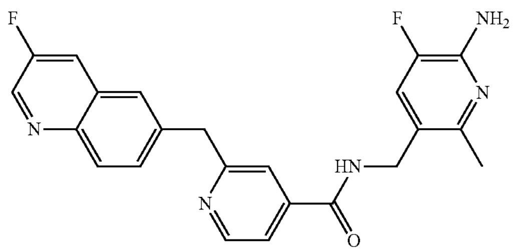 [SMILES: Cc1nc(N)c(F)cc1CNC(=O)c1ccnc(Cc2ccc3ncc(F)cc3c2)c1] |
| N-((6-amino-5-chloro-2-methylpyridin-3-yl)methyl)-2-((3-fluoroquinolin-6-yl)methyl)isonicotinamide | 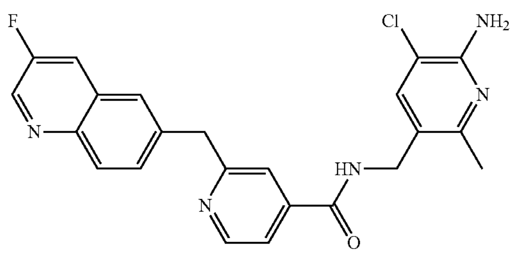 |
| N-((6-amino-2-methyl-5-(trifluoromethyl)pyridin-3-yl)methyl)-2-((3-fluoroquinolin-6-yl)methyl)isonicotinamide | 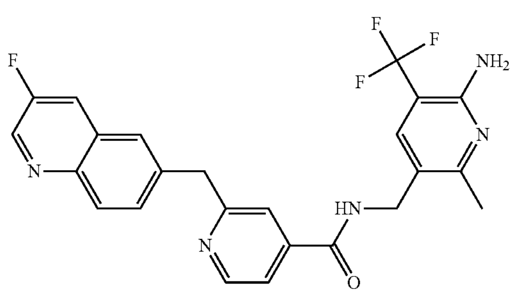 [SMILES: Cc1nc(N)c(C(F)(F)F)cc1CNC(=O)c1ccnc(Cc2ccc3ncc(F)cc3c2)c1] |
| N-((6-amino-5-cyano-2-methylpyridin-3-yl)methyl)-2-((3-fluoroquinolin-6-yl)methyl)isonicotinamide | 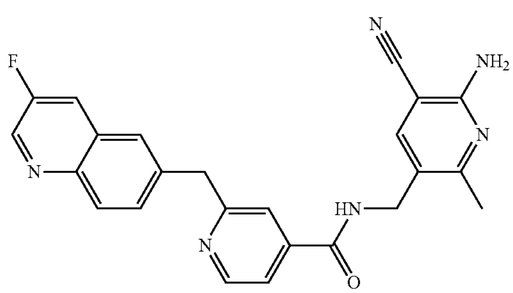 [SMILES: Cc1nc(N)c(C#N)cc1CNC(=O)c1ccnc(Cc2ccc3ncc(F)cc3c2)c1] |
| N-((6-amino-2-cyano-4-methylpyridin-3-yl)methyl)-2-((3-fluoroquinolin-6-yl)methyl)isonicotinamide | 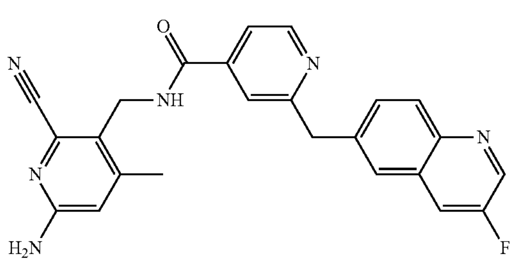 [SMILES: Cc1cc(N)nc(C#N)c1CNC(=O)c1ccnc(Cc2ccc3ncc(F)cc3c2)c1] |

TABLE 2-continued

| Name | Structure |
|---|---|
| N-((6-amino-4-methyl-2-(trifluoromethyl)pyridin-3-yl)methyl)-2-((3-fluoroquinolin-6-yl)methyl)isonicotinamide | 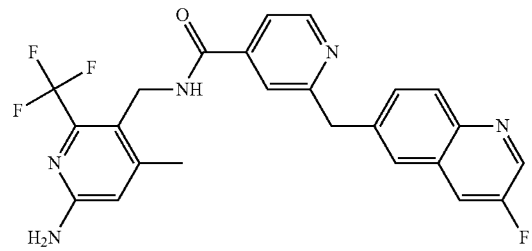 [SMILES: Cc1cc(N)nc(C(F)(F)F)c1CNC(=O)c1ccnc(Cc2ccc3ncc(F)cc3c2)c1] |
| N-((1-aminoimidazo[1,5-a]pyridin-6-yl)methyl)-2-((3-chloroquinolin-6-yl)methyl)isonicotinamide | 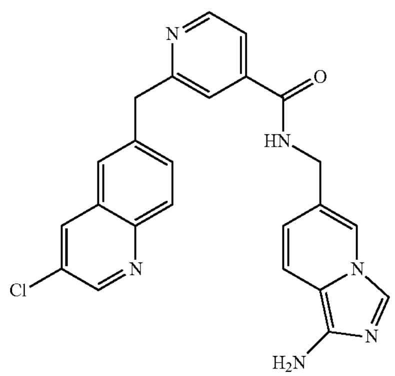 |
| N-((8-aminoimidazo[1,5-a]pyrimidin-3-yl)methyl)-2-((3-chloroquinolin-6-yl)methyl)isonicotinamide | 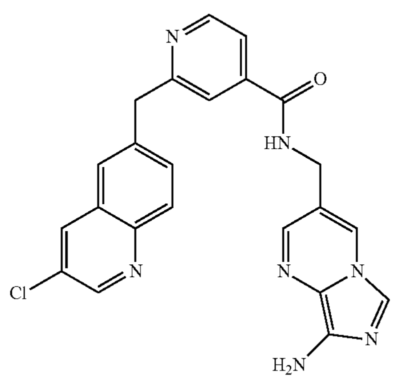 [SMILES: Nc1ncn2cc(CNC(=O)c3ccnc(Cc4ccc5ncc(Cl)cc5c4)c3)cnc12] |
| N-((3-aminoimidazo[1,5-a]pyridin-7-yl)methyl)-2-((3-chloroquinolin-6-yl)methyl)isonicotinamide | 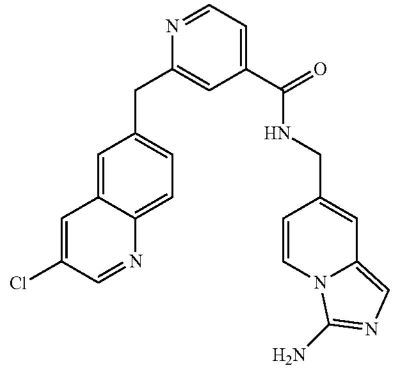 [SMILES: Nc1ncc2cc(CNC(=O)c3ccnc(Cc4ccc5ncc(Cl)cc5c4)c3)ccn12] |

TABLE 2-continued

| Name | Structure |
|---|---|
| N-((6-aminoimidazo[1,5-a]pyrimidin-2-yl)methyl)-2-((3-chloroquinolin-6-yl)methyl)isonicotinamide | 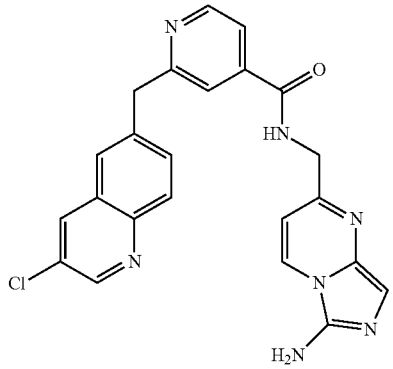 |
| N-((3-aminoimidazo[1,5-c]pyrimidin-7-yl)methyl)-2-((3-chloroquinolin-6-yl)methyl)isonicotinamide | 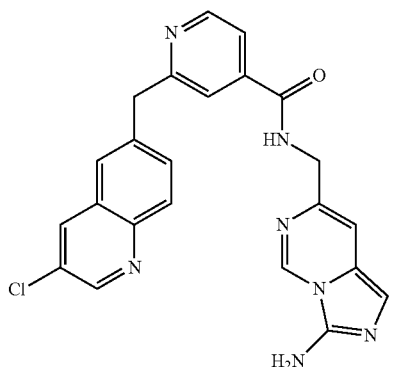 |
| N-((7-aminoimidazo[1,5-b]pyridazin-3-yl)methyl)-2-((3-chloroquinolin-6-yl)methyl)isonicotinamide | 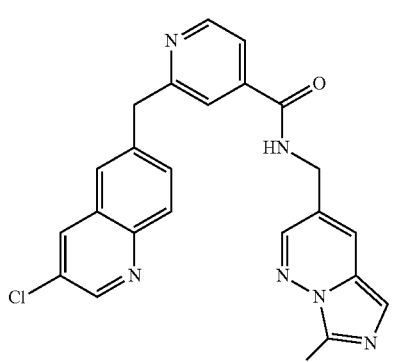 |
| N-((1-amino-3-methylimidazo[1,5-a]pyridin-6-yl)methyl)-2-((3-chloroquinolin-6-yl)methyl)isonicotinamide | 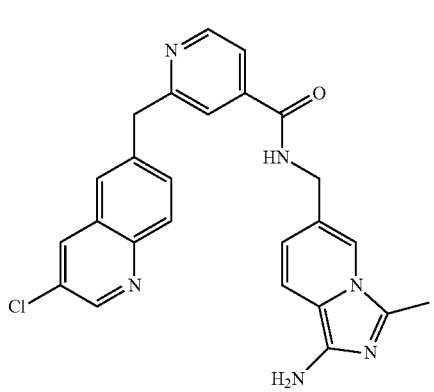 |

TABLE 2-continued

| Name | Structure |
|---|---|
| N-((8-amino-6-methylimidazo[1,5-a]pyrimidin-3-yl)methyl)-2-((3-chloroquinolin-6-yl)methyl)isonicotinamide | 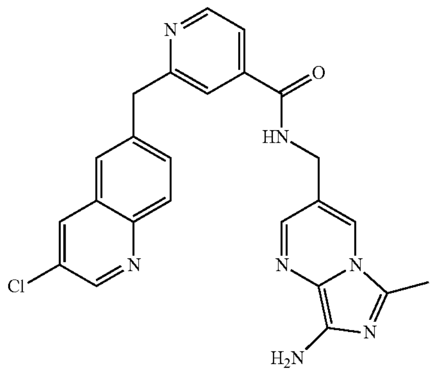 [SMILES: Cc1nc(N)c2ncc(CNC(=O)c3ccnc(Cc4ccc5ncc(Cl)cc5c4)c3)cn12] |
| N-((1-amino-3-methyl-2H-isoindol-5-yl)methyl)-2-((3-chloroquinolin-6-yl)methyl)isonicotinamide | 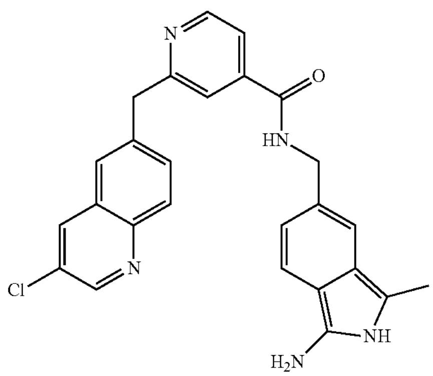 [SMILES: Cc1[nH]c(N)c2ccc(CNC(=O)c3ccnc(Cc4ccc5ncc(Cl)cc5c4)c3)cc12] |
| N-((3-amino-1-methylimidazo[1,5-a]pyridin-7-yl)methyl)-2-((3-chloroquinolin-6-yl)methyl)isonicotinamide | 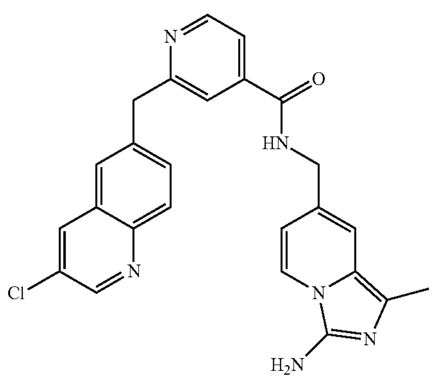 |
| N-((6-amino-8-methylimidazo[1,5-a]pyrimidin-2-yl)methyl)-2-((3-chloroquinolin-6-yl)methyl)isonicotinamide | 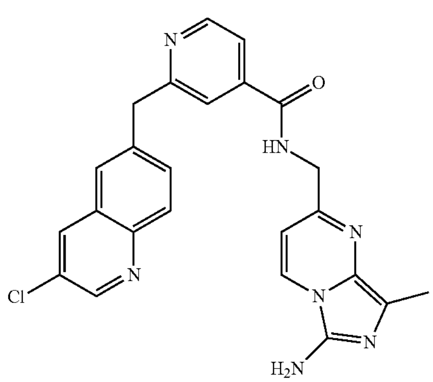 [SMILES: Cc1nc(N)n2ccc(CNC(=O)c3ccnc(Cc4ccc5ncc(Cl)cc5c4)c3)cc12] |

TABLE 2-continued

| Name | Structure |
|---|---|
| N-((3-amino-1-methylimidazo[1,5-c]pyrimidin-7-yl)methyl)-2-((3-chloroquinolin-6-yl)methyl)isonicotinamide | 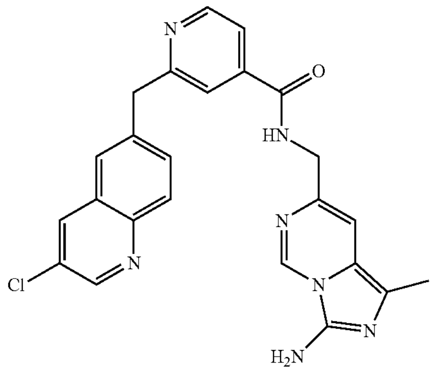 [SMILES: Cc1nc(N)n2cnc(CNC(=O)c3ccnc(Cc4ccc5ncc(Cl)cc5c4)c3)cc12] |
| N-((7-amino-5-methylimidazo[1,5-b]pyridazin-3-yl)methyl)-2-((3-chloroquinolin-6-yl)methyl)isonicotinamide | 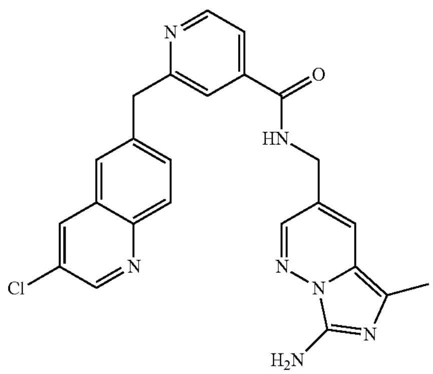 [SMILES: Cc1nc(N)n2ncc(CNC(=O)c3ccnc(Cc4ccc5ncc(Cl)cc5c4)c3)cc12] |
| N-((2-amino-3-methyl-1H-pyrrolo[2,3-b]pyridin-5-yl)methyl)-2(3-chloroquinolin-6-yl)methyl)isonicotinamide | 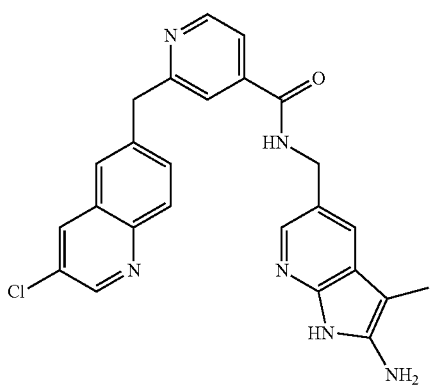 [SMILES: Cc1c(N)[nH]c2ncc(CNC(=O)c3ccnc(Cc4ccc5ncc(Cl)cc5c4)c3)cc12] |
| N-((2-amino-3-chloro-1H-pyrrolo[2,3-b]pyridin-5-yl)methyl)-2-((3-chloroquinolin-6-yl)methyl)isonicotinamide | 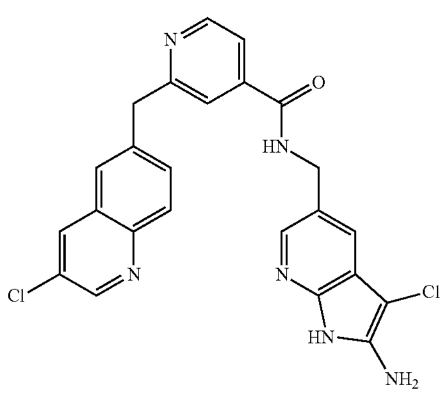 [SMILES: Nc1[nH]c2ncc(CNC(=O)c3ccnc(Cc4ccc5ncc(Cl)cc5c4)c3)cc2c1Cl] |

TABLE 2-continued

| Name | Structure |
|------|-----------|
| N-((6-chloroimidazo[1,2-a]pyridin-3-yl)methyl)-2-((3-chloroquinolin-6-yl)methyl)isonicotinamide | 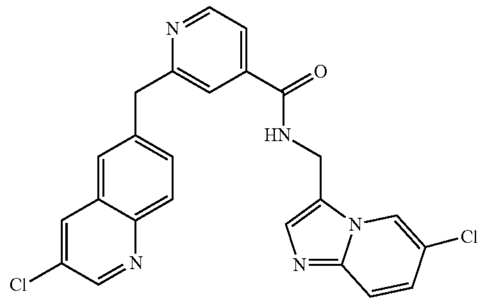 [SMILES: O=C(NCc1cnc2ccc(Cl)cn12)c1ccnc(Cc2ccc3ncc(Cl)cc3c2)c1] |
| N-((3-chloropyrrolo[1,2-a]pyrimidin-6-yl)methyl)-2-((3-chloroquinolin-6-yl)methyl)isonicotinamide | 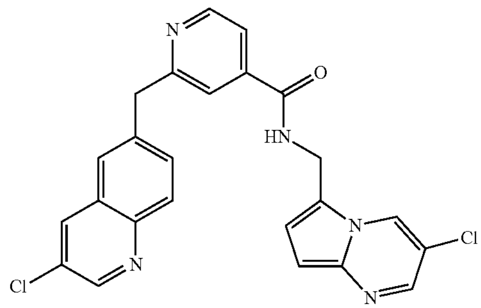 [SMILES: O=C(NCc1ccc2ncc(Cl)cn12)c1ccnc(Cc2ccc3ncc(Cl)cc3c2)c1] |
| N-((6-chloroimidazo[1,2-a]pyrimidin-3-yl)methyl)-2-((3-chloroquinolin-6-yl)methyl)isonicotinamide | 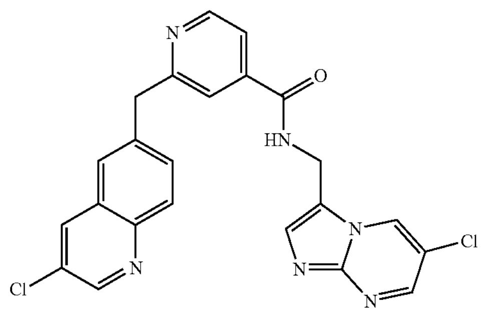 [SMILES: O=C(NCc1cnc2ncc(Cl)cn12)c1ccnc(Cc2ccc3ncc(Cl)cc3c2)c1] |
| N-((6-chloro-[1,2,4]triazolo[4,3-a]pyridin-3-yl)methyl)-2-((3-chloroquinolin-6-yl)methyl)isonicotinamide | 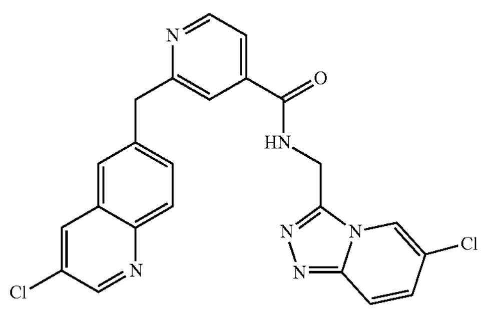 [SMILES: O=C(NCc1nnc2ccc(Cl)cn12)c1ccnc(Cc2ccc3ncc(Cl)cc3c2)c1] |
| N-((7-chloroimidazo[1,5-a]pyridin-1-yl)methyl)-2-((3-chloroquinolin-6-yl)methyl)isonicotinamide | 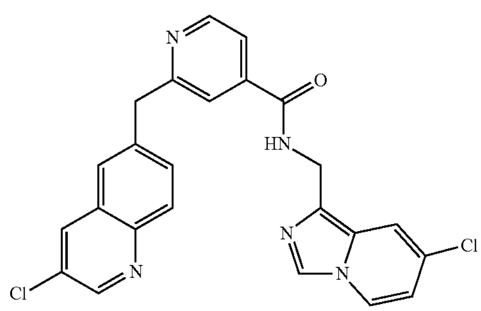 |

TABLE 2-continued

| Name | Structure |
|---|---|
| N-((5-chloro-[1,2,3]triazolo[1,5-a]pyridin-3-yl)methyl)-2-((3-chloroquinolin-6-yl)methyl)isonicotinamide | 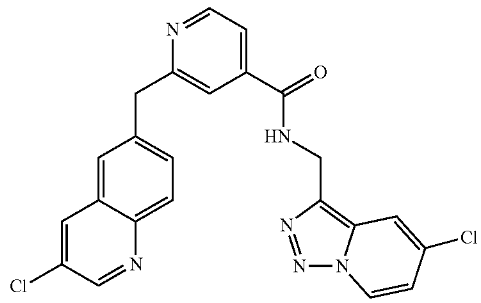 [SMILES: O=C(NCc1nnn2ccc(Cl)cc12)c1ccnc(Cc2ccc3ncc(Cl)cc3c2)c1] |
| N-((1-aminoimidazo[1,5-a]pyridin-6-yl)methyl)-2-((3-chloroquinolin-6-yl)methyl)isonicotinamide | 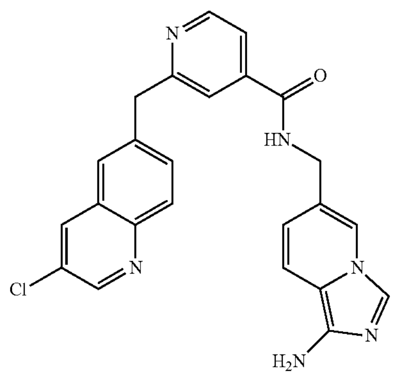 |
| N-((3-aminoimidazo[1,5-a]pyridin-7-yl)methyl)-2-((3-chloroquinolin-6-yl)methyl)isonicotinamide | 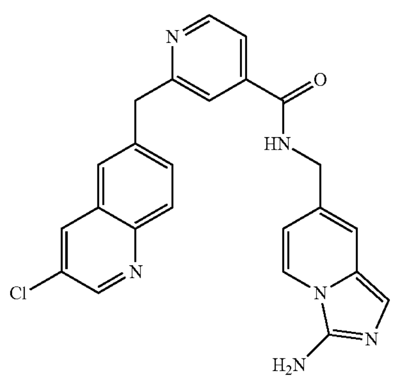 |
| N-((3-amino-1-methylimidazo[1,5-a]pyridin-7-yl)methyl)-2-((3-chloroquinolin-6-yl)methyl)isonicotinamide | 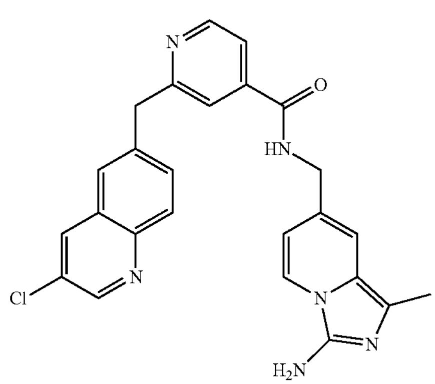 |

TABLE 2-continued

| Name | Structure |
|---|---|
| N-((3-chloropyrrolo[1,2-a]pyrimidin-6-yl)methyl)-2-((3-chloroquinolin-6-yl)methyl)isonicotinamide | 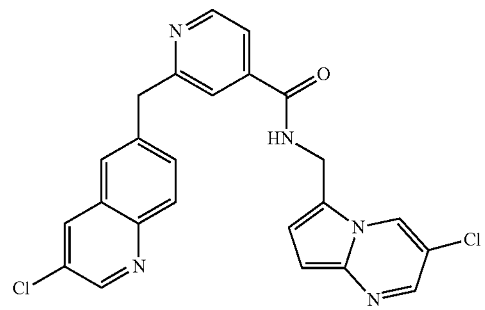 [SMILES: O=C(NCc1ccc2ncc(Cl)cn12)c1ccnc(Cc2ccc3ncc(Cl)cc3c2)c1] |

Preparation of Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa.), Aldrich Chemical (Milwaukee, Wis., including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire, UK), Frontier Scientific (Logan, Utah), ICN Biomedicals, Inc. (Costa Mesa, Calif.), Key Organics (Cornwall, U.K.), Lancaster Synthesis (Windham, N.H.), Maybridge Chemical Co. Ltd. (Cornwall, U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hanover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

Specific and analogous reactants are optionally identified through the indices of known chemicals prepared by the Chemical Abstract Service of the American Chemical Society, which are available in most public and university libraries, as well as through on-line databases (contact the American Chemical Society, Washington, D.C. for more details). Chemicals that are known but not commercially available in catalogs are optionally prepared by custom chemical synthesis houses, where many of the standard chemical supply houses (e.g., those listed above) provide custom synthesis services. A reference for the preparation and selection of pharmaceutical salts of the kallikrein inhibitory compound described herein is P. H. Stahl & C. G. Wermuth "Handbook of Pharmaceutical Salts", Verlag Helvetica Chimica Acta, Zurich, 2002.

Pharmaceutical Compositions

In certain embodiments, the kallikrein inhibitory compound as described herein is administered as a pure chemical. In other embodiments, the kallikrein inhibitory compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, 21$^{st}$ Ed. Mack Pub. Co., Easton, Pa. (2005)).

Provided herein is a pharmaceutical composition comprising at least one kallikrein inhibitory compound, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a compound of Formula (I), or a pharmaceutically acceptable salt thereof, and a pharmaceutically acceptable excipient. One embodiment provides a pharmaceutical composition comprising a compound of Formula (Ia), or a pharmaceutically acceptable salt thereof, and a pharmaceutically acceptable excipient.

In certain embodiments, the kallikrein inhibitory compound as described by Formula (I) or (Ia) is substantially pure, in that it contains less than about 5%, or less than about 1%, or less than about 0.1%, of other organic small molecules, such as unreacted intermediates or synthesis by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. In some embodiments, suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. (See, e.g., Remington: The Science and Practice of Pharmacy (Gennaro, 21$^{st}$ Ed. Mack Pub. Co., Easton, Pa. (2005)).

The dose of the composition comprising at least one kallikrein inhibitory compound as described herein differ, depending upon the patient's (e.g., human) condition, that is, stage of the disease, general health status, age, and other factors.

Pharmaceutical compositions are administered in a manner appropriate to the disease to be treated (or prevented). An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. The optimal dose depends upon the body mass, weight, or blood volume of the patient.

Oral doses typically range from about 1.0 mg to about 1000 mg, one to four times, or more, per day.

Kallikrein-Kinin System

Modulation of vascular permeability is important in regulating the passage of small molecules or blood cells between blood vessels and surrounding tissues. Vascular permeability depends upon the physiological states of tissues such as during inflammation, changes in blood pressure, and fluctuations in ion and nutrient gradients. The junctions between the endothelial cells that line blood vessels are the immediate controllers of vascular permeability. The strength of these junctions is tightly regulated by the kinin-kallikrein system of polypeptides and enzymes. Abnormalities in the kinin-kallikrein system lead to a range of pathologies including angioedema, macular edema and brain edema. Angioedema is a potentially fatal blood disorder characterized by swelling that may occur in the face, gastrointestinal tract, extremities, genitals and upper airways. Genetic hereditary angioedema attacks result from the unregulated activation of the kallikrein system with uncontrolled increases in vascular permeability. Currently there is a need for agents that are useful for the treatment of angioedema and for agents that inhibit plasma kallikrein.

The kallikrein-kinin system represents a metabolic cascade that, when activated, triggers the release of vasoactive kinins. The kinin-kallikrein system (KKS) consists of serine proteases involved in the production of kinins, principally bradykinin and Lys-bradykinin (kallidin). The KKS contributes to a variety of physiological processes including inflammation, blood pressure control and coagulation. The activation of this system is particularly important in blood pressure regulation and in inflammatory reactions, due to the ability of bradykinin to elevate vascular permeability and to cause vasodilatation of arteries and veins of the gut, aorta, uterus and urethra. The kinin-kallikrein system, also referred to as the contact system, consists of three serine proenzymes (factor XII (FXII) or Hageman factor, factor IX (FIX), and prekallikrein), and the kinin precursor high molecular weight kinin (HK). Contact activation is triggered by the binding of FXII to a negatively charged surface and involves the formation of α-FXIIa via autocatalysis. Bound α-FXIIa converts prekallikrein into kallikrein. Kallikrein can further convert α-FXIIa to β-FXIIa by an additional cleavage at R334-N335, a positive feedback mechanism that leads to sufficient kallikrein production to drive downstream processes. α-FXIIa consists of a heavy and light chain that are disulphide linked, whereas β-FXIIa lacks the heavy chain and loses its capacity to bind to negatively charged surfaces (Stavrou E, Schmaier A H., Thrombosis Research, 2010, 125(3) pp. 210-215). The N-terminal region of FXII (α-FXIIa heavy chain) shows strong homology with tissue-type plasminogen activator (tPA), with the presence of fibronectin type I, epidermal growth factor, and Kringle domains (Ny et al., Proc Natl Acad Sci USA, 1984, 81(17) pp. 5355-5359; Cool D E, MacGillivray R T, The Journal of Biological Chemistry, 1987, 262(28) pp. 13662-13673). Kallikrein is a trypsin-like serine protease enzyme that cleaves high molecular weight kinin (HK) to produce bradykinin. Bradykinin then binds to the bradykinin 2R receptors (BK2R) on endothelial cells to trigger an increase in vascular permeability.

Protease inhibitors regulate the activation of the contact system. Several known serpins of plasma are C1-inhibitor (C1INH), antithrombin III, α2-macroglobulin, α1-protease inhibitor, and α2-antiplasmin (Kaplan et al., Advances in Immunology, 1997 (66) pp. 225-72; Pixley et al., The Journal of Biological Chemistry, 1985, 260(3) pp. 1723-9). However, C1INH is the major regulator of the intrinsic system, interfering with the activities of factor XIIa and of kallikrein (Cugno et al., The Journal of Laboratory and Clinical Medicine, 1993, 121(1) pp. 38-43). Both C1INH and α2-macroglobulin account for more than 90% of the kallikrein inhibitory activity of plasma. Thus, the FXII-dependent kallikrein-kinin system is tightly regulated by the C1NH and when regulation of the FXII-dependent kallikrein-kinin system fails, in a subject, the subject is believed to suffer from hereditary angioedema (HAE) that is characterized by invalidating edema attacks.

Angioedema is a potentially fatal blood disorder characterized by swelling that may occur in the face, gastrointestinal tract, extremities, genitals and upper airways. Angioedema attacks begin in the deeper layers of the skin and mucous membranes with localized blood vessel dilatation and increased permeability. Symptoms of the disease result from the leakage of plasma from blood vessels into surrounding tissues. Genetic hereditary angioedema attacks result from unregulated activation of the kallikrein system with consequent overproduction of bradykinin and uncontrolled increases in vascular permeability. As vascular permeability rises beyond normal, plasma leaks out of the vasculature into surrounding tissue, causing swelling (Mehta D and Malik A B, *Physiol. Rev.*, 86 (1), 279-367, 2006; Sandoval R et al., *J. Physiol.*, 533(pt 2), 433-45, 2001; Kaplan A P and Greaves M W, Angioedema. *J. Am. Acad. Dermatol.*, 2005).

HAE results from mutations in the genes that code for elements of the coagulation and inflammation pathways. The three forms of HAE are distinguished by their underlying causes and levels of the C1-esterase inhibitor (C1NH, serpin peptidase inhibitor, clade G, member 1) protein in the blood, which inhibits the activity of plasma kallikrein. In type I, patients have insufficient levels of functional C1INH, while type II patients have dysfunctional C1INH. While type I and II affect men and women at equal rates, type III, which primarily affects women, results from a mutation in coagulation factor XII (Hageman factor; HAE-FXII). The underlying causes of type I and II HAE are autosomal dominant mutations in C1INH gene (SERPING1 gene) on chromosome 11 (11q12-q13.1).

C1INH accounts for 90% of inhibition of FXIIa and 50% of inhibition of plasma kallikrein (Pixley R A et al., *J. Biol. Chem.*, 260, 1723-9, 1985; Schapira M et al., *Biochemistry*, 20, 2738-43, 1981). In addition, C1INH also inactivates prekallikrein (Colman R W et al, *Blood*, 65, 311-8, 1985). When C1INH levels are normal, its activity blocks FXIIa from converting prekallikrein to kallikrein and blocks kallikrein's conversion to HK, thus preventing the production of bradykinin and the edemic episodes. When C1NH levels are low, or levels of dysfunctional C1INH are high, this inhibition fails and the pathogenic process ensues.

In addition to HAE, plasma kallikrein also contributes to non-hereditary angioedema, high altitude cerebral edema, cytotoxic cerebral edema, osmotic cerebral edema, diabetic macular edema (DME), clinically significant macular edema, cystoid macular edema (CME, Gao B B, *Nat Med.*, 13(2), 181-8, 2007), retinal edema, radiation induced edema, lymph edema, glioma-associated edema, allergic edema e.g. airflow obstruction in chronic allergic sinusitis or perennial rhinitis. Other disorders of the plasma kallikrein system include retinopathy and diabetic retinopathy (Liu J and Feener E P, *Biol. Chem.* 394(3), 319-28, 2013), proliferative and non-proliferative retinopathy (Liu J et al, *Invest. Ophthalmol. Vis. Sci.*, 54(2), 2013), CME following cataract extraction, CME induced by cryotherapy, CME induced by uveitis, CME following vascular occlusion (e.g., central retinal vein occlusion, branch retinal vein occlusion or hemiretinal vein occlusion), complications related to cataract surgery in diabetic retinopathy, hypertensive retinopathy (J A Phillips et al., *Hypertension*, 53, 175-181, 2009), retinal trauma, dry and wet age-related macular degeneration (AMD), ischemic reperfusion injuries (C Storoni et al., *JPET*, 381, 849-954, 2006), e.g., in a variety of contexts associated with tissue and/or organ transplantation.

Current treatments for angioedema, and those under development, target different elements in the HAE pathway. Three classes of therapies are currently available: (a) replacement therapy with C1INH concentrates (e.g., Cinryze, Berinert), (b) administration of selective kallikrein inhibitors (e.g., Ecallantide) and (c) bradykinin receptors antagonists (e.g., Firazyr).

Replacement therapies have proven useful for both acute attacks, including emergency situations, such as laryngeal edema (Bork K et al., *Transfusion*, 45, 1774-1784, 2005; Bork K and Barnstedt S E, *Arch. Intern. Med.*, 161, 714-718, 2001) and prophylaxis. Selective C1INH inhibitors inactivate both α-FXIIa and β-FXIIa molecules active early in the HAE pathway that catalyze the production of kallikrein (Muller F and Renne T, *Curr. Opin. Hematol.*, 15, 516-21, 2008; Cugno M et al., *Trends Mol. Med.* 15(2):69-78, 2009). In addition to HAE, plasma kallikrein inhibitors are considered to be useful in the treatment of other edemas such as macular edema and brain edema, and retinopathy, e.g., retinopathy associated with diabetes and/or hypertension. There is evidence that plasma kallikrein inhibitors are also effective in the treatment of edema formation in diseases, e.g., edema formation related to ischemic reperfusion injuries. The bradykinin receptors antagonists prevent bradykinin from activating the vascular permeability pathway and stop the initiation of swelling.

Methods of Treatment

Disclosed herein are methods of treating diseases or disorders wherein the inhibition of plasma kallikrein is indicated. Such diseases and disorders include but are not limited to angioedema, including hereditary and non-hereditary.

In some embodiments, the methods disclosed herein are useful for the treatment of angioedema. In some embodiments, the angioedema is hereditary angioedema (HAE). One embodiment provides a method of treating angioedema in a patient in need thereof comprising administration of a composition comprising a compound of Formula (I), or a pharmaceutically acceptable salt thereof. Another embodiment provides the method wherein the angioedema is hereditary angioedema.

One embodiment provides a method of treating angioedema in a patient in need thereof comprising administration of a composition comprising a compound of Formula (Ia), or a pharmaceutically acceptable salt thereof. Another embodiment provides the method wherein the angioedema is hereditary angioedema.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants, J are reported in Hertz. For proton spectra the solvent peak was used as the reference peak.

The following abbreviations and terms have the indicated meanings throughout:

AcOH=acetic acid
$B_2pin_2$=bis(pinacolato)diboron
Boc=tert-butoxycarbonyl
DCC=dicyclohexylcarbodiimide
DIEA=N,N-diisopropylethylamine
DMAP=4-dimethylaminopyridine
EDC=1-ethyl-3-(3-dimethylaminopropyl) carbodiimide eq=equivalent(s)
Et=ethyl
EtOAc or EA=ethyl acetate
EtOH=ethanol
g=gram
h or hr=hour
HBTU=O-(benzotriazol-1-yl)-N,N,N',N'-tetramethyluronium hexafluorophosphate
HOBt=hydroxybenzotriazole
HPLC=high pressure liquid chromatography
kg or Kg=kilogram
L or l=liter
LC/MS=LCMS=liquid chromatography-mass spectrometry
LRMS=low resolution mass spectrometry
m/z=mass-to-charge ratio
Me=methyl
MeOH=methanol
mg=milligram
min=minute
mL=milliliter
mmol=millimole
NaOAc=sodium acetate
PE=petroleum ether
Ph=phenyl
Prep=preparative
quant.=quantitative
RP-HPLC=reverse phase-high pressure liquid chromatography
rt or RT=room temperature
THF=tetrahydrofuran
UV=ultraviolet Intermediate 1: Preparation of 2-((2-cyanoquinolin-6-yl)methyl)isonicotinic acid

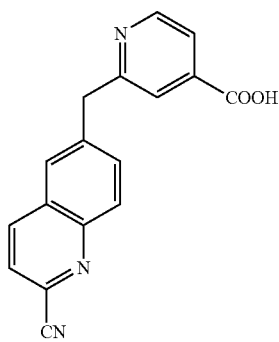 [SMILES: N#Cc1ccc2cc(Cc3cc(C(=O)O)ccn3)ccc2n1]

Step 1: Preparation of 6-methylquinoline 1-oxide

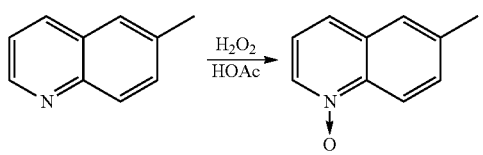

To a solution of 6-methylquinoline (10.0 g, 69.9 mmol, 1.0 eq) in HOAc (150 mL) was added 30% $H_2O_2$ (100 mL). The reaction mixture was heated to 70° C. and stirred overnight, then cooled, and water (100 mL) was added, then $Na_2SO_3$ was added portion wise to quench excess $H_2O_2$ while cooling in ice bath. The reaction mixture was extracted with DCM and the organic phase was washed with water, brine, dried over anhydrous sodium sulfate, filtered and concentrated to dryness to afford 6-methylquinoline 1-oxide as a brown oil (7.2 g, 64%).

Step 2: Preparation of 6-methylquinoline-2-carbonitrile

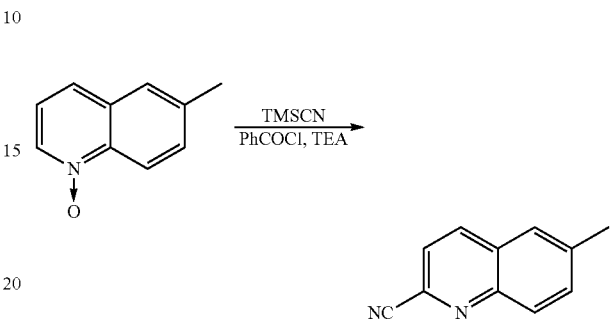

To a solution of 6-methylquinoline 1-oxide (7.2 g, 45.2 mmol, 1.0 eq) in trimethylsilycyanide (17.0 mL, 135.8 mmol, 3.0 eq) was added benzoyl chloride (15.6 mL, 135.8 mmol, 3.0 eq) while cooling in ice-water bath followed by triethylamine (18.9 mL, 135.8 mmol, 3.0 eq). The reaction was stirred for 1 h. The mixture was diluted with DCM, washed once with saturated aqueous $NaHCO_3$ carefully, then washed with water, brine, dried over anhydrous sodium sulfate, and purified on silica gel column (PE/DCM/EtOAc=10/1/1) and then triturated from EtOH to afford 6-methylquinoline-2-carbonitrile as a yellow solid (6.0 g, 78%).

Step 3: Preparation of 6-(bromomethyl)quinoline-2-carbonitrile

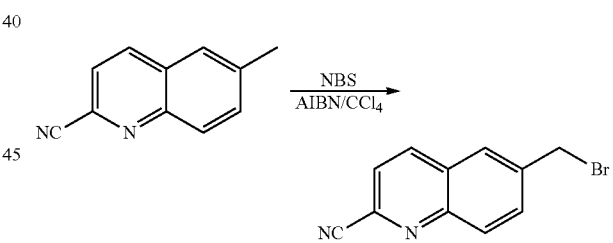

The mixture of 6-methylquinoline-2-carbonitrile (3.7 g, 22.0 mmol, 1.0 eq), NBS (3.9 g, 22.0 mmol, 1.0 eq) and AIBN (72 mg, 2 mol %) in tetrachloride carbon (100 mL) was refluxed for 3 h, then cooled and concentrated to dryness. The residue was triturated from DCM, filtered and dried to afford 6-(bromomethyl)quinoline-2-carbonitrile as a white solid (4.0 g, 74%).

Step 4: Preparation of ethyl 2-((2-cyanoquinolin-6-yl)methyl)isonicotinate

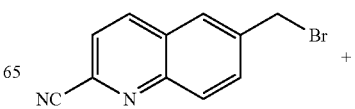

-continued

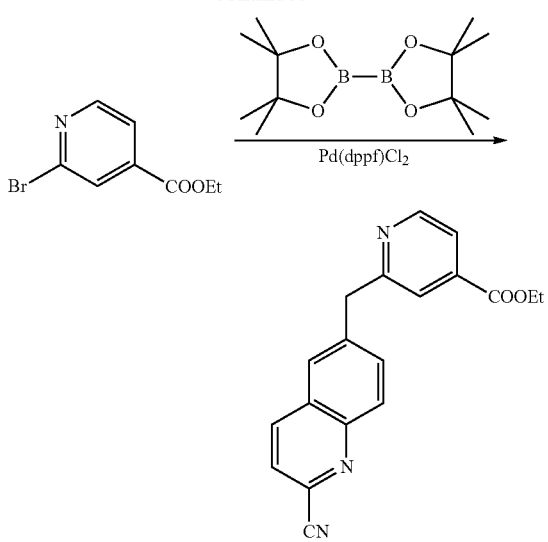

The mixture of ethyl 2-bromoisonicotinate (1.86 g, 8.1 mmol, 1.0 eq), BPDB (2.06 g, 8.1 mmol, 1.0 eq), potassium acetate (2.38 g, 24.3 mmol, 3.0 eq) and [1,1'-bis(diphenylphosphino)ferrocene]dichloropalladium(II) (296 mg, 5 mol %) were mixed in 1,4-dioxane (100 mL). The mixture was degassed with nitrogen, heated to 85° C. and stirred for 16 h, then cooled to rt, and 6-(bromomethyl)quinoline-2-carbonitrile (2.0 g, 8.1 mmol, 1.0 eq), [1,1'-bis(diphenylphosphino)ferrocene]dichloropalladium(II) (296 mg, 5 mol %) and sodium carbonate (2.57 g, 24.3 mmol, 3.0 eq, dissolved in 30 mL of water) were added. The mixture was degassed, heated to 95° C. and stirred overnight. The mixture was cooled and filtered through celite. Water (100 mL) and DCM (100 mL) were added to the filtrate. The DCM layer was separated and washed with brine, dried over anhydrous sodium sulfate, and purified on silica gel column to afford ethyl 2-((2-cyanoquinolin-6-yl)methyl)isonicotinate as a red solid (670 mg, 26%).

Step 5: Preparation of 2-((2-cyanoquinolin-6-yl)methyl)isonicotinic acid

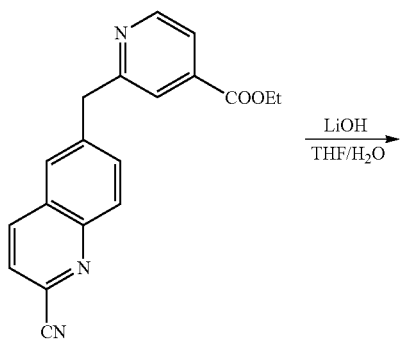

-continued

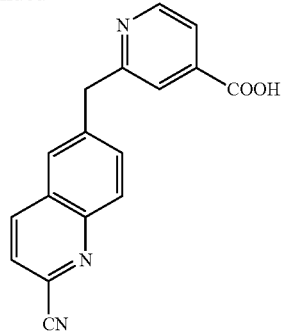

To the solution of ethyl 2-((2-cyanoquinolin-6-yl)methyl)isonicotinate (670 mg, 2.1 mmol, 1.0 eq) in THF (6 mL) was added an aqueous solution of lithium hydroxide monohydrate (177 mg, 4.2 mmol, 2.0 eq) in water (3 mL). The reaction was stirred for 2 h, then acidified with 2 N HCl to pH 3. DCM (50 mL) and water (50 mL) were added, and the DCM layer was separated and washed with brine, dried over anhydrous sodium sulfate, and purified via flash chromatography to afford 2-((2-cyanoquinolin-6-yl)methyl)isonicotinic acid as a brown solid (250 mg, 80% purity).

Intermediate 2: Preparation of 2-((3-chloroquinolin-6-yl)methyl)isonicotinic acid

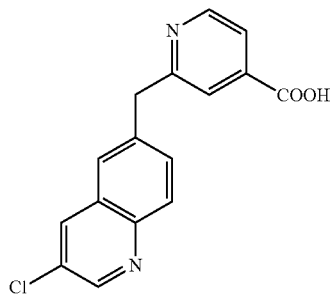 [SMILES: O=C(O)c1ccnc(Cc2ccc3ncc(Cl)cc3c2)c1]

Step 1: Preparation of methyl 3-chloroquinoline-6-carboxylate

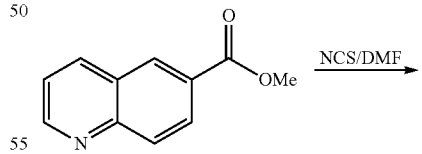

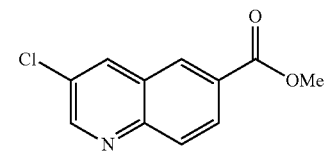

To a solution of methyl quinoline-6-carboxylate (15.0 g, 80.2 mmol, 1.0 eq) in DMF (200 ml) was added N-chlorosuccinimide (21.4 g, 0.16 mol, 2.0 eq) and the reaction mixture was stirred at 120° C. for 20 h. The reaction mixture was allowed to cool to rt, treated with brine and the mixture was extracted with ethyl acetate. The organic layer was dried over Na$_2$SO$_4$, filtered and concentrated under vacuum. The crude product was purified by chromatography on silica gel (EtOAc/PE=1/8, v/v) to afford methyl 3-chloroquinoline-6-carboxylate (9.1 g, 51%) as a yellow solid.

Step 2: Preparation of methyl (3-chloro-quinolin-6-yl)-methanol

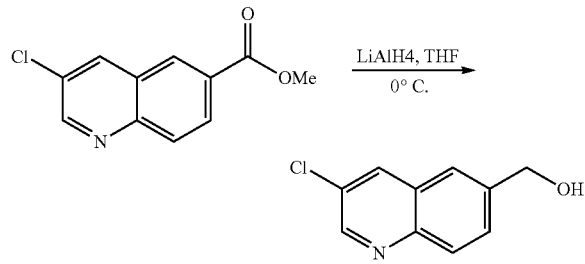

To a solution of methyl 3-chloroquinoline-6-carboxylate (8 g, 36.0 mmol, 1.0 eq) in dry THF was added LiAlH$_4$ (2.5M in THF, 5.8 mL, 0.4 eq). The resulting mixture was stirred at 0° C. for 1 h. After which period, additional LiAlH$_4$ (2.5M in THF, 2.8 mL, 0.2 eq) was added. The system was stirred for another 30 min at 0° C. and quenched by the slow addition of 1N aqueous NaOH. The resulting precipitate was filtered, and the filtrate was extracted with ethyl acetate. The combined organic layers were dried and concentrated. The residue was purified by silica gel chromatography (PE/EtOAc=20/1~5/1, v/v) to afford (3-chloro-quinolin-6-yl)-methanol (4.8 g, 69%) as a white solid.

Step 3: Preparation of 3-chloro-6-chloromethyl-quinoline

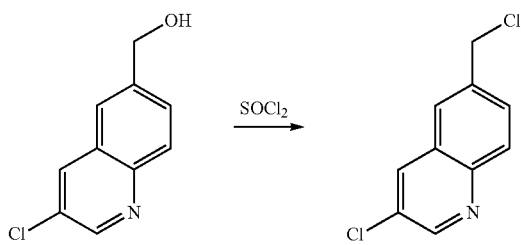

To (3-chloro-quinolin-6-yl)-methanol (3.3 g, 17.1 mmol, 1.0 eq) was added SOCl$_2$ (50 mL) and the mixture was stirred at rt for 1 h. The volatiles were then removed under vacuum and the residue was dissolved in DCM. The mixture was washed with saturated aq. NaHCO$_3$, dried and concentrated to give 3-chloro-6-chloromethyl-quinoline (3.4 g, 94%) as a yellow solid.

Step 4: Preparation of methyl 2-(trimethylstannyl)isonicotinate

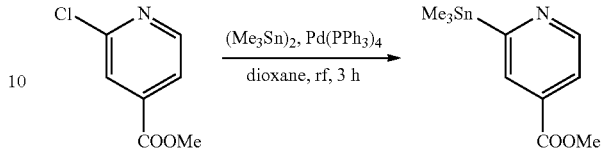

Hexamethyldistannane (0.21 mL, 334 mg, 1.02 mmol) and tetrakis(triphenylphosphine)palladium(0) (70 mg, 0.06 mmol) were added to a solution of methyl 2-chloroisonicotinate (100 mg, 0.58 mmol) in dry dioxane (10 mL) and the resulting mixture was refluxed for 3 h under N$_2$. EtOAc (50 mL) and water (100 mL) were then added. The layers were separated and the organic layer was washed with water (5×100 mL), dried (Na$_2$SO$_4$), and the solvent removed by rotary evaporation to leave crude residue which was used in the next step without further purification.

Step 4: Preparation of methyl 2-((3-chloroquinolin-6-yl)methyl)isonicotinate

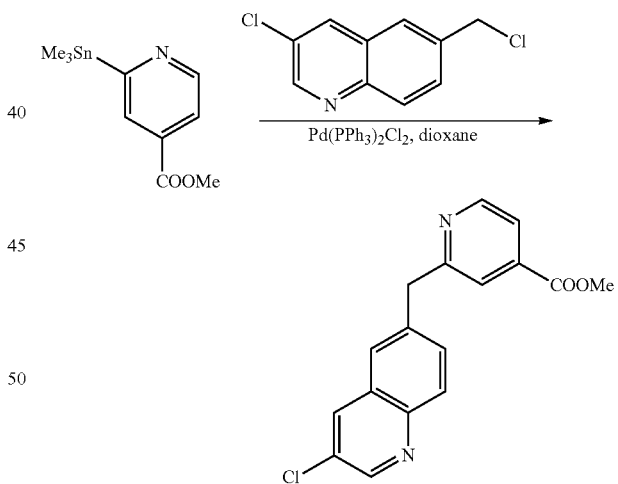

To a solution of 3-chloro-6-chloromethyl-quinoline (110 mg, 0.52 mmol, 1.0 eq) and crude methyl 2-(trimethylstannyl)isonicotinate in dioxane (10 mL) Pd(PPh$_3$)$_2$Cl$_2$ (36 mg, 0.05 mmol, 0.1 eq). The mixture was stirred at 90° C. for 3 h under nitrogen atmosphere, stripped of solvent and purified by silica gel chromatography (EtOAc/PE=10/1~5:1, v/v) to afford methyl 2-((3-chloroquinolin-6-yl)methyl) isonicotinate (70 mg) as a yellow solid. $^1$H NMR (400 MHz, DMSO-d$_6$) δ 8.83 (m, 2H), 8.53 (d, 1H), 7.98 (d, 1H), 7.85 (d, 1H), 7.73 (dd, 1H), 7.58 (s, 1H), 7.57 (s, 1H), 4.36 (s, 2H), 3.85 (s, 3H).

Step 5: Preparation of 2-((3-chloroquinolin-6-yl)methyl)isonicotinic acid

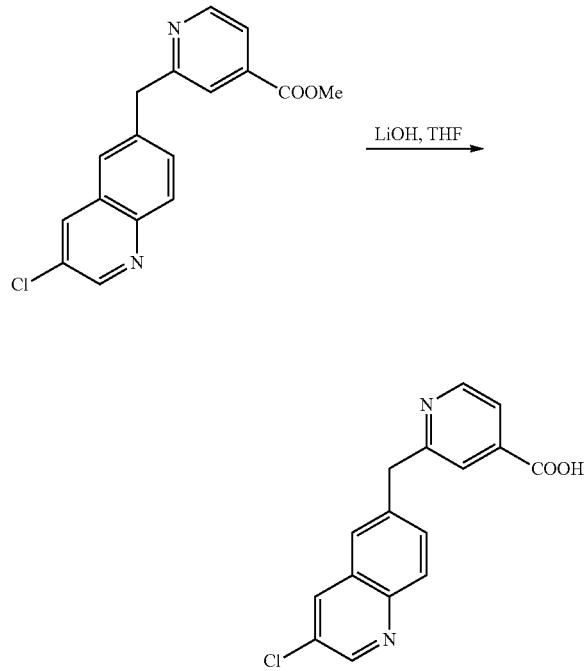

To a solution of methyl 2-((3-chloroquinolin-6-yl)methyl) isonicotinate (70 mg, 0.22 mmol, 1.0 eq.) in THF/H$_2$O (5 mL/1 mL) was added LiOH (71 mg, 2.1 mmol, 10 eq.). The resulting mixture was stirred for 1 h at room temperature; all starting material had been consumed (assessed by TLC). Volatile solvent was removed on rotavap, the aqueous residue was neutralized with 1M HCl and extracted with EtOAc (10 mL×3). The combined organic layers were washed with brine, dried over Na$_2$SO$_4$ and concentrated to furnish crude acid (50 mg, 75%), which was used directly without further purification.

Intermediate 3: Preparation of 2-((3-chloro-8-fluoroquinolin-6-yl)methyl)isonicotinic acid

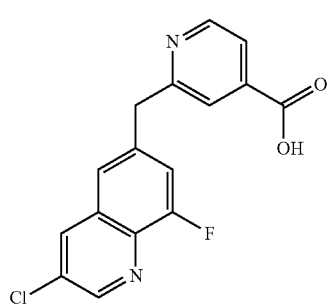 [SMILES: O=C(O)c1ccnc(Cc2cc(F)c3ncc(Cl)cc3c2)c1]

Step 1: Preparation of methyl 8-fluoroquinoline-6-carboxylate

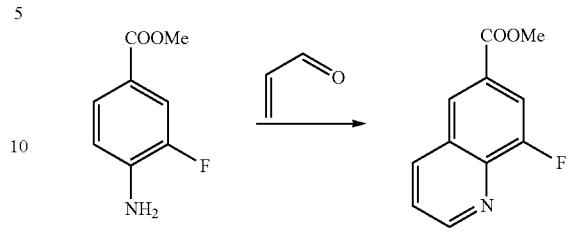

A mixture of methyl 4-amino-3-fluorobenzoate (35 g, 0.207 mmol, 1 eq), acrolein (17.4 g, 0.311 mol, 1.5 eq) and 6 N HCl (600 mL) was stirred at 100° C. for 10 min. Then the mixture was cooled and adjusted to pH ~5-6 using NaHCO$_3$ (aq). The mixture was extracted with DCM. The combined organic layers were washed with brine, dried over MgSO$_4$, filtered then concentrated and purified by column chromatography (EtOAc/PE=1/20, v/v) to give methyl 8-fluoroquinoline-6-carboxylate (11 g, 21%) as a yellow solid.

Step 2: Preparation of methyl 3-chloro-8-fluoroquinoline-6-carboxylate

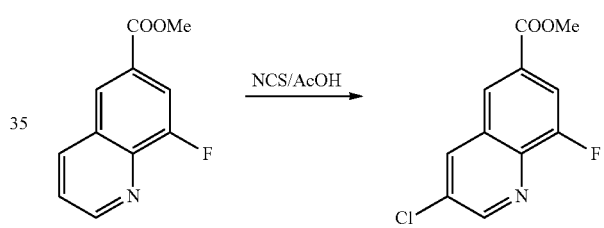

To a solution of methyl 8-fluoroquinoline-6-carboxylate (11 g, 53.7 mmol, 1 eq) in DMF was added NCS (21.4 g, 0.161 mol, 3 eq). The reaction mixture was stirred at 120° C. overnight. The reaction mixture was allowed to cool to ambient temperature, treated with water, neutralized with solid NaHCO$_3$ and further stirred at rt for 30 min. Finally, powdered sodium thiosulfate was carefully added to remove excess of NCS. The mixture was extracted with ethyl acetate. The organic layer was dried and concentrated under vacuum. The crude product was purified by flash-chromatography on silica gel to afford methyl 3-chloro-8-fluoroquinoline-6-carboxylate (11.5 g, 90%) as a yellow solid.

Step 3: Preparation of (3-chloro-8-fluoro-quinolin-6-yl)-methanol

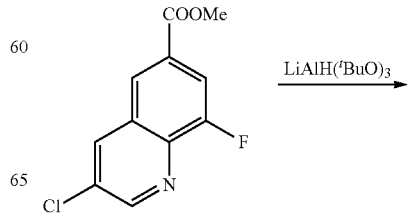

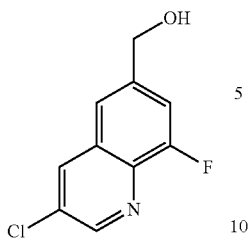

To a solution of methyl 3-chloro-8-fluoroquinoline-6-carboxylate (4.5 g, 18.8 mmol, 1 eq) was added LiAlH(t-BuO)₃ (12.0 g, 47.1 mmol, 2.5 eq). The resulting mixture was stirred at 40° C. for 12 h and then quenched by the addition of water. The mixture was extracted with ethyl acetate. The combined extracts were dried and concentrated. The residue was purified by silica gel chromatography (PE/EtOAc=2/1, v/v) to afford (3-chloro-8-fluoro-quinolin-6-yl)-methanol (2.1 g, 53%) as a yellow solid.

Step 4: Preparation of 3-chloro-6-chloromethyl-8-fluoro-quinoline

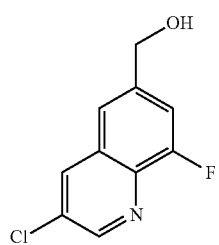 SOCl₂ → 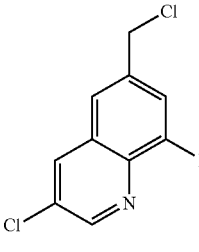

A mixture of 3-chloro-8-fluoro-6-hydroxymethyl-quinoline (2.1 g, 9.95 mmol, 1.0 eq) in SOCl₂ (50 mL) was stirred at rt for 1 h and concentrated. The residue was dissolved in DCM and treated with sat. NaHCO₃ solution to give 3-chloro-6-chloromethyl-8-fluoro-quinoline (2.2 g, 96%) as a yellow solid.

Step 5: Preparation of methyl 2-((3-chloro-8-fluoro-quinolin-6-yl)methyl)isonicotinate

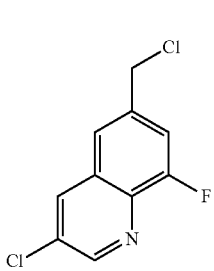 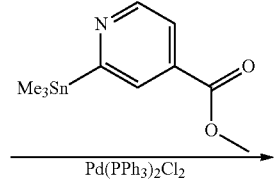 Pd(PPh₃)₂Cl₂ →

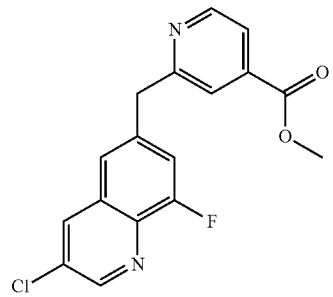

To a solution of 3-chloro-6-chloromethyl-8-fluoro-quinoline (2.2 g, 9.61 mmol, 1.0 eq) in dioxane (60 mL) was added methyl 2-(trimethylstannyl)isonicotinate (3.18 g, 10.6 mmol, 1.1 eq) and Pd(PPh₃)₂Cl₂ (674 mg, 0.96 mmol, 0.1 eq). The mixture was stirred at 90° C. for 3 h under nitrogen atmosphere, concentrated and purified by silica gel chromatography (DCM/MeOH=200/1, v/v) to afford methyl 2-((3-chloro-8-fluoroquinolin-6-yl)methyl)isonicotinate (1.6 g, 50%) as a yellow solid.

Step 6: Preparation of 2-((3-chloro-8-fluoroquinolin-6-yl)methyl)isonicotinic acid

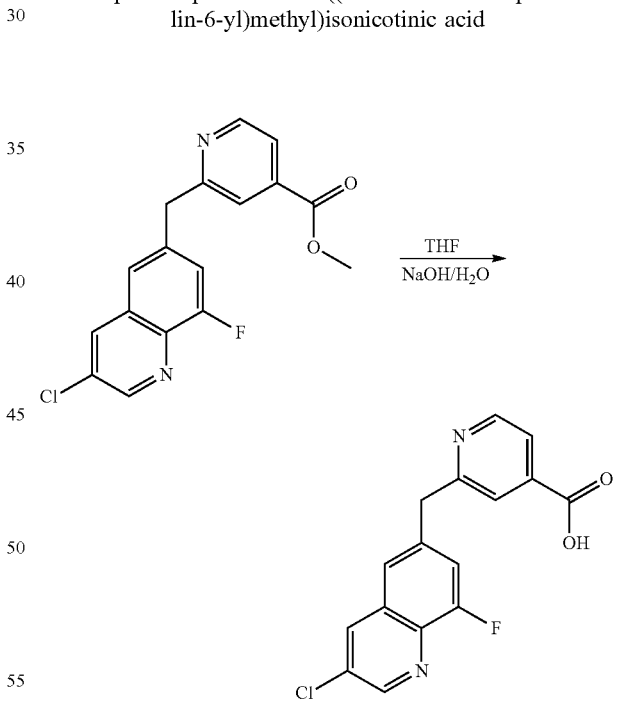

To a solution of methyl 2-((3-chloro-8-fluoroquinolin-6-yl)methyl)isonicotinate (800 mg, 2.4 mmol, 1 eq) in THF (20 ml)/water (10 ml) was added NaOH (116 mg, 0.29 mmol, 1.2 eq). The mixture was stirred at rt for 3 h. Then aqueous HCl (2 N) was added to the reaction mixture until pH 6-7. The mixture was extracted with ethyl acetate, and the organic layer was concentrated under pressure. The gray compound was directly used in next step (500 mg, 76%).

Intermediate 4: Preparation of
2-((3,8-dichloroquinolin-6-yl)methyl)isonicotinic acid

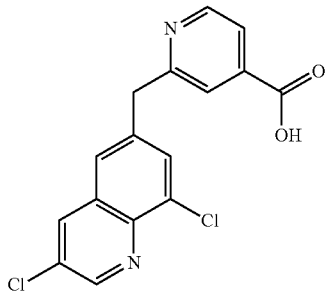 [SMILES: O=C(O)c1ccnc(Cc2cc(Cl)c3ncc(Cl)cc3c2)c1]

The title compound was synthesized as described for Intermediate 3 using methyl 4-amino-3-chlorobenzoate as a starting material.

Intermediate 5: Preparation of
2-((4-cyanoquinolin-6-yl)methyl)isonicotinic acid

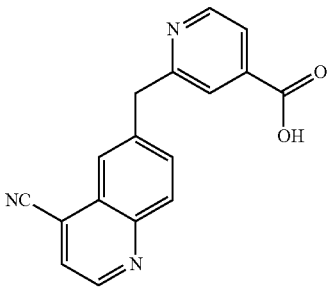 [SMILES: N#Cc1ccnc2ccc(Cc3cc(C(=O)O)ccn3)cc12]

Step 1: Preparation of
6-(methoxycarbonyl)quinoline 1-oxide

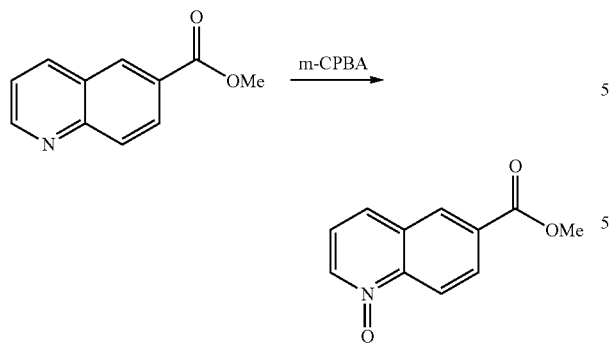

A mixture of methyl quinoline-6-carboxylate (10 g, 53.5 mmol, 1 eq) and m-CPBA (18.4 g, 0.106 mol, 2 eq) in DCM (50 mL) was stirred at rt overnight. Saturated aq. NaHCO₃ (40 mL) was added to the reaction mixture and it was stirred for 30 min. The organic layer was separated, dried, filtered and concentrated to obtain a residue, which was re-crystallized by ethyl acetate (5 mL) to afford 6-(methoxycarbonyl) quinoline 1-oxide (8.0 g, 74%) as a light yellow solid.

Step 2: Preparation of methyl
2-chloroquinoline-6-carboxylate and methyl
4-chloroquinoline-6-carboxylate

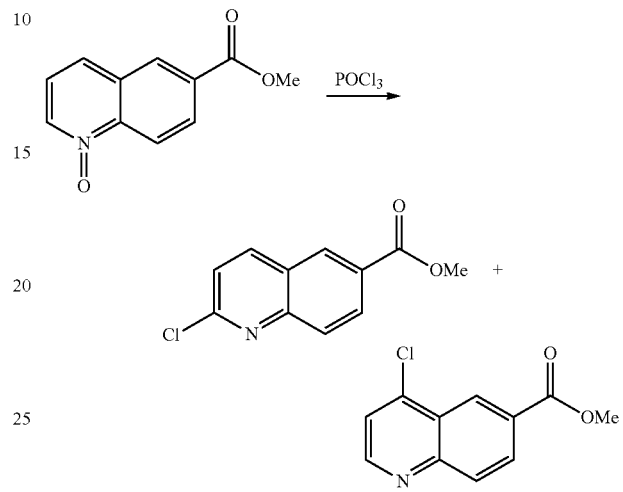

To 6-(methoxycarbonyl)quinoline 1-oxide (4.0 g, 19.7 mmol, 1 eq) was added phosphoryl trichloride (20 mL). The resulting mixture was then stirred at rt under N₂ for 2 h. The volatiles were then removed under vacuum and the residue was dissolved in DCM. The mixture was washed with saturated aq. NaHCO₃, dried and concentrated. The residue was purified by silica gel chromatography (PE/EtOAc=10/1, v/v) to afford methyl 2-chloroquinoline-6-carboxylate (1.2 g, 28%) and methyl 4-chloroquinoline-6-carboxylate (2.5 g, 57%).

Step 3: Preparation of
(4-chloro-quinolin-6-yl)-methanol

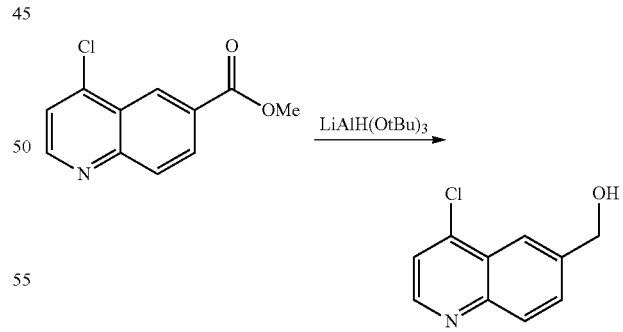

To a solution of methyl 4-chloroquinoline-6-carboxylate (2.2 g, 10 mmol, 1 eq) was added LiAlH(t-BuO)₃ (7.62 g, 30 mmol, 3 eq). The resulting mixture was stirred at 60° C. for 2 h and then quenched by the addition of water. The mixture was extracted with EtOAc. The combined extracts were dried and concentrated. The residue was purified by silica gel chromatography (PE/EtOAc=1/1, v/v) to afford (4-chloro-quinolin-6-yl)-methanol (1.54 g, 80%) as a yellow solid.

Step 4: Preparation of 6-hydroxymethyl-quinoline-4-carbonitrile

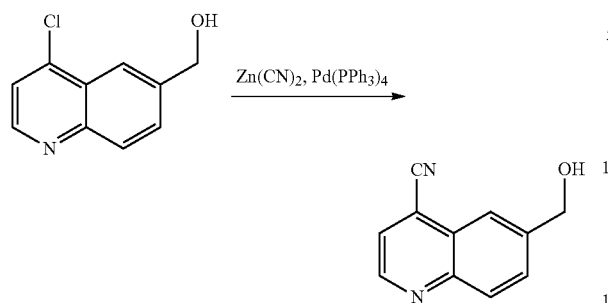

To a mixture of (4-chloroquinolin-6-yl)methanol and zinc cyanide in DMF (30 mL) was added palladium tetrakis (triphenylphosphine). The mixture was degassed and then heated to 90° C. for 3 h. After this time, the mixture was diluted with water and EtOAc, filtered and the resulting layers were separated. The aqueous layer was further extracted with EtOAc. The combined extracts were washed with water, dried over $MgSO_4$, filtered and the solvent removed in vacuo. The resulting residue was purified by chromatograph on silica gel column to afford 6-hydroxymethyl-quinoline-4-carbonitrile as an off-white solid (1.1 g, 77%).

Step 5: Preparation of 2-((4-cyanoquinolin-6-yl)methyl)isonicotinic acid

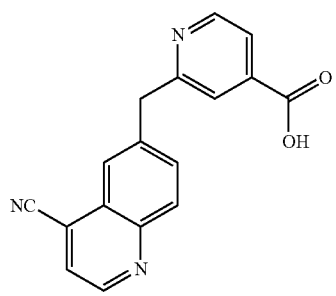 [SMILES: N#Cc1ccnc2ccc(Cc3cc(C(=O)O)ccn3)cc12]

The title compound was synthesized as described for Intermediate 3, Steps 4, 5 and 6.

Intermediate 6: Preparation of 2-((7-chloroquinolin-3-yl)methyl)isonicotinic acid

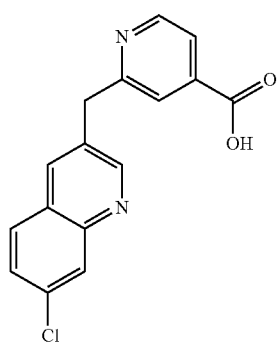 [SMILES: O=C(O)c1ccnc(Cc2cnc3cc(Cl)ccc3c2)c1]

Step 1: Preparation of N'-(7-chloroquinoline-3-carbonyl)-4-methylbenzenesulfonohydrazide

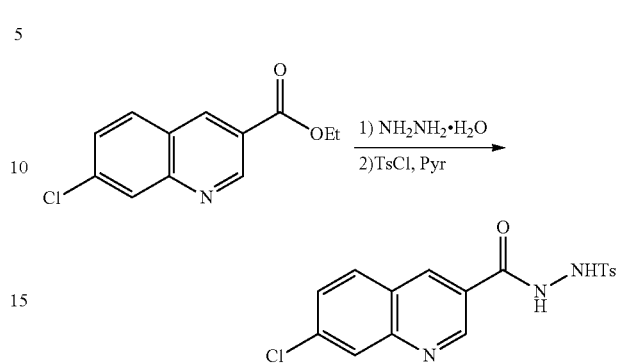

To a solution of ethyl 7-chloroquinoline-3-carboxylate (3.5 g, 14.90 mmol, 1.0 eq) in EtOH (60 mL) was added hydrazine monohydrate (7.2 mL, 149 mmol, 10 eq). The reaction mixture was stirred at 80° C. for 2 h, and then concentrated under reduced pressure. Water was added to the reaction flask and the solid was filtered and washed with cold water. The solid was dried in air and then dissolved in pyridine (30 mL). To the mixture was added TsCl (3.4 g, 17.90 mmol, 1.2 eq). After stirring at rt for 1 h, the mixture was concentrated in vacuo. The residue was poured into water and the resulting precipitate was collected by filtration to give N'-(7-chloroquinoline-3-carbonyl)-4-methylbenzenesulfonohydrazide (5.0 g, 90%) as a yellow solid.

Step 2: Preparation of (7-chloro-quinolin-3-yl)-methanol

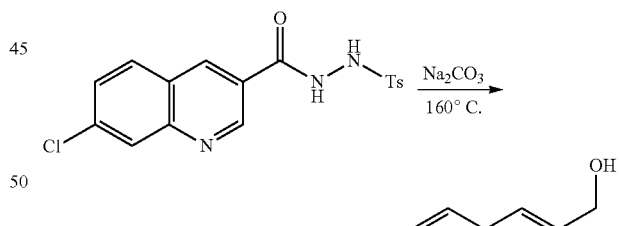

A mixture of N'-(7-chloroquinoline-3-carbonyl)-4-methylbenzenesulfonohydrazide (5.0 g, 13.30 mmol, 1.0 eq) and $Na_2CO_3$ (4.24 g, 40 mmol, 3 eq) in ethylene glycol (30 mL) was heated at 160° C. for 20 min. After cooling to rt the mixture was diluted with water and extracted with $Et_2O$. The combined extracts were dried and concentrated. The residue was purified by flash chromatography on a silica gel column (PE/EtOAc=1/1, v/v) to give (7-chloro-quinolin-3-yl)-methanol (600 mg, 23%) as a yellow solid.

Step 3: Preparation of 2-((7-chloroquinolin-3-yl)methyl)isonicotinic acid

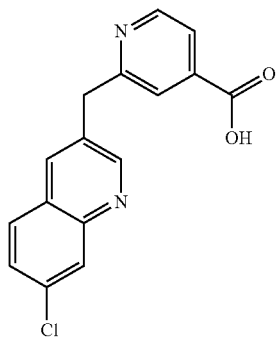 [SMILES: O=C(O)c1ccnc(Cc2cnc3cc(Cl)ccc3c2)c1]

The title compound was synthesized as described for Intermediate 3, Steps 4, 5 and 6.

Intermediate 7: Preparation of 2-((3-methylisoquinolin-6-yl)methyl)isonicotinic acid

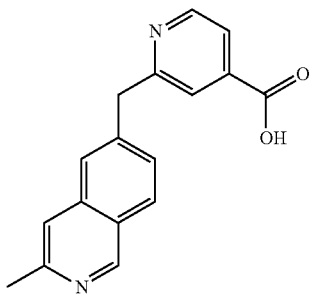 [SMILES: Cc1cc2cc(Cc3cc(C(=O)O)ccn3)ccc2cn1]

Step 1: Preparation of 6-bromo-3-methyl-isoquinoline

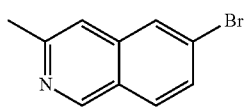

To a solution of 4-bromo-benzylamine (10.0 g, 54 mmol, 1.0 eq) in DCE (100 mL) was added 1,1-dimethoxy-propan-2-one (7.0 g, 59 mmol, 1.1 eq) and MgSO$_4$ (20 g). The mixture was stirred at 40° C. overnight. Then to the mixture was added NaBH$_3$CN (4.08 g, 64.8 mmol, 1.2 eq). After stirring at rt for 5 h the mixture was filtered. The filtrate was concentrated to give a yellow oil. Chlorosulfonic acid (30 mL) was cooled to −10° C. and the above crude product was added dropwise. The reaction mixture was heated to 100° C. for 10 min, then cooled and poured into ice. The mixture was neutralized with 2M NaOH and extracted with ethyl acetate. The combined extracts were dried and concentrated. The residue was purified by silica gel chromatography (PE/EtOAc=2/1, v/v) to afford 6-bromo-3-methyl-isoquinoline (4.0 g, 34% yield for 3 steps) as a yellow solid.

Step 2: Preparation of methyl 3-methylisoquinoline-6-carboxylate

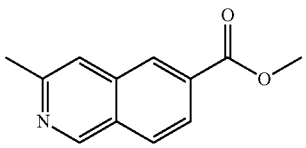

An autoclave vessel was charged with 6-bromo-3-methyl-isoquinoline (4.0 g, 18 mmol), Pd(dppf)Cl$_2$ (735 mg, 0.9 mmol, 0.05 eq) and triethylamine (5.0 mL, 36 mmol, 2 eq) in 40 mL of methanol. The vessel was purged with nitrogen three times and carbon monoxide three times. The vessel was pressurized to 3 MPa with carbon monoxide and heated to 100° C. The reaction was thus stirred overnight, then allowed to cool to room temperature. The resulting solution was concentrated and purified by flash chromatography on silica gel (PE/EtOAc=1/1, v/v) to afford methyl 3-methyl-isoquinoline-6-carboxylate (3.4 g, 94%) as a white solid.

Step 3: Preparation of (3-methyl-isoquinolin-6-yl)-methanol

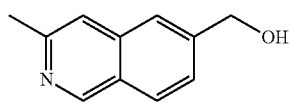

To a solution of methyl 3-methylisoquinoline-6-carboxylate (3.3 g, 16.42 mmol, 1 eq) in dry THF (100 mL) was added LiAlH(t-BuO)$_3$ (12.5 g, 45.25 mmol, 3 eq). The resulting mixture was stirred at 60° C. for 5 h and then quenched by the addition of water. The mixture was extracted with ethyl acetate. The combined extracts were dried and concentrated. The residue was purified by silica gel chromatography (PE/EtOAc=1/1, v/v) to afford (3-methyl-isoquinolin-6-yl)-methanol (2.5 g, 89%) as a white solid.

Step 4: Preparation of 2-((3-methylisoquinolin-6-yl)methyl)isonicotinic acid

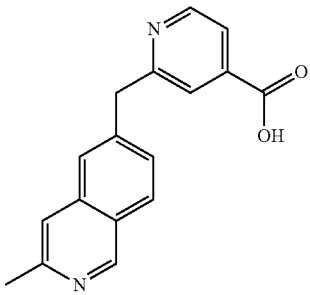 [SMILES: Cc1cc2cc(Cc3cc(C(=O)O)ccn3)ccc2cn1]

The title compound was synthesized as described for Intermediate 3, Steps 4, 5 and 6.

Intermediates 8-14

The title compounds were synthesized as described for Intermediate 7.

| Intermediate | Structure | Name |
|---|---|---|
| 8 | 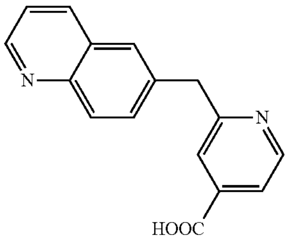 [SMILES: O=C(O)c1ccnc(Cc2ccc3ncccc3c2)c1] | 2-(quinolin-6-ylmethyl)isonicotinic acid |
| 9 | 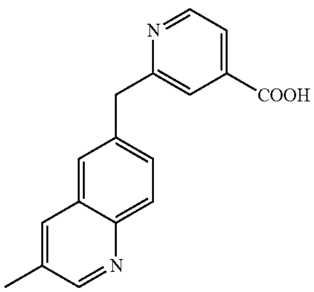 [SMILES: Cc1cnc2ccc(Cc3cc(C(=O)O)ccn3)cc2c1] | 2-((3-methylquinolin-6-yl)methyl)isonicotinic acid |
| 10 | 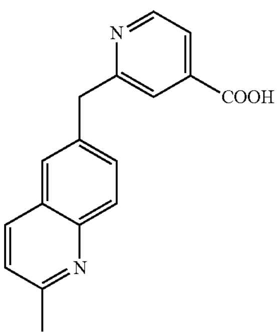 [SMILES: Cc1ccc2cc(Cc3cc(C(=O)O)ccn3)ccc2n1] | 2-((2-methylquinolin-6-yl)methyl)isonicotinic acid |
| 11 | 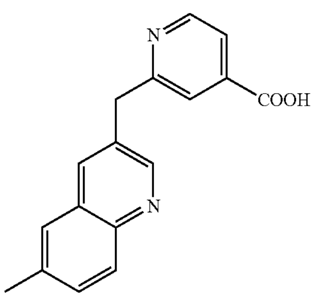 [SMILES: Cc1ccc2ncc(Cc3cc(C(=O)O)ccn3)cc2c1] | 2-((6-methylquinolin-3-yl)methyl)isonicotinic acid |
| 12 | 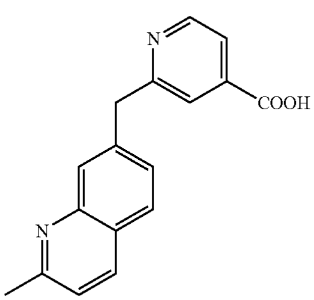 [SMILES: Cc1ccc2ccc(Cc3cc(C(=O)O)ccn3)cc2n1] | 2-((2-methylquinolin-7-yl)methyl)isonicotinic acid |
| 13 | | 2-((6-fluoroquinolin-3-yl)methyl)isonicotinic acid |
| 14 | | 2-((7-fluoroquinolin-3-yl)methyl)isonicotinic acid |

Intermediate 15: Preparation of 5-(aminomethyl)-4,6-dimethylpyridin-2-amine hydrochloride

Step 1: Preparation of 5-iodo-4,6-dimethyl-pyridin-2-ylamine

A mixture of 4,6-dimethyl-pyridin-2-ylamine (6 g, 49.1 mmol, 1.0 eq), periodic acid (1.6 g, 7.37 mmol, 0.15 eq) and iodine (6.2 g, 24.5 mmol, 0.5 eq) was added in a mixed solution of acetic acid (120 mL), $H_2O_2$ (6 mL) and $H_2SO_4$ (1 mL) at 80° C. for 4 h, then reaction mixture was poured into 10% aqueous Na₂S₂O₃ solution to quench any unreacted iodine and extracted with ether. The extract was washed with 10% aqueous NaOH, dried over Na₂SO₄ and concentrated, the resulting residue was purified by silica gel chromatography (DCM/MeOH=100/1, v/v) to afford 5-iodo-4,6-dimethyl-pyridin-2-ylamine (10 g, 80%) as a yellow solid.

Step 2: Preparation of
6-amino-2,4-dimethyl-nicotinonitrile

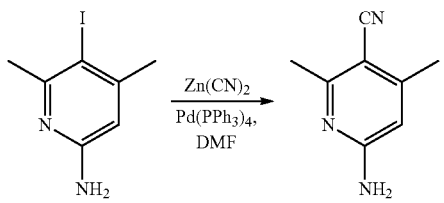

To a solution of 5-iodo-4,6-dimethyl-pyridin-2-ylamine (10 g, 40.3 mmol, 1.0 eq) in DMF (300 mL) was added Zn(CN)₂ (14 g, 120.9 mmol, 3.0 eq) and Pd(PPh₃)₄ (4.65 g, 4.03 mmol, 0.1 eq) carefully. The mixture was stirred at 90° C. overnight under N₂. ethyl acetate and water was added. The organic layer was separated and concentrated. The resulting residue was purified by silica gel chromatography (DCM/MeOH=100/1, v/v) to afford 6-amino-2,4-dimethyl-nicotinonitrile (5 g, 84%) as a yellow solid.

Step 3: Preparation of tert-butyl
(6-amino-2,4-dimethylpyridin-3-yl)methylcarbamate

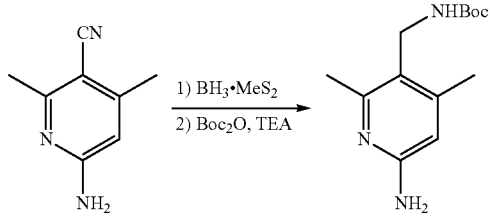

To a solution of 6-amino-2,4-dimethyl-nicotinonitrile (8.1 g, 55 mmol, 1.0 eq) in THF (300 mL) was added BH₃·MeS₂ (10 M, 55 mL, 550 mmol, 10.0 eq) at rt slowly. The mixture was stirred under reflux for 48 h. After cooling to rt, the mixture was quenched by the addition of concentrated HCl. The mixture was basified to pH 8 with sat. NaHCO₃ solution. To the mixture were added TEA (9.2 mL, 66 mmol, 1.2 eq) and Boc₂O (14.4 g, 66 mmol, 1.2 eq). The reaction mixture was stirred at rt for 1 h and then extracted with ethyl acetate. The combined organic layers were dried over Na₂SO₄, filtered, and concentrated. The residue was purified on silica gel column (PE/EtOAc=1/1) to give tert-butyl (6-amino-2,4-dimethylpyridin-3-yl)methylcarbamate (4.1 g, 30%) as a yellow solid.

Step 4: Preparation of
5-aminomethyl-4,6-dimethyl-pyridin-2-ylamine
hydrochloride

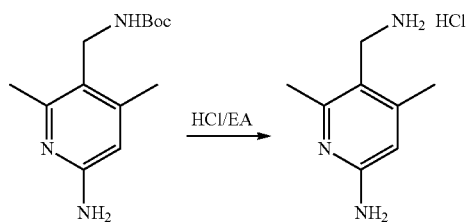

To a solution of tert-butyl (6-amino-2,4-dimethylpyridin-3-yl)methylcarbamate (4.1 g, 16.3 mmol, 1.0 eq) in ethyl acetate (20 mL) was added a solution of HCl in ethyl acetate (10 M, 50 mL). The mixture was stirred at rt for 1 h, and the precipitate was collected by filtration to afford 5-aminomethyl-4,6-dimethyl-pyridin-2-ylamine hydrochloride (2.0 g, 66%) as a white solid.

Intermediate 16: Preparation of
6-(aminomethyl)isoquinolin-1-amine

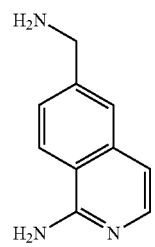

Step 1: Preparation of
6-bromo-1-chloroisoquinoline

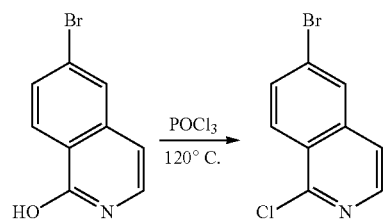

To a solution of 6-bromoisoquinolin-1-ol (10 g, 44.4 mmol, 1.0 eq) in POCl₃ (200 mL). The mixture was stirred at 120° C. for overnight. The mixture was concentrated and extracted with DCM and the combined extracts were washed with brine, dried and concentrated to give 6-bromo-1-chloroisoquinoline as a yellow solid (10 g, crude).

Step 2: Preparation of 6-bromoisoquinolin-1-amine

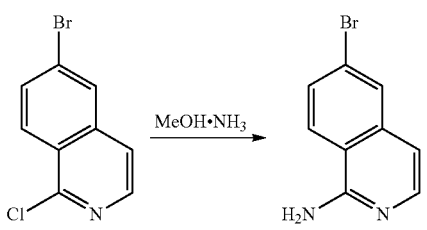 [SMILES: "MeOH·NH3" ; Clc1nccc2cc(Br)ccc12 ; Nc1nccc2cc(Br)ccc12]

To a solution of 6-bromo-1-chloroisoquinoline (10 g, 41.50 mmol, 1.0 eq) in MeOH/NH₃ (500 mL) and was stirred at 30° C. for 48 h. The mixture was concentrated to give 6-bromoisoquinolin-1-amine as a yellow solid (10 g, crude).

Step 3: Preparation of 1-aminoisoquinoline-6-carbonitrile

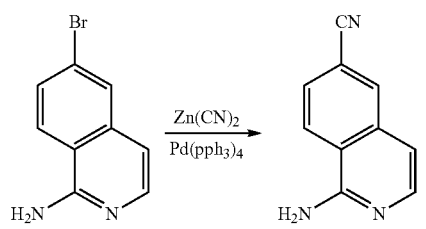

To a solution of 6-bromoisoquinolin-1-amine (10 g, 45.04 mmol, 1.0 eq) in DMF (400 mL) was added Zn(CN)₂ (13.22 g, 112.3 mmol, 2.5 eq) and Pd(pph₃)₄ (5.2 g, 4.51 mmol, 0.1 eq). The mixture was stirred at 120° C. for 4 h. The mixture was concentrated and extracted with DCM. The combined extracts were dried and concentrated. The residue was purified by flash chromatography on a silica gel column (DCM/MeOH=50/1, v/v) to give 1-aminoisoquinoline-6-carbonitrile (4.5 g, 59%) as a yellow oil.

Step 4: Preparation of 6-(aminomethyl)isoquinolin-1-amine

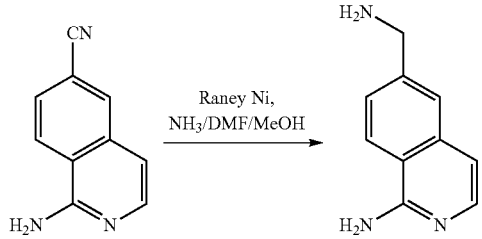

To a solution of 1-aminoisoquinoline-6-carbonitrile (4.5 g, 26.47 mmol, 1 eq) in MeOH (200 mL), DMF (200 mL) and ammonium hydroxide (100 mL) was added Raney Ni (4.0 g). The mixture was stirred at 40° C. overnight under hydrogen atmosphere. Raney Ni was filtered off and the filtrate was concentrated in vacuo to give 6-(aminomethyl) isoquinolin-1-amine (3 g, crude) as a yellow solid.

Intermediate 17: Preparation of (6-fluoro-1H-indol-5-yl)methanamine

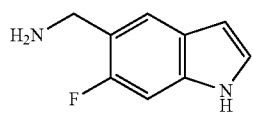 [SMILES: NCc1cc2cc[nH]c2cc1F]

Step 1: Preparation of 6-fluoro-1-(triisopropylsilyl)-1H-indole-5-carbaldehyde

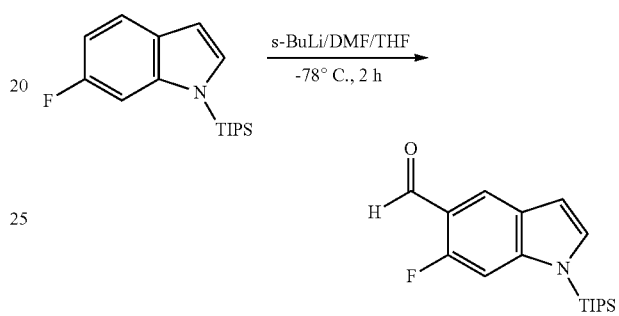

To a solution of 6-fluoro-1-(triisopropylsilyl)-1H-indole (2 g, 6.9 mmol, 1.0 eq) in THF (30 mL) was added s-BuLi (6.3 mL, 1.3 M, 1.2 eq) at −78° C. slowly. Then the mixture was stirred at this temperature for 1 h. DMF (1.5 g, 20.7 mmol, 3.0 eq) was added dropwise. The mixture was stirred at −78° C. for 1 h. Then the reaction was quenched by saturated aqueous NH₄Cl. The obtained mixture was extracted with EtOAc (50 mL×3). The organic layers were combined and washed with brine, dried over Na₂SO₄, filtered and concentrated. The residue was purified on silica gel column (PE/EtOAc=100/1) to give 6-fluoro-1-(triisopropylsilyl)-1H-indole-5-carbaldehyde as a yellow oil (950 mg, 57%).

Step 2: Preparation of 6-fluoro-1H-indole-5-carbaldehyde oxime

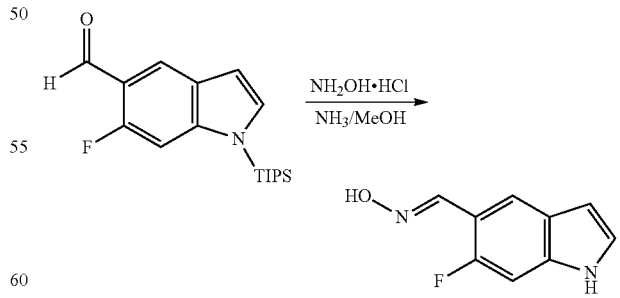

A mixture of 6-fluoro-1-(triisopropylsilyl)-1H-indole-5-carbaldehyde (780 mg, 2.45 mmol, 1.0 eq) and NH₂OH.HCl (340 mg, 4.89 mmol, 2.0 eq) in NH₃/MeOH (15% w/w, 10 mL) was stirred at rt overnight. The mixture was concentrated. The residue was purified directly on silica gel column (PE/EtOAc=50/1) to afford 6-fluoro-1H-indole-5-carbaldehyde oxime as a yellow solid (460 mg, crude).

Step 3: Preparation of (6-fluoro-1H-indol-5-yl)methanamine

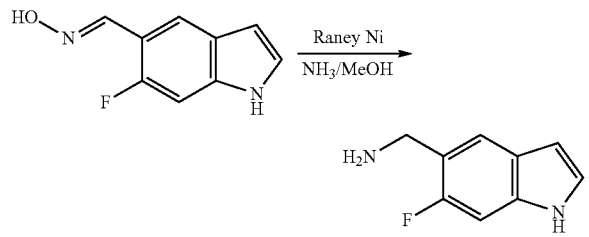

A mixture of 6-fluoro-1H-indole-5-carbaldehyde oxime (460 mg, 1.38 mmol, 1.0 eq) and Raney Ni (100 mg) in NH$_3$/MeOH (15% w/w, 10 mL) was stirred at rt under H$_2$ atmosphere (1 atm) overnight. Then the mixture was filtered and concentrated to afford (6-fluoro-1H-indol-5-yl)methanamine as a gray solid (420 mg, 95%). The solid was used for the next step without further purification.

Intermediate 18: Preparation of (5-chloro-1H-pyrrolo[2,3-b]pyridin-3-yl)methanamine

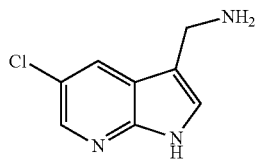 [SMILES: NCc1c[nH]c2ncc(Cl)cc12]

Step 1: Preparation of 5-chloro-1H-pyrrolo[2,3-b]pyridine-3-carbaldehyde

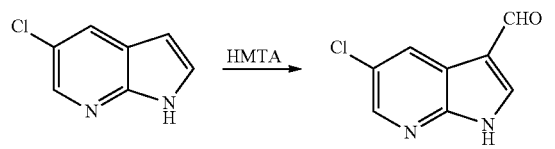

To a suspension of 5-chloro-1H-pyrrolo[2,3-b]pyridine (10.0 g, 65.5 mmol, 1 eq) in AcOH (56.7 mL) and water (28.3 mL) was added hexamethylenetetramine (11.9 g, 85.2 mmol, 1.3 eq). The mixture was stirred under reflux overnight, followed by addition of 200 mL of water. After stirring for 30 min, the reaction mixture was filtered to recover the solid, then dried under air to give 5-chloro-1H-pyrrolo[2,3-b]pyridine-3-carbaldehyde (6.2 g, 53%) as a yellow solid.

Step 2: Preparation of 5-chloro-1H-pyrrolo[2,3-b]pyridine-3-carbaldehyde oxime

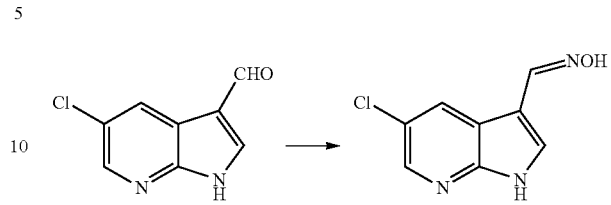

To a solution of 5-cloro-1H-pyrrolo[2,3-b]pyridine-3-carbaldehyde (1.0 g, 5.55 mmol, 1 eq) in EtOH (40 mL) and water (10 mL) was added hydroxylammonium chloride (575 mg, 8.33 mmol, 1.5 eq) and Na$_2$CO$_3$ (1.06 g, 10.0 mmol, 1.8 eq). The mixture was stirred under reflux for 3 h and then cooled to rt. The precipitate was collected by filtration to give 5-chloro-1H-pyrrolo[2,3-b]pyridine-3-carbaldehyde oxime (1.0 g, 92%) as an off white solid.

Step 3: Preparation of (5-chloro-1H-pyrrolo[2,3-b]pyridin-3-yl)methanamine

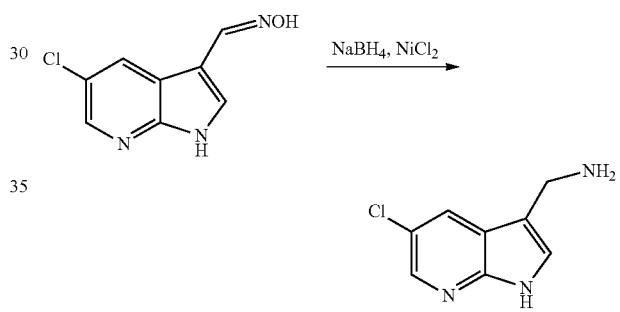

To a solution of 5-chloro-1H-pyrrolo[2,3-b]pyridine-3-carbaldehyde oxime (200 mg, 2 mmol, 1 eq) in MeOH (5 mL) was added NiCl$_2$ (128 mg, 1 mmol, 1 eq) and NaBH$_4$ (228 mg, 6 mmol, 6 eq). The mixture was stirred at rt for 5 h under hydrogen atmosphere. NiCl$_2$ was filtered off and the filtrate was concentrated in vacuo to give (5-chloro-1H-pyrrolo[2,3-b]pyridin-3-yl)methanamine (65 mg, 30%) as a yellow solid.

Intermediate 19: Preparation of (5-chloro-1-(tetrahydro-2H-pyran-2-yl)-1H-indazol-3-yl)methanamine

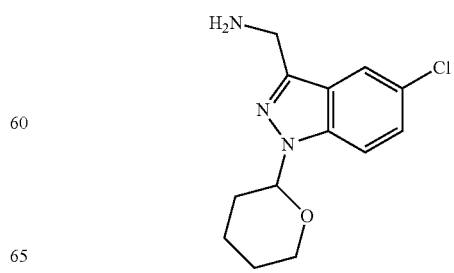

Step 1: Preparation of 1-(2-amino-5-chlorophenyl)-2-chloroethanone

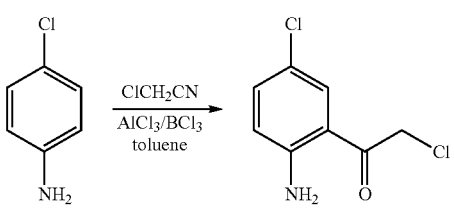

To a stirred solution of boron trichloride in toluene (200 mL, 1 M, 0.2 mol, 1.16 eq), a solution of 4-chloroaniline (22.0 g, 0.172 mol, 1.0 eq) in dry toluene (200 mL) was added dropwise under nitrogen at a temperature ranging from 5° C. to 10° C. To the resulting mixture, chloroacetonitrile (15 mL, 0.237 mol, 1.38 eq) and aluminum trichloride (29.0 g, 0.217 mol, 1.26 eq) were added successively. The mixture was refluxed for 18 h. After cooling, ice-cold hydrochloric acid (2 N, 500 mL) was added and a yellow precipitate was formed. The mixture was warmed at 80° C. with stirring, until the precipitate was dissolved. The cooled solution was extracted with dichloromethane (250 mL×3). The organic layer was washed with water, dried ($Na_2SO_4$), and concentrated. The resulting residue was purified on silica gel column (PE/EtOAc=50/1~PE/EtOAc/DCM=1/8/1, v/v/v) to afford 1-(2-amino-5-chlorophenyl)-2-chloroethanone as a yellow brown solid (18.3 g, 52%).

Step 2: Preparation of 5-chloro-3-(chloromethyl)-1H-indazole

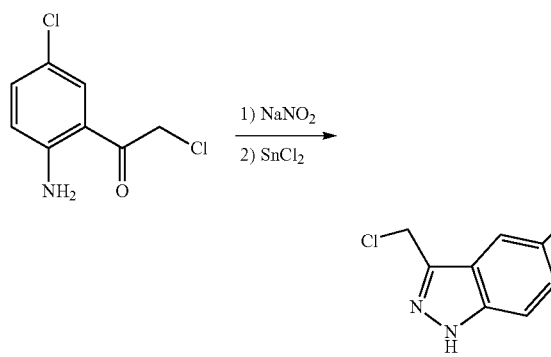

To a stirred suspension of 1-(2-amino-5-chlorophenyl)-2-chloroethanone (16 g, 78 mmol, 1.0 eq) in conc. hydrochloric acid (120 mL) was added a solution of sodium nitrite (5.9 g, 86 mmol, 1.1 eq) in water (30 mL) at 0° C. After 1 h, a solution of $SnCl_2.2H_2O$ (42.3 g, 187 mmol, 2.4 eq) in conc. hydrochloric acid (60 mL) was added to the reaction mixture and stirred for 1 h. Ice-water was added to the reaction mixture. The precipitate was collected by filtration, washed with water and dried to afford crude 5-chloro-3-(chloromethyl)-1H-indazole, which was used in the next step without further purification (13.5 g, 86%).

Step 3: Preparation of 5-chloro-3-(chloromethyl)-1-(tetrahydro-2H-pyran-2-yl)-1H-indazole

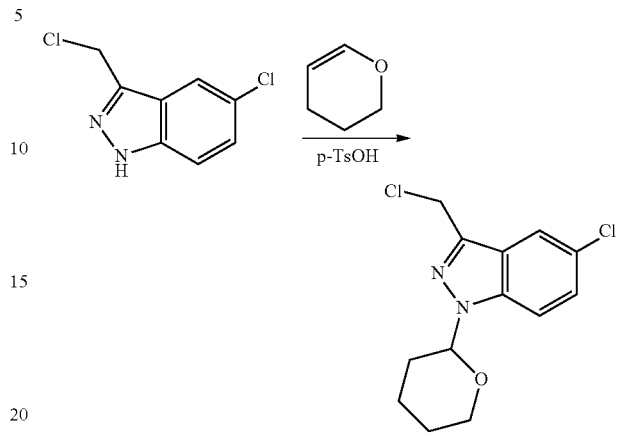

A solution of 5-chloro-3-(chloromethyl)-1H-indazole (13.5 g, 67 mmol, 1.0 eq), 3,4-dihydro-2H-pyran (11.3 g, 134 mmol, 2.0 eq) and p-toluenesulfonic acid monohydrate (1.27 g, 6.7 mmol, 0.1 eq) in THF (300 mL) was stirred at 70° C. for 12 h. After cooling to rt (~22° C.), the reaction mixture was mixed with water (300 mL) and extracted with ethyl acetate (200 mL×2). The organic layer was washed with brine, dried over anhydrous $Na_2SO_4$, and concentrated to afford 5-chloro-3-(chloromethyl)-1-(tetrahydro-2H-pyran-2-yl)-1H-indazole as a yellow solid (16 g, 84%).

Step 4: Preparation of 2-((5-chloro-1-(tetrahydro-2H-pyran-2-yl)-1H-indazol-3-yl)methyl)isoindoline-1,3-dione

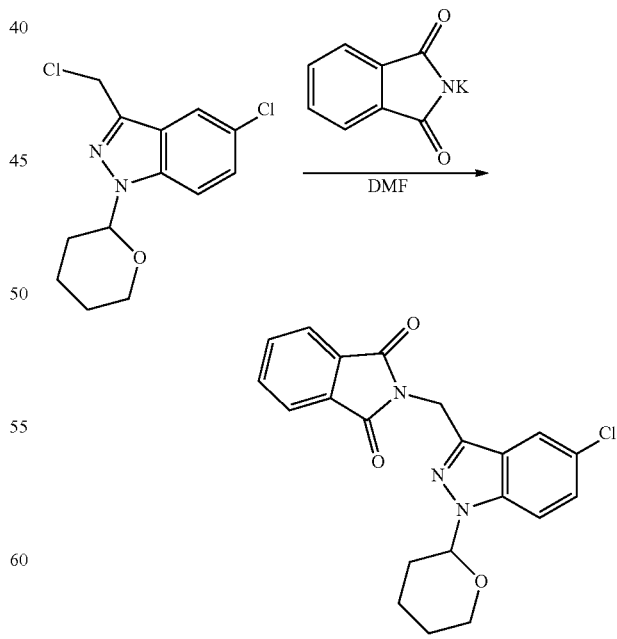

To a solution of 5-chloro-3-(chloromethyl)-1-(tetrahydro-2H-pyran-2-yl)-1H-indazole (18 g, 63 mmol, 1 eq) in anhydrous DMF (200 mL) under $N_2$, potassium phthalimide (17.5 g, 94 mmol, 1.5 eq) was added and the resulting mixture was heated at 90° C. for 2 h. The mixture was poured into water and extracted with DCM (200 mL×2). The combined organic layers were washed with water and brine, dried over anhydrous $Na_2SO_4$ and concentrated. The crude product was washed with EtOH to afford 2-((5-chloro-1-(tetrahydro-2H-pyran-2-yl)-1H-indazol-3-yl)methyl)isoindoline-1,3-dione as a white solid (15 g, 60%).

Step 5: Preparation of (5-chloro-1-(tetrahydro-2H-pyran-2-yl)-1H-indazol-3-yl)methanamine

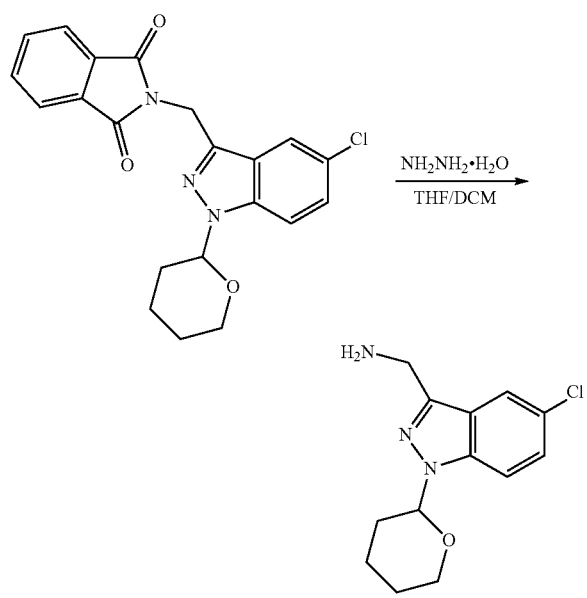

To a solution of 2-((5-chloro-1-(tetrahydro-2H-pyran-2-yl)-1H-indazol-3-yl)methyl)isoindoline-1,3-dione (15 g, 37.9 mmol, 1.0 eq) in THF (300 mL) and DCM (60 mL) was added hydrazine hydrate (9.5 g, 189 mmol, 5 eq). The white suspension was stirred at 48° C. for 12 h and phthalyl hydrazide was removed by filtration. The filtrate was concentrated in vacuo and the crude material was dissolved in DCM and washed with 1 N NaOH solution. The organic layer was dried over anhydrous $Na_2SO_4$ and concentrated to afford (5-chloro-1-(tetrahydro-2H-pyran-2-yl)-1H-indazol-3-yl)methanamine as a yellow solid (9.9 g, 99%).

Intermediate 20: Preparation of 5-(aminomethyl)-6-methylpyridin-2-amine

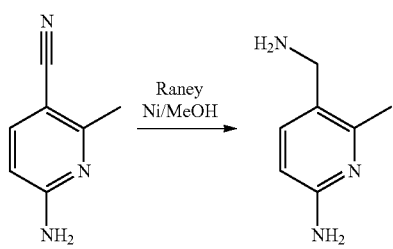

The solution of 6-amino-2-methylnicotinonitrile (200 mg, 1.5 mmol, 1.0 eq) and Raney Ni (50 mg) in MeOH (10 mL) was stirred at rt under $H_2$ (1 atm) overnight. Then the mixture was filtered and the filtrate was concentrated to give 5-(aminomethyl)-6-methylpyridin-2-amine as a yellow solid (210 mg, quant). The solid was used without further purification.

Intermediate 21: Preparation of 5-(aminomethyl)-4-methylpyridin-2-amine

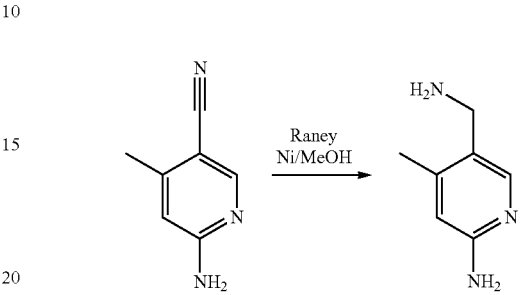

The solution of 6-amino-4-methylnicotinonitrile (200 mg, 1.5 mmol, 1.0 eq) and Raney Ni (50 mg) in MeOH (10 mL) was stirred at rt under $H_2$ (1 atm) overnight. Then the mixture was filtered and the filtrate was concentrated to give 5-(aminomethyl)-4-methylpyridin-2-amine as a yellow solid (210 mg, quant). The solid was used without further purification.

Intermediate 22: Preparation of 5-(aminomethyl)-6-(trifluoromethyl)pyridin-2-amine

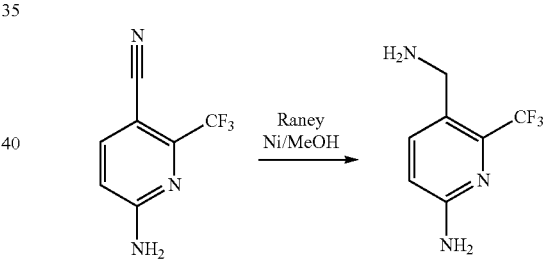

The solution of 6-amino-2-(trifluoromethyl)nicotinonitrile (200 mg, 1.06 mmol, 1.0 eq) and Raney Ni (50 mg) in MeOH (10 mL) was stirred at rt under $H_2$ (1 atm) overnight. Then the mixture was filtered and the filtrate was concentrated to give 5-(aminomethyl)-6-(trifluoromethyl)pyridin-2-amine as a yellow solid (204 mg, quant). The solid was used without further purification.

Intermediate 23: Preparation of tert-butyl 5-(aminomethyl)benzo[d]isoxazol-3-ylcarbamate

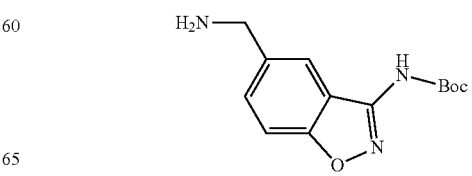

Step 1: Preparation of 5-methylbenzo[d]isoxazol-3-amine

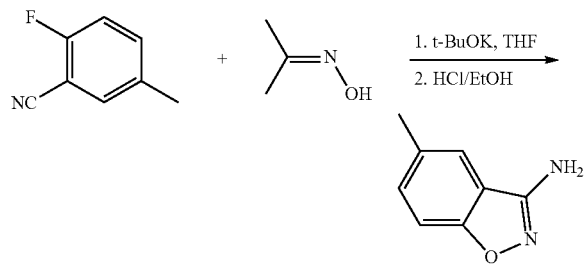

Potassium tert-butylate (4.57 g, 40.8 mmol, 1.1 eq.) was suspended in THF (40 mL). Acetone oxime (2.97 g, 40.7 mmol, 1.1 eq.) was added and the mixture was stirred at rt for 20 min., followed by the addition of a solution of 2-fluoro-5-methylbenzonitrile (5.00 g, 37 mmol, 1.0 eq.) in THF (30 mL) dropwise. The mixture was stirred at rt for 3 h and then refluxed overnight. The dark brown solution was quenched with water (10 mL). The mixture was partitioned between saturated $NaHCO_3$ aqueous solution (50 mL) and ethyl acetate (150 mL). The aqueous layer was extracted with ethyl acetate (50 mL). The combined organic layers were dried over anhydrous $Na_2SO_4$ and concentrated to afford brown oil. The crude oil was dissolved in EtOH (80 mL). $H_2O$ (53 mL) and conc. HCl (27 mL) was added and the mixture was stirred at 90° C. for 2 h. Cooled to rt and the mixture was basified with NaOH aqueous solution to pH 10. The aqueous layer was extracted with ethyl acetate (100 mL×3). The combined organic layers were dried over anhydrous $Na_2SO_4$ and concentrated. The residue was purified via flash chromatography (PE/EtOAc=5/1, v/v) to afford 5-methylbenzo[d]isoxazol-3-amine as a white solid (2.5 g, 45.6%).

Step 2: Preparation of 5-methylbenzo[d]isoxazol-3-amine di(tert-butyl carbamate)

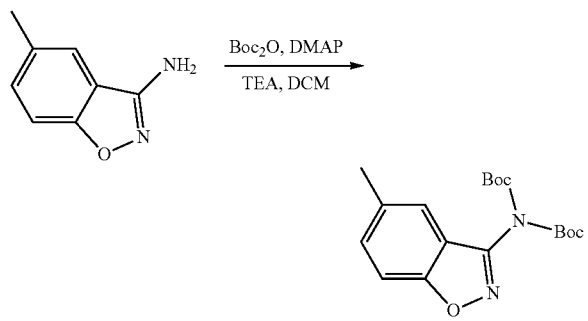

A mixture of 5-methylbenzo[d]isoxazol-3-amine (1.48 g, 10 mmol, 1.0 eq.), $Boc_2O$ (6.54 g, 30 mmol, 3.0 eq.), DMAP (122 mg, 1.0 mmol, 0.1 eq.), TEA (4.2 mL, 30 mmol, 3.0 eq.) in DCM (30 mL) was refluxed for 18 h. The mixture was washed with water (30 mL×2), dried over anhydrous $Na_2SO_4$ and concentrated. The residue was purified via flash chromatography (PE/EtOAc/DCM=1/20/1-1/7/1, v/v/v) to 5-methylbenzo[d]isoxazol-3-amine di(tert-butyl carbamate) as a white solid (3.2 g, 92%).

Step 3: Preparation of 5-(bromomethyl)benzo[d]isoxazol-3-amine di(tert-butyl carbamate)

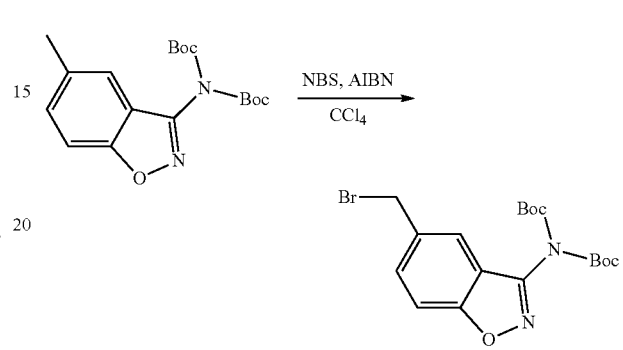

A mixture of 5-methylbenzo[d]isoxazol-3-amine di(tert-buytl carbamate) (1.04 g, 3 mmol, 1.0 eq.), NBS (536 mg, 3 mmol, 1.0 eq.), AIBN (53 mg, 0.32 mmol, 0.1 eq.) in $CCl_4$ (30 mL) was stirred at 85° C. for 5 h. Cooled to rt and the mixture was filtered. The filtrate was concentrated and the residue was purified via flash chromatography (PE/EtOAc=10/1, v/v) to afford 5-(bromomethyl)benzo[d]isoxazol-3-amine di(tert-butyl carbamate) as a white solid (970 mg, 75.8%).

Step 4: Preparation of 2-((3-aminobenzo[d]isoxazol-5-yl)methyl)isoindoline-1,3-dione di(tert-butyl carbamate)

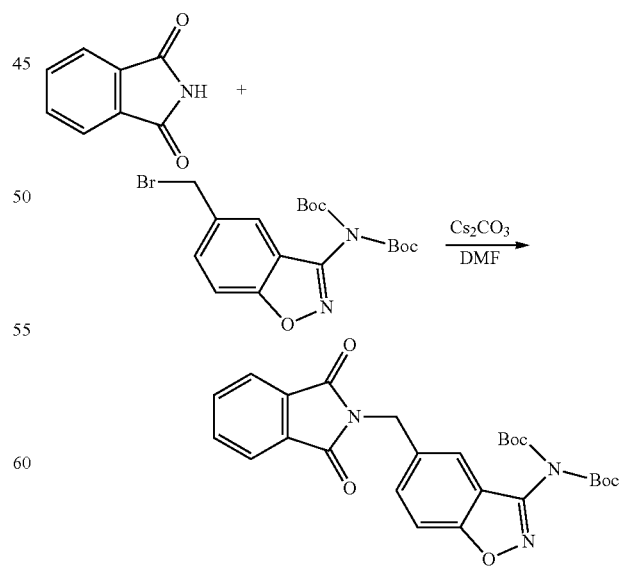

A mixture of 5-(bromomethyl)benzo[d]isoxazol-3-amine di(tert-butyl carbamate) (602 mg, 1.4 mmol, 1.0 eq.), isoindoline-1,3-dione (310 mg, 2.1 mmol, 1.5 eq.), Cs₂CO₃ (1.1 g, 3.4 mmol, 2.4 eq.) in DMF (10 mL) was stirred at 20° C. overnight. The mixture was partitioned between ethyl acetate (20 mL) and water (20 mL). The aqueous layer was extracted with ethyl acetate (20 mL×2). The combined organic layers were dried over anhydrous Na₂SO₄ and concentrated. The residue was purified via flash chromatography (PE/EtOAc=5/1, v/v) to afford 2-((3-aminobenzo[d]isoxazol-5-yl)methyl)isoindoline-1,3-dione di(tert-butyl carbamate) as a white solid (616 mg, 88.8%).

Step 5: Preparation of tert-butyl 5-(aminomethyl)benzo[d]isoxazol-3-ylcarbamate

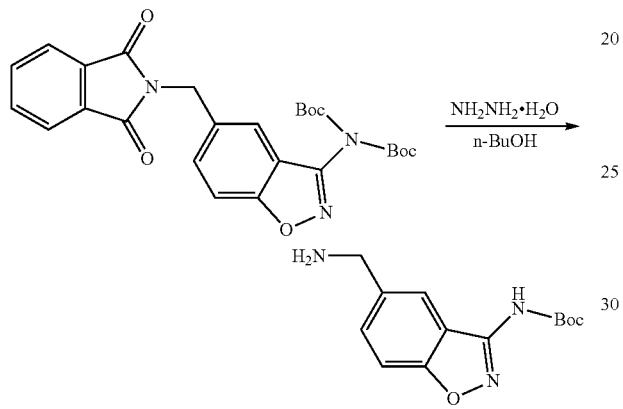

To a solution of 2-((3-aminobenzo[d]isoxazol-5-yl)methyl)isoindoline-1,3-dione di(tert-butyl carbamate) (320 mg, 0.65 mmol, 1.0 eq.) in n-BuOH (10 mL) was added NH₂NH₂.H₂O (0.20 mL). The mixture was stirred at rt overnight. The white slurry was diluted with DCM (10 mL) and filtered. The filtrate was evaporated and to the residue was triturated with Et₂O and dried to afford tert-butyl 5-(aminomethyl)benzo[d]isoxazol-3-ylcarbamate as a white solid (120 mg, 70.6%).

Intermediate 24: Preparation of 2-((6-methyl-2-(methylsulfonyl)quinolin-3-yl)methyl)isonicotinic acid

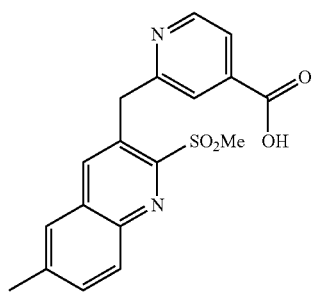 [SMILES: Cc1ccc2nc(S(C)(=O)=O)c(Cc3cc(C(=O)O)ccn3)cc2c1]

Step 1: Preparation of 2-methanesulfonyl-6-methyl-quinoline-3-carbaldehyde

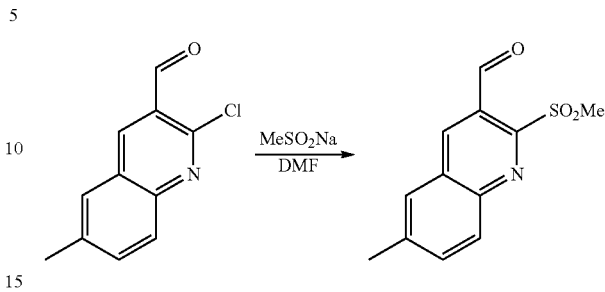

To a suspension of 2-chloro-6-methyl-quinoline-3-carbaldehyde (1.0 g, 4.88 mmol, 1 eq) in DMF (30 mL) was added sodium methanesulfinate (1.49 g, 14.6 mmol, 3 eq). The reaction mixture was stirred at 100° C. for 1 h under nitrogen. The cooled mixture was partitioned between EtOAc and water. The organic layer was separated and concentrated, and the resulting residue was purified by chromatography on silica gel column (EtOAc/PE=1/2, v/v) to give 2-methanesulfonyl-6-methyl-quinoline-3-carbaldehyde (1.1 g, 90%) as a yellow solid.

Step 2: Preparation of (2-methanesulfonyl-6-methyl-quinolin-3-yl)-methanol

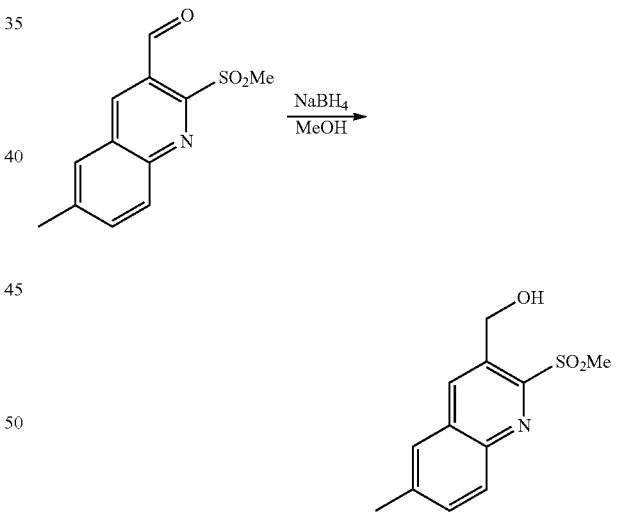

To a solution of 2-methanesulfonyl-6-methyl-quinoline-3-carbaldehyde (400 mg, 1.61 mmol, 1 eq) in MeOH (20 mL) was added NaBH₄ (67 mg, 1.77 mmol, 1.1 eq). The reaction mixture was stirred at 0° C. for 1 h. The mixture was partitioned between DCM and water. The organic layer was separated and concentrated. The resulting residue was purified by chromatography on silica gel column (EtOAc/PE=1/2, v/v) to give (2-methanesulfonyl-6-methyl-quinolin-3-yl)-methanol (395 mg, 97%) as a yellow solid.

Step 3: Preparation of 3-chloromethyl-2-methane-sulfonyl-6-methyl-quinoline

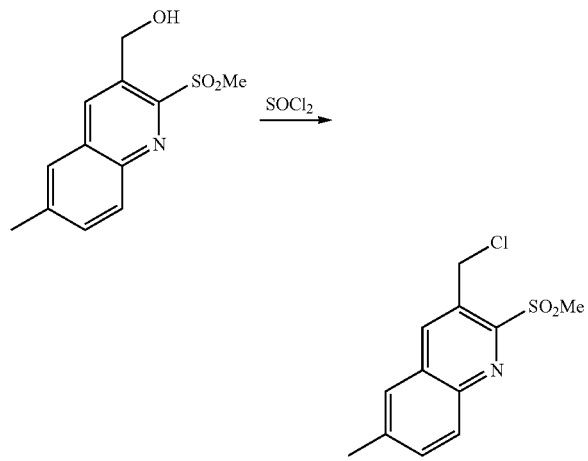

A mixture of (2-methanesulfonyl-6-methyl-quinolin-3-yl)-methanol (395 mg, 1.57 mmol, 1.0 eq) in SOCl$_2$ (10 mL) was stirred at rt for 1 h and concentrated. The resulting residue was dissolved in DCM and treated with saturated NaHCO$_3$ solution. The organic layer was concentrated to give 3-chloromethyl-2-methanesulfonyl-6-methyl-quinoline (400 mg, 95%) as a yellow solid.

Step 4: Preparation of methyl 2-((6-methyl-2-(methylsulfonyl)quinolin-3-yl)methyl)isonicotinate

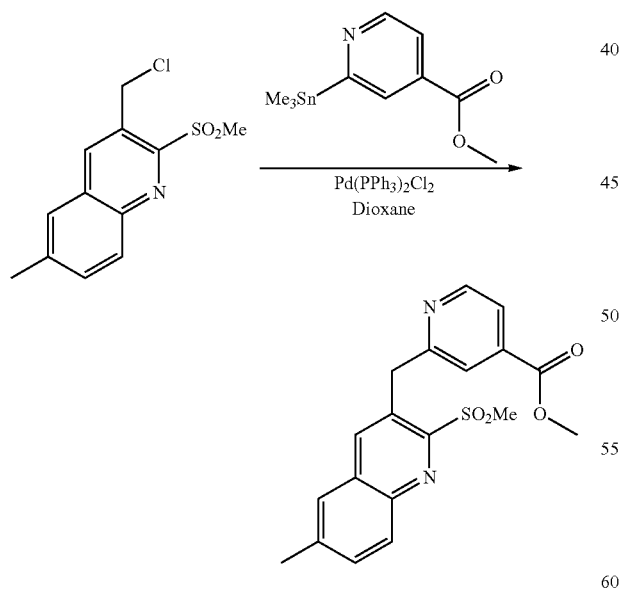

To a solution of 3-chloromethyl-2-methanesulfonyl-6-methyl-quinoline (400 mg, 1.49 mmol, 1.0 eq) in dioxane (15 mL) was added methyl 2-(trimethylstannyl)isonicotinate (492 mg, 1.64 mmol, 1.1 eq) and Pd(PPh$_3$)$_2$Cl$_2$ (105 mg, 0.15 mmol, 0.1 eq). The mixture was stirred at 90° C. for 3 h under nitrogen atmosphere, stripped of solvent and finally purified by chromatography on silica gel column (DCM/MeOH=100/1, v/v) to afford methyl 2-((6-methyl-2-(methylsulfonyl)quinolin-3-yl)methyl)isonicotinate (100 mg, 18%) as a yellow solid.

Step 5: Preparation of 2-((6-methyl-2-(methylsulfonyl)quinolin-3-yl)methyl)isonicotinic acid

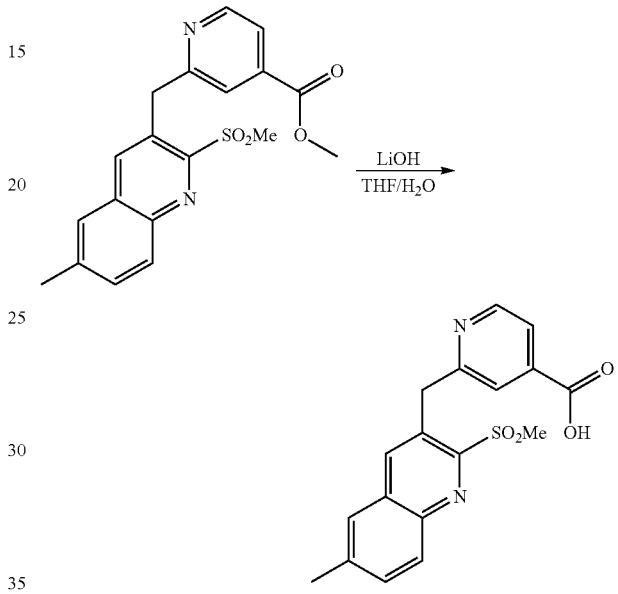

To a solution of 2-((6-methyl-2-(methylsulfonyl)quinolin-3-yl)methyl)isonicotinate (100 mg, 0.27 mmol, 1 eq) in THF/H$_2$O (5 mL, 1:1) was added LiOH.H$_2$O (17 mg, 0.41 mmol, 1.5 eq). The mixture was stirred at rt for 1 h and the mixture was acidified to pH 3 with 1 N HCl solution. The solvent was removed to give 2-((6-methyl-2-(methylsulfonyl)quinolin-3-yl)methyl)isonicotinic acid as a yellow solid which was used in the next step without further purification.

Intermediate 25: Preparation of 2-((3-cyanoquinolin-6-yl)methyl)isonicotinic acid

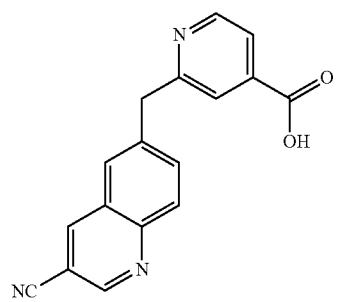 [SMILES: N#Cc1cnc2ccc(Cc3cc(C(=O)O)ccn3)cc2c1]

Step 1: Preparation of (3-bromo-quinolin-6-yl)-methanol

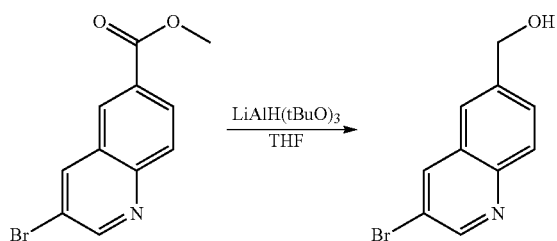

To a solution of methyl 3-bromoquinoline-6-carboxylate (4.5 g, 17.0 mmol, 1 eq) in THF (200 mL) was added LiAlH(t-BuO)$_3$ (10.78 g, 42.5 mmol, 2.5 eq). The resulting mixture was stirred at 40° C. for 12 h and then quenched by the addition of water. The mixture was extracted with EtOAc. The combined extracts were dried and concentrated. The resulting residue was purified by chromatography on silica gel column (PE/EtOAc=2/1, v/v) to afford (3-bromo-quinolin-6-yl)-methanol (3.1 g, 78%) as a yellow solid.

Step 2: Preparation of 6-hydroxymethyl-quinoline-3-carbonitrile

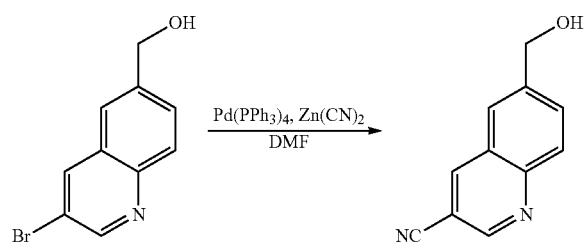

To a solution of (3-bromo-quinolin-6-yl)-methanol (3.1 g, 13.1 mmol, 1 eq) in DMF (60 mL) was added Zn(CN)$_2$ (1.52 g, 13.1 mmol, 1 eq) and Pd(PPh$_3$)$_4$ (757 mg, 0.66 mmol, 0.05 eq). The mixture was stirred at 90° C. overnight and then cooled to rt. The precipitate was filtered off and the filtrate was concentrated. The residue was purified by flash chromatography on silica gel column (PE/EtOAc=2/1, v/v) to give 6-hydroxymethyl-quinoline-3-carbonitrile (1.95 g, 81%) as a yellow solid.

Step 3: Preparation of 6-chloromethyl-quinoline-3-carbonitrile

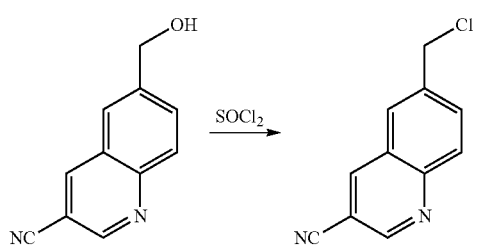

A mixture of 6-hydroxymethyl-quinoline-3-carbonitrile (1.95 g, 10.6 mmol, 1.0 eq) in SOCl$_2$ (50 mL) was stirred at rt for 1 h and concentrated. The residue was dissolved in DCM and treated with saturated NaHCO$_3$ solution. The organic layer was concentrated to give 6-chloromethyl-quinoline-3-carbonitrile (2.0 g, 93%) as a yellow solid.

Step 4: Preparation of methyl 2-((3-cyanoquinolin-6-yl)methyl)isonicotinate

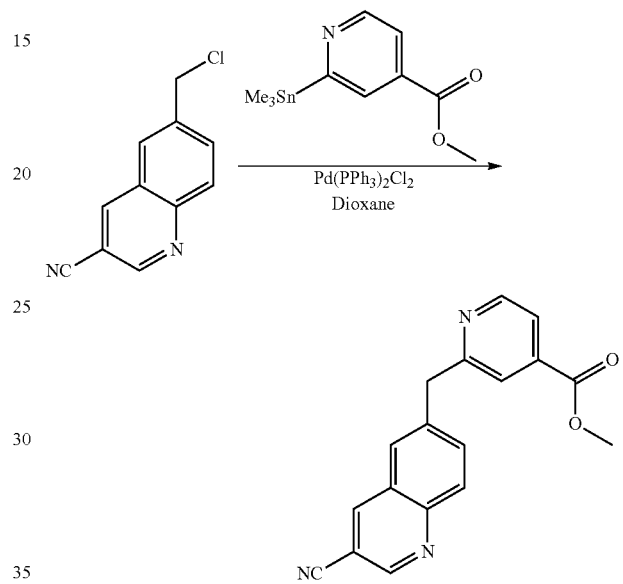

To a solution of 6-chloromethyl-quinoline-3-carbonitrile (2.0 g, 10.9 mmol, 1 eq) in dioxane (60 mL) was added methyl 2-(trimethylstannyl)isonicotinate (3.60 g, 12.0 mmol, 1.1 eq) and Pd(PPh$_3$)$_2$Cl$_2$ (770 mg, 0.11 mmol, 0.1 eq). The mixture was stirred at 90° C. for 3 h under nitrogen atmosphere, stripped of solvent and finally purified by chromatography on silica gel column (DCM/MeOH=100/1, v/v) to afford methyl 2-((3-cyanoquinolin-6-yl)methyl)isonicotinate (750 mg, 23%) as a yellow solid.

Step 5: Preparation of 2-((3-cyanoquinolin-6-yl)methyl)isonicotinic

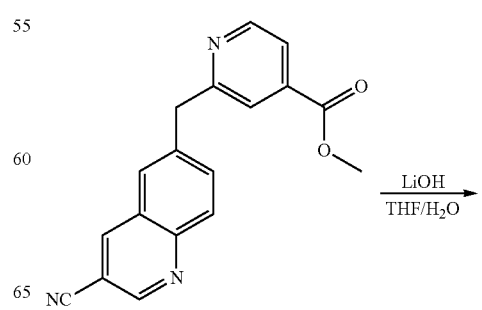

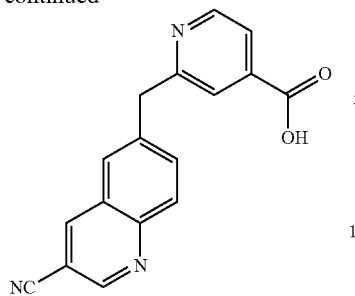

To a solution of methyl 2-((3-cyanoquinolin-6-yl)methyl) isonicotinate (750 mg, 2.47 mmol, 1 eq) in THF/H₂O (20 mL, 1:1) was added LiOH.H₂O (156 mg, 3.71 mmol, 1.5 eq). The mixture was stirred at rt for 1 h, and then it was acidified to pH 3 with 1 N HCl solution. The solvent was concentrated to give 2-((3-cyanoquinolin-6-yl)methyl)isonicotinic acid as a yellow solid which was used in the next step without further purification.

Intermediate 26: Preparation of 2-((3-chloro-8-(methoxycarbonyl)quinolin-6-yl)methyl)isonicotinic acid

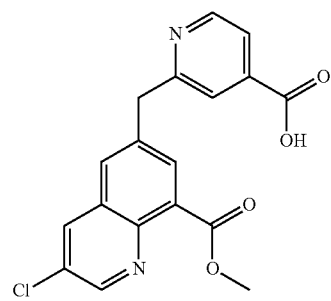 [SMILES: COC(=O)c1cc(Cc2cc(C(=O)O)ccn2)cc2cc(Cl)cnc12]

Step 1: Preparation of methyl 3-chloro-8-iodoquinoline-6-carboxylate

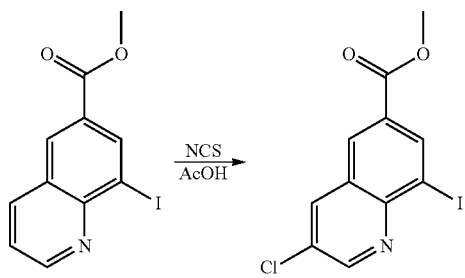 [SMILES: "AcOH" ; COC(=O)c1cc(I)c2ncccc2c1 ; "NCS" ; COC(=O)c1cc(I)c2ncc(Cl)cc2c1]

To a solution of methyl 8-iodoquinoline-6-carboxylate (30 g, 96 mmol, 1.0 eq) in AcOH (1.0 L) was added NCS (38 g, 293 mmol, 3 eq). The mixture was stirred at 100° C. overnight, The mixture was concentrated in vacuo and the residue was purified by chromatography on silica gel column (PE/DCM=1/1, v/v) to afford methyl 3-chloro-8-iodo-quinoline-6-carboxylate (15 g, 49%) as yellow solid.

Step 2: Preparation of (3-chloro-8-iodo-quinolin-6-yl)-methanol

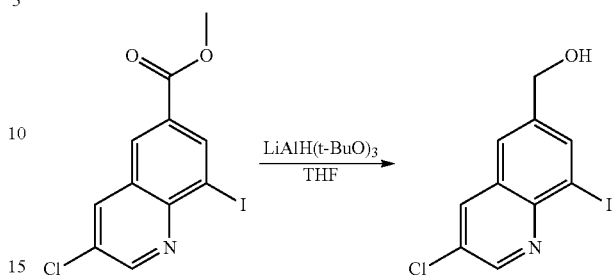

To a solution of methyl 3-chloro-8-iodoquinoline-6-carboxylate (12 g, 34.5 mmol, 1.0 eq) in dry THF (200 mL) was added lithium tri-tert-butoxyaluminum hydride (22 g, 70 mmol, 3.4 eq) carefully. The mixture was stirred at 50° C. for 5 h under N₂ protected. Then EtOAc and water was added. The organic layer was concentrated, and purified by chromatography on silica gel column (PE/DCM=1/1, v/v) to afford (3-chloro-8-iodo-quinolin-6-yl)-methanol (7.6 g, 69%) as white solid.

Step 3: Preparation of 3-chloro-6-hydroxymethyl-quinoline-8-carbonitrile

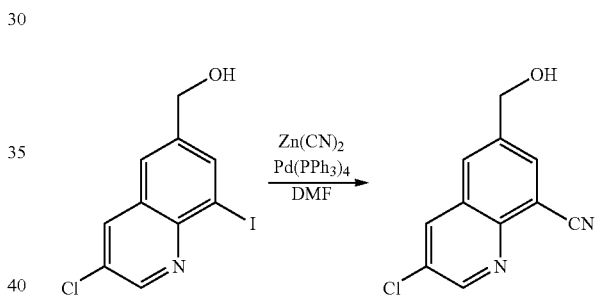

To a solution of (3-chloro-8-iodo-quinolin-6-yl)-methanol (7.6 g, 23.8 mmol, 1.0 eq) in DMF (100 mL) was added Zn(CN)₂ (2.79 g, 23.8 mmol, 1.0 eq) and Pd(PPh₃)₄ (2.75 g, 2.38 mmol, 0.1 eq) carefully. The mixture was stirred at 50° C. overnight under N₂ protected. Then EtOAc and water was added. The organic layer was concentrated, and purified by chromatography on silica gel column (PE/DCM=1/2, v/v) to afford 3-chloro-6-hydroxymethyl-quinoline-8-carbonitrile (5.0 g, 96%) as yellow solid.

Step 4: Preparation of 3-chloro-6-chloromethyl-quinoline-8-carbonitrile

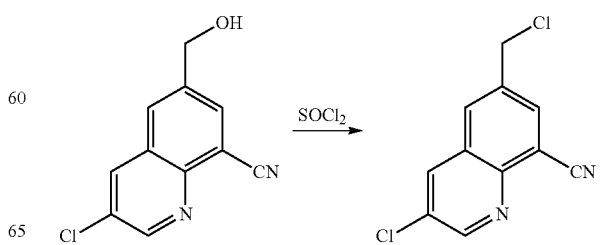

A mixture of 3-chloro-6-hydroxymethyl-quinoline-8-carbonitrile (2.9 g, 13.3 mmol, 1.0 eq) in SOCl$_2$ (50 mL) was stirred at rt for 1 h and concentrated. The residue was dissolved in DCM and treated with saturated NaHCO$_3$ solution to give 3-chloro-6-chloromethyl-quinoline-8-carbonitrile (2.2 g, 70%) as a yellow solid.

Step 5: Preparation of methyl 2-((3-chloro-8-cyanoquinolin-6-yl)methyl)isonicotinate

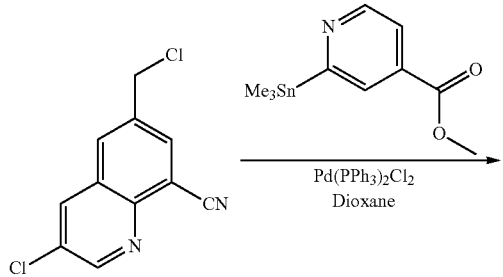

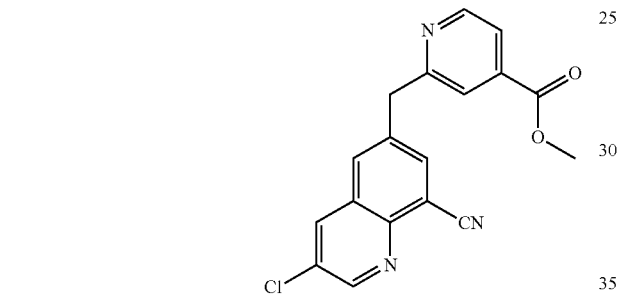

To a solution of 3-chloro-6-chloromethyl-quinoline-8-carbonitrile (2.0 g, 8.47 mmol, 1.0 eq) in dioxane (40 mL) was added methyl 2-(trimethylstannyl)isonicotinate (2.8 g, 9.32 mmol, 1.1 eq) and Pd(PPh$_3$)$_2$Cl$_2$ (597 mg, 0.85 mmol, 0.1 eq). The mixture was stirred at 90° C. for 3 h under nitrogen atmosphere, concentrated and purified by chromatography on silica gel column (DCM/MeOH=100/1, v/v) to afford methyl 2-((3-chloro-8-cyanoquinolin-6-yl)methyl) isonicotinate (1.4 g, 49%) as a yellow solid.

Step 6: Preparation of methyl 3-chloro-6-((4-(methoxycarbonyl)pyridin-2-yl)methyl)quinoline-8-carboxylate

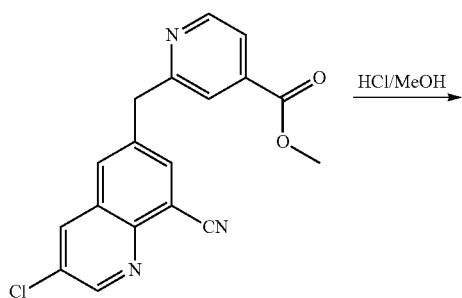

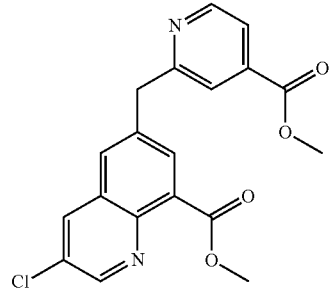

A mixture of methyl 2-((3-chloro-8-cyanoquinolin-6-yl) methyl)isonicotinate (1.20 g, 3.56 mmol, 1 eq) in HCl/MeOH (10 N, 100 mL) was heated under 80° C. for 7 days and then concentrated. The residue was dissolved in DCM and treated with saturated NaHCO$_3$ solution. The organic layer was concentrated and the residue was purified by flash chromatography on silica gel column (PE/EtOAc=1/1, v/v) to give methyl 3-chloro-6-((4-(methoxycarbonyl)pyridin-2-yl)methyl)quinoline-8-carboxylate (900 mg, 68%) as a yellow solid.

Step 7: Preparation of 2-((3-chloro-8-(methoxycarbonyl)quinolin-6-yl)methyl)isonicotinic acid

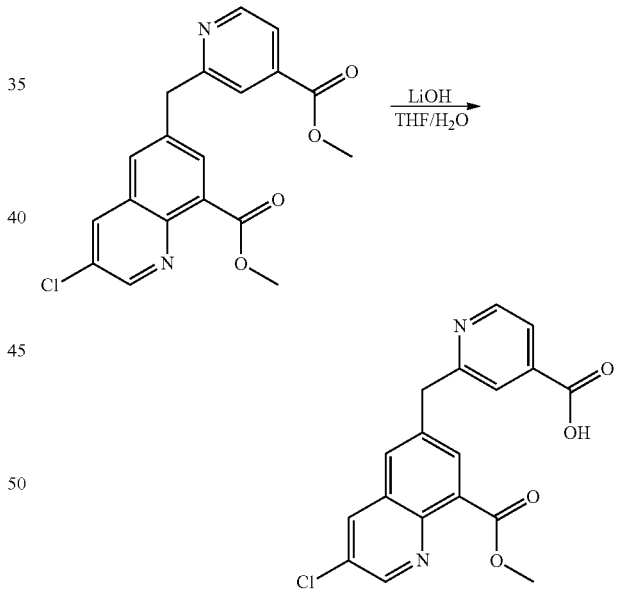

To a solution of methyl 3-chloro-6-((4-(methoxycarbonyl)pyridin-2-yl)methyl)quinoline-8-carboxylate (900 mg, 2.43 mmol, 1 eq) in THF/H$_2$O (20 mL, 1:1) was added LiOH.H$_2$O (102 mg, 2.43 mmol, 1.0 eq). The mixture was stirred at rt for 1 h and the mixture was acidified to pH 3 with 1 N HCl solution. The mixture was extracted with DCM and the combined organic layers were dried and concentrated. The residue was purified by flash chromatography on silica gel column (DCM/MeOH=10/1, v/v) to give 2-((3-chloro-8-(methoxycarbonyl)quinolin-6-yl)methyl)isonicotinic acid (400 mg, 46%) as a yellow solid.

Intermediate 27: Preparation of 2-((8-cyano-3-methylquinolin-6-yl)methyl)isonicotinic acid

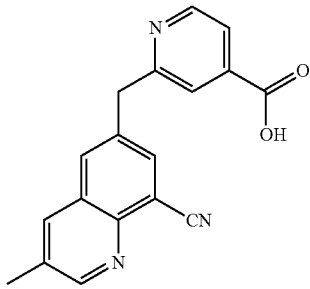 [SMILES: Cc1cnc2c(C#N)cc(Cc3cc(C(=O)O)ccn3)cc2c1]

Step 1: Preparation of methyl 4-amino-3-iodobenzoate

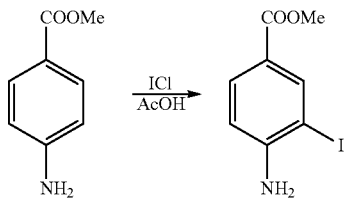

To a solution of methyl 4-aminobenzoate (20 g, 0.132 mol, 1 eq) in AcOH (500 mL) was added a solution of ICl (23.6 g, 0.146 mol, 1.1 eq) in AcOH (500 mL) at 0° C. The mixture was stirred at rt for 2 h. AcOH was concentrated under reduced pressure. The residue was diluted with DCM and washed with saturated $NaHCO_3$. The aqueous layer was extracted with DCM and the combined extracts were dried and concentrated. The resulting residue was purified by chromatography on silica gel column (EtOAc/PE=1/15, v/v) to give methyl 4-amino-3-iodobenzoate (27.4 g, 75%) as an off-white solid.

Step 2: Preparation of methyl 8-iodo-3-methylquinoline-6-carboxylate

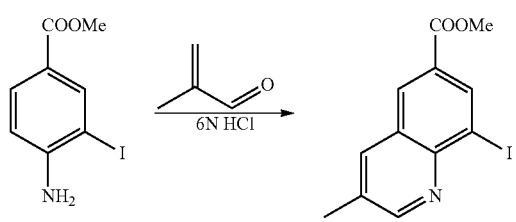

A mixture of methyl 4-amino-3-iodobenzoate (26 g, 93.5 mmol), 2-methyl-propenal (24.5 g, 0.28 mol, 3 eq) and 6 N HCl (95 mL) was heated to reflux for 24 h. Then the mixture was cooled and adjusted to pH ~5-6 using saturated $NaHCO_3$. The mixture was extracted with DCM. The combined organic layers were washed with brine, dried over $MgSO_4$, filtered then concentrated and purified by chromatography on silica gel column (EtOAc/PE=1/20, v/v) to give methyl 8-iodo-3-methylquinoline-6-carboxylate (10.2 g, 33%) as a yellow solid.

Step 3: Preparation of (8-iodo-3-methyl-quinolin-6-yl)-methanol

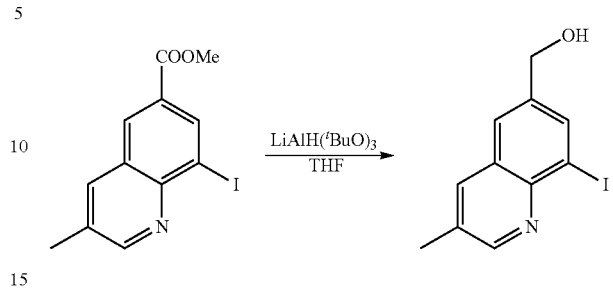

To a solution of methyl 8-iodo-3-methylquinoline-6-carboxylate (7.5 g, 22.9 mmol, 1 eq) in THF (200 mL) was added $LiAlH(t-BuO)_3$ (14.6 g, 57.3 mmol, 2.5 eq). The resulting mixture was stirred at 40° C. for 12 h and then quenched by the addition of water. The mixture was extracted with EtOAc. The combined extracts were dried and concentrated. The resulting residue was purified by chromatography on silica gel column (PE/EtOAc=2/1, v/v) to afford (8-iodo-3-methyl-quinolin-6-yl)-methanol (6.5 g, 95%) as a yellow solid.

Step 4: Preparation of 6-hydroxymethyl-3-methyl-quinoline-8-carbonitrile

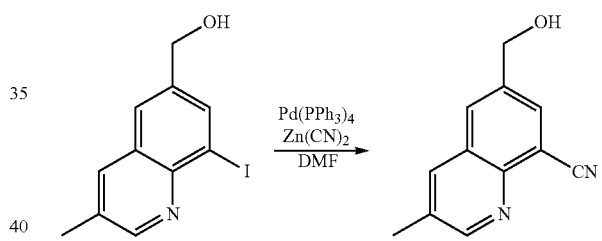

To a solution of (8-iodo-3-methyl-quinolin-6-yl)-methanol (2.1 g, 7.0 mmol, 1 eq) in DMF (50 mL) was added $Zn(CN)_2$ (815 mg, 7.0 mmol, 1 eq) and $Pd(PPh_3)_4$ (404 mg, 0.35 mmol, 0.05 eq). The mixture was stirred at 90° C. overnight and then cooled to rt. The precipitate was filtered off and the filtrate was concentrated. The resulting residue was purified by flash chromatography on silica gel column (PE/EtOAc=2/1, v/v) to give 6-hydroxymethyl-3-methyl-quinoline-8-carbonitrile (1.2 g, 86%) as a yellow solid.

Step 5: Preparation of 6-chloromethyl-quinoline-3-carbonitrile

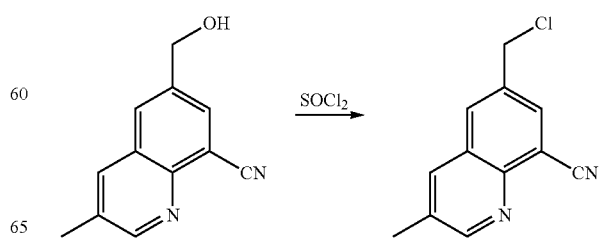

A mixture of 6-hydroxymethyl-3-methyl-quinoline-8-carbonitrile (1.2 g, 6.06 mmol, 1.0 eq) in SOCl₂ (30 mL) was stirred at rt for 1 h and concentrated. The residue was dissolved in DCM and treated with saturated NaHCO₃ solution. The organic layer was concentrated to give 6-chloromethyl-quinoline-3-carbonitrile (1.2 g, 92%) as a yellow solid.

Step 6: Preparation of methyl 2-((8-cyano-3-methylquinolin-6-yl)methyl)isonicotinate

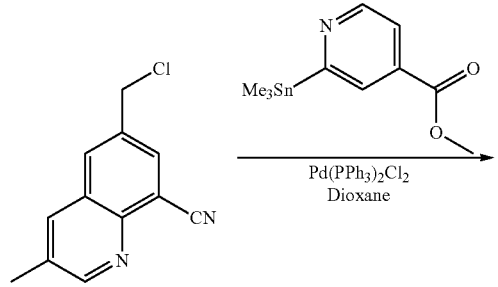

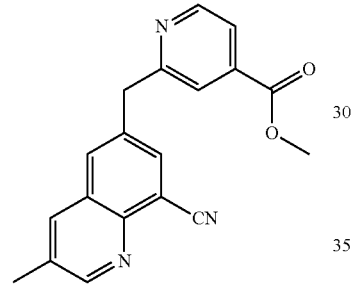

To a solution of 6-chloromethyl-quinoline-3-carbonitrile (1.2 g, 5.55 mmol, 1 eq) in dioxane (60 mL) was added methyl 2-(trimethylstannyl)isonicotinate (1.84 g, 6.11 mmol, 1.1 eq) and Pd(PPh₃)₂Cl₂ (428 mg, 0.61 mmol, 0.1 eq). The mixture was stirred at 90° C. for 3 h under nitrogen atmosphere, stripped of solvent and finally purified by chromatography on silica gel column (DCM/MeOH=100/1, v/v) to afford methyl 2-((8-cyano-3-methylquinolin-6-yl)methyl)isonicotinate (1.1 g, 62%) as a yellow solid.

Step 7: Preparation of 2-((8-cyano-3-methylquinolin-6-yl)methyl)isonicotinic acid

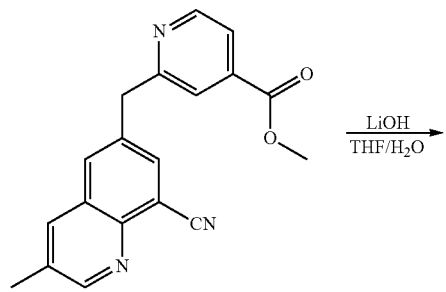

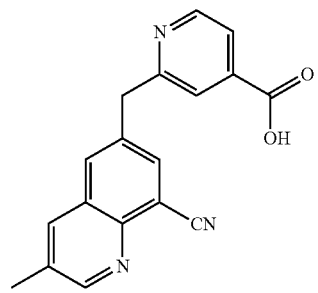

To a solution of methyl 2-((8-cyano-3-methylquinolin-6-yl)methyl)isonicotinate (1.1 g, 3.47 mmol, 1 eq) in THF/H₂O (30 mL, 1:1) was added LiOH.H₂O (219 mg, 5.21 mmol, 1.5 eq). The mixture was stirred at rt for 1 h and the mixture was acidified to pH 3 with 1 N HCl solution. The mixture was extracted with DCM, and the combined organic layers were dried and concentrated give 2-((8-cyano-3-methylquinolin-6-yl)methyl)isonicotinic acid (950 mg, 91%) as a white solid which was used without further purification.

Intermediate 28: Preparation of 2-((3-methyl-1H-indol-5-yl)methyl)isonicotinic acid

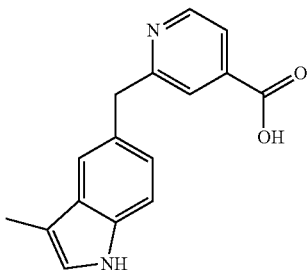 [SMILES: Cc1c[nH]c2ccc(Cc3cc(C(=O)O)ccn3)cc12]

Step 1: Preparation of methyl 3-chloro-1H-indole-5-carboxylate

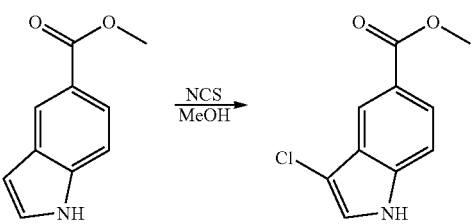

To a solution of methyl 1H-indole-5-carboxylate (10.0 g, 57.1 mmol, 1.0 eq) in MeOH was added NCS (8.4 g, 62.8 mmol, 1.1 eq). The mixture was stirred at rt for 3 h. MeOH was removed, and the resulting residue was dissolved in EtOAc. The mixture was washed with brine twice. The organic layer was dried and concentrated to give methyl 3-chloro-1H-indole-5-carboxylate (quant.) as a yellow solid.

Step 2: Preparation of 1-tert-butyl 5-methyl 3-chloro-1H-indole-1,5-dicarboxylate

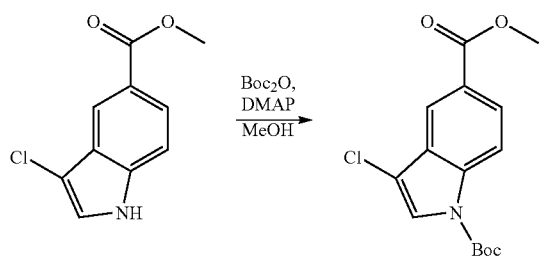 [SMILES: "MeOH" ; COC(=O)c1ccc2[nH]cc(Cl)c2c1 ; COC(=O)c1ccc2c(c1)c(Cl)cn2C(=O)OC(C)(C)C]

To a solution of methyl 3-chloro-1H-indole-5-carboxylate (11.9 g, 57.1 mmol, 1.0 eq) in MeOH was added Boc₂O (18.7 g, 86.7 mmol, 1.5 eq) and DMAP (348 mg, 2.86 mmol, 0.05 eq). The mixture was stirred at rt for 2 h. The mixture was concentrated and purified by chromatography on silica gel column (EtOAc/PE=1/10, v/v) to give 1-tert-butyl 5-methyl 3-chloro-1H-indole-1,5-dicarboxylate (13.4 g, 76%) as an off-white solid.

Step 3: Preparation of tert-butyl 3-chloro-5-(hydroxymethyl)-1H-indole-1-carboxylate

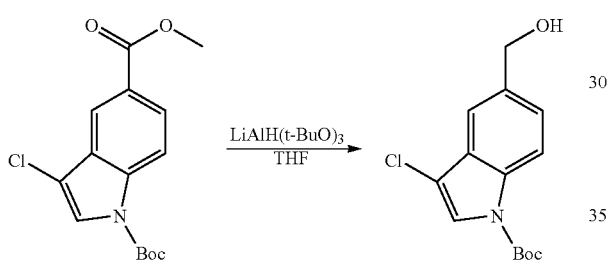

To a solution of 1-tert-butyl 5-methyl 3-chloro-1H-indole-1,5-dicarboxylate (7.0 g, 22.6 mmol, 1 eq) in THF (100 mL) was added LiAlH(t-BuO)₃ (14.4 g, 56.6 mmol, 2.5 eq). The resulting mixture was stirred at 60° C. for 12 h and then quenched by the addition of water. The mixture was extracted with EtOAc. The combined extracts were dried and concentrated. The resulting residue was purified by chromatography on silica gel column (PE/EtOAc=2/1, v/v) to afford tert-butyl 3-chloro-5-(hydroxymethyl)-1H-indole-1-carboxylate (4.3 g, 68%) as a white solid.

Step 4: Preparation of tert-butyl 3-chloro-5-(chloromethyl)-1H-indole-1-carboxylate

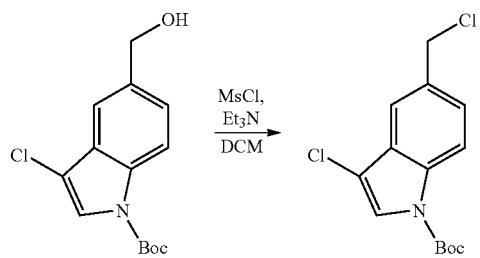 [SMILES: CC(C)(C)OC(=O)n1cc(Cl)c2cc(CO)ccc21 ; CC(C)(C)OC(=O)n1cc(Cl)c2cc(CCl)ccc21]

To a solution of tert-butyl 3-chloro-5-(hydroxymethyl)-1H-indole-1-carboxylate (1.5 g, 5.34 mmol, 1 eq) in dry DCM (30 mL) was added Et₃N (1.5 mL, 10.68 mmol, 2 eq) and MsCl (0.62 mL, 8.01 mmol, 1.5 eq). The resulting mixture was stirred at rt for 24 h and then quenched by the addition of water. The mixture was extracted with DCM. The combined extracts were dried and concentrated. The resulting residue was purified by chromatography on silica gel column (PE/EtOAc=20/1, v/v) to afford tert-butyl 3-chloro-5-(chloromethyl)-1H-indole-1-carboxylate (1.17 g, 73%) as a white solid.

Step 5: Preparation of tert-butyl 3-chloro-5-((4-(methoxycarbonyl)pyridin-2-yl)methyl)-1H-indole-1-carboxylate

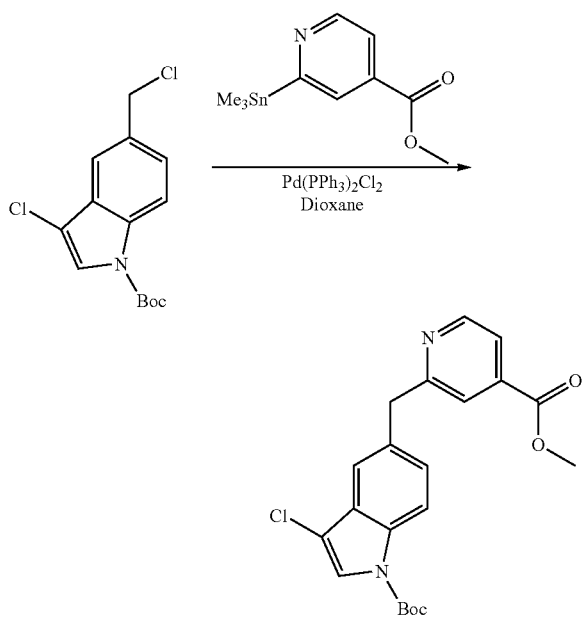

To a solution of tert-butyl 3-chloro-5-(chloromethyl)-1H-indole-1-carboxylate (1.1 g, 3.68 mmol, 1.0 eq) in dioxane (20 mL) were added methyl 2-(trimethylstannyl)isonicotinate (1.22 g, 4.05 mmol, 1.1 eq) and Pd(PPh₃)₂Cl₂ (260 mg, 0.37 mmol, 0.1 eq). The mixture was stirred at 90° C. for 3 h under nitrogen atmosphere, concentrated and purified by chromatography on silica gel column (PE/EtOAc=20/1, v/v) to afford tert-butyl 3-chloro-5-((4-(methoxycarbonyl)pyridin-2-yl)methyl)-1H-indole-1-carboxylate (690 mg, 47%) as an off-white solid.

Step 6: Preparation of tert-butyl 5-((4-(methoxycarbonyl)pyridin-2-yl)methyl)-3-methyl-1H-indole-1-carboxylate

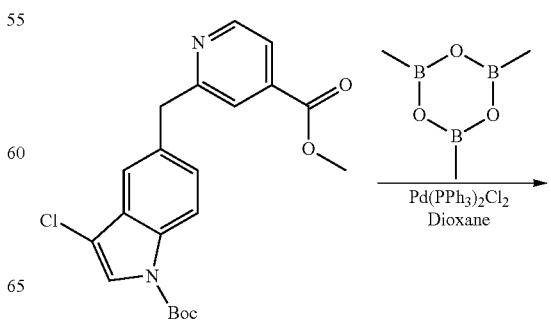

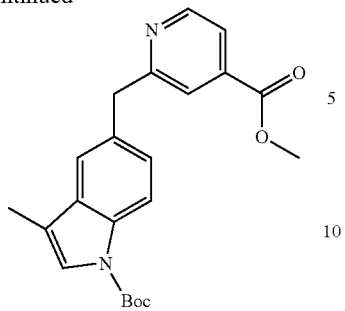

To a solution of tert-butyl 3-chloro-5-((4-(methoxycarbonyl)pyridin-2-yl)methyl)-1H-indole-1-carboxylate (400 mg, 1.0 mmol, 1 eq) in 1,4-dioxane (10 mL) was added potassium phosphate (424 mg, 2 mmol, 2 eq), trimethylboroxine (504 mg, 2 mmol, 2 eq, 50% purity in THF), tris(dibenzylideneacetone)dipalladium (46 mg, 0.05 mmol, 0.05 eq) and 2-dicyclohexylphosphino-2',4',6'-triisopropyl-1,1'-biphenyl (X-Phos) (134 mg, 0.30 mmol, 0.30 eq) under argon, and the mixture was heated to 110° C. and stirred for 4 h. Ice cooled water was then added, and the mixture was extracted with ethyl acetate. The organic layer was washed with brine, dried, and then concentrated under reduced pressure. The resulting residue was purified by chromatography on silica gel column (EtOAc/PE=1/5, v/v) to give tert-butyl 5-((4-(methoxycarbonyl)pyridin-2-yl)methyl)-3-methyl-1H-indole-1-carboxylate (280 mg, 74%) as a yellow solid.

Step 7: Preparation of 2-((3-methyl-1H-indol-5-yl)methyl)isonicotinic acid

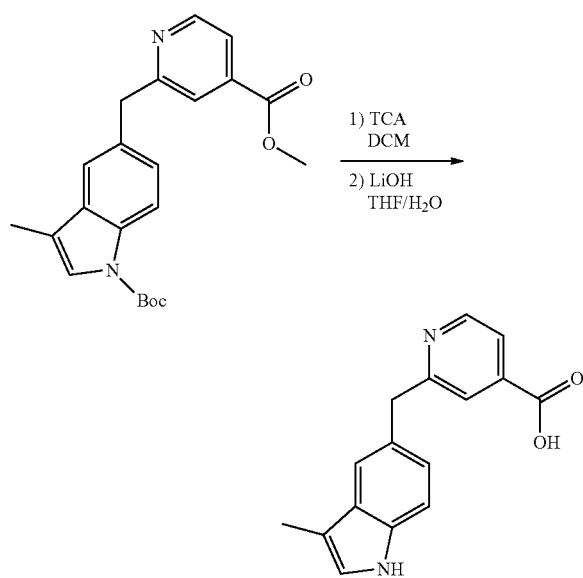

To a solution of tert-butyl 5-((4-(methoxycarbonyl)pyridin-2-yl)methyl)-3-methyl-1H-indole-1-carboxylate (280 mg, 0.74 mmol, 1 eq) in DCM (3 mL) was added TFA (3 mL). The mixture was stirred at rt for 2 h and then concentrated. The residue was diluted with DCM and washed with saturated NaHCO₃. The organic layer was concentrated and the residue was dissolved in THF/H₂O (10 mL, 1:1). To the mixture was added LiOH.H₂O (47 mg, 1.11 mmol, 1.5 eq). The mixture was stirred at rt for 1 h and the mixture was acidified to pH 3 with 1 N HCl solution. The mixture was extracted with DCM, and the combined organic layers were dried and concentrated give 2-((3-methyl-1H-indol-5-yl)methyl)isonicotinic acid (99 mg, 50%) as a yellow solid.

Intermediate 29: Preparation of 2-((2-(acetamidomethyl)quinolin-6-yl)methyl)isonicotinic acid

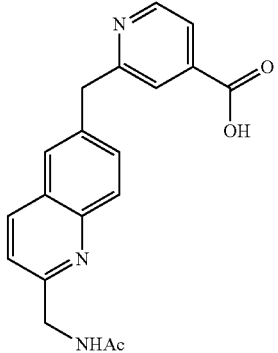 [SMILES: CC(=O)NCc1ccc2cc(Cc3cc(C(=O)O)ccn3)ccc2n1]

Step 1: Preparation of 6-(methoxycarbonyl)quinoline 1-oxide

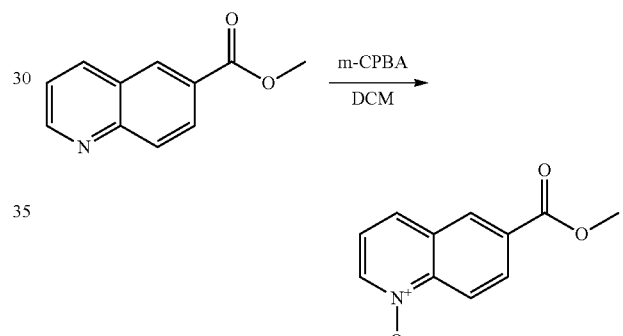

A mixture of methyl quinoline-6-carboxylate (10 g, 53.5 mmol, 1 eq) and m-CPBA (18.4 g, 0.106 mol, 2 eq) in DCM (50 mL) was stirred at rt overnight. Saturated aq. NaHCO₃ (40 mL) was added to the reaction mixture, and the resulting mixture was stirred for 30 min. The organic layer was separated, dried, filtered and concentrated. The resulting residue was recrystallized in EtOAc (5 mL) to afford 6-(methoxycarbonyl)quinoline 1-oxide (8.0 g, 74%) as a light yellow solid.

Step 2: Preparation of methyl 2-chloroquinoline-6-carboxylate and methyl 4-chloroquinoline-6-carboxylate

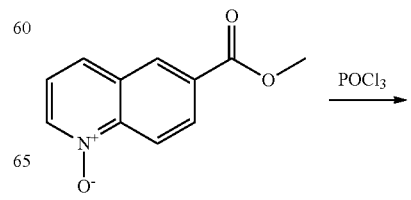

-continued

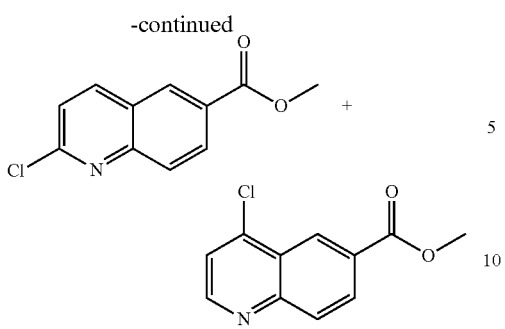

To 6-(methoxycarbonyl)quinoline 1-oxide (4.0 g, 19.7 mmol, 1 eq) was added phosphoryl trichloride (20 mL). The resulting mixture was then stirred at rt under $N_2$ for 2 h. The volatiles were then removed under vacuum and the residue was dissolved in DCM. The mixture was washed with saturated aq. $NaHCO_3$, dried and concentrated. The resulting residue was purified by chromatography on silica gel column (PE/EtOAc=10/1, v/v) to afford methyl 2-chloroquinoline-6-carboxylate (1.2 g, 28%) and methyl 4-chloroquinoline-6-carboxylate (2.5 g, 57%).

Step 3: Preparation of methyl 2-cyanoquinoline-6-carboxylate

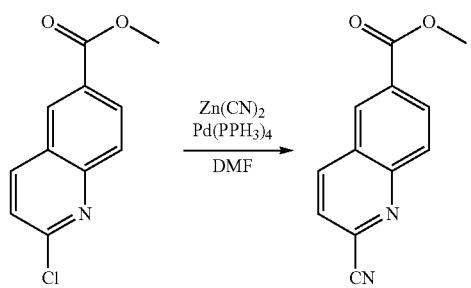

To a suspension of methyl 2-chloroquinoline-6-carboxylate (1.2 g, 5.43 mmol, 1 eq) in DMF (15 mL) was added $Zn(CN)_2$ (1.11 g, 10.86 mmol, 2 eq) and $Pd(PPh_3)_4$ (628 mg, 0.54 mmol, 0.1 eq). The reaction mixture was stirred at 100° C. for 3 h under nitrogen. The cooled mixture was partitioned between EtOAc and water. The organic layer was separated and concentrated. The resulting residue was purified by chromatography on silica gel column to give methyl 2-cyanoquinoline-6-carboxylate (980 mg, 85%) as a yellow solid.

Step 4: Preparation of 6-hydroxymethyl-quinoline-2-carbonitrile

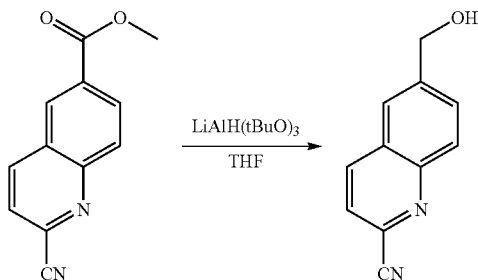 [SMILES: COC(=O)c1ccc2nc(C#N)ccc2c1 ; N#Cc1ccc2cc(CO)ccc2n1 ; "THF" ; "LiAlH(tBuO)3"]

To a suspension of methyl 2-cyanoquinoline-6-carboxylate (980 mg, 4.62 mmol, 1 eq) in dry THF (30 mL) was added LiAlH(t-BuO)$_3$ (2.94 g, 11.56 mmol, 2.5 eq). The resulting mixture was stirred at 60° C. for 12 h and then quenched by the addition of water. The mixture was extracted with EtOAc. The combined extracts were dried and concentrated. The resulting residue was purified by chromatography on silica gel column (PE/EtOAc=1/2, v/v) to afford 6-hydroxymethyl-quinoline-2-carbonitrile (722 mg, 83%) as a yellow solid.

Step 5: Preparation of 6-chloromethyl-quinoline-2-carbonitrile

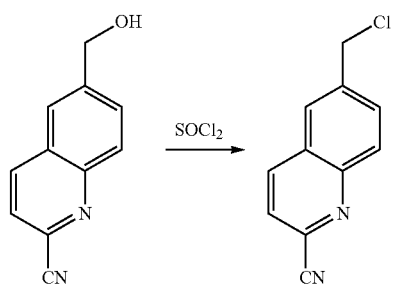

To 6-hydroxymethyl-quinoline-2-carbonitrile (2.1 g, 11.41 mmol, 1 eq) was added $SOCl_2$ (50 mL) and the mixture was stirred at rt for 3 h. The volatiles were then removed at 40° C. under vacuum and the residue was dissolved in DCM. The mixture was washed with saturated $NaHCO_3$ solution, dried and concentrated to give 6-chloromethyl-quinoline-2-carbonitrile (2.10 g, 91%) as a yellow solid.

Step 6: Preparation of methyl 2-((2-cyanoquinolin-6-yl)methyl)isonicotinate

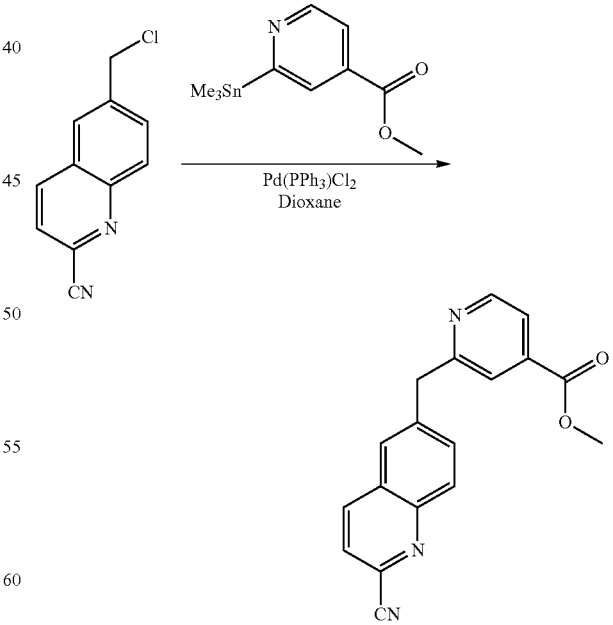

To a solution of 6-chloromethyl-quinoline-2-carbonitrile (2.10 g, 10.40 mmol, 1.0 eq) in dioxane (50 mL) was added methyl 2-(trimethylstannyl)isonicotinate (3.44 g, 11.44 mmol, 1.1 eq) and $Pd(PPh_3)_2Cl_2$ (730 mg, 1.04 mmol, 0.1 eq). The mixture was stirred at 90° C. for 3 h under nitrogen, concentrated and purified by chromatography on silica gel column (DCM/MeOH=100/1, v/v) to afford methyl 2-((2-cyanoquinolin-6-yl)methyl)isonicotinate (1.42 g, 45%) as a yellow solid.

Step 7: Preparation of methyl 2-((2-((tert-butoxycarbonylamino)methyl)quinolin-6-yl)methyl)isonicotinate

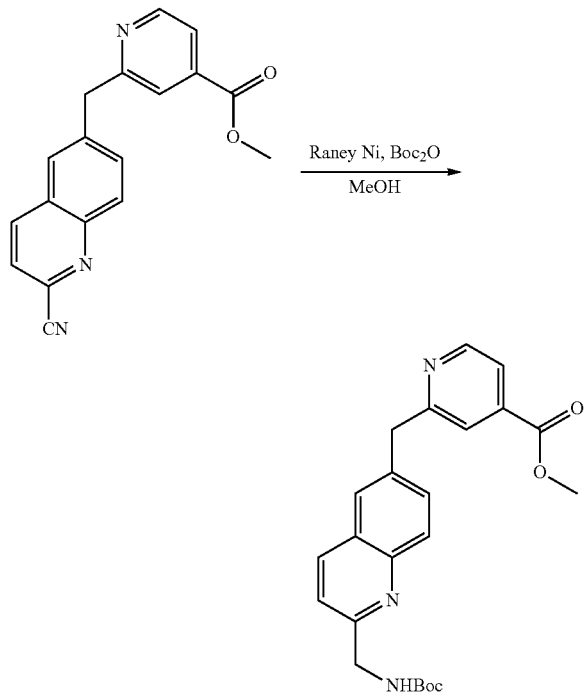

To a solution of methyl 2-((2-cyanoquinolin-6-yl)methyl)isonicotinate (1.0 g, 3.30 mmol, 1 eq) in MeOH (30 mL) were added Boc$_2$O (1.08 g, 5.00 mmol, 1.5 eq) and Raney Ni (200 mg). The mixture was stirred at rt for 5 h under hydrogen. Raney Ni was removed by filtration and the filtrate was concentrated. The resulting residue was purified by chromatography on silica gel column (EtOAc/PE=1/2, v/v) to afford methyl 2-((2-((tert-butoxycarbonylamino)methyl)quinolin-6-yl)methyl)isonicotinate (1.1 g, 82%) as a yellow solid.

Step 8: Preparation of methyl 2-((2-(acetamidomethyl)quinolin-6-yl)methyl)isonicotinate

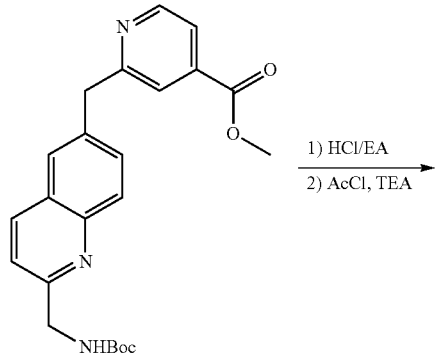

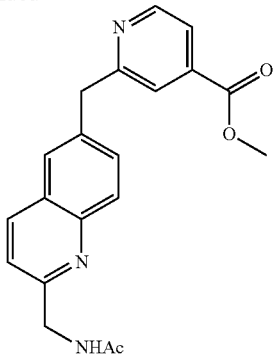

To a solution of methyl 2-((2-((tert-butoxycarbonylamino)methyl)quinolin-6-yl)methyl)isonicotinate (1.1 g, 2.70 mmol, 1 eq) in EtOAc (5 mL) was added a solution of HCl/EtOAc (30 mL, 10 N). The mixture was stirred at rt for 2 h, and the precipitate was collected by filtration. To a suspension of the above obtained crude product in DCM (30 mL) were added TEA (818 mg, 8.10 mmol, 3 eq) and AcCl (316 mg, 4.05 mmol, 1.5 eq). The mixture was stirred at rt for 1 h and the mixture was concentrated. The resulting residue was purified by chromatography on silica gel column (EtOAc/PE=1/2, v/v) to afford methyl 2-((2-(acetamidomethyl)quinolin-6-yl)methyl)isonicotinate (744 mg, 79% for 2 steps) as a yellow solid.

Step 9: Preparation of 2-[2-(acetylamino-methyl)-quinolin-6-ylmethyl]-isonicotinic acid

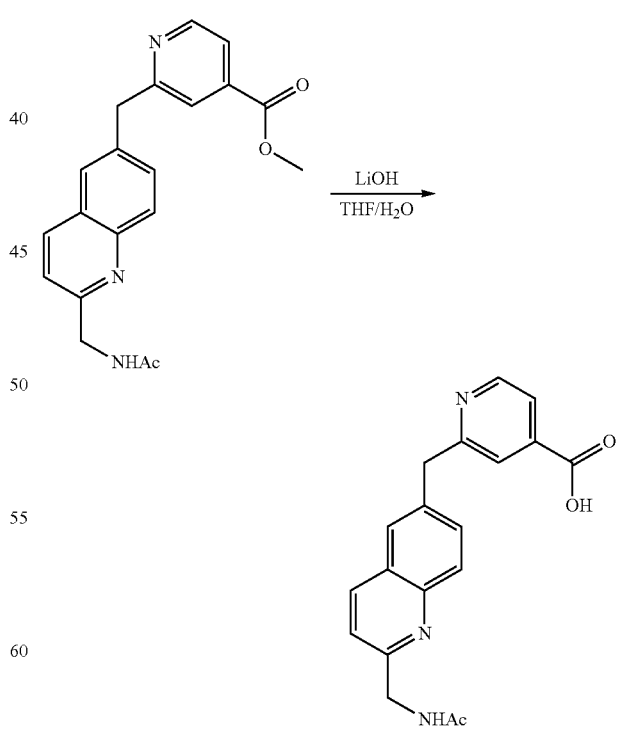

To a solution of methyl 2-((2-(acetamidomethyl)quinolin-6-yl)methyl)isonicotinate (744 mg, 2.13 mmol, 1 eq) in THF/H$_2$O (30 mL, 1:1) was added LiOH.H$_2$O (134 mg, 3.20 mmol, 1.5 eq). The mixture was stirred at rt for 1 h, and acidified to pH 3 with 1 N HCl solution. The mixture was extracted with DCM. The organic layer was washed with brine and then dried and concentrated to give 2-[2-(acetylamino-methyl)-quinolin-6-ylmethyl]-isonicotinic acid (649 mg, 91%) as a yellow solid which was used without further purification.

Intermediate 30: Preparation of 2-((2-(methylsulfonyl)quinolin-6-yl)methyl)isonicotinic acid

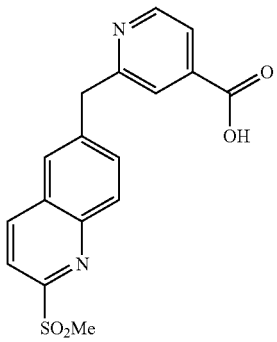 [SMILES: CS(=O)(=O)c1ccc2cc(Cc3cc(C(=O)O)ccn3)ccc2n1]

Step 1: Preparation of methyl 2-(methylsulfonyl)quinoline-6-carboxylate

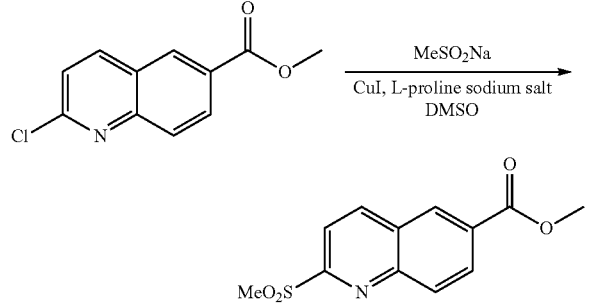

A mixture of methyl 2-chloroquinoline-6-carboxylate (1.2 g, 5.43 mmol, 1 eq), sodium methanesulphinate (665 mg, 6.51 mmol, 1.2 eq), copper iodide (103 mg, 0.54 mol, 0.1 eq), L-proline sodium salt (148 mg, 1.08 mol, 0.2 eq) in 110 mL of DMSO was heated to 110° C. under nitrogen and stirred for 15 h. The cooled mixture was partitioned between ethyl acetate and water. The organic layer was separated, and the aqueous layer was extracted with ethyl acetate twice. The combined organic layers were washed with brine, dried over MgSO$_4$, and concentrated in vacuo. The resulting residue was purified by chromatography on silica gel column (EtOAc/PE=1/2, v/v) to give methyl 2-(methylsulfonyl)quinoline-6-carboxylate (830 mg, 58%) as a yellow solid.

Step 2: Preparation of (2-methanesulfonyl-quinolin-6-yl)-methanol

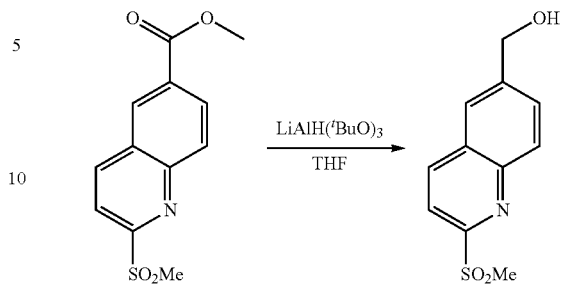

To a solution of methyl 2-(methylsulfonyl)quinoline-6-carboxylate (830 mg, 3.13 mmol, 1 eq) in THF (40 mL) was added LiAlH(t-BuO)$_3$ (2.0 g, 7.83 mmol, 2.5 eq). The resulting mixture was stirred at 40° C. for 12 h and then quenched by the addition of water. The mixture was extracted with EtOAc. The combined extracts were dried and concentrated. The resulting residue was purified by chromatography on silica gel column (PE/EtOAc=1/1, v/v) to afford (2-methanesulfonyl-quinolin-6-yl)-methanol (600 mg, 81%) as a yellow solid.

Step 3: Preparation of 6-chloromethyl-2-methanesulfonyl-quinoline

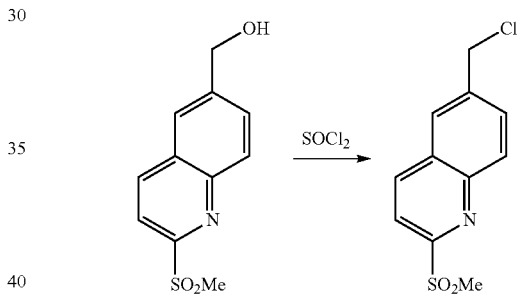

A mixture of (2-methanesulfonyl-quinolin-6-yl)-methanol (580 mg, 2.48 mmol, 1.0 eq) in SOCl$_2$ (10 mL) was stirred at rt for 1 h and concentrated. The residue was dissolved in DCM and treated with saturated NaHCO$_3$ solution. The organic layer was concentrated to give 6-chloromethyl-2-methanesulfonyl-quinoline (570 mg, 90%) as a yellow solid.

Step 4: Preparation of methyl 2-((2-(methylsulfonyl)quinolin-6-yl)methyl)isonicotinate

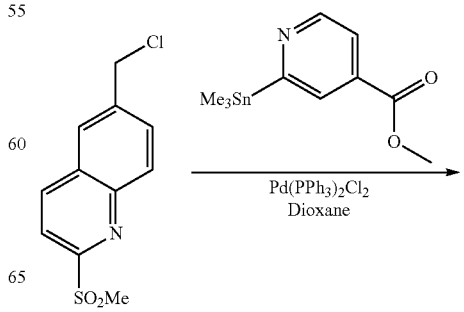

211

-continued

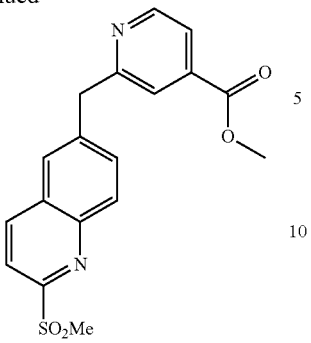

To a solution of 6-chloromethyl-2-methanesulfonyl-quinoline (560 mg, 2.20 mmol, 1.0 eq) in dioxane (15 mL) was added methyl 2-(trimethylstannyl)isonicotinate (727 mg, 2.42 mmol, 1.1 eq) and Pd(PPh₃)₂Cl₂ (154 mg, 0.22 mmol, 0.1 eq). The mixture was stirred at 90° C. for 3 h under nitrogen, concentrated and purified by chromatography on silica gel column (DCM/MeOH=100/1, v/v) to afford methyl 2-((2-(methylsulfonyl)quinolin-6-yl)methyl)isonicotinate (140 mg, 18%) as a yellow solid.

Step 5: Preparation of 2-((2-(methylsulfonyl)quinolin-6-yl)methyl)isonicotinic acid

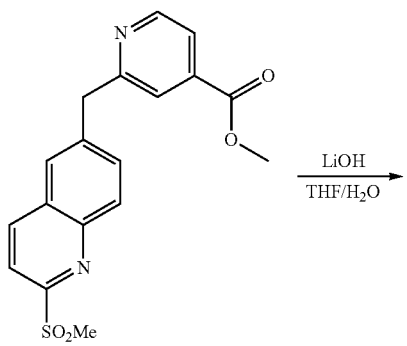

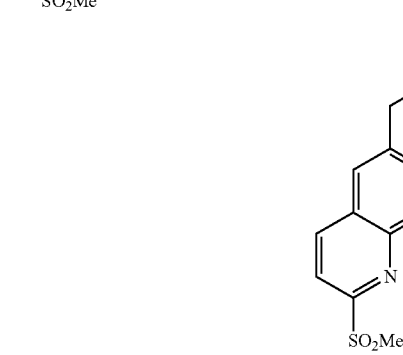

To a solution of methyl 2-((2-(methylsulfonyl)quinolin-6-yl)methyl)isonicotinate (140 mg, 0.39 mmol, 1 eq) in THF/H₂O (5 mL, 1:1) was added LiOH.H₂O (25 mg, 0.59 mmol, 1.5 eq). The mixture was stirred at rt for 1 h, and acidified to pH 3 with 1 N HCl solution. The solvent was removed to give 2-((2-(methylsulfonyl)quinolin-6-yl)methyl)isonicotinic acid as a yellow solid which was used in the next step without further purification.

212

Intermediate 31: Preparation of (3-chloro-4-fluoro-1H-indol-5-yl)methanamine hydrochloride

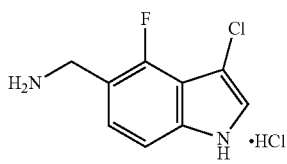 [SMILES: NCc1ccc2[nH]cc(Cl)c2c1F ; Cl]

Step 1: Preparation of 4-fluoro-1-triisopropylsilanyl-1H-indole

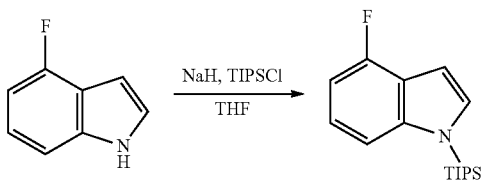

To a solution of 4-fluoro-1H-indole (5.0 g, 37.04 mmol, 1.0 eq) in dry THF (200 mL) was added a solution of NaH (1.63 g, 40.74 mmol, 1.1 eq, 60% purity) at 0° C. After stirring for 0.5 h, TIPSCl (7.8 g, 40.74 mmol, 1.1 eq) was added. Then the mixture was stirred at rt for 1 h and quenched by the addition of water. The mixture was extracted with EtOAc. The combined organic layers were dried and concentrated. The resulting residue was purified by chromatography on silica gel column (PE/EtOAc=10/1, v/v) to afford 4-fluoro-1-triisopropylsilanyl-1H-indole (10.0 g, 84%) as a yellow oil.

Step 2: Preparation of 4-fluoro-1-(triisopropylsilyl)-1H-indole-5-carbaldehyde

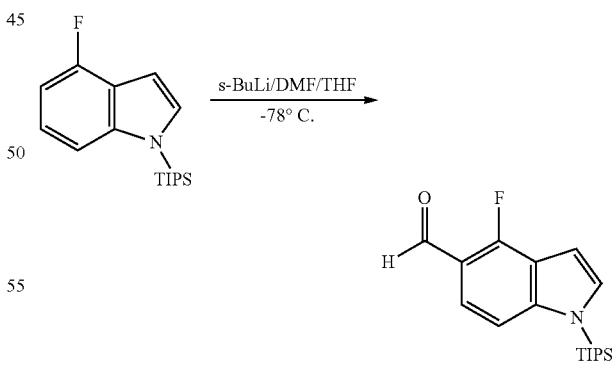

To a solution of 4-fluoro-1-triisopropylsilanyl-1H-indole (10 g, 34.36 mmol, 1.0 eq) in THF (30 mL) was added s-BuLi (27.5 mL, 41.24 mmol, 1.5 M, 1.2 eq) at −78° C. slowly. The mixture was stirred for 1 h. DMF (7.52 g, 103 mmol, 3.0 eq) was added dropwise. The mixture was stirred at −78° C. for 1 h. The reaction was quenched by saturated aq. NH₄Cl. The mixture was extracted with EtOAc (50 mL×3). The organic layers were combined and washed with brine, dried over Na₂SO₄, filtered and concentrated. The residue was purified by chromatography on silica gel column (PE/EtOAc=100/1) to give 4-fluoro-1-(triisopropylsilyl)-1H-indole-5-carbaldehyde (6.6 g, 60%) as a yellow oil.

Step 3: Preparation of 4-fluoro-1H-indole-5-carbaldehyde oxime

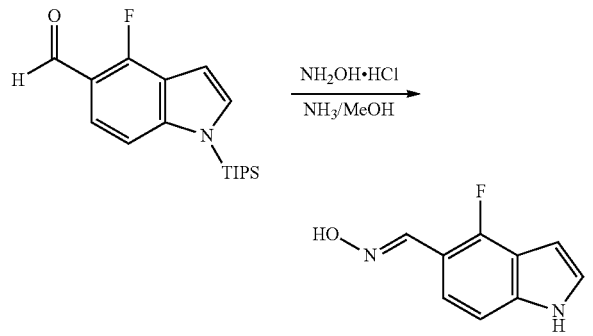

A mixture of 4-fluoro-1-(triisopropylsilyl)-1H-indole-5-carbaldehyde (6.5 g, 20.4 mmol, 1.0 eq) and NH₂OH.HCl (2.82 g, 40.8 mmol, 2.0 eq) in NH₃/MeOH (15% w/w, 200 mL) was stirred at rt overnight. The mixture was concentrated. The residue was purified by chromatography on silica gel column (PE/EtOAc=50/1) to afford 4-fluoro-1H-indole-5-carbaldehyde oxime (3.6 g, crude) as a yellow solid.

Step 4: Preparation of (4-fluoro-1H-indol-5-yl)methanamine

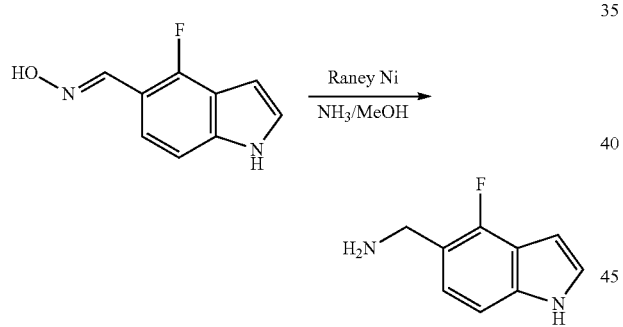

A mixture of 4-fluoro-1H-indole-5-carbaldehyde oxime (3.6 g, 20.2 mmol, 1.0 eq) and Raney Ni (600 mg) in NH₃/MeOH (15% w/w, 200 mL) was stirred at rt under H₂ atmosphere (1 atm) overnight. The mixture was filtered and concentrated to afford (4-fluoro-1H-indol-5-yl)methanamine (3.0 g, 92%) as a gray solid, which was used in the next step without further purification.

Step 5: Preparation of tert-butyl (4-fluoro-1H-indol-5-yl)methylcarbamate

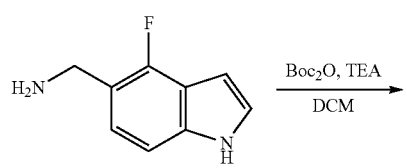

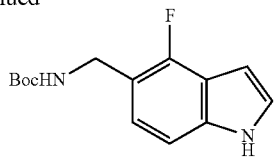

To a solution of (4-fluoro-1H-indol-5-yl)methanamine (3.0 g, 18.3 mmol, 1.0 eq) in DCM (150 mL) was added TEA (2.22 g, 22.0 mmol, 1.2 eq) and Boc₂O (4.80 g, 22.0 mmol, 1.2 eq). The mixture was stirred at rt for 2 h and concentrated. The residue was purified by chromatography on silica gel column (PE/EtOAc=10/1, v/v) to afford tert-butyl (4-fluoro-1H-indol-5-yl)methylcarbamate (4.2 g, 87%) as a yellow solid.

Step 6: Preparation of tert-butyl (3-chloro-4-fluoro-1H-indol-5-yl)methylcarbamate

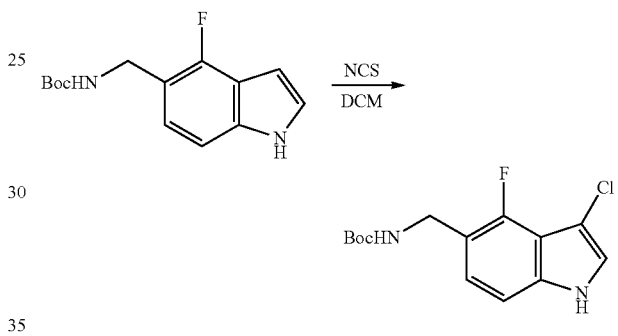

To a solution of tert-butyl (4-fluoro-1H-indol-5-yl)methylcarbamate (4.2 g, 15.9 mmol, 1.0 eq) in DCM (150 mL) was added NCS (2.22 g, 16.7 mmol, 1.05 eq). The mixture was stirred at rt for 1 h and concentrated. The residue was purified by chromatography on silica gel column (PE/EtOAc=10/1, v/v) to afford tert-butyl (3-chloro-4-fluoro-1H-indol-5-yl)methylcarbamate (4.0 g, 85%) as a yellow solid.

Step 7: Preparation of (3-chloro-4-fluoro-1H-indol-5-yl)methanamine hydrochloride

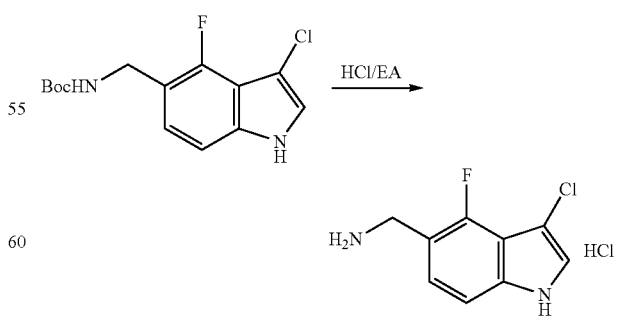

To a solution of tert-butyl (3-chloro-4-fluoro-1H-indol-5-yl)methylcarbamate (4.0 g, 13.4 mmol, 1.0 eq) in EtOAc (20 mL) was added a solution of HCl in EtOAc (10 N, 80 mL).

The mixture was stirred at rt for 1 h, and the precipitate was collected by filtration to afford (3-chloro-4-fluoro-1H-indol-5-yl)methanamine hydrochloride (2.57 g, 82%) as a yellow solid.

Intermediate 32: Preparation of (3-chloro-6-fluoro-1H-indol-5-yl)methanamine hydrochloride

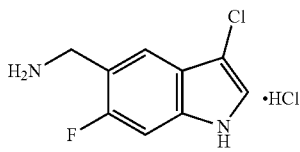

Step 1: Preparation of 6-fluoro-1-triisopropylsilanyl-1H-indole

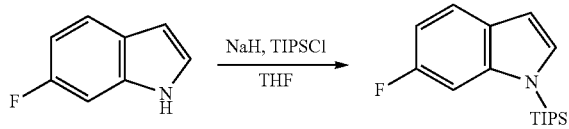

To a solution of 6-fluoro-1H-indole (5.0 g, 37.04 mmol, 1.0 eq) in dry THF (200 mL) was added a solution of NaH (1.63 g, 40.74 mmol, 1.1 eq, 60% purity) in THF (50 mL) at 0° C. After stirring for 0.5 h, TIPSCl (7.8 g, 40.74 mmol, 1.1 eq) was added. The mixture was stirred at rt for 1 h, and quenched by the addition of water. The mixture was extracted with EtOAc. The combined organic layers were dried and concentrated. The resulting residue was purified by chromatography on silica gel column (PE/EtOAc=10/1, v/v) to afford 6-fluoro-1-triisopropylsilanyl-1H-indole (10.3 g, 87%) as a yellow oil.

Step 2: Preparation of 6-fluoro-1-(triisopropylsilyl)-1H-indole-5-carbaldehyde

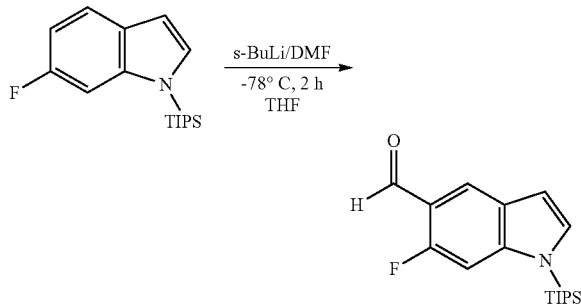

To a solution of 6-fluoro-1-(triisopropylsilyl)-1H-indole (2 g, 6.9 mmol, 1.0 eq) in THF (30 mL) was added s-BuLi (6.3 mL, 1.3 M, 1.2 eq) at −78° C. slowly. The mixture was stirred at this temperature for 1 h. DMF (1.5 g, 20.7 mmol, 3.0 eq) was added dropwise. The mixture was stirred at −78° C. for 1 h. The reaction was quenched by saturated aqueous NH₄Cl. The obtained mixture was extracted with EtOAc (50 mL×3). The organic layers were combined and washed with brine, dried over Na₂SO₄, filtered and concentrated. The resulting residue was purified by chromatography on silica gel column (PE/EtOAc=100/1) to give 6-fluoro-1-(triisopropylsilyl)-1H-indole-5-carbaldehyde (950 mg, 57%) as a yellow oil.

Step 3: Preparation of 6-fluoro-1H-indole-5-carbaldehyde oxime

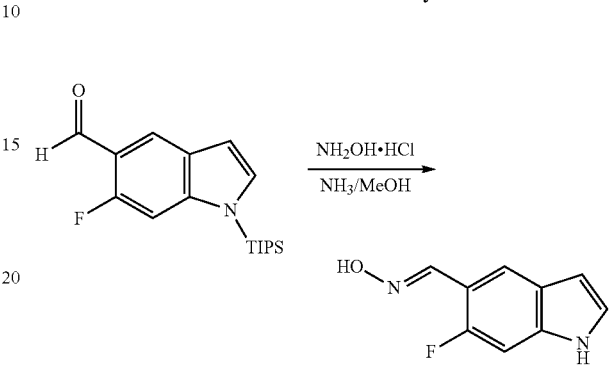

A mixture of 6-fluoro-1-(triisopropylsilyl)-1H-indole-5-carbaldehyde (780 mg, 2.45 mmol, 1.0 eq) and NH₂OH.HCl (340 mg, 4.89 mmol, 2.0 eq) in NH₃/MeOH (15% w/w, 10 mL) was stirred at rt overnight. The mixture was concentrated. The resulting residue was purified by chromatography on silica gel column (PE/EtOAc=50/1) to afford 6-fluoro-1H-indole-5-carbaldehyde oxime (460 mg, crude) as a yellow solid.

Step 4: Preparation of (6-fluoro-1H-indol-5-yl)methanamine

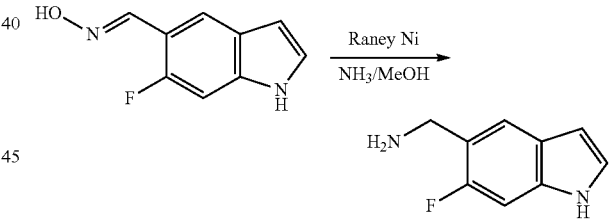

A mixture of 6-fluoro-1H-indole-5-carbaldehyde oxime (460 mg, 1.38 mmol, 1.0 eq) and Raney Ni (100 mg) in NH₃/MeOH (15% w/w, 10 mL) was stirred at rt under H₂ atmosphere (1 atm) overnight. The mixture was filtered and concentrated to afford (6-fluoro-1H-indol-5-yl)methanamine (420 mg, 95%) as a gray solid, which was used in the next step without further purification.

Step 5: Preparation of tert-butyl (6-fluoro-1H-indol-5-yl)methylcarbamate

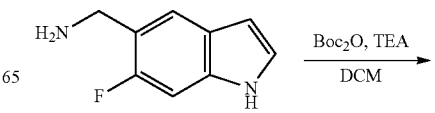

-continued

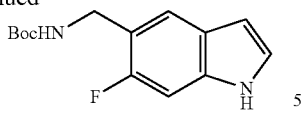

To a solution of (6-fluoro-1H-indol-5-yl)methanamine (420 mg, 2.56 mmol, 1.0 eq) in DCM (25 mL) was added TEA (0.43 mL, 3.07 mmol, 1.2 eq) and Boc$_2$O (670 mg, 3.07 mmol, 1.2 eq). The mixture was stirred at rt for 2 h and concentrated. The resulting residue was purified by chromatography on silica gel column (PE/EtOAc=10/1, v/v) to afford tert-butyl (6-fluoro-1H-indol-5-yl)methylcarbamate (608 mg, 90%) as a yellow solid.

Step 6: Preparation of tert-butyl (3-chloro-6-fluoro-1H-indol-5-yl)methylcarbamate

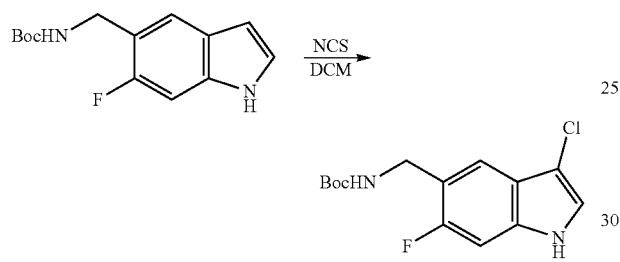

To a solution of tert-butyl (6-fluoro-1H-indol-5-yl)methylcarbamate (600 mg, 2.27 mmol, 1.0 eq) in DCM (20 mL) was added NCS (317 mg, 2.39 mmol, 1.05 eq). The mixture was stirred at rt for 1 h and concentrated. The resulting residue was purified by chromatography on silica gel column (PE/EtOAc=10/1, v/v) to afford tert-butyl (3-chloro-6-fluoro-1H-indol-5-yl)methylcarbamate (547 mg, 81%) as a yellow solid.

Step 7: Preparation of (3-chloro-6-fluoro-1H-indol-5-yl)methanamine hydrochloride

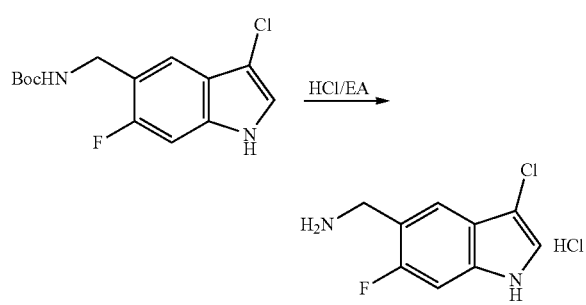

To a solution of tert-butyl (3-chloro-6-fluoro-1H-indol-5-yl)methylcarbamate (547 mg, 1.84 mmol, 1.0 eq) in EtOAc (5 mL) was added a solution of HCl in EtOAc (10 N, 10 mL). The mixture was stirred at rt for 1 h, and the precipitate was collected by filtration to afford (3-chloro-6-fluoro-1H-indol-5-yl)methanamine hydrochloride as a yellow solid.

Example 1: Preparation of 6-((4-(((3-chloro-6-fluoro-1H-indol-5-yl)methyl)carbamoyl)pyridin-2-yl)methyl)quinoline-2-carboxamide

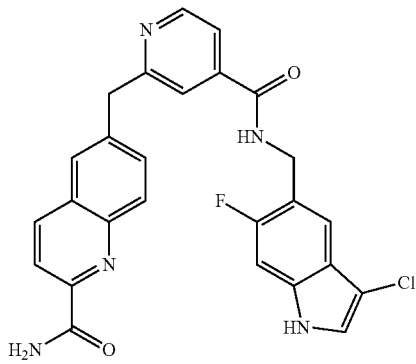

6-((4-(((3-chloro-6-fluoro-1H-indol-5-yl)methyl)carbamoyl)pyridin-2-yl)methyl)quinoline-2-carboxamide

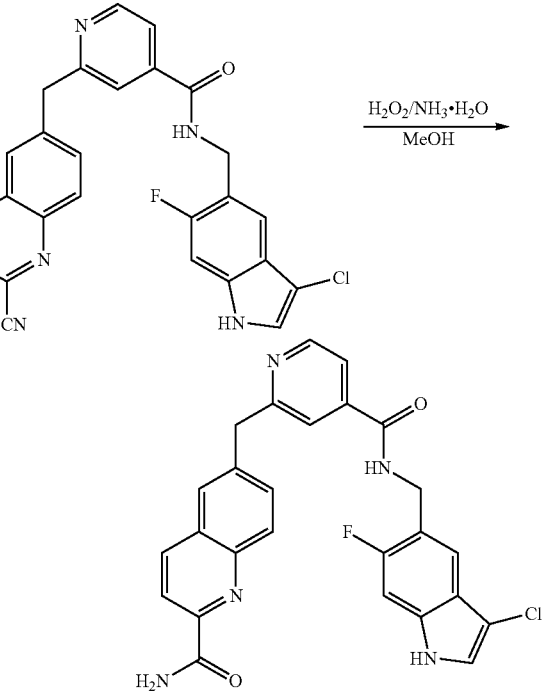

To a solution of N-(3-chloro-6-fluoro-1H-indol-5-ylmethyl)-2-(2-cyano-quinolin-6-ylmethyl)-isonicotinamide (synthesized as described in Example 3, 70 mg, 0.15 mmol, 1.0 eq) in MeOH (1.5 mL)/H$_2$O (0.6 mL) was added ammonium hydroxide (2.1 mL) and hydrogen peroxide (0.1 mL). The mixture was stirred at 30° C. for 3 h. The mixture was concentrated in vacuum and the residue was purified by prep-HPLC to give 6-((4-(((3-chloro-6-fluoro-1H-indol-5-yl) methyl) carbamoyl)pyridin-2-yl)methyl)quinoline-2-carboxamide (18 mg, 25%) as a white solid. LRMS (M+H$^+$) m/z calculated 488.1. found 487.8.

$^1$H NMR (DMSO-d$_6$, 400 MHz) δ 11.41 (s, 1H), 9.27 (s, 1H), 8.67 (d, 1H), 8.49 (d, 1H), 8.26 (s, 1H), 8.13 (d, 1H), 8.01 (d, 1H), 7.95 (s, 1H), 7.82 (s, 1H), 7.78 (d, 2H), 7.67 (d, 1H), 7.51 (s, 1H), 7.46 (d, 1H), 7.24 (d, 1H), 4.59 (d, 2H), 4.40 (s, 2H).

Example 2: Preparation of 6-((4-(((6-amino-2,4-dimethylpyridin-3-yl)methyl)carbamoyl)pyridin-2-yl)methyl)quinoline-2-carboxamide

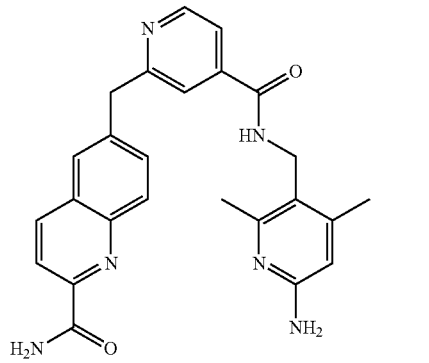

6-((4-(((6-amino-2,4-dimethylpyridin-3-yl)methyl)carbamoyl)pyridin-2-yl)methyl)quinoline-2-carboxamide

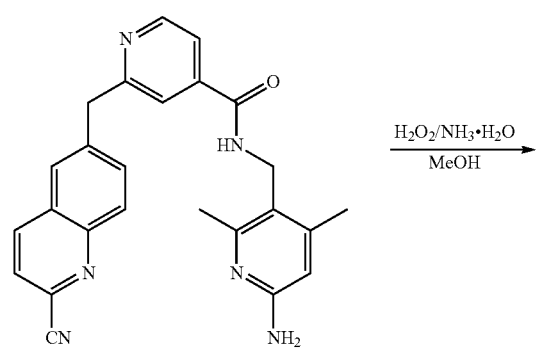

$\xrightarrow{\text{H}_2\text{O}_2/\text{NH}_3 \cdot \text{H}_2\text{O}}{\text{MeOH}}$

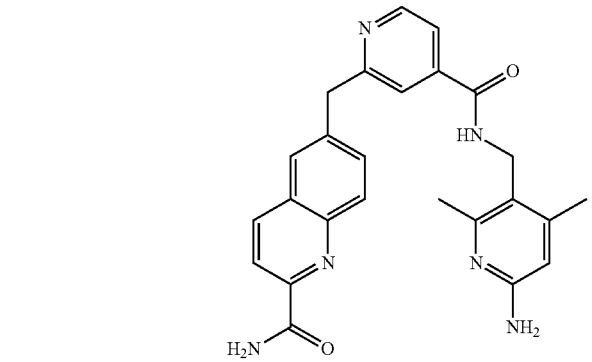

6-((4-(((6-Amino-2,4-dimethylpyridin-3-yl)methyl)carbamoyl)pyridin-2-yl)methyl)quinoline-2-carboxamide (18 mg, 19%) was prepared as described for 6-((4-(((3-chloro-6-fluoro-1H-indol-5-yl)methyl) carbamoyl)pyridin-2-yl)methyl)quinoline-2-carboxamide (Example 1) as a white solid. LRMS (M+H$^+$) m/z calculated 441.2. found 440.9.

$^1$H NMR (DMSO-d$_6$, 400 MHz) δ 8.66-8.61 (m, 2H), 8.49 (d, 1H), 8.27 (s, 1H), 8.13 (d, 1H), 8.06 (d, 1H), 7.94 (s, 1H), 7.80 (s, 1H), 7.78 (s, 1H), 7.62 (d, 1H), 6.13 (s, 1H), 5.71 (s, 2H), 4.38 (s, 1H), 4.35 (d, 2H), 2.30 (s, 3H), 2.17 (s, 3H).

Example 3: Preparation of N-((1-aminoisoquinolin-6-yl)methyl)-2-((2-cyanoquinolin-6-yl)methyl)isonicotinamide

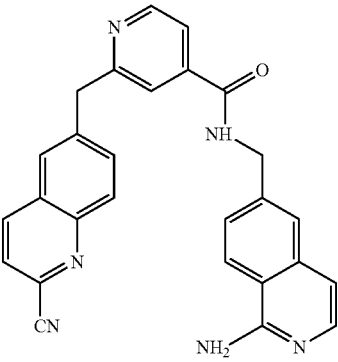

N-((1-aminoisoquinolin-6-yl)methyl)-2-((2-cyanoquinolin-6-yl)methyl)isonicotinamide

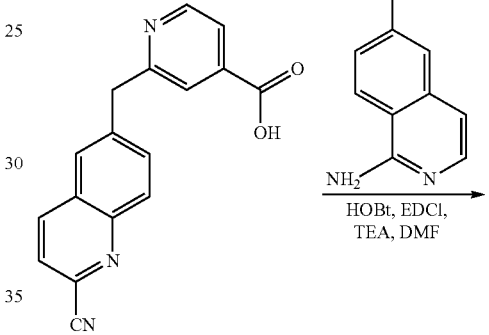

$\xrightarrow{\text{HOBt, EDCl,}}{\text{TEA, DMF}}$

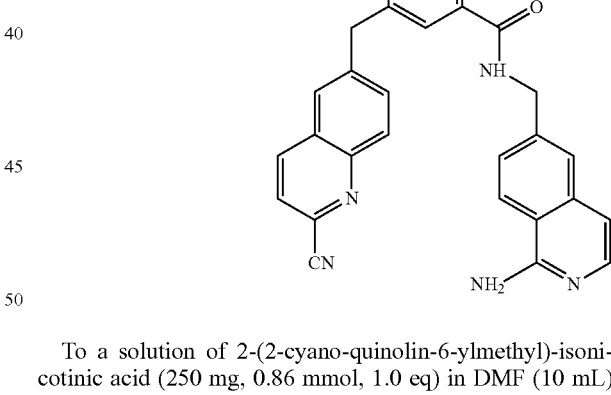

To a solution of 2-(2-cyano-quinolin-6-ylmethyl)-isonicotinic acid (250 mg, 0.86 mmol, 1.0 eq) in DMF (10 mL) was added 6-aminomethyl-isoquinolin-1-ylamine (148.7 mg, 0.86 mmol, 1.0 eq) followed by EDCI (280.7 mg, 1.46 mmol, 1.7 eq), HOBT (174.2 mg, 1.29 mmol, 1.5 eq) and TEA (0.47 mL, 3.4 mmol, 4.0 eq). The reaction mixture was heated to 45° C. kept stirring overnight. Water was added, and the mixture was extracted with DCM. The organic layer was washed with water, dried over Na$_2$SO$_4$, filtered and concentrated. The residue was purified by prep-HPLC to give N-((1-aminoisoquinolin-6-yl) methyl)-2-((2-cyanoquinolin-6-yl) methyl) isonicotinamide (95 mg, 25%) as a yellow solid. LRMS (M+H$^+$) m/z calculated 445.2. found 445.2.

$^1$H NMR (DMSO-d$_6$, 400 MHz): δ 9.41 (t, 1H), 8.58 (d, 1H), 8.62 (d, 1H), 8.15 (d, 1H), 8.09 (d, 1H), 8.01 (t, 2H), 7.91 (d, 1H), 7.89 (d, 1H), 7.84 (s, 1H), 7.77 (d, 1H), 7.70 (dd, 1H), 7.56 (s, 1H), 7.41 (dd, 1H), 6.85 (d, 1H), 6.76 (s, 2H), 4.62 (d, 2H), 4.44 (s, 2H).

Example 4: Preparation of 6-((4-((((6-amino-2,4-dimethylpyridin-3-yl)methyl)carbamoyl)pyridin-2-yl)methyl)quinoline-2-carboxamide

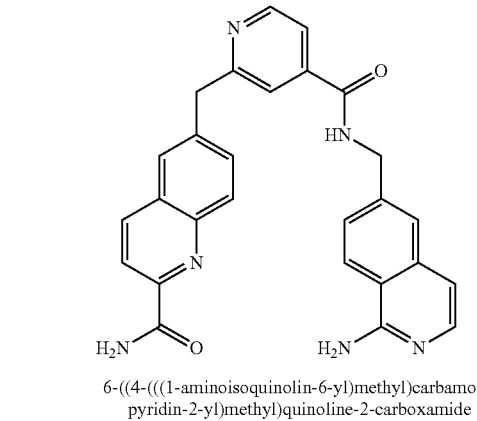

6-((4-(((1-aminoisoquinolin-6-yl)methyl)carbamoyl)pyridin-2-yl)methyl)quinoline-2-carboxamide

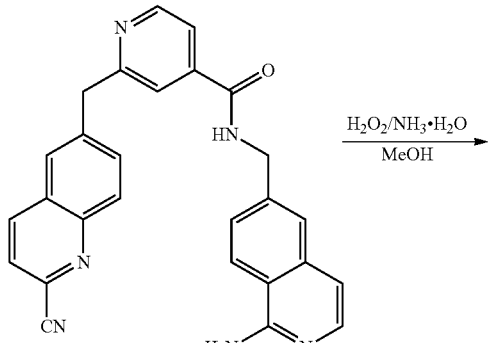

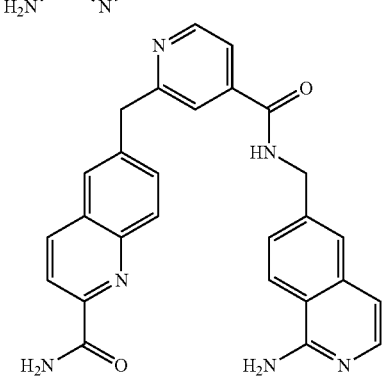

6-((4-((((6-Amino-2,4-dimethylpyridin-3-yl)methyl)carbamoyl)pyridin-2-yl)methyl)quinoline-2-carboxamide (17 mg, 23%) was prepared as described for 6-((4-(((3-chloro-6-fluoro-1H-indol-5-yl) methyl)carbamoyl)pyridin-2-yl)methyl) quinoline-2-carboxamide (Example 1) as a white solid. LRMS (M+H⁺) m/z calculated 463.2. found 462.8.

¹H NMR (DMSO-d₆, 400 MHz) δ 9.43 (t, 1H), 8.69 (d, 1H), 8.51 (d, 1H), 8.23 (s, 1H), 8.16 (t, 2H), 8.07 (d, 1H), 7.97 (s, 1H), 7.84-7.76 (m, 4H), 7.71 (d, 1H), 7.57 (s, 1H), 7.43 (d, 1H), 6.86 (d, 1H), 6.80 (s, 2H), 4.63 (d, 2H), 4.42 (s, 2H).

Example 5: Preparation of N-((3-chloro-6-fluoro-1H-indol-5-yl)methyl)-2-((3-cyanoquinolin-6-yl)methyl)isonicotinamide

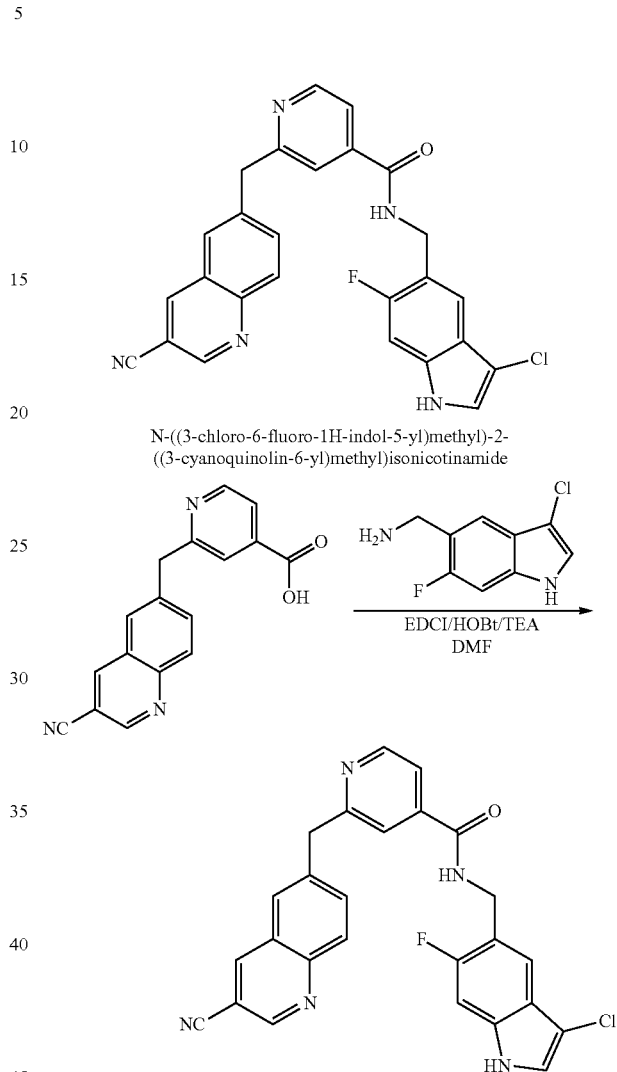

To a solution of 2-(3-isocyano-quinolin-6-ylmethyl)-isonicotinic acid (100 mg, 0.346 mmol, 1.0 eq) and (3-chloro-6-fluoro-1H-indol-5-yl)-methylamine (81 mg, 0.346 mmol, 1.0 eq) in DMF (8 mL) were added HOBT (70 mg, 0.519 mmol, 1.5 eq), EDCI (99.5 mg, 0.519 mmol, 1.5 eq) and Et₃N (140 mg, 1.384 mmol, 4 eq). The mixture was stirred at rt for 15 h and diluted with water. The organic layer was separated and the aqueous layer was extracted with DCM. The combined extracts were dried and concentrated. The residue was purified by prep-HPLC to give N-((3-chloro-6-fluoro-1H-indol-5-yl)methyl)-2-((3-cyanoquinolin-6-yl)methyl)isonicotinamide (15 mg, 9%) as an off-white solid. LRMS (M+H⁺) m/z calculated 470.1. found 470.1.

¹H NMR (DMSO-d₆, 400 MHz) δ 11.37 (s, 1H), 9.23 (t, 1H), 9.07 (d, 1H), 8.99 (s, 1H), 8.61 (d, 1H), 8.02 (d, 1H), 7.93 (s, 1H), 7.88 (d, 1H), 7.77 (s, 1H), 7.62 (d, 1H), 7.47 (d, 1H), 7.40 (d, 1H), 7.18 (d, 1H), 4.54 (d, 2H), 4.37 (s, 2H).

Example 6: Preparation of N-((1-aminoisoquinolin-6-yl)methyl)-2-((3-cyanoquinolin-6-yl)methyl)isonicotinamide

Example 7: Preparation of N-((6-amino-2,4-dimethylpyridin-3-yl)methyl)-2-((3-cyanoquinolin-6-yl)methyl)isonicotinamide

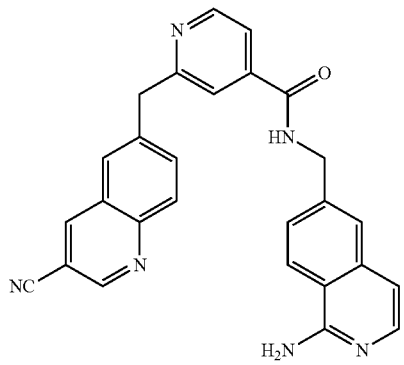

N-((1-aminoisoquinolin-6-yl)methyl)-2-((3-cyanoquinolin-6-yl)methyl)isonicotinamide

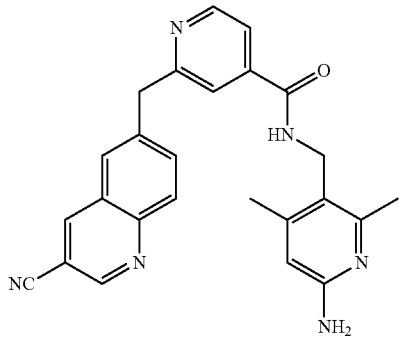

N-((6-amino-2,4-dimethylpyridin-3-yl)methyl)-2-((3-cyanoquinolin-6-yl)methyl-isonicotinamide

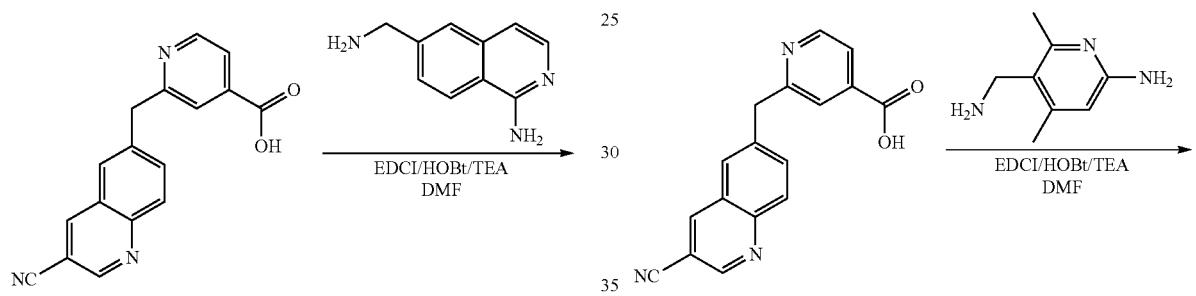

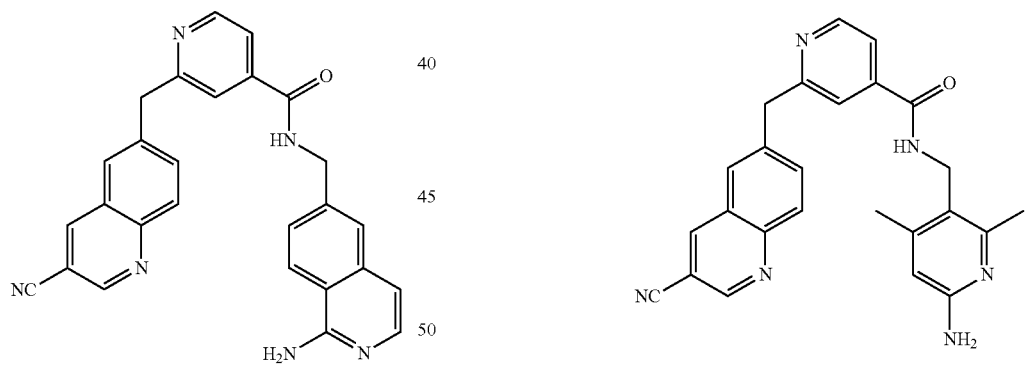

N-((1-aminoisoquinolin-6-yl)methyl)-2-((3-cyanoquinolin-6-yl)methyl)isonicotinamide (58 mg, 23.7%) was prepared as described for N-((3-chloro-6-fluoro-1H-indol-5-yl)methyl)-2-((3-cyanoquinolin-6-yl)methyl)isonicotinamide (Example 5) as an off-white solid. LRMS (M+H+) m/z calculated 445.2. found 444.9.

$^1$H NMR (DMSO-d$_6$, 400 MHz) δ 13.20-13.12 (m, 1H), 9.51 (t, 1H), 9.12 (d, 1H), 9.06-8.99 (m, 2H), 8.69 (d, 1H), 8.50 (d, 1H), 8.07 (d, 1H), 7.99 (s, 1H), 7.93 (dd, 1H), 7.83 (s, 2H), 7.73-7.71 (m, 2H), 7.66 (d, 1H), 7.22 (d, 1H), 4.68 (d, 2H), 4.44 (s, 2H).

N-((6-amino-2,4-dimethylpyridin-3-yl)methyl)-2-((3-cyanoquinolin-6-yl)methyl)isonicotinamide (45 mg, 32.3%) was prepared as described for N-((3-chloro-6-fluoro-1H-indol-5-yl)methyl)-2-((3-cyanoquinolin-6-yl)methyl)isonicotinamide (Example 5) as a off white solid. LRMS (M+H+) m/z calculated 423.2. found 422.9. $^1$H NMR (DMSO-d$_6$, 300 MHz) δ 9.12 (s, 1H), 9.03 (s, 1H), 8.69-8.65 (m, 1H), 8.61-8.59 (m, 1H), 8.05 (dd, 1H), 7.96-7.89 (m, 2H), 7.77 (s, 1H), 7.61-7.60 (m, 1H), 6.16 (d, 1H), 5.91-5.87 (m, 2H), 4.38-4.33 (m, 4H), 2.31 (s, 3H), 2.18 (s, 3H).

Example 8: Preparation of N-((1-aminoisoquinolin-6-yl)methyl)-2-((7-fluoroquinoxalin-2-yl)methyl)isonicotinamide

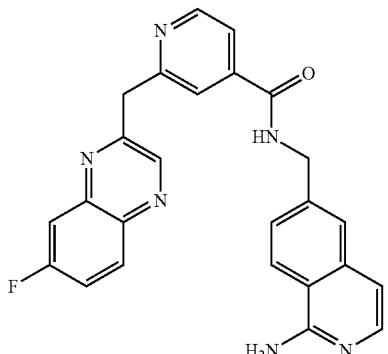

N-((1-aminoisoquinolin-6-yl)methyl)-2-((7-fluoroquinoxalin-2-yl)methyl)isonicotinamide

Step 1: Preparation of 7-fluoro-3,4-dihydro-1H-quinoxalin-2-one

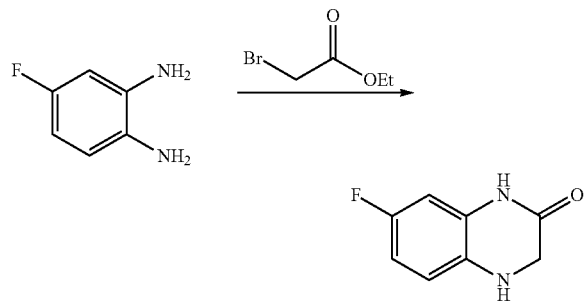

To a solution of 4-fluoro-benzene-1,2-diamine (20 g, 0.159 mol, 1 eq) in DMF (150 mL) was added Et$_3$N (44 mL, 0.318 mol, 2 eq), followed by ethyl 2-bromoacetate (29 g, 0.175 mol, 1.1 eq). The reaction mixture was stirred at rt for 16 h, then at 80° C. for 3 h. The DMF was evaporated by distillation. The reaction mixture was partitioned between H$_2$O and EtOAc. The organic layer was washed with sat. NaHCO$_3$, brine, and dried over Na$_2$SO$_4$. The solvent was evaporated under reduced pressure. The desired product was precipitated in a mixture of CH$_2$Cl$_2$ and hexane (1 to 1 ratio). Filtered and the filtrate was concentrated to dryness to afford 7-fluoro-3,4-dihydro-1H-quinoxalin-2-one (22 g, 83%).

Step 2: Preparation of 7-fluoro-quinoxalin-2-ol

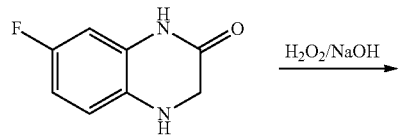

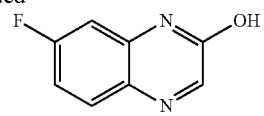

A mixture of 7-fluoro-3,4-dihydro-1H-quinoxalin-2-one (4.0 g, 24 mmol, 1.0 eq), sodium hydroxide (1.93 g, 48 mmol, 2.0 eq) and of 3% hydrogen peroxide solution (50 mL) was refluxed for 2 h, then it was acidified by slow addition of acetic acid. The resulting mixture is cooled to room temperature. The precipitated solid is collected by filtration, washed with ice-water, and dried in vacuum. The resulting residue was purified by column chromatography (DCM/MeOH=50:1, v/v) to afford 7-fluoro-quinoxalin-2-ol (2.60 g, 69%).

Step 3: Preparation of 2-chloro-7-fluoro-quinoxaline

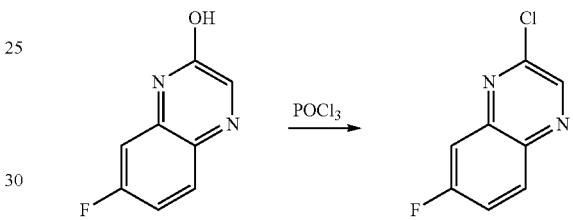

To the suspension of 7-fluoro-quinoxalin-2-ol (2 g, 12 mmol, 1 eq) in neat phosphorus oxychloride (10 mL) was added DMF (2 drops). The mixture was heated to 100° C. for 3 h. Then it was cooled to room temperature. Phosphorus oxychloride was removed in vacuum, and the residue was dissolved into EtOAc and dropped into ice water with stirring. The mixture was extracted with EtOAc for three times, the combined organic layers were washed with saturated NaHCO$_3$ solution. The organic layer was concentrated to afford 2-chloro-7-fluoro-quinoxaline (1.7 g, 77%).

Step 4: Preparation of 7-fluoro-2-(trimethylstannyl)quinoxaline

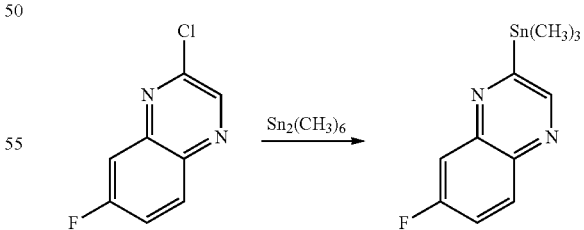

To a solution of 2-chloro-7-fluoro-quinoxaline (2.0 g, 11 mmol, 1 eq) in toluene (50 mL) was added hexamethylditin (7.2 g, 22 mmol, 2 eq) and Pd(PPh$_3$)$_4$ (635 mg, 0.55 mmol, 0.05 eq). The mixture was stirred at 90° C. for 12 h under nitrogen. The reaction mixture was concentrated, and the resulting residue was used in next step without further purification.

Step 5: Preparation of methyl 2-((7-fluoroquinoxalin-2-yl)methyl)isonicotinate

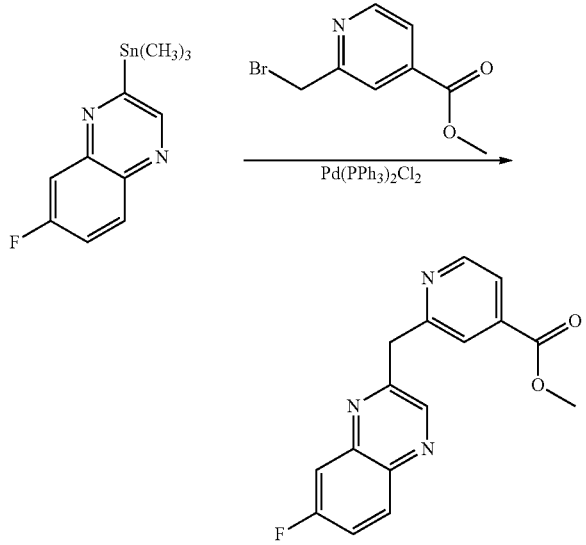

To a solution of 7-fluoro-2-trimethylstannanyl-quinoxaline (3.43 g, 11 mmol, 1.0 eq) in dioxane (60 mL) was added methyl 2-(bromomethyl)isonicotinate (2.5 g, 11 mmol, 1.0 eq) and Pd(PPh$_3$)$_2$Cl$_2$ (386 mg, 0.55 mmol, 0.05 eq). The mixture was stirred at 90° C. for 3 h under nitrogen atmosphere, concentrated and purified by silica gel chromatography (PE/EtOAc=3/1, v/v) to afford methyl 2-((7-fluoroquinoxalin-2-yl)methyl)isonicotinate (300 mg, 9% for 2 steps) as an off-white solid.

Step 6: Preparation of N-((1-aminoisoquinolin-6-yl) methyl)-2-((7-fluoroquinoxalin-2-yl) methyl) isonicotinamide

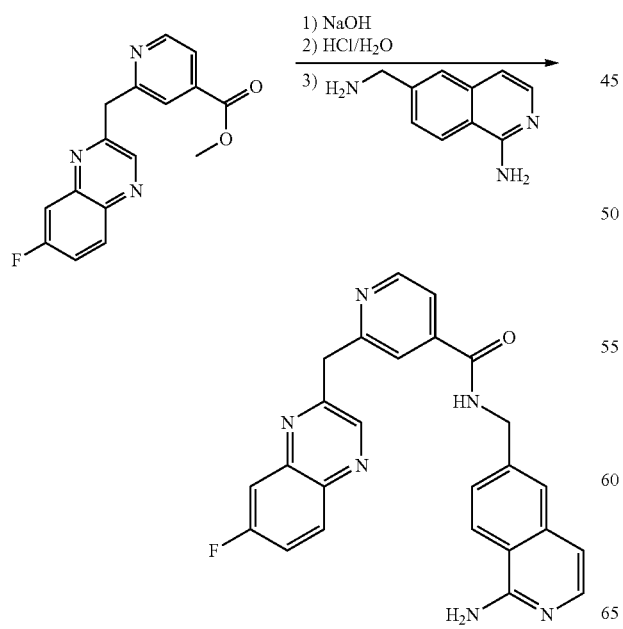

To a solution of methyl 2-((7-fluoroquinoxalin-2-yl)methyl)isonicotinate (70 mg, 0.235 mmol, 1.0 eq) in THF (10 mL)/H$_2$O (2 mL) was added NaOH (11.3 mg, 0.282 mmol, 1.2 eq). The mixture was stirred at 45° C. for 2 h and was acidified to pH 5-6 with 1 N HCl solution. The mixture was concentrated in vacuum, and the resulting residue was used in the next step without further purification. To a solution of this crude product and 6-aminomethyl-isoquinolin-1-ylamine (55.2 mg, 0.235 mmol, 1.0 eq) in DMF (8 mL) were added HOBT (47.6 mg, 0.352 mmol, 1.5 eq), EDCI (67.5 mg, 0.352 mmol, 1.5 eq) and Et$_3$N (95.1 mg, 0.940 mmol, 4 eq). The mixture was stirred at 45° C. for 15 h, and then concentrated. The resulting residue was purified by prep-HPLC to give N-((1-aminoisoquinolin-6-yl) methyl)-2-((7-fluoroquinoxalin-2-yl) methyl) isonicotinamide (15 mg, 14.6%) as a yellow solid. LRMS (M+H$^+$) m/z calculated 439.2. found 438.8. $^1$H NMR (CD$_3$OD, 400 MHz) δ 8.79 (s, 1H), 8.50 (d, 1H), 7.95-7.89 (m, 2H), 7.77 (s, 1H), 7.58-7.47 (m, 5H), 7.36 (d, 1H), 6.79 (d, 1H), 4.60 (s, 2H), 4.51 (s, 2H)

Example 9: Preparation of 2-[2-(acetylamino-methyl)-quinolin-6-ylmethyl]-N-(3-chloro-6-fluoro-1H-indol-5-ylmethyl)-isonicotinamide

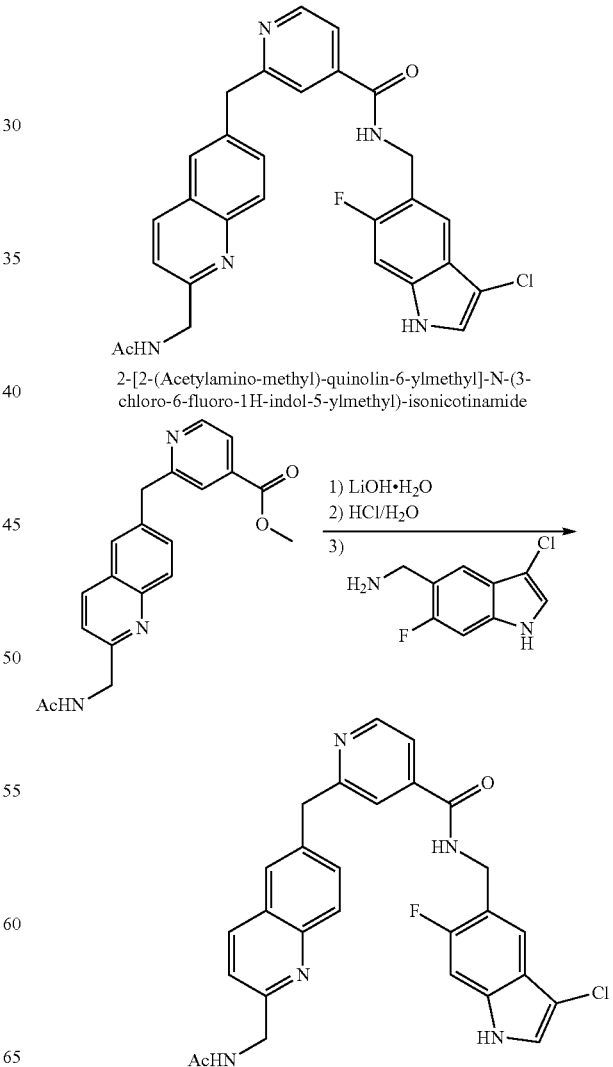

2-[2-(Acetylamino-methyl)-quinolin-6-ylmethyl]-N-(3-chloro-6-fluoro-1H-indol-5-ylmethyl)-isonicotinamide To a solution of methyl 2-((2-(acetamidomethyl)quinolin-6-yl)methyl)isonicotinate (100 mg, 0.287 mmol, 1.0 eq) in THF (10 mL)/H$_2$O (2 mL) was added LiOH.H$_2$O (14.4 mg, 0.344 mmol, 1.2 eq). The mixture was stirred at 45° C. for 2 h, and was acidified to pH 5~6 with 1 N HCl solution. The mixture was concentrated in vacuum, and the residue was directly used without further purification. To a solution of this crude product and (3-chloro-6-fluoro-1H-indol-5-yl)-methylamine (67.3 mg, 0.287 mmol, 1.0 eq) in DMF (8 mL) were added HOBT (58 mg, 0.430 mmol, 1.5 eq), EDCI (82.4 mg, 0.430 mmol, 1.5 eq) and Et$_3$N (116 mg, 1.146 mmol, 4 eq). The mixture was stirred at 45° C. for 15 h then concentrated. The resulting residue was purified by prep-HPLC to give 2-[2-(acetylamino-methyl)-quinolin-6-ylmethyl]-N-(3-chloro-6-fluoro-1H-indol-5-ylmethyl)-isonicotinamide (15 mg, 10.2%) as a yellow solid. LRMS (M+H$^+$) m/z calculated 516.2. found 515.8. $^1$H NMR (DMSO-d$_6$, 400 MHz) δ 11.43 (s, 1H), 9.30 (t, 1H), 9.01 (s, 1H), 8.69-8.64 (m, 2H), 8.48 (d, 1H), 7.98 (d, 1H), 7.93 (s, 1H), 7.84-7.78 (m, 2H), 7.71 (d, 1H), 7.56-7.51 (m, 3H), 7.45 (d, 1H), 7.23 (d, 1H), 4.60-4.56 (m, 4H), 4.41 (s, 2H), 1.94 (s, 3H).

Example 10: Preparation of 2-[2-(acetylamino-methyl)-quinolin-6-ylmethyl]-N-(1-amino-isoquinolin-6-ylmethyl)-isonicotinamide

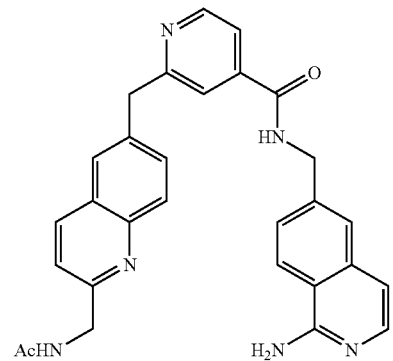

2-[2-(Acetylamino-methyl)-quinolin-6-ylmethyl]-N-(1-amino-isoquinolin-6-ylmethyl)-isonicotinamide (15 mg, 10.7%) was prepared as described for 2-[2-(acetylamino-methyl)-quinolin-6-ylmethyl]-N-(3-chloro-6-fluoro-1H-indol-5-ylmethyl)-isonicotinamide (Example 9) as an off white solid. LRMS (M+H$^+$) m/z calculated 491.2. found 490.9. $^1$H NMR (DMSO-d$_6$, 400 MHz) δ 8.97 (d, 1H), 8.76 (d, 1H), 8.41 (d, 1H), 8.24-8.20 (m, 2H), 8.08 (dd, 1H), 7.99 (s, 1H), 7.94-7.87 (m, 3H), 7.78 (dd, 1H), 7.57 (d, 1H), 7.21 (d, 1H), 4.88 (s, 2H), 4.82 (s, 2H), 4.63 (s, 2H), 2.13 (s, 3H).

Example 11: Preparation of 2-[2-(acetylamino-methyl)-quinolin-6-ylmethyl]-N-(6-amino-2,4-dimethyl-pyridin-3-ylmethyl)-isonicotinamide

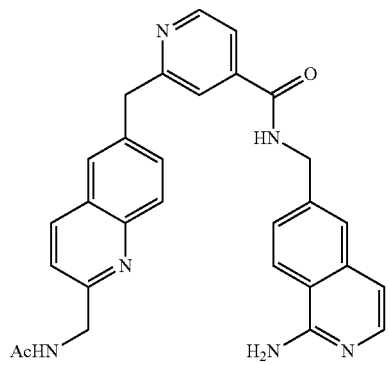

2-[2-(Acetylamino-methyl)-quinolin-6-ylmethyl]-N-(1-amino-isoquinolin-6-ylmethyl)-isonicotinamide

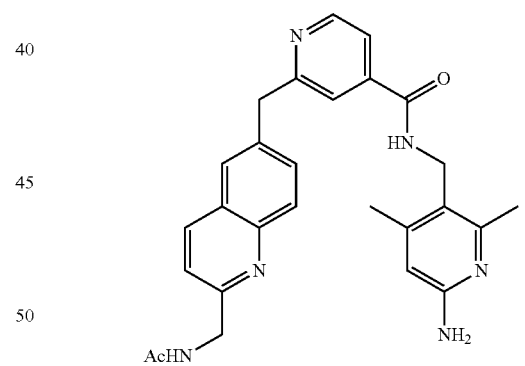

2-[2-(Acetylamino-methyl)-quinolin-6-ylmethyl]-N-(6-amino-2,4-dimethyl-pyridin-3-ylmethyl)-isonicotinamide

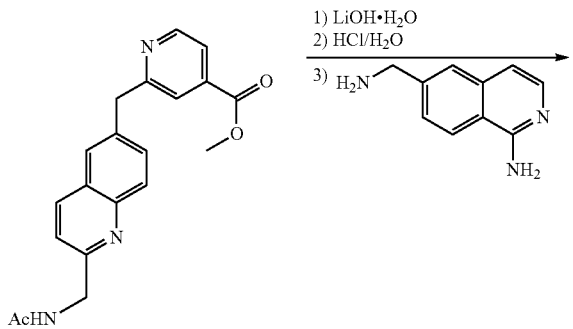

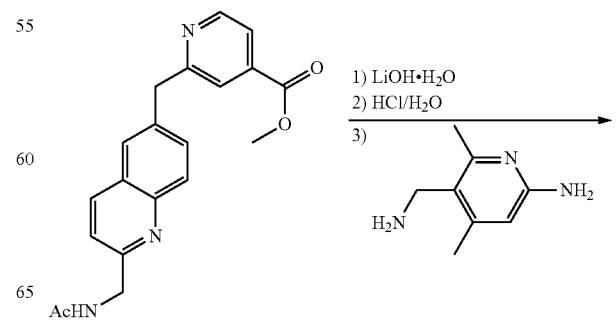

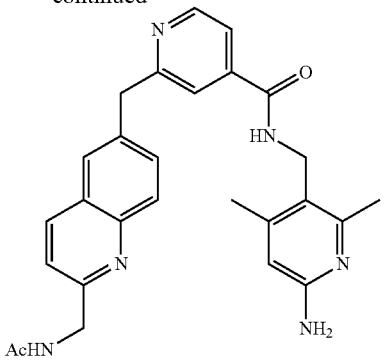

2-[2-(Acetylamino-methyl)-quinolin-6-ylmethyl]-N-(6-amino-2,4-dimethyl-pyridin-3-ylmethyl)-isonicotinamide (10 mg, 7.46%) was prepared as described for 2-[2-(acetylamino-methyl)-quinolin-6-ylmethyl]-N-(3-chloro-6-fluoro-1H-indol-5-ylmethyl)-isonicotinamide (Example 9) as a yellow solid. LRMS (M+H$^+$) m/z calculated 469.2. found 469.2.

$^1$H NMR (DMSO-d$_6$, 400 MHz) δ 8.48 (m, 1H), 8.13 (d, 1H), 7.82 (d, 1H), 7.66 (s, 1H), 7.59-7.54 (m, 2H), 7.48 (dd, 1H), 7.35 (d, 1H), 6.18 (s, 1H), 4.53 (s, 2H), 4.37 (s, 2H), 4.26 (s, 2H), 2.27 (s, 3H), 2.13 (s, 3H), 1.96 (s, 3H).

Example 12: Preparation of N-((3-chloro-6-fluoro-1H-indol-5-yl)methyl)-2-((6-(methylsulfonyl)quinolin-3-yl)methyl)isonicotinamide

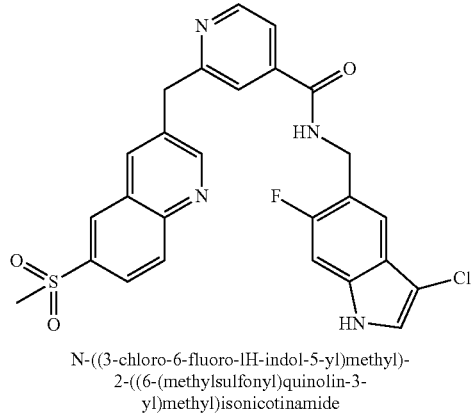 [SMILES: CS(=O)(=O)c1ccc2ncc(Cc3cc(C(=O)NCc4cc5c(Cl)c[nH]c5cc4F)ccn3)cc2c1]

N-((3-chloro-6-fluoro-1H-indol-5-yl)methyl)-
2-((6-(methylsulfonyl)quinolin-3-
yl)methyl)isonicotinamide Step 1: Preparation of 6-methanesulfonyl-quinoline

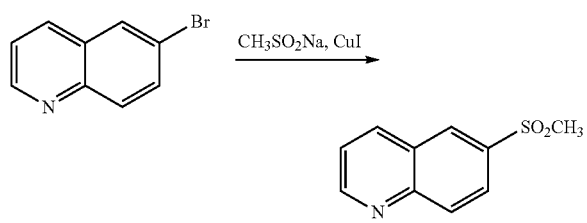

A mixture of 6-bromo-quinoline (20.7 g, 0.1 mol, 1 eq), sodium methanesulphinate (12.2 g, 0.12 mol, 1.2 eq), copper iodide (1.9 g, 0.01 mol, 0.1 eq), L-proline sodium salt (2.74 g, 0.02 mol, 0.2 eq) in 200 mL of DMSO was heated to 110° C. under nitrogen for 15 h. The cooled mixture was partitioned between ethyl acetate and water. The organic layer was separated, and the aqueous layer was extracted with ethyl acetate twice. The combined organic layers were washed with brine, dried over MgSO$_4$, and concentrated in vacuum. The resulting residue was purified by silica gel column (EtOAc/PE=1/2, v/v) to give 6-methanesulfonyl-quinoline (13.5 g, 65%) as a yellow solid.

Step 2: Preparation of 3-bromo-6-methanesulfonyl-quinoline

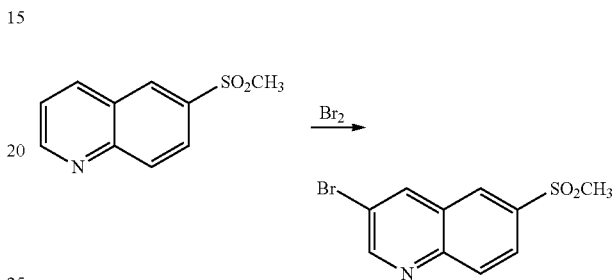

To a mixture of 6-methanesulfonyl-quinoline (6.0 g, 29.0 mmol, 1 eq) and pyridine (4.7 mL, 58.0 mmol, 2 eq) in CCl$_4$ (250 mL) was added Br$_2$ (0.9 mL, 34.8 mmol, 1.2 eq) drop wise. The mixture was heated to reflux for 2 h before being cooled to room temperature. The liquid in the flask was decanted and washed with saturated aqueous NaHCO$_3$ and water. The dark solid on the bottom of the flask was partitioned between aqueous NaHCO$_3$ and dichloromethane. The combined organic layers were washed with water again and dried before being evaporated to dryness in vacuum. The crude product was purified by silica gel column (EtOAc/PE=1/10, v/v) to give 3-bromo-6-methanesulfonyl-quinoline (6.2 g, 75%) as a yellow solid.

Step 3: Preparation of 6-methanesulfonyl-3-vinyl-quinoline

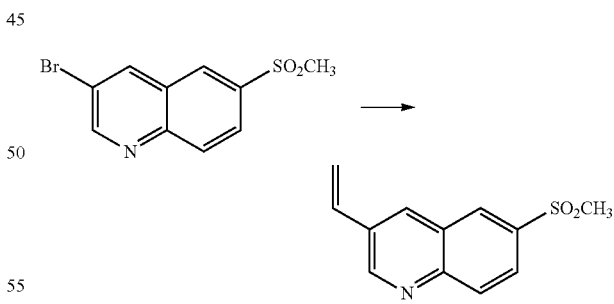

To a solution of 3-bromo-6-methanesulfonyl-quinoline (2.9 g, 10.2 mmol, 1 eq) and vinylboronic acid pinacol cyclic ester (2.1 g, 12.2 mmol, 1.2 eq) in dioxane (50 mL) and water (10 mL) was added Na$_2$CO$_3$ (3.24 g, 30.6 mmol, 3 eq) and Pd(dppf)Cl$_2$·CH$_2$Cl$_2$ (833 mg, 1.02 mmol, 0.1 eq). The mixture was stirred at 95° C. for 3 h. After cooling to rt, the solvent was removed in vacuum. The residue was purified by flash chromatography on a silica gel column (EtOAc/PE=1/10, v/v) to afford 6-methanesulfonyl-3-vinyl-quinoline as a yellow solid (2.1 g, 88%).

Step 4: Preparation of 6-methanesulfonyl-quinoline-3-carbaldehyde

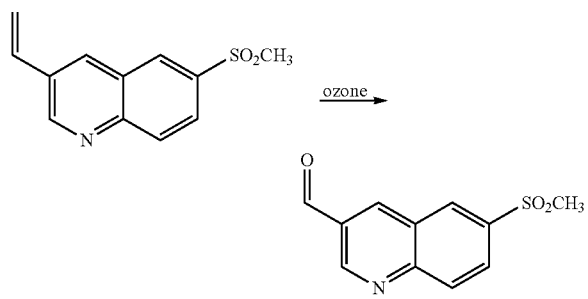

A 3-neck round-bottom flask was charged with 6-methanesulfonyl-3-vinyl-quinoline (2.1 g, 9.0 mmol, 1 eq) and dichloromethane (40 mL) and cooled to −78° C. Ozone was bubbled into the reaction mixture until blue color persisted (30 min). The reaction mixture was sparged with oxygen until blue color faded and quenched with methyl sulfide (6 mL). The mixture was stirred at rt for 1 h, then concentrated and purified by flash column chromatography (EtOAc/PE=1/8, v/v) to give 6-methanesulfonyl-quinoline-3-carbaldehyde (1.0 g, 47%) as a white solid.

Step 5: Preparation of (6-methanesulfonyl-quinolin-3-yl)-methanol

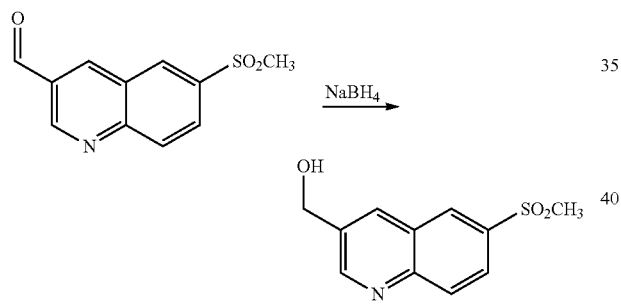

To a solution of 6-methanesulfonyl-quinoline-3-carbaldehyde (1.0 g, 4.25 mmol, 1 eq) in dry MeOH (20 mL) was added NaBH₄ (162 mg, 4.25 mmol, 1 eq) at 0° C. The mixture was stirred at the same temperature for 10 min. The reaction was quenched by the addition of water. The mixture was extracted with EtOAc. The combined extracts were dried and concentrated. The residue was purified by chromatography on a silica gel column (EtOAc/PE=1/2, v/v) to afford (6-methanesulfonyl-quinolin-3-yl)-methanol as a yellow solid (290 mg, 29%).

Step 6: Preparation of 3-chloromethyl-6-methanesulfonyl-quinoline

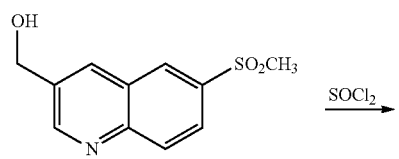

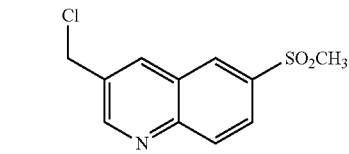

To (6-methanesulfonyl-quinolin-3-yl)-methanol (290 mg, 1.22 mmol, 1.0 eq) was added SOCl₂ (5 mL) and the mixture was stirred at rt for 2 h. The volatiles were then removed at 40° C. under vacuum, and the residue was dissolved in DCM. The mixture was washed with saturated aq. NaHCO₃, dried and concentrated to give 3-chloromethyl-6-methanesulfonyl-quinoline (310 mg, 99%) as a yellow solid.

Step 7: Preparation of methyl 2-((6-(methylsulfonyl)quinolin-3-yl)methyl)isonicotinate

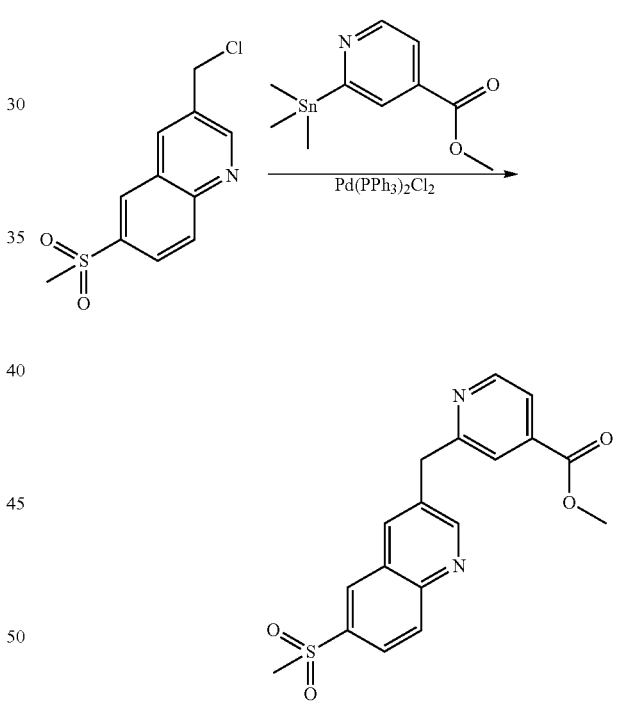

To a solution of 3-chloromethyl-6-methanesulfonyl-quinoline (310 mg, 2.61 mmol, 1.0 eq) in dioxane (20 mL) was added methyl 2-(trimethylstannyl)isonicotinate (864 mg, 2.87 mmol, 1.1 eq) and Pd(PPh₃)₂Cl₂ (183 mg, 0.26 mmol, 0.1 eq). The mixture was stirred at 90° C. for 3 h under nitrogen atmosphere, concentrated and purified by silica gel chromatography (DCM/MeOH=100/1, v/v) to afford methyl 2-((6-(methylsulfonyl)quinolin-3-yl)methyl)isonicotinate (290 mg, 67%) as a yellow solid.

Step 8: Preparation of N-((3-chloro-6-fluoro-1H-indol-5-yl)methyl)-2-((6-(methylsulfonyl)quinolin-3-yl)methyl)isonicotinamide

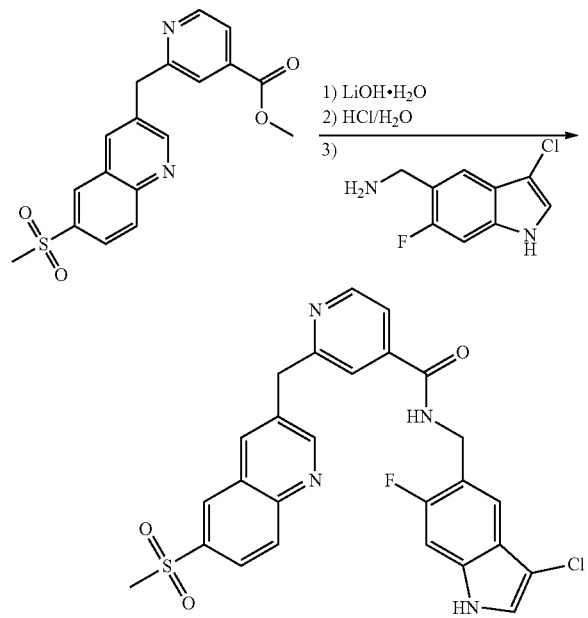

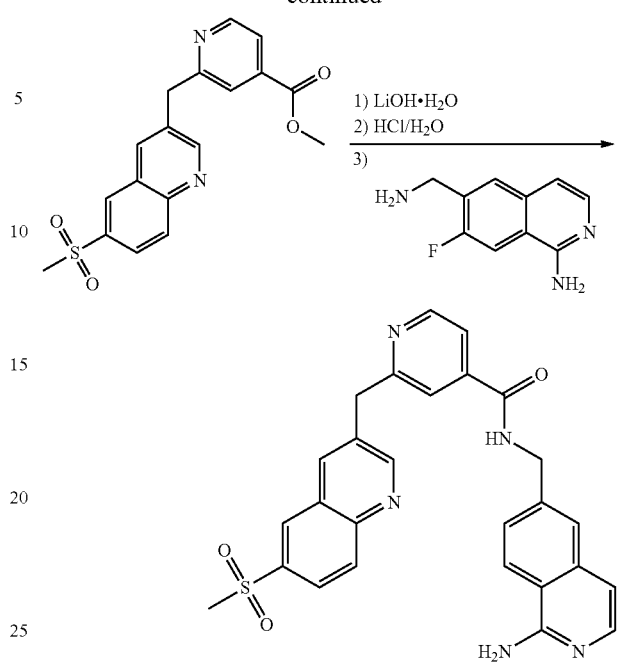

To a solution of methyl 2-((6-(methylsulfonyl)quinolin-3-yl)methyl)isonicotinate (85 mg, 0.24 mmol, 1.0 eq) in THF (3 mL)/H$_2$O (2 mL) was added LiOH.H$_2$O (15 mg, 0.36 mmol, 1.5 eq). The mixture was stirred at 40° C. for 1 h and was acidified to pH 5 with 1 N HCl solution. The mixture was concentrated in vacuum and the residue was directly used without further purification. To a solution of the above crude product and (3-chloro-6-fluoro-1H-indol-5-yl)-methylamine hydrochloride (68 mg, 0.29 mmol, 1.2 eq) in DMF (5 mL) was added HATU (137 mg, 0.36 mmol, 1.5 eq) and Et$_3$N (97 mg, 0.96 mmol, 4 eq). The mixture was stirred at rt for 1 h and concentrated. The residue was purified by prep-HPLC to give N-((3-chloro-6-fluoro-1H-indol-5-yl)methyl)-2-((6-(methylsulfonyl)quinolin-3-yl) methyl)isonicotinamide (53 mg, 43% for 2 steps) as an off-white solid. LRMS (M+H$^+$) m/z calculated 523.1. found 522.8. $^1$H NMR (DMSO-d6, 400 MHz) δ 11.90 (s, 1H), 9.29 (s, 1H), 9.10 (s, 1H), 8.66 (d, 1H), 8.63 (s, 1H), 8.50 (s, 1H), 8.22 (d, 1H), 8.14 (d, 1H), 7.85 (s, 1H), 7.68 (d, 1H), 7.52 (s, 1H), 7.47 (d, 1H), 4.61 (d, 2H), 4.46 (s, 2H), 3.37 (s, 3H).

Example 13: Preparation of N-((1-aminoisoquinolin-6-yl)methyl)-2-((6-(methylsulfonyl)quinolin-3-yl)methyl)isonicotinamide

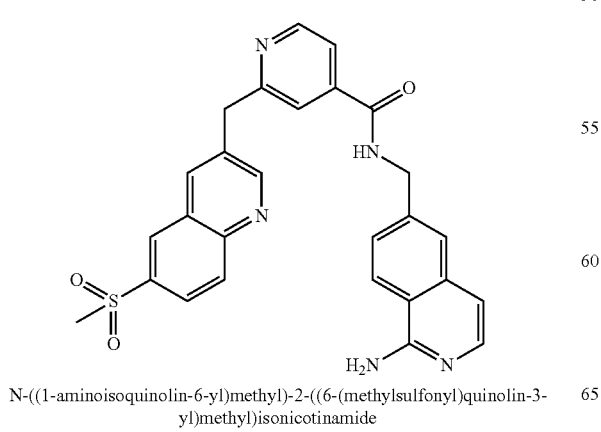

N-((1-aminoisoquinolin-6-yl)methyl)-2-((6-(methylsulfonyl)quinolin-3-yl)methyl)isonicotinamide N-((1-aminoisoquinolin-6-yl)methyl)-2-((6-(methylsulfonyl)quinolin-3-yl)methyl)isonicotinamide (56 mg, 46% for 2 steps) was prepared as described for N-((3-chloro-6-fluoro-1H-indol-5-yl)methyl)-2-((6-(methylsulfonyl)quinolin-3-yl)methyl)isonicotinamide (Example 12) as an off-white solid. LRMS (M+H$^+$) m/z calculated 498.2. found 497.9.

$^1$H NMR (CD$_3$OD, 400 MHz) δ 8.85 (s, 1H), 8.51 (d, 1H), 8.37 (s, 1H), 8.21 (s, 1H), 7.99 (s, 1H), 7.89 (d, 1H), 7.71 (s, 1H), 7.55 (s, 1H), 7.53 (d, 1H), 7.45 (s, 1H), 7.32 (d, 1H), 6.74 (d, 1H), 4.56 (s, 2H), 4.32 (s, 2H), 3.07 (s, 3H).

Example 14: Preparation of N-((6-amino-2,4-dimethylpyridin-3-yl)methyl)-2-((6-(methylsulfonyl)quinolin-3-yl)methyl)isonicotinamide

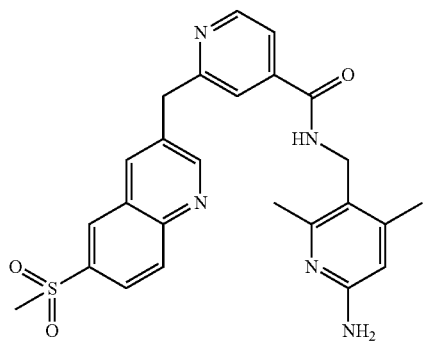

N-((6-amino-2,4-dimethylpyridin-3-yl)methyl)-2-((6-(methylsulfonyl)quinolin-3-yl)methyl)isonicotinamide

237

-continued

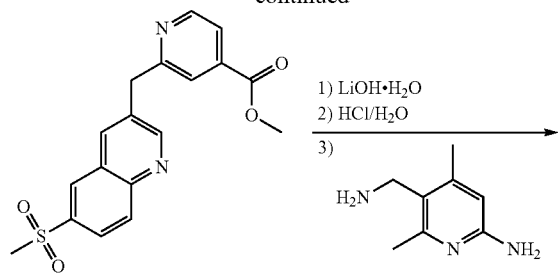

1) LiOH·H₂O
2) HCl/H₂O
3) 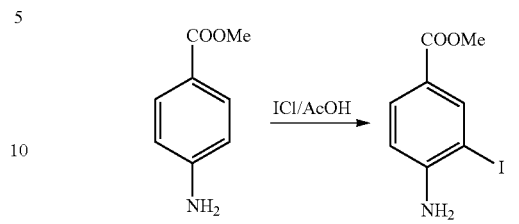

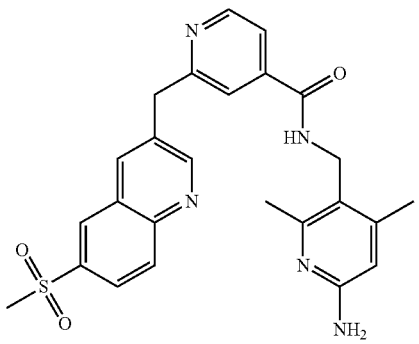

N-((6-amino-2,4-dimethylpyridin-3-yl)methyl)-2-((6-(methylsulfonyl)quinolin-3-yl)methyl)isonicotinamide (35 mg, 32% for 2 steps) was prepared as described for N-((3-chloro-6-fluoro-1H-indol-5-yl)methyl)-2-((6-(methylsulfonyl)quinolin-3-yl)methyl)isonicotinamide (Example 12) as an off-white solid. LRMS (M+H⁺) m/z calculated 476.2. found 476.0.

$^1$H NMR (CD$_3$OD, 400 MHz) δ 8.91 (d, 1H), 8.51 (d, 1H), 8.47 (s, 1H), 8.31 (s, 1H), 8.09 (d, 1H), 8.08 (d, 1H), 7.67 (s, 1H), 7.51 (d, 1H), 6.20 (s, 1H), 4.40 (s, 2H), 4.37 (s, 2H), 3.11 (s, 3H), 2.29 (s, 3H), 2.16 (s, 3H).

Example 15: Preparation of N-((6-amino-2,4-dimethylpyridin-3-yl)methyl)-2-((3-methyl-8-(methylsulfonyl)quinolin-6-yl)methyl)isonicotinamide

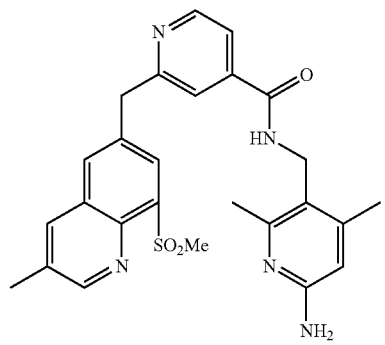

N-((6-amino-2,4-dimethylpyridin-3-yl)methyl)-
2-((3-methyl-8-(methylsulfonyl)quinolin-
6-yl)methyl)isonicotinamide

238

Step 1: Preparation of methyl 4-amino-3-iodobenzoate

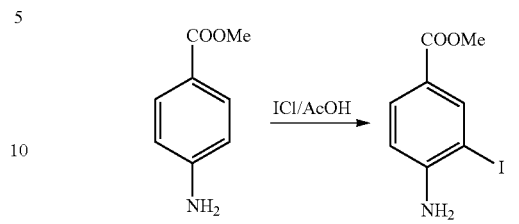

To a solution of methyl 4-aminobenzoate (20 g, 0.132 mol, 1 eq) in AcOH (500 mL) was added a solution of ICl (23.6 g, 0.146 mol, 1.1 eq) in AcOH (500 mL) at 0° C. The mixture was stirred at rt for 2 h. AcOH was evaporated under reduced pressure. The residue was diluted with DCM and washed with sat. NaHCO₃. The aqueous layer was extracted with DCM and the combined extracts were dried and concentrated. The residue was purified by chromatography on a silica gel column (EtOAc/PE=1/15, v/v) to give methyl 4-amino-3-iodobenzoate (27.4 g, 75%) as an off-white solid.

Step 2: Preparation of methyl 8-iodo-3-methylquinoline-6-carboxylate

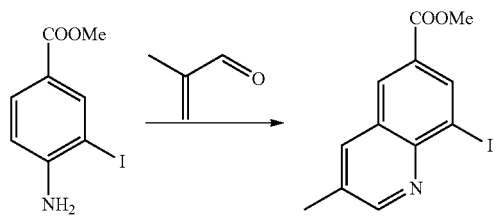

A mixture of methyl 4-amino-3-iodobenzoate (26 g, 93.5 mmol), 2-methyl-propenal (24.5 g, 0.28 mol, 3 eq) and 6 N HCl (95 mL) was heated to reflux for 24 h. Then the mixture was cooled and adjusted to pH ~5-6 using NaHCO₃ (aq). The mixture was extracted with DCM. The combined organic layers were washed with brine, dried over MgSO₄, filtered then concentrated and purified by column chromatography (EtOAc/PE=1/20, v/v) to give methyl 8-iodo-3-methylquinoline-6-carboxylate (10.2 g, 33%) as a yellow solid.

Step 3: Preparation of (8-iodo-3-methyl-quinolin-6-yl)-methanol

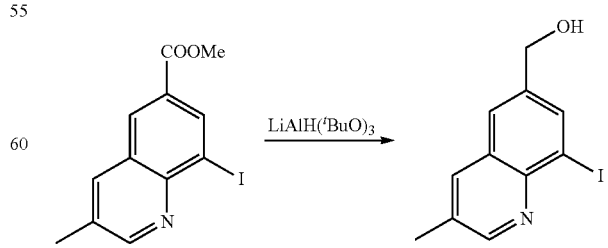

To a solution of methyl 8-iodo-3-methylquinoline-6-carboxylate (7.5 g, 22.9 mmol, 1 eq) was added LiAlH(t-BuO)₃

(14.6 g, 57.3 mmol, 2.5 eq). The resulting mixture was stirred at 40° C. for 12 h and then quenched by the addition of water. The mixture was extracted with EtOAc. The combined extracts were dried and concentrated. The residue was purified by silica gel chromatography (PE/EtOAc=2/1, v/v) to afford (8-iodo-3-methyl-quinolin-6-yl)-methanol (6.5 g, 95%) as a yellow solid.

Step 4: Preparation of (8-methanesulfonyl-3-methyl-quinolin-6-yl)-methanol

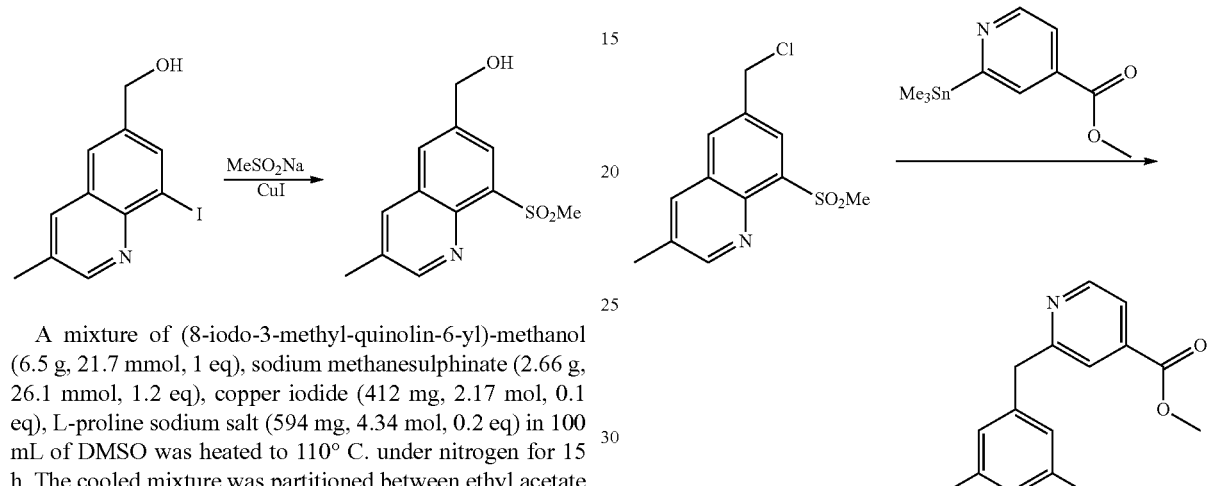

A mixture of (8-iodo-3-methyl-quinolin-6-yl)-methanol (6.5 g, 21.7 mmol, 1 eq), sodium methanesulphinate (2.66 g, 26.1 mmol, 1.2 eq), copper iodide (412 mg, 2.17 mol, 0.1 eq), L-proline sodium salt (594 mg, 4.34 mol, 0.2 eq) in 100 mL of DMSO was heated to 110° C. under nitrogen for 15 h. The cooled mixture was partitioned between ethyl acetate and water. The organic layer was separated, and the aqueous layer was extracted with ethyl acetate twice. The combined organic layers were washed with brine, dried over MgSO$_4$, and concentrated in vacuum. The residue was purified by silica gel column (EtOAc/PE=1/2, v/v) to give (8-methanesulfonyl-3-methyl-quinolin-6-yl)-methanol (3.3 g, 60%) as a yellow solid.

Step 5: Preparation of 6-chloromethyl-8-methanesulfonyl-3-methyl-quinoline

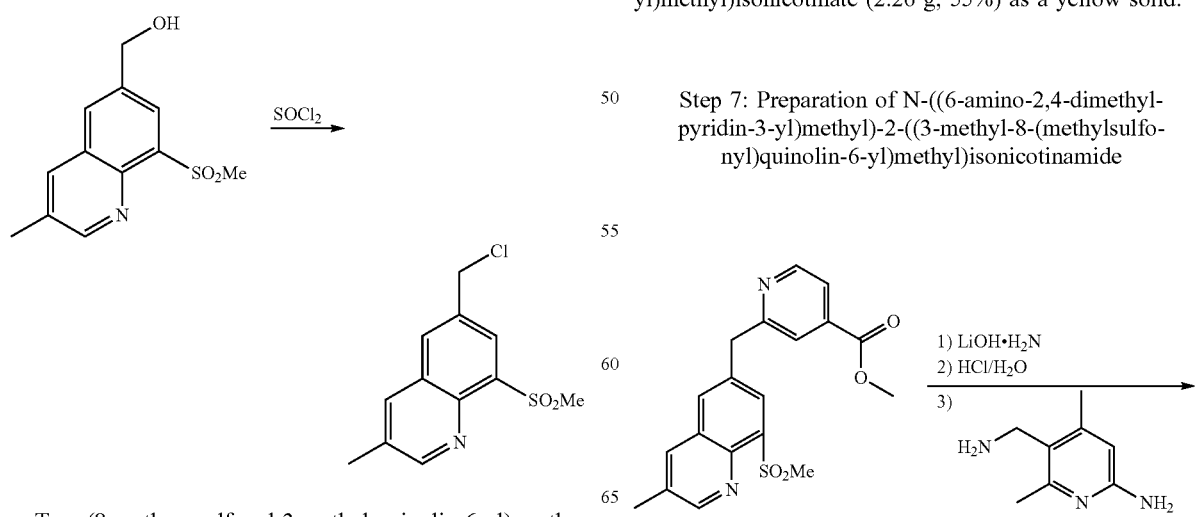

To (8-methanesulfonyl-3-methyl-quinolin-6-yl)-methanol (3.3 g, 13.1 mmol, 1.0 eq) was added SOCl$_2$ (50 mL) and the mixture was stirred at rt for 1 h. The volatiles were then removed under vacuum and the residue was dissolved in DCM. The mixture was washed with saturated aq. NaHCO$_3$, dried and concentrated to give 6-chloromethyl-8-methanesulfonyl-3-methyl-quinoline (3.4 g, 96%) as a yellow solid.

Step 6: Preparation of methyl 2-((3-methyl-8-(methylsulfonyl)quinolin-6-yl)methyl)isonicotinate

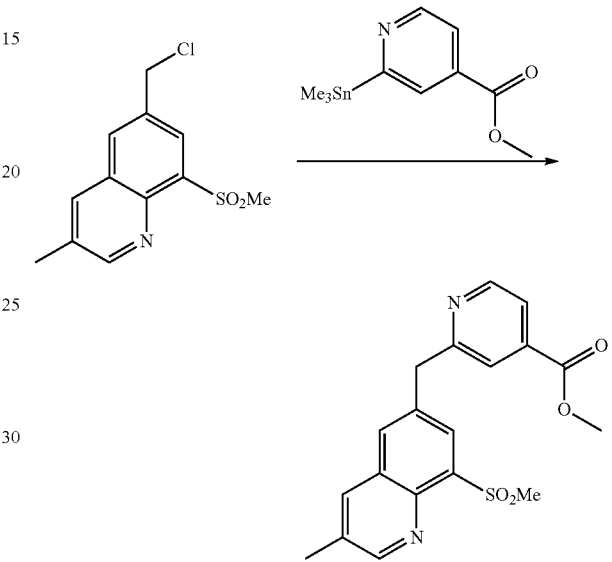

To a solution of 6-chloromethyl-8-methanesulfonyl-3-methyl-quinoline (3.0 g, 11.1 mmol, 1.0 eq) in dioxane (60 mL) was added methyl 2-(trimethylstannyl)isonicotinate (3.70 g, 12.3 mmol, 1.1 eq) and Pd(PPh$_3$)$_2$Cl$_2$ (779 mg, 1.11 mmol, 0.1 eq). The mixture was stirred at 90° C. for 3 h under nitrogen atmosphere, concentrated and purified by silica gel chromatography (DCM/MeOH=100/1, v/v) to afford methyl 2-((3-methyl-8-(methylsulfonyl)quinolin-6-yl)methyl)isonicotinate (2.26 g, 55%) as a yellow solid.

Step 7: Preparation of N-((6-amino-2,4-dimethyl-pyridin-3-yl)methyl)-2-((3-methyl-8-(methylsulfonyl)quinolin-6-yl)methyl)isonicotinamide

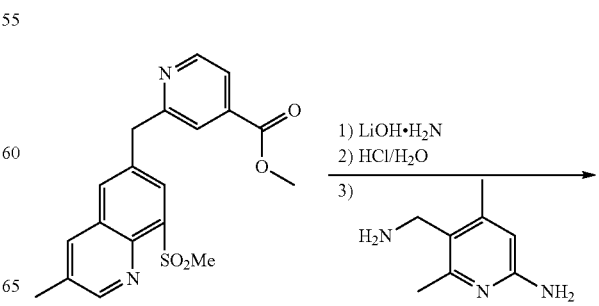

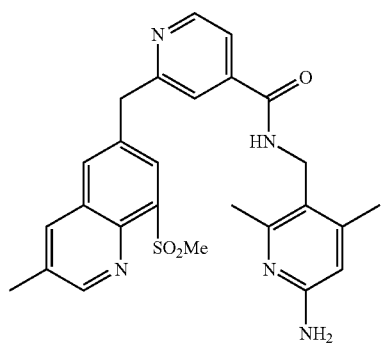

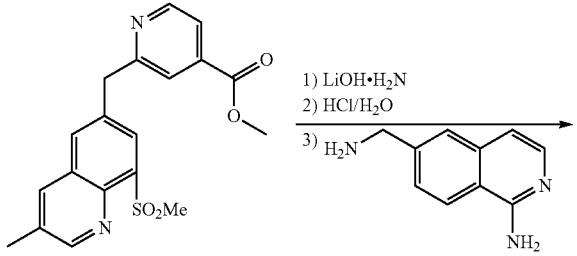

To a solution of methyl 2-((3-methyl-8-(methylsulfonyl)quinolin-6-yl)methyl)isonicotinate (120 mg, 0.32 mmol, 1.0 eq) in THF (3 mL)/H$_2$O (2 mL) was added LiOH.H$_2$O (26.88 mg, 0.64 mmol, 2.0 eq). The mixture was stirred at 40° C. for 1 h and was acidified to pH 5 with 1 N HCl solution. The mixture was concentrated in vacuo and the residue was directly used without further purification. To a solution of the above crude product and 5-aminomethyl-4,6-dimethyl-pyridin-2-ylamine (96.64 mg, 0.64 mmol, 2.0 eq) in DMF (5 mL) was added HOBT (64.8 mg, 0.48 mmol, 1.5 eq), EDCI (104.45 mg, 0.54 mmol, 1.7 eq) and Et$_3$N (0.17 mL, 1.28 mmol, 4 eq). The mixture was stirred at rt for overnight and diluted with water. The organic layer was separated and the aqueous layer was extracted with DCM. The combined extracts were dried and concentrated. The residue was purified by prep-HPLC to give N-((6-amino-2,4-dimethylpyridin-3-yl)methyl)-2-((3-methyl-8-(methylsulfonyl)quinolin-6-yl)methyl)isonicotinamide (30 mg, 18% for 2 steps) as an off-white solid. LRMS (M+H$^+$) m/z calculated 490.2. found 490.0. $^1$H NMR (DMSO-d$_6$, 400 MHz) δ: 8.93 (s, 1H), 8.67 (d, 2H), 8.27 (s, 2H), 8.16 (s, 1H), 7.82 (s, 1H), 7.63 (d, 1H), 6.13 (s, 1H), 5.70 (s, 2H), 4.44 (s, 2H), 4.35 (s, 2H), 3.58 (s, 3H), 2.52 (s, 3H), 2.31 (s, 3H), 2.17 (s, 3H).

Example 16: Preparation of N-((1-aminoisoquinolin-6-yl)methyl)-2-((3-methyl-8-(methylsulfonyl)quinolin-6-yl)methyl)isonicotinamide

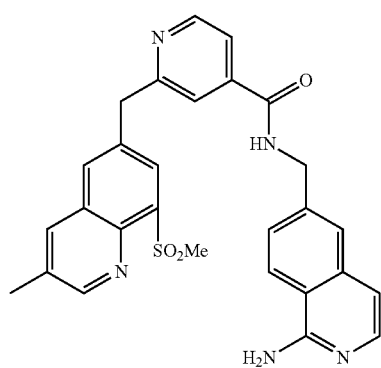

N-((1-aminoisoquinolin-6-yl)methyl)-2-((3-methyl-8-(methylsulfonyl)quinolin-6-yl)methyl)isonicotinamide N-((1-aminoisoquinolin-6-yl)methyl)-2-((3-methyl-8-(methylsulfonyl)quinolin-6-yl)methyl)isonicotinamide (60 mg, 35% for 2 steps) was prepared as described for N-((6-amino-2,4-dimethylpyridin-3-yl)methyl)-2-((3-methyl-8-(methylsulfonyl)quinolin-6-yl)methyl)isonicotinamide (Example 15) as yellow solid. LRMS (M+H$^+$) m/z calculated 512.2. found 512.0.

$^1$H NMR (DMSO-d$_6$, 400 MHz) δ 8.85 (s, 1H), 8.64 (d, 1H), 8.31 (s, 1H), 8.11 (s, 1H), 8.05 (d, 2H), 7.81 (s, 1H), 7.69 (d, 2H), 7.60 (s, 1H), 7.47 (d, 1H), 6.91 (d, 1H), 4.69 (s, 2H), 4.45 (s, 2H), 3.52 (s, 3H), 2.52 (s, 3H).

Example 17: Preparation of N-((3-chloro-6-fluoro-1H-indol-5-yl)methyl)-2-((3-methyl-8-(methylsulfonyl)quinolin-6-yl)methyl)isonicotinamide

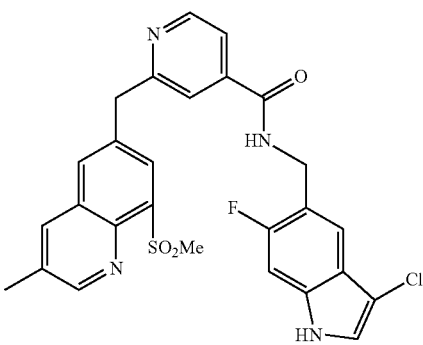

N-((3-chloro-6-fluoro-1H-indol-5-yl)methyl)-2-((3-methyl-8-(methylsulfonyl)quinolin-6-yl)methyl)isonicotinamide

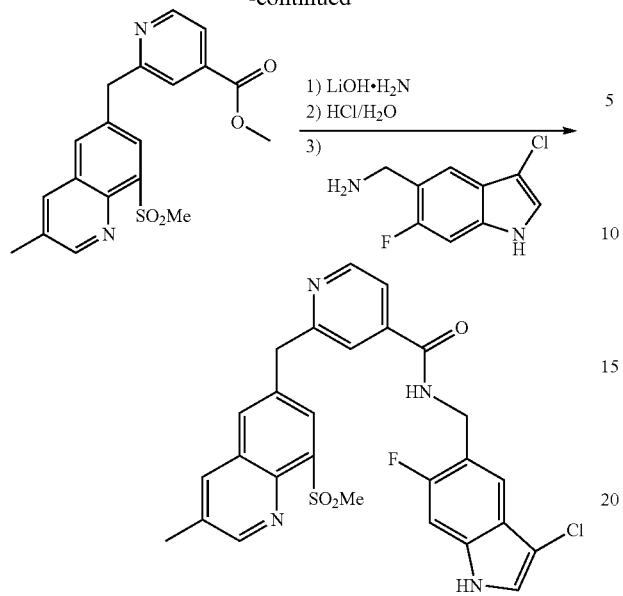

N-((3-chloro-6-fluoro-1H-indol-5-yl)methyl)-2-((3-methyl-8-(methylsulfonyl)quinolin-6-yl)methyl)isonicotinamide (30 mg, 17% for 2 steps) was prepared as described for N-((6-amino-2,4-dimethylpyridin-3-yl)methyl)-2-((3-methyl-8-(methylsulfonyl)quinolin-6-yl)methyl)isonicotinamide (Example 15) as yellow solid. LRMS (M+H$^+$) m/z calculated 537.1. found 537.1.

$^1$H NMR (DMSO-d$_6$, 400 MHz) δ 11.40 (s, 1H), 9.26 (t, 1H), 8.93 (d, 1H), 8.67 (d, 1H), 8.28 (d, 2H), 8.16 (s, 1H), 7.86 (s, 1H), 7.68 (d, 1H), 7.51 (d, 1H), 7.46 (d, 1H), 7.24 (d, 1H), 4.60 (d, 2H), 4.45 (s, 2H), 3.57 (s, 3H), 2.50 (s, 3H).

Example 18: Preparation of N-((6-fluoro-1H-indol-5-yl)methyl)-2-((3-methyl-8-(methylsulfonyl)quinolin-6-yl)methyl)isonicotinamide

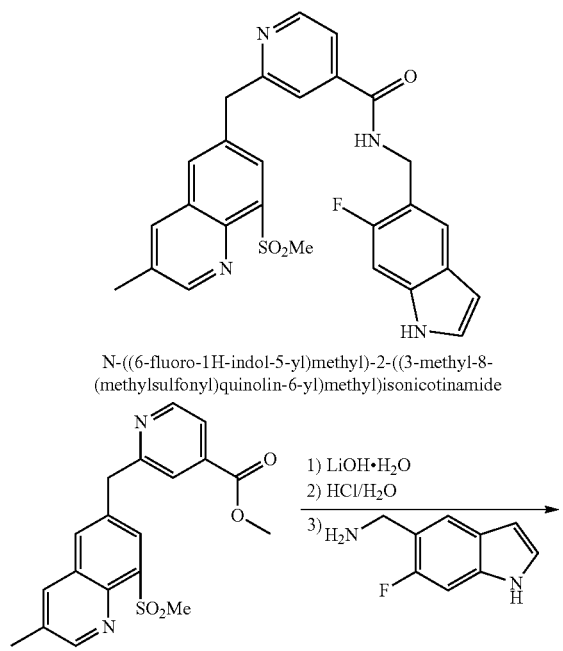

N-((6-fluoro-1H-indol-5-yl)methyl)-2-((3-methyl-8-(methylsulfonyl)quinolin-6-yl)methyl)isonicotinamide

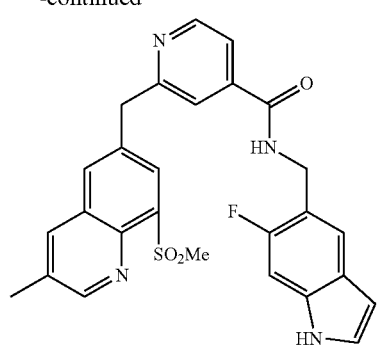

N-((6-fluoro-1H-indol-5-yl)methyl)-2-((3-methyl-8-(methylsulfonyl)quinolin-6-yl)methyl)isonicotinamide (40 mg, 28% for 2 steps) was prepared as described for N-((6-amino-2,4-dimethylpyridin-3-yl)methyl)-2-((3-methyl-8-(methylsulfonyl)quinolin-6-yl)methyl)isonicotinamide (Example 15) as an off-white solid. LRMS (M+H$^+$) m/z calculated 503.2. found 503.0. $^1$H NMR (DMSO-d$_6$, 400 MHz) δ 11.12 (s, 1H), 9.24 (t, 1H), 8.92 (d, 1H), 8.68 (d, 1H), 8.28 (d, 2H), 8.16 (s, 1H), 7.89 (s, 1H), 7.70 (d, 1H), 7.52 (d, 1H), 7.32 (s, 1H), 7.19 (d, 1H), 6.41 (d, 1H), 4.59 (d, 2H), 4.46 (s, 1H), 3.58 (s, 3H), 2.51 (s, 3H).

Example 19: Preparation of N-((3-chloro-1H-pyrrolo[2,3-b]pyridin-5-yl)methyl)-2-((3-methyl-8-(methylsulfonyl)quinolin-6-yl)methyl)isonicotinamide

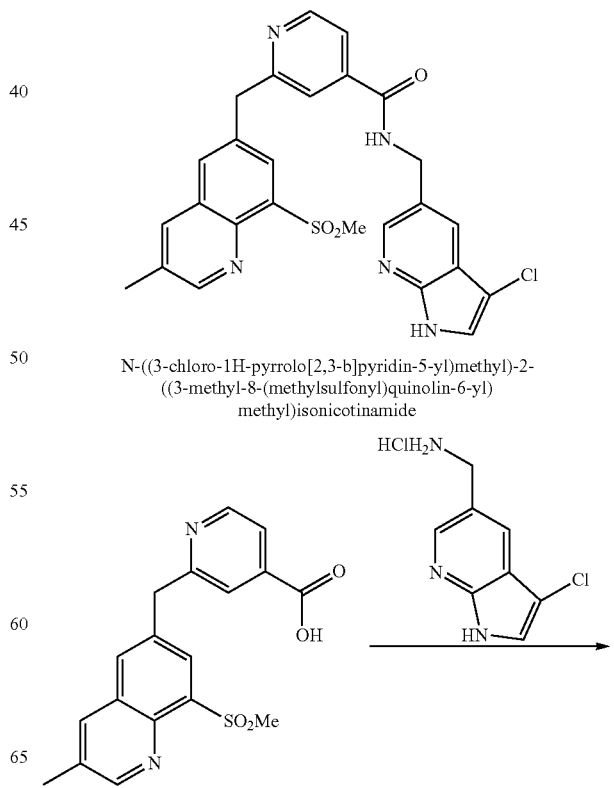

N-((3-chloro-1H-pyrrolo[2,3-b]pyridin-5-yl)methyl)-2-((3-methyl-8-(methylsulfonyl)quinolin-6-yl)methyl)isonicotinamide

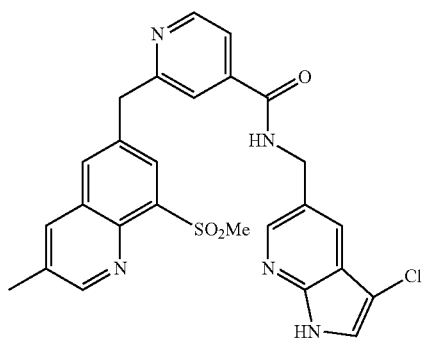

N-((3-chloro-1H-pyrrolo[2,3-b]pyridin-5-yl)methyl)-2-((3-methyl-8-(methylsulfonyl)quinolin-6-yl)methyl)isonicotinamide (55 mg, 38%) was prepared as described for N-((6-amino-2,4-dimethylpyridin-3-yl)methyl)-2-((3-methyl-8-(methylsulfonyl)quinolin-6-yl)methyl)isonicotinamide (Example 15) as a white solid. LRMS (M+H$^+$) m/z calculated 520.1. found 519.8.

$^1$H NMR (DMSO-d$_6$, 400 MHz) δ 9.35 (t, 1H), 8.92 (s, 1H), 8.66 (d, 1H), 8.26-8.32 (m, 3H), 8.16 (s, 1H), 7.88 (s, 1H), 7.85 (s, 1H), 7.65-7.68 (m, 2H), 4.59 (d, 2H), 4.45 (s, 2H), 3.56 (s, 3H), 2.51 (s, 3H).

Example 20: Preparation of N-((5-chloro-1H-indazol-3-yl)methyl)-2-((3-methyl-8-(methylsulfonyl)quinolin-6-yl)methyl)isonicotinamide

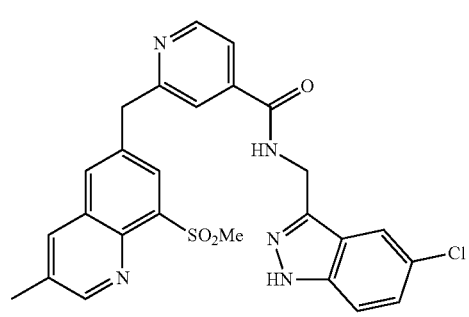

N-((5-chloro-1H-indazol-3-yl)methyl)-2-((3-methyl-8-(methylsulfonyl)quinolin-6-yl)methyl)isonicotinamide

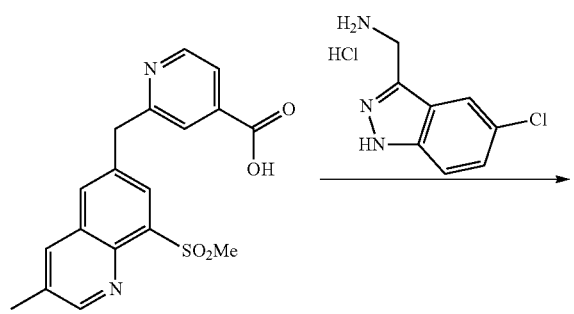

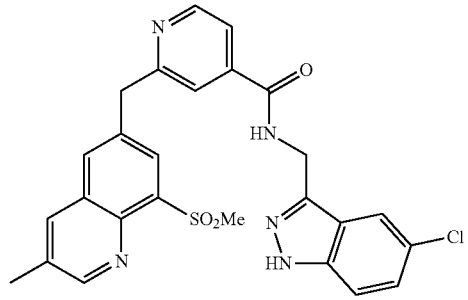

N-((5-chloro-1H-indazol-3-yl)methyl)-2-((3-methyl-8-(methylsulfonyl)quinolin-6-yl)methyl)isonicotinamide (30 mg, 21%) was prepared as described for N-((6-amino-2,4-dimethylpyridin-3-yl)methyl)-2-((3-methyl-8-(methylsulfonyl)quinolin-6-yl)methyl)isonicotinamide (Example 15) as a yellow solid. LRMS (M+H$^+$) m/z calculated 520.1. found 519.8. $^1$H NMR (DMSO-d$_6$, 400 MHz) δ 9.41 (t, 1H), 8.92 (s, 1H), 8.66 (d, 1H), 8.27 (d, 2H), 8.15 (s, 1H), 7.91 (s, 1H), 7.86 (s, 1H), 7.65 (d, 1H), 7.53 (d, 1H), 7.33 (d, 1H), 4.79 (d, 2H), 4.45 (s, 2H), 3.56 (s, 3H), 2.51 (s, 3H).

Example 21: Preparation of N-((3-chloro-4-fluoro-1H-indol-5-yl)methyl)-2-((3-methyl-8-(methylsulfonyl)quinolin-6-yl)methyl)isonicotinamide

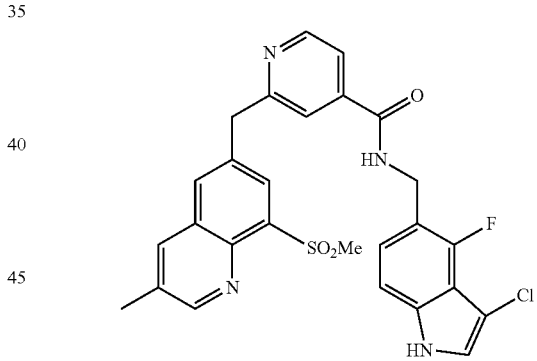

N-((3-chloro-4-fluoro-1H-indol-5-yl)methyl)-2-((3-methyl-8-(methylsulfonyl)quinolin-6-yl)methyl)isonicotinamide

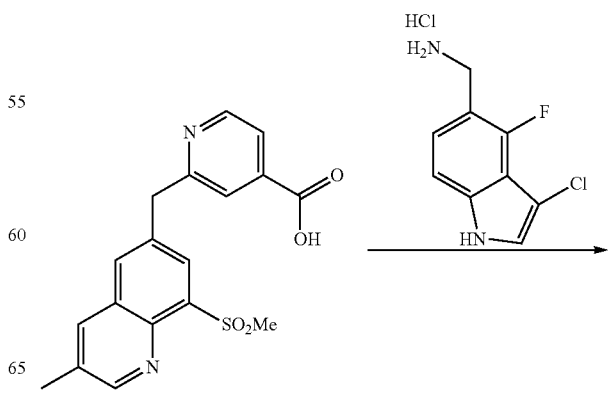

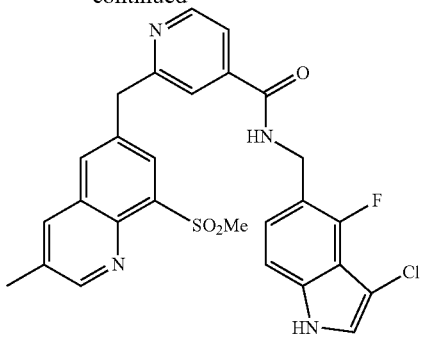

N-((3-chloro-4-fluoro-1H-indol-5-yl)methyl)-2-((3-methyl-8-(methylsulfonyl)quinolin-6-yl)methyl)isonicotinamide (40 mg, 27%) was prepared as described for N-((6-amino-2,4-dimethylpyridin-3-yl)methyl)-2-((3-methyl-8-(methylsulfonyl)quinolin-6-yl)methyl)isonicotinamide (Example 15) as a white solid. LRMS (M+H⁺) m/z calculated 537.1. found 536.7.

$^1$H NMR (DMSO-d$_6$, 400 MHz) δ 11.60 (s, 1H), 9.26 (t, 1H), 8.92 (s, 1H), 8.66 (d, 1H), 8.27 (d, 2H), 8.16 (s, 1H), 7.85 (s, 1H), 7.65 (d, 1H), 7.52 (d, 1H), 7.12-7.21 (m, 2H), 4.58 (d, 2H), 4.45 (s, 2H), 3.57 (s, 3H), 2.51 (s, 3H).

Example 22: Preparation of N-(6-Amino-2,4-dimethyl-pyridin-3-ylmethyl)-2-(5-chloro-1-oxo-1H-isoquinolin-2-ylmethyl)-isonicotinamide

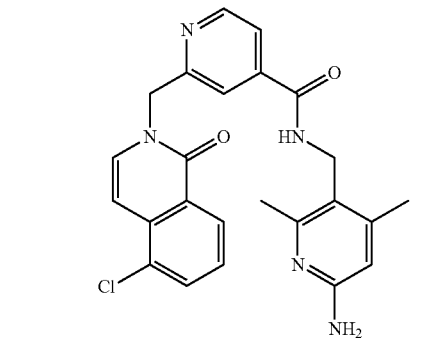

N-(6-Amino-2,4-dimethyl-pyridin-3-ylmethyl)-2-(5-chloro-1-oxo-1H-isoquinolin-2-ylmethyl)-isonicotinamide Step 1: Preparation of methyl 2-chlorophenethylcarbamate

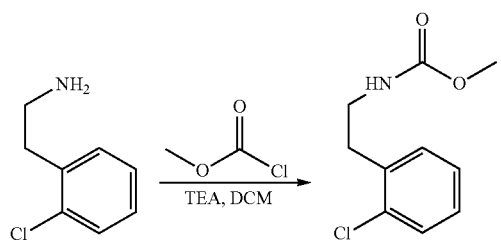

To a solution of 2-(2-chloro-phenyl)-ethylamine (10 g, 64 mmol, 1.0 eq) in DCM (150 mL) was added TEA (12.9 g, 128 mmol, 2.0 eq). The mixture was stirred at 0° C., and methyl chloroformate (9.07 g, 96 mmol, 1.5 eq) was added under nitrogen atmosphere. The mixture was allowed to warm to rt and stirred for 1 h, concentrated and purified by silica gel chromatography (PE/EtOAc=5/1, v/v) to afford methyl 2-chlorophenethylcarbamate (9.0 g, 66%) as a colorless oil.

Step 2: Preparation of 5-chloro-3,4-dihydro-2H-isoquinolin-1-one

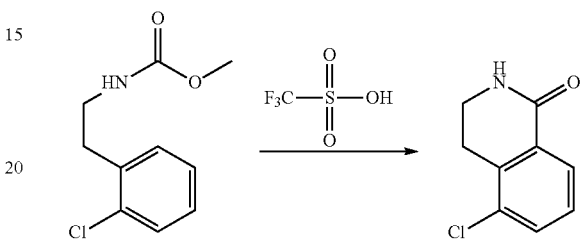

Trifluoromethanesulfonic acid (170 mL, 2.2 mol, 50 eq) was added to N-(6-amino-2,4-dimethyl-pyridin-3-ylmethyl)-2-(5-chloro-1-oxo-1H-isoquinolin-2-ylmethyl)-isonicotinamide (9.0 g, 44.2 mmol, 1.0 eq) at 0° C. The mixture was stirred at 70° C. for 24 h under nitrogen. Then the mixture was poured into ice-water to afford 5-chloro-3,4-dihydro-2H-isoquinolin-1-one (5.1 g, 67%) as a yellow oil.

Step 3: Preparation of 5-chloro-2H-isoquinolin-1-one

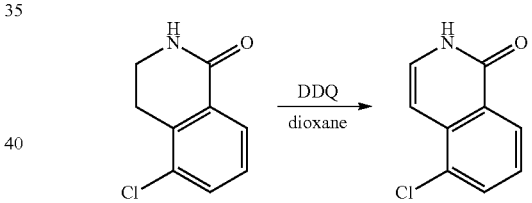

To a solution of 5-chloro-3,4-dihydro-2H-isoquinolin-1-one (5.1 g, 28 mmol, 1.0 eq) in dioxane (150 mL) was added DDQ (22 g, 70 mmol, 3.4 eq). The mixture was stirred at 100° C. for 72 h. The solvent was removed and EtOAc was added. Then washed with 10% NaOH, the organic layer was concentrated, and purified by silica gel chromatography (PE/EtOAc=3/1, v/v) to afford 5-chloro-2H-isoquinolin-1-one (1.3 g, 25%) as an orange oil.

Step 4: Preparation of methyl 2-((5-chloro-1-oxoisoquinolin-2(1H)-yl)methyl)isonicotinate

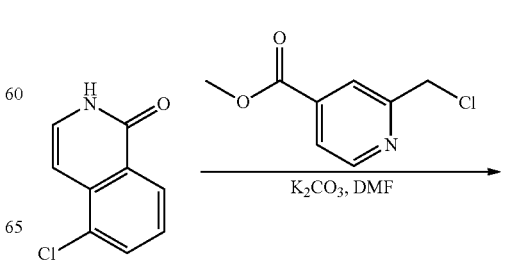

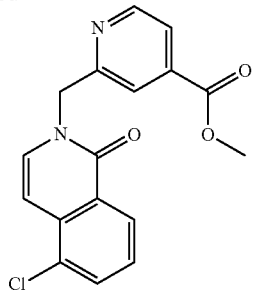

To a solution of 5-chloro-2H-isoquinolin-1-one (470 mg, 2.6 mmol, 1.0 eq) in DMF (10 mL) was added K₂CO₃ (723 mg, 5.2 mmol, 2.0 eq) and methyl 2-(chloromethyl)isonicotinate (722 mg, 3.9 mmol, 1.5 eq). The mixture was stirred at 30° C. for 4 h. The solvent was removed and purified by silica gel chromatography (PE/EtOAc=3/1, v/v) to afford methyl 2-((5-chloro-1-oxoisoquinolin-2(1H)-yl)methyl)isonicotinate (710 mg, 83%) as a yellow solid.

Step 5: Preparation of N-(6-amino-2,4-dimethyl-pyridin-3-ylmethyl)-2-(5-chloro-1-oxo-1H-isoquinolin-2-ylmethyl)-isonicotinamide

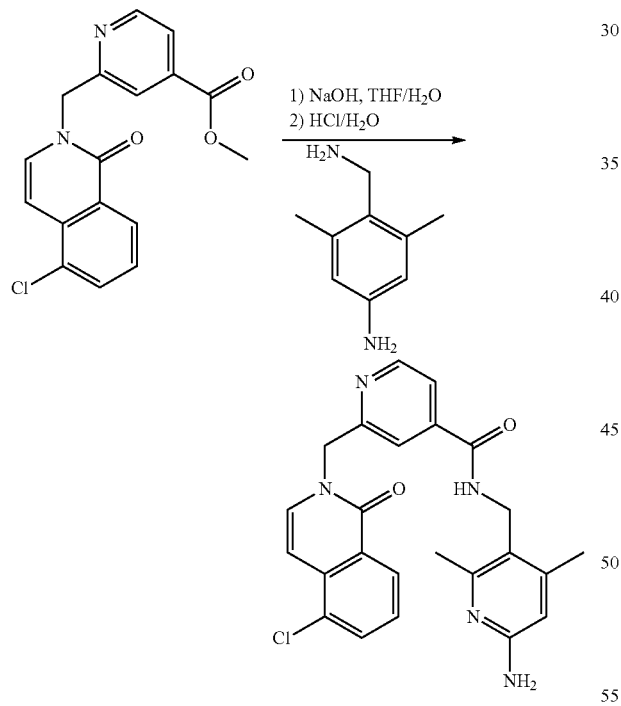

To a solution of methyl 2-((5-chloro-1-oxoisoquinolin-2 (1H)-yl)methyl)isonicotinate (210 mg, 0.54 mmol, 1.0 eq) in THF (5 mL)/H₂O (5 mL) was added NaOH (43 mg, 1.08 mmol, 2.0 eq). The mixture was stirred at 40° C. for 1 h and was acidified to pH 5 with 1 N HCl solution. The mixture was concentrated in vacuum and the residue was directly used without further purification. To a solution of the above crude product and 4-aminomethyl-3,5-dimethyl-phenylamine (122 mg, 0.81 mmol, 1.5 eq) in DMF (8 mL) was added HATU (230 mg, 0.6 mmol, 1.2 eq) and Et₃N (0.3 mL, 1.62 mmol, 3 eq). The mixture was stirred at rt for overnight, concentrated and purified by flash chromatography on a silica gel column (DCM/MeOH=10/1, v/v) to give N-(6-amino-2,4-dimethyl-pyridin-3-ylmethyl)-2-(5-chloro-1-oxo-1H-isoquinolin-2-ylmethyl)-isonicotinamide (31 mg, 13% for 2 steps) as a white solid. LRMS (M+H⁺) m/z calculated 448.2. found 448.0. ¹H NMR (DMSO-d₆, 400 MHz) δ 8.71 (m, 1H), 8.56-8.57 (d, 1H), 8.16-8.18 (d, 1H), 7.88-7.90 (d, 1H), 7.74-7.76 (d, 1H), 7.70 (s, 1H), 7.64-7.65 (d, 1H), 7.48-7.52 (t, 1H), 6.81-6.83 (d, 1H), 6.14 (s, 1H), 5.80 (m, 2H), 5.34 (s, 2H), 4.33-4.34 (d, 2H), 2.30 (s, 3H), 2.17 (s, 3H).

Example 23: Preparation of N-((6-amino-2,4-dimethylpyridin-3-yl)methyl)-2-((6-chloro-1-oxoisoquinolin-2(1H)-yl)methyl)isonicotinamide

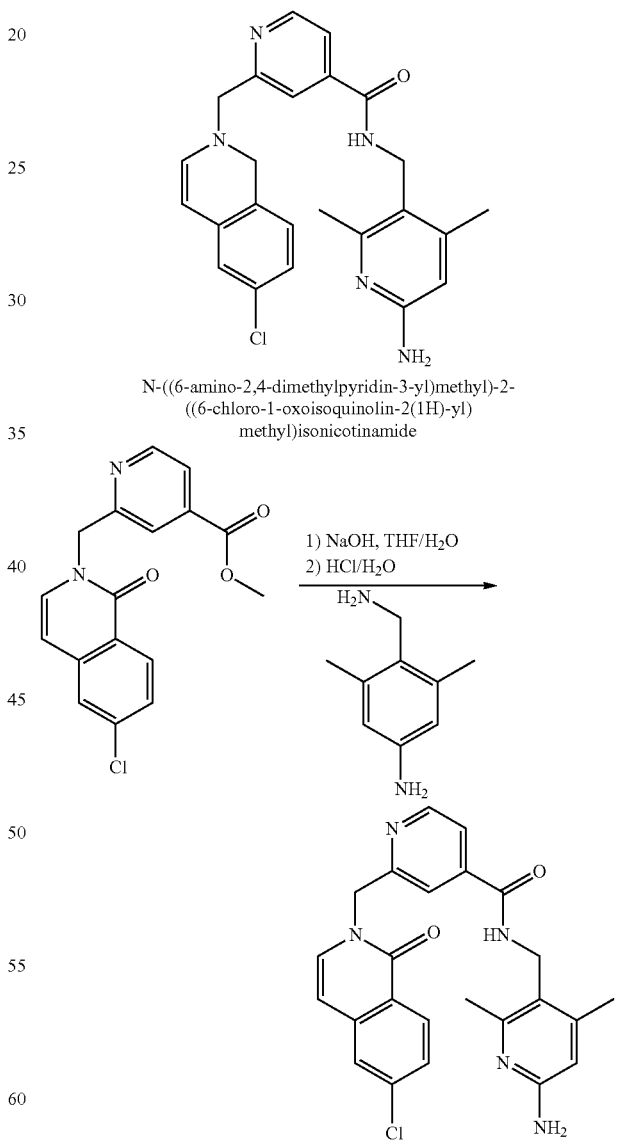

N-((6-amino-2,4-dimethylpyridin-3-yl)methyl)-2-((6-chloro-1-oxoisoquinolin-2(1H)-yl)methyl)isonicotinamide (45 mg, 33%) was prepared as described for N-(6-amino-2,4-dimethyl-pyridin-3-ylmethyl)-2-(5-chloro-1-oxo-1H- isoquinolin-2-ylmethyl)-isonicotinamide (Example 22) as a white solid. LRMS (M+H$^+$) m/z calculated 448.2. found 447.8.

$^1$H NMR (DMSO-d$_6$, 400 MHz) δ 8.71 (s, 1H), 8.58 (d, 1H), 8.17 (d, 1H), 7.83 (s, 1H), 7.68-7.65 (m, 3H), 7.54 (dd, 1H), 6.67 (d, 1H), 6.15 (s, 1H), 5.74 (br, 2H), 4.35 (d, 2H), 2.31 (s, 3H), 2.17 (s, 3H).

Example 24: Preparation of N-((6-amino-2,4-dimethylpyridin-3-yl)methyl)-2-((3-chloro-1H-indol-5-yl)methyl)isonicotinamide

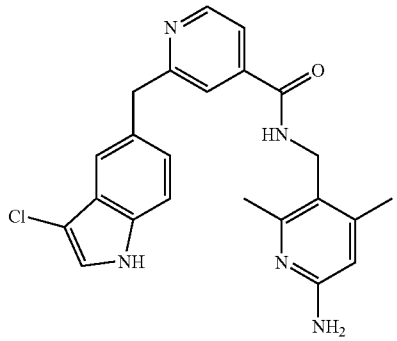

N-((6-amino-2,4-dimethylpyridin-3-yl)methyl)-2-((3-chloro-1H-indol-5-yl)methyl)isonicotinamide Step 1: Preparation of methyl 3-chloro-1H-indole-5-carboxylate

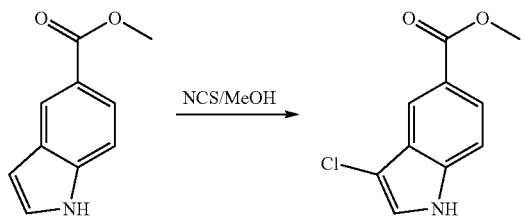

To a solution of methyl 1H-indole-5-carboxylate (10.0 g, 57.1 mmol, 1.0 eq) in MeOH was added NCS (8.4 g, 62.8 mmol, 1.1 eq). The mixture was stirred at rt for 3 h. MeOH was removed by evaporation and the residue was re-dissolved in EtOAc. The mixture was washed with brine twice. The organic layer was dried and concentrated to give methyl 3-chloro-1H-indole-5-carboxylate (quant) as a yellow solid.

Step 2: Preparation of 1-tert-butyl 5-methyl 3-chloro-1H-indole-1,5-dicarboxylate

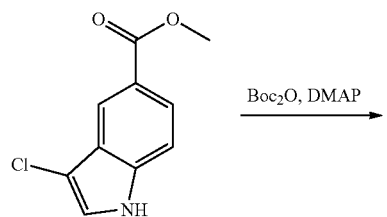

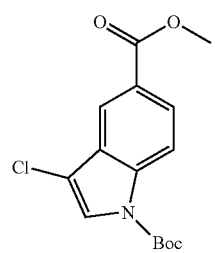

To a solution of methyl 3-chloro-1H-indole-5-carboxylate (11.9 g, 57.1 mmol, 1.0 eq) in MeOH was added Boc$_2$O (18.7 g, 86.7 mmol, 1.5 eq) and DMAP (348 mg, 2.86 mmol, 0.05 eq). The mixture was stirred at rt for 2 h. The mixture was concentrated and purified by chromatography on a silica gel column (EtOAc/PE=1/10, v/v) to give 1-tert-butyl 5-methyl 3-chloro-1H-indole-1,5-dicarboxylate (13.4 g, 76%) as an off-white solid.

Step 3: Preparation of tert-butyl 3-chloro-5-(hydroxymethyl)-1H-indole-1-carboxylate

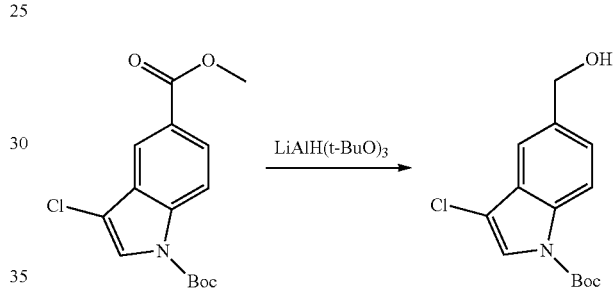

To a solution of 1-tert-butyl 5-methyl 3-chloro-1H-indole-1,5-dicarboxylate (7.0 g, 22.6 mmol, 1 eq) in THF (100 mL) was added LiAlH(t-BuO)$_3$ (14.4 g, 56.6 mmol, 2.5 eq). The resulting mixture was stirred at 60° C. for 12 h and then quenched by the addition of water. The mixture was extracted with EtOAc. The combined extracts were dried and concentrated. The residue was purified by silica gel chromatography (PE/EtOAc=2/1, v/v) to afford tert-butyl 3-chloro-5-(hydroxymethyl)-1H-indole-1-carboxylate (4.3 g, 68%) as a white solid.

Step 4: Preparation of tert-butyl 3-chloro-5-(chloromethyl)-1H-indole-1-carboxylate

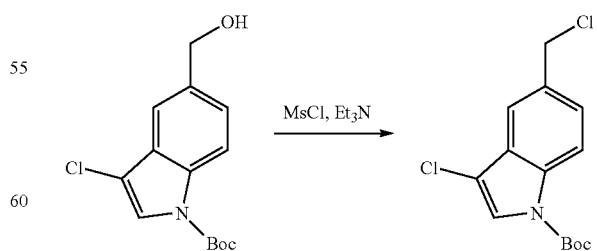

To a solution of tert-butyl 3-chloro-5-(hydroxymethyl)-1H-indole-1-carboxylate (1.5 g, 5.34 mmol, 1 eq) in dry DCM (30 mL) was added Et$_3$N (1.5 mL, 10.68 mmol, 2 eq) and MsCl (0.62 mL, 8.01 mmol, 1.5 eq). The resulting mixture was stirred at rt for 24 h and then quenched by the addition of water. The mixture was extracted with DCM. The combined extracts were dried and concentrated. The residue was purified by silica gel chromatography (PE/EtOAc=20/1, v/v) to afford tert-butyl 3-chloro-5-(chloromethyl)-1H-indole-1-carboxylate (1.17 g, 73%) as a white solid.

Step 5: Preparation of tert-butyl 3-chloro-5-((4-(methoxycarbonyl)pyridin-2-yl)methyl)-1H-indole-1-carboxylate

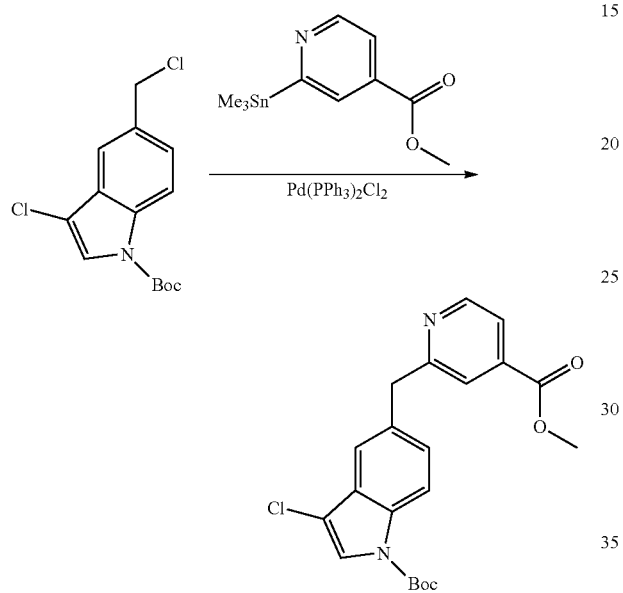

To a solution of tert-butyl 3-chloro-5-(chloromethyl)-1H-indole-1-carboxylate (1.1 g, 3.68 mmol, 1.0 eq) in dioxane (20 mL) was added methyl 2-(trimethylstannyl)isonicotinate (1.22 g, 4.05 mmol, 1.1 eq) and Pd(PPh₃)₂Cl₂ (260 mg, 0.37 mmol, 0.1 eq). The mixture was stirred at 90° C. for 3 h under nitrogen atmosphere, concentrated and purified by silica gel chromatography (PE/EtOAc=20/1, v/v) to afford tert-butyl 3-chloro-5-((4-(methoxycarbonyl)pyridin-2-yl) methyl)-1H-indole-1-carboxylate (690 mg, 47%) as an off-white solid.

Step 6: Preparation of 2-(3-chloro-1H-indol-5-ylmethyl)-isonicotinic acid

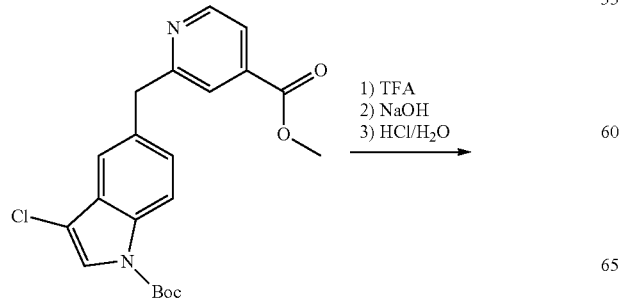

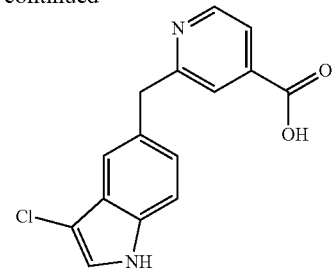

To a solution of tert-butyl 3-chloro-5-((4-(methoxycarbonyl)pyridin-2-yl)methyl)-1H-indole-1-carboxylate (690 mg, 1.72 mmol, 1.0 eq) in DCM (3 mL) was added TFA (5 mL). The mixture was stirred at rt for 2 h. Then the mixture was concentrated and the residue was re-dissolved in DCM and washed with sat. NaHCO₃ aq. The organic layer was concentrated. The residue was dissolved in THF/H₂O (5 mL, v/v=1:1). To the mixture was added NaOH. The mixture was stirred at rt for 0.5 h. Then the mixture was acidified to pH 5 with 1N HCl. The mixture was extracted with EtOAc. The combined organic layers were dried and concentrated to give 2-(3-chloro-1H-indol-5-ylmethyl)-isonicotinic acid (220 mg, 45%) as a yellow solid.

Step 7: Preparation of N-((6-amino-2,4-dimethylpyridin-3-yl)methyl)-2-((3-chloro-1H-indol-5-yl)methyl)isonicotinamide

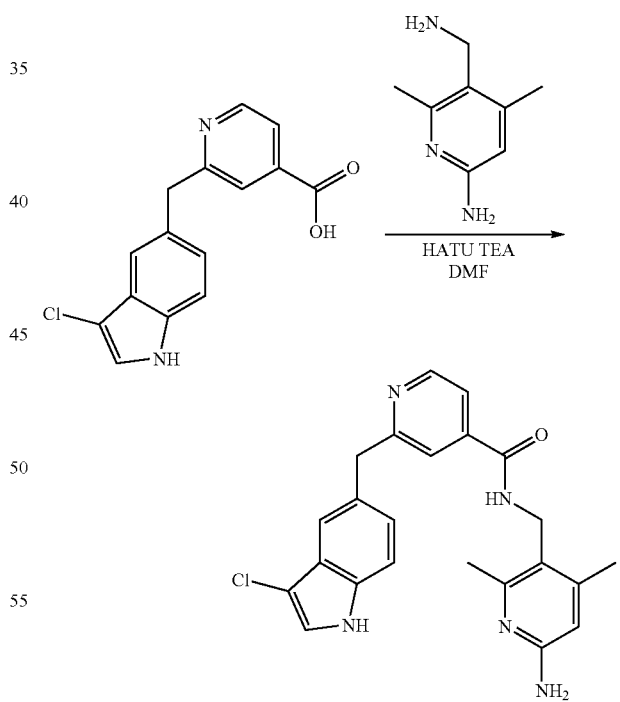

To a solution of 2-(3-chloro-1H-indol-5-ylmethyl)-isonicotinic acid (100 mg, 0.35 mmol, 1 eq) and 4-aminomethyl-3,5-dimethyl-phenylamine (117 mg, 0.52 mmol, 1.5 eq) in DMF (5 mL) was added HATU (160 mg, 0.42 mmol, 1.2 eq) and Et₃N (140 mg, 1.40 mmol, 4 eq). The mixture was stirred at rt for 1 h, concentrated and purified by prep-HPLC to give N-((6-amino-2,4-dimethylpyridin-3-yl)methyl)-2-

((3-chloro-1H-indol-5-yl) methyl)isonicotinamide (35 mg, 24%) as an off-white solid. LRMS (M+H⁺) m/z calculated 420.2. found 419.8.

$^1$H NMR (CD$_3$OD, 400 MHz) δ 8.54 (d, 1H), 7.61 (s, 1H), 7.54 (dd, 1H), 7.38 (s, 1H), 7.29 (d, 1H), 7.20 (s, 1H), 7.06 (dd, 1H), 6.28 (s, 1H), 4.45 (s, 2H), 4.25 (d, 2H), 2.36 (s, 3H), 2.22 (s, 3H).

Example 25: Preparation of N-((6-amino-2,4-dimethylpyridin-3-yl)methyl)-2-((3-methyl-1H-indol-5-yl)methyl)isonicotinamide

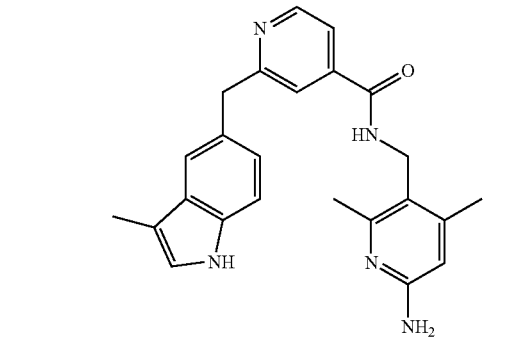

N-((6-amino-2,4-dimethylpyridin-3-yl)methyl)-2-((3-methyl-1H-indol-5-yl)methyl)isonicotinamide

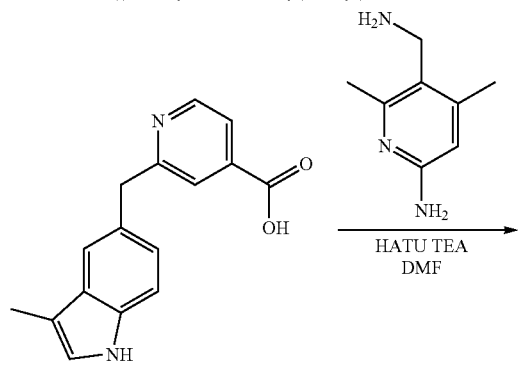

N-((6-amino-2,4-dimethylpyridin-3-yl)methyl)-2-((3-methyl-1H-indol-5-yl)methyl)isonicotinamide (25 mg, 16%) was prepared as described in Example 24, Step 7 as a white solid. LRMS (M+H⁺) m/z calculated 400.2. found 399.9. $^1$H NMR (CD$_3$OD, 400 MHz) δ 8.53 (d, 1H), 7.59 (s, 1H), 7.52 (d, 1H), 7.37 (s, 1H), 7.23 (d, 1H), 6.97 (d, 1H), 6.95 (s, 1H), 6.27 (s, 1H), 4.45 (s, 2H), 4.24 (d, 2H), 2.35 (s, 3H), 2.25 (s, 3H), 2.22 (s, 3H).

Example 26: Preparation of N-((6-amino-5-cyano-2-methylpyridin-3-yl)methyl)-2-((3-chloroquinolin-6-yl)methyl)isonicotinamide

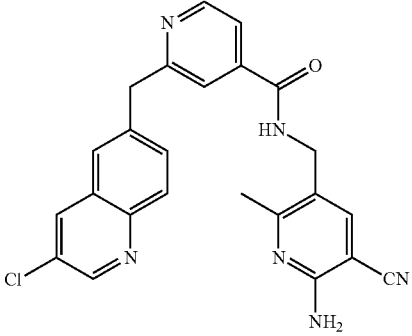

N-((6-amino-5-cyano-2-methylpryidin-3-yl)methyl)-2-((3-cholorquinolin-6-yl)methyl)isonicotinamide Step 1: Preparation of 5-aminomethyl-6-methyl-pyridin-2-ylamine hydrochloride

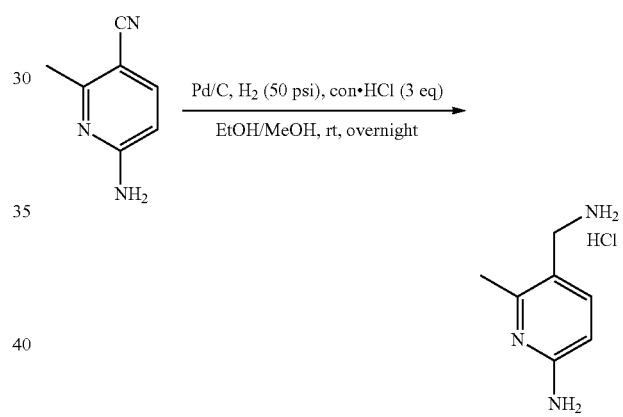

The mixture of 6-amino-2-methyl-nicotinonitrile (2 g, 15.0 mmol, 1 eq), Pd/C (10%, 500 mg), and con. HCl (3 mL) in a solution of EtOH/MeOH (10 mL/10 mL) was stirred at rt under H$_2$ (50 psi) for overnight. The reaction mixture was filtered, and the filtrate was concentrated to give crude 5-aminomethyl-6-methyl-pyridin-2-ylamine hydrochloride (3.5 g) as a yellow solid. LRMS (M+H⁺) m/z calculated 138. found 138.

Step 2: Preparation of tert-butyl (6-amino-2-methylpyridin-3-yl)methylcarbamate

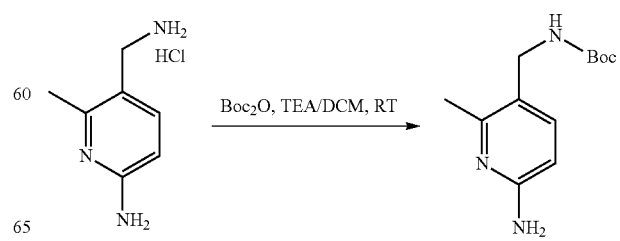

The mixture of 5-aminomethyl-6-methyl-pyridin-2-ylamine hydrochloride (3.5 g, crude) in DCM (50 mL) was added TEA (4.5 g, 45.0 mmol, 3 eq) followed by Boc$_2$O (4.9 g, 22.5 mmol, 1.5 eq). The reaction mixture was stirred at rt overnight. The reaction mixture was concentrated. The residue was purified by column chromatography on a silica gel (DCM/MeOH=20/1, v/v) to give tert-butyl (6-amino-2-methylpyridin-3-yl)methylcarbamate (3 g) as a white solid. LRMS (M+H$^+$) m/z calculated 238. found 238.

Step 3: Preparation of tert-butyl (6-amino-5-bromo-2-methylpyridin-3-yl)methylcarbamate

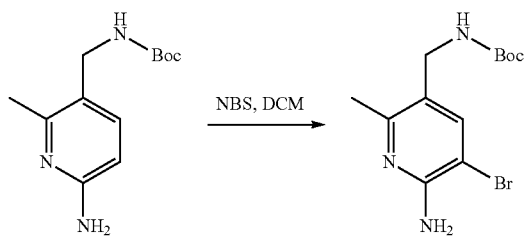 [SMILES: Cc1nc(N)ccc1CNC(=O)OC(C)(C)C ; Cc1nc(N)c(Br)cc1CNC(=O)OC(C)(C)C]

To the solution of tert-butyl (6-amino-2-methylpyridin-3-yl)methylcarbamate (3 g, 13.7 mmol, 1 eq) in DCM (30 mL) was added NBS (2.5 g, 13.9 mmol, 1.1 eq). The resulting mixture was concentrated. The residue was purified by column chromatography on a silica gel (PE/EtOAc=10/1 to EtOAc, v/v) to give tert-butyl (6-amino-5-bromo-2-methyl-pyridin-3-yl)methylcarbamate (2 g, 50%) as a white solid. LRMS (M+H$^+$) m/z calculated 316,318. found 316,318.

Step 4: Preparation of tert-butyl (6-amino-5-cyano-2-methylpyridin-3-yl)methylcarbamate

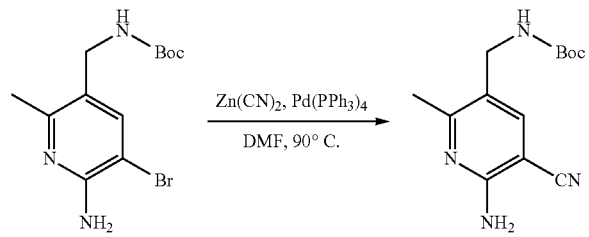 [SMILES: Cc1nc(N)c(Br)cc1CNC(=O)OC(C)(C)C ; Cc1nc(N)c(C#N)cc1CNC(=O)OC(C)(C)C]

The mixture of tert-butyl (6-amino-5-bromo-2-methyl-pyridin-3-yl)methylcarbamate (500 mg, 1.58 mmol, 1 eq), Zn(CN)$_2$ (185 mg, 1.58 mmol, 1.0 eq) and Pd(PPh$_3$)$_4$ (182 mg, 0.16 mmol, 0.1 eq) in DMF (20 mL) was heated to 95° C. and kept stirring for 3 h. Then it was cooled to rt, filtered, and the filtrate was concentrated. The residue was purified by column chromatography on a silica gel (PE/EtOAc=2/1, v/v) to give tert-butyl (6-amino-5-cyano-2-methylpyridin-3-yl)methylcarbamate (300 mg, 72%) as a white solid. LRMS (M+H$^+$) m/z calculated 263. found 263.

Step 5: Preparation of 2-amino-5-aminomethyl-6-methyl-nicotinonitrile hydrochloride

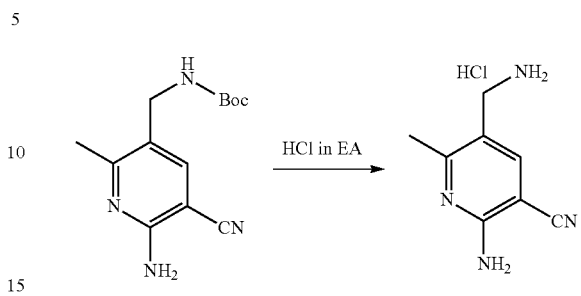

To the mixture of tert-butyl (6-amino-5-cyano-2-methyl-pyridin-3-yl)methylcarbamate (1.2 g, 4.6 mmol, 1 eq) in EtOAc (10 mL) was added 10 mL of 6 N HCl in EtOAc and kept stirring for 2 h. The reaction mixture was filtered, and the filter cake was washed with EtOAc to give 2-amino-5-aminomethyl-6-methyl-nicotinonitrile hydrochloride (600 mg, 67%) as a white solid. LRMS (M+H$^+$) m/z calculated 163. found 163.

Step 6: Preparation of N-((6-amino-5-cyano-2-methylpyridin-3-yl)methyl)-2-((3-chloroquinolin-6-yl)methyl)isonicotinamide

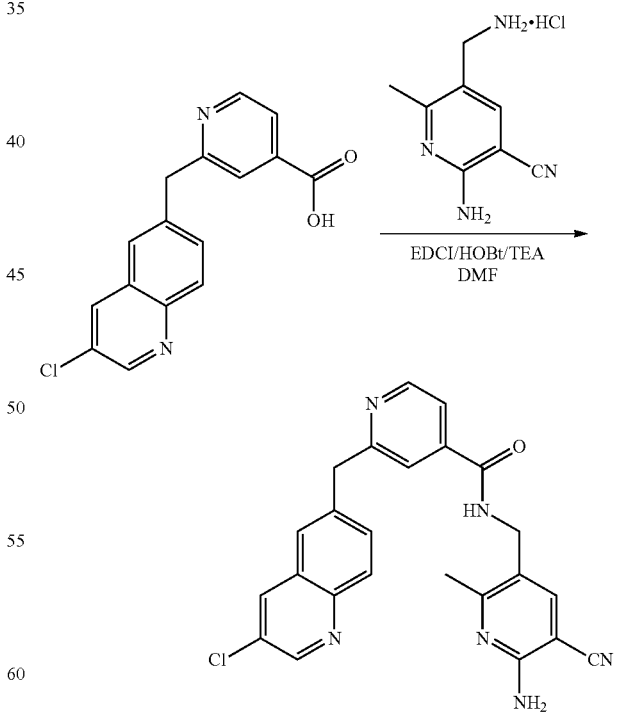

To a solution of 2-(3-chloro-quinolin-6-ylmethyl)-isonicotinic acid (80 mg, 0.27 mmol, 1 eq) in DMF (10 mL) was added 2-amino-5-aminomethyl-6-methyl-nicotinonitrile hydrochloride (54 mg, 0.27 mmol, 1 eq) followed by EDCI (78 mg, 0.41 mmol, 1.5 eq), HOBT (55 mg, 0.41 mmol, 1.5 eq) and TEA (82 mg, 0.81 mmol, 3.0 eq). The reaction mixture was heated to 45° C. kept stirring for overnight. Water was added, and the mixture was extracted with DCM. The organic layer was washed with water, dried over $Na_2SO_4$, filtered, and concentrated. The residue was purified by prep-HPLC to give N-((6-amino-5-cyano-2-methylpyridin-3-yl)methyl)-2-((3-chloroquinolin-6-yl)methyl)isonicotinamide (60 mg, 50%) as a white solid. LRMS (M+H$^+$) m/z calculated 443.1. found 442.8.

$^1$H NMR (DMSO-d$_6$, 400 MHz): δ 9.04 (t, 1H), 8.83 (d, 1H), 8.64 (d, 1H), 8.53 (s, 1H), 7.98 (d, 1H), 7.85 (s, 1H), 7.77 (s, 1H), 7.74 (d, 1H), 7.68 (s, 1H), 7.63 (s, 1H), 6.78 (s, 2H), 4.37 (s, 2H), 4.31 (d, 2H), 2.36 (s, 3H).

Example 27: Preparation of 2-amino-5-((2-((3-chloroquinolin-6-yl)methyl)isonicotinamido)methyl)-6-methylnicotinamide

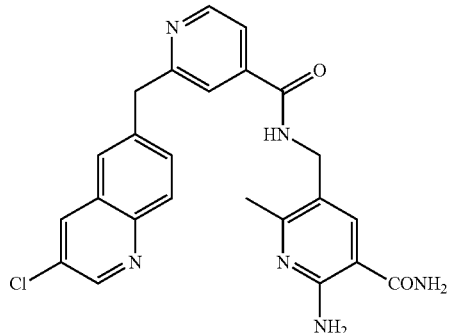

2-amino-5-((2-((3-chloroquinolin-6-yl)methyl)isonicotinamido)methyl)-6-methylnicotinamide

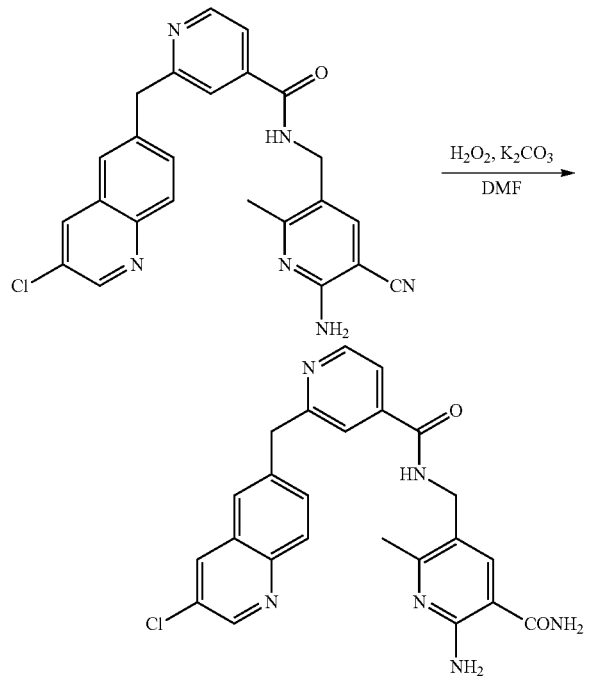

To a solution of N-((6-amino-5-cyano-2-methylpyridin-3-yl)methyl)-2-((3-chloroquinolin-6-yl)methyl)isonicotinamide (80 mg, 0.18 mmol, 1 eq) in DMF (5 mL) was added $K_2CO_3$ (50 mg, 0.36 mmol, 2.0 eq) followed by 30% of $H_2O_2$ (2 mL). The reaction mixture was heated to 50° C. kept stirring for 3 h. The reaction mixture was concentrated. The residue was purified by prep-HPLC to give 2-amino-5-((2-((3-chloroquinolin-6-yl)methyl)isonicotinamido)methyl)-6-methylnicotinamide (45 mg, 54%) as a white solid. LRMS (M+H$^+$) m/z calculated 461.1. found 461.1.

$^1$H NMR (DMSO-d$_6$, 400 MHz) δ 8.91 (t, 1H), 8.83 (d, 1H), 8.63 (d, 1H), 8.53 (d, 1H), 7.98 (d, 1H), 7.86 (s, 3H), 7.78 (s, 1H), 7.74 (d, 1H), 7.64 (d, 1H), 7.13-7.21 (m, 3H), 4.36 (s, 2H), 4.32 (d, 2H), 2.31 (s, 3H).

Example 28: Preparation of N-((6-amino-5-chloro-2-methylpyridin-3-yl)methyl)-2-((3-chloroquinolin-6-yl)methyl)isonicotinamide

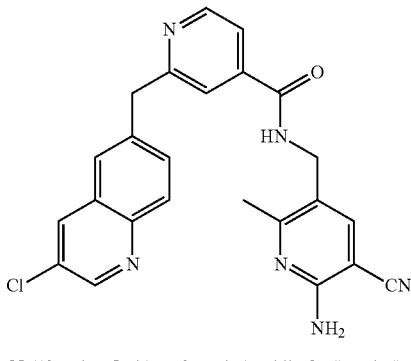

N-((6-amino-5-chloro-2-methylpryidin-3-yl)methyl)-2-((3-cholorquinolin-6-yl)methyl)isonicotinamide Step 1: Preparation of 6-amino-5-chloro-2-methyl-nicotinonitrile

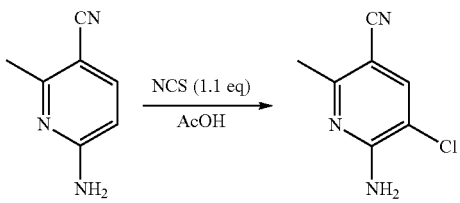

The mixture of 6-amino-2-methyl-nicotinonitrile (500 mg, 3.76 mmol, 1 eq) and NCS (1 g, 7.52 mmol, 2 eq) in AcOH (10 mL) was heated to 60° C. and kept stirring for 2 h. The reaction mixture was concentrated. The residue was purified by column chromatography on a silica gel (PE/EtOAc=10/1 to EtOAcv/v) to give 6-amino-5-chloro-2-methyl-nicotinonitrile (400 mg, 64%) as a white solid. LRMS (M+H$^+$) m/z calculated 168. found 168.

Step 2: Preparation of 5-aminomethyl-3-chloro-6-methyl-pyridin-2-ylamine hydrochloride

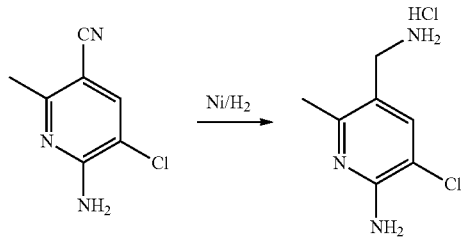

The mixture of 6-amino-5-chloro-2-methyl-nicotinonitrile (400 mg, 2.4 mmol, 1 eq), Rany Ni (400 mg) and conc. HCl (1 mL) in EtOH/MeOH (10 mL/10 mL) was stirred under $H_2$ (1 atm) at rt for overnight. The reaction mixture was filtered, and the filtrate was concentrated to give crude 5-aminomethyl-3-chloro-6-methyl-pyridin-2-ylamine hydrochloride (1 g) as a yellow solid. LRMS (M+H$^+$) m/z calculated 172. found 172.

Step 3: Preparation of N-((6-amino-5-cyano-2-methylpyridin-3-yl)methyl)-2-((3-chloroquinolin-6-yl)methyl)isonicotinamide

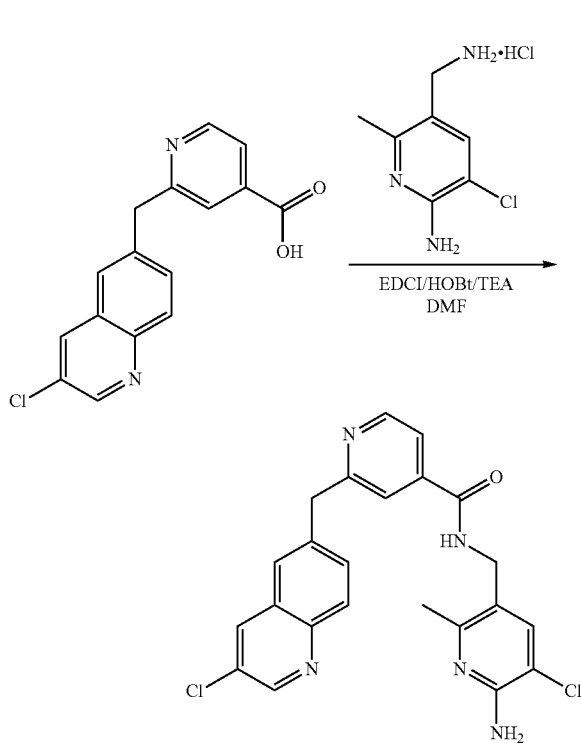

N-((6-amino-5-chloro-2-methylpyridin-3-yl)methyl)-2-((3-chloroquinolin-6-yl)methyl)isonicotinamide (15 mg, 12%) was prepared as described for N-((6-amino-5-cyano-2-methylpyridin-3-yl)methyl)-2-((3-chloroquinolin-6-yl)methyl)isonicotinamide (Example 26) as a white solid. LRMS (M+H$^+$) m/z calculated 452.1. found 451.8.

$^1$H NMR (DMSO-d$_6$, 400 MHz) δ 9.03 (t, 1H), 8.83 (d, 1H), 8.63 (d, 1H), 8.52 (d, 1H), 7.98 (d, 1H), 7.85 (s, 1H), 7.72-7.76 (m, 2H), 7.62 (d, 1H), 7.41 (s, 1H), 6.11 (s, 2H), 4.36 (s, 2H), 4.29 (d, 2H), 2.29 (s, 3H).

Example 29: Preparation of N-((6-amino-4-methyl-pyridin-3-yl)methyl)-2-((3-chloroquinolin-6-yl)methyl)isonicotinamide

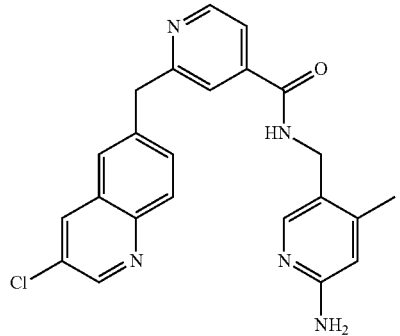

N-((6-amino-4-methylpyridin-3-yl)methyl)-2-((3-chloroquinolin-6-yl)methyl)isonicotinamide

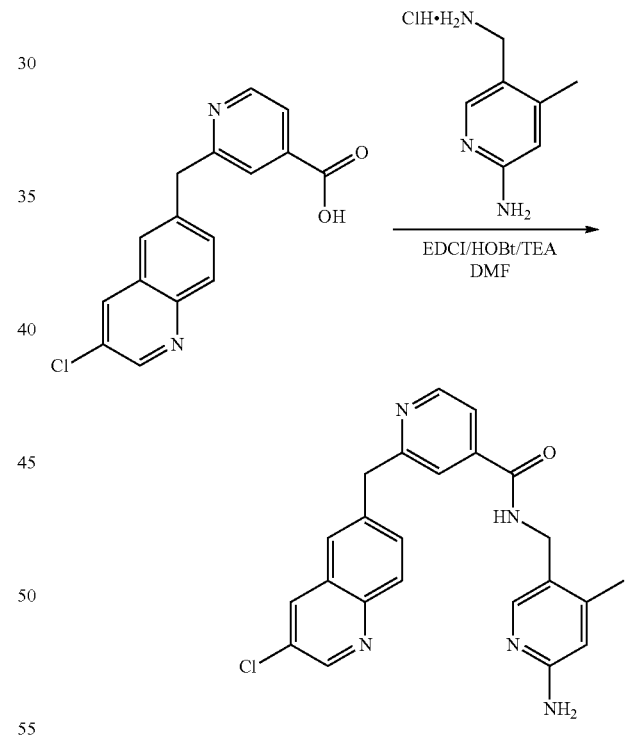

N-((6-amino-4-methylpyridin-3-yl)methyl)-2-((3-chloroquinolin-6-yl)methyl)isonicotinamide (25 mg, 22%) was prepared as described for N-((6-amino-5-cyano-2-methylpyridin-3-yl)methyl)-2-((3-chloroquinolin-6-yl)methyl)isonicotinamide (Example 26) as a white solid. LRMS (M+H$^+$) m/z calculated 418.1. found 417.8.

$^1$H NMR (DMSO-d$_6$, 300 MHz) δ 8.93 (t, 1H), 8.83 (d, 1H), 8.62 (d, 1H), 8.52 (d, 1H), 7.98 (d, 1H), 7.84 (s, 1H), 7.71-7.77 (m, 2H), 7.61 (d, 1H), 6.24 (s, 1H), 5.75 (s, 2H), 4.37 (s, 2H), 4.29 (d, 2H), 2.14 (s, 3H).

Example 30: Preparation of N-((6-amino-2-(trifluoromethyl)pyridin-3-yl)methyl)-2-((3-chloroquinolin-6-yl)methyl)isonicotinamide

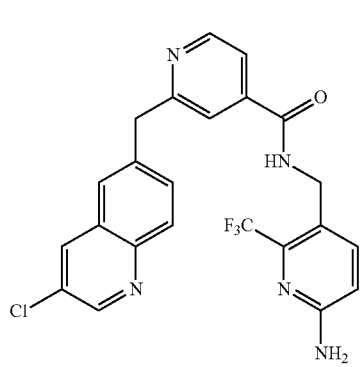

N-((6-amino-2-(trifluoromethyl)pyridin-3-yl)methyl)-2-((3-chloroquinolin-6-yl)methyl)isonicotinamide

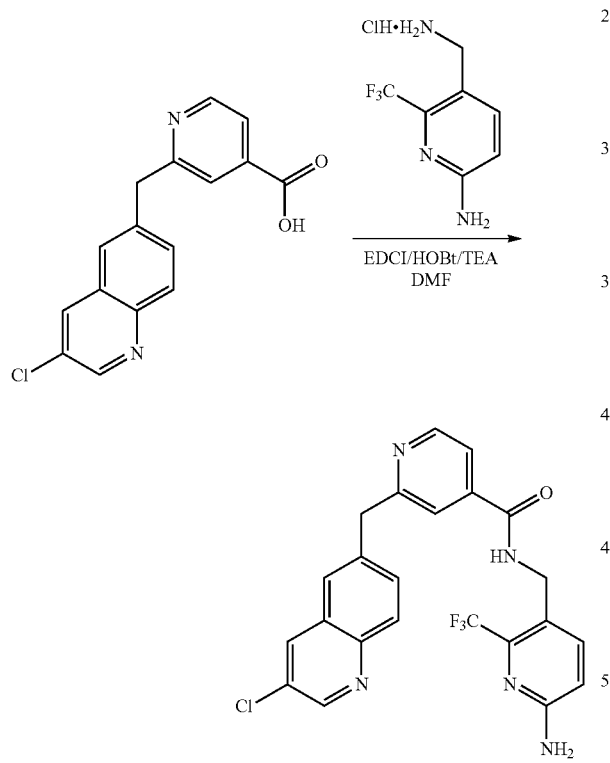

N-((6-amino-2-(trifluoromethyl)pyridin-3-yl)methyl)-2-((3-chloroquinolin-6-yl)methyl)isonicotinamide (45 mg, 35%) was prepared as described for N-((6-amino-5-cyano-2-methylpyridin-3-yl)methyl)-2-((3-chloroquinolin-6-yl)methyl)isonicotinamide (Example 26) as a white solid. LRMS (M+H$^+$) m/z calculated 472.1. found 471.8.

$^1$H NMR (DMSO-d$_6$, 400 MHz) δ 9.13 (t, 1H), 8.83 (d, 1H), 8.65 (d, 1H), 8.53 (d, 1H), 7.98 (d, 1H), 7.86 (s, 1H), 7.77 (s, 1H), 7.74 (d, 1H), 7.64 (d, 1H), 7.52 (d, 1H), 6.65 (d, 1H), 6.44 (s, 2H), 4.44 (d, 2H), 4.37 (s, 2H).

Example 31: Preparation of N-((1-aminoisoquinolin-6-yl)methyl)-2-((3-chloroquinolin-6-yl)methyl)isonicotinamide

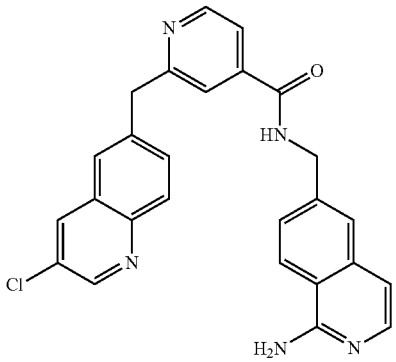

N-((1-aminoisoquinolin-6-yl)methyl)-2-((3-chloroquinolin-6-yl)methyl)isonicotinamide

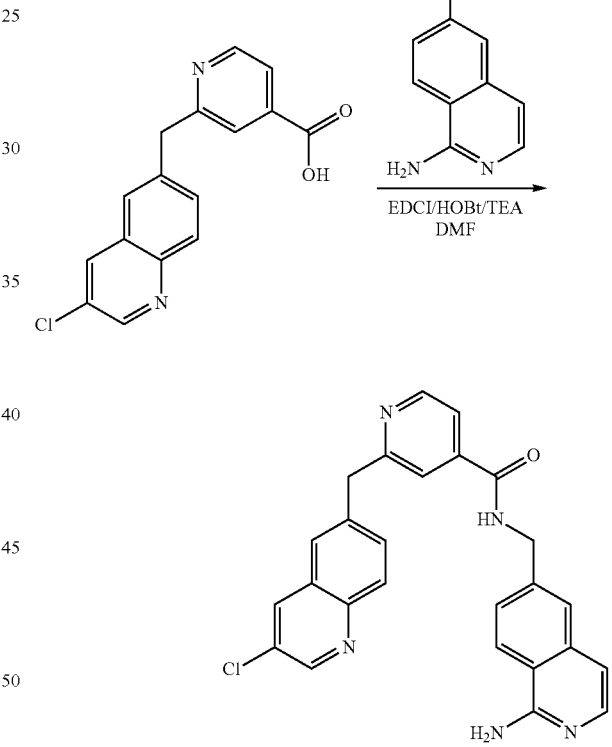

N-((1-aminoisoquinolin-6-yl)methyl)-2-((3-chloroquinolin-6-yl)methyl)isonicotinamide (65 mg, 45%) was prepared as described for N-((6-amino-5-cyano-2-methylpyridin-3-yl)methyl)-2-((3-chloroquinolin-6-yl)methyl)isonicotinamide (Example 26) as a white solid. LRMS (M+H$^+$) m/z calculated 454.1. found 453.9.

$^1$H NMR (DMSO-d$_6$, 400 MHz) δ 9.40 (t, 1H), 8.83 (d, 1H), 8.67 (d, 1H), 8.54 (s, 1H), 8.13 (d, 1H), 7.97 (d, 1H), 7.87 (s, 1H), 7.81 (s, 1H), 7.74-7.76 (m, 2H), 7.69 (d, 1H), 7.55 (s, 1H), 7.40 (d, 1H), 6.84 (d, 1H), 6.74 (s, 2H), 4.61 (d, 2H), 4.38 (s, 2H).

Example 32: Preparation of 2-(3-chloro-quinolin-6-ylmethyl)-N-(6-fluoro-1H-indazol-5-ylmethyl)-isonicotinamide

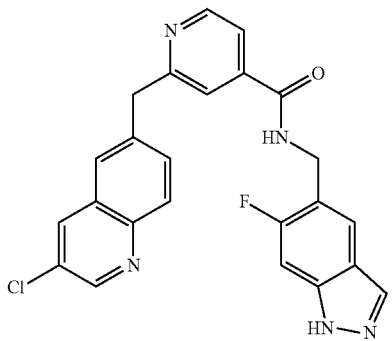

2-(3-chloro-quinolin-6-ylmethyl)-N-(6-fluoro-1H-indazol-5-ylmethyl)-isonicotinamide

Step 1: Preparation of 4-amino-2-fluoro-5-methyl-benzonitrile

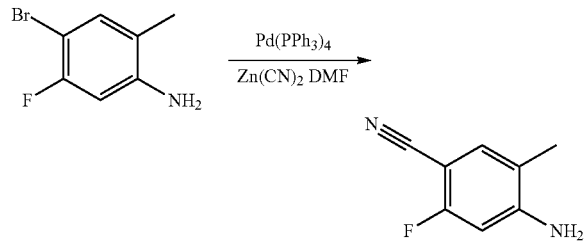

To a solution of 4-bromo-5-fluoro-2-methyl-phenylamine (20 g, 98.0 mmol, 1.0 eq) in DMF (100 mL) was added Zn(CN)2 (28.7 g, 245 mmol, 2.5 eq), followed by addition of Pd(PPh$_3$)$_4$ under N$_2$. The mixture was stirred at 90° C. for overnight. The mixture was concentrated in vacuo and the residue was dissolved in water, extracted with EtOAc. The combined extracts were dried and concentrated. The residue was purified by column chromatography on a silica gel column (PE/EtOAc=10/1, v/v) to afford 4-amino-2-fluoro-5-methyl-benzonitrile as a yellow solid (13.68 g, 92%).

Step 2: Preparation of 6-fluoro-1H-indazole-5-carbonitrile

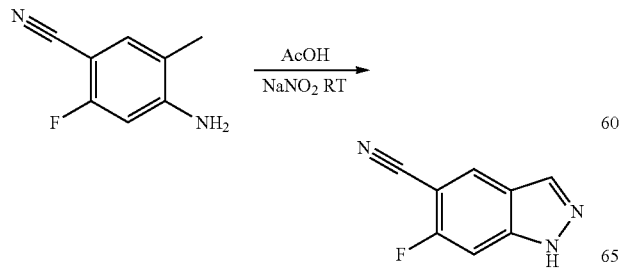

To a solution of 4-amino-2-fluoro-5-methyl-benzonitrile (13.68 g, 90.59 mmol, 1.0 eq) in AcOH (450 mL) was added NaNO$_2$ (7.5 g, 108.7 mmol, 1.2 eq). The mixture was stirred at rt for overnight. Upon completion, aqueous NaOH (50%) was added to the reaction mixture until pH 7-8. The mixture was extracted with EtOAc. The organic layer was concentrated under pressure. The residue was purified by column chromatography on a silica gel column (PE/EtOAc=15/1, v/v) to afford 6-fluoro-1H-indazole-5-carbonitrile as a white solid (5 g, 34%).

Step 3: Preparation of 6-fluoro-1-(tetrahydro-pyran-2-yl)-1H-indazole-5-carbonitrile

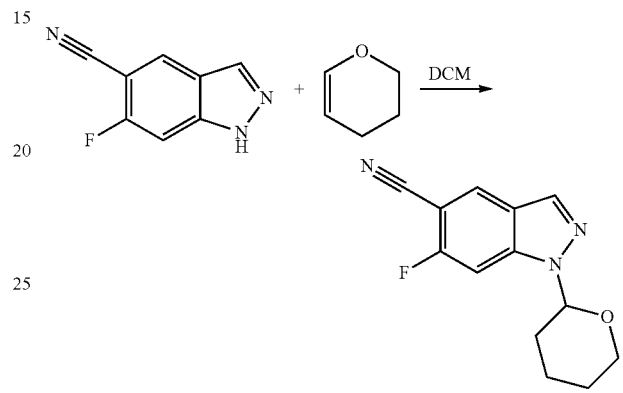

To a solution of 6-fluoro-1H-indazole-5-carbonitrile (5 g, 31.05 mmol, 1.0 eq) and 3,4-dihydro-2H-pyran (5.25 g, 62.1 mmol, 2 eq) in DCM (50 mL) was added PTSA (590 mg, 3.11 mmol, 0.1 eq) and the mixture was stirred at rt overnight. Solvent was removed in vacuo. The residue was dissolved in EtOAc, washed with water, brine and dried over Na$_2$SO$_4$. The combined extracts were dried and concentrated. The residue was purified by chromatography on a silica gel column (PE/EtOAc=15/1, v/v) to afford 6-fluoro-1-(tetrahydro-pyran-2-yl)-1H-indazole-5-carbonitrile as a brown solid (4.39 g, 57%).

Step 4: Preparation of (6-fluoro-1-(tetrahydro-2H-pyran-2-yl)-1H-indazol-5-yl)methanamine

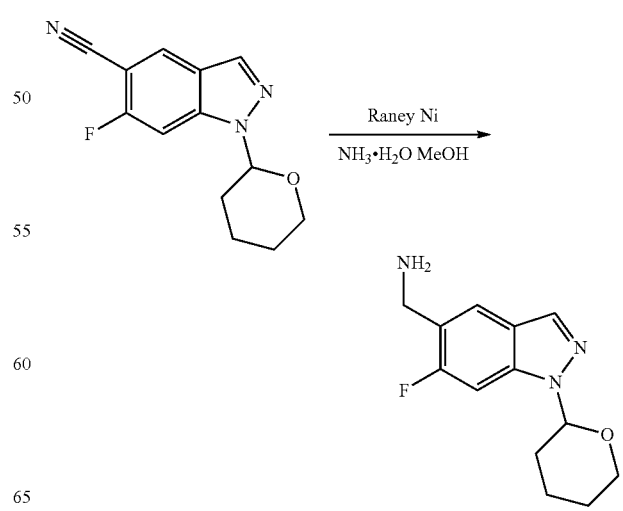

To a solution of 6-fluoro-1-(tetrahydro-pyran-2-yl)-1H-indazole-5-carbonitrile (4.39 g, 17.92 mmol, 1.0 eq) in MeOH (20 mL) was added Raney Ni (800 mg) under H₂. The mixture was stirred at rt overnight. The reaction mixture was filtered and the filtrate was purified by chromatography on a silica gel column (PE/EtOAc=15/1, v/v) to give (6-fluoro-1-(tetrahydro-2H-pyran-2-yl)-1H-indazol-5-yl)methanamine (3.8 g, 85%) as a white solid.

Step 5: Preparation of (6-fluoro-1H-indazol-5-yl)methanamine hydrochloride

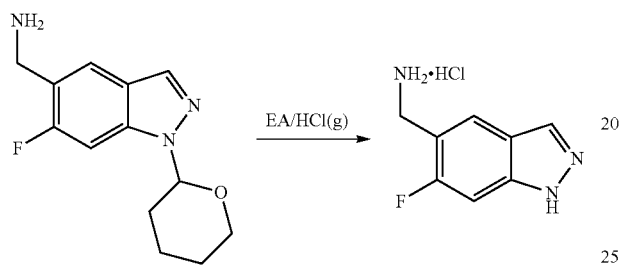

To a solution of (6-fluoro-1-(tetrahydro-2H-pyran-2-yl)-1H-indazol-5-yl)methanamine (3.43 g, 15.26 mmol, 1 eq) in EtOAc was added EtOAc/HCl (10 M). The mixture was stirred at rt for 3 h. The reaction mixture was filtered and the filtrate was concentrated to give (6-fluoro-1H-indazol-5-yl)methanamine hydrochloride (3.43 mg, crude).

Step 6: Preparation of 2-(3-Chloro-quinolin-6-ylmethyl)-N-(6-fluoro-1H-indazol-5-ylmethyl)-isonicotinamide

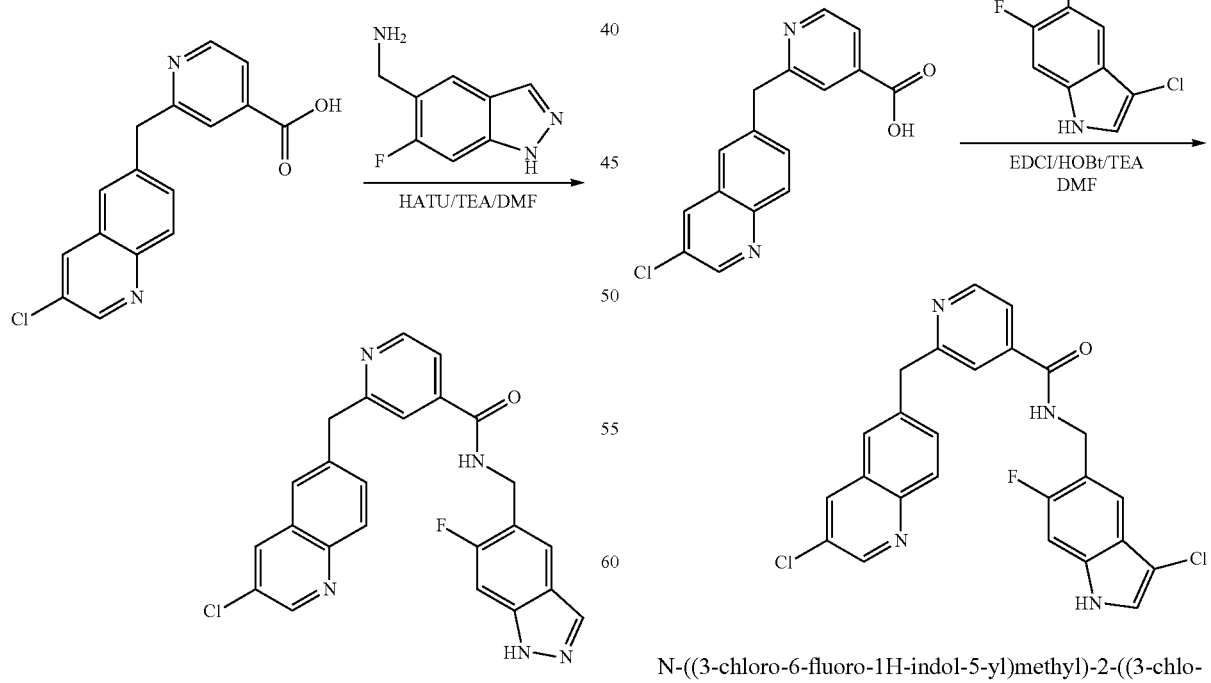

To a solution of (6-fluoro-1H-indazol-5-yl)-methylamine hydrochloride (80 mg, 0.4 mmol, 1.5 eq) in DMF (10 mL) was added 2-(3-chloro-quinolin-6-ylmethyl)-isonicotinic acid (80 mg, 0.26 mmol, 1 eq), HATU (122 mg, 0.32 mmol/1.2 eq), and TEA (1 mL). The reaction mixture was stirred at rt for 3 h. Then it was quenched with water, extracted with DCM. The combined extracts were dried and concentrated, and the residue was purified by prep-HPLC to give 2-(3-Chloro-quinolin-6-ylmethyl)-N-(6-fluoro-1H-indazol-5-ylmethyl)-isonicotinamide (30 mg, 27%) as a white solid. LCMS (M+H⁺) m/z calculated 446.1. found 446.0.
¹H NMR (DMSO-d6, 400 MHz) δ 13.09 (s, 1H), 9.26-9.28 (t, 1H), 8.83-8.84 (d, 1H), 8.65-8.66 (d, 1H), 8.52-8.53 (d, 1H), 8.06 (s, 1H), 7.97-7.99 (d, 1H), 7.86 (s, 1H), 7.80 (s, 1H), 7.68-7.76 (m, 2H), 7.67-7.68 (d, 1H), 7.32-7.35 (d, 1H), 4.56-4.57 (d, 2H), 4.38 (s, 2H), 2.50 (s, 3H).

Example 33: Preparation of N-((3-chloro-6-fluoro-1H-indol-5-yl)methyl)-2-((3-chloroquinolin-6-yl)methyl)isonicotinamide

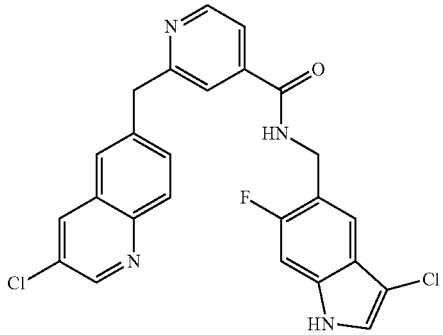

N-((3-chloro-6-fluoro-1H-indol-5-yl)methyl)-2-((3-chloroquinolin-6-yl)methyl)isonicotinamide

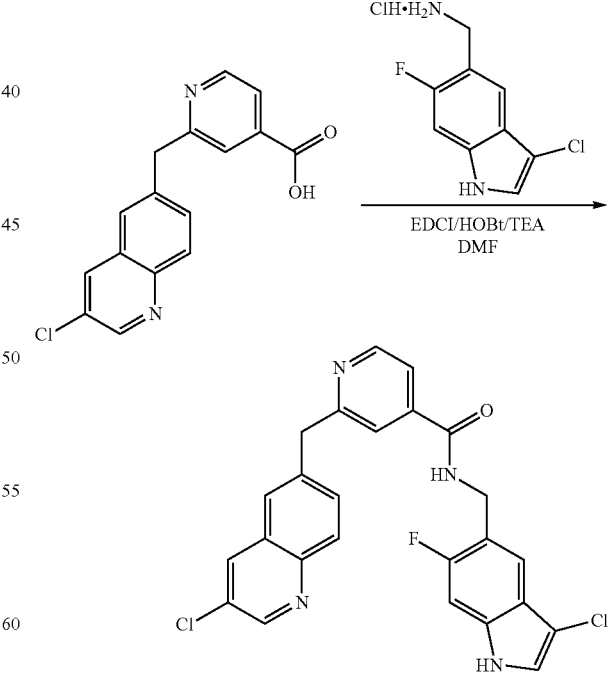

N-((3-chloro-6-fluoro-1H-indol-5-yl)methyl)-2-((3-chloroquinolin-6-yl)methyl)isonicotinamide (50 mg, 33%) was prepared as described for N-((6-amino-5-cyano-2-methylpyridin-3-yl)methyl)-2-((3-chloroquinolin-6-yl)methyl)

isonicotinamide (Example 26) as a yellow solid. LRMS (M+H⁺) m/z calculated 479.1. found 478.9.

¹H NMR (DMSO-d$_6$, 400 MHz): δ 11.42 (br, 1H), 9.25 (t, 1H), 8.83 (s, 1H), 8.65 (d, 1H), 8.53 (s, 1H), 7.98 (d, 1H), 7.85 (s, 1H), 7.79 (s, 1H), 7.74 (d, 1H), 7.66 (d, 1H), 7.51 (s, 1H), 7.44 (d, 1H), 7.22 (d, 1H), 4.58 (d, 2H), 4.37 (s, 2H).

Example 34: Preparation of N-((6-amino-2-methyl-pyridin-3-yl)methyl)-2-((3-chloroquinolin-6-yl)methyl)isonicotinamide

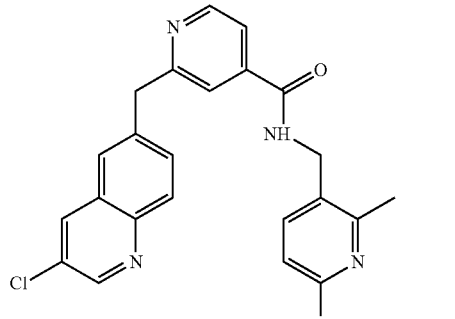

N-((6-amino-2-methylpyridin-3-yl)methyl)-2-((3-chloroquinolin-6-yl)methyl)isonicotinamide

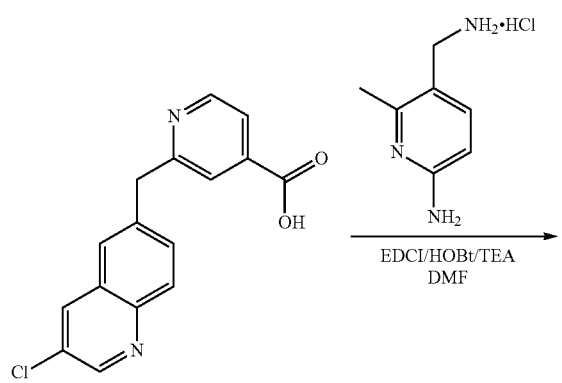

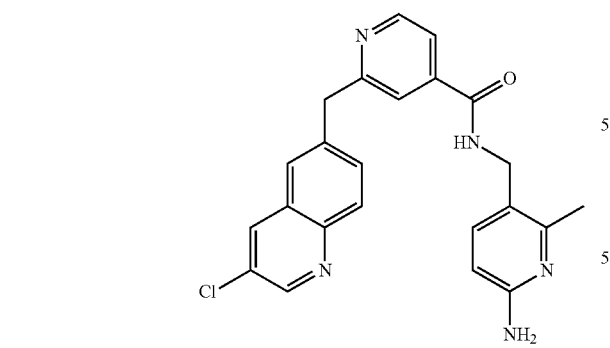

N-((6-amino-2-methylpyridin-3-yl)methyl)-2-((3-chloroquinolin-6-yl)methyl)isonicotinamide N-((6-amino-2-methylpyridin-3-yl)methyl)-2-((3-chloroquinolin-6-yl)methyl)isonicotinamide (60 mg, 45%) was prepared as described for N-((6-amino-5-cyano-2-methyl-pyridin-3-yl)methyl)-2-((3-chloroquinolin-6-yl)methyl)isonicotinamide (Example 26) as a yellow solid. LRMS (M+H⁺) m/z calculated 418.1. found 417.8.

¹H NMR (DMSO-d$_6$, 400 MHz) δ 9.00 (t, 1H), 8.83 (d, 1H), 8.63 (d, 1H), 8.53 (d, 1H), 7.98 (d, 1H), 7.85 (s, 1H), 7.73-7.76 (m, 2H), 7.62 (d, 1H), 7.77 (d, 1H), 6.26 (d, 1H), 5.85 (s, 2H), 4.36 (s, 2H), 4.28 (d, 2H), 2.28 (s, 3H).

Example 35: Preparation of N-((6-amino-2,4-dimethylpyridin-3-yl)methyl)-2-((3-chloroquinolin-6-yl)methyl)isonicotinamide

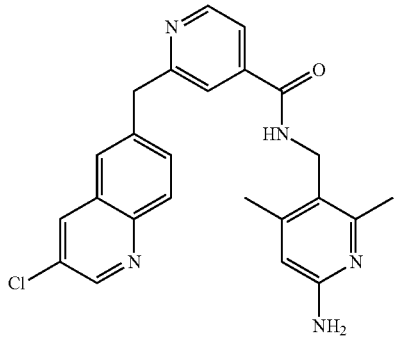

N-((6-amino-2,4-dimethylpyridin-3-yl)methyl)-2-((3-chloroquinolin-6-yl)methyl)isonicotinamide

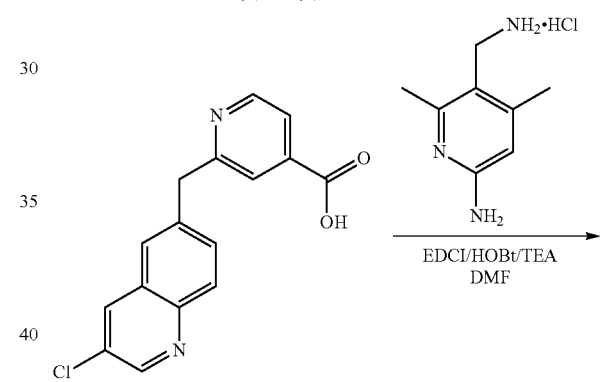

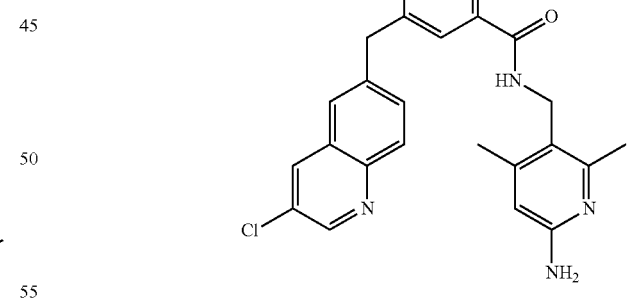

N-((6-amino-2,4-dimethylpyridin-3-yl)methyl)-2-((3-chloroquinolin-6-yl)methyl)isonicotinamide (40 mg, 29%) was prepared as described for N-((6-amino-5-cyano-2-methylpyridin-3-yl)methyl)-2-((3-chloroquinolin-6-yl)methyl)isonicotinamide (Example 26) as a yellow solid. LRMS (M+H⁺) m/z calculated 432.2. found 432.0.

¹H NMR (DMSO-d$_6$, 400 MHz) δ 8.83 (d, 1H), 8.64 (t, 1H), 8.60 (d, 1H), 8.53 (s, 1H), 7.97 (d, 1H), 7.84 (s, 2H), 7.72-7.75 (m, 2H), 7.60 (d, 1H), 6.11 (s, 1H), 5.67 (s, 2H), 4.33-4.35 (m, 4H), 2.29 (s, 3H), 2.15 (s, 3H).

Example 36: Preparation of N-((3-aminobenzo[d]isoxazol-6-yl)methyl)-2-((3-chloroquinolin-6-yl)methyl)isonicotinamide

Example 37: Preparation of N-(5-chloro-1H-indazol-3-ylmethyl)-2-(3-chloro-quinolin-6-ylmethyl)-isonicotinamide

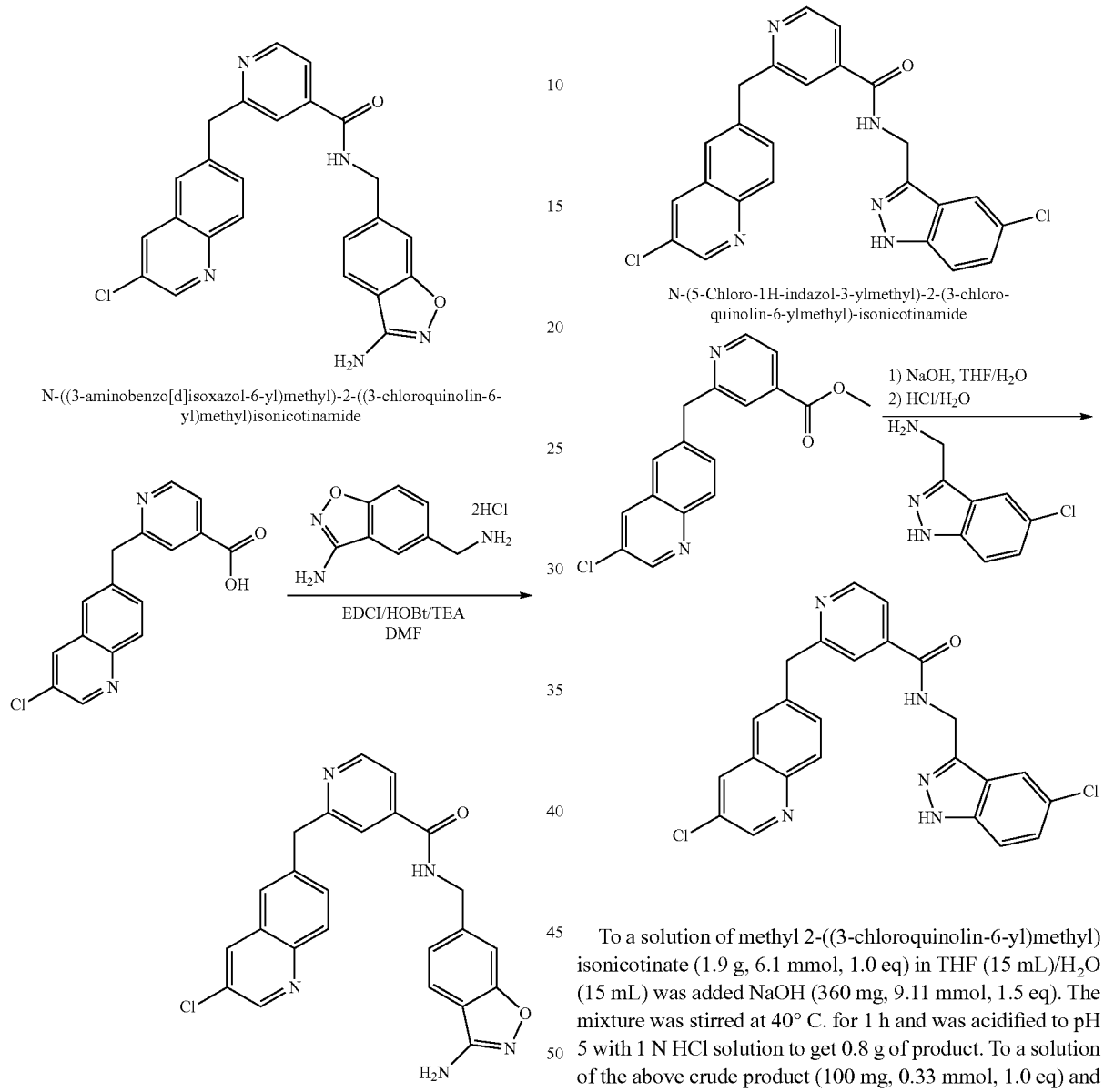

N-((3-aminobenzo[d]isoxazol-6-yl)methyl)-2-((3-chloroquinolin-6-yl)methyl)isonicotinamide (65 mg, 46%) was prepared as described for N-((6-amino-5-cyano-2-methyl-pyridin-3-yl)methyl)-2-((3-chloroquinolin-6-yl)methyl)isonicotinamide (Example 26) as a yellow solid. LRMS (M+H⁺) m/z calculated 444.1. found 443.9.

¹H NMR (DMSO-d₆, 400 MHz) δ 9.38 (t, 1H), 8.83 (d, 1H), 8.67 (s, 1H), 8.53 (d, 1H), 7.99 (d, 1H), 7.86 (s, 1H), 7.81 (s, 1H), 7.76 (d, 2H), 7.67 (d, 1H), 7.36 (s, 1H), 7.21 (d, 1H), 6.38 (s, 2H), 4.60 (d, 2H), 4.38 (s, 2H).

To a solution of methyl 2-((3-chloroquinolin-6-yl)methyl)isonicotinate (1.9 g, 6.1 mmol, 1.0 eq) in THF (15 mL)/H₂O (15 mL) was added NaOH (360 mg, 9.11 mmol, 1.5 eq). The mixture was stirred at 40° C. for 1 h and was acidified to pH 5 with 1 N HCl solution to get 0.8 g of product. To a solution of the above crude product (100 mg, 0.33 mmol, 1.0 eq) and (5-chloro-1H-indazol-3-yl)-methylamine (120 mg, 0.66 mmol, 2.0 eq) in DMF (8 mL) was added HATU (152 mg, 0.4 mmol, 1.2 eq) and Et₃N (0.15 mL, 0.99 mmol, 3 eq). The mixture was stirred at rt for overnight, concentrated and purified was purified by flash chromatography on a silica gel column (DCM/MeOH=10/1, v/v) to give N-(5-chloro-1H-indazol-3-ylmethyl)-2-(3-chloro-quinolin-6-ylmethyl)-isonicotinamide (46 mg, 30% for 2 steps) as a white solid. LRMS (M+H⁺) m/z calculated 462.1. found 461.9.

¹H NMR (DMSO-d₆, 400 MHz) δ 13.09 (s, 1H), 9.40 (m, 1H), 8.82-8.83 (d, 1H), 8.63-8.64 (d, 1H), 8.51-8.52 (d, 1H), 7.96-7.98 (d, 1H), 7.89 (s, 1H), 7.84 (s, 1H), 7.78 (s, 1H), 7.74 (d, 1H), 7.64 (d, 1H), 7.52-7.54 (d, 1H), 7.32-7.34 (dd, 1H), 4.77-4.78 (d, 2H), 4.36 (s, 2H).

Example 38: Preparation of N-(3-Chloro-1H-pyrrolo[2,3-b]pyridin-5-ylmethyl)-2-(3-chloro-quinolin-6-ylmethyl)-isonicotinamide

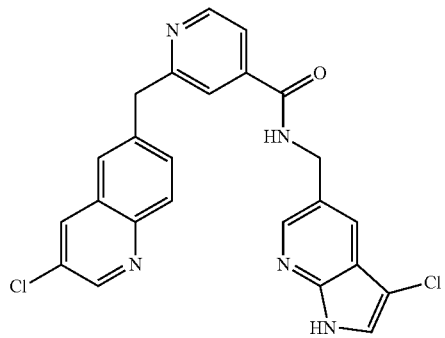

N-(3-Chloro-1H-pyrrolo[2,3-b]pyridin-5-ylmethyl)-2-(3-chloro-quinolin-6-ylmethyl)-isonicotinamide

Example 39: Preparation of N-(6-Amino-2-methyl-pyridin-3-ylmethyl)-2-(3-chloro-quinolin-6-ylmethyl)-isonicotinamide

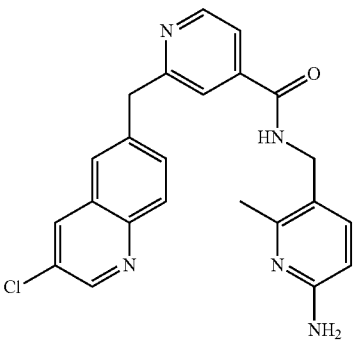

N-(6-Amino-2-methyl-pyridin-3-ylmethyl)-2-(3-chloro-quinolin-6-ylmethyl)-isonicotinamide

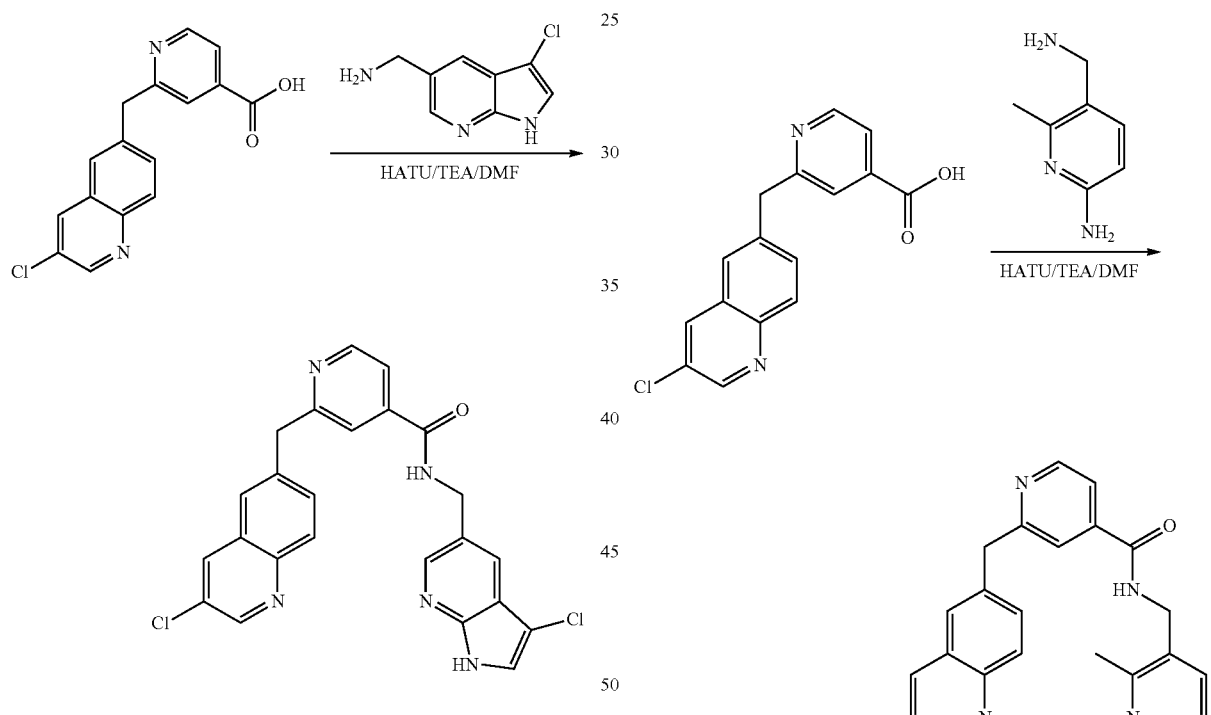

To a solution of 2-(3-chloro-quinolin-6-ylmethyl)-isonicotinic acid (100 mg, 0.33 mmol, 1.0 eq) and (3-chloro-1H-pyrrolo[2,3-b]pyridin-5-yl)-methylamine (120 mg, 0.66 mmol, 2.0 eq) in DMF (8 mL) was added HATU (152 mg, 0.4 mmol, 1.2 eq) and Et$_3$N (0.15 mL, 0.99 mmol, 3 eq). The mixture was stirred at rt for overnight, concentrated and purified was purified by flash chromatography on a silica gel column (DCM/MeOH=10/1, v/v) to give N-(5-chloro-1H-indazol-3-ylmethyl)-2-(3-chloro-quinolin-6-ylmethyl)-isonicotinamide (13 mg, 8.5%) as a white solid. LRMS (M+H$^+$) m/z calculated 462.1. found 461.9.

$^1$H NMR (DMSO-d$_6$, 400 MHz) δ 11.96 (s, 1H), 9.33 (m, 1H), 8.82 (d, 1H), 8.65 (d, 1H), 8.51-8.52 (d, 1H), 8.30 (d, 1H), 7.98 (d, 1H), 7.86 (m, 2H), 7.63-7.77 (m, 4H), 4.57-4.59 (d, 2H), 4.36 (s, 2H).

N-(6-amino-2-methyl-pyridin-3-ylmethyl)-2-(3-chloro-quinolin-6-ylmethyl)-isonicotinamide (41 mg, 30%) was prepared as described for N-(5-chloro-1H-indazol-3-ylmethyl)-2-(3-chloro-quinolin-6-ylmethyl)-isonicotinamide (Example 37) as a white solid. LRMS (M+H$^+$) m/z calculated 418.1. found 418.0.

$^1$H NMR (DMSO-d$_6$, 400 MHz) δ 8.99 (m, 1H), 8.83 (d, 1H), 8.62-8.63 (d, 1H), 8.53 (d, 1H), 7.96-7.99 (d, 1H), 7.85 (s, 1H), 7.72-7.76 (m, 2H), 7.61-7.63 (d, 1H), 6.21-6.23 (d, 2H), 5.75 (s, 2H), 4.36 (s, 2H), 4.27 (d, 2H), 2.27 (s, 2H).

Example 40: Preparation of N-(3-Chloro-4-fluoro-1H-indol-5-ylmethyl)-2-(3-chloro-quinolin-6-ylmethyl)-isonicotinamide

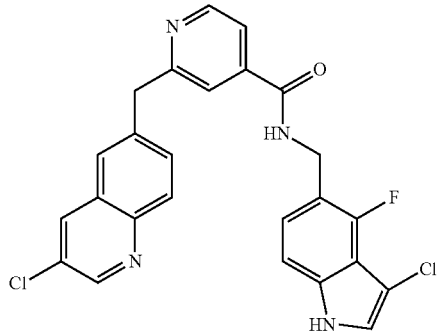

N-(3-Chloro-4-fluoro-1H-indol-5-ylmethyl)-2-(3-chloro-quinolin-6-ylmethyl)-isonicotinamide

Example 41: Preparation of 2-(3-chloro-quinolin-6-ylmethyl)-N-(6-fluoro-1H-indol-5-ylmethyl)-isonicotinamide

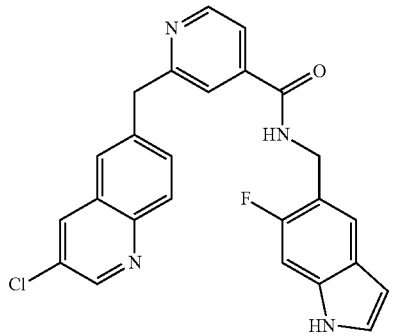

2-(3-Chloro-quinolin-6-ylmethyl)-N-(6-fluoro-1H-indol-5-ylmethyl)-isonictinamide

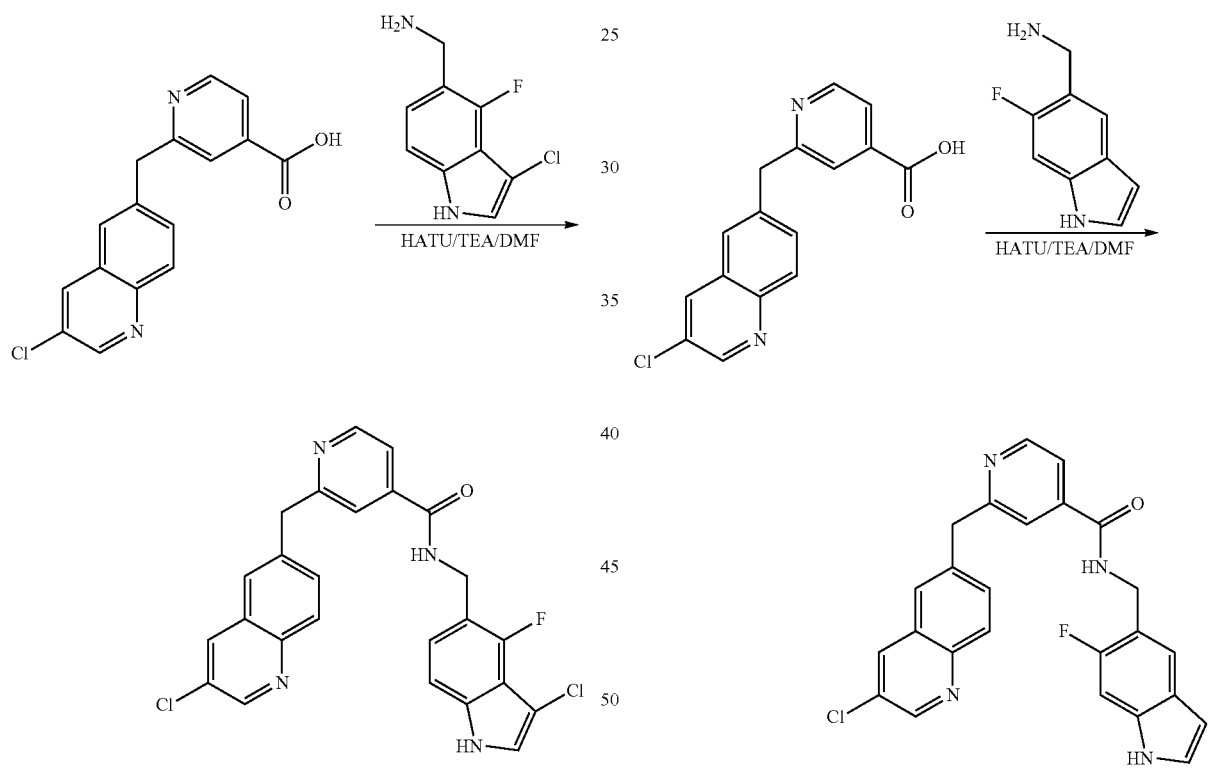

N-(3-chloro-4-fluoro-1H-indol-5-ylmethyl)-2-(3-chloro-quinolin-6-ylmethyl)-isonicotinamide (41 mg, 26%) was prepared as described for N-(5-chloro-1H-indazol-3-ylmethyl)-2-(3-chloro-quinolin-6-ylmethyl)-isonicotinamide (Example 37) as a white solid. LRMS (M+H$^+$) m/z calculated 479.1. found 479.0.

$^1$H NMR (DMSO-d$_6$, 400 MHz) δ 11.59 (s, 1H), 9.23 (m, 1H), 8.82 (d, 1H), 8.63 (d, 1H), 8.52 (d, 1H), 7.98 (d, 1H), 7.84 (s, 1H), 7.78 (s, 1H), 7.72-7.74 (d, 1H), 7.63-7.64 (d, 1H), 7.50-7.51 (d, 1H), 7.12-7.19 (m, 2H), 4.55-4.57 (d, 2H), 4.36 (s, 2H).

2-(3-Chloro-quinolin-6-ylmethyl)-N-(6-fluoro-1H-indol-5-ylmethyl)-isonicotinamide (71 mg, 48%) was prepared as described for N-(5-chloro-1H-indazol-3-ylmethyl)-2-(3-chloro-quinolin-6-ylmethyl)-isonicotinamide (Example 37) as a white solid. LRMS (M+H$^+$) m/z calculated 445.1. found 445.0.

$^1$H NMR (DMSO-d$_6$, 400 MHz) δ 11.11 (s, 1H), 9.21 (m, 1H), 8.82 (d, 1H), 8.63 (d, 1H), 8.53 (d, 1H), 7.96 (d, 1H), 7.66-7.85 (m, 4H), 7.47 (d, 1H), 7.17-7.31 (m, 1H), 7.13 (d, 1H), 6.38 (d, 2H), 4.56 (d, 2H), 4.36 (s, 2H).

Example 42: Preparation of 2-((3-chloroquinolin-6-yl)methyl)-N-((2-methyl-6-(methylamino)pyridin-3-yl)methyl)isonicotinamide

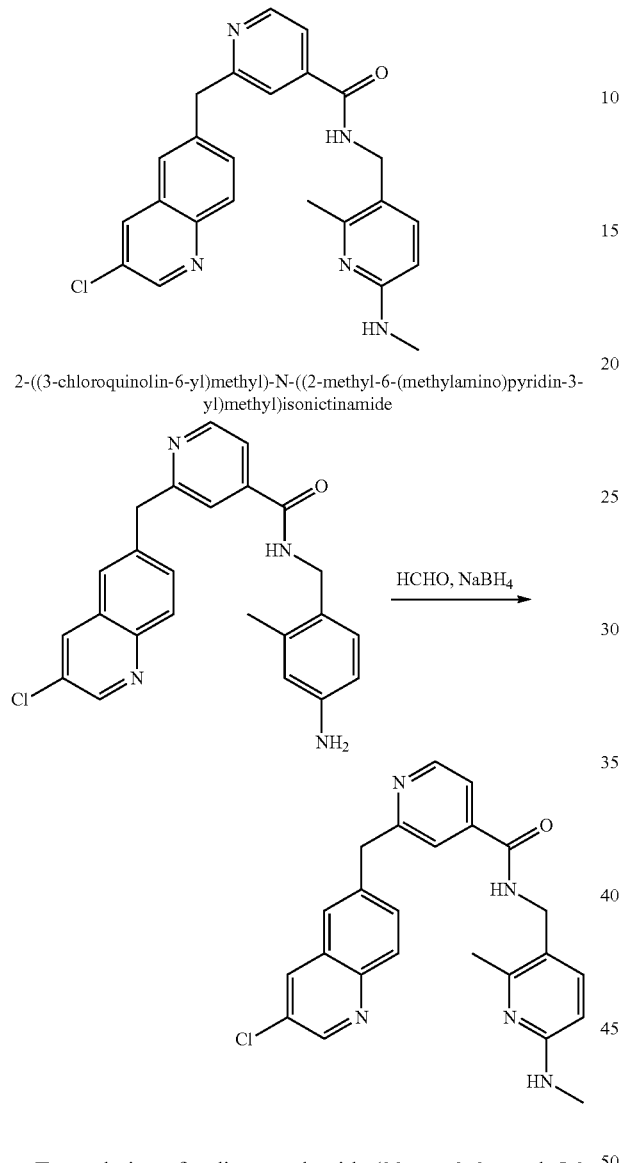

2-((3-chloroquinolin-6-yl)methyl)-N-((2-methyl-6-(methylamino)pyridin-3-yl)methyl)isonictinamide To a solution of sodium methoxide (33 mg, 0.6 mmol, 5.0 eq) in MeOH (20 mL), were added paraformaldehyde (36 mg, 1.2 mmol, 10.0 eq) and N-(6-amino-2-methyl-pyridin-3-ylmethyl)-2-(3-chloro-quinolin-6-ylmethyl)-isonicotinamide (50 mg, 0.12 mmol, 1.0 eq). The mixture was stirred at rt for 24 h until TLC indicated the starting material was consumed. Then sodium borohydride (14 mg, 0.36 mmol, 3.0 eq) was added, and the mixture was stirred at 40° C. for additional 3 h. The resulting mixture was concentrated and dissolved in EtOAc. The organic phase was washed with water and brine, dried and concentrated in vacuum. The residue was purified by prep-HPLC to give 2-((3-chloroquinolin-6-yl)methyl)-N-((2-methyl-6-(methylamino)pyridin-3-yl)methyl)isonicotinamide (13 mg, 25%). LRMS (M+H$^+$) m/z calculated 432.2. found 431.8.

$^1$H NMR (DMSO-d6, 400 MHz) δ 8.98 (t, 1H), 8.82 (d, 1H), 8.63 (d, 1H), 8.52 (d, 1H), 7.98 (d, 1H), 7.85 (s, 1H), 7.74 (d, 1H), 7.72 (d, 1H), 7.62 (d, 1H), 7.26 (d, 1H), 6.23 (d, 1H), 6.19 (d, 1H), 4.36 (s, 2H), 4.29 (d, 2H), 2.72 (d, 3H), 2.31 (s, 3H).

Example 43: Preparation of N-((6-amino-2-cyclopropylpyridin-3-yl)methyl)-2-((3-chloroquinolin-6-yl)methyl)isonicotinamide

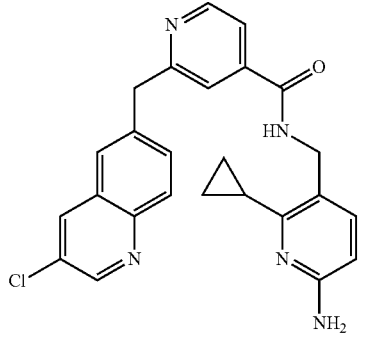

N-((6-amino-2-cyclopropylpyridin-3-yl)methyl)-2-((3-chloroquinolin-6-yl)methyl)isonicotinamide

Step 1: Preparation of 6-amino-2-chloro-nicotinonitrile

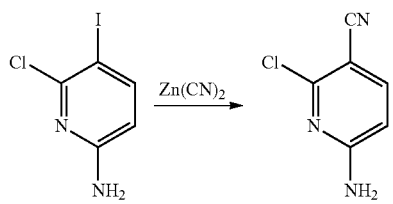

To a solution of 6-chloro-5-iodo-pyridin-2-ylamine (25.0 g, 98 mmol, 1.0 eq) in DMF (200 mL) was added Zn(CN)$_2$ (5.7 g, 49 mmol, 0.5 eq) and Pd(PPh$_3$)$_4$ (5.66 g, 4.9 mmol, 0.05 eq). The mixture was stirred at 65° C. overnight under N$_2$. Then EtOAc and water was added. The organic layer was concentrated, and purified by silica gel chromatography (EA/PE=1/1, v/v) to afford 6-amino-2-chloro-nicotinonitrile (12.2 g, 81%) as a yellow solid.

Step 2: Preparation of 6-amino-2-cyclopropyl-nicotinonitrile

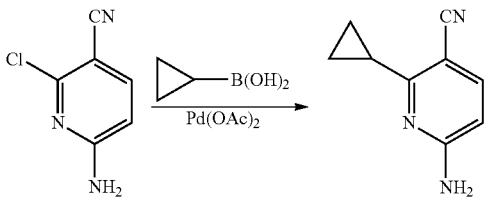

To a mixture of 6-amino-2-chloro-nicotinonitrile (3.0 g, 19.6 mmol, 1 eq), cyclopropylboronic acid (2.2 g, 25.5 mmol, 1.3 eq), K$_3$PO$_4$ (12.4 g, 58.8 mmol, 3 eq), tricyclohexylphosphine (550 mg, 1.96 mmol, 0.1 eq) in 200 mL of toluene and 10 mL of water was added Pd(OAc)$_2$ (220 mg, 0.98 mmol, 0.05 eq). The reaction mixture was stirred under reflux for 48 h. After cooling to rt, the solvent was removed by evaporation. The residue was diluted with water and extracted with EtOAc. The combined organic layers were dried and concentrated. The residue was purified by chromatography on silica gel column (EtOAc/PE=1/1, v/v) to give 6-amino-2-cyclopropyl-nicotinonitrile (1.6 g, 51%) as a yellow solid.

Step 3: Preparation of 5-(aminomethyl)-6-cyclopropylpyridin-2-amine hydrochloride

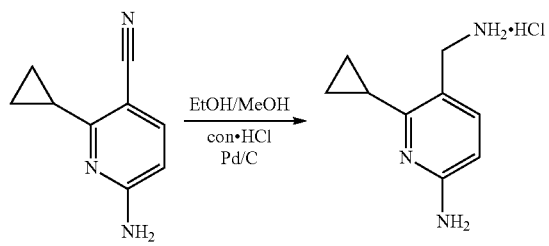

To a solution of 6-amino-2-cyclopropyl-nicotinonitrile (700 mg, 4.4 mmol, 1 eq) was added in MeOH (10 mL) and EtOH (10 mL), followed by addition of conc. HCl. Then Pd/C was added under N$_2$ and the stirring was continued at 40° C. overnight. After filtration and washed with MeOH, the organic phase was concentrated under reduce pressure to give the crude product (500 mg, 69%), which was used directly in the next reaction without further purification.

Step 4: Preparation of tert-butyl (6-amino-2-cyclopropylpyridin-3-yl)methylcarbamate

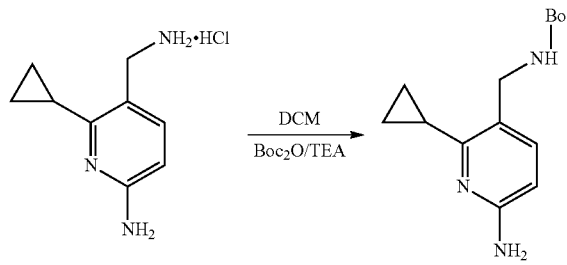

To a solution of 5-aminomethyl-6-cyclopropyl-pyridin-2-ylamine (500 mg, 3.06 mmol, 1 eq) and Boc$_2$O (920 mg, 3.68 mmol, 1.2 eq) in DCM was added TEA (1 mL) kept stirring at rt for 2 h. Then it was washed with water and extracted with EtOAc. After concentration under reduce pressure, the residue was purified by chromatography on silica gel column (EtOAc/PE=1/2, v/v) to give the target compound (300 mg, 37%).

Step 5: Preparation of 5-(aminomethyl)-6-cyclopropylpyridin-2-amine hydrochloride

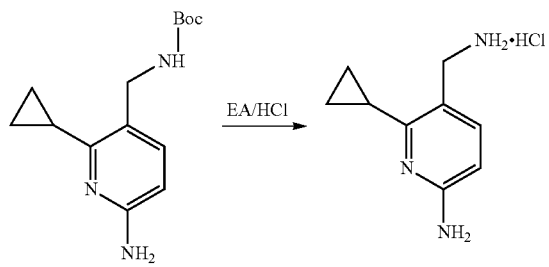

To a solution of tert-butyl (6-amino-2-cyclopropylpyridin-3-yl)methylcarbamate in EtOAc was added EtOAc/HCl with stirring at rt for 2 h. After filtration and washing with EtOAc, the product (120 mg, 53%) was obtained as white solid, which was used without purification.

Step 6: Preparation of N-((6-amino-2-cyclopropylpyridin-3-yl)methyl)-2-((3-chloroquinolin-6-yl)methyl)isonicotinamide

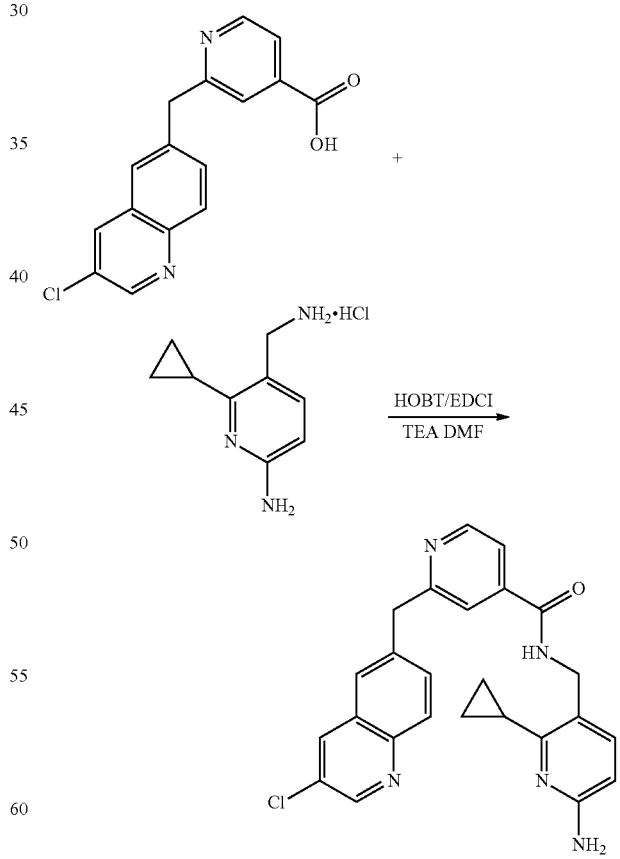

To a solution of 5-aminomethyl-6-cyclopropyl-pyridin-2-ylamine (46 mg, 0.2 mmol, 1.5 eq) in DMF (10 mL) was added 2-(3-chloro-quinolin-6-ylmethyl)-isonicotinic acid (40 mg, 0.13 mmol, 1 eq), HOBT (22 mg, 0.16 mmol, 1.2 eq), and EDCI (30 mg, 0.16 mmol, 1.2 eq). The reaction mixture was stirred at rt overnight. Then it was quenched with water, extracted with DCM. The combined extracts were dried and concentrated, and the residue was purified by prep-HPLC to give N-((6-amino-2-cyclopropylpyridin-3-yl)methyl)-2-((3-chloroquinolin-6-yl)methyl)isonicotinamide (7.7 mg, 13%) as a white solid. LRMS (M+H$^+$) m/z calculated 444.2. found 444.1.

$^1$H NMR (DMSO-d6, 400 MHz) δ 9.00 (t, 1H), 8.82 (d, 1H), 8.62 (d, 1H), 8.51 (d, 1H), 7.97 (d, 2H), 7.85 (s, 1H), 7.72 (d, 2H), 7.61 (d, 2H), 7.19 (d, 1H), 6.15 (d, 2H), 5.61 (s, 2H), 4.42 (d, 2H), 4.36 (s, 2H), 0.83 (s, 2H), 0.71-0.74 (m, 2H).

Example 44: Preparation of 2-((3-chloroquinolin-6-yl)methyl)-N-((6-(dimethylamino)-2-methylpyridin-3-yl)methyl)isonicotinamide

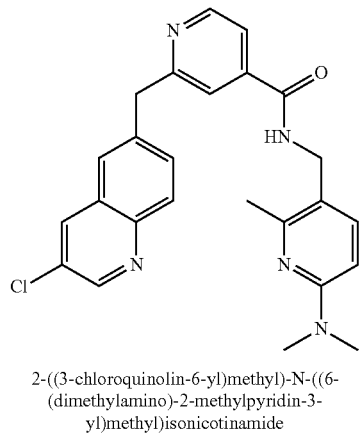 [SMILES: Cc1nc(N(C)C)ccc1CNC(=O)c1ccnc(Cc2ccc3ncc(Cl)cc3c2)c1]

2-((3-chloroquinolin-6-yl)methyl)-N-((6-(dimethylamino)-2-methylpyridin-3-yl)methyl)isonicotinamide Step 1: Preparation of 6-(dimethylamino)-2-methylnicotinonitrile

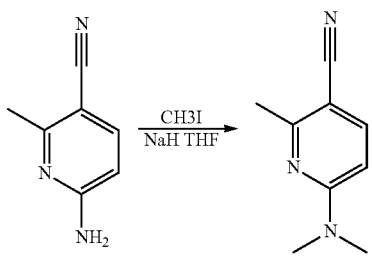

To a solution of 6-amino-2-methyl-nicotinonitrile (2 g, 15 mmol, 1.0 eq) and CH$_3$I (21 mg, 150 mmol, 10 eq) in THF (10 mL) was added NaH (1.8 mg, 75 mmol, 5.0 eq) under N$_2$. The mixture was stirred at rt overnight. The mixture was quenched with water, extracted with DCM. The combined extracts were dried and concentrated in vacuum to provide the compound (2.2 g, 91%), which was not further purified for next step.

Step 2: Preparation of 5-(aminomethyl)-N,N,6-trimethylpyridin-2-amine

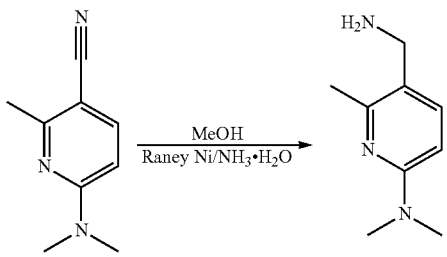

To a solution of 6-dimethylamino-2-methyl-nicotinonitrile (200 mg, 1.19 mmol, 1.0 eq) in MeOH (10 mL) was added Raney Ni (400 mg) under H$_2$. The mixture was stirred at rt overnight. The reaction mixture was filtered and the filtrate was concentrated to provide the product (180 mg, 91%), which was directly used in next step without further purification.

Step 3: Preparation of 2-((3-chloroquinolin-6-yl)methyl)-N-((6-(dimethylamino)-2-methylpyridin-3-yl)methyl)isonicotinamide

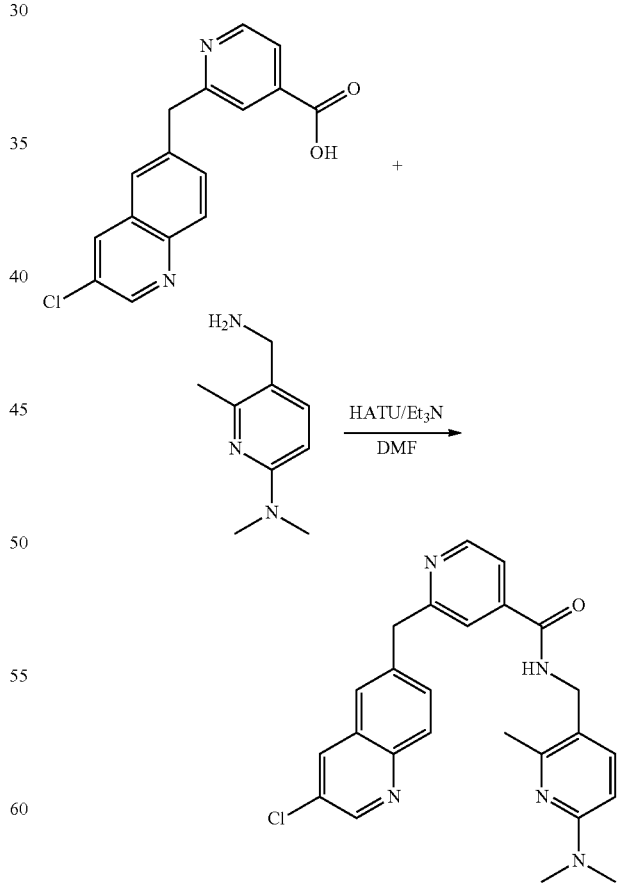

To a solution of 2-(3-chloro-quinolin-6-ylmethyl)-isonicotinic acid (326 mg, 1.09 mmol, 1 eq) in DMF (10 mL) was added (5-aminomethyl-6-methyl-pyridin-2-yl)-dimethylamine (180 mg, 1.09 mmol, 1 eq), HATU (497 mg, 1.3 mmol, 1.2 eq), and Et₃N (1 mL). The reaction mixture was stirred at rt for 3 h. Then it was quenched with water, extracted with DCM. The combined extracts were dried and concentrated. The residue was purified by prep-HPLC to give 2-((3-chloroquinolin-6-yl)methyl)-N-((6-(dimethylamino)-2-methylpyridin-3-yl)methyl)isonicotinamide (130 mg, 30%) as a gray solid. LRMS (M+H⁺) m/z calculated 446.2. found 445.8.

¹H NMR (DMSO, 400 MHz) δ 9.00-9.02 (m, 1H), 8.82 (d, 1H), 8.62 (d, 1H), 8.51 (d, 1H), 7.96-7.98 (m, 1H), 7.84 (s, 1H), 7.72-7.75 (m, 2H), 7.61-7.62 (m, 1H), 7.34-7.37 (m, 1H), 6.40-6.41 (m, 1H), 4.31 (d, 4H), 2.96 (s, 6H), 2.35 (s, 3H).

Example 45: Preparation of 2-((2-(aminomethyl)quinolin-6-yl)methyl)-N-((3-chloro-6-fluoro-1H-indol-5-yl)methyl)isonicotinamide

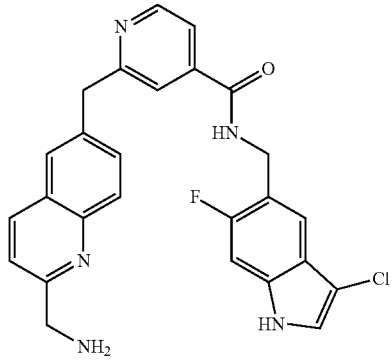 [SMILES: NCc1ccc2cc(Cc3cc(C(=O)NCc4cc5c(Cl)c[nH]c5cc4F)ccn3)ccc2n1]

2-((2-(Aminomethyl)quinolin-6-yl)methyl)-N-((3-chloro-6-fluoro-1H-indol-5-yl)methyl)isonicotinamide (60 mg, 79%) was prepared as described for Example 146. LRMS (M+H⁺) m/z calculated 474.1. found 474.1. ¹H NMR (DMSO-d₆, 400 MHz) δ 11.53 (s, 1H), 9.58 (s, 1H), 8.83 (d, 1H), 8.60 (br, 1H), 8.43 (d, 1H), 8.10 (d, 1H), 8.02-8.00 (m, 3H), 7.85 (d, 1H), 7.62 (d, 1H), 7.51 (s, 1H), 7.47 (d, 1H), 7.44 (d, 1H), 7.31 (s, 1H), 7.24 (d, 1H), 7.20 (d, 1H), 4.60 (d, 2H), 4.57 (s, 2H), 4.40 (q, 2H).

Example 46: Preparation of N-((6-amino-2,4-dimethylpyridin-3-yl)methyl)-2-((2-(aminomethyl)quinolin-6-yl)methyl)isonicotinamide

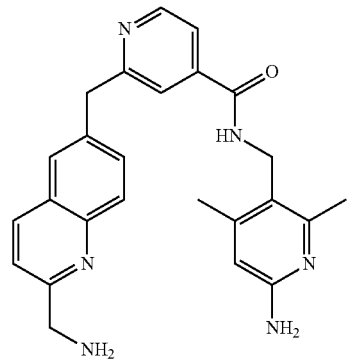 [SMILES: Cc1cc(N)nc(C)c1CNC(=O)c1ccnc(Cc2ccc3nc(CN)ccc3c2)c1]

N-((6-amino-2,4-dimethylpyridin-3-yl)methyl)-2-((2-(aminomethyl)quinolin-6-yl)methyl)isonicotinamide (35 mg, 53%) was prepared as described for Example 146. LRMS (M+H⁺) m/z calculated 427.2. found 427.2. ¹H NMR (CD₃OD, 400 MHz) δ 8.99 (d, 1H), 8.69 (d, 1H), 8.39 (s, 1H), 8.35 (d, 1H), 8.25 (d, 1H), 8.16 (s, 1H), 7.98 (d, 1H), 7.80 (d, 1H), 6.74 (s, 1H), 4.82 (s, 2H), 4.63 (s, 2H), 4.59 (s, 2H), 2.63 (s, 3H), 2.50 (s, 3H).

Example 47: Preparation of N-((3-aminobenzo[d]isoxazol-6-yl)methyl)-2-((3-methylquinolin-6-yl)methyl)isonicotinamide

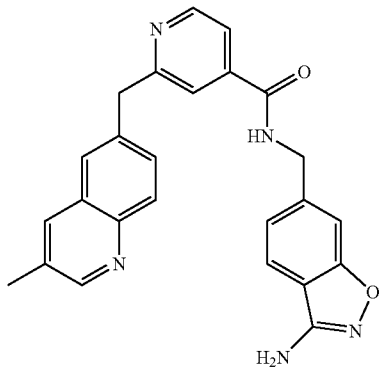

N-((3-aminobenzo[d]isoxazol-6-yl)methyl-2-((3-methylquinolin-6-yl)methyl)isonicotinamide Step 1: Preparation of 5-(aminomethyl)benzo[d]isoxazol-3-amine di(tert-butyl carbamate)

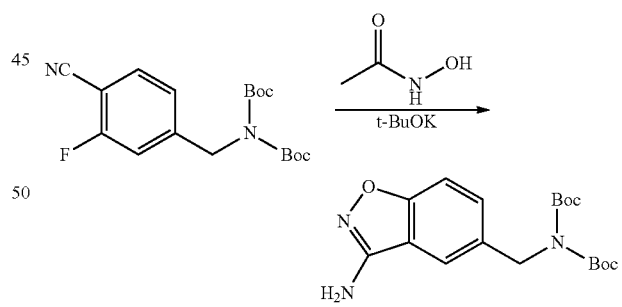

To a mixture of N-hydroxy-acetamide (964 mg, 12.86 mmol, 1.5 eq) in DMF (40 mL) was added t-BuOK (1.4 g, 12.86 mmol, 1.5 eq). After stirring for 30 min at rt, 4-(aminomethyl)-2-fluorobenzonitrile di(tert-butyl carbamate) (3 g, 8.57 mmol, 1.0 eq) was added. The reaction mixture was stirred for 5 h at rt and then concentrated. The residue was purified by column chromatography on a silica gel (PE/EtOAc=4/1 to 3/1, v/v) to give 5-(aminomethyl)benzo[d]isoxazol-3-amine di(tert-butyl carbamate) (2 g, 64%) as a white solid. LRMS (M+H⁺) m/z calculated 364. found 364.

Step 2: Preparation of 5-aminomethyl-benzo[d]isoxazol-3-ylamine dihydrochloride

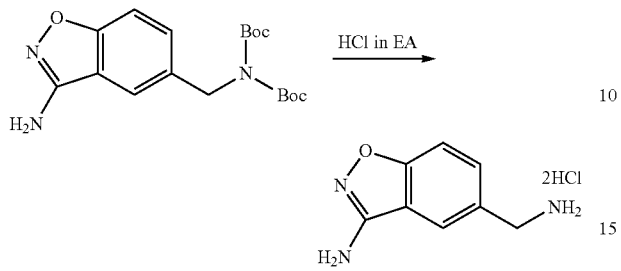

To a mixture of 5-(aminomethyl)benzo[d]isoxazol-3-amine di(tert-butyl carbamate) (2 g, 5.51 mmol, 1.0 eq) in MeOH (20 mL) was added 3 N of HCl in EtOAc (5 mL). After stirring for 2 h at rt, the reaction mixture was filtered and the filter cake was washed with Et$_2$O to give the crude 5-aminomethyl-benzo[d]isoxazol-3-ylamine dihydrochloride (1.5 g) as a white solid. LRMS (M+H$^+$) m/z calculated 164. found 164.

Step 3: Preparation of N-((3-aminobenzo[d]isoxazol-6-yl)methyl)-2-((3-methylquinolin-6-yl)methyl)isonicotinamide

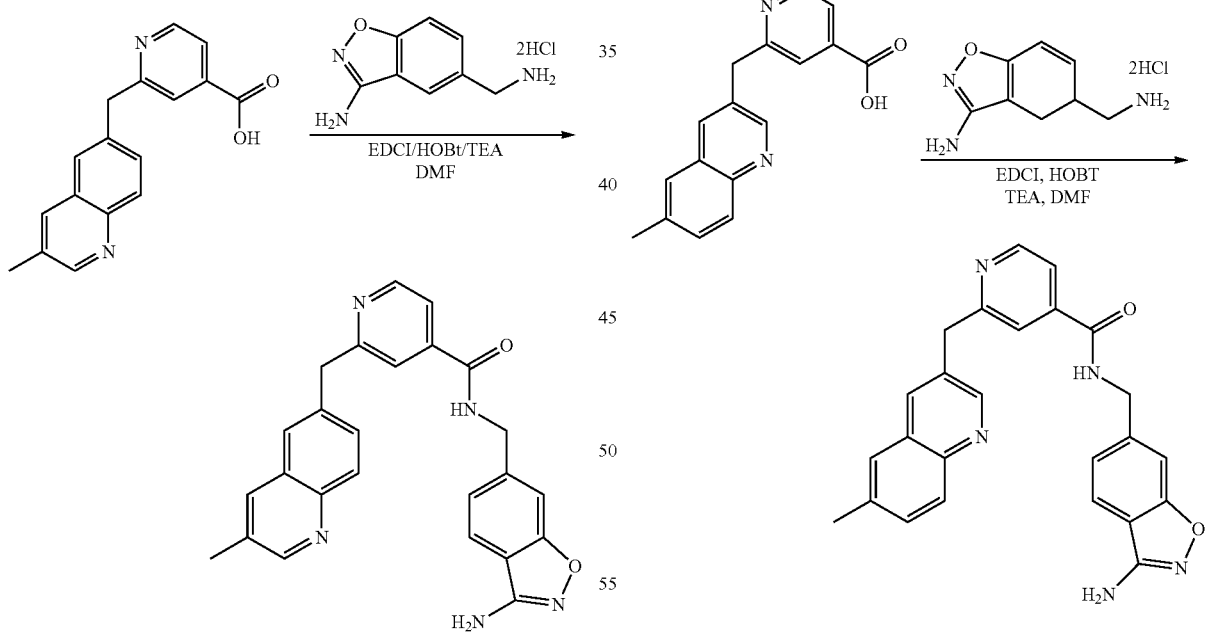

To a solution of 2-(3-methyl-quinolin-6-ylmethyl)-isonicotinic acid (150 mg, crude) in DMF (15 mL) was added 5-aminomethyl-benzo[d]isoxazol-3-ylamine dihydrochloride (80 mg, 0.34 mmol, 1.0 eq) followed by EDCI (98 mg, 0.51 mmol, 1.5 eq), HOBT (69 mg, 0.51 mmol, 1.5 eq) and TEA (103 mg, 1.02 mmol, 3.0 eq). The reaction mixture was heated to 45° C. kept stirring for overnight. Water was added, and the mixture was extracted with DCM. The organic layer was washed with water, dried over Na$_2$SO$_4$, filtered, and concentrated. The residue was purified by prep-HPLC to give N-((3-aminobenzo[d]isoxazol-6-yl)methyl)-2-((3-methylquinolin-6-yl)methyl)isonicotinamide (30 mg, 21%) as a yellow solid. LRMS (M+H$^+$) m/z calculated 424.2. found 424.0.

$^1$H NMR (DMSO-d$_6$, 400 MHz): δ 9.37 (t, 1H), 8.71 (s, 1H), 8.66 (d, 1H), 8.06 (s, 1H), 7.89 (d, 1H), 7.74-7.78 (m, 3H), 7.66 (d, 1H), 7.61 (d, 1H), 7.35 (s, 1H), 7.21 (d, 1H), 6.37 (s, 2H), 4.58 (d, 2H), 4.35 (s, 2H), 2.46 (s, 3H).

Example 48: Preparation of N-((3-aminobenzo[d]isoxazol-6-yl)methyl)-2-((6-methylquinolin-3-yl)methyl)isonicotinamide

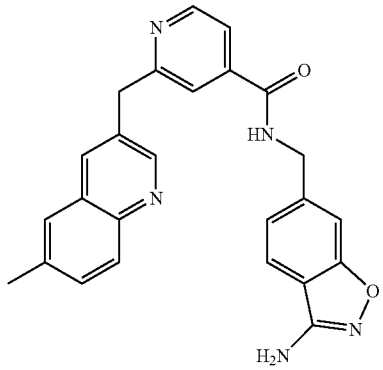

N-((3-aminobenzo[d]isoxazol-6-yl)methyl)-2-((6-methylquinolin-3-yl)methyl)isonicotinamide

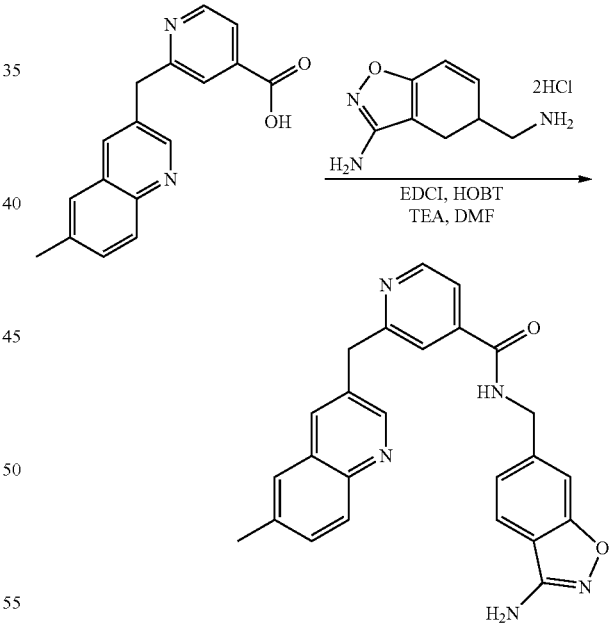

N-((3-aminobenzo[d]isoxazol-6-yl) methyl)-2-((6-methylquinolin-3-yl) methyl) isonicotinamide (30 mg, 21%) was prepared as described for N-((3-aminobenzo[d]isoxazol-6-yl)methyl)-2-((3-methylquinolin-6-yl)methyl)isonicotinamide (Example 47) as a yellow solid. LRMS (M+H$^+$) m/z calculated 424.2. found 423.9. $^1$H NMR (DMSO-d$_6$, 400 MHz) δ 9.40 (t, 1H), 8.81 (s, 1H), 8.66 (d, 1H), 8.10 (s, 1H), 7.89 (d, 1H), 7.82 (s, 1H), 7.76 (d, 1H), 7.68 (t, 2H), 7.55 (d, 1H), 7.35 (s, 1H), 7.22 (d, 1H), 6.38 (s, 2H), 4.60 (d, 2H), 4.37 (s, 2H), 2.48 (s, 3H).

Example 49: Preparation of N-((3-chloro-6-fluoro-1H-indol-5-yl)methyl)-2-((3-chloro-8-cyanoquinolin-6-yl)methyl)isonicotinamide

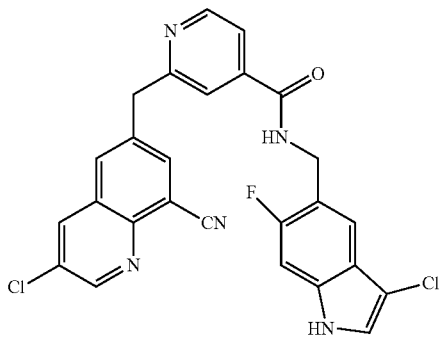

N-((3-chloro-6-fluoro-1H-indol-5-yl)methyl)-2-((3-chloro-8-cyanquinolin-6-yl)methyl)isonicotinamide

Step 1: Preparation of methyl 3-chloro-8-iodoquinoline-6-carboxylate

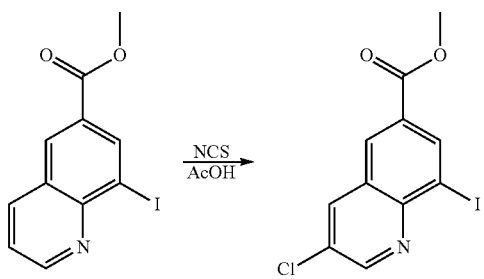 [SMILES: "AcOH" ; COC(=O)c1cc(I)c2ncccc2c1 ; "NCS" ; COC(=O)c1cc(I)c2ncc(Cl)cc2c1]

To a solution of methyl 8-iodoquinoline-6-carboxylate (30 g, 96 mmol, 1.0 eq) in AcOH (1.0 L) was added NCS (38 g, 293 mmol, 3 eq). The mixture was stirred at 100° C. overnight, The mixture was concentrated in vacuo and the residue was purified by silica gel chromatography (PE/DCM=1/1, v/v) to afford methyl 3-chloro-8-iodoquinoline-6-carboxylate (15 g, 49%) as yellow solid.

Step 2: Preparation of (3-chloro-8-iodo-quinolin-6-yl)-methanol

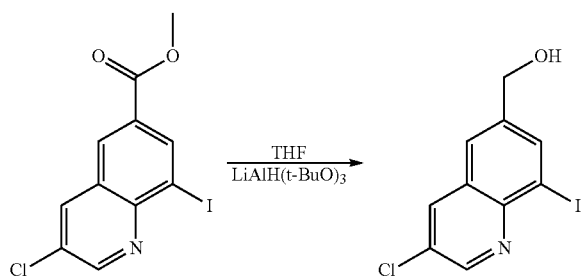 [SMILES: COC(=O)c1cc(I)c2ncc(Cl)cc2c1 ; OCc1cc(I)c2ncc(Cl)cc2c1 ; "LiAlH(t-BuO)3" ; "THF"]

To a solution of methyl 3-chloro-8-iodoquinoline-6-carboxylate (12 g, 34.5 mmol, 1.0 eq) in dry THF (200 mL) was added lithium tri-tert-butoxyaluminum hydride (22 g, 70 mmol, 3.4 eq) carefully. The mixture was stirred at 50° C. for 5 h under $N_2$ protected. Then EtOAc and water were added. The organic layer was concentrated, and purified by silica gel chromatography (PE/DCM=1/1, v/v) to afford (3-chloro-8-iodo-quinolin-6-yl)-methanol (7.6 g, 69%) as white solid.

Step 3: Preparation of 3-chloro-6-hydroxymethyl-quinoline-8-carbonitrile

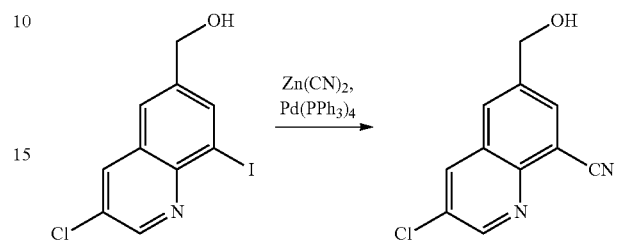

To a solution of (3-chloro-8-iodo-quinolin-6-yl)-methanol (7.6 g, 23.8 mmol, 1.0 eq) in DMF (100 mL) was added $Zn(CN)_2$ (2.79 g, 23.8 mmol, 1.0 eq) and $Pd(PPh_3)_4$ (2.75 g, 2.38 mmol, 0.1 eq) carefully. The mixture was stirred at 50° C. overnight under $N_2$ protected. Then EtOAc and water was added. The organic layer was concentrated, and purified by silica gel chromatography (PE/DCM=1/2, v/v) to afford 3-chloro-6-hydroxymethyl-quinoline-8-carbonitrile (5.0 g, 96%) as yellow solid.

Step 4: Preparation of 3-chloro-6-chloromethyl-quinoline-8-carbonitrile

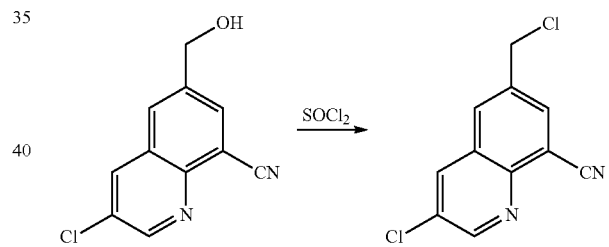

A mixture of 3-chloro-6-hydroxymethyl-quinoline-8-carbonitrile (2.9 g, 13.3 mmol, 1.0 eq) in $SOCl_2$ (50 mL) was stirred at rt for 1 h and concentrated. The residue was dissolved in DCM and treated with sat. $NaHCO_3$ solution to give 3-chloro-6-chloromethyl-quinoline-8-carbonitrile (2.2 g, 70%) as a yellow solid.

Step 5: Preparation of methyl 2-((3-chloro-8-cyano-quinolin-6-yl)methyl)isonicotinate

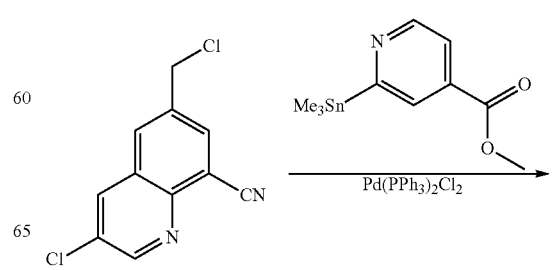

-continued

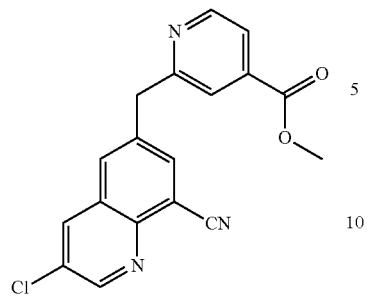

To a solution of 3-chloro-6-chloromethyl-quinoline-8-carbonitrile (2.0 g, 8.47 mmol, 1.0 eq) in dioxane (40 mL) was added methyl 2-(trimethylstannyl)isonicotinate (2.8 g, 9.32 mmol, 1.1 eq) and Pd(PPh$_3$)$_2$Cl$_2$ (597 mg, 0.85 mmol, 0.1 eq). The mixture was stirred at 90° C. for 3 h under nitrogen atmosphere, concentrated and purified by silica gel chromatography (DCM/MeOH=100/1, v/v) to afford methyl 2-((3-chloro-8-cyanoquinolin-6-yl)methyl)isonicotinate (1.4 g, 49%) as a yellow solid.

Step 6: Preparation of 2-(3-chloro-8-cyano-quinolin-6-ylmethyl)-isonicotinic acid

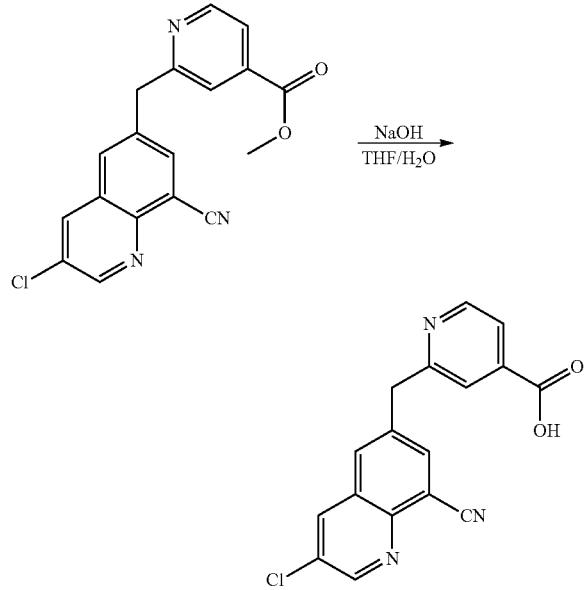

To a solution of methyl 2-((3-chloro-8-cyanoquinolin-6-yl)methyl)isonicotinate (1.4 g, 4.2 mmol, 1.0 eq) in THF (5 mL) and H$_2$O (5 mL) was added NaOH (200 mg, 5 mmol, 1.2 eq). The mixture was stirred at rt for 2 h. Then it was acidified by 1 N HCl to PH=6 and extracted by EtOAc. The organic layer was concentrated to afford 2-(3-chloro-8-cyano-quinolin-6-ylmethyl)-isonicotinic acid (1.1 g, 37%) as a white solid.

Step 7: Preparation of N-((3-chloro-6-fluoro-1H-indol-5-yl) methyl)-2-((3-chloro-8-cyanoquinolin-6-yl)methyl) isonicotinamide

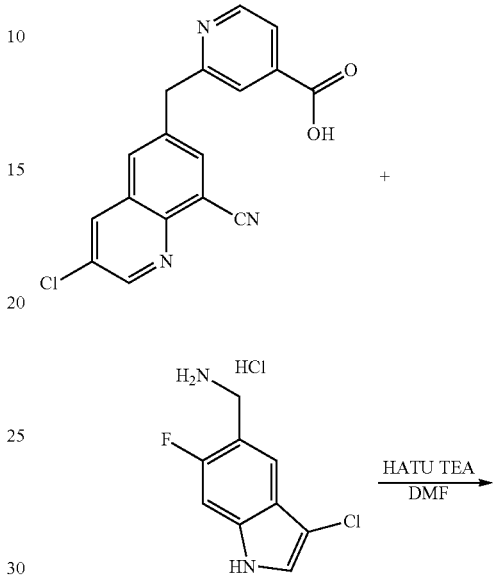

To a solution of 2-(3-chloro-quinolin-6-ylmethyl)-isonicotinic acid (120 mg, 0.37 mmol, 1.0 eq) and (3-chloro-6-fluoro-1H-indol-5-yl)-methylamine hydrochloride (200 mg, 0.73 mmol, 2.0 eq) in DMF (10 mL) was added HATU (170 mg, 4.4 mmol, 1.2 eq) and Et$_3$N (1.0 mL, 7.1 mmol, 19 eq). The mixture was stirred at rt overnight, Then EtOAc and water was added. The organic layer was concentrated and the residue was purified by pre-HPLC to give N-((3-chloro-6-fluoro-1H-indol-5-yl) methyl)-2-((3-chloro-8-cyanoquinolin-6-yl)methyl) isonicotinamide (170 mg, 91%) as a yellow solid. LRMS (M+H$^+$) m/z calculated 504.1. found 503.8.

1H NMR (DMSO-d6, 400 MHz) δ 11.39 (s, 1H), 9.24 (m, 1H), 9.03-9.04 (d, 1H), 8.71-8.72 (d, 1H), 8.64-8.66 (d, 1H), 8.40 (d, 1H), 8.19 (d, 1H), 7.84 (s, 1H), 7.66-7.68 (d, 1H), 7.44-7.51 (m, 2H), 7.21-7.24 (d, 1H), 4.59-4.60 (d, 2H), 4.43 (s, 2H).

Example 50: Preparation of N-((6-amino-2,4-dimethylpyridin-3-yl)methyl)-2-((3-chloro-8-cyanoquinolin-6-yl)methyl)isonicotinamide Example 51: Preparation of N-((3-chloro-4-fluoro-1H-indol-5-yl)methyl)-2-((3-chloro-8-cyanoquinolin-6-yl)methyl)isonicotinamide

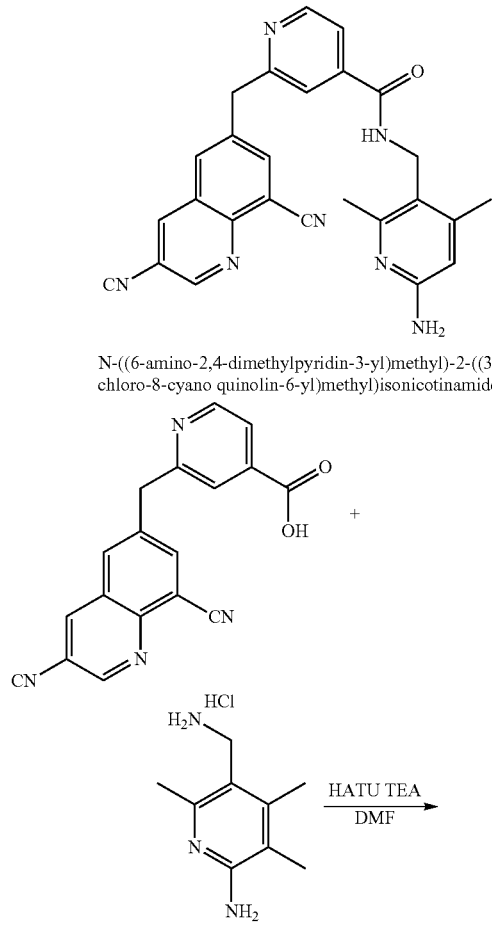

N-((6-amino-2,4-dimethylpyridin-3-yl)methyl)-2-((3-chloro-8-cyano quinolin-6-yl)methyl)isonicotinamide

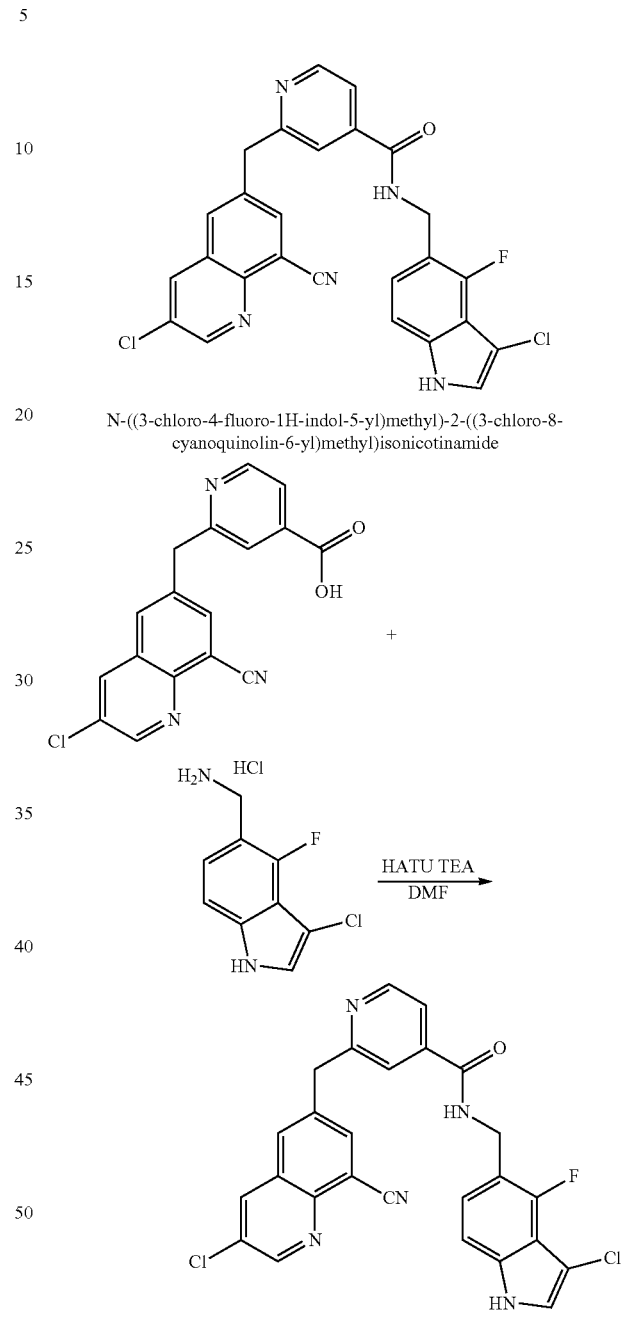

N-((3-chloro-4-fluoro-1H-indol-5-yl)methyl)-2-((3-chloro-8-cyanoquinolin-6-yl)methyl)isonicotinamide N-((6-amino-2,4-dimethylpyridin-3-yl)methyl)-2-((3-chloro-8-cyanoquinolin-6-yl)methyl)isonicotinamide (130 mg, 77%) was prepared as described for N-((3-chloro-6-fluoro-1H-indol-5-yl) methyl)-2-((3-chloro-8-cyanoquinolin-6-yl)methyl) isonicotinamide (Example 49) as white solid. LRMS (M+H$^+$) m/z calculated 456.2. found 456.8.

1H NMR (DMSO-d6, 400 MHz) δ 9.03-9.04 (d, 1H), 8.72-8.73 (d, 1H), 8.59-8.66 (m, 3H), 8.38-8.39 (d, 1H), 8.18-8.19 (d, 1H), 7.79 (s, 1H), 7.60-7.62 (dd, 1H), 6.15 (s, 1H), 5.77 (s, 1H), 4.41 (s, 2H), 4.34-4.35 (d, 2H), 2.31 (s, 3H), 2.18 (s, 3H).

N-((3-chloro-4-fluoro-1H-indol-5-yl)methyl)-2-((3-chloro-8-cyanoquinolin-6-yl)methyl)isonicotinamide (80 mg, 43%) was prepared as described for N-((3-chloro-6-fluoro-1H-indol-5-yl) methyl)-2-((3-chloro-8-cyanoquinolin-6-yl)methyl) isonicotinamide (Example 49) as white solid. LRMS (M+H$^+$) m/z calculated 504.1. found 503.8.

$^1$H NMR (DMSO-d6, 400 MHz) δ 11.58 (s, 1H), 9.22 (m, 1H), 9.03-9.04 (d, 1H), 8.71-8.72 (d, 1H), 8.63-8.65 (d, 1H), 8.39-8.40 (d, 1H), 8.19 (s, 1H), 7.83 (s, 1H), 7.65-7.66 (m, 1H), 7.50-7.51 (d, 2H), 7.14-7.21 (m, 2H). 4.57-4.59 (d, 2H), 4.42 (s, 1H)

Example 52: Preparation of 2-((3-chloro-8-cyano-quinolin-6-yl)methyl)-N-((6-fluoro-1H-indol-5-yl)methyl)isonicotinamide Example 53: Preparation of N-((6-amino-4-methyl-pyridin-3-yl)methyl)-2-((3-chloro-8-cyanoquinolin-6-yl)methyl)isonicotinamide

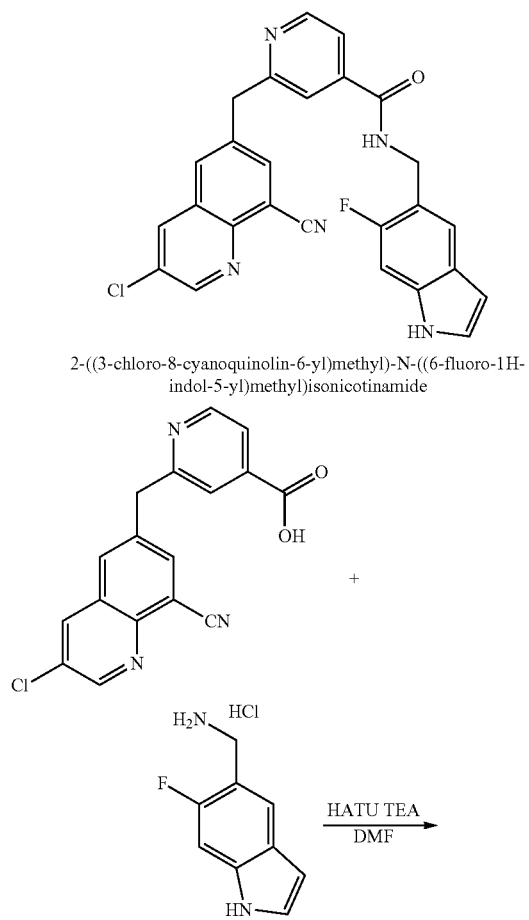

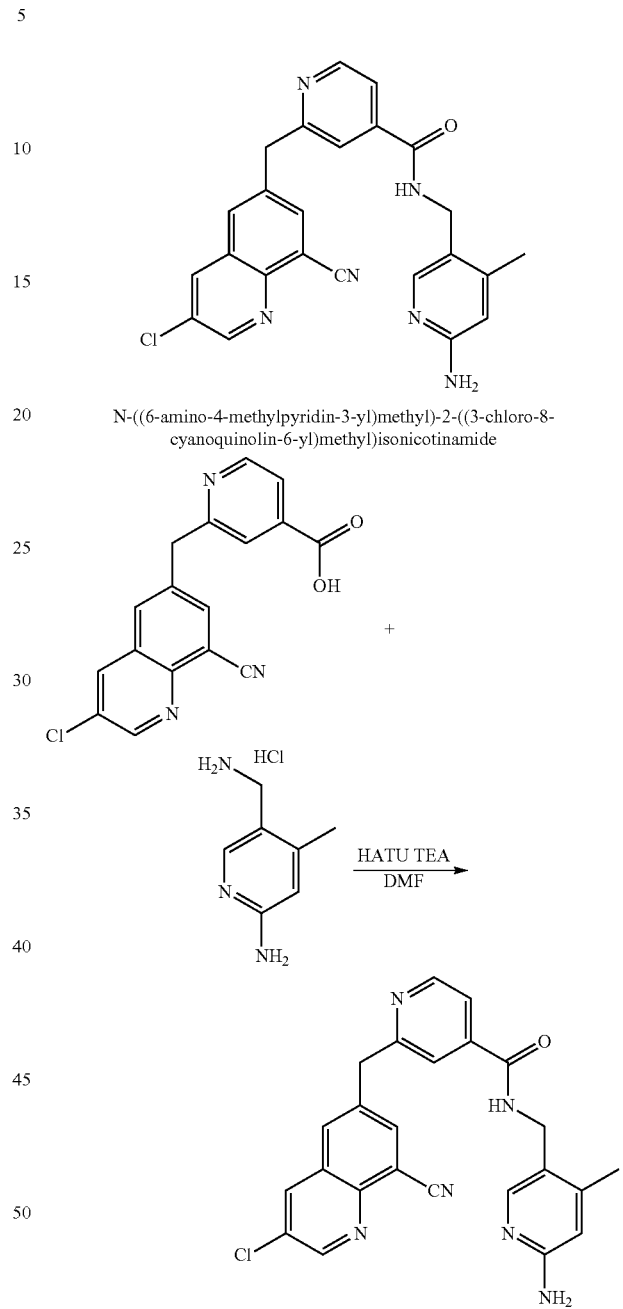

N-((3-chloro-4-fluoro-1H-indol-5-yl)methyl)-2-((3-chloro-8-cyanoquinolin-6-yl)methyl)isonicotinamide (80 mg, 46%) was prepared as described for N-((3-chloro-6-fluoro-1H-indol-5-yl) methyl)-2-((3-chloro-8-cyanoquinolin-6-yl)methyl) isonicotinamide (Example 49) as white solid. LRMS (M+H$^+$) m/z calculated 469.7. found 469.7.

$^1$H NMR (DMSO-d6, 400 MHz) δ 11.09 (s, 1H), 9.19 (m, 1H), 9.03-9.04 (d, 1H), 8.72-8.73 (d, 1H), 8.64-8.65 (d, 1H), 8.39-8.40 (d, 1H), 8.19 (s, 1H), 7.84 (s, 1H), 7.67-7.69 (m, 1H), 7.49-7.50 (d, 2H), 7.31-7.32 (t, 1H) 7.14-7.18 (m, 2H), 6.39 (s, 1H), 4.56-4.58 (d, 2H), 4.42 (s, 1H).

N-((6-amino-2,4-dimethylpyridin-3-yl)methyl)-2-((3-chloro-8-cyanoquinolin-6-yl)methyl)isonicotinamide (120 mg, 73%) was prepared as described for N-((3-chloro-6-fluoro-1H-indol-5-yl)methyl)-2-((3-chloro-8-cyanoquinolin-6-yl)methyl) isonicotinamide (Example 49) as yellow solid. LRMS (M+H+) m/z calculated 443.1. found 443.0.

$^1$H NMR (DMSO-d6, 400 MHz) δ 9.03-9.04 (d, 1H), 8.92-8.93 (t, 1H), 8.72-8.73 (d, 1H), 8.61-8.63 (m, 3H), 8.39-8.40 (d, 1H), 8.18-8.19 (d, 1H), 7.79 (s, 2H), 7.61-7.63 (dd, 1H), 6.27 (s, 1H), 5.77 (s, 1H), 4.41 (s, 2H), 4.29-4.32 (d, 2H), 2.15 (s, 3H).

Example 54: Preparation of 2-(3-chloro-8-cyano-quinolin-6-ylmethyl)-N-(5-chloro-1H-indazol-3-ylmethyl)-isonicotinamide

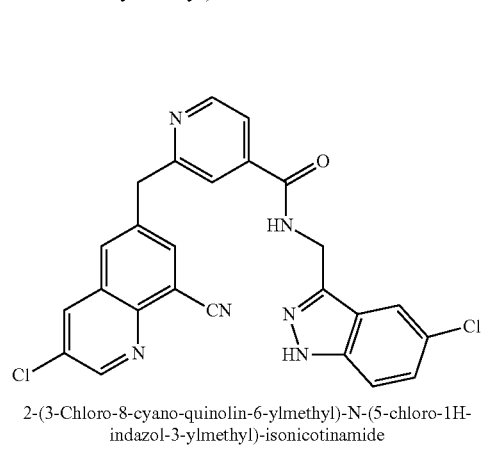

2-(3-Chloro-8-cyano-quinolin-6-ylmethyl)-N-(5-chloro-1H-indazol-3-ylmethyl)-isonicotinamide

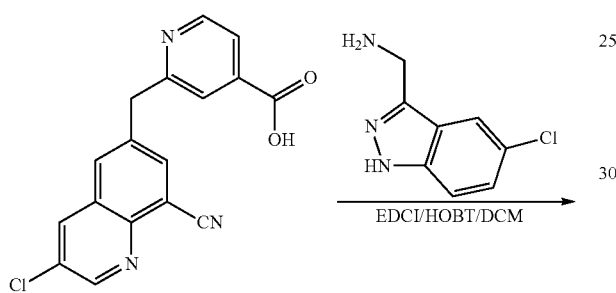

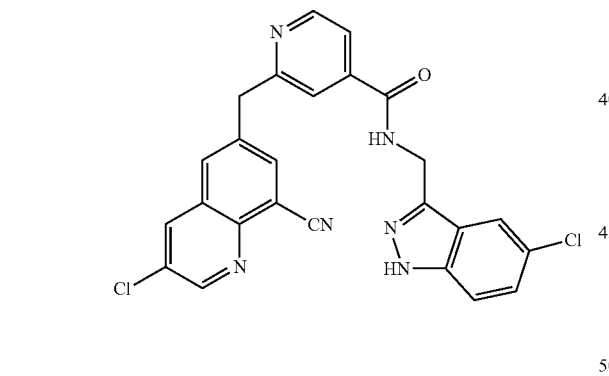

To a solution of 2-(3-chloro-8-cyano-quinolin-6-ylmethyl)-isonicotinic acid (100 mg, 0.31 mmol, 1.0 eq) in DCM (8 mL) was added HOBT (53 mg, 0.39 mmol, 1.3 eq), EDCI (86 mg, 0.45 mmol, 1.5 eq), Et$_3$N (0.13 mL, 0.9 mmol, 3.0 eq) and (5-chloro-1H-indazol-3-yl)-methylamine (67 mg, 0.37 mmol, 1.2 eq). The mixture was stirred at rt for 12 h and diluted with water. The organic layer was separated and the aqueous layer was extracted with DCM. The combined extracts were dried and concentrated. The residue was purified by flash chromatography on a silica gel column (DCM/MeOH=10/1, v/v) to give 2-(3-chloro-8-cyano-quinolin-6-ylmethyl)-N-(5-chloro-1H-indazol-3-ylmethyl)-isonicotinamide (50 mg, 34%) as a white solid. LRMS (M+H$^+$) m/z calculated 487.1. found 486.8.

$^1$H NMR (DMSO-d$_6$, 400 MHz) δ 13.07 (s, 1H), 9.36 (m, 1H), 9.04 (d, 1H), 8.70 (d, 1H), 8.63 (d, 1H), 8.38 (d, 1H), 8.18 (s, 1H), 7.89 (d, 1H), 7.82 (s, 1H), 7.64 (d, 1H), 7.53 (d, 1H), 7.31-7.34 (d, 1H), 4.78 (d, 2H), 4.42 (s, 2H).

Example 55: Preparation of 2-(3-chloro-8-cyano-quinolin-6-ylmethyl)-N-(3-chloro-1H-pyrrolo[2,3-b]pyridin-5-ylmethyl)-isonicotinamide

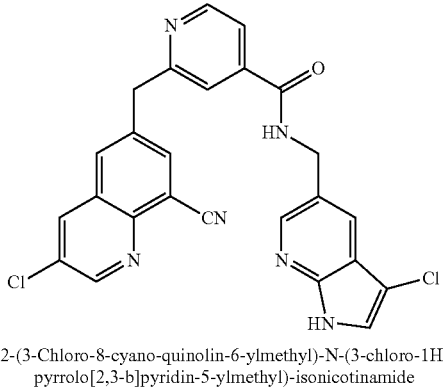

2-(3-Chloro-8-cyano-quinolin-6-ylmethyl)-N-(3-chloro-1H-pyrrolo[2,3-b]pyridin-5-ylmethyl)-isonicotinamide

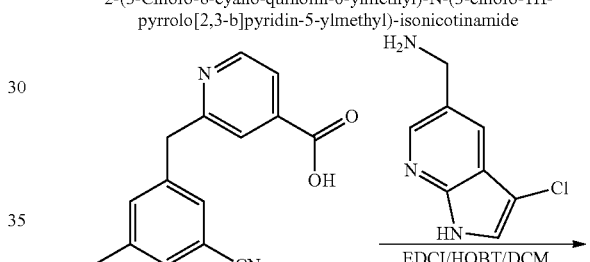

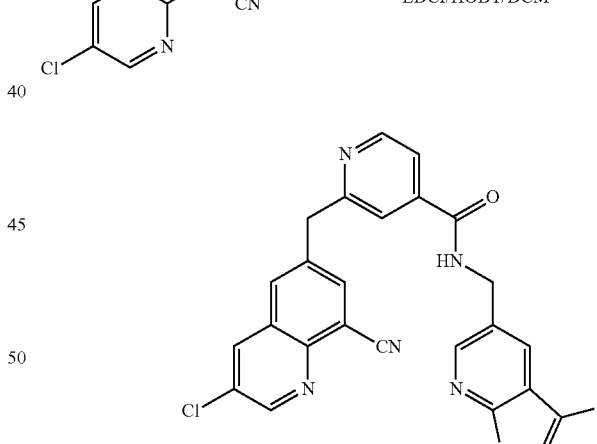

2-(3-Chloro-8-cyano-quinolin-6-ylmethyl)-N-(3-chloro-1H-pyrrolo[2,3-b]pyridin-5-ylmethyl)-isonicotinamide (90 mg, 66%) was prepared as described for 2-(3-chloro-8-cyano-quinolin-6-ylmethyl)-N-(5-chloro-1H-indazol-3-yl-methyl)-isonicotinamide (Example 54) as a white solid. LRMS (M+H$^+$) m/z calculated 487.1. found 486.8.

$^1$H NMR (DMSO-d$_6$, 400 MHz) δ 11.95 (s, 1H), 9.34 (m, 1H), 9.04 (d, 1H), 8.71 (d, 1H), 8.64 (d, 1H), 8.39 (d, 1H), 8.31 (s, 1H), 8.19 (s, 1H), 7.87 (s, 1H), 7.83 (d, 1H), 7.65-7.67 (m, 2H), 4.59-4.61 (d, 2H), 4.42 (s, 2H).

Example 56: Preparation of N-(6-amino-2-methyl-pyridin-3-ylmethyl)-2-(3-chloro-8-cyano-quinolin-6-ylmethyl)-isonicotinamide

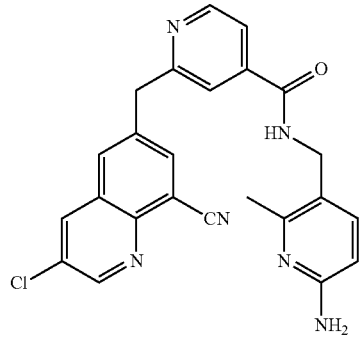

N-(6-Amino-2-methyl-pyridin-3-ylmethyl)-2-(3-chloro-8-cyano-quinolin-6-ylmethyl)-isonicotinamide

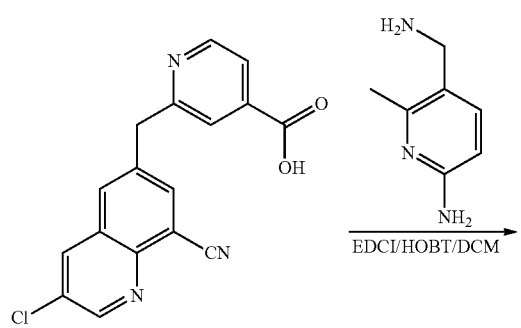

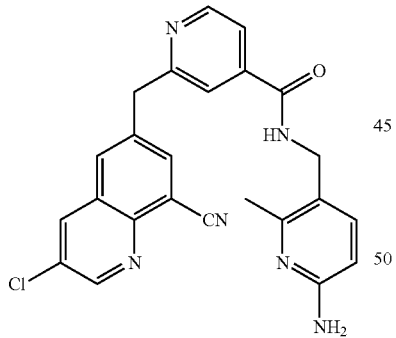

N-(6-amino-2-methyl-pyridin-3-ylmethyl)-2-(3-chloro-8-cyano-quinolin-6-ylmethyl)-isonicotinamide (50 mg, 38%) was prepared as described for 2-(3-chloro-8-cyano-quinolin-6-ylmethyl)-N-(5-chloro-1H-indazol-3-ylmethyl)-isonicotinamide (Example 54) as a white solid. LRMS (M+H$^+$) m/z calculated 441.9. found 441.9.

$^1$H NMR (DMSO-d$_6$, 400 MHz) δ 9.04 (m, 2H), 8.72 (d, 1H), 8.64 (d, 1H), 8.39 (d, 1H), 8.19 (s, 1H), 7.80 (s, 1H), 7.63 (d, 1H), 7.38 (m, 1H), 6.38 (m, 1H), 6.25 (m, 1H), 4.42 (s, 2H), 4.30 (d, 2H).

Example 57: Preparation of N-(1-amino-isoquinolin-6-ylmethyl)-2-(3-chloro-8-cyano-quinolin-6-ylmethyl)-isonicotinamide

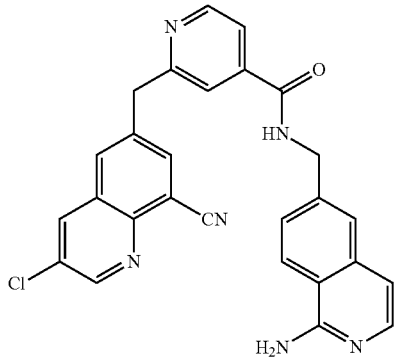

N-(1-Amino-isoquinolin-6-ylmethyl)-2-(3-chloro-8-cyano-quinolin-6-ylmethyl)-isonicotinamide

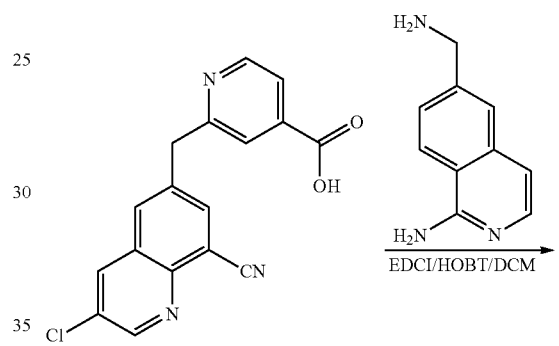

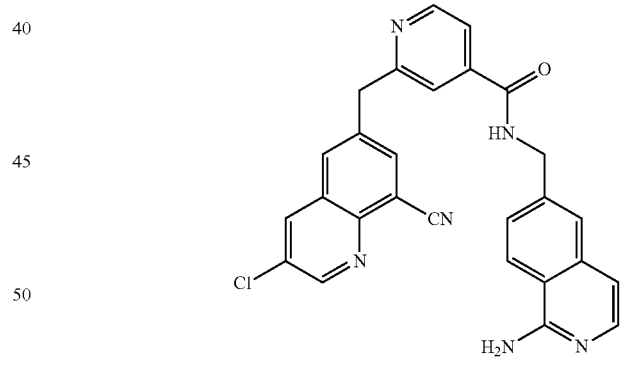

N-(1-amino-isoquinolin-6-ylmethyl)-2-(3-chloro-8-cyano-quinolin-6-ylmethyl)-isonicotinamide (100 mg, 73%) was prepared as described for 2-(3-chloro-8-cyano-quinolin-6-ylmethyl)-N-(5-chloro-1H-indazol-3-ylmethyl)-isonicotinamide (Example 54) as a white solid. LRMS (M+H$^+$) m/z calculated 479.1. found 479.0.

$^1$H NMR (DMSO-d$_6$, 400 MHz) δ 9.39 (m, 2H), 9.04 (d, 1H), 8.72 (d, 1H), 8.66 (d, 1H), 8.40 (s, 1H), 8.20 (s, 1H), 8.12-8.15 (d, 1H), 7.86 (s, 1H), 7.75-7.76 (d, 1H), 7.69-7.70 (d, 1H), 7.56 (s, 1H), 7.39-7.41 (d, 1H), 6.84-6.85 (d, 1H), 6.72 (s, 1H), 4.62 (d, 2H), 4.44 (s, 2H).

Example 58: Preparation of 6-((4-(((6-amino-2,4-dimethylpyridin-3-yl)methyl)carbamoyl)pyridin-2-yl)methyl)-3-chloroquinoline-8-carboxamide

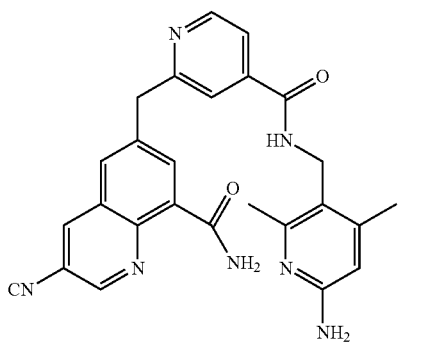

6-((4-(((6-amino-2,4-dimethylpyridin-3-yl)methyl)carbamoyl)pyridin-2-yl)methyl)-3-chloroquinoline-8-carboxamide

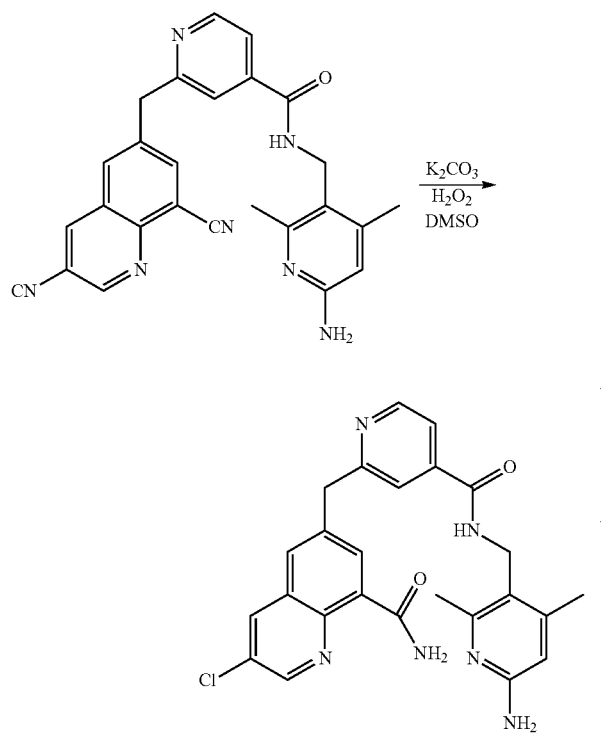

To a solution of N-(((6-amino-2,4-dimethylpyridin-3-yl)methyl)-2-((3-chloro-8-cyanoquinolin-6-yl)methyl)isonicotinamide hydrochloride (100 mg, 0.22 mmol, 1.0 eq) and K$_2$CO$_3$ (215 mg, 1.56 mmol, 7.3 eq) in DMSO (10 mL) was added H$_2$O$_2$ (1 mL). The mixture was stirred at 50° C. for 3 h, Then EtOAc and water was added, The organic layer was concentrated and purified by pre-HPLC to give 6-((4-(((6-amino-2,4-dimethylpyridin-3-yl)methyl)carbamoyl)pyridin-2-yl)methyl)-3-chloroquinoline-8-carboxamide (71 mg, 48%) as a white solid. LRMS (M+H+) m/z calculated 475.2. found 474.8.

$^1$H NMR (DMSO-d6, 400 MHz) δ 9.62 (d, 1H), 8.96-8.98 (d, 1H), 8.59-8.70 (m, 3H), 8.43-8.48 (d, 1H), 8.03-8.04 (d, 1H), 7.94 (s, 1H), 7.79 (s, 1H), 7.60-7.62 (dd, 1H), 6.11 (s, 1H), 5.66 (s, 1H), 4.40 (s, 2H), 4.33-4.35 (d, 2H), 2.30 (s, 3H), 2.16 (s, 3H).

Example 59: Preparation of 3-chloro-6-((4-(((3-chloro-6-fluoro-1H-indol-5-yl)methyl)carbamoyl)pyridin-2-yl)methyl)quinoline-8-carboxamide

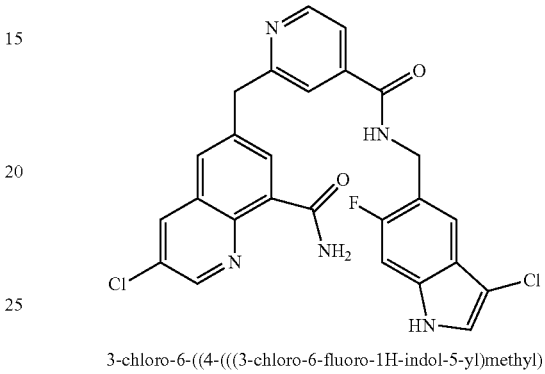

3-chloro-6-((4-(((3-chloro-6-fluoro-1H-indol-5-yl)methyl)carbamoyl)pyridin-2-yl)methyl)quinoline-8-carboxamide

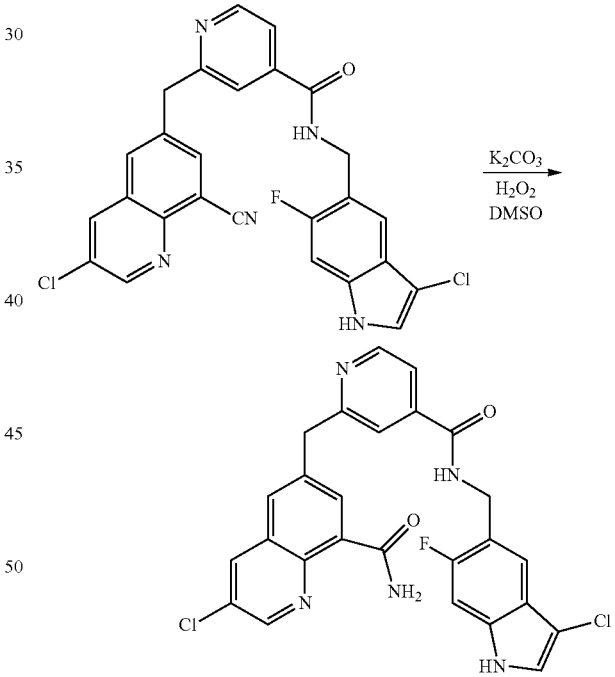

3-Chloro-6-((4-(((3-chloro-6-fluoro-1H-indol-5-yl)methyl)carbamoyl)pyridin-2-yl)methyl)quinoline-8-carboxamide (30 mg, 58%) was prepared as described for 6-((4-(((6-amino-2,4-dimethylpyridin-3-yl)methyl)carbamoyl)pyridin-2-yl)methyl)-3-chloroquinoline-8-carboxamide (Example 58) as a white solid. LRMS (M+H+) m/z calculated 522.1. found 521.9. $^1$H NMR (DMSO-d6, 400 MHz) δ 11.39 (s, 1H), 9.63 (s, 1H), 9.24-9.26 (t, 1H), 8.97-8.98 (d, 1H), 8.64-8.70 (dd, 2H), 8.44-8.45 (d, 1H), 8.04-8.05 (d, 1H), 7.95-7.96 (d, 1H), 7.66-7.68 (d, 1H), 7.43-7.50 (m, 1H), 7.20-7.24 (d, 1H), 4.57-4.59 (d, 2H), 4.42 (s, 2H).

Example 60: Preparation of 3-chloro-6-((4-(((5-chloro-1H-indazol-3-yl)methyl)carbamoyl)pyridin-2-yl)methyl)quinoline-8-carboxamide

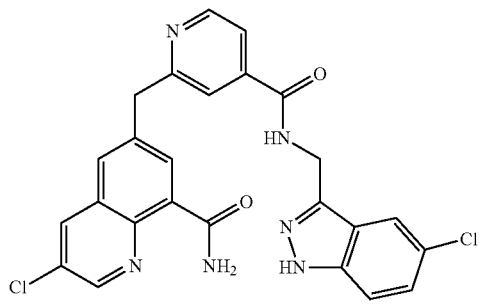

3-chloro-6-((4-(((5-chloro-1H-indazol-3-yl)
carbamoyl)pyridin-2-yl)methyl)quinoline-8-carboxamide

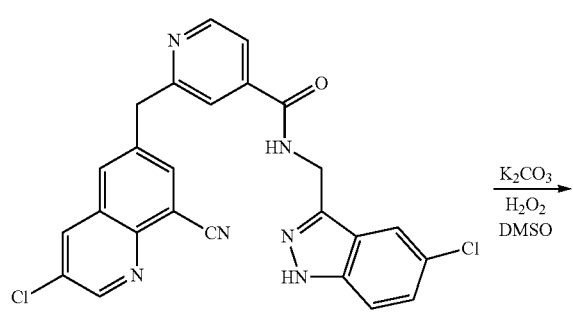

3-Chloro-6-((4-(((5-chloro-1H-indazol-3-yl)methyl)carbamoyl)pyridin-2-yl)methyl)quinoline-8-carboxamide (20 mg, 66%) was prepared as described for 6-((4-(((6-amino-2,4-dimethylpyridin-3-yl)methyl)carbamoyl)pyridin-2-yl)methyl)-3-chloroquinoline-8-carboxamide (Example 58) as a white solid. LRMS (M+H+) m/z calculated 505.1. found 504.9. $^1$H NMR (DMSO-d$_6$, 400 MHz) δ 13.09 (s, 1H), 9.63 (s, 1H), 9.40-9.41 (t, 1H), 8.97-8.98 (d, 1H), 8.64-8.70 (dd, 2H), 8.43 (s, 1H), 7.84-8.02 (m, 3H), 7.64-7.65 (d, 1H), 7.51-7.54 (d, 1H), 7.31-7.32 (m, 1H), 4.77-4.79 (d, 2H), 4.41 (s, 2H).

Example 61: Preparation of 3-chloro-6-((4-(((3-chloro-1H-pyrrolo[2,3-b]pyridin-5-yl)methyl)carbamoyl)pyridin-2-yl)methyl)quinoline-8-carboxamide

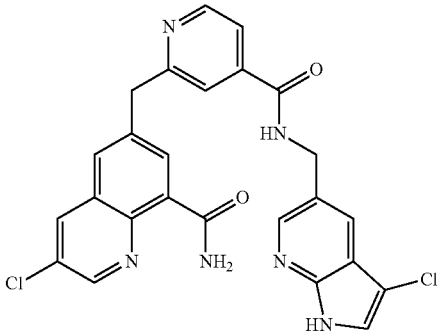

3-chloro-6-((4-(((3-chloro-1H-pyrrolo[2,3-b]pyridin-5-yl)
methyl)carbamoyl)pyridin-2-yl)methyl)quinoline-8-carboxamide

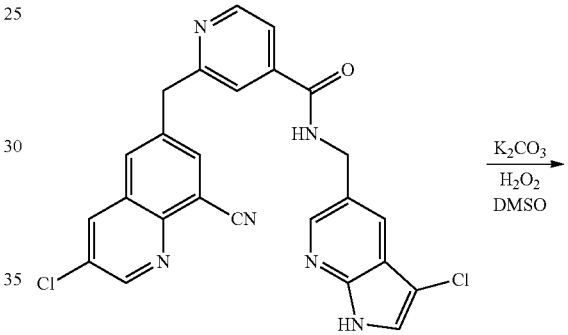

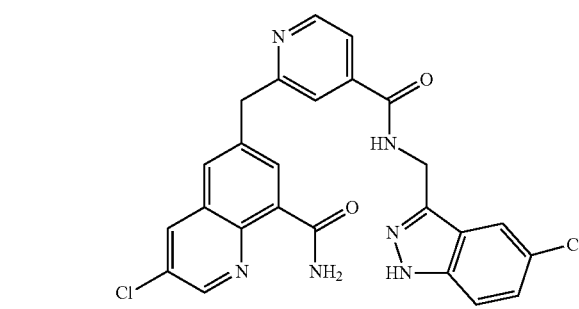

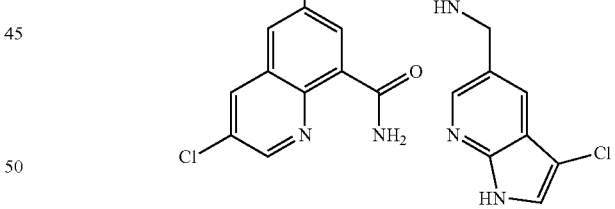

3-Chloro-6-((4-(((3-chloro-1H-pyrrolo[2,3-b]pyridin-5-yl)methyl)carbamoyl)pyridin-2-yl)methyl)quinoline-8-carboxamide (30 mg, 37%) was prepared as described for 6-((4-(((6-amino-2,4-dimethylpyridin-3-yl)methyl)carbamoyl)pyridin-2-yl)methyl)-3-chloroquinoline-8-carboxamide (Example 58) as a white solid. LRMS (M+H+) m/z calculated 505.1. found 505.0. $^1$H NMR (DMSO-d$_6$, 400 MHz) δ 9.63 (s, 1H), 9.34-9.35 (t, 1H), 8.96-8.97 (d, 1H), 8.69-8.70 (d, 1H), 8.64-8.66 (d, 1H), 8.44 (s, 1H), 8.31 (s, 1H), 8.04 (s, 1H), 7.95 (s, 1H), 7.87 (s, 1H), 7.82 (s, 1H), 7.65-7.67 (d, 2H), 4.58-4.60 (d, 2H), 4.42 (s, 2H).

Example 62: Preparation of 6-((4-(((6-amino-2-methylpyridin-3-yl)methyl)carbamoyl)pyridin-2-yl)methyl)-3-chloroquinoline-8-carboxamide

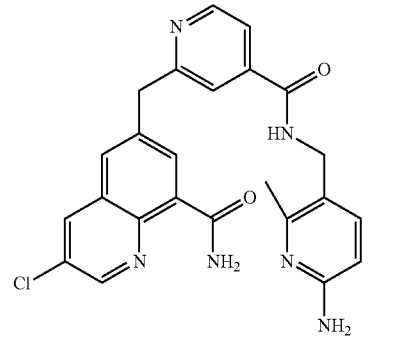

6-((4-(((6-amino-2-methylpyridin-3-yl)methyl)carbamoyl)pyridin-2-yl)methyl)-3-chloroquinoline-8-carboxamide

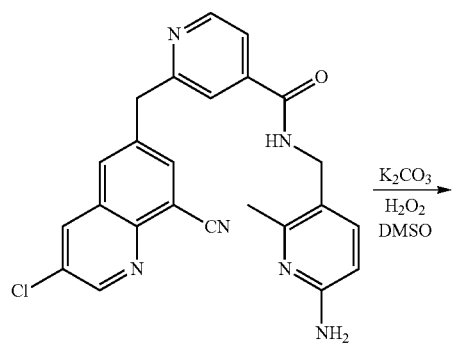

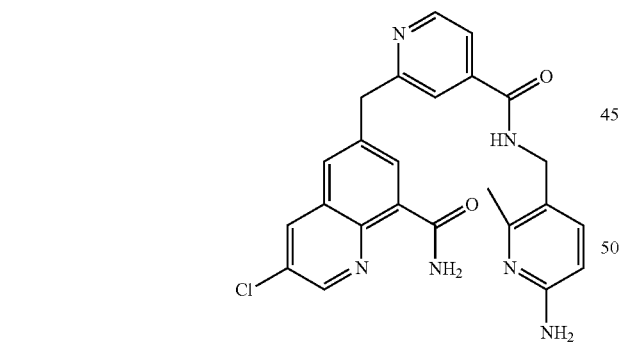

6-((4-(((6-Amino-2-methylpyridin-3-yl)methyl)carbamoyl)pyridin-2-yl)methyl)-3-chloroquinoline-8-carboxamide (28 mg, 44%) was prepared as described for 6-((4-(((6-amino-2,4-dimethylpyridin-3-yl)methyl)carbamoyl)pyridin-2-yl)methyl)-3-chloroquinoline-8-carboxamide (Example 58) as a white solid. LRMS (M+H+) m/z calculated 461.1. found 461.1. $^1$H NMR (DMSO-d$_6$, 400 MHz) δ 9.63 (s, 1H), 8.97-9.00 (m, 2H), 8.70-8.71 (d, 1H), 8.62-8.64 (d, 1H), 8.44-8.46 (d, 1H), 8.04 (s, 1H), 7.96 (s, 1H), 7.63-7.65 (dd, 1H), 7.23-7.25 (d, 1H), 6.22-6.25 (dd, 1H), 5.77 (s, 1H), 4.42 (s, 2H), 4.28-4.30 (d, 2H), 2.28 (s, 3H).

Example 63: Preparation of 6-((4-(((6-amino-4-methylpyridin-3-yl)methyl)carbamoyl)pyridin-2-yl)methyl)-3-chloroquinoline-8-carboxamide

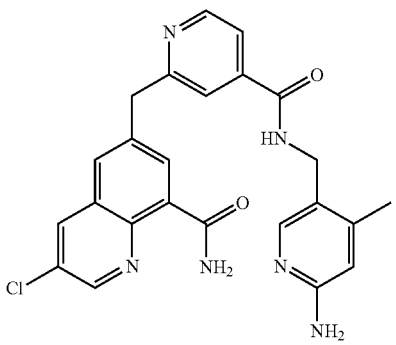

6-((4-(((6-amino-4-methylpyridin-3-yl)methyl)carbamoyl)pyridin-2-yl)methyl)-3-chloroquinoline-8-carboxamide

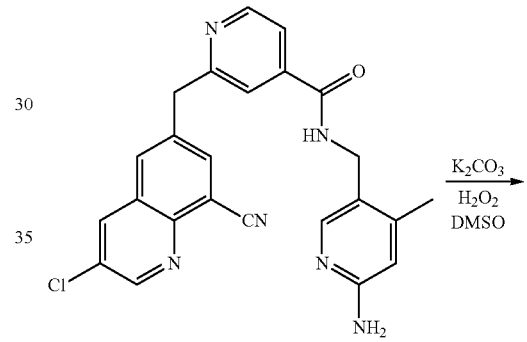

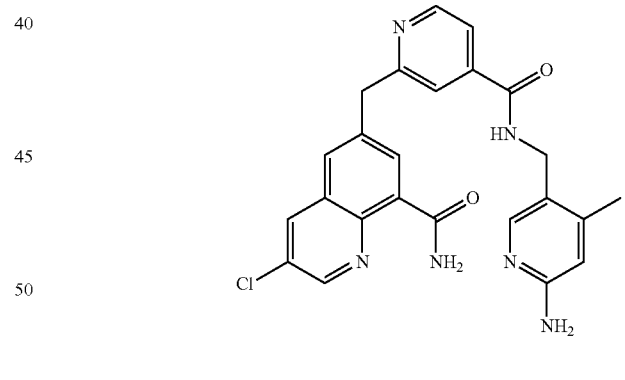

6-((4-(((6-Amino-4-methylpyridin-3-yl)methyl)carbamoyl)pyridin-2-yl)methyl)-3-chloroquinoline-8-carboxamide (70 mg, 69%) was prepared as described for 6-((4-(((6-amino-2,4-dimethylpyridin-3-yl)methyl)carbamoyl)pyridin-2-yl)methyl)-3-chloroquinoline-8-carboxamide (Example 58) as a white solid. LRMS (M+H+) m/z calculated 461.1. found 461.1. $^1$H NMR (DMSO-d$_6$, 400 MHz) δ 9.63 (s, 1H), 8.92-9.00 (m, 2H), 8.70-8.71 (d, 1H), 8.62-8.64 (d, 1H), 8.43-8.45 (d, 1H), 8.05 (s, 1H), 7.96 (s, 1H), 7.78-7.80 (dd, 1H), 7.61-7.63 (d, 1H), 6.26 (s, 1H), 5.81 (s, 1H), 4.41 (s, 2H), 4.29-4.31 (d, 2H), 2.15 (s, 3H).

Example 64: Preparation of 6-((4-(((1-aminoisoqui-nolin-6-yl)methyl)carbamoyl)pyridin-2-yl)methyl)-3-chloroquinoline-8-carboxamide

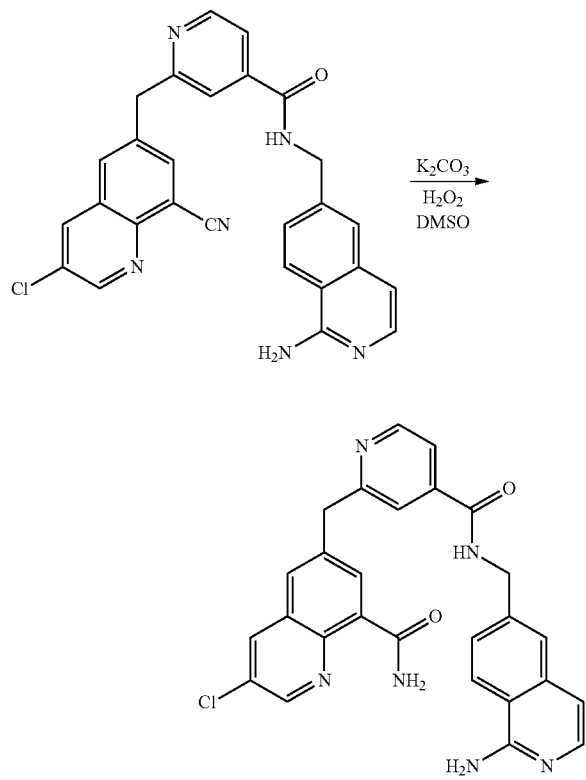

6-((4-(((1-aminoisoquinolin-6-yl)methyl)carbamoyl)pyridin-2-yl)methyl)-3-chloroquinoline-8-carboxamide 6-((4-(((1-Aminoisoquinolin-6-yl)methyl)carbamoyl)pyridin-2-yl)methyl)-3-chloroquinoline-8-carboxamide (25 mg, 16%) was prepared as described for 6-((4-(((6-amino-2,4-dimethylpyridin-3-yl)methyl)carbamoyl)pyridin-2-yl)methyl)-3-chloroquinoline-8-carboxamide (Example 58) as a white solid. LRMS (M+H+) m/z calculated 497.1. found 497.0. $^1$H NMR (DMSO-$d_6$, 400 MHz) δ 9.63 (s, 1H), 9.37-9.39 (t, 1H), 8.97-8.98 (m, 2H), 8.70-8.71 (d, 1H), 8.67-8.68 (d, 1H), 8.45-8.46 (d, 1H), 8.13-8.15 (d, 1H), 8.06 (s, 1H), 7.95 (s, 1H), 7.85 (s, 1H), 7.75-7.76 (d, 1H), 7.69-7.70 (dd, 1H), 7.54-7.56 (dd, 1H), 7.42 (s, 1H), 7.39- 7.40 (d, 1H), 6.84-6.86 (d, 1H), 6.76 (s, 2H), 4.60-4.62 (d, 2H), 4.40 (s, 2H).

Example 65: Preparation of 3-chloro-6-((4-(((3-chloro-4-fluoro-1H-indol-5-yl)methyl)carbamoyl)pyridin-2-yl)methyl)quinoline-8-carboxamide

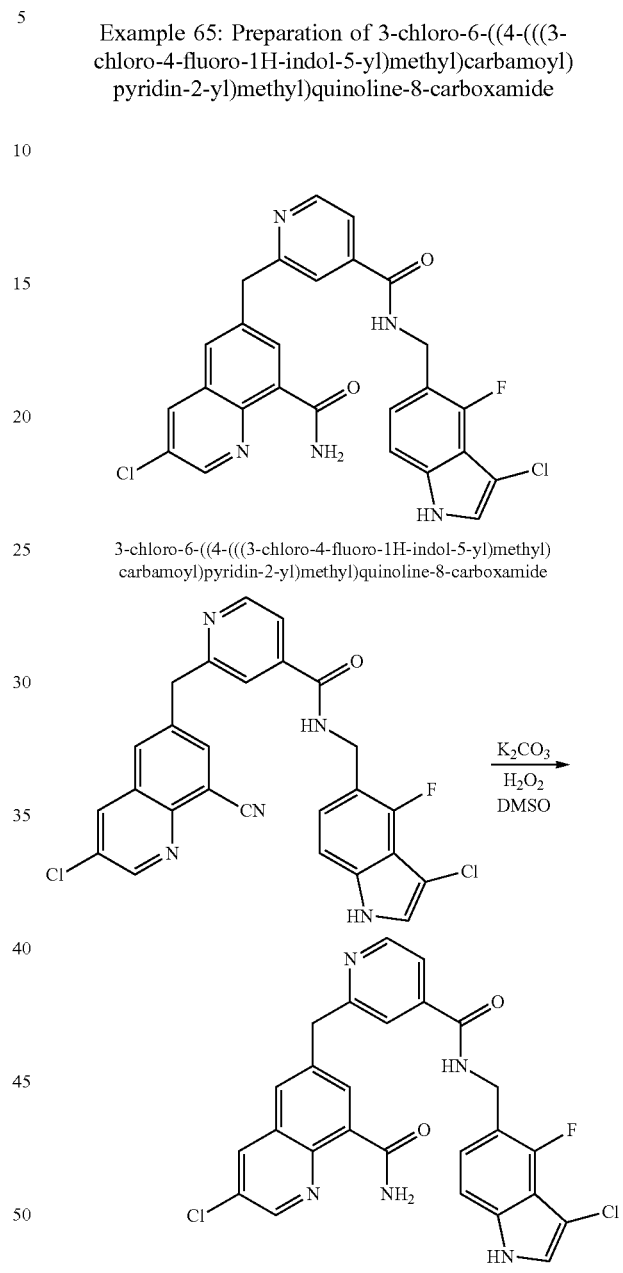

3-chloro-6-((4-(((3-chloro-4-fluoro-1H-indol-5-yl)methyl)carbamoyl)pyridin-2-yl)methyl)quinoline-8-carboxamide 3-Chloro-6-((4-(((3-chloro-4-fluoro-1H-indol-5-yl)methyl)carbamoyl)pyridin-2-yl)methyl)quinoline-8-carboxamide (35 mg, 16%) was prepared as described for 6-((4-(((6-amino-2,4-dimethylpyridin-3-yl)methyl)carbamoyl)pyridin-2-yl)methyl)-3-chloroquinoline-8-carboxamide (Example 58) as a white solid. LRMS (M+H+) m/z calculated 522.1. found 522.0. $^1$H NMR (DMSO-$d_6$, 400 MHz) δ 11.58 (s, 1H), 9.62 (s, 1H), 9.22-9.25 (t, 1H), 8.97-8.98 (d, 2H), 8.69-8.70 (d, 1H), 8.63-8.65 (d, 1H), 8.43-8.44 (d, 1H), 8.04 (s, 1H), 7.94 (s, 1H), 7.82 (s, 1H), 7.65-7.66 (d, 1H), 7.51 (s, 1H), 7.14-7.20 (m, 2H), 4.56-4.57 (d, 2H), 4.41 (s, 2H).

Example 66: Preparation of 3-chloro-6-((4-(((6-fluoro-1H-indol-5-yl)methyl)carbamoyl)pyridin-2-yl)methyl)quinoline-8-carboxamide

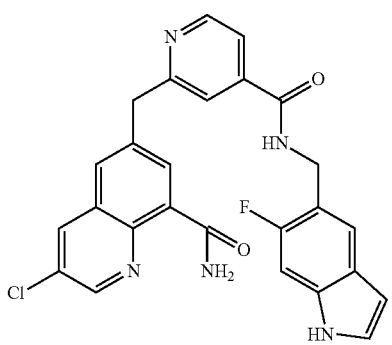

3-chloro-6-((4-(((6-fluoro-1H-indol-5-yl)methyl)carbamoyl)pyridin-2-yl)methyl)quinoline-8-carboxamide 3-Chloro-6-((4-(((6-fluoro-1H-indol-5-yl)methyl)carbamoyl)pyridin-2-yl)methyl)quinoline-8-carboxamide (35 mg, 42%) was prepared as described for 6-((4-(((6-amino-2,4-dimethylpyridin-3-yl)methyl)carbamoyl)pyridin-2-yl)methyl)-3-chloroquinoline-8-carboxamide (Example 58) as a white solid. LRMS (M+H+) m/z calculated 488.1 found 488.0. $^1$H NMR (DMSO-$d_6$, 400 MHz) δ 11.09 (s, 1H), 9.62 (s, 1H), 9.19-9.22 (t, 1H), 8.97-8.98 (d, 2H), 8.69-8.70 (d, 1H), 8.64-8.66 (d, 1H), 8.44-8.45 (d, 1H), 8.05 (s, 1H), 7.95 (s, 1H), 7.84 (s, 1H), 7.67-7.69 (d, 1H), 7.48-7.50 (s, 1H), 7.30-7.31 (t, 2H), 7.14-7.17 (1, 1H), 4.55-4.57 (d, 2H), 4.42 (s, 2H).

Example 67: Preparation of N-((6-amino-2,4-dimethylpyridin-3-yl)methyl)-2-((3-chloro-8-(methylsulfonyl)quinolin-6-yl)methyl)isonicotinamide

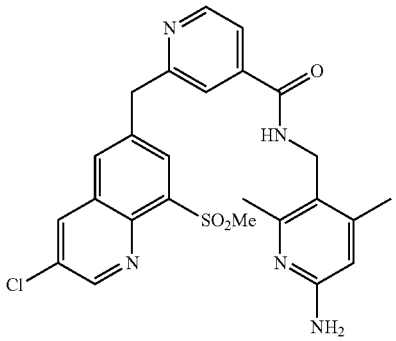

N-((6-amino-2,3-dimethylpyridin-3-yl)methyl)-2-((3-chloro-8-(methylsulfonyl)quinolin-6-yl)methyl)isonicotinamide

Step 1: Preparation of (3-chloro-8-methanesulfonyl-quinolin-6-yl)-methanol

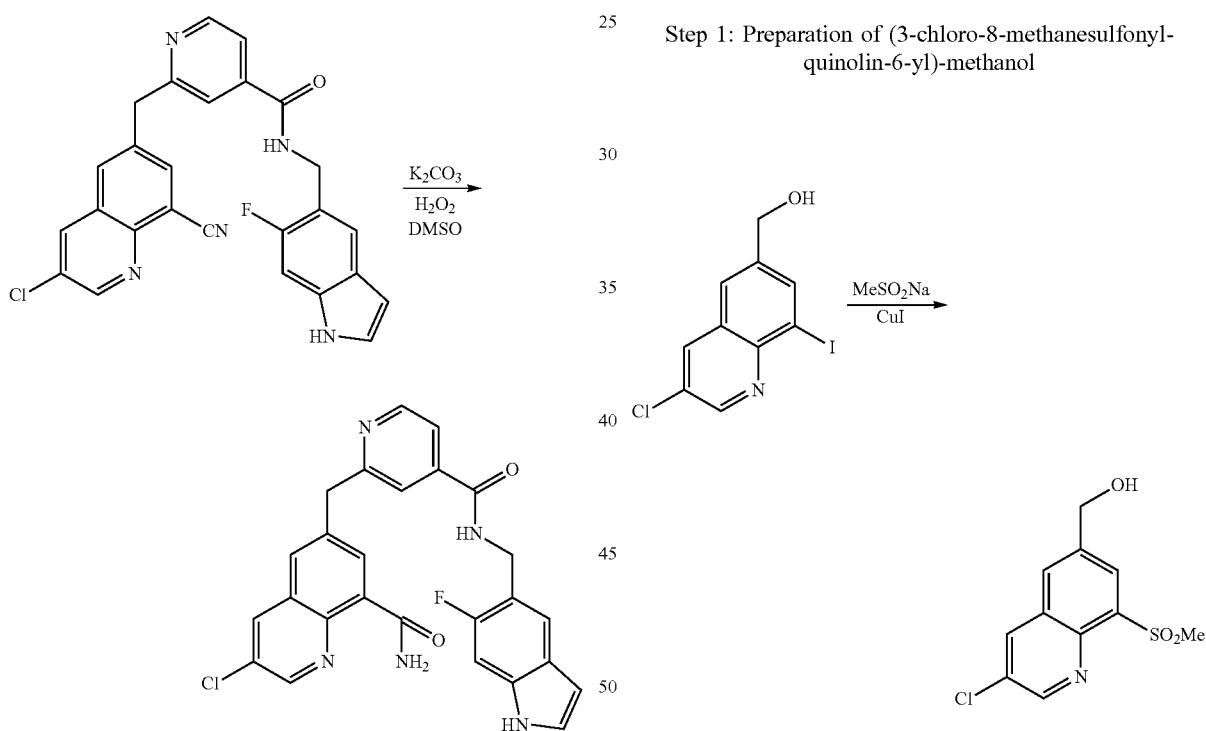

A mixture of (3-chloro-8-iodo-quinolin-6-yl)-methanol (7.6 g, 23.8 mmol, 1 eq), sodium methanesulphinate (2.92 g, 28.6 mmol, 1.2 eq), copper iodide (452 mg, 2.38 mol, 0.1 eq), L-proline sodium salt (652 mg, 4.76 mol, 0.2 eq) in 110 mL of DMSO was heated to 110° C. under nitrogen for 15 h. The cooled mixture was partitioned between ethyl acetate and water. The organic layer was separated, and the aqueous layer was extracted with ethyl acetate twice. The combined organic layers were washed with brine, dried over MgSO$_4$, and concentrated in vacuum. The residue was purified by silica gel column (EtOAc/PE=1/2, v/v) to give (3-chloro-8-methanesulfonyl-quinolin-6-yl)-methanol (4.1 g, 64%) as a yellow solid.

Step 2: Preparation of 3-chloro-6-chloromethyl-8-methanesulfonyl-quinoline

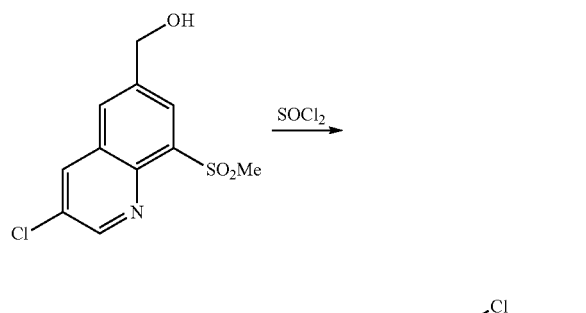

To (3-chloro-8-methanesulfonyl-quinolin-6-yl)-methanol (4.1 g, 15.1 mmol, 1.0 eq) was added $SOCl_2$ (50 mL) and the mixture was stirred at rt for 1 h. The volatiles were then removed under vacuum and the residue was dissolved in DCM. The mixture was washed with saturated aq. $NaHCO_3$, dried and concentrated to give 3-chloro-6-chloromethyl-8-methanesulfonyl-quinoline (4.3 g, 99%) as a yellow solid.

Step 3: Preparation of methyl 2-((3-chloro-8-(methylsulfonyl)quinolin-6-yl)methyl)isonicotinate

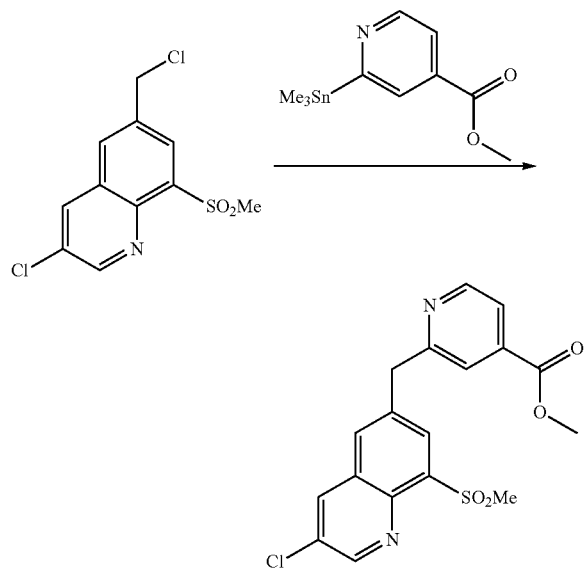

To a solution of 3-chloro-6-chloromethyl-8-methanesulfonyl-quinoline (4.3 g, 14.9 mmol, 1.0 eq) in dioxane (70 mL) was added methyl 2-(trimethylstannyl)isonicotinate (4.93 g, 16.4 mmol, 1.1 eq) and $Pd(PPh_3)_2Cl_2$ (1.04 g, 1.49 mmol, 0.1 eq). The mixture was stirred at 90° C. for 3 h under nitrogen atmosphere, concentrated and purified by silica gel chromatography (DCM/MeOH=50/1, v/v) to afford methyl 2-((3-chloro-8-(methylsulfonyl)quinolin-6-yl)methyl)isonicotinate (2.3 g, 40%) as a yellow solid.

Step 4: Preparation of N-((6-amino-2,4-dimethylpyridin-3-yl)methyl)-2-((3-chloro-8-(methylsulfonyl)quinolin-6-yl)methyl)isonicotinamide

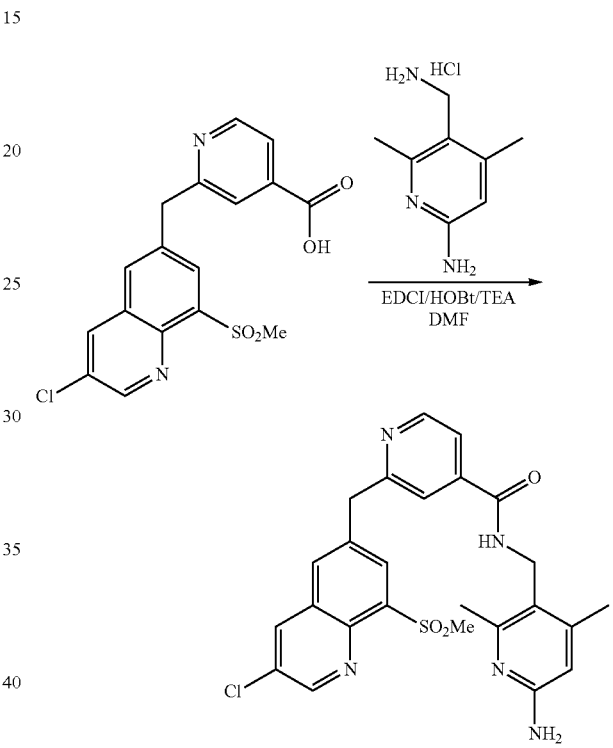

To a solution of 2-(3-chloro-8-methanesulfonyl-quinolin-6-ylmethyl)-isonicotinic acid (80 mg, 0.21 mmol, 1 eq) in DMF (10 mL) was added 5-aminomethyl-4,6-dimethyl-pyridin-2-ylamine hydrochloride (40 mg, 0.21 mmol, 1.0 eq) followed by EDCI (61 mg, 0.32 mmol, 1.5 eq), HOBT (43 mg, 0.32 mmol, 1.5 eq) and TEA (64 mg, 0.64 mmol, 3.0 eq). The reaction mixture was heated to 45° C. kept stirring for overnight. Water was added, and the mixture was extracted with DCM. The organic layer was washed with water, dried over $Na_2SO_4$, filtered, and concentrated. The residue was purified by prep-HPLC to give N-((6-amino-2,4-dimethylpyridin-3-yl)methyl)-2-((3-chloro-8-(methylsulfonyl)quinolin-6-yl)methyl)isonicotinamide (40 mg, 37%) as a yellow solid. LRMS (M+H$^+$) m/z calculated 510.1. found 509.8.

$^1$H NMR (DMSO-d$_6$, 400 MHz) δ 9.07 (d, 1H), 8.76 (d, 1H), 8.66 (t, 1H), 8.62 (d, 1H), 8.36 (d, 1H), 8.23 (s, 1H), 7.83 (s, 1H), 7.62 (d, 1H), 6.12 (s, 1H), 5.70 (s, 2H), 4.47 (s, 2H), 4.34 (d, 2H), 3.56 (s, 3H), 2.30 (s, 3H), 2.17 (s, 3H).

Example 68: Preparation of N-((3-chloro-6-fluoro-1H-indol-5-yl)methyl)-2-((3-chloro-8-(methylsulfonyl)quinolin-6-yl)methyl)isonicotinamide

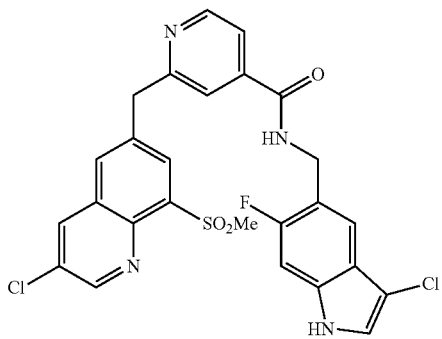

N-((3-chloro-6-fluoro-1H-indol-5-yl)methyl)-2-((3-chloro-8-(methylsulfonyl)quinolin-6-yl)methyl)isonicotinamide

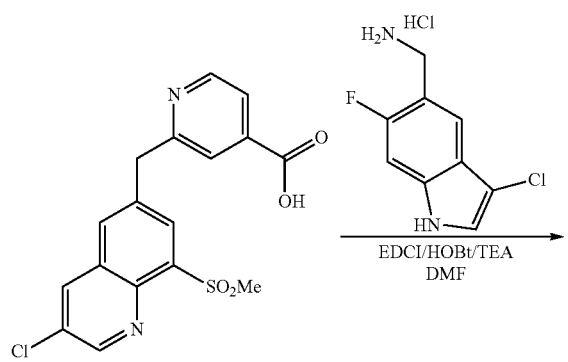

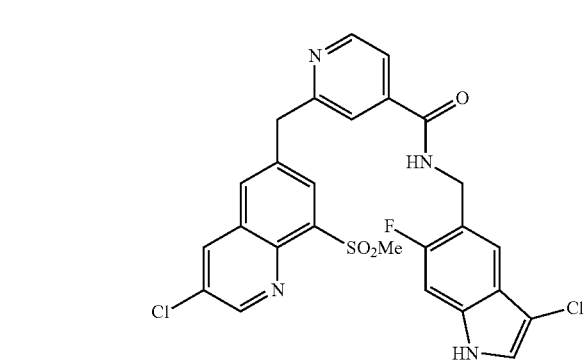

N-((3-chloro-6-fluoro-1H-indol-5-yl)methyl)-2-((3-chloro-8-(methylsulfonyl) quinolin-6-yl)methyl)isonicotinamide (40 mg, 34%) was prepared as described for N-((6-amino-2,4-dimethylpyridin-3-yl)methyl)-2-((3-chloro-8-(methylsulfonyl)quinolin-6-yl)methyl)isonicotinamide (Example 67) as a white solid. LRMS (M+H⁺) m/z calculated 557.1. found 557.0.

$^1$H NMR (DMSO-$d_6$, 400 MHz) δ 11.41 (s, 1H), 9.27 (t, 1H), 9.07 (d, 1H), 8.76 (d, 1H), 8.67 (d, 1H), 8.37 (s, 1H), 8.23 (s, 1H), 7.88 (s, 1H), 7.68 (d, 1H), 7.51 (d, 2H), 7.46 (d, 1H), 7.23 (d, 2H), 4.59 (d, 2H), 4.49 (s, 2H), 3.56 (s, 3H).

Example 69: Preparation of N-((6-amino-2-methylpyridin-3-yl)methyl)-2-((3-chloro-8-(methylsulfonyl)quinolin-6-yl)methyl)isonicotinamide

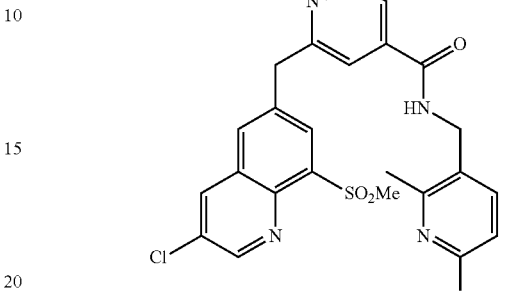

N-((6-amino-2-methylpyridin-3-yl)methyl)-2-((3-chloro-8-(methylsulfonyl)quinolin-6-yl)methyl)isonicotinamide

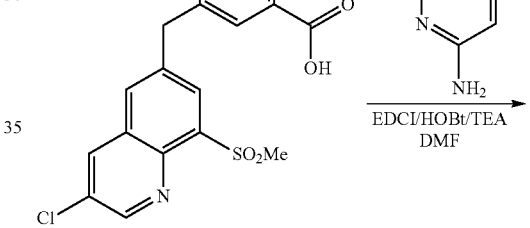

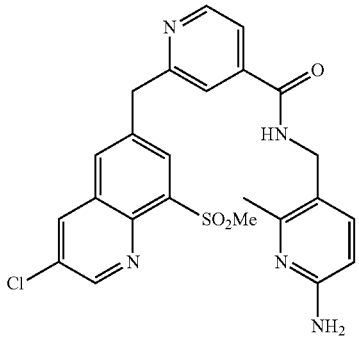

N-((6-amino-2-methylpyridin-3-yl)methyl)-2-((3-chloro-8-(methylsulfonyl)quinolin-6-yl)methyl)isonicotinamide (40 mg, 34%) was prepared as described for N-((6-amino-2,4-dimethylpyridin-3-yl)methyl)-2-((3-chloro-8-(methylsulfonyl)quinolin-6-yl)methyl)isonicotinamide (Example 67) as a white solid. LRMS (M+H⁺) m/z calculated 496.1. found 495.7.

$^1$H NMR (DMSO-$d_6$, 400 MHz) δ 9.07 (d, 1H), 9.01 (t, 1H), 8.76 (d, 1H), 8.64 (d, 1H), 8.36 (d, 1H), 8.23 (s, 1H), 7.85 (s, 1H), 7.65 (d, 1H), 7.24 (d, 1H), 6.23 (d, 1H), 5.75 (s, 2H), 4.48 (s, 2H), 4.30 (d, 2H), 3.56 (s, 3H), 2.28 (s, 3H).

Example 70: Preparation of N-((6-amino-2,4-dimethylpyridin-3-yl)methyl)-2-((8-cyano-3-methylquinolin-6-yl)methyl)isonicotinamide

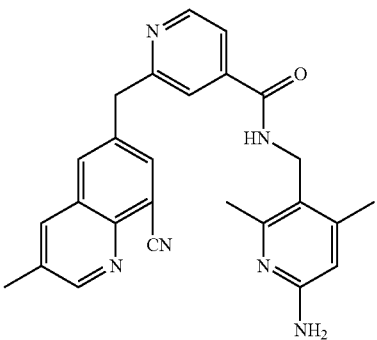

N-((6-amino-2,4-dimethylpyridin-3-yl)methyl)-2-((8-cyano-3-methylquinolin-6-yl)methyl)isonicotinamide

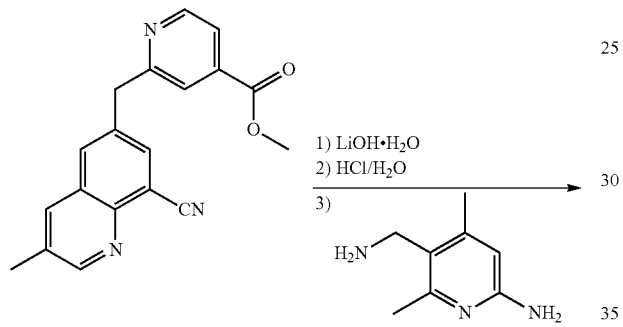

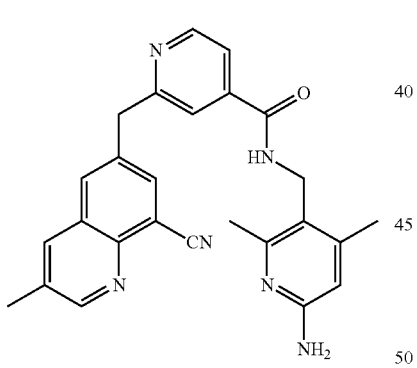

To a solution of methyl 2-((8-cyano-3-methylquinolin-6-yl)methyl)isonicotinate (300 mg, 0.95 mmol, 1.0 eq) in THF (16 mL)/H$_2$O (4 mL) was added LiOH.H$_2$O (79.49 mg, 1.89 mmol, 2.0 eq). The mixture was stirred at 40° C. for 1 h and was acidified to pH 5 with 1 N HCl solution. The mixture was concentrated in vacuo and the residue was directly used without further purification. To a solution of the above crude product and 5-aminomethyl-4,6-dimethyl-pyridin-2-ylamine (285 mg, 1.89 mmol, 2.0 eq) in DMF 10 mL) was added HOBT (192.37 mg, 1.43 mmol, 1.5 eq), EDCI (310.08 mg, 1.62 mmol, 1.7 eq) and Et$_3$N (0.53 mL, 3.8 mmol, 4 eq). The mixture was stirred at rt for overnight and diluted with water. The organic layer was separated and the aqueous layer was extracted with DCM. The combined extracts were dried and concentrated. The residue was purified by prep-HPLC to give N-((6-amino-2,4-dimethylpyridin-3-yl)methyl)-2-((8-cyano-3-methylquinolin-6-yl) methyl)isonicotinamide (90 mg, 21% for 2 steps) as an off-white solid. LRMS (M+H$^+$) m/z calculated 437.2. found 437.0.

$^1$H NMR (DMSO-d$_6$, 400 MHz) δ 8.89 (s, 1H), 8.61 (t, 2H), 8.23 (s, 2H), 8.10 (s, 1H), 7.78 (s, 1H), 7.61 (t, 1H), 6.12 (s, 1H), 5.67 (s, 2H), 4.37 (s, 2H), 4.35 (d, 2H), 2.50 (s, 3H), 2.30 (s, 3H), 2.16 (s, 3H).

Example 71: Preparation of N-((1-aminoisoquinolin-6-yl)methyl)-2-((8-cyano-3-methylquinolin-6-yl)methyl)isonicotinamide

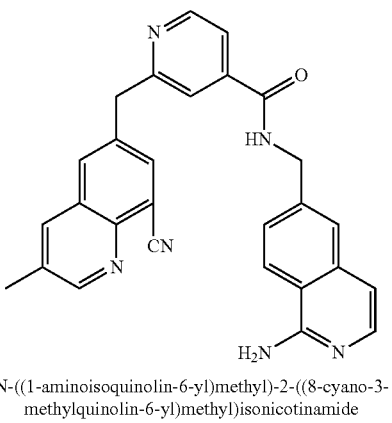

N-((1-aminoisoquinolin-6-yl)methyl)-2-((8-cyano-3-methylquinolin-6-yl)methyl)isonicotinamide

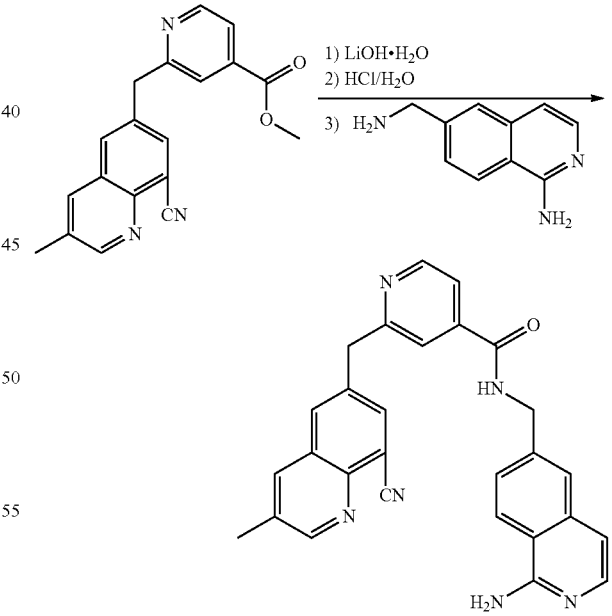

N-((1-aminoisoquinolin-6-yl)methyl)-2-((8-cyano-3-methylquinolin-6-yl)methyl)isonicotinamide (105 mg, 24% for 2 steps) was prepared as described for N-((6-amino-2,4-dimethylpyridin-3-yl)methyl)-2-((8-cyano-3-methylquinolin-6-yl)methyl)isonicotinamide (Example 70) as an off-white solid. LRMS (M+H$^+$) m/z calculated 459.2. found 459.0.

¹H NMR (DMSO-d₆, 400 MHz) δ 9.41 (t, 1H), 8.90 (s, 1H), 8.69 (d, 1H), 8.28 (d, 2H), 8.16 (d, 2H), 7.86 (s, 1H), 7.78 (d, 1H), 7.71 (d, 1H), 7.57 (s, 1H), 7.43 (d, 1H), 6.87 (d, 1H), 6.78 (s, 2H), 4.64 (d, 2H), 4.42 (s, 2H), 2.50 (s, 3H).

Example 72: Preparation of N-((3-chloro-6-fluoro-1H-indol-5-yl)methyl)-2-((8-cyano-3-methylquinolin-6-yl)methyl)isonicotinamide

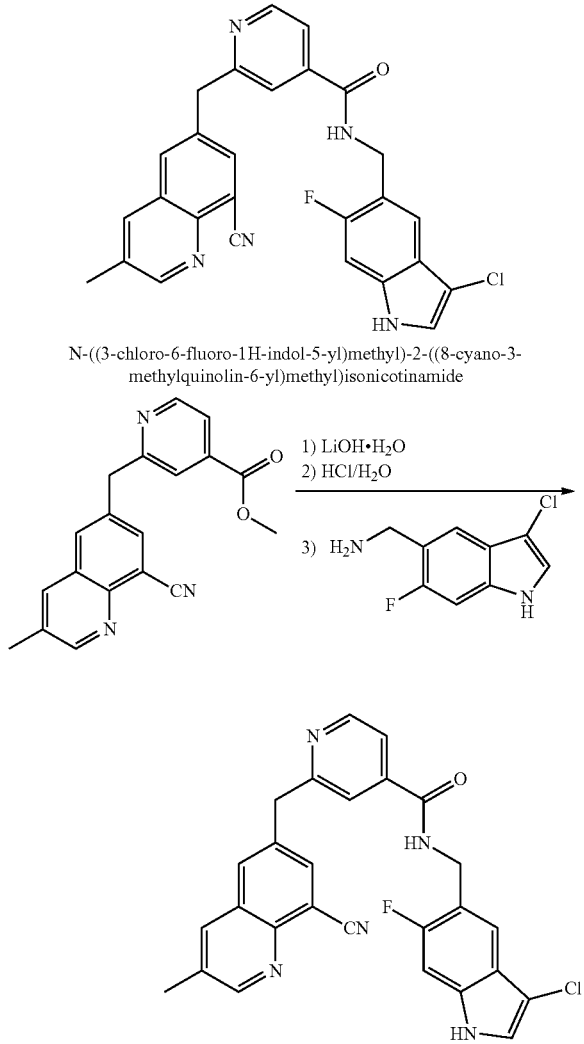

N-((3-chloro-6-fluoro-1H-indol-5-yl)methyl)-2-((8-cyano-3-methylquinolin-6-yl)methyl)isonicotinamide (100 mg, 21% for 2 steps) was prepared as described for N-((6-amino-2,4-dimethylpyridin-3-yl)methyl)-2-((8-cyano-3-methylquinolin-6-yl)methyl)isonicotinamide (Example 70) as an off-white solid. LRMS (M+H⁺) m/z calculated 484.1. found 483.9.

¹H NMR (DMSO-d₆, 400 MHz) δ 11.32 (s, 1H), 8.90 (t, 1H), 8.67 (d, 1H), 8.62 (d, 1H), 8.27 (d, 2H), 8.12 (s, 1H), 7.83 (s, 1H), 7.68 (d, 1H), 7.52 (d, 1H), 7.46 (d, 1H), 7.25 (d, 1H), 4.61 (d, 2H), 4.41 (s, 2H), 2.50 (s, 3H).

Example 73: Preparation of N-((3-chloro-1H-pyrrolo[2,3-b]pyridin-5-yl)methyl)-2-((8-cyano-3-methylquinolin-6-yl)methyl)isonicotinamide

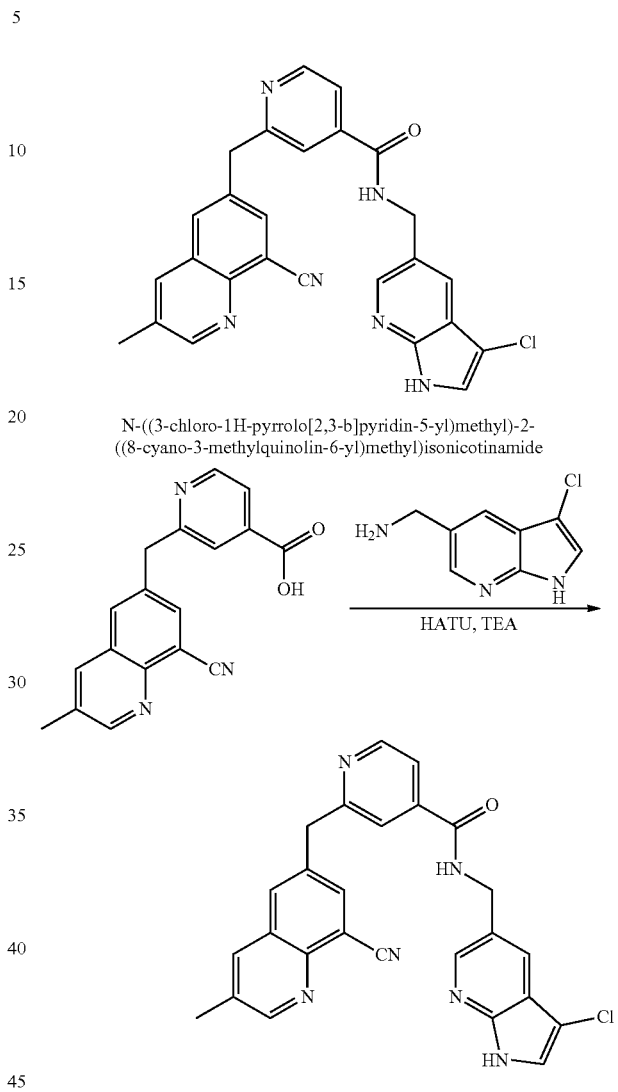

To a solution of 2-(8-cyano-3-methyl-quinolin-6-ylmethyl)-isonicotinic acid (100 mg, 0.33 mmol, 1.0 eq) and (3-chloro-1H-pyrrolo[2,3-b]pyridin-5-yl)-methylamine hydrochloride (144 mg, 0.66 mmol, 2.0 eq) in DMF (5 mL) was added HATU (188 mg, 0.50 mmol, 1.5 eq) and Et₃N (134 mg, 1.32 mmol, 4 eq). The mixture was stirred at rt for 2 h and diluted with water. The organic layer was separated and the aqueous layer was extracted with DCM. The combined extracts were dried and concentrated. The residue was purified by prep-HPLC to give N-((3-chloro-1H-pyrrolo[2,3-b]pyridin-5-yl)methyl)-2-((8-cyano-3-methylquinolin-6-yl)methyl)isonicotinamide (66 mg, 43%) as an off-white solid. LRMS (M+H⁺) m/z calculated 467.1. found 466.8. ¹H NMR (DMSO-d₆, 400 MHz) δ: 11.97 (s, 1H), 9.34 (t, 1H), 8.89 (s, 1H), 8.66 (d, 1H), 8.32 (s, 1H), 8.26 (s, 1H), 8.23 (s, 1H), 8.11 (s, 1H), 7.88 (s, 1H), 7.82 (s, 1H), 7.68 (d, 1H), 7.66 (d, 1H), 4.61 (d, 2H), 4.40 (s, 2H), 2.50 (s, 3H).

Example 74: Preparation of N-((3-chloro-4-fluoro-1H-indol-5-yl)methyl)-2-((8-cyano-3-methylquinolin-6-yl)methyl)isonicotinamide

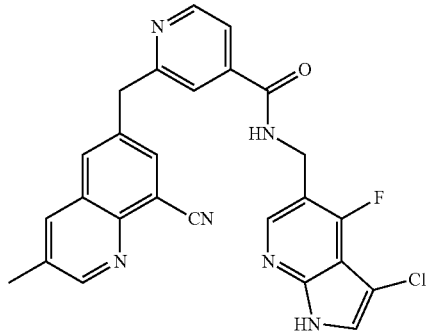

N-((3-chloro-4-fluoro-1H-indol-5-yl)methyl)-2-((8-cyano-3-methylquinolin-6-yl)methyl)isonicotinamide

Example 75: Preparation of N-((5-chloro-1H-indazol-3-yl)methyl)-2-((8-cyano-3-methylquinolin-6-yl)methyl)isonicotinamide

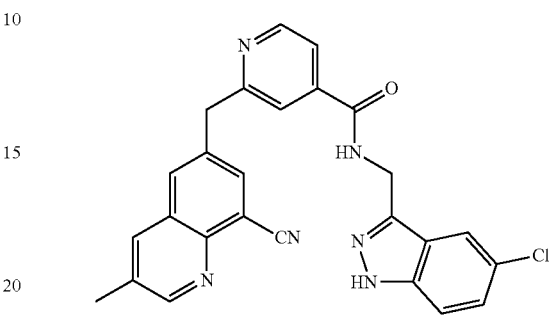

N-((5-chloro-1H-indazol-3-yl)methyl)-2-((8-cyano-3-methylquinolin-6-yl)methyl)isonicotinamide

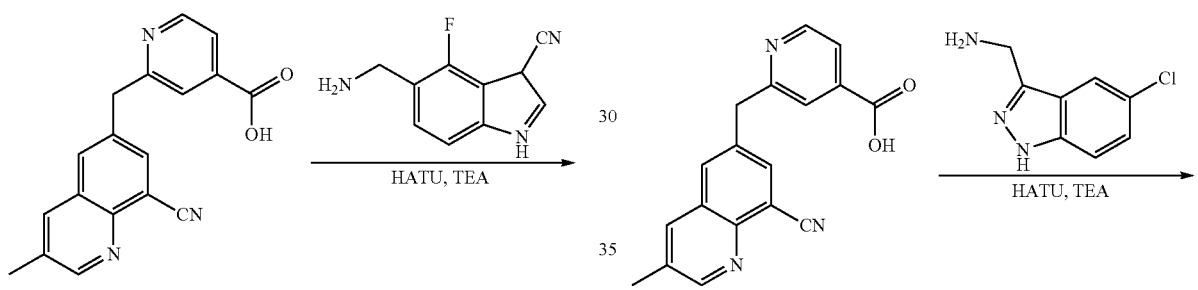

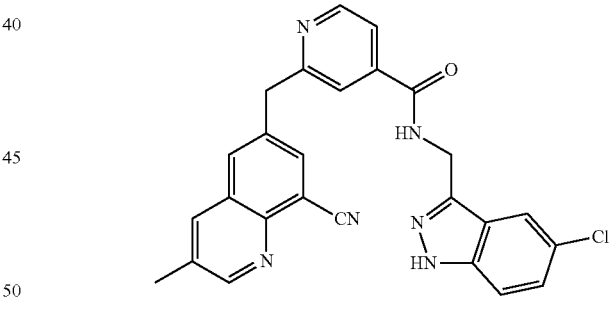

N-((3-chloro-4-fluoro-1H-indol-5-yl)methyl)-2-((8-cyano-3-methylquinolin-6-yl)methyl)isonicotinamide (70 mg, 44%) was prepared as described for N-((3-chloro-1H-pyrrolo[2,3-b]pyridin-5-yl)methyl)-2-((8-cyano-3-methylquinolin-6-yl)methyl)isonicotinamide (Example 73) as an off-white solid. LRMS (M+H$^+$) m/z calculated 484.1. found 483.8.

$^1$H NMR (DMSO-d$_6$, 400 MHz) δ 11.59 (s, 1H), 9.23 (t, 1H), 8.80 (d, 1H), 8.65 (d, 1H), 8.25 (s, 1H), 8.12 (s, 1H), 7.81 (s, 1H), 7.65 (d, 1H), 7.52 (d, 1H), 7.20 (d, 1H), 7.15 (d, 1H), 4.58 (d, 2H), 4.39 (s, 2H), 2.50 (s, 3H).

N-((5-chloro-1H-indazol-3-yl)methyl)-2-((8-cyano-3-methylquinolin-6-yl)methyl)isonicotinamide (74 mg, 48%) was prepared as described for N-((3-chloro-1H-pyrrolo[2,3-b]pyridin-5-yl)methyl)-2-((8-cyano-3-methylquinolin-6-yl)methyl)isonicotinamide (Example 73) as an off-white solid. LRMS (M+H$^+$) m/z calculated 467.1. found 466.8.

$^1$H NMR (DMSO-d$_6$, 400 MHz) δ 13.09 (s, 1H), 9.38 (t, 1H), 8.90 (d, 1H), 8.65 (d, 1H), 8.25 (s, 2H), 8.12 (s, 1H), 7.89 (s, 1H), 7.81 (s, 1H), 7.64 (d, 1H), 7.53 (d, 1H), 7.34 (d, 1H), 7.32 (d, 1H), 4.79 (d, 2H), 4.39 (s, 2H), 2.50 (s, 3H).

Example 76: Preparation of 2-((8-cyano-3-methylquinolin-6-yl)methyl)-N-((6-fluoro-1H-indol-5-yl)methyl)isonicotinamide

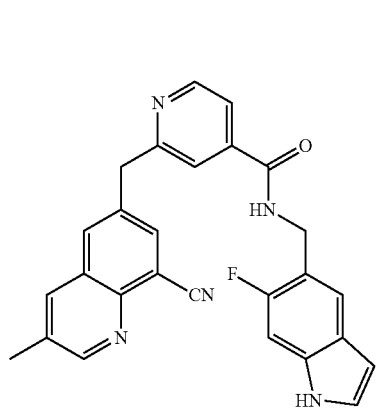

2-((8-cyano-3-methylquinolin-6-yl)methyl)-N-((6-fluoro-1H-indol-5-yl)methyl)isonicotinamide

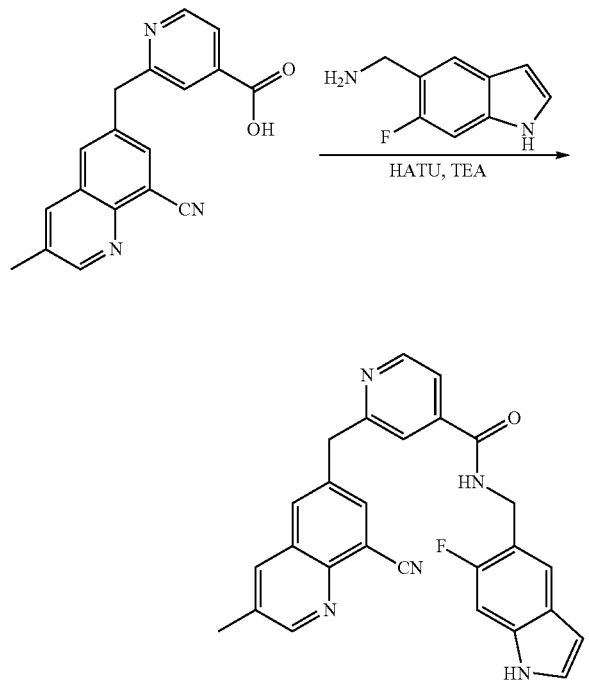

2-((8-Cyano-3-methylquinolin-6-yl)methyl)-N-((6-fluoro-1H-indol-5-yl)methyl)isonicotinamide (70 mg, 46%) was prepared as described for N-((3-chloro-1H-pyrrolo[2,3-b]pyridin-5-yl)methyl)-2-((8-cyano-3-methylquinolin-6-yl)methyl)isonicotinamide (Example 73) as an off-white solid. LRMS (M+H$^+$) m/z calculated 450.2. found 449.8.

$^1$H NMR (DMSO-d$_6$, 400 MHz) δ 11.11 (s, 1H), 9.20 (t, 1H), 8.90 (d, 1H), 8.65 (d, 1H), 8.26 (t, 2H), 8.13 (s, 1H), 7.83 (s, 1H), 7.68 (d, 1H), 7.31 (d, 1H), 7.17 (d, 1H), 6.40 (s, 1H), 4.57 (d, 2H), 4.40 (s, 2H), 2.50 (s, 3H).

Example 77: Preparation of 6-((4-(((6-amino-2,4-dimethylpyridin-3-yl)methyl)carbamoyl)pyridin-2-yl)methyl)-3-methylquinoline-8-carboxamide

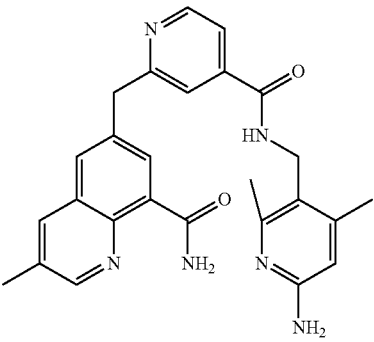

6-((4-(((6-amino-2,4-dimethylpyridin-3-yl)methyl)carbamoyl)pyridin-2-yl)methyl)-3-methylquinoline-8-carboxamide

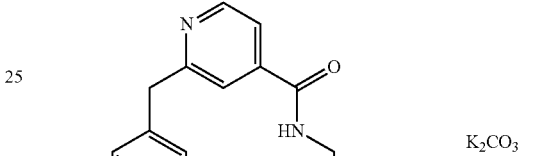

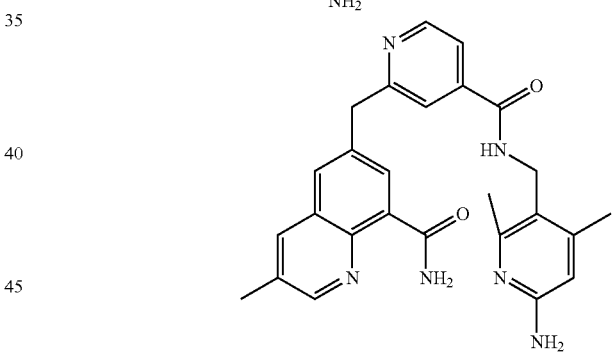

To a solution of N-(6-amino-2,4-dimethyl-pyridin-3-ylmethyl)-2-(8-cyano-3-methyl-quinolin-6-ylmethyl)-isonicotinamide (80 mg, 0.18 mmol, 1.0 eq) and K$_2$CO$_3$ (180.7 mg, 1.31 mmol, 7.3 eq) in DMSO (10 mL) was added H$_2$O$_2$ (1 mL). The mixture was stirred at 50° C. for 3 h, then EtOAc and water was added, the organic layer was concentrated and purified by pre-HPLC to give 6-((4-(((6-amino-2,4-dimethylpyridin-3-yl)methyl)carbamoyl)pyridin-2-yl)methyl)-3-methylquinoline-8-carboxamide (4 mg, 4.8%) as a white solid. LRMS (M+H+) m/z calculated 455.2. found 454.9.

$^1$H NMR (DMSO-d$_6$, 400 MHz) δ 10.20 (s, 1H), 8.84 (s, 1H), 8.66 (s, 1H), 8.63 (s, 1H), 8.41 (s, 1H), 8.25 (s, 1H), 7.98 (s, 1H), 7.90 (s, 1H), 7.78 (s, 1H), 7.61 (s, 1H), 6.12 (s, 1H), 5.68 (s, 2H), 4.38 (d, 2H), 4.34 (s, 2H), 2.50 (s, 3H), 2.29 (s, 3H), 2.21 (s, 3H).

Example 78: Preparation of 6-((4-(((3-chloro-6-fluoro-1H-indol-5-yl)methyl)carbamoyl)pyridin-2-yl)methyl)-3-methylquinoline-8-carboxamide

Example 79: Preparation of 6-((4-(((1-aminoisoquinolin-6-yl)methyl)carbamoyl)pyridin-2-yl)methyl)-3-methylquinoline-8-carboxamide

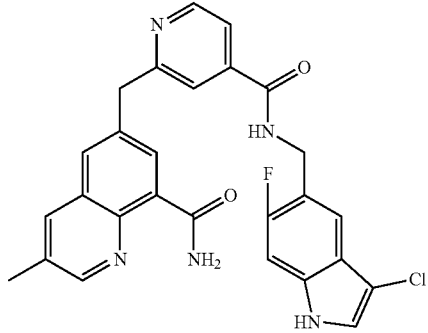

6-((4-(((3-chloro-6-fluoro-1H-indol-5-yl)methyl)carbamoyl)pyridin-2-yl)methyl)-3-methylquinoline-8-carboxamide

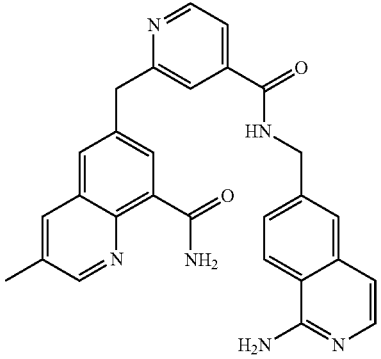

6-((4-(((1-aminoisoquinolin-6-yl)methyl)carbamoyl)pyridin-2-yl)methyl)-3-methylquinoline-8-carboxamide

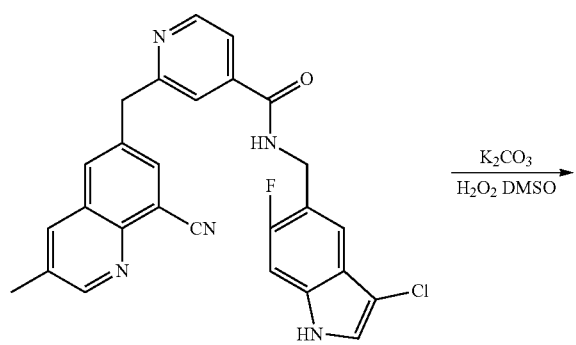

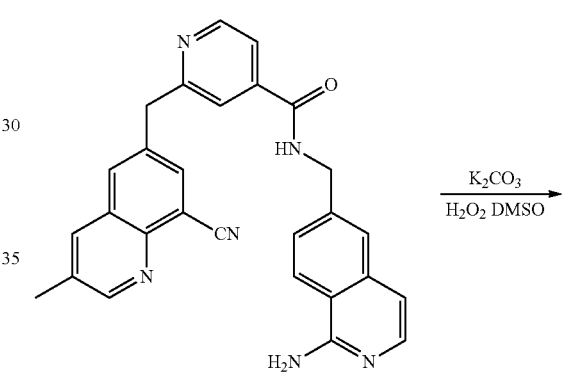

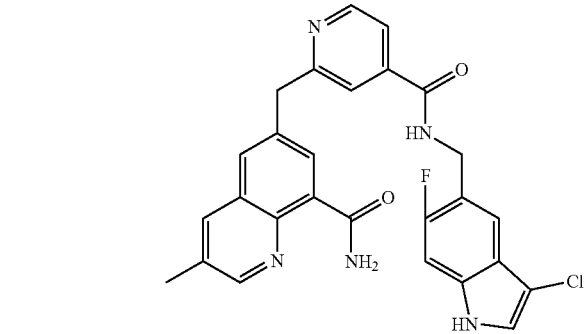

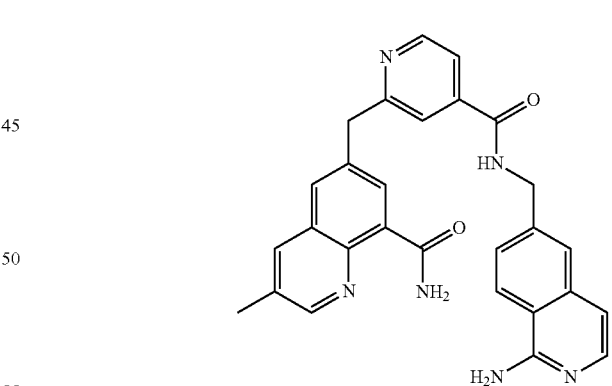

6-((4-(((3-chloro-6-fluoro-1H-indol-5-yl)methyl)carbamoyl)pyridin-2-yl)methyl)-3-methylquinoline-8-carboxamide (40 mg, 32%) was prepared as described for 6-((4-(((6-amino-2,4-dimethylpyridin-3-yl)methyl)carbamoyl)pyridin-2-yl)methyl)-3-methylquinoline-8-carboxamide (Example 77) as a off-white solid. LRMS (M+H$^+$) m/z calculated 502.1. found 501.8. $^1$H NMR (DMSO-d$_6$, 400 MHz) δ 11.44 (s, 1H), 10.28 (d, 1H), 9.31 (t, 1H), 8.89 (s, 1H), 8.71 (d, 1H), 8.48 (s, 1H), 8.28 (s, 1H), 8.02 (s, 1H), 7.93 (s, 1H), 7.86 (s, 1H), 7.72 (d, 1H), 7.55 (d, 1H), 7.50 (d, 1H), 7.29 (d, 1H), 4.64 (d, 2H), 4.45 (s, 2H), 2.54 (s, 3H).

6-((4-(((1-Aminoisoquinolin-6-yl)methyl)carbamoyl)pyridin-2-yl)methyl)-3-methylquinoline-8-carboxamide (35 mg, 48%) was prepared as described for 6-((4-(((6-amino-2,4-dimethylpyridin-3-yl)methyl)carbamoyl)pyridin-2-yl)methyl)-3-methylquinoline-8-carboxamide (Example 77) as a white solid. LRMS (M+H$^+$) m/z calculated 477.2. found 476.9. $^1$H NMR (DMSO-d$_6$, 400 MHz) δ 10.22 (s, 1H), 9.40 (t, 1H), 8.85 (d, 1H), 8.68 (d, 1H), 8.43 (s, 1H), 8.26 (s, 1H), 8.15 (d, 1H), 8.00 (s, 1H), 7.89 (d, 1H), 7.76 (d, 1H), 7.70 (d, 1H), 7.56 (s, 1H), 7.42 (d, 2H), 6.86 (d, 1H), 6.76 (s, 2H), 4.62 (d, 2H), 4.42 (s, 2H), 2.50 (s, 3H).

Example 80: Preparation of 6-((4-(((3-chloro-1H-pyrrolo[2,3-b]pyridin-5-yl)methyl)carbamoyl)pyridin-2-yl)methyl)-3-methylquinoline-8-carboxamide

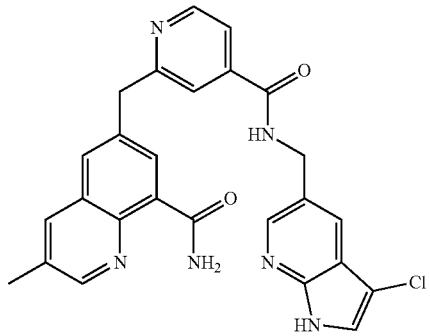

6-((4-(((3-chloro-1H-pyrrolo[2,3-b]pyridin-5-yl)methyl)carbamoyl)pyridin-2-yl)methyl)-3-methylquinoline-8-carboxamide

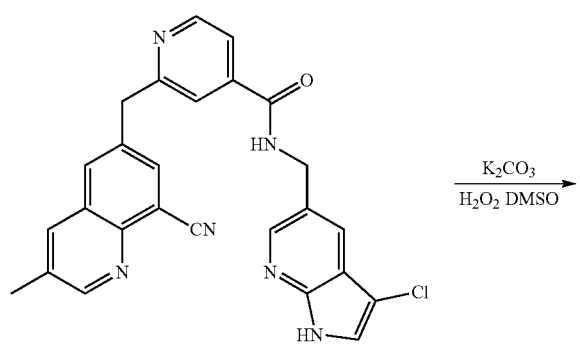

6-((4-(((3-Chloro-1H-pyrrolo[2,3-b]pyridin-5-yl)methyl)carbamoyl)pyridin-2-yl)methyl)-3-methylquinoline-8-carboxamide (20 mg, 38%) was prepared as described for 6-((4-(((6-amino-2,4-dimethylpyridin-3-yl)methyl)carbamoyl)pyridin-2-yl)methyl)-3-methylquinoline-8-carboxamide (Example 77) as a white solid. LRMS (M+H$^+$) m/z calculated 485.1. found 484.8. $^1$H NMR (DMSO-d$_6$, 400 MHz) δ 10.23 (s, 1H), 9.36 (t, 1H), 8.84 (d, 1H), 8.66 (d, 1H), 8.43 (d, 1H), 8.31 (d, 1H), 8.24 (s, 1H), 7.98 (d, 1H), 7.88 (s, 2H), 7.80 (s, 1H), 7.67 (s, 1H), 7.66 (d, 1H), 4.60 (d, 2H), 4.40 (s, 2H), 2.51 (s, 3H).

Example 81: Preparation of 6-((4-(((3-chloro-4-fluoro-1H-indol-5-yl)methyl)carbamoyl)pyridin-2-yl)methyl)-3-methylquinoline-8-carboxamide

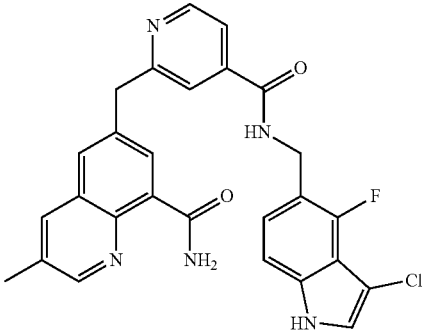

6-((4-(((3-chloro-4-fluoro-1H-indol-5-yl)methyl)carbamoyl)pyridin-2-yl)methyl)-3-methylquinoline-8-carboxamide

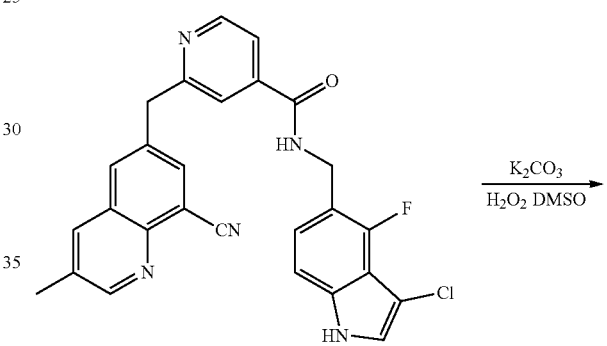

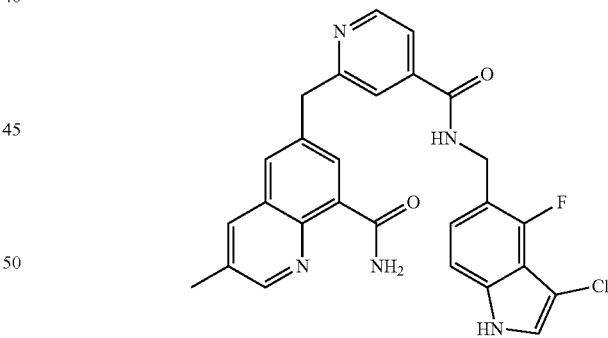

6-((4-(((3-Chloro-4-fluoro-1H-indol-5-yl)methyl)carbamoyl)pyridin-2-yl)methyl)-3-methylquinoline-8-carboxamide (30 mg, 41%) was prepared as described for 6-((4-(((6-amino-2,4-dimethylpyridin-3-yl)methyl)carbamoyl)pyridin-2-yl)methyl)-3-methylquinoline-8-carboxamide (Example 77) as a white solid. LRMS (M+H+) m/z calculated 502.1. found 501.8. $^1$H NMR (DMSO-d$_6$, 400 MHz) δ 11.59 (s, 1H), 10.23 (s, 1H), 9.26 (t, 1H), 8.85 (d, 1H), 8.65 (d, 1H), 8.42 (d, 1H), 8.25 (s, 1H), 7.98 (d, 1H), 7.88 (d, 1H), 7.80 (s, 1H), 7.66 (d, 1H), 7.51 (d, 1H), 7.21 (d, 1H), 7.16 (d, 1H), 4.58 (d, 2H), 4.40 (s, 2H), 2.51 (s, 3H).

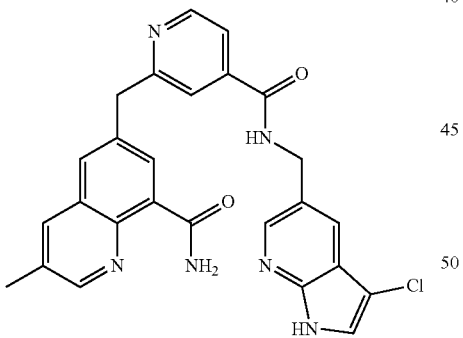

Example 82: Preparation of 6-((4-(((5-chloro-1H-indazol-3-yl)methyl)carbamoyl)pyridin-2-yl)methyl)-3-methylquinoline-8-carboxamide

Example 83: Preparation of 6-((4-(((6-fluoro-1H-indol-5-yl)methyl)carbamoyl)pyridin-2-yl)methyl)-3-methylquinoline-8-carboxamide

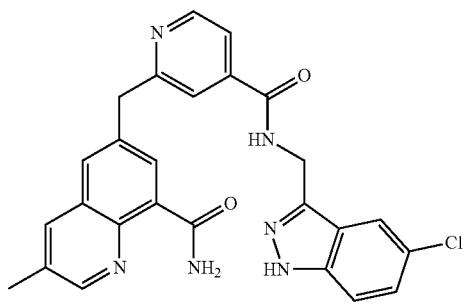

6-((4-(((5-chloro-1H-indazol-3-yl)methyl)carbamoyl)pyridin-2-yl)methyl)-3-methylquinoline-8-carboxamide

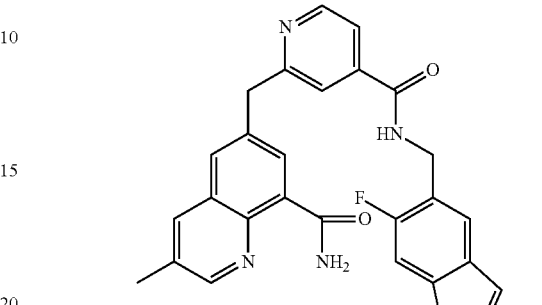

6-((4-(((6-fluoro-1H-indol-5-yl)methyl)carbamoyl)pyridin-2-yl)methyl)-3-methylquinoline-8-carboxamide

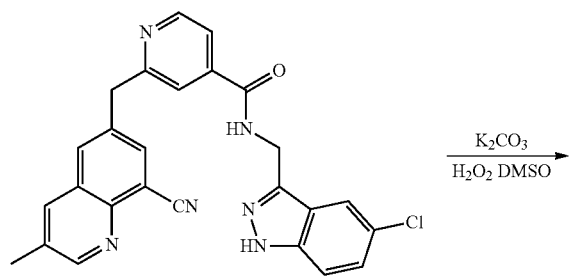

$\xrightarrow{\text{K}_2\text{CO}_3}{\text{H}_2\text{O}_2 \text{ DMSO}}$

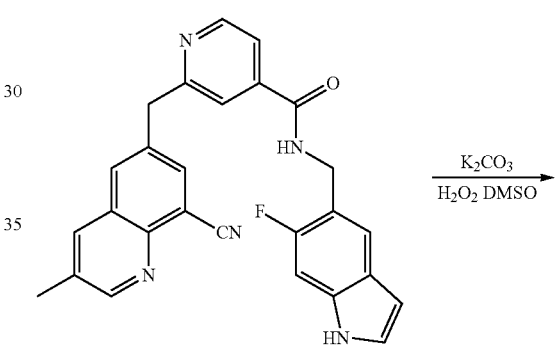

$\xrightarrow{\text{K}_2\text{CO}_3}{\text{H}_2\text{O}_2 \text{ DMSO}}$

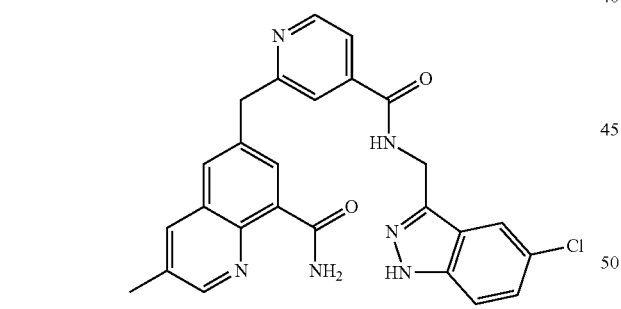

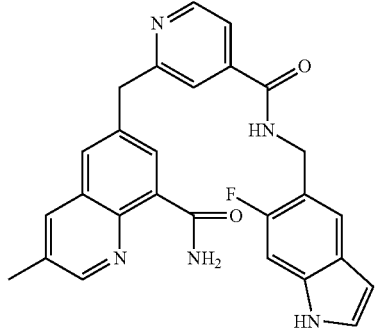

6-((4-(((5-Chloro-1H-indazol-3-yl)methyl)carbamoyl)pyridin-2-yl)methyl)-3-methylquinoline-8-carboxamide (20 mg, 48%) was prepared as described for 6-((4-(((6-amino-2,4-dimethylpyridin-3-yl)methyl)carbamoyl)pyridin-2-yl)methyl)-3-methylquinoline-8-carboxamide (Example 77) as a white solid. LRMS (M+H+) m/z calculated 485.1. found 484.8. $^1$H NMR (DMSO-$d_6$, 400 MHz) δ 13.08 (s, 1H), 10.21 (s, 1H), 9.39 (s, 1H), 8.84 (s, 1H), 8.65 (d, 1H), 8.42 (s, 1H), 8.25 (s, 1H), 7.97 (s, 1H), 7.89 (s, 2H), 7.80 (s, 1H), 7.64 (d, 1H), 7.53 (d, 1H), 7.34 (d, 1H), 4.78 (d, 2H), 4.39 (s, 2H), 2.50 (s, 3H).

6-((4-(((6-fluoro-1H-indol-5-yl)methyl)carbamoyl)pyridin-2-yl)methyl)-3-methylquinoline-8-carboxamide (20 mg, 35%) was prepared as described for 6-((4-(((6-amino-2,4-dimethylpyridin-3-yl)methyl)carbamoyl)pyridin-2-yl)methyl)-3-methylquinoline-8-carboxamide (Example 77) as a white solid. LRMS (M+H+) m/z calculated 468.2. found 467.8. $^1$H NMR (DMSO-$d_6$, 400 MHz) δ 11.11 (s, 1H), 10.23 (s, 1H), 9.23 (t, 1H), 8.84 (s, 1H), 8.66 (d, 1H), 8.44 (s, 1H), 8.26 (s, 1H), 7.99 (s, 1H), 7.90 (s, 1H), 7.83 (s, 1H), 7.69 (d, 1H), 7.51 (d, 1H), 7.18 (s, 1H), 7.18 (d, 1H), 6.40 (s, 1H), 4.57 (d, 2H), 4.41 (s, 2H), 2.51 (s, 3H).

Example 84: Preparation of 6-((4-(((6-amino-2,4-dimethylpyridin-3-yl)methyl)carbamoyl)pyridin-2-yl)methyl)-3-methylquinoline-8-carboxylic acid

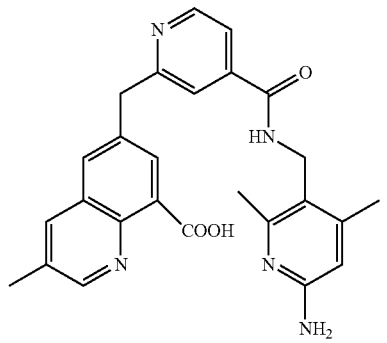

6-((4-(((6-amino-2,4-dimethylpyridin-3-yl)methyl)carbamoyl)pyridin-2-yl)methyl-3-methylquinoline-8-carboxylic acid Step 1: Preparation of methyl 6-((4-(methoxycarbonyl)pyridin-2-yl)methyl)-3-methylquinoline-8-carboxylate

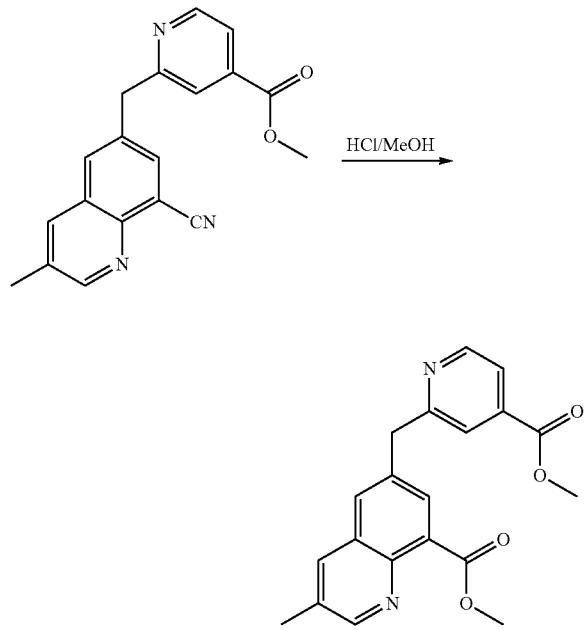

A mixture of methyl 2-((8-cyano-3-methylquinolin-6-yl)methyl)isonicotinate (500 mg, 1.58 mmol, 1 eq) in HCl/MeOH (10 M, 25 mL) was heated under reflux for one week. After cooling to rt, solvent was removed by evaporation. The residue was diluted with DCM and washed with sat. NaHCO₃. The organic phase was separated, dried and concentrated. The residue was purified by chromatography on silica gel column (EtOAc/PE=2/1, v/v) to give methyl 6-((4-(methoxycarbonyl)pyridin-2-yl)methyl)-3-methylquinoline-8-carboxylate (100 mg, 18%) as a yellow solid.

Step 2: Preparation of 6-((4-(((6-amino-2,4-dimethylpyridin-3-yl)methyl)carbamoyl)pyridin-2-yl)methyl)-3-methylquinoline-8-carboxylic acid

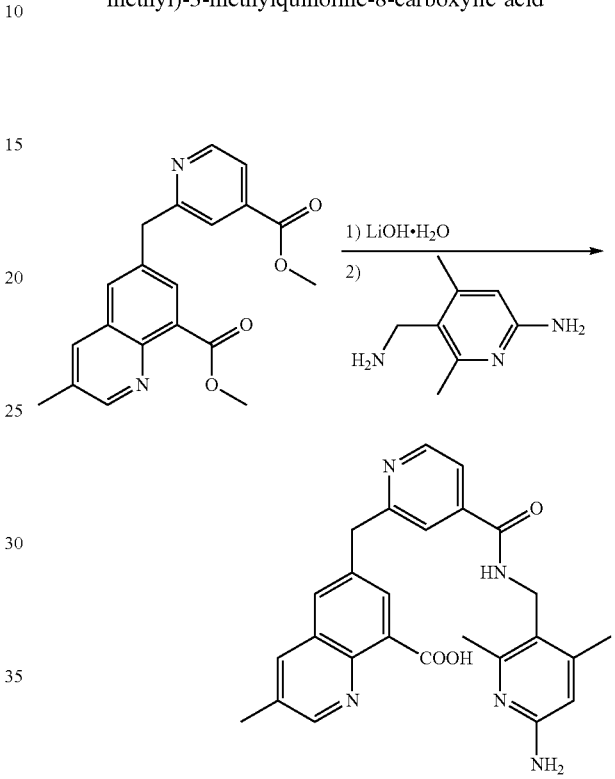

To a solution of methyl 6-((4-(methoxycarbonyl)pyridin-2-yl)methyl)-3-methylquinoline-8-carboxylate (100 mg, 0.31 mmol, 1.0 eq) in THF/H₂O (5 mL, 1:1) was added LiOH.H₂O (39 mg, 0.93 mmol, 3 eq). The mixture was stirred at rt for 5 h and then concentrated. To a solution of the above crude product and 5-aminomethyl-4,6-dimethylpyridin-2-ylamine hydrochloride (88 mg, 0.47 mmol, 1.5 eq) in DMF (5 mL) was added HATU (188 mg, 0.50 mmol, 1.5 eq) and Et₃N (134 mg, 1.32 mmol, 4 eq). The mixture was stirred at rt for 2 h and diluted with water. The organic layer was separated and the aqueous layer was extracted with DCM, the combined extracts were dried and concentrated. The residue was purified by prep-HPLC to give 6-((4-(((6-amino-2,4-dimethylpyridin-3-yl)methyl)carbamoyl)pyridin-2-yl)methyl)-3-methylquinoline-8-carboxylic acid (2 mg, 1.4% for 2 steps) as an off-white solid. LRMS (M+H⁺) m/z calculated 456.2. found 455.9.

¹H NMR (CD₃OD, 400 MHz) δ 8.80 (s, 1H), 8.60 (d, 1H), 8.33 (s, 1H), 8.27 (s, 1H), 7.99 (s, 1H), 7.73 (s, 1H), 7.31 (d, 1H), 6.32 (s, 1H), 4.49 (s, 2H), 4.43 (s, 2H), 2.57 (s, 3H), 2.39 (s, 3H), 2.26 (s, 3H).

Example 85

Preparation of N-((6-amino-4-methylpyridin-3-yl)methyl)-2-((7-chloro-3-oxoisoquinolin-2(3H)-yl)methyl)isonicotinamide

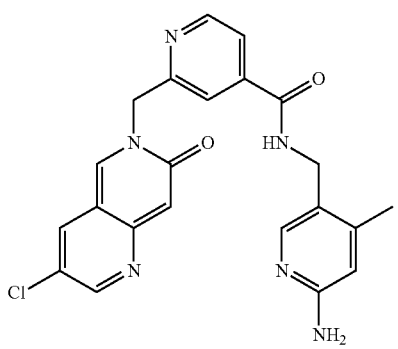

N-((6-amino-4-methylpyridin-3-yl)methyl)-2-((7-chloro-3-oxoisoqiunolin-2(3H)-yl)methyl)isonicotinamide Step 1: Preparation of dimethoxy-acetic acid

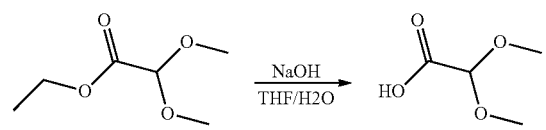

To a solution of ethyl 2,2-dimethoxyacetate (30 g, 170 mmol, 1.0 eq) in THF (100 mL) and H₂O (100 mL) was added NaOH (8.2 g, 205 mmol, 1.2 eq). The mixture was stirred at rt for 2 h. Then it was acidified by 1 N HCl to PH=6 and extracted by EtOAc. The organic layer was concentrated to afford dimethoxy-acetic acid (15 g, 59%) as a yellow oil.

Step 2: Preparation of N-(3-chloro-benzyl)-2,2-dimethoxy-acetamide

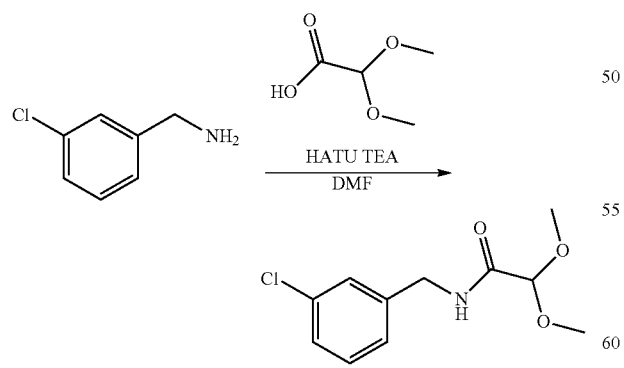

To a solution of dimethoxy-acetic acid (15 g, 100 mmol, 1.1 eq) and 3-chloro-benzylamine (13 g, 92 mmol, 1.0 eq) in DMF (200 mL) was added HATU (40 g, 100 mmol, 1.1 eq) and Et₃N (38 mL, 300 mmol, 3 eq). The mixture was stirred at rt overnight. Then EtOAc and water was added, the organic layer was concentrated and the residue was purified by chromatography on a silica gel column (PE/EtOAc=10/1-1/1, v/v) to give N-(3-chloro-benzyl)-2,2-dimethoxy-acetamide (13.5 g, 50%) as a yellow oil.

Step 3: Preparation of 2-(3-chloro-8-cyano-quinolin-6-ylmethyl)-isonicotinic acid

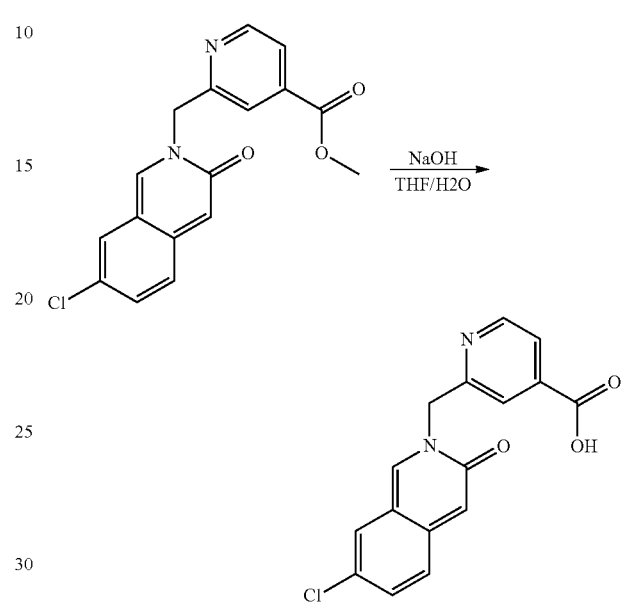

To a solution of methyl 2-((7-chloro-3-oxoisoquinolin-2(3H)-yl)methyl)isonicotinate (350 mg, 1.1 mmol, 1.0 eq) in THF (5 mL) and H₂O (5 mL) was added NaOH (51 mg, 1.3 mmol, 1.2 eq). The mixture was stirred at rt for 2 h. Then it was acidified by 1 N HCl to PH=6 and extracted by EtOAc. The organic layer was concentrated to afford 2-(3-chloro-8-cyano-quinolin-6-ylmethyl)-isonicotinic acid (320 mg, 91%) as a white solid.

Step 4: Preparation of N-((6-amino-4-methylpyridin-3-yl)methyl)-2-((7-chloro-3-oxoisoquinolin-2(3H)-yl)methyl)isonicotinamide

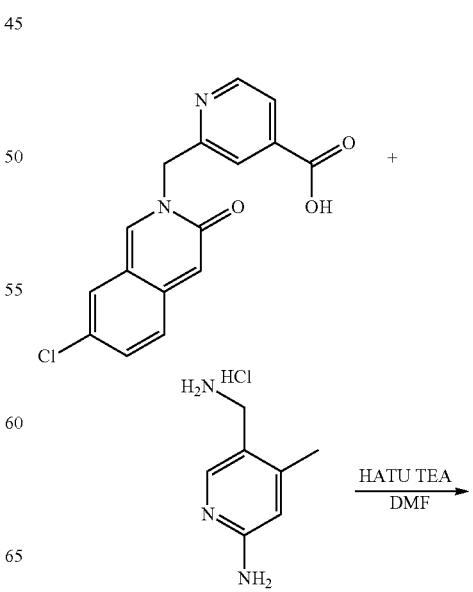

-continued

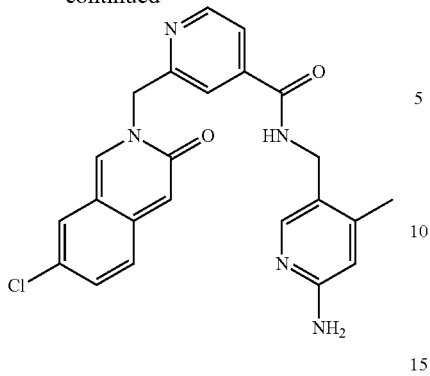

To a solution of 2-(7-chloro-3-oxo-3H-isoquinolin-2-yl-methyl)-isonicotinic acid (50 mg, 0.16 mmol, 1.0 eq) and 5-aminomethyl-4-methyl-pyridin-2-ylamine hydrochloride (57 mg, 0.33 mmol, 2.0 eq) in DMF (10 mL) was added HATU (73 mg, 0.19 mmol, 1.2 eq) and Et$_3$N (1.0 mL, 7.1 mmol, 44 eq). The mixture was stirred at rt for overnight, then EtOAc and water was added. The organic layer was concentrated and the residue was purified by pre-HPLC to give N-((6-amino-4-methylpyridin-3-yl)methyl)-2-((7-chloro-3-oxoisoquinolin-2(3H)-yl)methyl)isonicotinamide (25 mg, 36%) as white solid. LRMS (M+H$^+$) m/z calculated 434.1. found 434.0.

$^1$H NMR (DMSO-d$_6$, 400 MHz) δ 9.05 (s, 1H), 9.88-9.90 (t, 1H), 8.68-8.69 (d, 1H), 8.88-8.93 (m, 1H), 7.77 (s, 1H), 7.67-7.72 (m, 3H), 7.41 (d, 1H), 6.25 (s, 1H), 5.76 (s, 2H), 5.57 (s, 2H), 4.29-4.30 (d, 2H), 2.13 (s, 3H).

Example 86: Preparation of N-((6-amino-2-methyl-pyridin-3-yl)methyl)-2-((7-chloro-3-oxoisoquinolin-2(3H)-yl)methyl)isonicotinamide

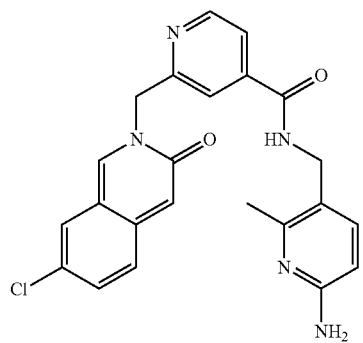

N-((6-amino-2-methylpyridin-3-yl)methyl)-2-((7-chloro-3-oxoisoquinolin-2(3H)-yl)methyl)isonicotinamide

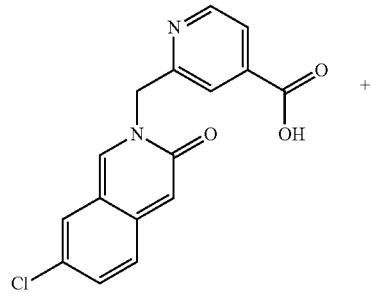

+

-continued

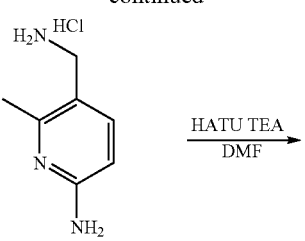

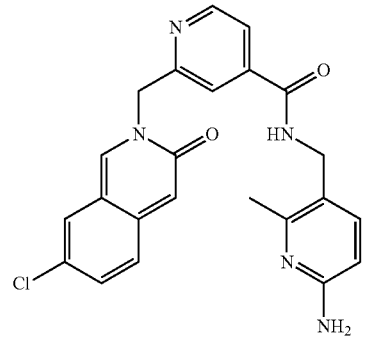

N-((6-amino-2-methylpyridin-3-yl)methyl)-2-((7-chloro-3-oxoisoquinolin-2(3H)-yl)methyl)isonicotinamide (27 mg, 37%) was prepared as described for N-((6-amino-4-methyl-pyridin-3-yl)methyl)-2-((7-chloro-3-oxoisoquinolin-2(3H)-yl)methyl)isonicotinamide (Example 85) as white solid. LRMS (M+H$^+$) m/z calculated 434.1. found 434.0.

$^1$H NMR (DMSO-d$_6$, 400 MHz) δ 9.05-9.07 (t, 1H), 9.04 (s, 1H), 8.69-8.70 (t, 1H), 8.17 (d, 1H), 7.90-7.92 (m, 1H), 7.67-7.63 (m, 2H), 7.41 (s, 3H), 7.23-7.26 (d, 1H), 6.22-6.24 (d, 1H), 5.76 (s, 1H), 5.57 (s, 2H), 4.28-4.30 (d, 2H), 2.27 (s, 3H).

Example 87: Preparation of N-((6-amino-2,4-dimethylpyridin-3-yl)methyl)-2-((7-chloro-3-oxoisoquinolin-2(3H)-yl)methyl)isonicotinamide

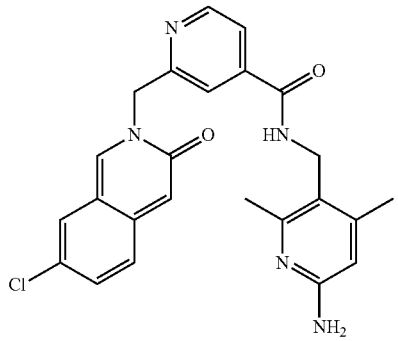

N-((6-amino-2,4-dimethylpyridin-3-yl)methyl)-2-((7-chloro-3-oxoisoquinolin-2(3H)-yl)methyl)isonicotinamide 333
-continued

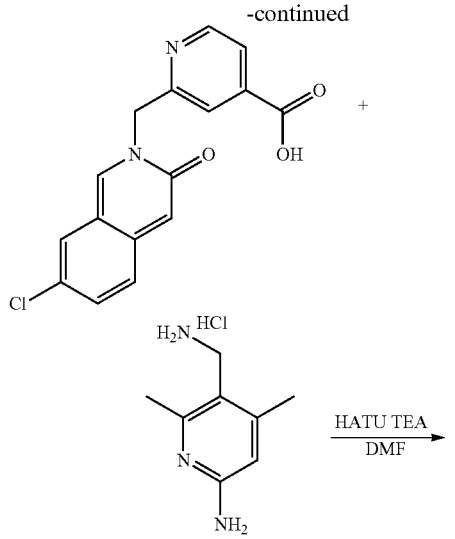

334
-continued

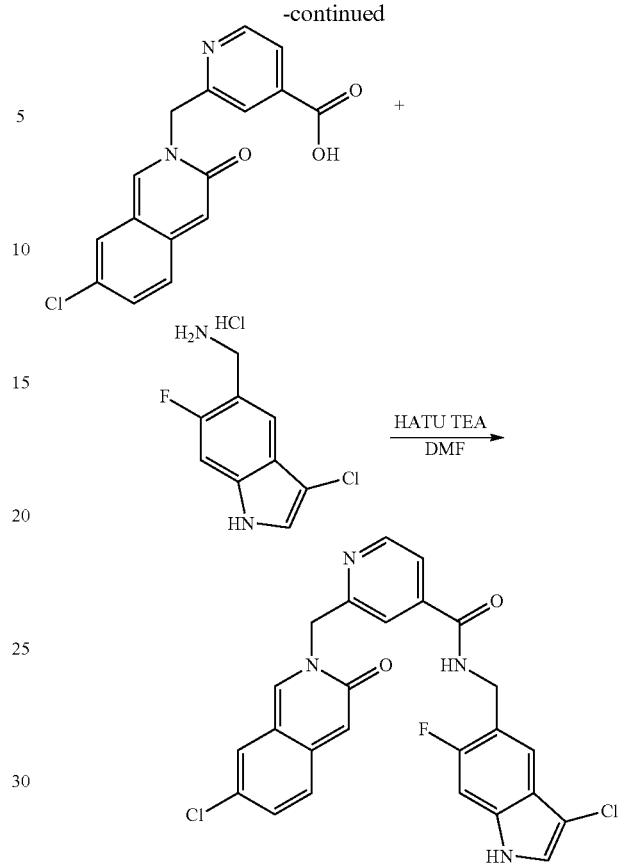

N-((6-amino-2,4-dimethylpyridin-3-yl)methyl)-2-((7-chloro-3-oxoisoquinolin-2(3H)-yl)methyl)isonicotinamide (30 mg, 42%) was prepared as described for N-((6-amino-4-methylpyridin-3-yl)methyl)-2-((7-chloro-3-oxoisoquinolin-2(3H)-yl)methyl)isonicotinamide (Example 85) as white solid. LRMS (M+H⁺) m/z calculated 448.1. found 448.0.
¹H NMR (DMSO-d₆, 400 MHz) δ 9.04 (s, 1H), 8.71-8.73 (t, 1H), 8.66-8.68 (d, 1H), 8.17-8.18 (d, 1H), 7.87-7.92 (m, 2H), 7.67-7.70 (m, 2H), 7.40 (s, 1H), 6.11 (s, 1H), 5.70 (s, 2H), 5.56 (s, 2H), 4.33-4.34 (d, 2H), 2.29 (s, 3H), 2.15 (s, 3H).

Example 88: Preparation of 2-((7-chloro-3-oxoisoquinolin-2(3H)-yl)methyl)-N-((3-chloro-6-fluoro-1H-indol-5-yl)methyl)isonicotinamide 2-((7-Chloro-3-oxoisoquinolin-2(3H)-yl)methyl)-N-((3-chloro-6-fluoro-1H-indol-5-yl)methyl)isonicotinamide (55 mg, 70%) was prepared as described for N-((6-amino-4-methylpyridin-3-yl)methyl)-2-((7-chloro-3-oxoisoquinolin-2(3H)-yl)methyl)isonicotinamide (Example 85) as white solid. LRMS (M+H⁺) m/z calculated 495.1. found 495.0.
¹H NMR (DMSO-d₆, 400 MHz) δ 11.40 (s, 1H), 9.33-9.35 (t, 1H), 9.04 (s, 1H), 8.72-8.73 (d, 1H), 8.17 (s, 1H), 8.89-8.94 (m, 2H), 7.69-7.70 (d, 1H), 7.66-7.67 (d, 1H), 7.50-7.51 (d, 1H), 7.24-7.45 (m, 2H), 7.21-7.24 (d, 1H), 5.59 (D, 2H), 4.58-4.60 (d, 2H).

Example 89: Preparation of N-(6-amino-2-methyl-pyridin-3-ylmethyl)-2-(3-chloro-quinolin-6-ylmethyl)-isonicotinamide

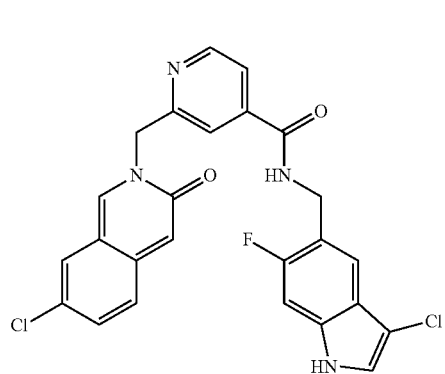

2-((7-chloro-3-oxoisoquinolin-2(3H)-yl)methyl)-N-((3-chloro-6-fluoro-1H-indol-5-yl)methyl)isonicotinamide

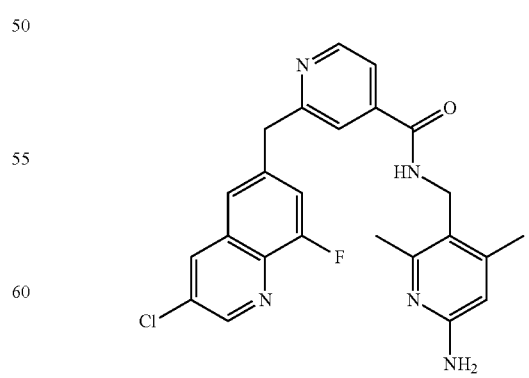

N-(6-Amino-2,4-dimethyl-pyridin-3-ylmethyl)-2-(3-chloro-8-fluoro-quinolin-6-ylmethyl)-isonicotinamide

Step 1: Preparation of methyl 8-fluoroquinoline-6-carboxylate

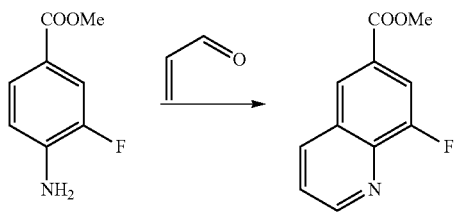

A mixture of methyl 4-amino-3-fluorobenzoate (35 g, 0.207 mmol, 1 eq), acrolein (17.4 g, 0.311 mol, 1.5 eq) and 6 N HCl (600 mL) was stirred at 100° C. for 10 min. Then the mixture was cooled and adjusted to pH ~5-6 using NaHCO₃ (aq). The mixture was extracted with DCM. The combined organic layers were washed with brine, dried over MgSO₄, filtered then concentrated and purified by column chromatography (EtOAc/PE=1/20, v/v) to give methyl 8-fluoroquinoline-6-carboxylate (11 g, 21%) as a yellow solid.

Step 2: Preparation of methyl 3-chloro-8-fluoroquinoline-6-carboxylate

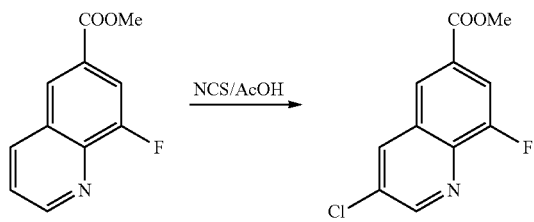 [SMILES: COC(=O)c1cc(F)c2ncccc2c1 ; COC(=O)c1cc(F)c2ncc(Cl)cc2c1]

To a solution of methyl 8-fluoroquinoline-6-carboxylate (11 g, 53.7 mmol, 1 eq) in DMF was added NCS (21.4 g, 0.161 mol, 3 eq). The reaction mixture was stirred at 120° C. overnight. The reaction mixture was allowed to cool to ambient temperature, treated with water, neutralized with solid NaHCO₃ and further stirred at rt for 30 min. Finally, powdered sodium thiosulfate was carefully added to remove excess of NCS. The mixture was extracted with EtOAc. The organic layer was dried and concentrated under vacuum. The crude product was purified by flash-chromatography on silica gel to afford methyl 3-chloro-8-fluoroquinoline-6-carboxylate (11.5 g, 90%) as a yellow solid.

Step 3: Preparation of (3-chloro-8-fluoro-quinolin-6-yl)-methanol

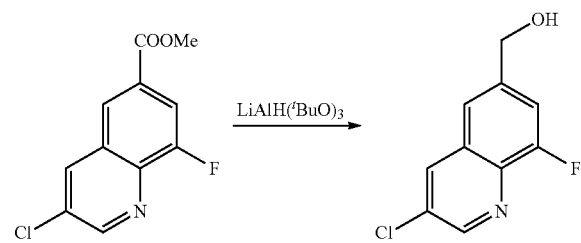 [SMILES: COC(=O)c1cc(F)c2ncc(Cl)cc2c1 ; OCc1cc(F)c2ncc(Cl)cc2c1]

To a solution of methyl 3-chloro-8-fluoroquinoline-6-carboxylate (4.5 g, 18.8 mmol, 1 eq) was added LiAlH(t-BuO)₃ (12.0 g, 47.1 mmol, 2.5 eq). The resulting mixture was stirred at 40° C. for 12 h and then quenched by the addition of water. The mixture was extracted with EtOAc. The combined extracts were dried and concentrated. The residue was purified by silica gel chromatography (PE/EtOAc=2/1, v/v) to afford (3-chloro-8-fluoro-quinolin-6-yl)-methanol (2.1 g, 53%) as a yellow solid.

Step 4: Preparation of 3-chloro-6-chloromethyl-8-fluoro-quinoline

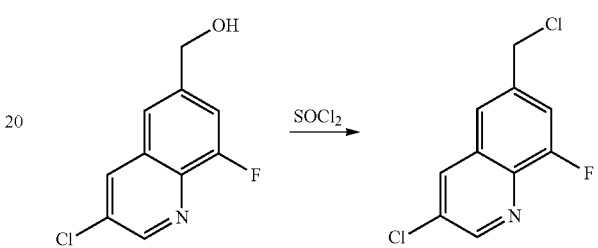

A mixture of 3-chloro-8-fluoro-6-hydroxymethyl-quinoline (2.1 g, 9.95 mmol, 1.0 eq) in SOCl₂ (50 mL) was stirred at rt for 1 h and concentrated. The residue was dissolved in DCM and treated with sat. NaHCO₃ solution to give 3-chloro-6-chloromethyl-8-fluoro-quinoline (2.2 g, 96%) as a yellow solid.

Step 5: Preparation of methyl 2-((3-chloro-8-fluoro-quinolin-6-yl)methyl)isonicotinate

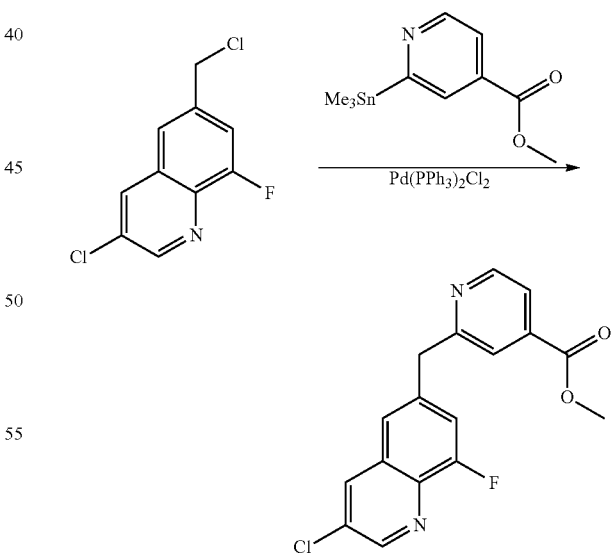

To a solution of 3-chloro-6-chloromethyl-8-fluoro-quinoline (2.2 g, 9.61 mmol, 1.0 eq) in dioxane (60 mL) was added methyl 2-(trimethylstannyl)isonicotinate (3.18 g, 10.6 mmol, 1.1 eq) and Pd(PPh₃)₂Cl₂ (674 mg, 0.96 mmol, 0.1 eq). The mixture was stirred at 90° C. for 3 h under nitrogen atmosphere, concentrated and purified by silica gel chromatography (DCM/MeOH=200/1, v/v) to afford methyl 2-((3-chloro-8-fluoroquinolin-6-yl)methyl)isonicotinate (1.6 g, 50%) as a yellow solid.

Step 6: Preparation of 2-((3-chloro-8-fluoroquinolin-6-yl)methyl)isonicotinic acid

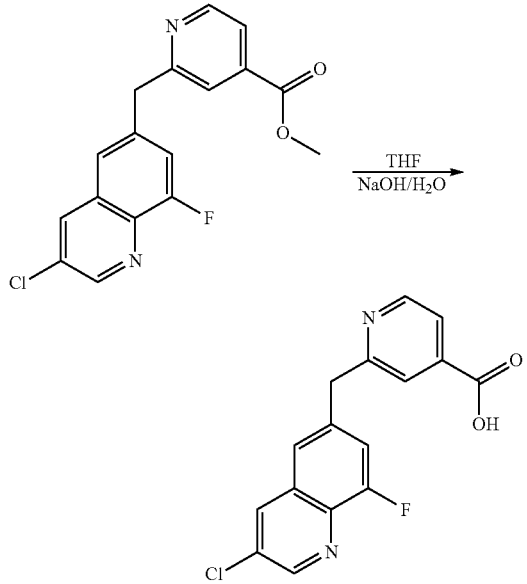

To a solution of methyl 2-((3-chloro-8-fluoroquinolin-6-yl)methyl)isonicotinate (800 mg, 2.4 mmol, 1 eq) in THF (20 ml)/water (10 ml) was added NaOH (116 mg, 0.29 mmol, 1.2 eq). The mixture was stirred at rt for 3 h. Then aqueous HCl (2 N) was added to the reaction mixture until pH 6-7. The mixture was extracted with EtOAc, and the organic layer was concentrated under pressure. The gray compound was directly used in next step (500 mg, 76%).

Step 7: Preparation of N-(6-amino-2,4-dimethyl-pyridin-3-ylmethyl)-2-(3-chloro-8-fluoro-quinolin-6-ylmethyl)-isonicotinamide

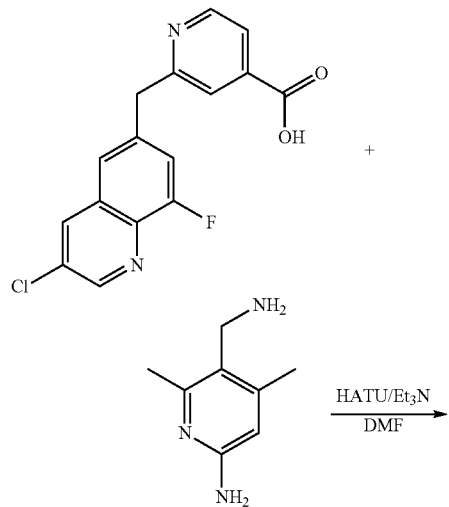

-continued

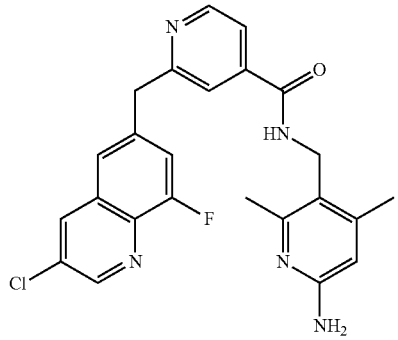

To a solution of 2-(3-chloro-quinolin-6-ylmethyl)-isonicotinic acid (100 mg, 0.3 mmol, 1 eq) in DMF (10 mL) was added 5-aminomethyl-4, 6-dimethyl-pyridin-2-ylamine (71 mg, 0.47 mmol, 1.5 eq), HATU (137 mg, 0.36 mmol, 1.2 eq) and Et₃N (1 mL). The mixture was stirred at rt for 3 h. Then it was quenched with water, extracted with DCM. The combined extracts were dried, concentrated, and the residue was purified by prep-HPLC to give N-(6-amino-2,4-dimethyl-pyridin-3-ylmethyl)-2-(3-chloro-8-fluoro-quinolin-6-ylmethyl)-isonicotinamide (39 mg, 29%) as a white solid. LRMS (M+H⁺) m/z calculated 450.1. found 449.8.

¹H NMR (DMSO-d6, 400 MHz) δ: 8.88 (d, 1H), 8.60-8.62 (m, 3H), 7.75 (s, 1H), 7.68 (s, 1H), 7.58-7.61 (m, 2H), 6.13 (s, 1H), 5.71 (s, 2H), 4.33 (s, 4H), 2.30 (s, 3H), 2.16 (s, 3H).

Example 90: Preparation of N-(3-chloro-6-fluoro-1H-indol-5-ylmethyl)-2-(3-chloro-8-fluoro-quinolin-6-ylmethyl)-isonicotinamide

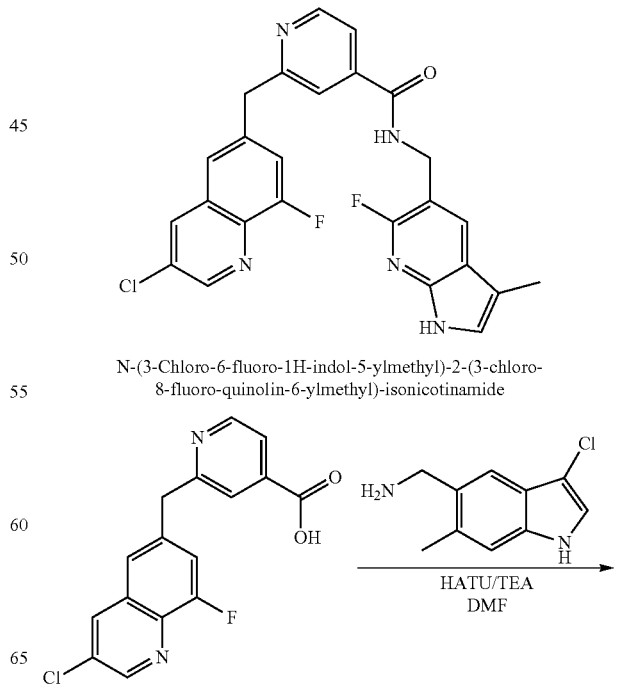

N-(3-Chloro-6-fluoro-1H-indol-5-ylmethyl)-2-(3-chloro-8-fluoro-quinolin-6-ylmethyl)-isonicotinamide

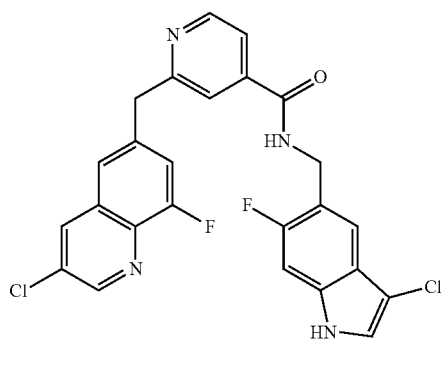

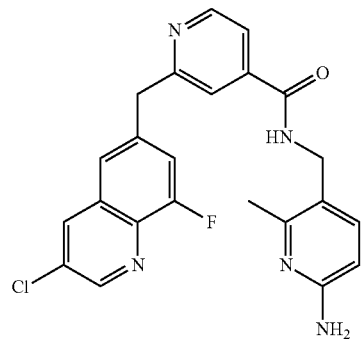

N-(3-chloro-6-fluoro-1H-indol-5-ylmethyl)-2-(3-chloro-8-fluoro-quinolin-6-ylmethyl)-isonicotinamide (47 mg, 20%) was prepared as described for N-(6-amino-2,4-dimethyl-pyridin-3-ylmethyl)-2-(3-chloro-8-fluoro-quinolin-6-ylmethyl)-isonicotinamide (Example 89) as a white solid; LRMS (M+H+) m/z calculated 497.1. found 497.7.

$^1$H NMR (DMSO-d6, 400 MHz) δ 11.38 (s, 1H), 9.23 (s, 1H), 8.88 (s, 1H), 8.61-8.66 (m, 2H), 7.80 (s, 1H), 7.59-7.69 (m, 3H), 7.43-7.50 (m, 2H), 7.20-7.23 (d, 1H), 4.57-4.59 (d, 2H), 4.36 (s, 2H).

Example 91: Preparation of N-(6-amino-2-methyl-pyridin-3-ylmethyl)-2-(3-chloro-8-fluoro-quinolin-6-ylmethyl)-isonicotinamide N-(6-amino-2-methyl-pyridin-3-ylmethyl)-2-(3-chloro-8-fluoro-quinolin-6-ylmethyl)-isonicotinamide (45 mg, 22%) was prepared as described for N-(6-amino-2,4-dimethyl-pyridin-3-ylmethyl)-2-(3-chloro-8-fluoro-quinolin-6-ylmethyl)-isonicotinamide (Example 89) as a white solid. LRMS (M+H+) m/z calculated 436.1. found 436.0.

$^1$H NMR (DMSO-d6, 400 MHz) δ 8.97 (s, 1H), 8.88 (s, 1H), 8.6-8.64 (m, 2H), 7.77 (s, 1H), 7.68 (s, 1H), 7.59-7.63 (m, 2H), 7.42 (d, 1H), 6.26 (d, 1H), 5.80 (d, 2H), 4.35 (s, 2H), 4.29 (d, 2H).

Example 92: Preparation of methyl 6-((4-(((6-amino-2,4-dimethylpyridin-3-yl)methyl)carbamoyl)pyridin-2-yl)methyl)-3-chloroquinoline-8-carboxylate

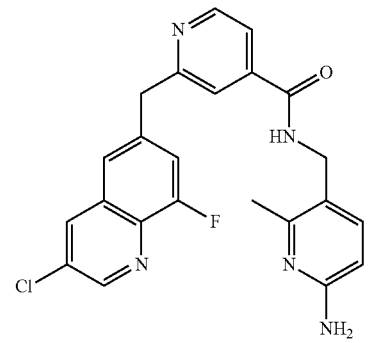

N-(6-Amino-2-methyl-pyridin-3-ylmethyl)-2-(3-chloro-8-fluoro-quinolin-6-ylmethyl)-isonicotinamide

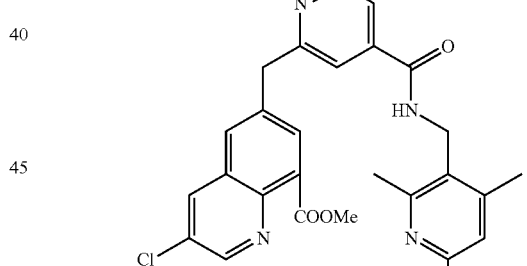

methyl 6-(((6-amino-2,4-dimethylpyridin-3-yl)methyl)carbamoyl)pyridin-2-yl)methyl)-3-chloroquinoline-8-carboxylate

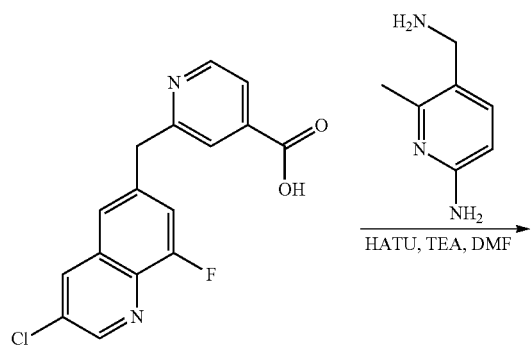

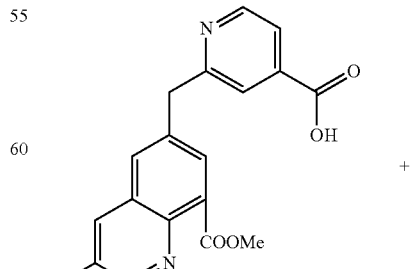

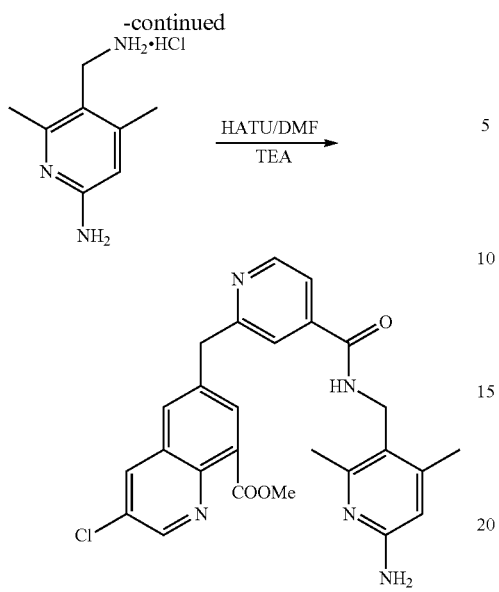

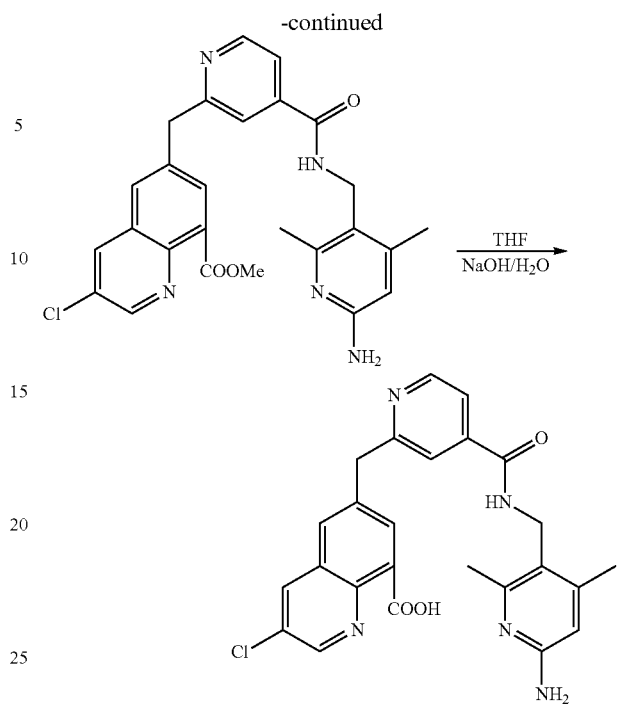

To a solution of 5-aminomethyl-4,6-dimethyl-pyridin-2-ylamine (95 mg, 0.43 mmol, 1.7 eq) in DMF (10 mL) was added 2-((3-chloro-8-(methoxycarbonyl)quinolin-6-yl)methyl)isonicotinic acid (90 mg, 0.25 mmol, 1 eq), HATU (123 mg, 0.32 mmol, 1.3 eq), and Et$_3$N (0.5 mL). The mixture was stirred at rt overnight. Then it was quenched with water, extracted with DCM. The combined extracts were dried, concentrated, and the residue was purified by column chromatography (DCM/MeOH=20/1, v/v) to give methyl 6-((4-(((6-amino-2,4-dimethylpyridin-3-yl)methyl) carbamoyl)pyridin-2-yl)methyl)-3-chloroquinoline-8-carboxylate (100 mg, 81.9%) as a yellow solid. LRMS (M+H$^+$) m/z calculated 490.2. found 490.1.

$^1$H NMR (DMSO-d6, 400 MHz) δ 8.89-8.90 (m, 1H), 8.59-8.63 (m, 3H), 8.00 (s, 1H), 7.91-7.92 (m, 1H), 7.77 (s, 1H), 7.60 (d, 1H), 6.15 (s, 1H), 4.37 (s, 2H), 4.33-4.34 (d, 2H), 3.88 (s, 3H), 2.31 (s, 3H), 2.18 (s, 3H).

Example 93: Preparation of 6-((4-(((6-amino-2,4-dimethylpyridin-3-yl)methyl)carbamoyl)pyridin-2-yl)methyl)-3-chloroquinoline-8-carboxylic acid

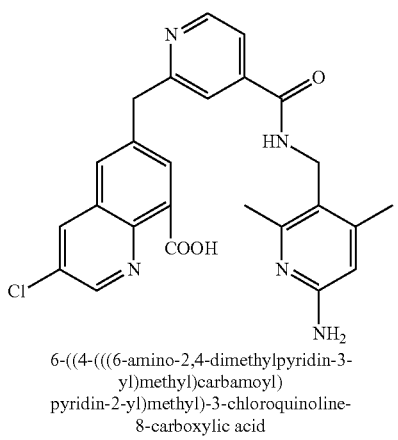

6-((4-(((6-amino-2,4-dimethylpyridin-3-yl)methyl)carbamoyl) pyridin-2-yl)methyl)-3-chloroquinoline-8-carboxylic acid To a solution of methyl 6-((4-((6-amino-2,4-dimethyl-pyridin-3-yl)methylcarbamoyl)pyridin-2-yl)methyl)-3-chloroquinoline-8-carboxylate (50 mg, 0.1 mmol, 1 eq) in THF (10 mL) was added a solution NaOH (4.9 mg, 0.12 mmol, 1.2 eq) in water (2 mL) and kept stirring at rt for 3 h. Then it was acidified to pH 5 with AcOH. The mixture was concentrated in vacuo and purified by a prep-HPLC to give 6-((4-(((6-amino-2,4-dimethylpyridin-3-yl)methyl)carbamoyl) pyridin-2-yl)methyl)-3-chloroquinoline-8-carboxylic acid (31.3 mg, 65.7%) as a gray solid. LRMS (M+H$^+$) m/z calculated 476.1. found 476.1.

$^1$H NMR (DMSO-d6, 400 MHz) δ 8.99 (s, 1H), 8.74 (s, 1H), 8.59-8.62 (m, 2H), 8.18 (s, 1H), 8.04 (s, 1H), 7.79 (s, 1H), 7.60 (d, 1H), 6.11 (s, 1H), 5.64 (s, 2H), 4.39 (s, 2H), 4.33 (d, 2H), 2.29 (s, 3H), 2.16 (s, 3H).

Example 94: Preparation of N-((6-amino-2,4-dimethylpyridin-3-yl)methyl)-2-((3-chloro-8-(hydroxymethyl)quinolin-6-yl)methyl)isonicotinamide

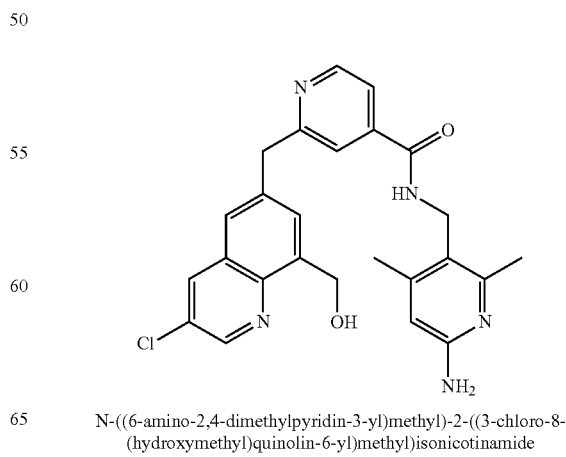

N-((6-amino-2,4-dimethylpyridin-3-yl)methyl)-2-((3-chloro-8-(hydroxymethyl)quinolin-6-yl)methyl)isonicotinamide

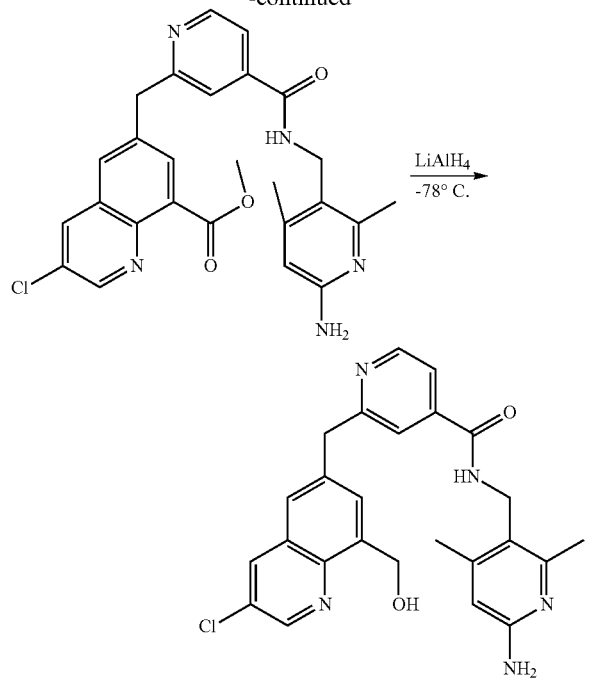

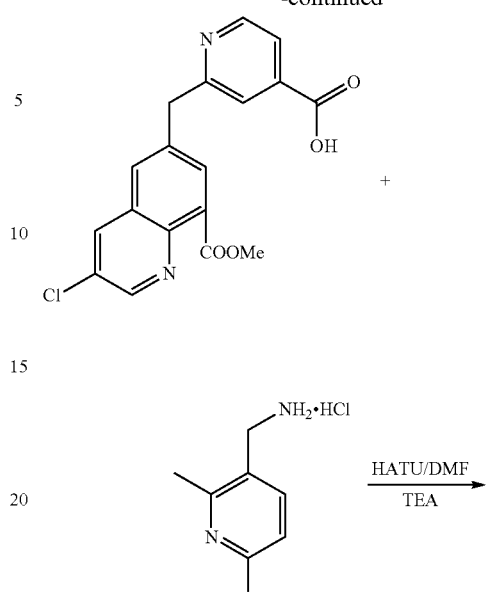

To a solution of methyl 6-((4-((6-amino-2,4-dimethyl-pyridin-3-yl)methylcarbamoyl)pyridin-2-yl)methyl)-3-chloroquinoline-8-carboxylate (100 mg, 0.2 mmol, 1 eq) in dry THF was added drop wise LiAlH$_4$ below −78° C. under N$_2$ over a period of 20 min. The reaction mixture was stirred for 5 h, and then it was quenched with potassium sodium tartrate and extracted with EtOAc. The combine extracts were dried, concentrated and the residue was purified by prep-HPLC to give N-((6-amino-2,4-dimethylpyridin-3-yl)methyl)-2-((3-chloro-8-(hydroxymethyl)quinolin-6-yl)methyl)isonicotinamide (6.5 mg, 7%) as a white solid. LRMS (M+H$^+$) m/z calculated 462.2. found 462.1.

$^1$H NMR (DMSO-d6, 400 MHz) δ 8.81 (d, 1H), 8.59-8.63 (m, 2H), 8.50 (d, 1H), 7.77 (s, 1H), 7.72 (d, 2H), 7.59 (d, 1H), 6.13 (s, 1H), 5.72 (s, 2H), 5.26-5.28 (t, 1H), 5.07 (d, 1H), 4.32-4.33 (m, 4H), 2.30 (s, 3H), 2.16 (s, 3H).

Example 95: Preparation of methyl 6-((4-(((6-amino-2-methylpyridin-3-yl)methyl)carbamoyl)pyridin-2-yl)methyl)-3-chloroquinoline-8-carboxylate

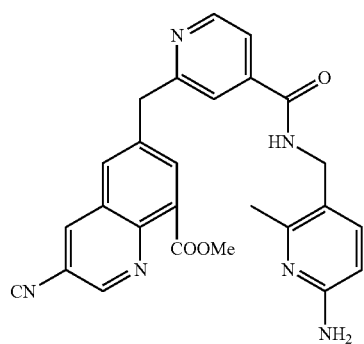

methyl 6-((4-(((6-amino-2-methylpyridin-3-yl)methyl)carbamoyl)pyridin-2-yl)methyl)-3-chloroquinoline-8-carboxylate To a solution of 5-aminomethyl-6-methyl-pyridin-2-ylamine (89 mg, 0.43 mmol, 1.7 eq) in DMF (10 mL) was added 2-((3-chloro-8-(methoxycarbonyl)quinolin-6-yl)methyl)isonicotinic acid (90 mg, 0.25 mmol, 1 eq), HATU (123 mg, 0.32 mmol, 1.3 eq), and Et$_3$N (0.5 mL). The mixture was stirred at rt overnight. Then it was quenched with water, extracted with DCM. The combined extracts were dried and concentrated, the residue was purified on a silica gel column (DCM/MeOH=20/1, v/v) to give methyl 6-((4-(((6-amino-2-methylpyridin-3-yl)methyl)carbamoyl)pyridin-2-yl)methyl)-3-chloroquinoline-8-carboxylate (100 mg, 84.7%) as a yellow solid. LRMS (M+H$^+$) m/z calculated 476.1. found 476.1.

$^1$H NMR (DMSO-d6, 400 MHz) δ 8.98 (t, 1H), 8.90 (m, 1H), 8.61-8.63 (m, 2H), 8.00 (d, 1H), 7.92 (d, 1H), 7.79 (s, 1H), 7.62 (d, 1H), 7.25 (d, 1H), 6.25 (d, 1H), 5.81 (s, 2H), 4.38 (s, 2H), 4.28 (d, 2H), 3.89 (s, 3H), 2.28 (s, 3H).

Example 96: Preparation of 6-((4-(((6-amino-2-methylpyridin-3-yl)methyl)carbamoyl)pyridin-2-yl)methyl)-3-chloroquinoline-8-carboxylic acid

Example 97: Preparation of N-((6-amino-2-methylpyridin-3-yl)methyl)-2-((3-chloro-8-(hydroxymethyl)quinolin-6-yl)methyl)isonicotinamide

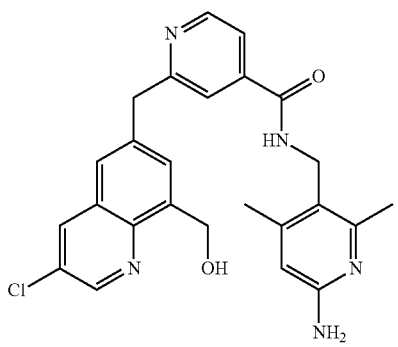

6-((4-(((6-amino-2-methylpyridin-3-yl)methyl)carbamoyl)pyridin-2-yl)methyl)-3-chloroquinoline-8-carboxylic acid

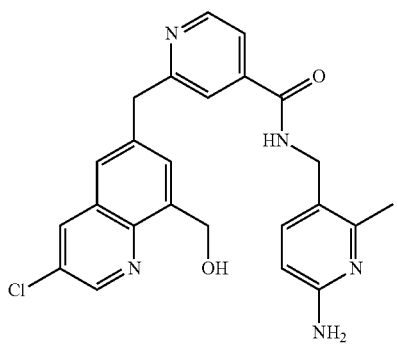

N-(6-Amino-2-methyl-pyridin-3-ylmethyl)-2-((3-chloro-8-hydroxymethyl-quinolin-6-ylmethyl)-isonicotinamide

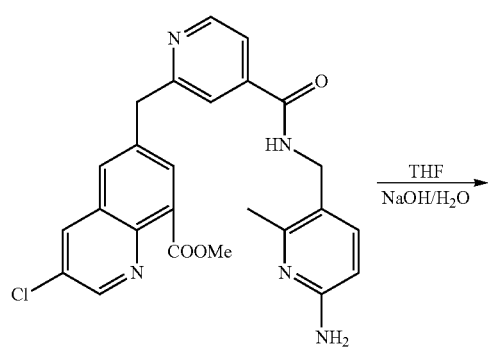

$\xrightarrow{\text{THF}}_{\text{NaOH/H}_2\text{O}}$

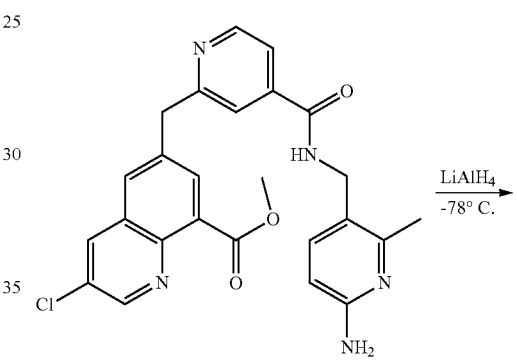

$\xrightarrow{\text{LiAlH}_4}_{-78^\circ \text{C.}}$

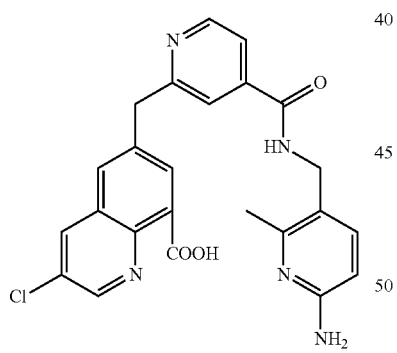

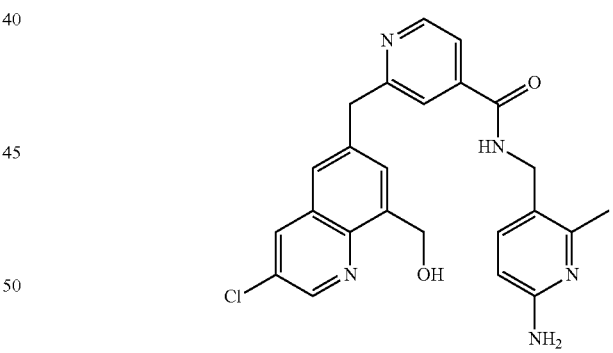

6-((4-(((6-Amino-2-methylpyridin-3-yl)methyl)carbamoyl)pyridin-2-yl)methyl)-3-chloroquinoline-8-carboxylic acid (54 mg, 83.59%) was prepared as described for 6-((4-(((6-amino-2,4-dimethylpyridin-3-yl)methyl)carbamoyl)pyridin-2-yl)methyl)-3-chloroquinoline-8-carboxylic acid (Example 93) as a white solid. LRMS (M+H$^+$) m/z calculated 462.1. found 462.1.

$^1$H NMR (DMSO-d6, 400 MHz) δ 9.07 (d, 1H), 8.99 (s, 1H), 8.83 (d, 1H), 8.62 (d, 1H), 8.41 (m, 1H), 8.17 (s, 1H), 7.82 (s, 1H), 7.62 (d, 1H), 7.24 (d, 2H), 6.21 (d, 1H), 5.72 (s, 1H), 4.45 (s, 2H), 4.28 (d, 2H), 2.27 (s, 3H).

N-((6-amino-2-methylpyridin-3-yl)methyl)-2-((3-chloro-8-(hydroxymethyl)quinolin-6-yl)methyl)isonicotinamide (12.8 mg, 13.6%) was prepared as described for N-((6-amino-2,4-dimethylpyridin-3-yl)methyl)-2-((3-chloro-8-(hydroxymethyl)quinolin-6-yl)methyl)isonicotinamide (Example 94) as a white solid. LRMS (M+H$^+$) m/z calculated 448.1. found 448.1.

$^1$H NMR (DMSO-d6, 400 MHz) δ 8.98 (m, 1H), 8.80 (d, 1H), 8.62 (d, 1H), 8.50 (d, 1H), 7.72 (t, 3H), 7.62 (d, 1H), 7.24 (d, 1H), 6.24 (d, 1H), 5.75 (s, 2H), 5.27 (m, 1H), 5.08 (d, 2H), 4.35 (s, 2H), 4.27 (d, 1H), 2.27 (s, 3H).

Example 98: Preparation of 6-amino-3-((2-((3-chloroquinolin-6-yl)methyl)isonicotinamido)methyl)-2,4-dimethylpyridine 1-oxide Example 99: Preparation of 6-((4-(((6-amino-2,4-dimethylpyridin-3-yl)methyl)carbamoyl)pyridin-2-yl)methyl)-3-chloroquinoline 1-oxide

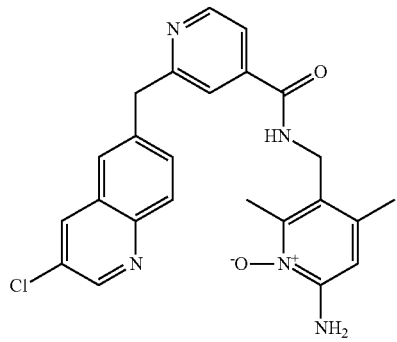

6-amino-3-((2-((3-chloroquinolin-6-yl)methyl)isonicotinamido)methyl)-2,4-dimethylpyridine 1-oxide

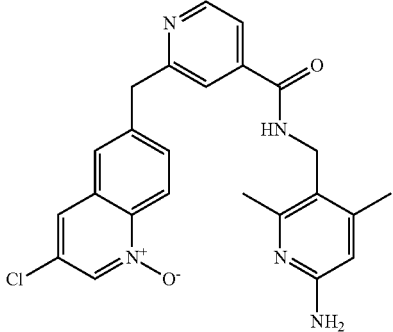

6-((4-(((6-amino-2,4-dimethylpyridin-3-yl)methyl)carbamoyl)pyridin-2-yl)methyl-3-chloroquinoline 1-oxide

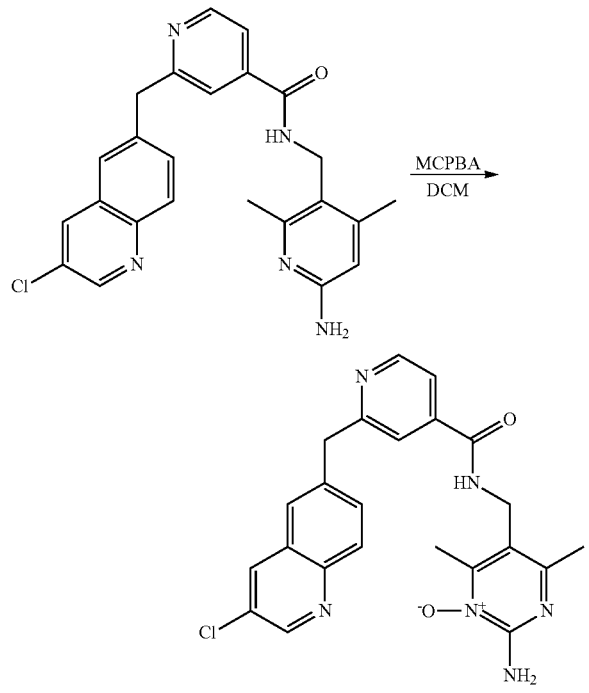

Step 1: Preparation of 3-chloro-6-chloromethyl-quinoline 1-oxide

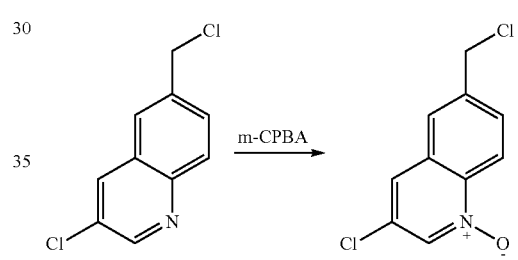

To a solution of 3-chloro-6-chloromethyl-quinoline (500 mg, 2.37 mmol, 1 eq) in dry DCM (20 mL) was added m-CPBA (1.23 g, 7.11 mmol, 3 eq). The mixture was stirred at 40° C. for 5 h. Then the reaction was quenched by sat. NaHCO$_3$ and extracted with DCM. The combined organic layers were dried and concentrated. The residue was purified by chromatography on a silica gel column (EtOAc/PE=1/3, v/v) to give 3-chloro-6-chloromethyl-quinoline 1-oxide (400 mg, 74%) as a yellow solid.

To a solution of N-((6-amino-2,4-dimethylpyridin-3-yl)methyl)-2-((3-chloroquinolin-6-yl)methyl) isonicotinamide (50 mg, 0.11 mmol, 1 eq) in dry DCM was added m-CPBA. The reaction mixture was stirred for 3 h. Then it was quenched with potassium sodium tartrate and extracted with DCM. The combine extracts were dried, concentrated and the residue was purified by prep-HPLC to give 6-amino-3-((2-((3-chloroquinolin-6-yl)methyl)isonicotinamido)methyl)-2,4-dimethylpyridine 1-oxide (12.8 mg, 13.6%) as a white solid. LRMS (M+H$^+$) m/z calculated 448.1. found 448.1.

$^1$H NMR (DMSO-d6, 400 MHz) δ 8.82 (s, 1H), 8.73 (t, 1H), 8.60-8.61 (d, 1H), 8.51 (d, 1H), 7.96 (d, 1H), 7.84 (s, 1H), 7.70-7.73 (m, 2H), 7.57 (d, 1H), 6.70 (s, 2H), 6.53 (s, 1H), 4.34 (m, 4H), 2.41 (s, 3H), 2.23 (s, 3H).

Step 2: Preparation of 3-chloro-6-((4-(methoxycarbonyl)pyridin-2-yl)methyl)quinoline 1-oxide

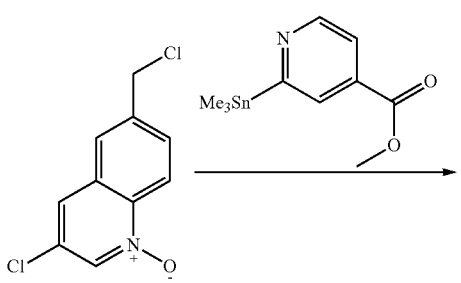

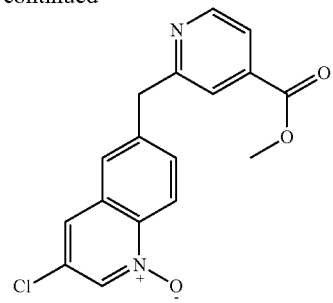

To a solution of 3-chloro-6-chloromethyl-quinoline 1-oxide (400 mg, 1.76 mmol, 1.0 eq) in dioxane (10 mL) was added methyl 2-(trimethylstannyl)isonicotinate (583 mg, 1.94 mmol, 1.1 eq) and Pd(PPh$_3$)$_2$Cl$_2$ (126 mg, 0.18 mmol, 0.1 eq). The mixture was stirred at 90° C. for 3 h under nitrogen atmosphere, then concentrated and purified by silica gel chromatography (DCM/MeOH=100/1, v/v) to afford 3-chloro-6-((4-(methoxycarbonyl)pyridin-2-yl)methyl)quinoline 1-oxide (210 mg, 36%) as a yellow solid.

Step 3: Preparation of 6-((4-(((6-amino-2,4-dimethylpyridin-3-yl)methyl)carbamoyl)pyridin-2-yl)methyl)-3-chloroquinoline 1-oxide

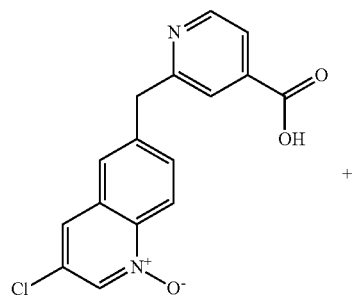

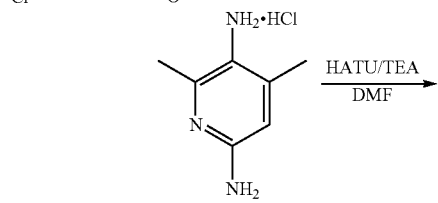

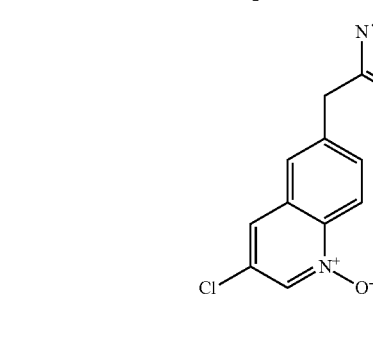

To a solution of 2-(3-chloro-1-oxy-quinolin-6-ylmethyl)-isonicotinic acid (100 mg, 0.32 mmol, 1 eq) in DMF (10 mL) was added 5-aminomethyl-4,6-dimethyl-pyridin-2-ylamin (106 mg, 0.48 mmol, 1.5 eq), HATU (182 mg, 0.48 mmol, 1.5 eq), and Et$_3$N (1 mL). The mixture was stirred at rt for 3 h. Then it was quenched with water, extracted with DCM. The combined extracts were dried, concentrated, and the residue was purified by prep-HPLC to give 6-((4-(((6-amino-2,4-dimethylpyridin-3-yl)methyl)carbamoyl)pyridin-2-yl)methyl)-3-chloroquinoline 1-oxide (30 mg, 21%) as a gray solid. LRMS (M+H$^+$) m/z calculated 448.1. found 447.8.

$^1$H NMR (DMSO-d6, 400 MHz) δ 8.74 (d, 1H), 8.59-8.63 (m, 2H), 8.38 (d, 1H), 8.10 (s, 1H), 7.91 (s, 1H), 7.73-7.75 (m, 2H), 7.59-7.61 (m, 1H), 6.13 (s, 1H), 5.71 (s, 2H), 4.33 (d, 4H), 2.30 (s, 3H), 2.16 (s, 3H).

Example 100: Preparation of N-((6-amino-2,4-dimethylpyridin-3-yl)methyl)-2-((3,8-dichloroquinolin-6-yl)methyl)isonicotinamide

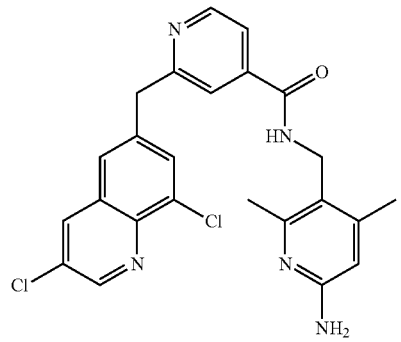

N-((6-amino-2,4-dimethylpyridin-3-yl)methyl)-2-((3,8-dichloroquinolin-6-yl)methyl)isonicotinamide Step 1: Preparation of 2-((3,8-dichloroquinolin-6-yl)methyl)isonicotinic acid

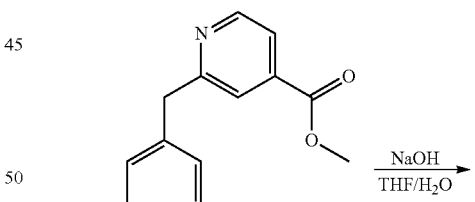

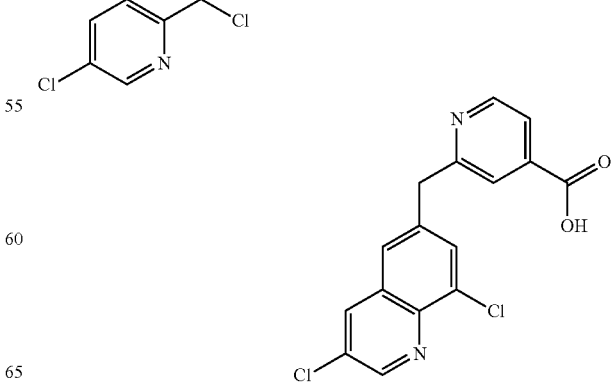

To a solution of methyl 2-((3,8-dichloroquinolin-6-yl)methyl)isonicotinate (300 mg, 0.86 mmol, 1 eq) in THF (10 mL)/water (5 mL) was added NaOH (42 mg, 1.05 mmol, 1.2 eq). The mixture was stirred at rt for 3 h and then aqueous HCl (2 N) was added to adjust pH 4. The mixture was extracted with EtOAc, and the organic layer was concentrated under pressure to provide the crude product (170 mg, 59%) without further purification.

Step 2: Preparation of N-((6-amino-2,4-dimethylpyridin-3-yl)methyl)-2-((3,8-dichloroquinolin-6-yl)methyl)isonicotinamide

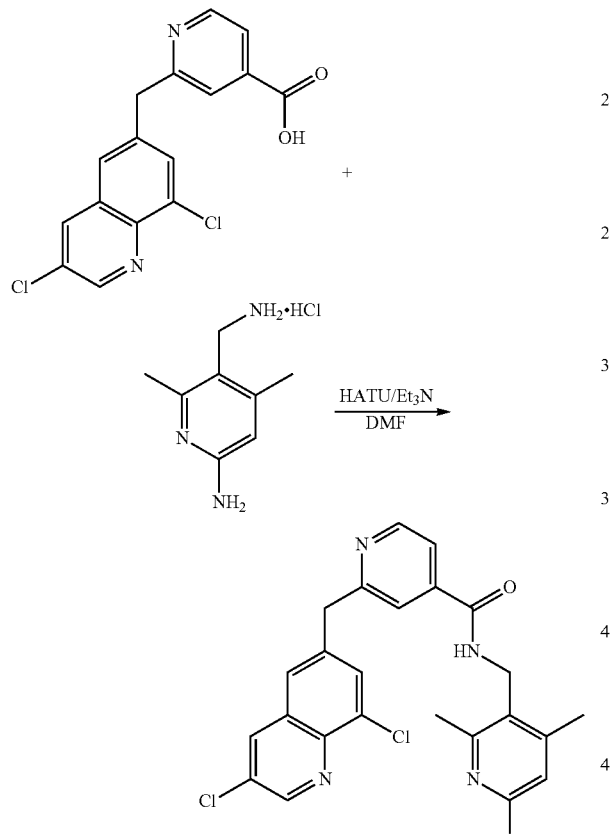

To a solution of 2-(3,8-dichloro-quinolin-6-ylmethyl)-isonicotinic acid (80 mg, 0.24 mmol, 1 eq) in DMF (10 mL) was added 5-aminomethyl-4, 6-dimethyl-pyridin-2-ylamine (83 mg, 0.36 mmol, 1.5 eq), HATU (110 mg, 0.29 mmol, 1.2 eq), and Et$_3$N (121.2 mg, 1.2 mmol, 5 eq). The mixture was stirred at rt for 3 h. Then it was quenched with water, extracted with DCM. The combined extracts were dried, concentrated, and the residue was purified by prep-HPLC to give N-((6-amino-2,4-dimethylpyridin-3-yl)methyl)-2-((3,8-dichloroquinolin-6-yl)methyl)isonicotinamide (16 mg, 14%) as a white solid. LRMS (M+H$^+$) m/z calculated 466.1. found 465.8.

$^1$H NMR (DMSO-d6, 400 MHz) δ 8.95 (s, 1H), 8.60-8.66 (m, 3H), 7.77-7.94 (m, 3H), 8.00 (s, 1H), 7.60 (d, 1H), 7.68-7.71 (m, 1H), 6.18 (s, 1H), 5.91 (s, 2H), 4.33-4.34 (m, 4H), 2.32 (s, 3H), 2.19 (s, 3H).

Example 101: Preparation of N-((6-amino-2-methylpyridin-3-yl)methyl)-2-((3,8-dichloroquinolin-6-yl)methyl)isonicotinamide

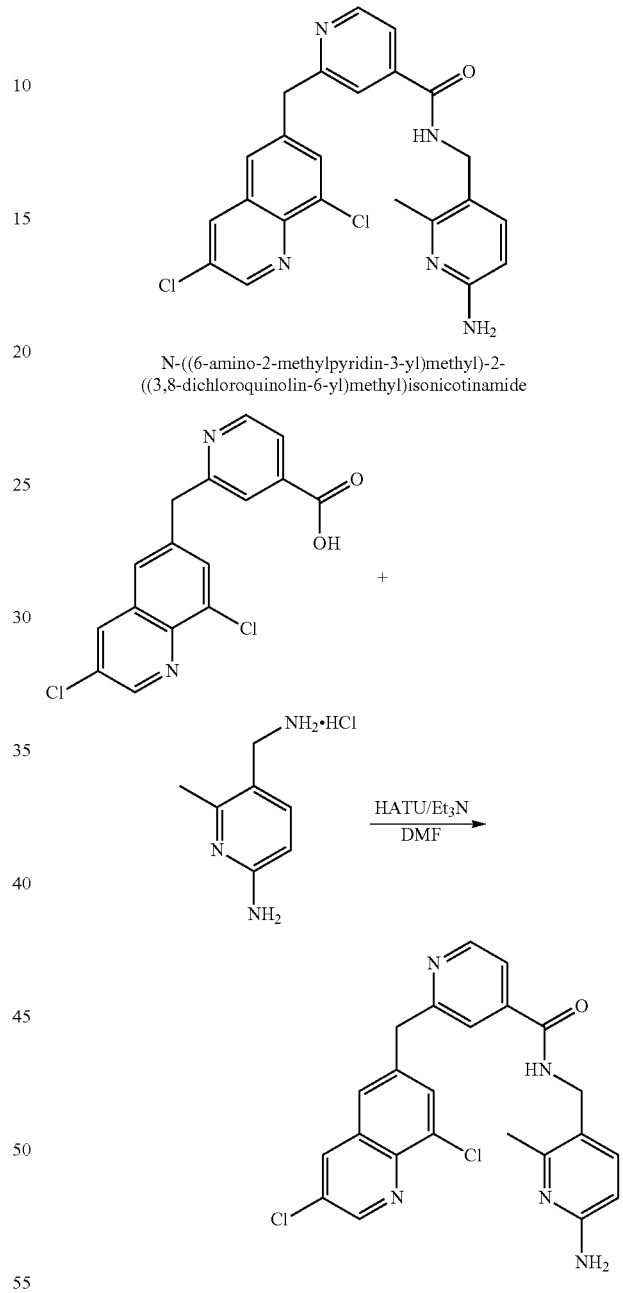

N-((6-amino-2-methylpyridin-3-yl)methyl)-2-((3,8-dichloroquinolin-6-yl)methyl)isonicotinamide N-((6-amino-2-methylpyridin-3-yl)methyl)-2-((3,8-dichloroquinolin-6-yl)methyl)isonicotinamide (25 mg, 23%) was prepared as described for N-((6-amino-2,4-dimethylpyridin-3-yl)methyl)-2-((3,8-dichloroquinolin-6-yl)methyl)isonicotinamide (Example 100) as a white solid. LRMS (M+H$^+$) m/z calculated 452.1. found 451.8.

$^1$H NMR (DMSO-d6, 400 MHz) δ 8.94-8.98 (m, 2H), 8.63-8.64 (m, 2H), 7.95 (m, 1H), 7.84-7.88 (m, 2H), 7.62 (d, 1H), 6.24-6.26 (m, 1H), 6.80 (s, 2H), 4.28-4.36 (m, 4H), 2.28 (s, 3H)

Example 102: Preparation of N-((6-amino-2-methylpyridin-3-yl)methyl)-2-((3-chloro-5-fluoroquinolin-6-yl)methyl)isonicotinamide

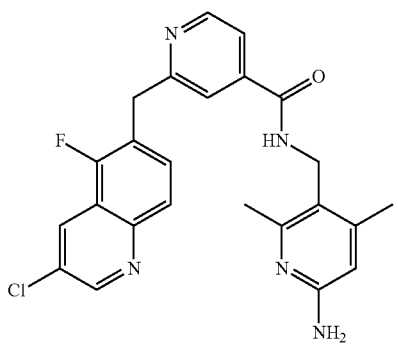

N-((6-amino-2,4-dimethylpyridin-3-yl)methyl)-2-((3-chloro-5-fluoroquinolin-6-yl)methyl)isonicotinamide

Step 1: Preparation of methyl 5-fluoroquinoline-6-carboxylate and methyl 7-fluoroquinoline-6-carboxylate

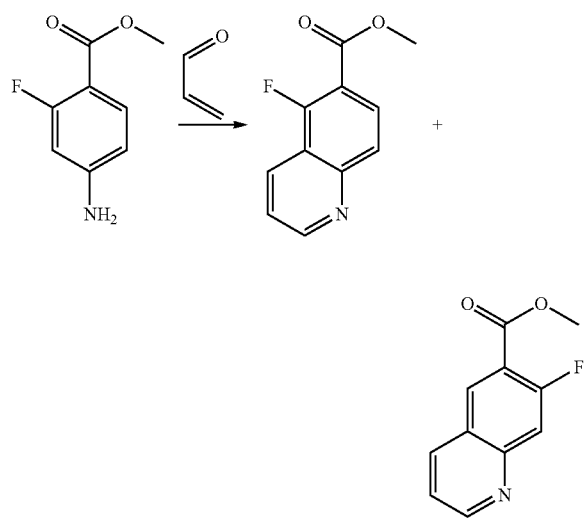

To a suspension of methyl 4-amino-2-fluorobenzoate (20.0 g, 0.129 mol, 1 eq) and p-chloranil (35.0 g, 0.142 mol, 1.1 eq) in 500 mL of 6 N HCl solution was added acrolein (13.5 g, 0.194 mol, 1.5 eq, 80% purity). The mixture was stirred at 100° C. for 10 min. After cooling to rt, the mixture was basified to pH 3 with sat. NaHCO₃. The precipitate was removed by filtration. The filtrate was extracted with CHCl₃. The combined organic layers were dried and concentrated. The residue was purified by chromatography on silica gel column (EtOAc/PE=1/10, v/v) to give methyl 5-fluoroquinoline-6-carboxylate and methyl 7-fluoroquinoline-6-carboxylate (3.0 g, 11%) as a yellow solid.

Step 2: Preparation of methyl 3-chloro-5-fluoroquinoline-6-carboxylate and methyl 3-chloro-7-fluoroquinoline-6-carboxylate

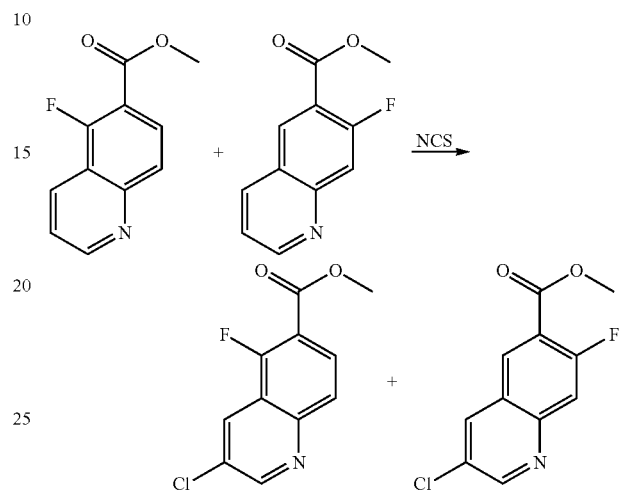

To a solution of mixture of methyl 5-fluoroquinoline-6-carboxylate and methyl 7-fluoroquinoline-6-carboxylate (3.7 g, 18.0 mmol, 1 eq) in DMF (90 mL) was added NCS (7.2 g, 54.0 mmol, 3 eq). The reaction mixture was stirred at 120° C. for 40 min under N₂. The reaction mixture was allowed to cool to ambient temperature, treated with water, neutralized with solid NaHCO₃ and stirred at rt for 30 min. Powdered sodium thiosulfate was carefully added to remove excess of NCS. The mixture was extracted with EtOAc. The organic layer was dried and concentrated under vacuum. The crude product was purified by flash-chromatography on silica gel column to afford the mixture of methyl 3-chloro-5-fluoroquinoline-6-carboxylate and methyl 3-chloro-7-fluoroquinoline-6-carboxylate (2.1 g, 49%) as a yellow solid.

Step 3: Preparation of N-((6-amino-2,4-dimethylpyridin-3-yl)methyl)-2-((3-chloro-5-fluoroquinolin-6-yl)methyl)isonicotinamide

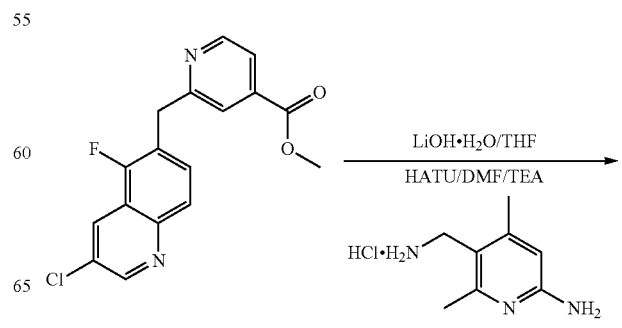

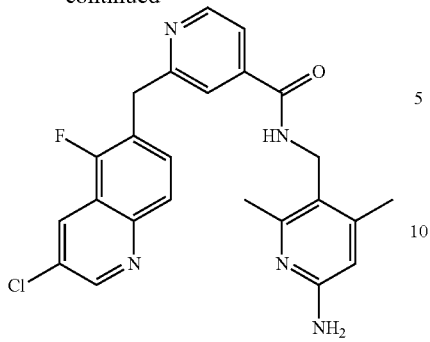

To a solution of methyl 3-chloro-5-fluoroquinoline-6-carboxylate (104.4 mg, 0.32 mmol, 1.0 eq) in THF (5 mL)/H₂O (5 mL) was added LiOH.H₂O (26.87 mg, 0.64 mmol, 2 eq). The mixture was stirred at 40° C. for 1 h and was acidified to pH 5 with 1 N HCl solution. The mixture was concentrated in vacuo and the residue was directly used without further purification. To a solution of the above crude product in DMF (10 mL) was added 5-aminomethyl-4,6-dimethyl-pyridin-2-ylamin (106 mg, 0.48 mmol, 1.5 eq), HATU (182 mg, 0.48 mmol, 1.5 eq), and Et₃N (1 mL). The mixture was stirred at rt for 3 h. Then it was quenched with water, extracted with DCM. The combined extracts were dried, concentrated, and the residue was purified by prep-HPLC to give N-((6-amino-2,4-dimethylpyridin-3-yl)methyl)-2-((3-chloro-5-fluoroquinolin-6-yl)methyl)isonicotinamide (17 mg, 12.4%) as a white solid. LRMS (M+H⁺) m/z calculated 450.1. found 450.1. ¹H NMR (DMSO-d6, 400 MHz) δ 8.87 (d, 1H), 8.55-8.58 (m, 3H), 7.93 (d, 1H), 7.73-7.81 (m, 2H), 7.60 (d, 1H), 6.11 (s, 1H), 5.66 (s, 2H), 4.33-4.38 (m, 4H), 2.29 (s, 3H), 2.16 (s, 3H).

Example 103: Preparation of N-((6-amino-2-methylpyridin-3-yl)methyl)-2-((3-chloro-5-fluoroquinolin-6-yl)methyl)isonicotinamide

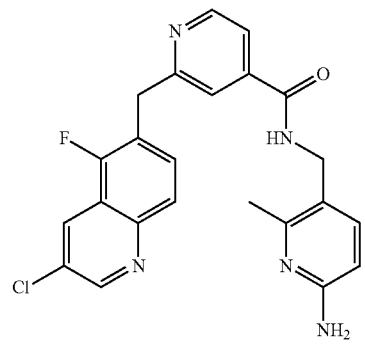

N-((6-amino-2-methylpyridin-3-yl)methyl)-2-((3-Chloro-5-fluoroquinolin-6-yl)methyl)isonicotinamide

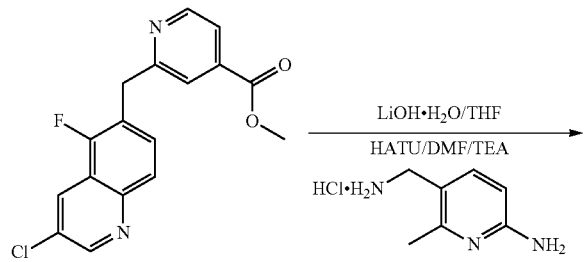

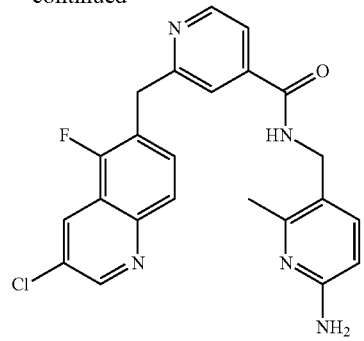

N-((6-amino-2-methylpyridin-3-yl)methyl)-2-((3-chloro-5-fluoroquinolin-6-yl)methyl)isonicotinamide (45 mg, 32%) was prepared as described for N-((6-amino-2,4-dimethyl-pyridin-3-yl)methyl)-2-((3-chloro-5-fluoroquinolin-6-yl)methyl)isonicotinamide (Example 102) as a white solid. LRMS (M+H⁺) m/z calculated 436.1. found 436.1. ¹H NMR (DMSO-d6, 400 MHz) δ 8.99 (m, 1H), 8.88 (s, 1H), 8.57 (d, 2H), 7.94 (d, 1H), 7.63-7.81 (m, 3H), 7.24 (s, 1H), 6.21 (d, 1H), 5.72 (s, 2H), 4.40 (s, 2H), 4.27 (d, 2H), 2.27 (s, 3H).

Example 104: Preparation of N-((6-amino-2-methylpyridin-3-yl)methyl)-2-((3-chloroquinolin-6-yl)methyl)isonicotinamide

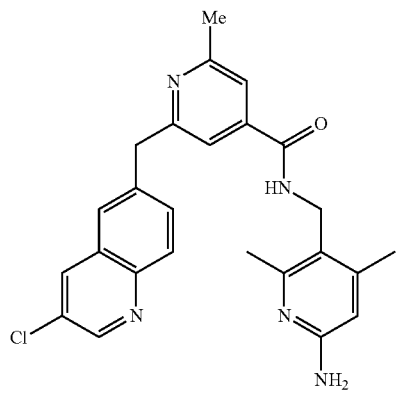

N-((6-amino-2,4-dimethylpyridin-3-yl)methyl)-2-((3-chloroquinolin-6-yl)methyl)-6-methylisonicotinamide Step 1: Preparation of methyl 3-chloroquinoline-6-carboxylate

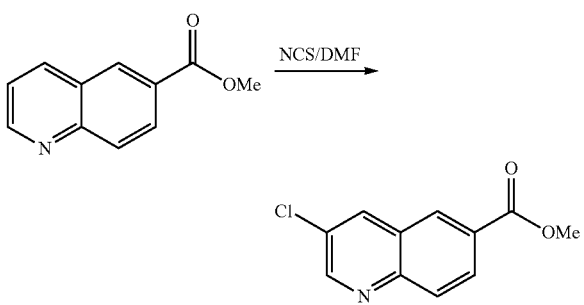

To a solution of methyl quinoline-6-carboxylate (15.0 g, 80.2 mmol, 1.0 eq) in DMF (200 ml) was added N-chlorosuccinimide (21.4 g, 0.16 mol, 2.0 eq) and the reaction mixture was stirred at 120° C. for 20 h. The reaction mixture was allowed to cool to rt, treated with brine and the mixture was extracted with EtOAc. The organic layer was dried over Na$_2$SO$_4$, filtered and concentrated under vacuum. The crude product was purified by chromatography on silica gel (EtOAc/PE=1/8, v/v) to afford methyl 3-chloroquinoline-6-carboxylate (9.1 g, 51%) as a yellow solid.

Step 2: Preparation of methyl (3-chloro-quinolin-6-yl)-methanol

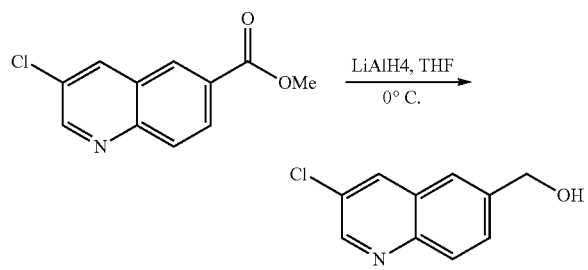

To a solution of methyl 3-chloroquinoline-6-carboxylate (8 g, 36.0 mmol, 1.0 eq) in dry THF was added LiAlH$_4$ (2.5M in THF, 5.8 mL, 0.4 eq). The resulting mixture was stirred at 0° C. for 1 h. After which period, additional LiAlH$_4$ (2.5M in THF, 2.8 mL, 0.2 eq) was added. The system was stirred for another 30 min at 0° C. and quenched by the slow addition of 1N aqueous NaOH. The resulting precipitate was filtered, and the filtrate was extracted with EtOAc. The combined organic layers were dried and concentrated. The residue was purified by silica gel chromatography (PE/EtOAc=20/1-5/1, v/v) to afford (3-chloro-quinolin-6-yl)-methanol (4.8 g, 69%) as a white solid.

Step 3: Preparation of 3-chloro-6-chloromethyl-quinoline

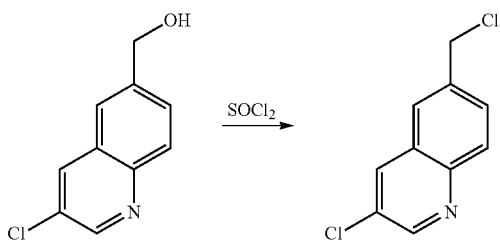

To (3-chloro-quinolin-6-yl)-methanol (3.3 g, 17.1 mmol, 1.0 eq) was added SOCl$_2$ (50 mL) and the mixture was stirred at rt for 1 h. The volatiles were then removed under vacuum and the residue was dissolved in DCM. The mixture was washed with saturated aq. NaHCO$_3$, dried and concentrated to give 3-chloro-6-chloromethyl-quinoline (3.4 g, 94%) as a yellow solid.

Step 4: Preparation of methyl 2-methyl-6-(trimethylstannyl)isonicotinate

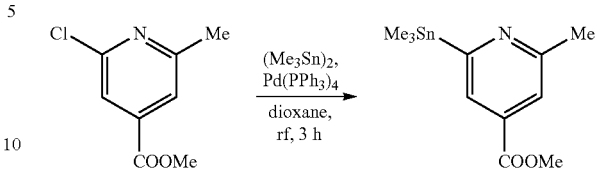

Hexamethyldistannane (0.21 mL, 334 mg, 1.02 mmol) and tetrakis(triphenylphosphine)palladium(0) (70 mg, 0.06 mmol) were added to a solution of methyl 2-chloro-6-methylisonicotinate (100 mg, 0.54 mmol) in dry dioxane (10 mL) and the resulting mixture was refluxed for 3 h under N$_2$. EtOAc (50 mL) and water (100 mL) were then added. The layers were separated and the organic layer was washed with water (5×100 mL), dried (Na$_2$SO$_4$), and the solvent removed by rotary evaporation to leave crude residue which was used in the next step without further purification.

Step 4: Preparation of methyl 2-((3-chloroquinolin-6-yl)methyl)-6-methylisonicotinate

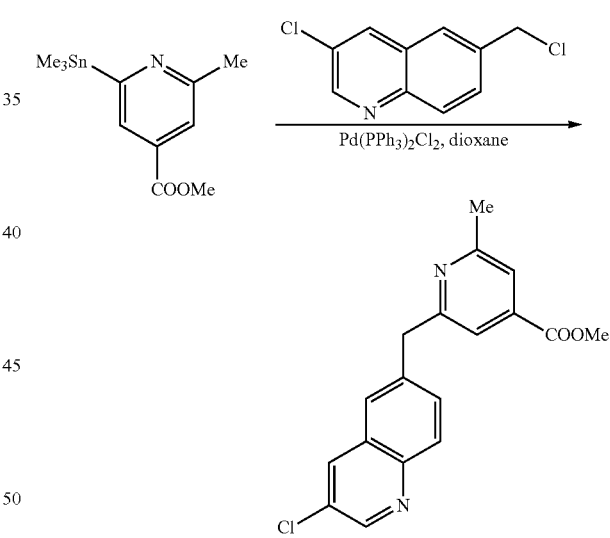

To a solution of 3-chloro-6-chloromethyl-quinoline (110 mg, 0.52 mmol, 1.0 eq) and crude methyl 2-methyl-6-(trimethylstannyl)isonicotinate in dioxane (10 mL) Pd(PPh$_3$)$_2$Cl$_2$ (36 mg, 0.05 mmol, 0.1 eq). The mixture was stirred at 90° C. for 3 h under nitrogen atmosphere, stripped of solvent and purified by silica gel chromatography (EtOAc/PE=10/1-5:1, v/v) to afford methyl 2-((3-chloroquinolin-6-yl)methyl)-6-methylisonicotinate (70 mg, 40%) as a yellow solid. $^1$H NMR (400 MHz, DMSO-d$_6$) δ 8.83 (d, 1H), 8.53 (d, 1H), 7.98 (d, 1H), 7.85 (d, 1H), 7.73 (dd, 1H), 7.58 (s, 1H), 7.57 (s, 1H), 4.36 (s, 2H), 3.85 (s, 3H), 2.53 (s, 3H).

Step 5: Preparation of 2-((3-chloroquinolin-6-yl)methyl)-6-methylisonicotinic acid

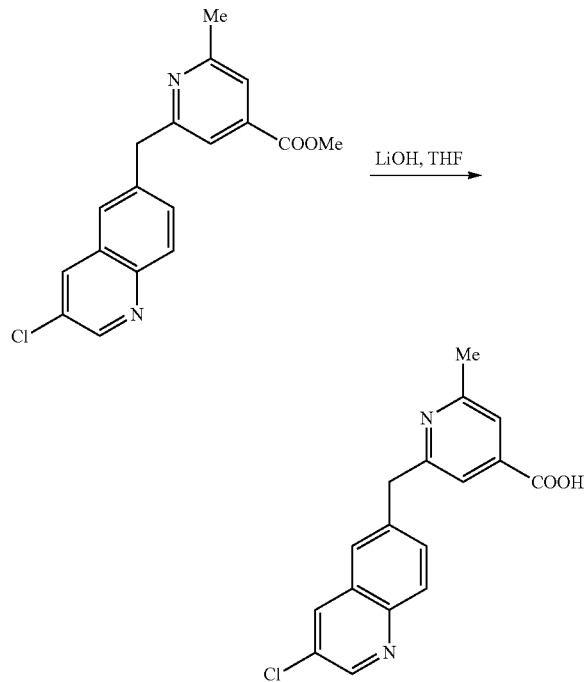

To a solution of 2-((3-chloroquinolin-6-yl)methyl)-6-methylisonicotinate (70 mg, 0.21 mmol, 1.0 eq.) in THF/H₂O (5 mL/1 mL) was added LiOH (71 mg, 2.1 mmol, 10 eq.). The resulting mixture was stirred for 1 h at room temperature; all starting material had been consumed (assessed by TLC). Volatile solvent was removed on rotavap, the aqueous residue was neutralized with 1M HCl and extracted with EtOAc (10 mL×3). The combined organic layers were washed with brine, dried over Na₂SO₄ and concentrated to furnish crude acid (50 mg, 75%), which was used directly in the next step without further purification.

Step 6: Preparation of N-((6-amino-2,4-dimethylpyridin-3-yl) methyl)-2-((3-chloroquinolin-6-yl)methyl)-6-methylisonicotinamide

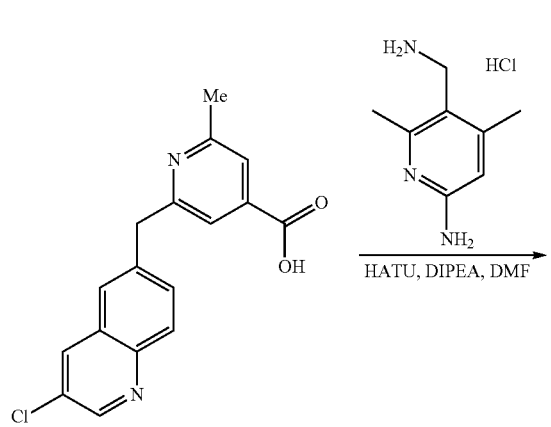

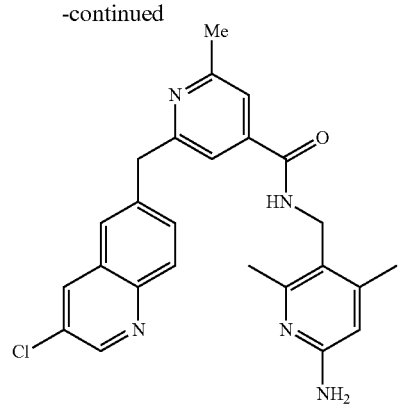

-continued

To a solution of 2-((3-chloroquinolin-6-yl)methyl)-6-methylisonicotinic acid (50 mg, 0.16 mmol, 1.0 eq.) in DMF (5 mL) was added 5-aminomethyl-6-methyl-pyridin-2-ylamine hydrochloride (33 mg, 0.0.19 mmol, 1.2 eq.) followed by HATU (91 mg, 0.24 mmol, 1.5 eq.) and DIPEA (0.08 mL, 0.48 mmol, 3.0 eq.) at 0° C. The reaction mixture was allowed to warm to room temperature and stirred for 2 h under N₂. Water (20 mL) was added, and the mixture was extracted with EtOAc (20 mL×3). The combined organic layers were washed with brine, dried over Na₂SO₄, filtered and concentrated. The residue was purified by prep-TLC (DCM: MeOH=15:1) to give N-((6-amino-2,4-dimethyl-pyridin-3-yl) methyl)-2-((3-chloroquinolin-6-yl)methyl)-6-methylisonicotinamide (24 mg, 34%) as a yellow solid. LRMS (M+H⁺) m/z calculated 446.2. found 446.2. ¹H NMR (DMSO-d₆, 400 MHz): δ 8.83 (d, 1H), 8.66 (s, 1H), 8.53 (d, 1H), 7.97 (d, 1H), 7.84 (d, 1H), 7.71 (dd, 1H), 7.50 (s, 1H), 7.47 (s, 1H), 6.32 (s, 2H), 4.32 (d, 2H), 4.29 (s, 2H), 2.48 (s, 3H), 2.37 (s, 3H), 2.23 (s, 3H).

Example 105: Preparation of N-((6-amino-2,4-dimethylpyridin-3-yl)methyl)-2-((5-chloro-1H-indazol-1-yl)methyl)isonicotinamide

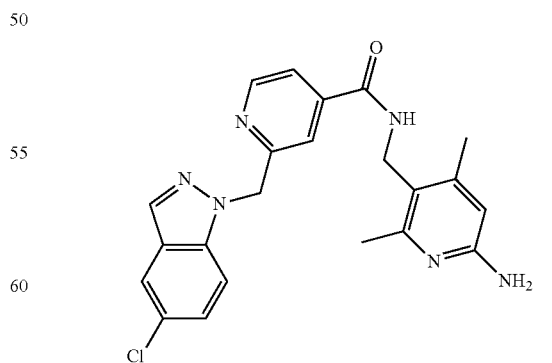

N-((6-amino-2,4-dimethylpyridin-3-yl)methyl)-2-((5-chloro-1H-indazol-1-yl)methyl)isonicotinamide

Step 1: Preparation of methyl 3-chloroquinoline-6-carboxylate

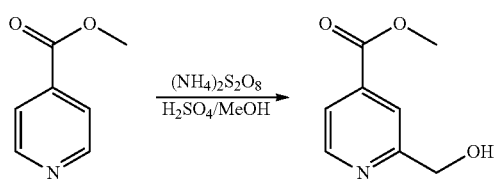

To a solution of methyl isonicotinate (5.0 g, 36.5 mmol, 1.0 eq) in MeOH (70 ml) was added conc. $H_2SO_4$ (300 mg, 3.1 mmol, 0.086 eq) dropwise at rt. The above mixture was heated at reflux, to which was added an aqueous solution of $(NH_4)_2S_2O_8$ (15.0 g, 65.7 mmol in 30 mL of water) dropwise. The reaction mixture was kept at reflux for additional 30 minutes, cooled to rt, treated with 4 M NaOH and aqueous $NaHCO_3$ to about pH 7. The aqueous mixture was concentrated under vacuum, and the residue was extracted with EtOAc (100 mL×2). The combined organic layers were washed with brine, dried over $Na_2SO_4$, filtered and concentrated under vacuum. The crude product was purified by chromatography on silica gel (PE/EtOAc=1/3 to 1/1, v/v) to afford methyl 3-chloroquinoline-6-carboxylate (1.5 g, 25%) as a white solid. LCMS (M+H$^+$) m/z calculated 168. found 168.0. $^1$H NMR (CDCl$_3$, 400 MHz): δ 8.71 (d, J=4.8 Hz, 1H), 7.84 (d, J=0.8 Hz, 1H), 7.77 (dd, 1H), 4.84 (s, 2H), 3.96 (s, 3H).

Step 2: Preparation of methyl 2-(((methylsulfonyl)oxy)methyl)isonicotinate

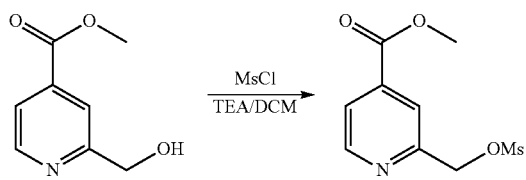 [SMILES: "MsCl" ; COC(=O)c1ccnc(CO)c1 ; "TEA/DCM" ; COC(=O)c1ccnc(COS(C)(=O)=O)c1]

To a stirred solution of methyl 2-(hydroxymethyl)isonicotinate (1.0 g, 6.0 mmol, 1.0 eq) and TEA (1.2 g, 12.0 mmol, 2.0 eq) in DCM (15 mL) was added MsCl (755 g, 6.6 mmol, 1.1 eq) at 0° C. The resulting mixture was stirred at rt for a further 30 minutes, diluted with DCM (60 mL), washed with water (30 mL), brine (30 mL×2), dried and concentrated to afford methyl 2-(((methylsulfonyl)oxy)methyl)isonicotinate (1.2 g, 82%) as a dark brown oil.

Step 3: Preparation of methyl 2-((5-chloro-1H-indazol-1-yl)methyl)isonicotinate

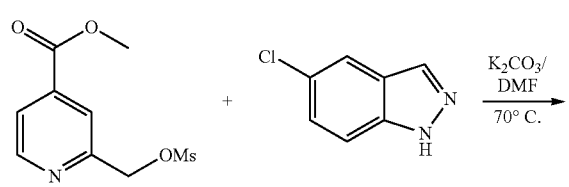

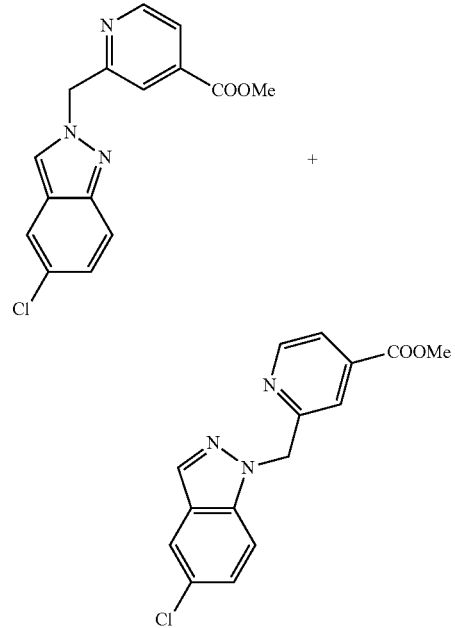

A mixture of methyl 2-(((methylsulfonyl)oxy)methyl) isonicotinate (300 mg, 1.22 mmol, 1.0 eq), 5-chloro-1H-indazole (280 mg, 1.84 mmol, 1.5 eq) and $K_2CO_3$ (337 mg, 2.44 mmol, 2 eq) in DMF (5 mL) was stirred at 70° C. for 2 hours. The mixture was cooled to rt, diluted with EtOAc (50 mL), washed with water (30 mL), brine (30 mL×2), dried and concentrated. The residue was purified by chromatography on silica gel (PE/EtOAc=10/1-5/1 v/v) to afford methyl 2-((5-chloro-1H-indazol-1-yl)methyl)isonicotinate (120 mg, 33%) as a white solid. $^1$H NMR (CDCl$_3$, 400 MHz): δ 8.68 (d, 1H), 8.00 (s, 1H), 7.73 (d, 1H), 7.69 (d, 1H), 7.48 (s, 1H), 7.34 (d, 1H), 7.28 (dd, 1H), 5.73 (s, 2H), 3.85 (s, 3H). Chromatography on silica gel (PE/EtOAc=5/1 to 3/1, v/v) to afford methyl 2-((5-chloro-2H-indazol-2-yl)methyl)isonicotinate (70 mg, 19%) as a white solid. $^1$H NMR (CDCl$_3$, 400 MHz): δ 8.73 (d, 1H), 8.05 (s, 1H), 7.79 (dd, 1H), 7.72 (s, 1H), 7.64-7.60 (m, 2H), 7.21 (dd, 1H), 5.75 (s, 2H), 3.90 (s, 3H).

Step 4: Preparation of 2-((5-chloro-1H-indazol-1-yl)methyl)isonicotinic acid

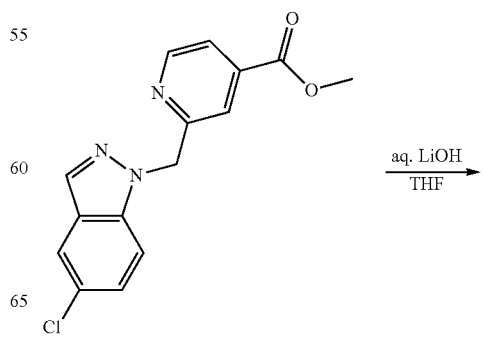

-continued

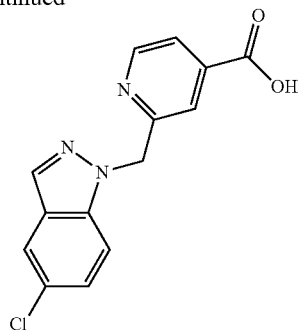

To a solution of methyl 2-((5-chloro-1H-indazol-1-yl)methyl)isonicotinate (270 mg, 0.89 mmol, 1.0 eq) in THF (5 mL) was added LiOH.H$_2$O (375 mg, 8.9 mmol, 10.0 eq) and water (5 mL). The mixture was stirred at rt for 2 hours, concentrated under vacuum to remove most THF. The aqueous mixture was adjusted with 1M HCl to about pH 7. The white suspension was filtered and the solid was washed with water (10 mL), evaporated under vacuum to dryness to afford 2-((5-chloro-1H-indazol-1-yl)methyl)isonicotinic acid (240 mg, 93%) as a white solid.

Step 5: Preparation of N-((6-amino-2,4-dimethyl-pyridin-3-yl)methyl)-2-((5-chloro-1H-indazol-1-yl)methyl)isonicotinamide

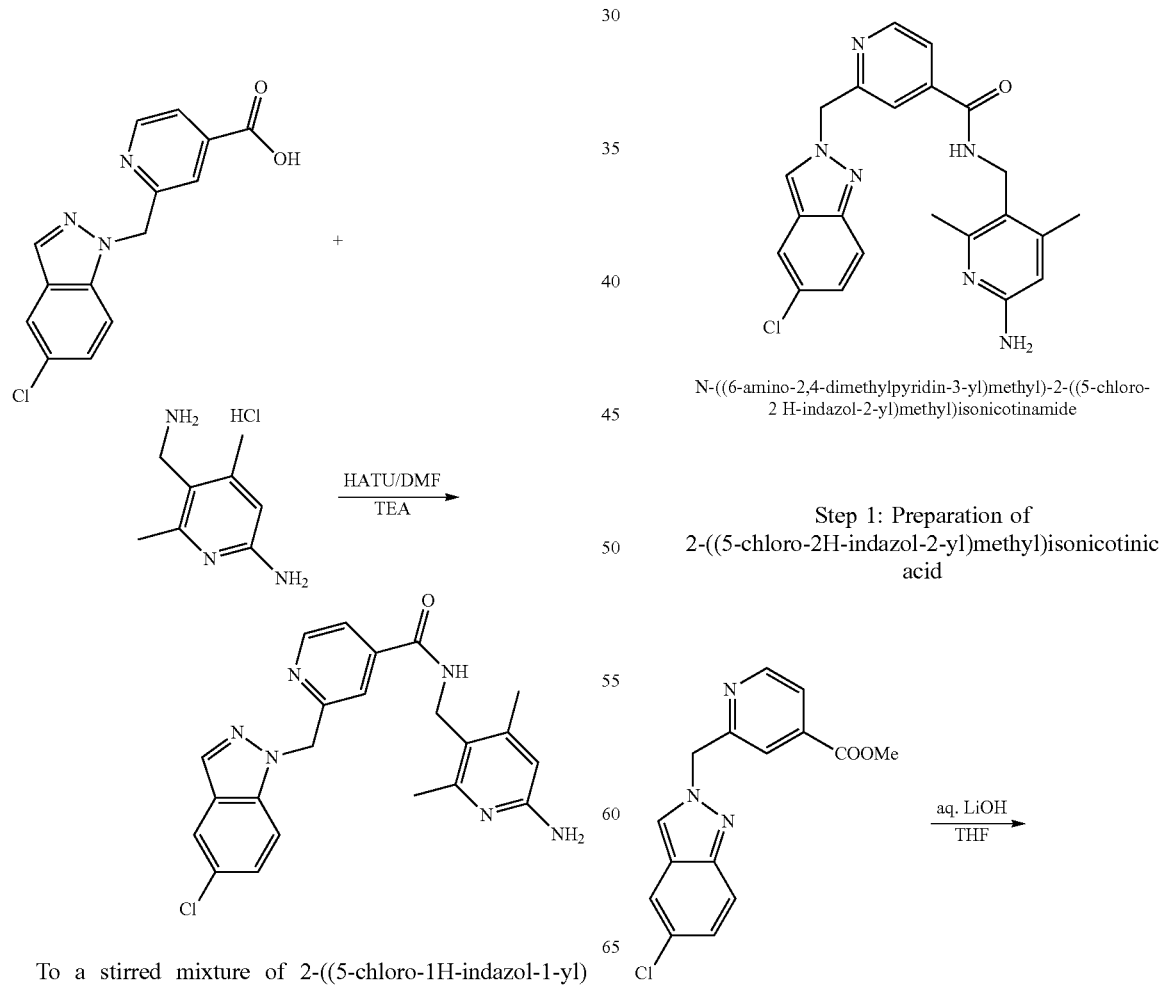

To a stirred mixture of 2-((5-chloro-1H-indazol-1-yl)methyl)isonicotinic acid (100 mg, 0.35 mmol, 1.0 eq), TEA (101 mg, 1.0 mmol, 3.0 eq) and 5-(aminomethyl)-4,6-dimethylpyridin-2-amine hydrochloride (65 mg, 0.35 mmol, 1.0 eq) in DMF (3 mL) was added HATU (264 mg, 0.7 mmol, 2.0 eq) at 0° C. The reaction mixture was stirred at rt for 16 h, and then diluted with EtOAc (50 mL). The new mixture was washed with water (30 mL), brine (30 mL×2), dried and concentrated. The residue was purified by chromatography on silica gel (DCM/MeOH=50/1 to 20/1, v/v) and then Prep-TLC (DCM/MeOH=20/1, v/v) to afford N-((6-amino-2,4-dimethylpyridin-3-yl)methyl)-2-((5-chloro-1H-indazol-1-yl)methyl)isonicotinamide (10 mg, 7%) as a white solid. LCMS (M+H$^+$) m/z calculated 421. found 421.0.

$^1$H NMR (DMSO-d$_6$, 400 MHz): δ 8.68 (t, 1H), 8.57 (d, 1H), 8.10 (d, 1H), 7.88 (d, 1H), 7.75 (d, 1H), 7.65 (dd, 1H), 7.49 (s, 1H), 7.40 (dd, 1H), 6.14 (s, 1H), 5.82-5.73 (m, 4H), 4.30 (d, 2H), 2.28 (s, 3H), 2.15 (s, 3H). LRMS (M+H$^+$) m/z calculated 421.2. found 421.0.

Example 106: Preparation of N-((6-amino-2,4-dimethylpyridin-3-yl)methyl)-2-((5-chloro-2H-indazol-2-yl)methyl)isonicotinamide

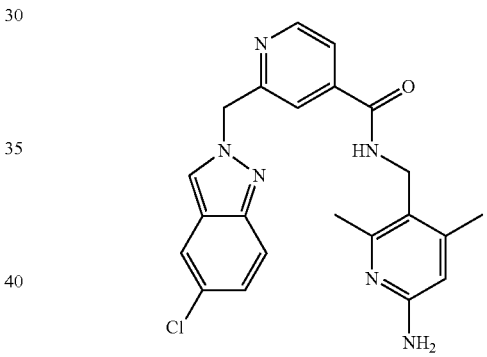

N-((6-amino-2,4-dimethylpyridin-3-yl)methyl)-2-((5-chloro-2H-indazol-2-yl)methyl)isonicotinamide Step 1: Preparation of 2-((5-chloro-2H-indazol-2-yl)methyl)isonicotinic acid

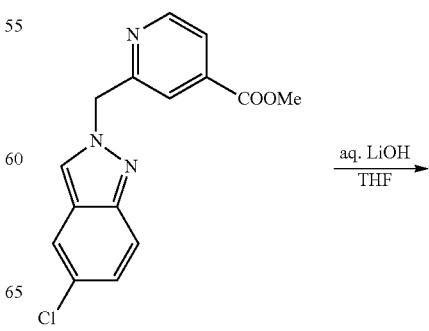

-continued

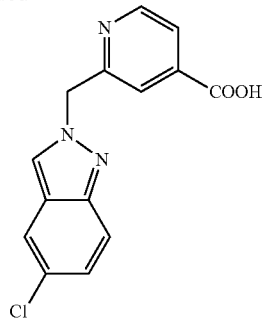

To a solution of methyl 2-((5-chloro-2H-indazol-2-yl)methyl)isonicotinate (150 mg, 0.50 mmol, 1.0 eq) in THF (5 mL) was added LiOH H$_2$O (208 mg, 5.0 mmol, 10.0 eq) and water (5 mL). The mixture was stirred at rt for 2 hours, concentrated under vacuum to remove most THF. The aqueous mixture was adjusted with 1M HCl to pH ~7. The white suspension was filtered and the solid was washed with water (10 mL), concentrated to afford 2-((5-chloro-2H-indazol-2-yl)methyl)isonicotinic acid (110 mg, 77%) as a white solid.

Step 2: Preparation of N-((6-amino-2,4-dimethylpyridin-3-yl)methyl)-2-((5-chloro-2H-indazol-2-yl)methyl)isonicotinamide

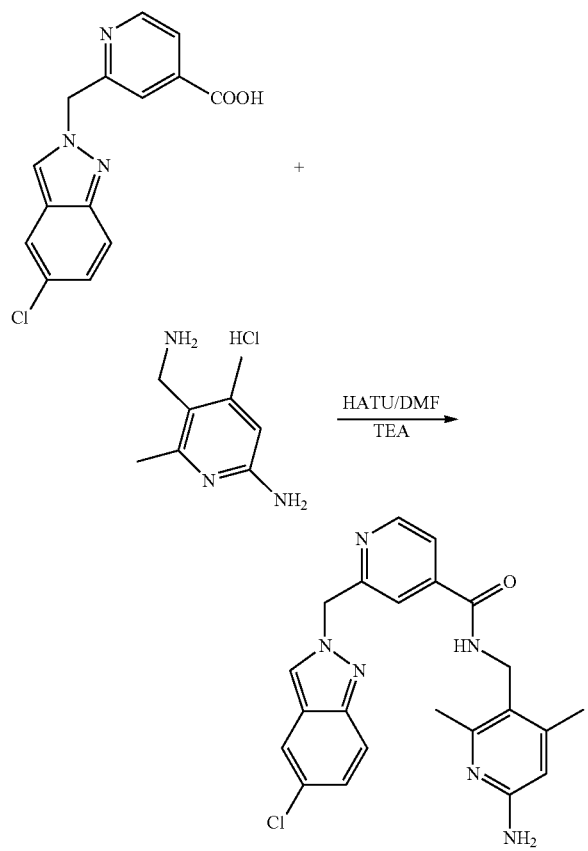

To a stirred mixture of 2-((5-chloro-2H-indazol-2-yl)methyl)isonicotinic acid (110 mg, 0.38 mmol, 1.0 eq), TEA (105 mg, 1.0 mmol, 3.0 eq) and 5-(aminomethyl)-4,6-dimethylpyridin-2-amine hydrochloride (71 mg, 0.38 mmol, 1.0 eq) in DMF (3 mL) was added HATU (290 mg, 0.76 mmol, 2.0 eq) at 0° C. The reaction mixture was stirred at rt for 16 h, and then diluted with EtOAc (50 mL). The new mixture was washed with water (30 mL), brine (30 mL×2), dried and concentrated. The residue was purified by chromatography on silica gel (DCM/MeOH=50/1 to 10/1, v/v) and then Prep-TLC (DCM/MeOH=10/1, v/v) to afford N-((6-amino-2,4-dimethylpyridin-3-yl)methyl)-2-((5-chloro-2H-indazol-2-yl)methyl)isonicotinamide (30 mg, 19%) as a white solid. LCMS (M+H$^+$) m/z calculated 421.2. found 421.0.

$^1$H NMR (DMSO-d$_6$, 400 MHz): δ 8.84 (s, 1H), 8.65 (d, 1H), 8.55 (d, 1H), 7.85 (dd, 1H), 7.69 (dd, 1H), 7.60-7.63 (m, 2H), 7.23 (dd, 1H), 6.38 (s, 1H), 5.81 (s, 2H), 4.33 (d, 2H), 2.41 (s, 3H), 2.27 (s, 3H).

Example 107: Preparation of N-((6-amino-2,4-dimethylpyridin-3-yl)methyl)-2-((5-methyl-2H-indazol-2-yl)methyl)isonicotinamide

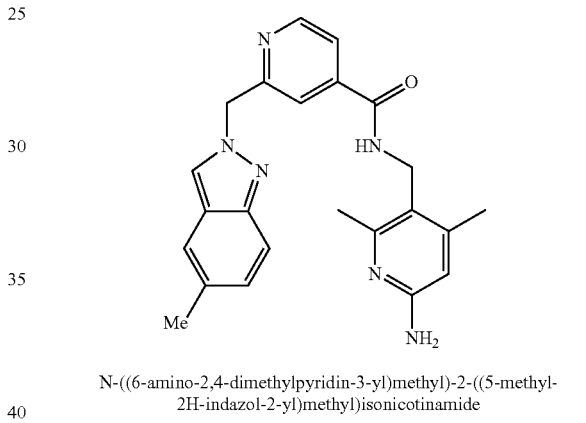

N-((6-amino-2,4-dimethylpyridin-3-yl)methyl)-2-((5-methyl-2H-indazol-2-yl)methyl)isonicotinamide Step 1: Preparation of methyl 2-((5-chloro-2H-indazol-2-yl)methyl)isonicotinate

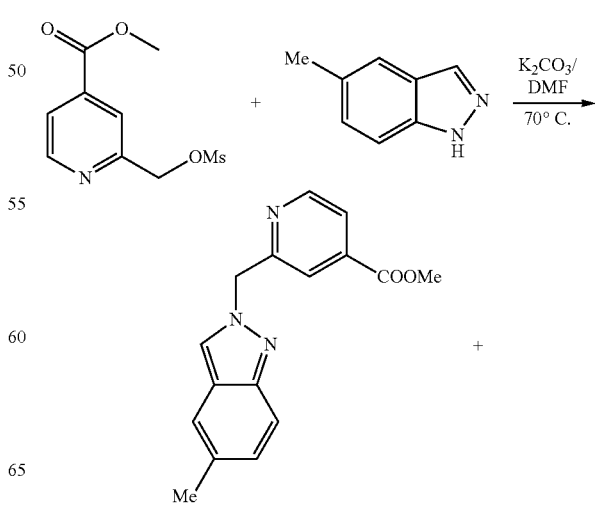

367
-continued

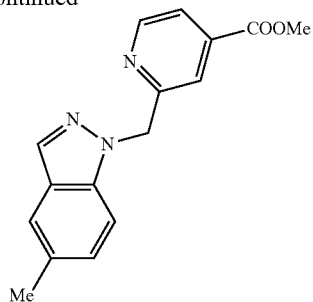

Methyl 2-((5-methyl-2H-indazol-2-yl)methyl)isonicotinate and methyl 2-((5-methyl-1H-indazol-1-yl)methyl)isonicotinate were prepared as described for methyl 2-((5-chloro-2H-indazol-2-yl)methyl)isonicotinate.

¹H NMR (CDCl₃, 400 MHz): δ 8.72 (d, 1H), 7.98 (s, 1H), 7.77 (dd, 1H), 7.67 (s, 1H), 7.61 (d, 1H), 7.39 (s, 1H), 7.12 (dd, 1H), 5.75 (s, 2H), 3.88 (s, 3H), 2.40 (s, 3H).

Methyl 2-((5-methyl-1H-indazol-1-yl)methyl)isonicotinate: ¹H NMR (CDCl₃, 400 MHz): δ 8.72 (d, 1H), 8.00 (s, 1H), 7.72 (d, 1H), 7.51 (s, 1H), 7.47 (s, 1H), 7.29 (d, 1H), 7.18 (d, 1H), 5.76 (s, 2H), 3.84 (s, 3H), 2.43 (s, 3H).

Step 2: Preparation of N-((6-amino-2,4-dimethylpyridin-3-yl)methyl)-2-((5-chloro-2H-indazol-2-yl)methyl)isonicotinamide

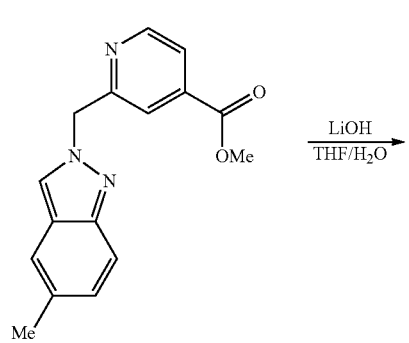

368
-continued

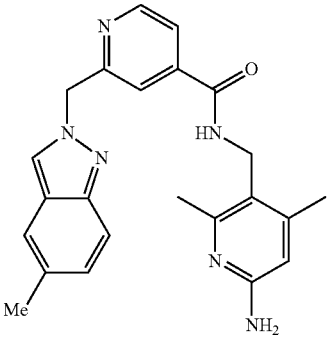

N-((6-amino-2,4-dimethylpyridin-3-yl)methyl)-2-((5-methyl-2H-indazol-2-yl)methyl)isonicotinamide was prepared as described for N-((6-amino-2,4-dimethylpyridin-3-yl)methyl)-2-((5-chloro-2H-indazol-2-yl)methyl)isonicotinamide. LCMS (M+H+) m/z calculated 401.2. found 401.0. 1H NMR (DMSO-d6, 400 MHz): δ 8.78 (s, 1H), 8.63 (d, 1H), 8.38 (s, 1H), 7.75-7.64 (m, 1H), 7.54 (s, 1H), 7.47 (d, 1H), 7.46 (s, 1H), 7.07 (dd, 1H), 6.29 (s, 2H), 5.75 (s, 2H), 4.32 (d, 2H), 2.35 (s, 6H), 2.22 (s, 3H).

Example 108: Preparation of N-((6-amino-2,4-dimethylpyridin-3-yl)methyl)-2-((5-methyl-3a,7a-dihydro-1H-indazol-1-yl)methyl)isonicotinamide

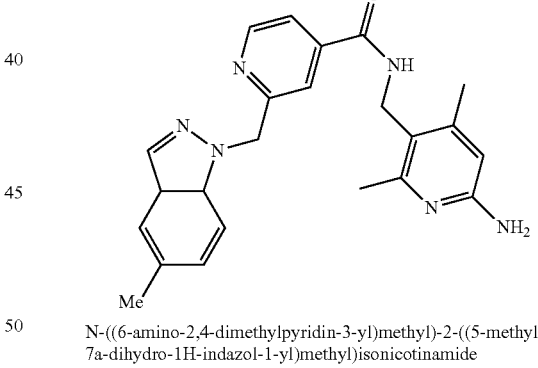

N-((6-amino-2,4-dimethylpyridin-3-yl)methyl)-2-((5-methyl-3a,7a-dihydro-1H-indazol-1-yl)methyl)isonicotinamide

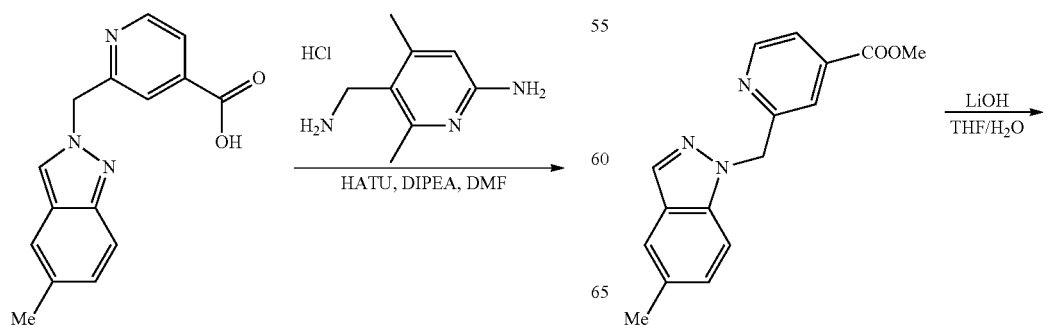

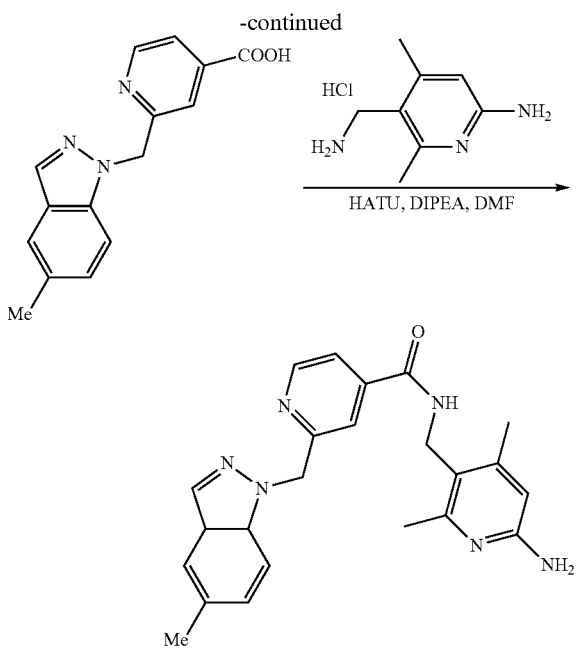

N-((6-amino-2,4-dimethylpyridin-3-yl)methyl)-2-((5-methyl-3a,7a-dihydro-1H-indazol-1-yl)methyl)isonicotinamide was prepared as described for N-((6-amino-2,4-dimethylpyridin-3-yl)methyl)-2-((5-chloro-1H-indazol-1-yl)methyl)isonicotinamide (Example 105). LCMS (M+H⁺) m/z calculated 401.2. found 401.0. ¹H NMR (DMSO-d₆, 400 MHz): δ 8.68 (t, 1H), 8.59 (d, 1H), 8.01 (d, 1H), 7.63 (dd, 1H), 7.54 (d, 1H), 7.53 (s, 1H), 7.38 (s, 1H), 7.26-7.13 (m, 1H), 6.16 (s, 1H), 5.87 (s, 2H), 5.75 (s, 2H), 4.29 (d, 2H), 2.40 (s, 3H), 2.29 (s, 3H), 2.15 (s, 3H).

Example 109: Preparation of N-((3-chloro-6-fluoro-1H-indol-5-yl)methyl)-2-((6-methyl-2-(methylsulfonyl)quinolin-3-yl)methyl)isonicotinamide

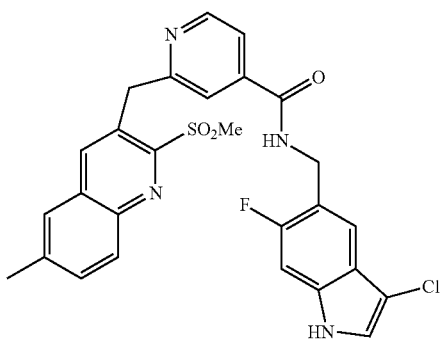 [SMILES: Cc1ccc2nc(S(C)(=O)=O)c(Cc3cc(C(=O)NCc4cc5c(Cl)c[nH]c5cc4F)ccn3)cc2c1]

N-((3-chloro-6-fluoro-1H-indol-5-yl)methyl)-2-((6-methyl-2-(methylsulfonyl)quinolin-3-yl)methyl)isonicotinamide (19 mg, 13% yields for 2 steps) was prepared as described for N-((6-amino-2,4-dimethylpyridin-3-yl)methyl)-2-((3-methyl-8-(methylsulfonyl)quinolin-6-yl)methyl)isonicotinamide (Example 15) as purple solid. LRMS (M+H⁺) m/z calculated 537.1. found 537.1. ¹H NMR (DMSO-d₆, 400 MHz) δ 11.40 (s, 1H), 9.27-9.24 (t, 1H), 8.63-8.62 (d, 1H), 8.31 (s, 1H), 8.02-8.00 (d, 1H), 7.82 (s, 1H), 7.75-7.45 (m, 5H), 7.24-7.21 (d, 1H), 4.78 (s, 2H), 4.60-4.58 (d, 2H), 3.52 (s, 3H), 2.52-2.51 (t, 3H).

Example 110: Preparation of N-((3-chloro-6-fluoro-1H-indol-5-yl)methyl)-2-((2-methylquinolin-6-yl)methyl)isonicotinamide

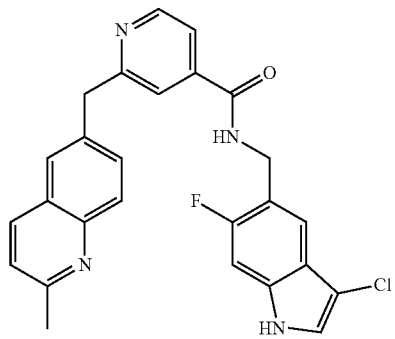 [SMILES: Cc1ccc2cc(Cc3cc(C(=O)NCc4cc5c(Cl)c[nH]c5cc4F)ccn3)ccc2n1]

N-((3-chloro-6-fluoro-1H-indol-5-yl)methyl)-2-((2-methylquinolin-6-yl)methyl)isonicotinamide (16 mg, 15%) was prepared as described in Example 24, Step 7 as a yellow solid. LRMS (M+H⁺) m/z calculated 459.1. found 459.1. ¹H NMR (DMSO-d₆, 300 MHz) δ 11.39 (s, 1H), 9.24 (t, 1H), 8.66-8.64 (d, 1H), 8.18-8.16 (d, 1H), 7.85-7.78 (m, 3H), 7.65-7.62 (m, 2H), 7.50-7.36 (m, 3H), 7.24-7.20 (d, 1H), 4.59-4.57 (d, 2H), 4.33 (s, 2H), 2.62 (s, 3H).

Example 111: Preparation of N-((1-aminoisoquinolin-6-yl)methyl)-2-((2-methylquinolin-6-yl)methyl)isonicotinamide

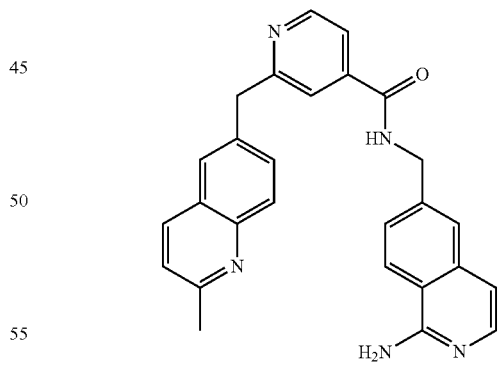

N-((1-aminoisoquinolin-6-yl)methyl)-2-((2-methylquinolin-6-yl)methyl)isonicotinamide (30 mg, 20% yield for 2 steps) was prepared as described for N-((1-aminoisoquinolin-6-yl)methyl)-2-((3-methylquinolin-6-yl)methyl)isonicotinamide (Example 142). LRMS (M+H⁺) m/z calculated 434.2. found 434.2. ¹H NMR (CD₃OD, 300 MHz) δ 8.64 (d, 1H), 8.14 (d, 1H), 8.06 (d, 1H), 7.88 (d, 1H), 7.77-7.59 (m, 6H), 7.47 (d, 1H), 7.37 (d, 1H), 6.90 (d, 1H), 4.69 (s, 2H), 4.38 (s, 2H), 2.68 (s, 3H).

Example 112: Preparation of N-((6-amino-2-methylpyridin-3-yl)methyl)-2-((2-methylquinolin-6-yl)methyl)isonicotinamide

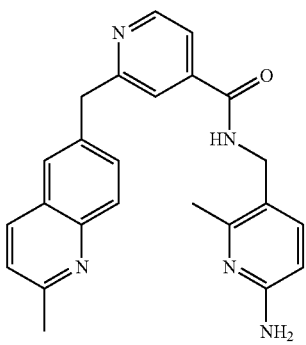 [SMILES: Cc1ccc2cc(Cc3cc(C(=O)NCc4ccc(N)nc4C)ccn3)ccc2n1]

N-((6-amino-2-methylpyridin-3-yl)methyl)-2-((2-methylquinolin-6-yl)methyl)isonicotinamide (29 mg, 14%) was prepared as described in Example 24, Step 7 as a yellow solid. LRMS (M+H$^+$) m/z calculated 398.1. found 398.1. $^1$H NMR (DMSO-d$_6$, 400 MHz) δ 9.02 (t, 1H), 8.65-8.63 (d, 1H), 8.18-8.16 (d, 1H), 7.86-7.63 (m, 5H), 7.38-7.36 (d, 2H), 7.26-7.24 (d, 1H), 6.25-6.23 (d, 1H), 5.77-5.76 (d, 2H), 4.33-4.29 (m, 4H), 2.63 (s, 3H), 2.23 (s, 3H).

Example 113: Preparation of N-((6-amino-2,4-dimethylpyridin-3-yl)methyl)-2-((2-methylquinolin-6-yl)methyl)isonicotinamide

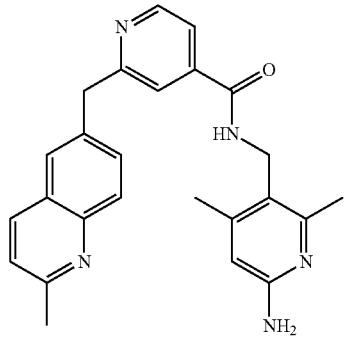

N-((6-amino-2,4-dimethylpyridin-3-yl)methyl)-2-((2-methylquinolin-6-yl)methyl)isonicotinamide (45 mg, 16%) was prepared as described in Example 24, Step 7. LRMS (M+H$^+$) m/z calculated 411.9. found 411.9. $^1$H NMR (DMSO-d$_6$, 300 MHz) δ 8.59-8.65 (m, 2H), 8.17 (d, 1H), 7.83 (d, 1H), 7.75 (d, 2H), 7.58-7.64 (m, 2H), 7.37 (d, 1H), 6.11 (s, 1H), 5.67 (s, 2H), 4.30-4.34 (m, 3H), 2.61 (d, 3H), 2.29 (s, 3H), 2.15 (s, 3H).

Example 114: Preparation of N-((6-amino-2,4-dimethylpyridin-3-yl)methyl)-2-((6-methylquinolin-3-yl)methyl)isonicotinamide

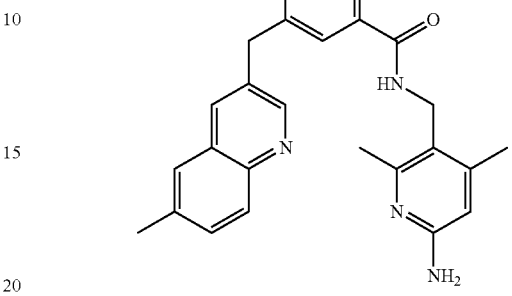

N-((6-amino-2,4-dimethylpyridin-3-yl)methyl)-2-((6-methylquinolin-3-yl)methyl)isonicotinamide (29 mg, 21%) was prepared as described in Example 24, Step 7 as a yellow solid. LRMS (M+H$^+$) m/z calculated 412.1. found 412.1. $^1$H NMR (DMSO-d$_6$, 400 MHz) δ 8.72 (s, 1H), 8.57-8.52 (d, 2H), 8.00 (s, 1H), 7.80-7.58 (m, 2H), 7.53-7.44 (m, 3H), 6.05 (s, 1H), 5.62 (s, 2H), 4.26 (s, 4H), 2.42-2.39 (m, 3H), 2.22 (s, 3H), 2.07 (s, 3H).

Example 115: Preparation of N-((1-aminoisoquinolin-6-yl)methyl)-2-((6-methylquinolin-3-yl)methyl)isonicotinamide

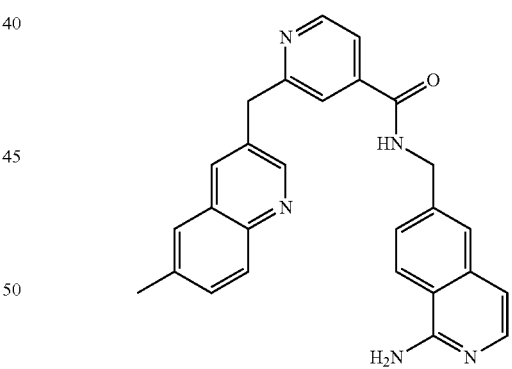

N-((1-aminoisoquinolin-6-yl)methyl)-2-((6-methylquinolin-3-yl)methyl)isonicotinamide (27 mg, 18% yield for 2 steps) was prepared as described for N-((1-aminoisoquinolin-6-yl)methyl)-2-((3-methylquinolin-6-yl)methyl)isonicotinamide (Example 142). LRMS (M+H$^+$) m/z calculated 434.2. found 434.2. $^1$H NMR (CD$_3$OD, 400 MHz) δ 8.74 (d, 1H), 8.66 (d, 1H), 8.11 (s, 1H), 8.07 (d, 1H), 7.88 (d, 1H), 7.83 (s, 1H), 7.72 (d, 1H), 7.69 (d, 1H), 7.61 (s, 2H), 7.51 (d, 1H), 7.49 (d, 1H), 6.92 (d, 1H), 4.71 (s, 2H), 4.41 (s, 2H), 2.51 (s, 3H).

Example 116: Preparation of N-((3-chloro-6-fluoro-1H-indol-5-yl)methyl)-2-((6-methylquinolin-3-yl)methyl) isonicotinamide

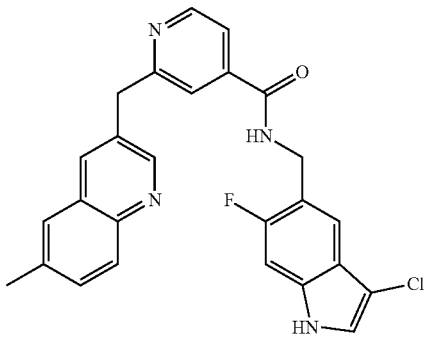 [SMILES: Cc1ccc2ncc(Cc3cc(C(=O)NCc4cc5c(Cl)c[nH]c5cc4F)ccn3)cc2c1]

N-((3-chloro-6-fluoro-1H-indol-5-yl)methyl)-2-((6-methyl quinolin-3-yl) methyl)isonicotinamide (62 mg, 40%) was prepared as described in Example 24, Step 7 as an off-white solid. LRMS (M+H⁺) m/z calculated 459. found 459. $^1$H NMR (DMSO-d$_6$, 400 MHz) δ 11.39 (s, 1H), 9.24 (t, 1H), 8.80 (s, 1H), 8.64 (d, 1H), 8.09 (s, 1H), 7.87 (d, 1H), 7.81 (s, 1H), 7.65-7.67 (m, 2H), 7.50-7.55 (m, 2H), 7.45 (d, 1H), 7.23 (d, 1H), 4.59 (d, 2H), 4.37 (s, 2H), 2.48 (s, 3H).

Example 117: Preparation of N-((6-amino-2-methylpyridin-3-yl)methyl)-2-((6-methylquinolin-3-yl)methyl)isonicotinamide

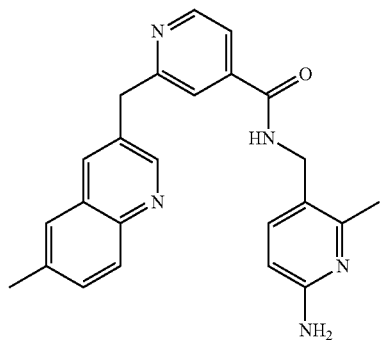

N-((6-amino-2-methylpyridin-3-yl)methyl)-2-((6-methylquinolin-3-yl)methyl)isonicotinamide was prepared as described in Example 24, Step 7.

Example 118: Preparation of N-((1-aminoisoquinolin-6-yl)methyl)-2-((6-fluoroquinolin-3-yl)methyl) isonicotinamide

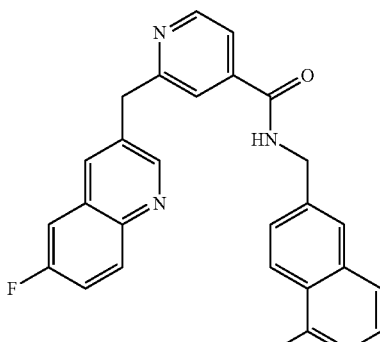

N-((1-aminoisoquinolin-6-yl)methyl)-2-((6-fluoroquinolin-3-yl)methyl)isonicotinamide (30 mg, 20% yield for 2 steps) was prepared as described for N-((1-aminoisoquinolin-6-yl)methyl)-2-((3-methylquinolin-6-yl)methyl)isonicotinamide (Example 142). LRMS (M+H⁺) m/z calculated 438.2. found 438.2. $^1$H NMR (CD$_3$OD, 300 MHz) δ 8.81 (d, 1H), 8.66 (d, 1H), 8.20 (d, 1H), 8.08 (d, 1H), 8.05 (dd, 1H), 7.83 (s, 1H), 7.71 (d, 1H), 7.70 (d, 1H), 7.62 (s, 1H), 7.57-7.47 (m, 3H), 6.93 (d, 1H), 4.72 (s, 2H), 4.44 (s, 2H).

Example 119: Preparation of N-((6-amino-2,4-dimethylpyridin-3-yl)methyl)-2-((6-fluoroquinolin-3-yl)methyl)isonicotinamide

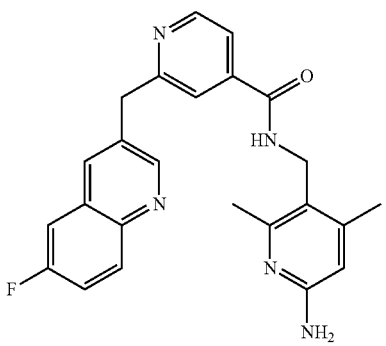

N-((6-amino-2,4-dimethylpyridin-3-yl)methyl)-2-((6-fluoroquinolin-3-yl)methyl)isonicotinamide (35 mg, 25%) was prepared as described in Example 24, Step 7 as an off-white solid. LRMS (M+H⁺) m/z calculated 416.1. found 416.1. $^1$H NMR (DMSO-d$_6$, 300 MHz) δ 8.87-8.86 (d, 1H), 8.66-8.58 (m, 2H), 8.18 (d, 1H), 8.06-8.02 (m, 1H), 7.78-7.72 (m, 2H), 7.64-7.58 (m, 2H), 6.11 (s, 2H), 5.68 (s, 2H), 4.36-4.33 (m, 4H), 2.30 (s, 3H), 2.16 (s, 3H).

Example 120: Preparation of N-((3-chloro-6-fluoro-1H-indol-5-yl)methyl)-2-((6-fluoroquinolin-3-yl)methyl)isonicotinamide

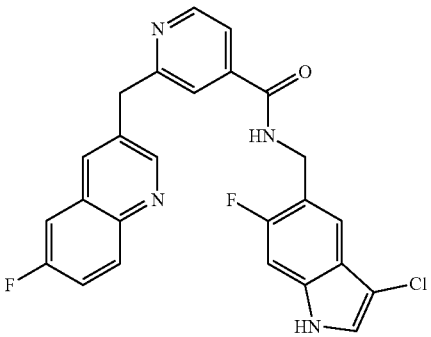 [SMILES: O=C(NCc1cc2c(Cl)c[nH]c2cc1F)c1ccnc(Cc2cnc3ccc(F)cc3c2)c1]

N-((3-chloro-6-fluoro-1H-indol-5-yl)methyl)-2-((6-fluoroquinolin-3-yl)methyl)isonicotinamide (42 mg, 26.8%) was prepared as described in Example 24, Step 7. LRMS (M+H⁺) m/z calculated 463.1. found 463.1. $^1$H NMR (DMSO-d$_6$, 300 MHz) δ 11.41 (s, 1H), 9.26 (t, 1H), 8.88 (d, 1H), 8.65 (d, 1H), 8.10 (d, 1H), 8.02-8.07 (m, 1H), 7.82 (s, 1H), 7.74 (dd, 1H), 7.61-7.67 (m, 2H), 7.51 (s, 1H), 7.45 (d, 1H), 7.22 (d, 1H), 4.59 (d, 2H), 4.39 (s, 2H).

Example 121: Preparation of N-((6-amino-2-methylpyridin-3-yl)methyl)-2-((6-fluoroquinolin-3-yl)methyl)isonicotinamide

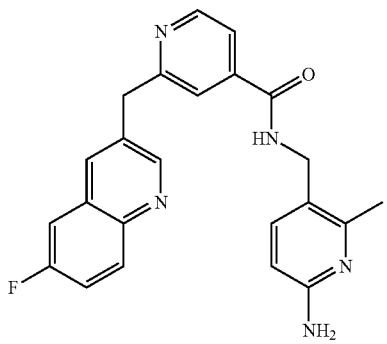 [SMILES: Cc1nc(N)ccc1CNC(=O)c1ccnc(Cc2cnc3ccc(F)cc3c2)c1]

N-((6-amino-2-methylpyridin-3-yl)methyl)-2-((6-fluoroquinolin-3-yl)methyl)isonicotinamide (18 mg, 13.2%) was prepared as described in Example 24, Step 7. LRMS (M+H$^+$) m/z calculated 401.9. found 401.9. $^1$H NMR (CD$_3$OD, 300 MHz) δ 8.80 (d, 1H), 8.63 (d, 1H), 8.20 (s, 1H), 8.01-8.04 (m, 1H), 7.78 (s, 1H), 7.63-7.64 (m, 1H), 7.52-7.58 (m, 3H), 7.40 (d, 1H), 4.43 (d, 4H), 2.38 (s, 3H).

Example 122: Preparation of N-((6-amino-2,4-dimethylpyridin-3-yl)methyl)-2-((7-fluoroquinolin-3-yl)methyl)isonicotinamide

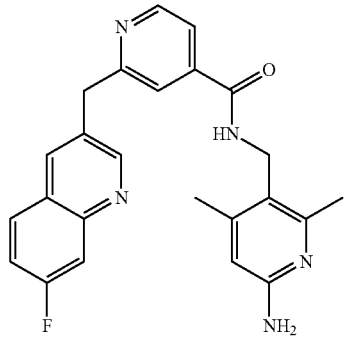 [SMILES: Cc1cc(N)nc(C)c1CNC(=O)c1ccnc(Cc2cnc3cc(F)ccc3c2)c1]

N-((6-amino-2,4-dimethylpyridin-3-yl)methyl)-2-((7-fluoroquinolin-3-yl)methyl)isonicotinamide (35 mg, 25%) was prepared as described in Example 24, Step 7. LRMS (M+H$^+$) m/z calculated 415.9. found 415.9. $^1$H NMR (DMSO-d$_6$, 300 MHz) δ 8.92 (d, 1H), 8.65 (t, 1H), 8.60 (d, 1H), 8.26 (s, 1H), 8.04 (dd, 1H), 7.79 (s, 1H), 7.73 (dd, 1H), 7.61 (d, 1H), 7.51-7.55 (m, 1H), 6.13 (s, 1H), 5.68 (s, 2H), 4.35-4.37 (m, 4H), 2.31 (s, 3H), 2.17 (s, 3H).

Example 123: Preparation of N-((3-chloro-6-fluoro-1H-indol-5-yl)methyl)-2-((7-fluoroquinolin-3-yl)methyl)isonicotinamide

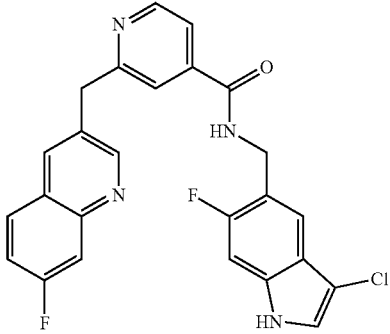 [SMILES: O=C(NCc1cc2c(Cl)c[nH]c2cc1F)c1ccnc(Cc2cnc3cc(F)ccc3c2)c1]

N-((3-chloro-6-fluoro-1H-indol-5-yl)methyl)-2-((7-fluoroquinolin-3-yl)methyl)isonicotinamide (45 mg, 28.7%) was prepared as described in Example 24, Step 7. LRMS (M+H$^+$) m/z calculated 462.8. found 462.8. $^1$H NMR (DMSO-d$_6$, 300 MHz) δ 11.39-11.42 (m, 1H), 9.26 (t, 1H), 8.92 (s, 1H), 8.64 (d, 1H), 8.27 (s, 1H), 8.04 (dd, 1H), 7.82 (s, 1H), 7.65-7.74 (m, 2H), 7.43-7.55 (m, 3H), 7.22 (d, 1H), 4.59 (d, 2H), 4.38 (s, 2H).

Example 124: Preparation of N-((1-aminoisoquinolin-6-yl)methyl)-2-((7-fluoroquinolin-3-yl)methyl)isonicotinamide

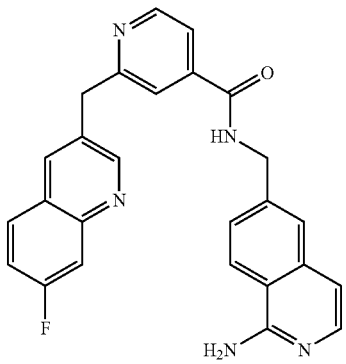

N-((1-aminoisoquinolin-6-yl)methyl)-2-((7-fluoroquinolin-3-yl)methyl)isonicotinamide (16 mg, 10.8%) was prepared as described for N-((1-aminoisoquinolin-6-yl)methyl)-2-((3-methylquinolin-6-yl)methyl)isonicotinamide (Example 142). LRMS (M+H$^+$) m/z calculated 437.8. found 437.8. $^1$H NMR (CD$_3$OD, 400 MHz) δ 8.72 (d, 1H), 8.52 (d, 1H), 8.09 (s, 1H), 7.93 (d, 1H), 7.77-7.80 (m, 1H), 7.70 (s, 1H), 7.56-7.58 (m, 2H), 7.47-7.50 (m, 2H), 7.35 (d, 2H), 7.26-7.31 (m, 1H), 6.78 (d, 1H), 4.58 (s, 2H), 4.29 (s, 2H).

Example 125: Preparation of N-((3-chloro-6-fluoro-1H-indol-5-yl)methyl)-2-(quinolin-3-ylmethyl)isonicotinamide

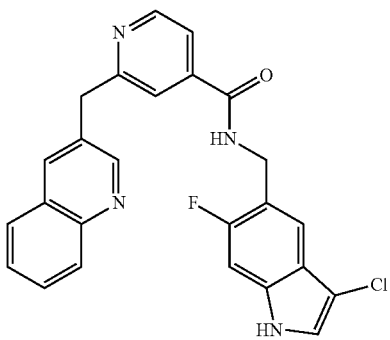 [SMILES: O=C(NCc1cc2c(Cl)c[nH]c2cc1F)c1ccnc(Cc2cnc3ccccc3c2)c1]

N-((3-chloro-6-fluoro-1H-indol-5-yl)methyl)-2-(quinolin-3-ylmethyl)isonicotinamide (24 mg, 17%) was prepared as described in Example 24, Step 7 as a yellow solid. LRMS (M+H$^{+}$) m/z calculated 445.1. found 445.1. $^1$H NMR (DMSO-d$_6$, 400 MHz) δ 11.40 (s, 1H), 9.26 (t, 1H), 9.01 (s, 1H), 8.66-8.65 (d, 1H), 8.40 (s, 1H), 8.05-8.00 (t, 2H), 7.85 (s, 1H), 7.80 (t, 1H), 7.69-7.66 (m, 2H), 7.51-7.44 (m, 2H), 7.24-7.21 (d, 1H), 4.60-4.59 (d, 2H), 4.44 (s, 2H).

Example 126: Preparation of N-((3-chloro-6-fluoro-1H-indol-5-yl)methyl)-2-((6-chloroquinolin-3-yl)methyl)isonicotinamide

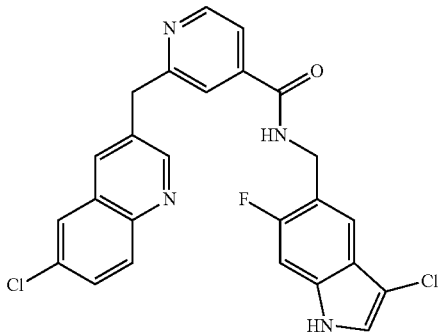 [SMILES: O=C(NCc1cc2c(Cl)c[nH]c2cc1F)c1ccnc(Cc2cnc3ccc(Cl)cc3c2)c1]

N-((3-chloro-6-fluoro-1H-indol-5-yl)methyl)-2-((6-chloro quinolin-3-yl)methyl) isonicotinamide (12 mg, 15%) was prepared as described in Example 24, Step 7 as an off-white solid. LRMS (M+H$^+$) m/z calculated 479. found 479. $^1$H NMR (DMSO-d$_6$, 400 MHz) δ 11.39 (s, 1H), 9.25 (t, 1H), 8.92 (d, 1H), 8.64 (d, 1H), 8.20 (s, 1H), 8.08 (d, 1H), 8.00 (d, 1H), 7.82 (s, 1H), 7.71 (d, 1H), 7.66 (d, 2H), 7.50 (d, 2H), 7.45 (d, 1H), 7.22 (d, 1H), 4.59 (d, 2H), 4.40 (s, 2H).

Example 127: Preparation of N-((1-aminoisoquinolin-6-yl)methyl)-2-((2-methylquinolin-7-yl)methyl)isonicotinamide

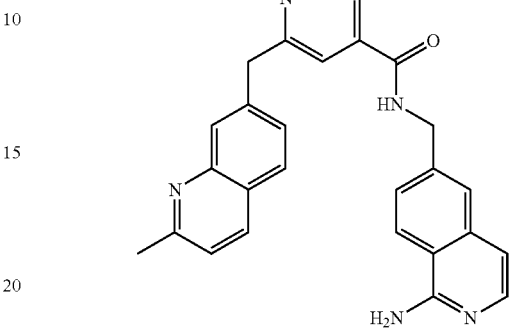

N-((1-aminoisoquinolin-6-yl)methyl)-2-((2-methylquinolin-7-yl)methyl)isonicotinamide (35 mg, 22%) was prepared as described for N-((1-aminoisoquinolin-6-yl)methyl)-2-((3-methylquinolin-6-yl)methyl)isonicotinamide (Example 142). LRMS (M+H$^{+)}$ m/z calculated 434. found 434. $^1$H NMR (DMSO-d$_6$, 400 MHz) δ 9.39 (t, 1H), 8.67 (d, 1H), 8.18 (d, 1H), 8.13 (d, 1H), 7.80-7.85 (m, 3H), 7.75 (d, 1H), 7.68 (d, 1H), 7.54 (s, 1H), 7.47 (d, 1H), 7.35-7.40 (m, 2H), 6.84 (d, 1H), 6.72 (s, 2H), 4.60 (d, 2H), 4.37 (s, 2H), 2.62 (s, 3H).

Example 128: Preparation of N-((3-chloro-6-fluoro-1H-indol-5-yl)methyl)-2-((2-methylquinolin-7-yl)methyl)isonicotinamide

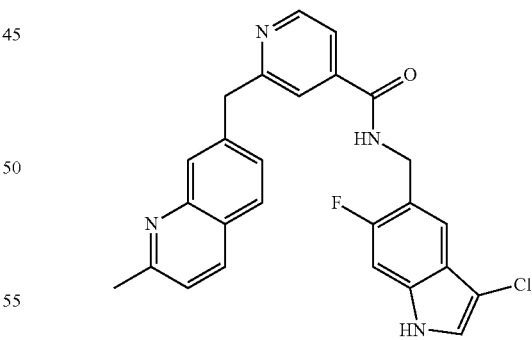

N-((3-chloro-6-fluoro-1H-indol-5-yl)methyl)-2-((2-methylquinolin-7-yl)methyl)isonicotinamide (25 mg, 15%) was prepared as described in Example 24, Step 7. LRMS (M+H+) m/z calculated 459. found 459. $^1$H NMR (DMSO-d$_6$, 300 MHz) δ 11.40 (br, 1H), 9.26 (t, 1H), 8.65 (d, 1H), 8.17 (d, 1H), 7.79-7.84 (m, 3H), 7.65 (d, 1H), 7.42-7.50 (m, 3H), 7.35 (d, 1H), 7.22 (d, 2H), 4.57 (d, 2H), 4.35 (s, 2H), 2.62 (s, 3H).

Example 129: Preparation of N-((6-amino-2,4-dimethylpyridin-3-yl)methyl)-2-((2-methylquinolin-7-yl)methyl)isonicotinamide

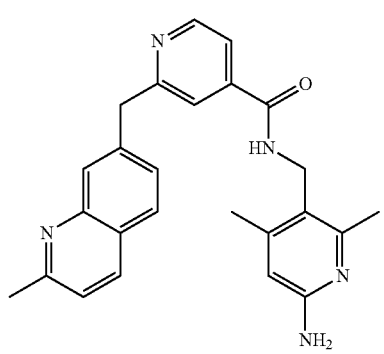

N-((6-amino-2,4-dimethylpyridin-3-yl)methyl)-2-((2-methylquinolin-7-yl)methyl)isonicotinamide (10 mg, 7%) was prepared as described in Example 24, Step 7. LRMS (M+H$^+$) m/z calculated 412. found 412. $^1$H NMR (DMSO-d$_6$, 300 MHz) δ 8.59-8.64 (m, 2H), 8.17 (d, 1H), 7.82 (d, 1H), 7.76 (d, 2H), 7.60 (d, 1H), 7.45 (d, 1H), 7.35 (d, 1H), 6.10 (s, 1H), 5.67 (s, 2H), 4.33 (s, 4H), 2.62 (s, 3H), 2.29 (s, 3H), 2.15 (s, 3H).

Example 130: Preparation of N-(3-chloro-6-fluoro-1H-indol-5-ylmethyl)-2-(2-cyano-quinolin-6-ylmethyl)-isonicotinamide

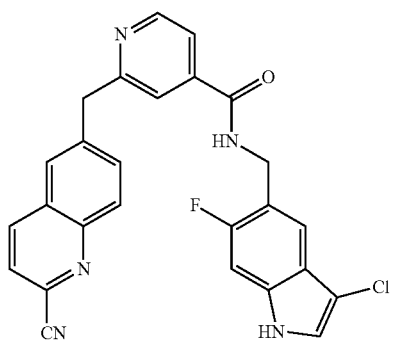 [SMILES: N#Cc1ccc2cc(Cc3cc(C(=O)NCc4cc5c(Cl)c[nH]c5cc4F)ccn3)ccc2n1]

N-(3-chloro-6-fluoro-1H-indol-5-ylmethyl)-2-(2-cyano-quinolin-6-ylmethyl)-isonicotinamide (90 mg, 22%) was prepared as described in Example 24, Step 7. LRMS (M+H$^+$) m/z calculated 570.1. found 570.1. $^1$H NMR (DMSO-d$_6$, 400 MHz) δ 11.41 (s, 1H), 9.26 (t, 1H), 8.60-8.65 (m, 2H), 8.00-8.08 (m, 3H), 7.87-7.89 (dd, 1H), 7.81 (s, 1H), 7.66-7.67 (dd, 1H), 7.50-7.51 (d, 1H), 7.43-7.45 (d, 1H), 7.21-7.24 (d, 1H), 4.58-4.59 (d, 2H), 4.42 (s, 2H).

Example 131: Preparation of N-(6-amino-2,4-dimethyl-pyridin-3-ylmethyl)-2-(2-cyano-quinolin-6-ylmethyl)-isonicotinamide

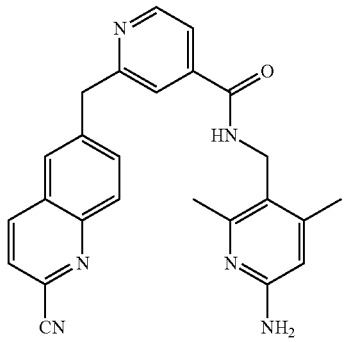 [SMILES: Cc1cc(N)nc(C)c1CNC(=O)c1ccnc(Cc2ccc3nc(C#N)ccc3c2)c1]

N-(6-amino-2,4-dimethyl-pyridin-3-ylmethyl)-2-(2-cyano-quinolin-6-ylmethyl)-isonicotinamide (90 mg, 26%) was prepared as described in Example 24, Step 7. LRMS (M+H$^+$) m/z calculated 423.1. found 423.1. $^1$H NMR (DMSO-d$_6$, 400 MHz) δ 8.60-8.64 (m, 3H), 8.00-8.07 (m, 3H), 7.86-7.88 (m, 1H), 7.78 (s, 1H), 7.61-7.62 (d, 1H), 6.12 (s, 1H), 5.68 (s, 2H), 4.33-4.40 (m, 4H), 2.30 (s, 3H), 2.16 (s, 3H).

Example 132: Preparation of N-((1-aminoisoquinolin-6-yl)methyl)-2-((3-methylisoquinolin-6-yl)methyl)isonicotinamide

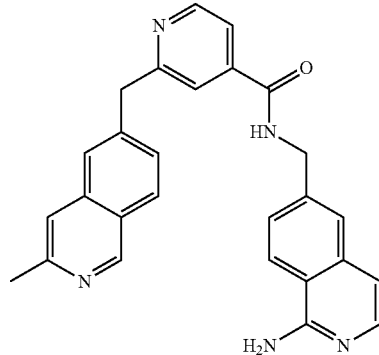 [SMILES: Cc1cc2cc(Cc3cc(C(=O)NCc4ccc5c(N)nccc5c4)ccn3)ccc2cn1]

Step 1: Preparation of 6-bromo-3-methyl-isoquinoline

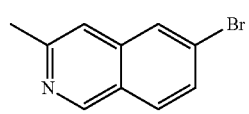

To a solution of 4-bromo-benzylamine (10.0 g, 54 mmol, 1.0 eq) in DCE (100 mL) was added 1,1-dimethoxy-propan-2-one (7.0 g, 59 mmol, 1.1 eq) and MgSO$_4$ (20 g). The mixture was stirred at 40° C. overnight. Then to the mixture was added NaBH$_3$CN (4.08 g, 64.8 mmol, 1.2 eq). After stirring at rt for 5 h the mixture was filtered. The filtrate was concentrated to give a yellow oil. Chlorosulfonic acid (30 mL) was cooled to −10° C. and the above crude product was added dropwise. The reaction mixture was heated to 100° C. for 10 min, then cooled and poured into ice. The mixture was neutralized with 2M NaOH and extracted with EtOAc. The combined extracts were dried and concentrated. The residue was purified by silica gel chromatography (PE/EtOAc=2/1, v/v) to afford 6-bromo-3-methyl-isoquinoline (4.0 g, 34% yield for 3 steps) as a yellow solid.

Step 2: Preparation of methyl 3-methylisoquinoline-6-carboxylate

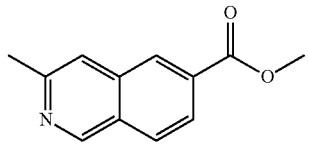

An autoclave vessel was charged with 6-bromo-3-methyl-isoquinoline (4.0 g, 18 mmol), Pd(dppf)Cl$_2$ (735 mg, 0.9 mmol, 0.05 eq) and triethylamine (5.0 mL, 36 mmol, 2 eq) in 40 mL of methanol. The vessel was purged with nitrogen three times and carbon monoxide three times. The vessel was pressurized to 3 MPa with carbon monoxide and heated to 100° C. The reaction was thus stirred overnight, then allowed to cool to room temperature. The resulting solution was concentrated and purified by flash chromatography on silica gel (PE/EtOAc=1/1, v/v) to afford methyl 3-methyl-isoquinoline-6-carboxylate (3.4 g, 94%) as a white solid.

Step 3: Preparation of (3-methyl-isoquinolin-6-yl)-methanol

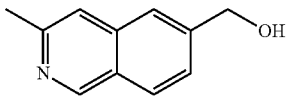

To a solution of methyl 3-methylisoquinoline-6-carboxylate (3.3 g, 16.42 mmol, 1 eq) in dry THF (100 mL) was added LiAlH(t-BuO)$_3$ (12.5 g, 45.25 mmol, 3 eq). The resulting mixture was stirred at 60° C. for 5 h and then quenched by the addition of water. The mixture was extracted with EtOAc. The combined extracts were dried and concentrated. The residue was purified by silica gel chromatography (PE/EtOAc=1/1, v/v) to afford (3-methyl-isoquinolin-6-yl)-methanol (2.5 g, 89%) as a white solid.

Step 4: Preparation of 6-chloromethyl-3-methyl-isoquinoline

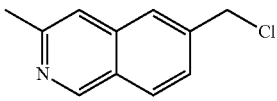

To (3-methyl-isoquinolin-6-yl)-methanol (1.5 g, 8.67 mmol, 1 eq) was added SOCl$_2$ (9 mL) and the mixture was stirred at rt for 3 h. The volatiles were then removed at 40° C. under vacuum and the residue was dissolved in DCM. The mixture was washed with saturated aq. NaHCO$_3$, dried and concentrated to give 6-chloromethyl-3-methyl-isoquinoline (1.4 g, 85%) as a white solid.

Step 5: Preparation of methyl 2-((3-methylisoquinolin-6-yl)methyl)isonicotinate

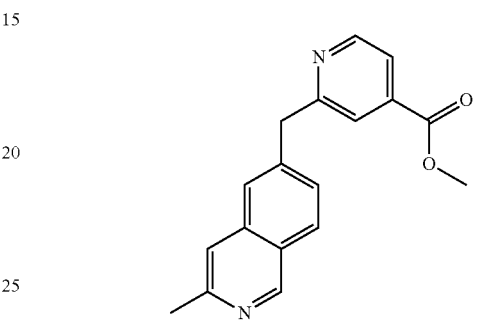

Methyl 2-((3-methylisoquinolin-6-yl)methyl)isonicotinate (1.0 g, 47%) was prepared as described for Example 24, Step 5.

Step 6: Preparation of N-((1-aminoisoquinolin-6-yl)methyl)-2-((3-methylisoquinolin-6-yl)methyl)isonicotinamide

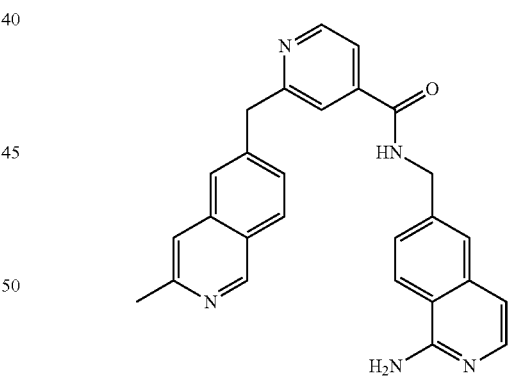

N-((1-aminoisoquinolin-6-yl)methyl)-2-((3-methylisoquinolin-6-yl)methyl)isonicotinamide (20 mg, 14% yield for 2 steps) was prepared as described for N-((1-aminoisoquinolin-6-yl)methyl)-2-((3-methylquinolin-6-yl)methyl)isonicotinamide (Example 142). LRMS (M+H$^+$) m/z calculated 434.2. found 434.2. $^1$H NMR (CD$_3$OD, 400 MHz) δ 9.06 (s, 1H), 8.66 (d, 1H), 8.08 (d, 1H), 7.97 (d, 1H), 7.80 (s, 1H), 7.71 (s, 2H), 7.70 (s, 1H), 7.62 (s, 1H), 7.56 (s, 1H), 7.50 (d, 1H), 7.47 (d, 1H), 6.92 (d, 1H), 4.71 (s, 2H), 4.11 (s, 2H), 2.64 (s, 3H).

Example 133: Preparation of N-((3-chloro-6-fluoro-1H-indol-5-yl)methyl)-2-((3-methylisoquinolin-6-yl)methyl)isonicotinamide

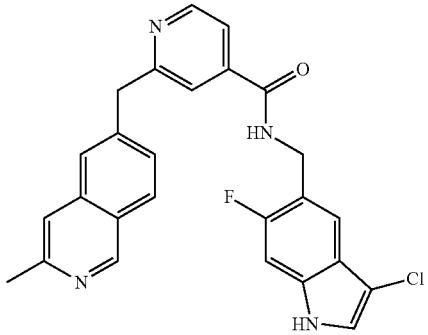 [SMILES: Cc1cc2cc(Cc3cc(C(=O)NCc4cc5c(Cl)c[nH]c5cc4F)ccn3)ccc2cn1]

N-((3-chloro-6-fluoro-1H-indol-5-yl)methyl)-2-((3-methylisoquinolin-6-yl)methyl)isonicotinamide (43 mg, 28% yield for 2 steps) was prepared as described for Example 132. LRMS (M+H$^+$) m/z calculated 459.1. found 459.1. $^1$H NMR (DMSO-d$_6$, 400 MHz) δ 11.42 (s, 1H), 9.26 (t, 1H), 9.15 (s, 1H), 8.67 (d, 1H), 8.00 (dd, 1H), 7.79 (s, 1H), 7.72 (s, 1H), 7.67 (d, 1H), 7.58 (s, 1H), 7.53 (d, 1H), 7.52 (s, 1H), 7.46 (d, 1H), 7.24 (d, 1H), 4.60 (d, 2H), 4.36 (s, 2H), 2.59 (s, 3H).

Example 134: Preparation of N-((1-aminoisoquinolin-6-yl)methyl)-2-((2-(methylsulfonyl)quinolin-6-yl)methyl)isonicotinamide

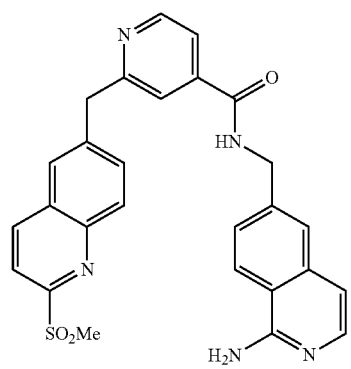 [SMILES: CS(=O)(=O)c1ccc2cc(Cc3cc(C(=O)NCc4ccc5c(N)nccc5c4)ccn3)ccc2n1]

N-((1-aminoisoquinolin-6-yl)methyl)-2-((2-(methylsulfonyl)quinolin-6-yl)methyl)isonicotinamide (34 mg, 34% yield for 2 steps) was prepared as described for N-((1-aminoisoquinolin-6-yl)methyl)-2-((3-methylquinolin-6-yl)methyl)isonicotinamide (Example 142). LRMS (M+H$^+$) m/z calculated 498.2. found 498.2. $^1$H NMR (CD$_3$OD, 400 MHz) δ 8.66 (d, 1H), 8.49 (d, 1H), 8.06 (d, 1H), 8.03 (d, 1H), 8.02 (s, 1H), 7.88 (s, 1H), 7.81 (s, 1H), 7.78 (d, 1H), 7.69 (d, 1H), 7.67 (d, 1H), 7.59 (s, 1H), 7.46 (d, 1H), 6.88 (d, 1H), 4.69 (s, 2H), 4.43 (s, 2H), 3.37 (s, 3H).

Example 135: Preparation of N-((3-chloro-6-fluoro-1H-indol-5-yl)methyl)-2-((2-(methylsulfonyl)quinolin-6-yl)methyl)isonicotinamide

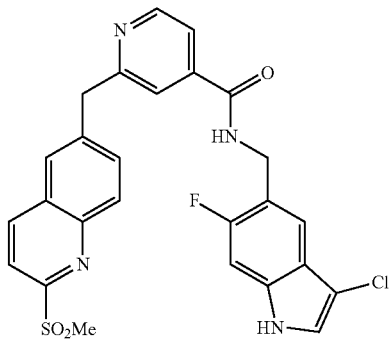 [SMILES: CS(=O)(=O)c1ccc2cc(Cc3cc(C(=O)NCc4cc5c(Cl)c[nH]c5cc4F)ccn3)ccc2n1]

N-((3-chloro-6-fluoro-1H-indol-5-yl)methyl)-2-((2-(methylsulfonyl)quinolin-6-yl)methyl)isonicotinamide (24 mg, 23%) was prepared as described in Example 24, Step 7. LRMS (M+H$^+$) m/z calculated 523.1. found 523.1. $^1$H NMR (CD$_3$OD, 400 MHz) δ 8.53 (d, 1H), 8.47 (d, 1H), 8.02 (d, 1H), 7.99 (d, 1H), 7.84 (s, 1H), 7.75 (d, 1H), 7.68 (s, 1H), 7.56 (d, 1H), 7.40 (d, 1H), 7.13 (s, 1H), 7.02 (s, 1H), 4.58 (s, 2H), 4.36 (s, 2H), 3.25 (s, 3H).

Example 136: Preparation of N-((1-aminoisoquinolin-6-yl)methyl)-2-((4-cyanoquinolin-6-yl)methyl)isonicotinamide

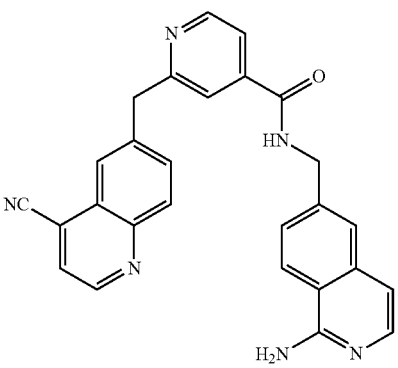 [SMILES: N#Cc1ccnc2ccc(Cc3cc(C(=O)NCc4ccc5c(N)nccc5c4)ccn3)cc12]

N-((1-aminoisoquinolin-6-yl)methyl)-2-((4-cyanoquinolin-6-yl)methyl)isonicotinamide (43 mg, 29% yield for 2 steps) was prepared as described for N-((1-aminoisoquinolin-6-yl)methyl)-2-((3-methylquinolin-6-yl)methyl)isonicotinamide (Example 142). LRMS (M+H$^+$) m/z calculated 445.2. found 445.2. $^1$H NMR (CD$_3$OD, 300 MHz) δ 9.40 (t, 1H), 9.06 (d, 1H), 8.69 (d, 1H), 8.15-8.11 (m, 3H), 8.06 (s, 1H), 7.92 (d, 1H), 7.87 (s, 1H), 7.77 (d, 1H), 7.71 (d, 1H), 7.56 (s, 1H), 7.41 (d, 1H), 6.85 (d, 1H), 6.73 (s, 2H), 4.62 (d, 2H), 4.50 (s, 2H).

Example 137: Preparation of N-((3-chloro-6-fluoro-1H-indol-5-yl)methyl)-2-((4-cyanoquinolin-6-yl)methyl)isonicotinamide

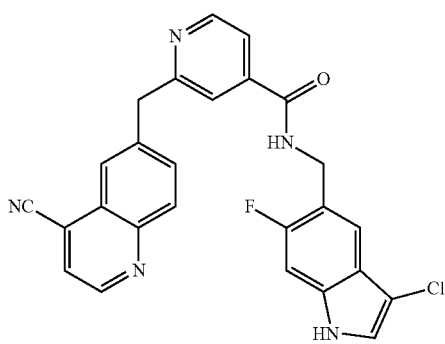 [SMILES: N#Cc1ccnc2ccc(Cc3cc(C(=O)NCc4cc5c(Cl)c[nH]c5cc4F)ccn3)cc12]

N-((3-chloro-6-fluoro-1H-indol-5-yl)methyl)-2-((4-cyanoquinolin-6-yl)methyl)isonicotinamide (45 mg, 29%) was prepared as described in Example 24, Step 7 as a yellow solid. LRMS (M+H$^+$) m/z calculated 470.1. found 470.1. $^1$H NMR (DMSO, 400 MHz) δ 11.42 (s, 1H), 9.28 (t, 1H), 9.07 (d, 1H), 8.68 (d, 1H), 8.14 (d, 1H), 8.12 (s, 1H), 8.06 (s, 1H), 7.91 (d, 1H), 7.86 (s, 1H), 7.68 (d, 1H), 7.51 (d, 1H), 7.46 (d, 1H), 7.24 (d, 1H), 4.60 (d, 1H), 4.49 (s, 2H).

Example 138: Preparation of N-((6-amino-2,4-dimethylpyridin-3-yl)methyl)-2-((4-cyanoquinolin-6-yl)methyl)isonicotinamide

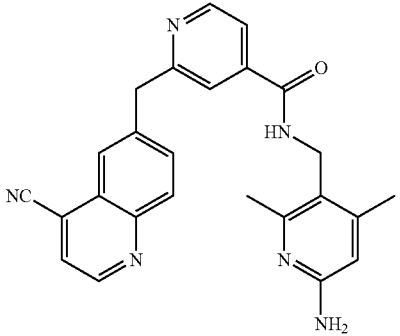 [SMILES: Cc1cc(N)nc(C)c1CNC(=O)c1ccnc(Cc2ccc3nccc(C#N)c3c2)c1]

N-((6-amino-2,4-dimethylpyridin-3-yl)methyl)-2-((4-cyanoquinolin-6-yl)methyl)isonicotinamide (23 mg, 17% yield) was prepared as described in Example 24, Step 7 as a yellow solid. LRMS (M+H$^+$) m/z calculated 423.2. found 423.2. $^1$H NMR (CD$_3$OD, 300 MHz) δ 8.98 (d, 1H), 8.63 (d, 1H), 8.10 (d, 1H), 8.07 (s, 1H), 7.93 (d, 1H), 7.86 (dd, 1H), 7.77 (s, 1H), 7.63 (dd, 1H), 6.29 (s, 1H), 4.50 (s, 2H), 4.49 (s, 2H), 2.38 (s, 3H), 2.26 (s, 3H).

Example 139: Preparation of N-((1-aminoisoquinolin-6-yl)methyl)-2-((7-chloroquinolin-3-yl)methyl)isonicotinamide

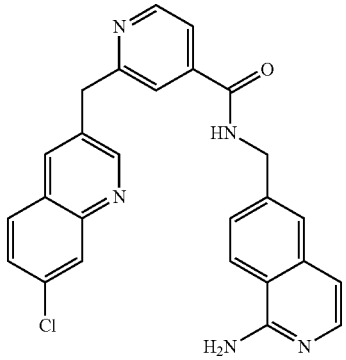 [SMILES: Nc1nccc2cc(CNC(=O)c3ccnc(Cc4cnc5cc(Cl)ccc5c4)c3)ccc12]

N-((1-aminoisoquinolin-6-yl)methyl)-2-((7-chloroquinolin-3-yl)methyl)isonicotinamide (34 mg, 23% yields for 2 steps) was prepared as described for N-((1-aminoisoquinolin-6-yl)methyl)-2-((3-methylquinolin-6-yl)methyl) isonicotinamide (Example 142). LRMS (M+H$^+$) m/z calculated 454.1. found 454.1. $^1$H NMR (DMSO-d$_6$, 400 MHz) δ 9.42 (d, 1H), 8.96 (s, 1H), 8.68 (d, 1H), 8.20 (s, 1H), 8.15 (d, 1H), 8.05 (s, 1H), 8.02 (d, 1H), 7.86 (s, 1H), 7.78 (d, 1H), 7.70 (d, 1H), 7.63 (dd, 1H), 7.56 (s, 1H), 7.42 (d, 1H), 6.86 (d, 1H), 4.63 (d, 2H), 4.42 (s, 2H).

Example 140: Preparation of N-((3-chloro-6-fluoro-1H-indol-5-yl)methyl)-2-((7-chloroquinolin-3-yl)methyl)isonicotinamide

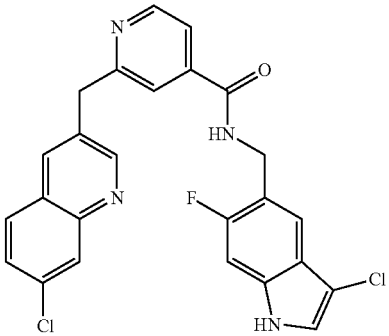 [SMILES: O=C(NCc1cc2c(Cl)c[nH]c2cc1F)c1ccnc(Cc2cnc3cc(Cl)ccc3c2)c1]

N-((3-chloro-6-fluoro-1H-indol-5-yl)methyl)-2-((7-chloroquinolin-3-yl)methyl)isonicotinamide (35 mg, 23%) was prepared as described in Example 24, Step 7 as a white solid. LRMS (M+H$^+$) m/z calculated 479.1. found 479.1. $^1$H NMR (DMSO-d$_6$, 400 MHz) δ 11.42 (s, 1H), 9.27 (t, 1H), 8.95 (d, 1H), 8.66 (d, 1H), 8.27 (s, 1H), 8.04 (d, 1H), 8.01 (d, 1H), 7.83 (s, 1H), 7.67 (d, 1H), 7.62 (dd, 1H), 7.52 (d, 1H), 7.46 (d, 1H), 7.25 (d, 1H), 4.60 (d, 2H), 4.40 (s, 2H).

Example 141: Preparation of N-((6-amino-2,4-dimethylpyridin-3-yl)methyl)-2-((7-chloroquinolin-3-yl)methyl)isonicotinamide

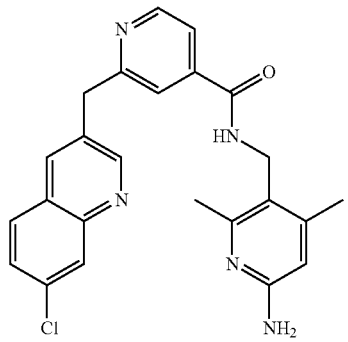 [SMILES: Cc1cc(N)nc(C)c1CNC(=O)c1ccnc(Cc2cnc3cc(Cl)ccc3c2)c1]

N-((6-amino-2,4-dimethylpyridin-3-yl)methyl)-2-((7-chloroquinolin-3-yl)methyl)isonicotinamide (10 mg, 7%) was prepared as described in Example 24, Step 7 as a white solid. LRMS (M+H$^+$) m/z calculated 432.2. found 432.2. $^1$H NMR (CD$_3$OD, 400 MHz) δ 8.87 (d, 1H), 8.63 (d, 1H), 8.25 (s, 1H), 8.00 (s, 1H), 7.91 (d, 1H), 7.78 (s, 1H), 7.63 (d, 1H), 7.60 (dd, 1H), 6.32 (s, 1H), 4.53 (d, 2H), 4.44 (s, 2H), 2.41 (s, 3H), 2.29 (s, 3H).

Example 142: Preparation of N-((1-aminoisoquinolin-6-yl)methyl)-2-((3-methylquinolin-6-yl)methyl)isonicotinamide

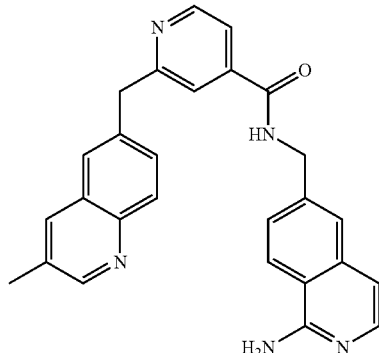

To a solution of 2-(3-methyl-quinolin-6-ylmethyl)-isonicotinic acid (150 mg, crude) in DMF (15 mL) was added 6-aminomethyl-isoquinolin-1-ylamine (62 mg, 0.36 mmol, 1.0 eq) followed by EDCI (104 mg, 0.54 mmol, 1.5 eq), HOBT (73 mg, 0.54 mmol, 1.5 eq) and TEA (109 mg, 1.08 mmol, 3.0 eq). The reaction mixture was heated to 40° C. kept stirring for overnight. Water was added, and the mixture was extracted with DCM. The organic layer was washed with water, dried over Na$_2$SO$_4$, filtered, and concentrated. The residue was purified by prep-HPLC to give N-((1-aminoisoquinolin-6-yl)methyl)-2-((3-methylquinolin-6-yl)methyl) isonicotinamide (30 mg, 19%) as a white solid. LRMS (M+H$^+$) m/z calculated 434. found 434. $^1$H NMR (DMSO-d$_6$, 400 MHz) δ 9.40 (t, 1H), 8.71 (s, 1H), 8.67 (d, 1H), 8.13 (d, 1H), 8.07 (s, 1H), 7.90 (d, 1H), 7.75-7.80 (m, 3H), 7.68 (d, 1H), 7.62 (d, 1H), 7.54 (s, 1H), 7.49 (d, 1H), 6.84 (d, 1H), 6.77 (s, 2H), 4.60 (d, 2H), 4.35 (s, 2H), 2.46 (s, 3H).

Example 143: Preparation of N-((3-chloro-6-fluoro-1H-indol-5-yl)methyl)-2-((3-methylquinolin-6-yl)methyl)isonicotinamide

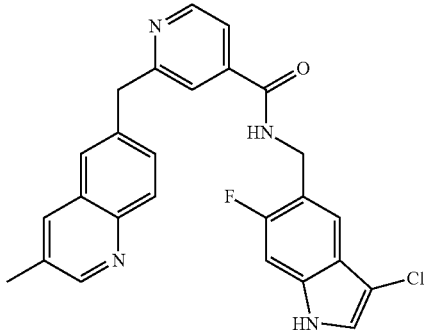 [SMILES: Cc1cnc2ccc(Cc3cc(C(=O)NCc4cc5c(Cl)c[nH]c5cc4F)ccn3)cc2c1]

N-((3-chloro-6-fluoro-1H-indol-5-yl)methyl)-2-((3-methylquinolin-6-yl)methyl)isonicotinamide (30 mg, 18%) was prepared as described for Example 24, Step 7 as a yellow solid. LRMS (M+H+) m/z calculated 459. found 459. 1H NMR (DMSO-d$_6$, 300 MHz) δ 11.42 (br, 1H), 9.25 (t, 1H), 8.71 (s, 1H), 8.65 (d, 1H), 8.05 (s, 1H), 7.89 (d, 1H), 7.76 (d, 2H), 7.60-7.66 (m, 2H), 7.51 (d, 1H), 7.43 (d, 1H), 7.22 (d, 2H), 4.58 (d, 2H), 4.34 (s, 2H), 2.46 (s, 3H).

Example 144: Preparation of N-((6-amino-2,4-dimethylpyridin-3-yl)methyl)-2-((3-methylquinolin-6-yl)methyl)isonicotinamide

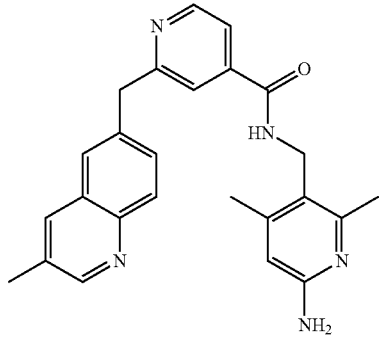

To a solution of 2-(3-methyl-quinolin-6-ylmethyl)-isonicotinic acid (150 mg, crude) in DMF (15 mL) was added 5-aminomethyl-4,6-dimethyl-pyridin-2-ylamine dihydrochloride (400 mg, crude) followed by EDCI (104 mg, 0.54 mmol, 1.5 eq), HOBT (73 mg, 0.54 mmol, 1.5 eq) and TEA (109 mg, 1.08 mmol, 3.0 eq). The reaction mixture was heated to 40° C. kept stirring for overnight. Water was added, and the mixture was extracted with DCM. The organic layer was washed with water, dried over Na₂SO₄, filtered, and concentrated. The residue was purified by prep-HPLC to give N-((6-amino-2,4-dimethylpyridin-3-yl)methyl)-2-((3-methylquinolin-6-yl)methyl)isonicotinamide (25 mg, 17%) as a yellow solid. LRMS (M+H⁺) m/z calculated 412. found 412. ¹H NMR (DMSO-d₆, 300 MHz) δ 8.71 (s, 1H), 8.65 (t, 1H), 8.60 (d, 1H), 8.06 (s, 1H), 7.89 (d, 1H), 7.74 (d, 2H), 7.60 (d, 2H), 6.10 (s, 1H), 5.70 (s, 2H), 4.32 (s, 4H), 2.46 (s, 3H), 2.29 (s, 3H), 2.15 (s, 3H).

Example 145: Preparation of N-((6-amino-2,4-dimethylpyridin-3-yl)methyl)-2-((3-methylisoquinolin-6-yl)methyl)isonicotinamide

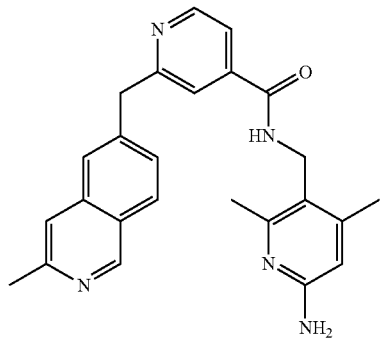

N-((6-amino-2,4-dimethylpyridin-3-yl)methyl)-2-((3-methylisoquinolin-6-yl)methyl)isonicotinamide (29 mg, 21%) was prepared as described for Example 24, Step 7. LRMS (M+H⁺) m/z calculated 412.2. found 412.2. ¹H NMR (CD₃OD, 400 MHz) δ 9.05 (s, 1H), 8.61 (d, 1H), 7.96 (s, 1H), 7.73 (s, 1H), 7.69 (s, 1H), 7.62 (dd, 1H), 7.55 (s, 1H), 7.52 (d, 1H), 6.30 (s, 1H), 4.49 (s, 2H), 4.38 (s, 2H), 2.64 (s, 3H), 2.39 (s, 3H), 2.26 (s, 3H).

Example 146: Preparation of N-((1-aminoisoquinolin-6-yl)methyl)-2-((2-(aminomethyl)quinolin-6-yl)methyl)isonicotinamide

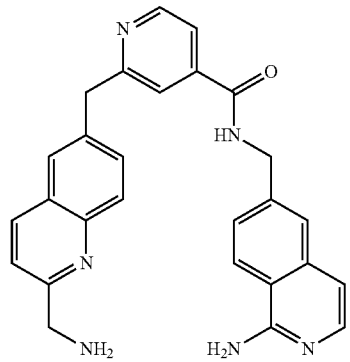 [SMILES: NCc1ccc2cc(Cc3cc(C(=O)NCc4ccc5c(N)nccc5c4)ccn3)ccc2n1]

Step 1: Preparation of tert-butyl (6-((4-((1-aminoisoquinolin-6-yl)methylcarbamoyl)pyridin-2-yl)methyl)quinolin-2-yl)methylcarbamate

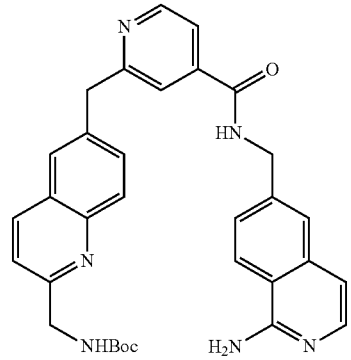 [SMILES: CC(C)(C)OC(=O)NCc1ccc2cc(Cc3cc(C(=O)NCc4ccc5c(N)nccc5c4)ccn3)ccc2n1]

tert-Butyl (6-((4-((1-aminoisoquinolin-6-yl)methylcarbamoyl)pyridin-2-yl)methyl)quinolin-2-yl)methylcarbamate (70 mg, 35%) was prepared as described for Example 24, Step 7.

Step 2: Preparation of N-((1-aminoisoquinolin-6-yl)methyl)-2-((2-(aminomethyl)quinolin-6-yl)methyl)isonicotinamide

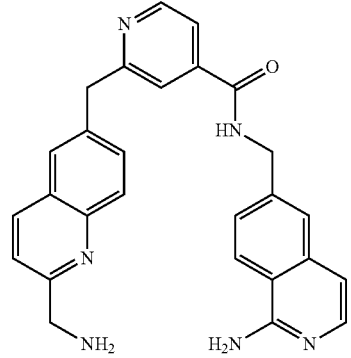 [SMILES: NCc1ccc2cc(Cc3cc(C(=O)NCc4ccc5c(N)nccc5c4)ccn3)ccc2n1]

To a solution of tert-butyl (6-((4-((1-aminoisoquinolin-6-yl)methylcarbamoyl)pyridin-2-yl)methyl)quinolin-2-yl)methylcarbamate (80 mg, 0.13 mmol) in EtOAc (1 mL) was added HCl/EtOAc solution. The mixture was stirred at rt for 1 h. The precipitate was collected by filtration to give N-((1-aminoisoquinolin-6-yl)methyl)-2-((2-(aminomethyl)quinolin-6-yl)methyl) isonicotinamide (50 mg, 66%) as an off-white solid. LRMS (M+H⁺) m/z calculated 449.2. found 449.2. ¹H NMR (DMSO-d₆, 400 MHz) δ 13.51 (s, 1H), 10.05 (s, 1H), 9.25 (br, 1H), 8.88 (d, 1H), 8.63-8.62 (m, 4H), 8.45 (d, 1H), 8.19 (s, 1H), 8.09-8.01 (m, 3H), 7.89 (d, 1H), 7.85 (s, 1H), 7.73-7.64 (m, 4H), 7.20 (d, 1H), 4.69 (d, 2H), 4.59 (s, 2H), 4.39 (t, 2H).

II. Biological Evaluation

Example 1: In Vitro Enzyme Inhibition

The ability of the compounds disclosed herein to inhibit human plasma kallikrein activity was quantified according to the procedures below.

A 10 mM solution of the test compound was made in DMSO. This solution was serially diluted 1:5 in DMSO to yield 2000, 400, 80, 16, 3.2, 0.64, 0.128, 0.0256 and 0.00512 µM compound test solutions. A control tube containing only DMSO is included. 16 µL of each compound test solution was combined with 384 µL of assay buffer (50 mM Tris-HCl pH 7.5, 150 mM NaCl, 0.01% Triton X-100) to yield a "4× test compound buffer stock".

Separately, a 40 nM solution of human Plasma Kallikrein (Abcam) and a 93.6 µM solution Pro-Phe-Arg-AMC (Bachem) were made using assay buffer. These solutions are hereby referred to as 4×hPK and 2×PFR-AMC, respectively.

60 µL of each 4× test compound buffer stock was combined with 60 µL of 4×hPK to yield 120 µL of "2× test compound buffer stock/2×hPK". 50 µL was removed from this mixture and placed into duplicate wells on a Microfluor 1Black U-bottom microtiter plate (Thermo Scientific). This plate was incubated for 5 minutes at 37° C. To each well, 50 µL of pre-warmed 2×PFR-AMC was added to start the enzymatic reaction. Cleavage of PFR-AMC was monitored in a Biotek Synergy H4 reader set at 37° C. Readings are taken every 43 seconds for 1 hour. The highest mean velocity over 20 reads (~15 minutes) is used to calculate the $IC_{50}$. The $IC_{50}$ is calculated using the Gen5 (Biotek Instruments).

The ability of the compounds in Table 3 to inhibit human plasma kallikrein activity was determined.

TABLE 3

| Chemical Synthesis Example | Name | hPK IC50 (µM) |
|---|---|---|
| 1 | 6-((4-(((3-chloro-6-fluoro-1H-indol-5-yl)methyl)carbamoyl)pyridin-2-yl)methyl)quinoline-2-carboxamide | B |
| 2 | 6-((4-(((6-amino-2,4-dimethylpyridin-3-yl)methyl)carbamoyl)pyridin-2-yl)methyl)quinoline-2-carboxamide | B |
| 3 | N-((1-aminoisoquinolin-6-yl)methyl)-2-((2-cyanoquinolin-6-yl)methyl)isonicotinamide | A |
| 4 | 6-((4-(((1-aminoisoquinolin-6-yl)methyl)carbamoyl)pyridin-2-yl)methyl)quinoline-2-carboxamide | B |
| 5 | N-((3-chloro-6-fluoro-1H-indol-5-yl)methyl)-2-((3-cyanoquinolin-6-yl)methyl)isonicotinamide | A |
| 6 | N-((1-aminoisoquinolin-6-yl)methyl)-2-((3-cyanoquinolin-6-yl)methyl)isonicotinamide | A |
| 7 | N-((6-amino-2,4-dimethylpyridin-3-yl)methyl)-2-((3-cyanoquinolin-6-yl)methyl)isonicotinamide | A |
| 8 | N-((1-aminoisoquinolin-6-yl)methyl)-2-((7-fluoroquinoxalin-2-yl)methyl)isonicotinamide | B |
| 9 | 2-((2-(acetamidomethyl)quinolin-6-yl)methyl)-N-((3-chloro-6-fluoro-1H-indol-5-yl)methyl)isonicotinamide | B |
| 10 | 2-((2-(acetamidomethyl)quinolin-6-yl)methyl)-N-((1-aminoisoquinolin-6-yl)methyl)isonicotinamide | B |
| 11 | 2-((2-(acetamidomethyl)quinolin-6-yl)methyl)-N-((6-amino-2,4-dimethylpyridin-3-yl)methyl)isonicotinamide | B |
| 12 | N-((3-chloro-6-fluoro-1H-indol-5-yl)methyl)-2-((6-(methylsulfonyl)quinolin-3-yl)methyl)isonicotinamide | A |
| 13 | N-((1-aminoisoquinolin-6-yl)methyl)-2-((6-(methylsulfonyl)quinolin-3-yl)methyl)isonicotinamide | B |
| 14 | N-((6-amino-2,4-dimethylpyridin-3-yl)methyl)-2-((6-(methylsulfonyl)quinolin-3-yl)methyl)isonicotinamide | B |
| 15 | N-((6-amino-2,4-dimethylpyridin-3-yl)methyl)-2-((3-methyl-8-(methylsulfonyl)quinolin-6-yl)methyl)isonicotinamide | A |
| 16 | N-((1-aminoisoquinolin-6-yl)methyl)-2-((3-methyl-8-(methylsulfonyl)quinolin-6-yl)methyl)isonicotinamide | A |
| 17 | N-((3-chloro-6-fluoro-1H-indol-5-yl)methyl)-2-((3-methyl-8-(methylsulfonyl)quinolin-6-yl)methyl)isonicotinamide | A |
| 18 | N-((6-fluoro-1H-indol-5-yl)methyl)-2-((3-methyl-8-(methylsulfonyl)quinolin-6-yl)methyl)isonicotinamide | A |
| 19 | N-((3-chloro-1H-pyrrolo[2,3-b]pyridin-5-yl)methyl)-2-((3-methyl-8-(methylsulfonyl)quinolin-6-yl)methyl)isonicotinamide | A |
| 20 | N-((5-chloro-1H-indazol-3-yl)methyl)-2-((3-methyl-8-(methylsulfonyl)quinolin-6-yl)methyl)isonicotinamide | A |
| 21 | N-((3-chloro-4-fluoro-1H-indol-5-yl)methyl)-2-((3-methyl-8-(methylsulfonyl)quinolin-6-yl)methyl)isonicotinamide | A |
| 22 | N-((6-amino-2,4-dimethylpyridin-3-yl)methyl)-2-((5-chloro-1-oxoisoquinolin-2(1H)-yl)methyl)isonicotinamide | B |
| 23 | N-((6-amino-2,4-dimethylpyridin-3-yl)methyl)-2-((6-chloro-1-oxoisoquinolin-2(1H)-yl)methyl)isonicotinamide | C |
| 24 | N-((6-amino-2,4-dimethylpyridin-3-yl)methyl)-2-((3-chloro-1H-indol-5-yl)methyl)isonicotinamide | B |

TABLE 3-continued

| Chemical Synthesis Example | Name | hPK IC50 (μM) |
|---|---|---|
| 25 | N-((6-amino-2,4-dimethylpyridin-3-yl)methyl)-2-((3-methyl-1H-indol-5-yl)methyl)isonicotinamide | B |
| 26 | N-((6-amino-5-cyano-2-methylpyridin-3-yl)methyl)-2-((3-chloroquinolin-6-yl)methyl)isonicotinamide | C |
| 27 | 2-amino-5-((2-((3-chloroquinolin-6-yl)methyl)isonicotinamido)methyl)-6-methylnicotinamide | D |
| 28 | N-((6-amino-5-chloro-2-methylpyridin-3-yl)methyl)-2-((3-chloroquinolin-6-yl)methyl)isonicotinamide | C |
| 29 | N-((6-amino-4-methylpyridin-3-yl)methyl)-2-((3-chloroquinolin-6-yl)methyl)isonicotinamide | A |
| 30 | N-((6-amino-2-(trifluoromethyl)pyridin-3-yl)methyl)-2-((3-chloroquinolin-6-yl)methyl)isonicotinamide | D |
| 31 | N-((1-aminoisoquinolin-6-yl)methyl)-2-((3-chloroquinolin-6-yl)methyl)isonicotinamide | A |
| 32 | 2-((3-chloroquinolin-6-yl)methyl)-N-((6-fluoro-1H-indazol-5-yl)methyl)isonicotinamide | C |
| 33 | N-((3-chloro-6-fluoro-1H-indol-5-yl)methyl)-2-((3-chloroquinolin-6-yl)methyl)isonicotinamide | A |
| 34 | N-((6-amino-2-methylpyridin-3-yl)methyl)-2-((3-chloroquinolin-6-yl)methyl)isonicotinamide | A |
| 35 | N-((6-amino-2,4-dimethylpyridin-3-yl)methyl)-2-((3-chloroquinolin-6-yl)methyl)isonicotinamide | A |
| 36 | N-((3-aminobenzo[d]isoxazol-6-yl)methyl)-2-((3-chloroquinolin-6-yl)methyl)isonicotinamide | C |
| 37 | N-((5-chloro-1H-indazol-3-yl)methyl)-2-((3-chloroquinolin-6-yl)methyl)isonicotinamide | A |
| 38 | N-((3-chloro-1H-pyrrolo[2,3-b]pyridin-5-yl)methyl)-2-((3-chloroquinolin-6-yl)methyl)isonicotinamide | A |
| 39 | N-((6-amino-2-methylpyridin-3-yl)methyl)-2-((3-chloroquinolin-6-yl)methyl)isonicotinamide | A |
| 40 | N-((3-chloro-4-fluoro-1H-indol-5-yl)methyl)-2-((3-chloroquinolin-6-yl)methyl)isonicotinamide | A |
| 41 | 2-((3-chloroquinolin-6-yl)methyl)-N-((6-fluoro-1H-indol-5-yl)methyl)isonicotinamide | A |
| 42 | 2-((3-chloroquinolin-6-yl)methyl)-N-((2-methyl-6-(methylamino)pyridin-3-yl)methyl)isonicotinamide | B |
| 43 | N-((6-amino-2-cyclopropylpyridin-3-yl)methyl)-2-((3-chloroquinolin-6-yl)methyl)isonicotinamide | B |
| 44 | 2-((3-chloroquinolin-6-yl)methyl)-N-((6-(dimethylamino)-2-methylpyridin-3-yl)methyl)isonicotinamide | D |
| 45 | 2-((2-(aminomethyl)quinolin-6-yl)methyl)-N-((3-chloro-6-fluoro-1H-indol-5-yl)methyl)isonicotinamide | B |
| 46 | N-((6-amino-2,4-dimethylpyridin-3-yl)methyl)-2-((2-(aminomethyl)quinolin-6-yl)methyl)isonicotinamide | A |
| 47 | N-((3-aminobenzo[d]isoxazol-6-yl)methyl)-2-((3-methylquinolin-6-yl)methyl)isonicotinamide | C |
| 48 | N-((3-aminobenzo[d]isoxazol-6-yl)methyl)-2-((6-methylquinolin-3-yl)methyl)isonicotinamide | D |
| 49 | N-((3-chloro-6-fluoro-1H-indol-5-yl)methyl)-2-((3-chloro-8-cyanoquinolin-6-yl)methyl)isonicotinamide | A |
| 50 | N-((6-amino-2,4-dimethylpyridin-3-yl)methyl)-2-((3-chloro-8-cyanoquinolin-6-yl)methyl)isonicotinamide | A |
| 51 | N-((3-chloro-4-fluoro-1H-indol-5-yl)methyl)-2-((3-chloro-8-cyanoquinolin-6-yl)methyl)isonicotinamide | A |
| 52 | 2-((3-chloro-8-cyanoquinolin-6-yl)methyl)-N-((6-fluoro-1H-indol-5-yl)methyl)isonicotinamide | A |
| 53 | N-((6-amino-4-methylpyridin-3-yl)methyl)-2-((3-chloro-8-cyanoquinolin-6-yl)methyl)isonicotinamide | B |
| 54 | N-((5-chloro-1H-indazol-3-yl)methyl)-2-((3-chloro-8-cyanoquinolin-6-yl)methyl)isonicotinamide | A |
| 55 | N-((3-chloro-1H-pyrrolo[2,3-b]pyridin-5-yl)methyl)-2-((3-chloro-8-cyanoquinolin-6-yl)methyl)isonicotinamide | A |
| 56 | N-((6-amino-2-methylpyridin-3-yl)methyl)-2-((3-chloro-8-cyanoquinolin-6-yl)methyl)isonicotinamide | A |
| 57 | N-((1-aminoisoquinolin-6-yl)methyl)-2-((3-chloro-8-cyanoquinolin-6-yl)methyl)isonicotinamide | A |
| 58 | 6-((4-(((6-amino-2,4-dimethylpyridin-3-yl)methyl)carbamoyl)pyridin-2-yl)methyl)-3-chloroquinoline-8-carboxamide | A |
| 59 | 3-chloro-6-((4-(((3-chloro-6-fluoro-1H-indol-5-yl)methyl)carbamoyl)pyridin-2-yl)methyl)quinoline-8-carboxamide | A |

TABLE 3-continued

| Chemical Synthesis Example | Name | hPK IC50 (μM) |
|---|---|---|
| 60 | 3-chloro-6-((4-(((5-chloro-1H-indazol-3-yl)methyl)carbamoyl)pyridin-2-yl)methyl)quinoline-8-carboxamide | A |
| 61 | 3-chloro-6-((4-(((3-chloro-1H-pyrrolo[2,3-b]pyridin-5-yl)methyl)carbamoyl)pyridin-2-yl)methyl)quinoline-8-carboxamide | A |
| 62 | 6-((4-(((6-amino-2-methylpyridin-3-yl)methyl)carbamoyl)pyridin-2-yl)methyl)-3-chloroquinoline-8-carboxamide | A |
| 63 | 6-((4-(((6-amino-4-methylpyridin-3-yl)methyl)carbamoyl)pyridin-2-yl)methyl)-3-chloroquinoline-8-carboxamide | A |
| 64 | 6-((4-(((1-aminoisoquinolin-6-yl)methyl)carbamoyl)pyridin-2-yl)methyl)-3-chloroquinoline-8-carboxamide | A |
| 65 | 3-chloro-6-((4-(((3-chloro-4-fluoro-1H-indol-5-yl)methyl)carbamoyl)pyridin-2-yl)methyl)quinoline-8-carboxamide | A |
| 66 | 3-chloro-6-((4-(((6-fluoro-1H-indol-5-yl)methyl)carbamoyl)pyridin-2-yl)methyl)quinoline-8-carboxamide | A |
| 67 | N-((6-amino-2,4-dimethylpyridin-3-yl)methyl)-2-((3-chloro-8-(methylsulfonyl)quinolin-6-yl)methyl)isonicotinamide | A |
| 68 | N-((3-chloro-6-fluoro-1H-indol-5-yl)methyl)-2-((3-chloro-8-(methylsulfonyl)quinolin-6-yl)methyl)isonicotinamide | A |
| 69 | N-((6-amino-2-methylpyridin-3-yl)methyl)-2-((3-chloro-8-(methylsulfonyl)quinolin-6-yl)methyl)isonicotinamide | A |
| 70 | N-((6-amino-2,4-dimethylpyridin-3-yl)methyl)-2-((8-cyano-3-methylquinolin-6-yl)methyl)isonicotinamide | A |
| 71 | N-((1-aminoisoquinolin-6-yl)methyl)-2-((8-cyano-3-methylquinolin-6-yl)methyl)isonicotinamide | A |
| 72 | N-((3-chloro-6-fluoro-1H-indol-5-yl)methyl)-2-((8-cyano-3-methylquinolin-6-yl)methyl)isonicotinamide | A |
| 73 | N-((3-chloro-1H-pyrrolo[2,3-b]pyridin-5-yl)methyl)-2-((8-cyano-3-methylquinolin-6-yl)methyl)isonicotinamide | A |
| 74 | N-((3-chloro-4-fluoro-1H-indol-5-yl)methyl)-2-((8-cyano-3-methylquinolin-6-yl)methyl)isonicotinamide | A |
| 75 | N-((5-chloro-1H-indazol-3-yl)methyl)-2-((8-cyano-3-methylquinolin-6-yl)methyl)isonicotinamide | A |
| 76 | 2-((8-cyano-3-methylquinolin-6-yl)methyl)-N-((6-fluoro-1H-indol-5-yl)methyl)isonicotinamide | A |
| 77 | 6-((4-(((6-amino-2,4-dimethylpyridin-3-yl)methyl)carbamoyl)pyridin-2-yl)methyl)-3-methylquinoline-8-carboxamide | A |
| 78 | 6-((4-(((3-chloro-6-fluoro-1H-indol-5-yl)methyl)carbamoyl)pyridin-2-yl)methyl)-3-methylquinoline-8-carboxamide | A |
| 79 | 6-((4-(((1-aminoisoquinolin-6-yl)methyl)carbamoyl)pyridin-2-yl)methyl)-3-methylquinoline-8-carboxamide | A |
| 80 | 6-((4-(((3-chloro-1H-pyrrolo[2,3-b]pyridin-5-yl)methyl)carbamoyl)pyridin-2-yl)methyl)-3-methylquinoline-8-carboxamide | A |
| 81 | 6-((4-(((3-chloro-4-fluoro-1H-indol-5-yl)methyl)carbamoyl)pyridin-2-yl)methyl)-3-methylquinoline-8-carboxamide | A |
| 82 | 6-((4-(((5-chloro-1H-indazol-3-yl)methyl)carbamoyl)pyridin-2-yl)methyl)-3-methylquinoline-8-carboxamide | A |
| 83 | 6-((4-(((6-fluoro-1H-indol-5-yl)methyl)carbamoyl)pyridin-2-yl)methyl)-3-methylquinoline-8-carboxamide | A |
| 84 | 6-((4-(((6-amino-2,4-dimethylpyridin-3-yl)methyl)carbamoyl)pyridin-2-yl)methyl)-3-methylquinoline-8-carboxylic acid | A |
| 85 | N-((6-amino-4-methylpyridin-3-yl)methyl)-2-((7-chloro-3-oxoisoquinolin-2(3H)-yl)methyl)isonicotinamide | B |
| 86 | N-((6-amino-2-methylpyridin-3-yl)methyl)-2-((7-chloro-3-oxoisoquinolin-2(3H)-yl)methyl)isonicotinamide | B |
| 87 | N-((6-amino-2,4-dimethylpyridin-3-yl)methyl)-2-((7-chloro-3-oxoisoquinolin-2(3H)-yl)methyl)isonicotinamide | B |
| 88 | 2-((7-chloro-3-oxoisoquinolin-2(3H)-yl)methyl)-N-((3-chloro-6-fluoro-1H-indol-5-yl)methyl)isonicotinamide | B |

TABLE 3-continued

| Chemical Synthesis Example | Name | hPK IC50 (μM) |
|---|---|---|
| 89 | N-((6-amino-2,4-dimethylpyridin-3-yl)methyl)-2-((3-chloro-8-fluoroquinolin-6-yl)methyl)isonicotinamide | A |
| 90 | N-((3-chloro-6-fluoro-1H-indol-5-yl)methyl)-2-((3-chloro-8-fluoroquinolin-6-yl)methyl)isonicotinamide | A |
| 91 | N-((6-amino-2-methylpyridin-3-yl)methyl)-2-((3-chloro-8-fluoroquinolin-6-yl)methyl)isonicotinamide | A |
| 92 | methyl 6-((4-(((6-amino-2,4-dimethylpyridin-3-yl)methyl)carbamoyl)pyridin-2-yl)methyl)-3-chloroquinoline-8-carboxylate | A |
| 93 | 6-((4-(((6-amino-2,4-dimethylpyridin-3-yl)methyl)carbamoyl)pyridin-2-yl)methyl)-3-chloroquinoline-8-carboxylic acid | A |
| 94 | N-((6-amino-2,4-dimethylpyridin-3-yl)methyl)-2-((3-chloro-8-(hydroxymethyl)quinolin-6-yl)methyl)isonicotinamide | A |
| 95 | methyl 6-((4-(((6-amino-2-methylpyridin-3-yl)methyl)carbamoyl)pyridin-2-yl)methyl)-3-chloroquinoline-8-carboxylate | A |
| 96 | 6-((4-(((6-amino-2-methylpyridin-3-yl)methyl)carbamoyl)pyridin-2-yl)methyl)-3-chloroquinoline-8-carboxylic acid | B |
| 97 | N-((6-amino-2-methylpyridin-3-yl)methyl)-2-((3-chloro-8-(hydroxymethyl)quinolin-6-yl)methyl)isonicotinamide | A |
| 98 | 6-amino-3-((2-((3-chloroquinolin-6-yl)methyl)isonicotinamido)methyl)-2,4-dimethylpyridine 1-oxide | B |
| 99 | 6-((4-(((6-amino-2,4-dimethylpyridin-3-yl)methyl)carbamoyl)pyridin-2-yl)methyl)-3-chloroquinoline 1-oxide | A |
| 100 | N-((6-amino-2,4-dimethylpyridin-3-yl)methyl)-2-((3,8-dichloroquinolin-6-yl)methyl)isonicotinamide | A |
| 101 | N-((6-amino-2-methylpyridin-3-yl)methyl)-2-((3,8-dichloroquinolin-6-yl)methyl)isonicotinamide | A |
| 102 | N-((6-amino-2,4-dimethylpyridin-3-yl)methyl)-2-((3-chloro-5-fluoroquinolin-6-yl)methyl)isonicotinamide | A |
| 103 | N-((6-amino-2-methylpyridin-3-yl)methyl)-2-((3-chloro-5-fluoroquinolin-6-yl)methyl)isonicotinamide | A |
| 104 | N-((6-amino-2,4-dimethylpyridin-3-yl)methyl)-2-((3-chloroquinolin-6-yl)methyl)-6-methylisonicotinamide | A |
| 105 | N-((6-amino-2,4-dimethylpyridin-3-yl)methyl)-2-((5-chloro-1H-indazol-1-yl)methyl)isonicotinamide | A |
| 106 | N-((6-amino-2,4-dimethylpyridin-3-yl)methyl)-2-((5-chloro-2H-indazol-2-yl)methyl)isonicotinamide | A |
| 107 | N-((6-amino-2,4-dimethylpyridin-3-yl)methyl)-2-((5-methyl-2H-indazol-2-yl)methyl)isonicotinamide | B |
| 108 | N-((6-amino-2,4-dimethylpyridin-3-yl)methyl)-2-((5-methyl-1H-indazol-1-yl)methyl)isonicotinamide | A |
| 109 | N-((3-chloro-6-fluoro-1H-indol-5-yl)methyl)-2-((6-methyl-2-(methylsulfonyl)quinolin-3-yl)methyl)isonicotinamide | B |
| 110 | N-((3-chloro-6-fluoro-1H-indol-5-yl)methyl)-2-((2-methylquinolin-6-yl)methyl)isonicotinamide | A |
| 111 | N-((1-aminoisoquinolin-6-yl)methyl)-2-((2-methylquinolin-6-yl)methyl)isonicotinamide | A |
| 112 | N-((6-amino-2-methylpyridin-3-yl)methyl)-2-((2-methylquinolin-6-yl)methyl)isonicotinamide | A |
| 113 | N-((6-amino-2,4-dimethylpyridin-3-yl)methyl)-2-((2-methylquinolin-6-yl)methyl)isonicotinamide | A |
| 114 | N-((6-amino-2,4-dimethylpyridin-3-yl)methyl)-2-((6-methylquinolin-3-yl)methyl)isonicotinamide | A |
| 115 | N-((1-aminoisoquinolin-6-yl)methyl)-2-((6-methylquinolin-3-yl)methyl)isonicotinamide | A |
| 116 | N-((3-chloro-6-fluoro-1H-indol-5-yl)methyl)-2-((6-methylquinolin-3-yl)methyl)isonicotinamide | A |
| 117 | N-((6-amino-2-methylpyridin-3-yl)methyl)-2-((6-methylquinolin-3-yl)methyl)isonicotinamide | A |
| 118 | N-((1-aminoisoquinolin-6-yl)methyl)-2-((6-fluoroquinolin-3-yl)methyl)isonicotinamide | A |
| 119 | N-((6-amino-2,4-dimethylpyridin-3-yl)methyl)-2-((6-fluoroquinolin-3-yl)methyl)isonicotinamide | A |
| 120 | N-((3-chloro-6-fluoro-1H-indol-5-yl)methyl)-2-((6-fluoroquinolin-3-yl)methyl)isonicotinamide | A |
| 121 | N-((6-amino-2-methylpyridin-3-yl)methyl)-2-((6-fluoroquinolin-3-yl)methyl)isonicotinamide | A |
| 122 | N-((6-amino-2,4-dimethylpyridin-3-yl)methyl)-2-((7-fluoroquinolin-3-yl)methyl)isonicotinamide | A |

TABLE 3-continued

| Chemical Synthesis Example | Name | hPK IC50 (µM) |
|---|---|---|
| 123 | N-((3-chloro-6-fluoro-1H-indol-5-yl)methyl)-2-((7-fluoroquinolin-3-yl)methyl)isonicotinamide | A |
| 124 | N-((1-aminoisoquinolin-6-yl)methyl)-2-((7-fluoroquinolin-3-yl)methyl)isonicotinamide | A |
| 125 | N-((3-chloro-6-fluoro-1H-indol-5-yl)methyl)-2-(quinolin-3-ylmethyl)isonicotinamide | A |
| 126 | N-((3-chloro-6-fluoro-1H-indol-5-yl)methyl)-2-((6-chloroquinolin-3-yl)methyl)isonicotinamide | A |
| 127 | N-((1-aminoisoquinolin-6-yl)methyl)-2-((2-methylquinolin-7-yl)methyl)isonicotinamide | A |
| 128 | N-((3-chloro-6-fluoro-1H-indol-5-yl)methyl)-2-((2-methylquinolin-7-yl)methyl)isonicotinamide | A |
| 129 | N-((6-amino-2,4-dimethylpyridin-3-yl)methyl)-2-((2-methylquinolin-7-yl)methyl)isonicotinamide | B |
| 130 | N-((3-chloro-6-fluoro-1H-indol-5-yl)methyl)-2-((2-isocyanoquinolin-6-yl)methyl)isonicotinamide | A |
| 131 | N-((6-amino-2,4-dimethylpyridin-3-yl)methyl)-2-((2-isocyanoquinolin-6-yl)methyl)isonicotinamide | A |
| 132 | N-((1-aminoisoquinolin-6-yl)methyl)-2-((3-methylisoquinolin-6-yl)methyl)isonicotinamide | A |
| 133 | N-((3-chloro-6-fluoro-1H-indol-5-yl)methyl)-2-((3-methylisoquinolin-6-yl)methyl)isonicotinamide | A |
| 134 | N-((1-aminoisoquinolin-6-yl)methyl)-2-((2-(methylsulfonyl)quinolin-6-yl)methyl)isonicotinamide | B |
| 135 | N-((3-chloro-6-fluoro-1H-indol-5-yl)methyl)-2-((2-(methylsulfonyl)quinolin-6-yl)methyl)isonicotinamide | B |
| 136 | N-((1-aminoisoquinolin-6-yl)methyl)-2-((4-cyanoquinolin-6-yl)methyl)isonicotinamide | A |
| 137 | N-((3-chloro-6-fluoro-1H-indol-5-yl)methyl)-2-((4-cyanoquinolin-6-yl)methyl)isonicotinamide | B |
| 138 | N-((6-amino-2,4-dimethylpyridin-3-yl)methyl)-2-((4-cyanoquinolin-6-yl)methyl)isonicotinamide | A |
| 139 | N-((1-aminoisoquinolin-6-yl)methyl)-2-((7-chloroquinolin-3-yl)methyl)isonicotinamide | A |
| 140 | N-((3-chloro-6-fluoro-1H-indol-5-yl)methyl)-2-((7-chloroquinolin-3-yl)methyl)isonicotinamide | A |
| 141 | N-((6-amino-2,4-dimethylpyridin-3-yl)methyl)-2-((7-chloroquinolin-3-yl)methyl)isonicotinamide | A |
| 142 | N-((1-aminoisoquinolin-6-yl)methyl)-2-((3-methylquinolin-6-yl)methyl)isonicotinamide | A |
| 143 | N-((3-chloro-6-fluoro-1H-indol-5-yl)methyl)-2-((3-methylquinolin-6-yl)methyl)isonicotinamide | A |
| 144 | N-((6-amino-2,4-dimethylpyridin-3-yl)methyl)-2-((3-methylquinolin-6-yl)methyl)isonicotinamide | A |
| 145 | N-((6-amino-2,4-dimethylpyridin-3-yl)methyl)-2-((3-methylisoquinolin-6-yl)methyl)isonicotinamide | A |
| 146 | N-((1-aminoisoquinolin-6-yl)methyl)-2-((2-(aminomethyl)quinolin-6-yl)methyl)isonicotinamide | B |

Note:
Biochemical assay $IC_{50}$ data are designated within the following ranges:
A: ≤0.10 µM
B: >0.10 µM to ≤1.0 µM
C: >1.0 µM to ≤10 µM
D: >10 µM

Example 2: In Vitro Cellular Assay

The ability of the compounds disclosed herein to inhibit cellular kallikrein activity was quantified and the respective $EC_{50}$ value was determined.

Materials:
Plasma kallikrein inhibitor C1NH (Athens Research & Technology, Cat#16-16-031509); Ellagic acid (Sigma, E2250); Substrate Z—FR-2-AMC (GL Biochem, Cat#55352); Nunc™ 96-Well Polypropylene MicroWell™ Plates (Nunc, Cat#267342)

Methods:
All dilutions were prepared in an assay buffer comprising 50 mM Tris-HCl pH 7.2, 150 mM NaCl, and 0.01% Triton X-100.

Four fold serial dilutions were prepared from a 107.53 µM plasma kallikrein inhibitor C1NH stock solution, to yield ten solutions with concentrations between 20 µM and 0.76 nM. Similarly, four fold serial dilutions were prepared from 10 mM stock solutions of various test compounds, to yield ten solutions with concentrations between 4 mM and 0.015 µM. The ten solutions of the test compounds, prepared by serial dilution, were further diluted 50-fold in the assay buffer.

Human plasma is thawed on ice and centrifuged for 15 min at 4° C. to remove platelets. A 1 mM stock solution of ellagic acid is diluted to 8 µM and mixed with human plasma, after removing platelets, at a ratio of 1:0.8. The mixture of human plasma and ellagic acid was further diluted 32-fold in the assay buffer, to yield the final mixture for use in the inhibition assay.

A 22.5 µL volume of the final mixture of human plasma and ellagic acid was added to a 96-well microwell plate and the plate was incubated for 15 min at 37° C.

The C1NH inhibitor at various concentrations, prepared by serial dilutions as described above, were added to the inhibitor control wells. The volume of C1NH inhibitor added to each inhibitor control well was 12.5 µL, to yield final concentrations of 5 µM, 1.25 µM, 312.5 nM, 78.125 nM, 19.531 nM, 4.883 nM, 1.221 nM, 0.305 nM, 0.076 nM, and 0.019 nM. Each C1NH concentration is tested in duplicates.

The test compounds at various concentrations, also prepared by serial dilutions as described above, are added to the test wells. The volume of test compound added to each test well was 12.5 µL, to yield final concentrations of 20 µM, 5 µM, 1.25 µM, 312.5 nM, 78.125 nM, 19.531 nM, 4.883 nM, 1.221 nM, 0.305 nM, and 0.076 nM. Each test compound concentration was tested in duplicates.

In addition to the inhibitor control and test wells, the 96 well assay plate includes positive control wells which contained the mixture of human plasma and ellagic acid without C1NH inhibitor or test compounds, and background wells which contained neither the mixture of human plasma and ellagic acid nor the test compounds. The total volume of liquid in positive control and background wells was brought up to 35 µL, using the assay buffer.

The assay plate containing C1NH inhibitors and test compounds mixed with human plasma and ellagic acid and appropriate controls was incubated at 37° C. for 5 min. A 10 mM stock solution of substrate Z—FR-2-AMC was diluted to 133.2 µM in the assay buffer, and 15 µL of the diluted substrate was added to each well, to yield a final substrate concentration of 40 µM in each well. The reagents were mixed well by shaking the plate gently for 30 sec.

The enzyme reaction was quantified by immediate kinetic reading of the assay plate using excitation/emission wavelengths of 330 nm/440 nm respectively. Fluorescence intensity was recorded for 60 min, using a time interval of 43 sec.

The inhibition activity of the test compounds were evaluated using the IC50 values, calculated according to the dose-response curve of the test compounds, fitted using the "log(inhibitor)-response (variable slope)" equation in GraphPadPrism software (GraphPad Software, Inc.).

The percentage inhibition was calculated using the following equation:

$$\text{Inhibition \%} = 100 - \frac{\text{Sample value} - \text{Mean}(BG)}{\text{Mean}(PC) - \text{Mean}(BG)} \times 100$$

where, Mean(BG) is the average value of the fluorescence intensity of the background wells and Mean(PC) is the average value of the fluorescence intensity of the positive control wells.

Table 4 provides the $EC_{50}$ values of various compounds disclosed herein.

TABLE 4

| Chemical Synthesis Example | Name | Contact Assay $EC_{50}$ (µM) |
|---|---|---|
| 15 | N-((6-amino-2,4-dimethylpyridin-3-yl)methyl)-2-((3-methyl-8-(methylsulfonyl)quinolin-6-yl)methyl)isonicotinamide | A |
| 16 | N-((1-aminoisoquinolin-6-yl)methyl)-2-((3-methyl-8-(methylsulfonyl)quinolin-6-yl)methyl)isonicotinamide | A |
| 17 | N-((3-chloro-6-fluoro-1H-indol-5-yl)methyl)-2-((3-methyl-8-(methylsulfonyl)quinolin-6-yl)methyl)isonicotinamide | A |
| 18 | N-((6-fluoro-1H-indol-5-yl)methyl)-2-((3-methyl-8-(methylsulfonyl)quinolin-6-yl)methyl)isonicotinamide | B |
| 19 | N-((3-chloro-1H-pyrrolo[2,3-b]pyridin-5-yl)methyl)-2-((3-methyl-8-(methylsulfonyl)quinolin-6-yl)methyl)isonicotinamide | A |
| 20 | N-((5-chloro-1H-indazol-3-yl)methyl)-2-((3-methyl-8-(methylsulfonyl)quinolin-6-yl)methyl)isonicotinamide | A |
| 21 | N-((3-chloro-4-fluoro-1H-indol-5-yl)methyl)-2-((3-methyl-8-(methylsulfonyl)quinolin-6-yl)methyl)isonicotinamide | A |
| 31 | N-((1-aminoisoquinolin-6-yl)methyl)-2-((3-chloroquinolin-6-yl)methyl)isonicotinamide | A |
| 33 | N-((3-chloro-6-fluoro-1H-indol-5-yl)methyl)-2-((3-chloroquinolin-6-yl)methyl)isonicotinamide | B |
| 34 | N-((6-amino-2-methylpyridin-3-yl)methyl)-2-((3-chloroquinolin-6-yl)methyl)isonicotinamide | A |
| 35 | N-((6-amino-2,4-dimethylpyridin-3-yl)methyl)-2-((3-chloroquinolin-6-yl)methyl)isonicotinamide | A |
| 38 | N-((3-chloro-1H-pyrrolo[2,3-b]pyridin-5-yl)methyl)-2-((3-chloroquinolin-6-yl)methyl)isonicotinamide | B |
| 39 | N-((6-amino-2-methylpyridin-3-yl)methyl)-2-((3-chloroquinolin-6-yl)methyl)isonicotinamide | A |
| 40 | N-((3-chloro-4-fluoro-1H-indol-5-yl)methyl)-2-((3-chloroquinolin-6-yl)methyl)isonicotinamide | B |
| 50 | N-((6-amino-2,4-dimethylpyridin-3-yl)methyl)-2-((3-chloro-8-cyanoquinolin-6-yl)methyl)isonicotinamide | A |

TABLE 4-continued

| Chemical Synthesis Example | Name | Contact Assay EC$_{50}$ (µM) |
|---|---|---|
| 56 | N-((6-amino-2-methylpyridin-3-yl)methyl)-2-((3-chloro-8-cyanoquinolin-6-yl)methyl)isonicotinamide | B |
| 57 | N-((1-aminoisoquinolin-6-yl)methyl)-2-((3-chloro-8-cyanoquinolin-6-yl)methyl)isonicotinamide | B |
| 58 | 6-((4-(((6-amino-2,4-dimethylpyridin-3-yl)methyl)carbamoyl)pyridin-2-yl)methyl)-3-chloroquinoline-8-carboxamide | A |
| 59 | 3-chloro-6-((4-(((3-chloro-6-fluoro-1H-indol-5-yl)methyl)carbamoyl)pyridin-2-yl)methyl)quinoline-8-carboxamide | B |
| 60 | 3-chloro-6-((4-(((5-chloro-1H-indazol-3-yl)methyl)carbamoyl)pyridin-2-yl)methyl)quinoline-8-carboxamide | B |
| 61 | 3-chloro-6-((4-(((3-chloro-1H-pyrrolo[2,3-b]pyridin-5-yl)methyl)carbamoyl)pyridin-2-yl)methyl)quinoline-8-carboxamide | B |
| 62 | 6-((4-(((6-amino-2-methylpyridin-3-yl)methyl)carbamoyl)pyridin-2-yl)methyl)-3-chloroquinoline-8-carboxamide | A |
| 64 | 6-((4-(((1-aminoisoquinolin-6-yl)methyl)carbamoyl)pyridin-2-yl)methyl)-3-chloroquinoline-8-carboxamide | A |
| 65 | 3-chloro-6-((4-(((3-chloro-4-fluoro-1H-indol-5-yl)methyl)carbamoyl)pyridin-2-yl)methyl)quinoline-8-carboxamide | A |
| 66 | 3-chloro-6-((4-(((6-fluoro-1H-indol-5-yl)methyl)carbamoyl)pyridin-2-yl)methyl)quinoline-8-carboxamide | B |
| 67 | N-((6-amino-2,4-dimethylpyridin-3-yl)methyl)-2-((3-chloro-8-(methylsulfonyl)quinolin-6-yl)methyl)isonicotinamide | A |
| 68 | N-((3-chloro-6-fluoro-1H-indol-5-yl)methyl)-2-((3-chloro-8-(methylsulfonyl)quinolin-6-yl)methyl)isonicotinamide | A |
| 69 | N-((6-amino-2-methylpyridin-3-yl)methyl)-2-((3-chloro-8-(methylsulfonyl)quinolin-6-yl)methyl)isonicotinamide | A |
| 70 | N-((6-amino-2,4-dimethylpyridin-3-yl)methyl)-2-((8-cyano-3-methylquinolin-6-yl)methyl)isonicotinamide | A |
| 71 | N-((1-aminoisoquinolin-6-yl)methyl)-2-((8-cyano-3-methylquinolin-6-yl)methyl)isonicotinamide | A |
| 72 | N-((3-chloro-6-fluoro-1H-indol-5-yl)methyl)-2-((8-cyano-3-methylquinolin-6-yl)methyl)isonicotinamide | B |
| 73 | N-((3-chloro-1H-pyrrolo[2,3-b]pyridin-5-yl)methyl)-2-((8-cyano-3-methylquinolin-6-yl)methyl)isonicotinamide | B |
| 77 | 6-((4-(((6-amino-2,4-dimethylpyridin-3-yl)methyl)carbamoyl)pyridin-2-yl)methyl)-3-methylquinoline-8-carboxamide | A |
| 78 | 6-((4-(((3-chloro-6-fluoro-1H-indol-5-yl)methyl)carbamoyl)pyridin-2-yl)methyl)-3-methylquinoline-8-carboxamide | A |
| 79 | 6-((4-(((1-aminoisoquinolin-6-yl)methyl)carbamoyl)pyridin-2-yl)methyl)-3-methylquinoline-8-carboxamide | A |
| 80 | 6-((4-(((3-chloro-1H-pyrrolo[2,3-b]pyridin-5-yl)methyl)carbamoyl)pyridin-2-yl)methyl)-3-methylquinoline-8-carboxamide | A |
| 81 | 6-((4-(((3-chloro-4-fluoro-1H-indol-5-yl)methyl)carbamoyl)pyridin-2-yl)methyl)-3-methylquinoline-8-carboxamide | B |
| 82 | 6-((4-(((5-chloro-1H-indazol-3-yl)methyl)carbamoyl)pyridin-2-yl)methyl)-3-methylquinoline-8-carboxamide | B |
| 83 | 6-((4-(((6-fluoro-1H-indol-5-yl)methyl)carbamoyl)pyridin-2-yl)methyl)-3-methylquinoline-8-carboxamide | B |
| 84 | 6-((4-(((6-amino-2,4-dimethylpyridin-3-yl)methyl)carbamoyl)pyridin-2-yl)methyl)-3-methylquinoline-8-carboxylic acid | A |
| 89 | N-((6-amino-2,4-dimethylpyridin-3-yl)methyl)-2-((3-chloro-8-fluoroquinolin-6-yl)methyl)isonicotinamide | A |

TABLE 4-continued

| Chemical Synthesis Example | Name | Contact Assay EC$_{50}$ (μM) |
|---|---|---|
| 91 | N-((6-amino-2-methylpyridin-3-yl)methyl)-2-((3-chloro-8-fluoroquinolin-6-yl)methyl)isonicotinamide | A |
| 100 | N-((6-amino-2,4-dimethylpyridin-3-yl)methyl)-2-((3,8-dichloroquinolin-6-yl)methyl)isonicotinamide | A |
| 110 | N-((3-chloro-6-fluoro-1H-indol-5-yl)methyl)-2-((2-methylquinolin-6-yl)methyl)isonicotinamide | B |
| 111 | N-((1-aminoisoquinolin-6-yl)methyl)-2-((2-methylquinolin-6-yl)methyl)isonicotinamide | B |
| 113 | N-((6-amino-2,4-dimethylpyridin-3-yl)methyl)-2-((2-methylquinolin-6-yl)methyl)isonicotinamide | A |
| 114 | N-((6-amino-2,4-dimethylpyridin-3-yl)methyl)-2-((6-methylquinolin-3-yl)methyl)isonicotinamide | A |
| 115 | N-((1-aminoisoquinolin-6-yl)methyl)-2-((6-methylquinolin-3-yl)methyl)isonicotinamide | A |
| 116 | N-((3-chloro-6-fluoro-1H-indol-5-yl)methyl)-2-((6-methylquinolin-3-yl)methyl)isonicotinamide | B |
| 117 | N-((6-amino-2-methylpyridin-3-yl)methyl)-2-((6-methylquinolin-3-yl)methyl)isonicotinamide | B |
| 118 | N-((1-aminoisoquinolin-6-yl)methyl)-2-((6-fluoroquinolin-3-yl)methyl)isonicotinamide | A |
| 132 | N-((1-aminoisoquinolin-6-yl)methyl)-2-((3-methylisoquinolin-6-yl)methyl)isonicotinamide | B |
| 142 | N-((1-aminoisoquinolin-6-yl)methyl)-2-((3-methylquinolin-6-yl)methyl)isonicotinamide | A |
| 143 | N-((3-chloro-6-fluoro-1H-indol-5-yl)methyl)-2-((3-methylquinolin-6-yl)methyl)isonicotinamide | B |
| 144 | N-((6-amino-2,4-dimethylpyridin-3-yl)methyl)-2-((3-methylquinolin-6-yl)methyl)isonicotinamide | A |
| 145 | N-((6-amino-2,4-dimethylpyridin-3-yl)methyl)-2-((3-methylisoquinolin-6-yl)methyl)isonicotinamide | A |

Note:
Assay EC$_{50}$ data are designated within the following ranges:
A: ≤0.10 μM
B: >0.10 μM to ≤1.0 μM
C: >1.0 μM to ≤10 μM
D: >10 μM III. Preparation of Pharmaceutical Dosage Forms Example 1: Oral Tablet A tablet is prepared by mixing 48% by weigh of a compound of Formula (I) or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

We claim:

1. A compound, or a pharmaceutically acceptable salt thereof, having the structure of Formula (Ia):

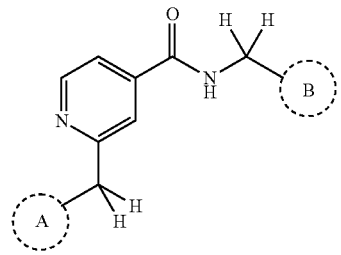

(Ia)

wherein,
Ring A is an optionally substituted bicyclic heteroaryl ring selected from optionally substituted quinolyl, optionally substituted indolyl, optionally substituted indazolyl, optionally substituted benzimidazolyl, optionally substituted isoquinolyl, optionally substituted cinnolinyl, optionally substituted phthalazinyl, optionally substituted quinazolinyl, optionally substituted naphthyridinyl, or optionally substituted benzoisoxazolyl; and Ring B is an optionally substituted monocyclic heteroaryl ring selected from optionally substituted imidazolyl, optionally substituted pyrazolyl, optionally substituted pyridinyl, optionally substituted pyridazinyl, optionally substituted pyrimidinyl, or optionally substituted pyrazinyl; or optionally substituted bicyclic heteroaryl ring selected from optionally substituted quinolinyl, optionally substituted isoquinolinyl, optionally substituted quinazolinyl, optionally substituted indolyl, optionally substituted indazolyl, optionally substituted 1H-pyrrolo[2,3-b]pyridinyl, optionally substituted benzoxazolyl, optionally substituted benzoisoxazolyl, or optionally substituted benzimidazolyl;

wherein each heteroaryl is independently optionally substituted by one or more substituents selected from alkyl optionally substituted with halogen, hydroxy, methoxy, or trifluoromethyl; halo, fluoroalkyl, oxo, thioxo, cyano, nitro, carbocyclyl optionally substituted with halogen, hydroxy, methoxy, or trifluoromethyl; carbocyclylalkyl optionally substituted with halogen, hydroxy, methoxy, or trifluoromethyl; heterocyclyl optionally substituted with halogen, hydroxy, methoxy, or trifluoromethyl; heterocyclylalkyl optionally substituted with halogen, hydroxy, methoxy, or trifluoromethyl; —$R^b$—$OR^a$, —$R^b$—$OC(O)$—$R^a$, —$R^b$—$OC(O)$—$OR^a$, —$R^b$—$OC(O)$—$N(R^a)_2$, —$R^b$—$N(R^a)_2$, —$R^b$—$C(O)R^a$, —$R^b$—$C(O)OR^a$, —$R^b$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tR^a$ (where t is 1 or 2), —$R^b$—$S(O)_tOR^a$ (where t is 1 or 2) and —$R^b$—$S(O)_tN(R^a)_2$ (where t is 1 or 2), where each $R^a$ is independently hydrogen, alkyl optionally substituted with halogen, hydroxy, methoxy, or trifluoromethyl; fluoroalkyl, cycloalkyl optionally substituted with halogen, hydroxy, methoxy, or trifluoromethyl; cycloalkylalkyl optionally substituted with halogen, hydroxy, methoxy, or trifluoromethyl; heterocyclyl optionally substituted with halogen, hydroxy, methoxy, or trifluoromethyl; heterocyclylalkyl optionally substituted with halogen, hydroxy, methoxy, or trifluoromethyl; and each $R^b$ is independently a direct bond or a straight or branched alkylene chain.

2. The compound of claim 1, or a pharmaceutically acceptable salt thereof, wherein Ring A is optionally substituted quinolyl, optionally substituted indolyl, optionally substituted isoquinolyl, optionally substituted quinazolinyl, or optionally substituted benzoisoxazolyl.

3. The compound of claim 1, or a pharmaceutically acceptable salt thereof, wherein Ring A is selected from optionally substituted benzo[d]isoxazol-7-yl, optionally substituted 4-aminoquinazolin-5-yl, optionally substituted indol-5-yl; optionally substituted quinolin-3-yl; quinoxalin-2-yl; optionally substituted isoquinolin-1(2H)-on-2-yl; or optionally substituted quinolin-6-yl.

4. The compound of claim 1, or a pharmaceutically acceptable salt thereof, wherein Ring A is an optionally substituted quinolin-6-yl or an optionally substituted quinolin-3-yl.

5. The compound of claim 4, or a pharmaceutically acceptable salt thereof, wherein the optionally substituted quinolin-6-yl or optionally substituted quinolin-3-yl is substituted with at least one substituent selected from optionally substituted C1-C3 alkyl, halogen, —CN, —$SO_2Me$, —$SO_2NH_2$, —$CONH_2$, —$CH_2NHAc$, —$CO_2Me$, —$CO_2H$, —$CH_2OH$, —$CH_2NH_2$, —$NH_2$, —OH, or —OMe.

6. The compound of claim 5, or a pharmaceutically acceptable salt thereof, wherein the optionally substituted quinolin-6-yl is substituted at least at the 3-position.

7. The compound of claim 6, or a pharmaceutically acceptable salt thereof, wherein the quinolin-6-yl is selected from 3-chloroquinolin-6-yl, 3-methylquinolin-6-yl, 3-trifluoromethylquinolin-6-yl, 3-fluoroquinolin-6-yl, or 3-cyanoquinolin-6-yl.

8. The compound of claim 5, or a pharmaceutically acceptable salt thereof, wherein the optionally substituted quinolin-3-yl is substituted at least at the 6-position or the 7-position.

9. The compound of claim 1, or a pharmaceutically acceptable salt thereof, wherein Ring B is optionally substituted imidazolyl.

10. The compound of claim 1, or a pharmaceutically acceptable salt thereof, wherein Ring B is selected from optionally substituted pyridazinyl, optionally substituted pyrimidinyl, or optionally substituted pyrazinyl.

11. The compound of claim h or a pharmaceutically acceptable salt thereof, wherein Ring B is an optionally substituted pyridinyl.

12. The compound of claim 11, or a pharmaceutically acceptable salt thereof, wherein the optionally substituted pyridinyl is an optionally substituted aminopyridinyl.

13. The compound of claim 12, or a pharmaceutically acceptable salt thereof, wherein the optionally substituted aminopyridinyl is an optionally substituted 6-aminopyridin-3-yl.

14. The compound of claim 1, or a pharmaceutically acceptable salt thereof, wherein Ring A is selected from optionally substituted quinolyl; and Ring B is an optionally substituted aminopyridinyl.

15. The compound of claim 1, or a pharmaceutically acceptable salt thereof, wherein Ring B is optionally substituted benzoxazolyl, optionally substituted benzoisoxazolyl, or optionally substituted benzimidazolyl.

16. The compound of claim 1, or a pharmaceutically acceptable salt thereof, wherein Ring B is an optionally substituted indolyl or an optionally substituted indazolyl.

17. The compound of claim 16, or a pharmaceutically acceptable salt thereof, wherein the optionally substituted indolyl is an optionally substituted indol-5-yl or an optionally substituted indazol-5-yl.

18. The compound of claim 1, or a pharmaceutically acceptable salt thereof, wherein Ring B is an optionally substituted 1H-pyrrolo[2,3-b]pyridinyl.

19. The compound of claim 1, or a pharmaceutically acceptable salt thereof, wherein Ring A is selected from optionally substituted quinolyl; and Ring B is selected from an optionally substituted indolyl, an optionally substituted indazolyl, or an optionally substituted 1H-pyrrolo[2,3-b]pyridinyl.

20. A pharmaceutical composition comprising a compound of Formula (Ia) as described in claim 1, or a pharmaceutically acceptable salt thereof, and a pharmaceutically acceptable excipient.

* * * * *